US007740871B2

(12) United States Patent
Ambinder et al.

(10) Patent No.: US 7,740,871 B2
(45) Date of Patent: Jun. 22, 2010

(54) CANCER IMMUNOTHERAPY WITH A VIRAL ANTIGEN-DEFINED, IMMUNOMODULATOR-SECRETING CELL VACCINE

(75) Inventors: Richard F. Ambinder, Lutherville, MD (US); Yiping Yang, Chapel Hill, NC (US); Ivan M. Borrello, Baltimore, MD (US); Hyam I. Levitsky, Owing Mills, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 1094 days.

(21) Appl. No.: 10/528,311

(22) PCT Filed: Sep. 19, 2003

(86) PCT No.: PCT/US03/29684

§ 371 (c)(1), (2), (4) Date: Mar. 24, 2006

(87) PCT Pub. No.: WO2004/027036

PCT Pub. Date: Apr. 1, 2004

(65) Prior Publication Data

US 2006/0233770 A1 Oct. 19, 2006

Related U.S. Application Data

(60) Provisional application No. 60/411,990, filed on Sep. 19, 2002.

(51) Int. Cl.
*A61K 35/12* (2006.01)
*A61K 48/00* (2006.01)
*C12P 21/00* (2006.01)

(52) U.S. Cl. .................. 424/277.1; 424/93.1; 424/85.1; 424/231.1; 435/325; 435/455; 514/44

(58) Field of Classification Search .................. 435/320
See application file for complete search history.

(56) References Cited

U.S. PATENT DOCUMENTS 6,464,973 B1 * 10/2002 Levitsky et al. .......... 424/93.21

FOREIGN PATENT DOCUMENTS

WO WO 99/38954 A1 8/1999

OTHER PUBLICATIONS

Morishima et al. J. Exp. Immunol. 1999, vol. 115, pp. 385-392.*
Draneff et al. 2002, vol. 188, pp. 147-154.*
Nedospasov et al. Molecular Biology 2007, vol. 41, No. 2, pp. 316-328.*
Borrello et al. Human Gen Therapy, 1999, vol. 10, pp. 1983-1991.*
Lee et al. J. Immunol. 1997, vol. 158, pp. 3325-3334.*
Nawrocki et al. Cancer Treatment Reviews, vol. 25, No. 1, Feb. 1999, pp. 29-46.*
Asada et al., "Significant Antitumor Effects Obtained by Autologous Tumor Cell Vaccine Engineered to Secrete Interleukin (IL)-12 and IL-18 by Means of the EBV/Lipoplex," *Molecular Therapy*, vol. 5(5), 609-616 (2002).
Khanna et al., "Immune Regulation in Epstein-Barr Virus-Associated Diseases," *Microbiological Reviews*, vol. 59(3), 387-405 (1995).

* cited by examiner

*Primary Examiner*—Mondesi Robert
*Assistant Examiner*—Bao Qun Li
(74) *Attorney, Agent, or Firm*—Barnes & Thornburg LLP

(57) ABSTRACT

A human cell line, which lacks major histocompatibility class I (MHC-I) antigens and major histocompatibility class II (MHC-II) antigens and which has been modified to comprise and express (i) a nucleotide sequence encoding an immunomodulator and (ii) a nucleotide sequence encoding a viral antigen, and a method of inducing or stimulating an immune response in a human to a viral-associated disease or cancer comprising administering to the human (i) the aforementioned human cell line in an amount sufficient to induce or stimulate an immune response to the viral associated disease or cancer, (ii) a human cell line, which lacks MHC-I and MHC-11 antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, simultaneously or sequentially in either order, by the same or different routes, in amounts sufficient to induce or stimulate an immune response to the viral-associated disease or cancer, or (iii) an immunomodulator and a human cell line, which lacks MHC-I and MHC-II antigens and which has been modified to comprise and express a nucleotide sequence encoding an antigen of EBV, simultaneously or sequentially in either order, by the same or different routes, in amounts sufficient to induce or stimulate an immune response to the viral associated disease or cancer.

18 Claims, 186 Drawing Sheets

Homo sapiens interferon, alpha 1 (IFNA1), mRNA.

ACCESSION NM_024013

VERSION NM_024013.1 GI:13128949

1 agaacctaga gcccaaggtt cagagtcacc catctcagca agcccagaag tatctgcaat
61 atctacgatg gcctcgccct ttgctttact gatggtcctg gtggtgctca gctgcaagtc
121 aagctgctct ctgggctgtg atctccctga gacccacagc ctggataaca ggaggacctt
181 gatgctcctg gcacaaatga gcagaatctc tccttcctcc tgtctgatgg acagacatga
241 ctttggattt ccccaggagg agtttgatgg caaccagttc cagaaggctc cagccatctc
301 tgtcctccat gagctgatcc agcagatctt caacctcttt accacaaaag attcatctgc
361 tgcttgggat gaggacctcc tagacaaatt ctgcaccgaa ctctaccagc agctgaatga
421 cttggaagcc tgtgtgatgc aggaggagag ggtgggagaa actcccctga tgaatgcgga
481 ctccatcttg gctgtgaaga aatacttccg aagaatcact ctctatctga cagagaagaa
541 atacagccct tgtgcctggg aggttgtcag agcagaaatc atgagatccc tctctttatc
601 aacaaacttg caagaaagat taaggaggaa ggaataacat ctggtccaac atgaaaacaa
661 ttcttattga ctcatacacc aggtcacgct ttcatgaatt ctgtcatttc aaagactctc
721 acccctgcta taactatgac catgctgata aactgattta tctatttaaa tatttattta
781 actattcata agatttaaat tatttttgtt catataacgt catgtgcacc tttacactgt
841 ggttagtgta ataaaacatg ttccttatat ttactc Homo sapiens interferon, alpha 2 (IFNA2), mRNA.

ACCESSION NM_000605

VERSION NM_000605.2 GI:11067750

1 gagaacctgg agcctaaggt ttaggctcac ccatttcaac cagtctagca gcatctgcaa
61 catctacaat ggccttgacc tttgctttac tggtggccct cctggtgctc agctgcaagt
121 caagctgctc tgtgggctgt gatctgcctc aaacccacag cctgggtagc aggaggacct
181 tgatgctcct ggcacagatg aggagaatct ctcttttctc ctgcttgaag gacagacatg
241 actttggatt tccccaggag gagtttggca accagttcca aaaggctgaa accatccctg
301 tcctccatga gatgatccag cagatcttca atctcttcag cacaaaggac tcatctgctg
361 cttgggatga gaccctccta gacaaattct acactgaact ctaccagcag ctgaatgacc
421 tggaagcctg tgtgatacag ggggtggggg tgacagagac tcccctgatg aaggaggact
481 ccattctggc tgtgaggaaa tacttccaaa gaatcactct ctatctgaaa gagaagaaat
541 acagcccttg tgcctgggag gttgtcagag cagaaatcat gagatctttt tctttgtcaa
601 caaacttgca agaaagttta agaagtaagg aatgaaaact ggttcaacat ggaaatgatt
661 ttcattgatt cgtatgccag ctcacctttt tatgatctgc catttcaaag actcatgttt
721 ctgctatgac catgacacga tttaaatctt ttcaaatgtt tttaggagta ttaatcaaca
781 ttgtattcag ctcttaaggc actagtccct tacagaggac catgctgact gatccattat
841 ctatttaaat atttttaaaa tattatttat ttaactattt ataaaacaac ttatttttgt
901 tcatattatg tcatgtgcac ctttgcacag tggttaatgt aataaaatgt gttctttgta

Fig. 3

961 tttggtaaat ttattttgtg ttgttcattg aacttttgct atggaacttt tgtacttgtt
1021 tattctttaa aatgaaattc caagcctaat tgtgcaacct gattacagaa taactggtac
1081 acttcatttg tccatcaata ttatattcaa gatataagta aaaataaact ttctgtaaac
1141 ca

Fig. 3 (cont.)

Homo sapiens interferon, gamma (IFNG), mRNA.

ACCESSION NM_000619

VERSION NM_000619.1 GI:10835170

1 tgaagatcag ctattagaag agaaagatca gttaagtcct ttggacctga tcagcttgat
61 acaagaacta ctgatttcaa cttctttggc ttaattctct cggaaacgat gaaatataca
121 agttatatct tggcttttca gctctgcatc gttttgggtt ctcttggctg ttactgccag
181 gacccatatg taaaagaagc agaaaacctt aagaaatatt ttaatgcagg tcattcagat
241 gtagcggata atggaactct tttcttaggc attttgaaga attggaaaga ggagagtgac
301 agaaaaataa tgcagagcca aattgtctcc ttttacttca aactttttaa aaactttaaa
361 gatgaccaga gcatccaaaa gagtgtggag accatcaagg aagacatgaa tgtcaagttt
421 ttcaatagca acaaaaagaa acgagatgac ttcgaaaagc tgactaatta ttcggtaact
481 gacttgaatg tccaacgcaa agcaatacat gaactcatcc aagtgatggc tgaactgtcg
541 ccagcagcta aaacagggaa gcgaaaaagg agtcagatgc tgtttcaagg tcgaagagca
601 tcccagtaat ggttgtcctg cctgcaatat ttgaatttta aatctaaatc tatttattaa
661 tatttaacat tatttatatg gggaatatat ttttagactc atcaatcaaa taagtattta
721 taatagcaac ttttgtgtaa tgaaaatgaa tatctattaa tatatgtatt atttataatt
781 cctatatcct gtgactgtct cacttaatcc tttgttttct gactaattag gcaaggctat
841 gtgattacaa ggctttatct caggggccaa ctaggcagcc aacctaagca agatcccatg
901 ggttgtgtgt ttatttcact tgatgataca atgaacactt ataagtgaag tgatactatc
961 cagttactgc cggtttgaaa atatgcctgc aatctgagcc agtgctttaa tggcatgtca
1021 gacagaactt gaatgtgtca ggtgaccctg atgaaaacat agcatctcag gagatttcat
1081 gcctggtgct tccaaatatt gttgacaact gtgactgtac ccaaatggaa agtaactcat
1141 ttgttaaaat tatcaatatc taatatatat gaataaagtg taagttcaca act

Fig. 3 (cont.)

Human papilloma virus type 59, complete viral genome.

ACCESSION X77858

VERSION X77858.1 GI:557236

JOURNAL Virology 203 (1), 158-161 (1994)

1 gttaagaccg aaaacggtgc atataaaggt agttgaaaag aaaagggcaa cggcatggca
61 cgctttgagg atcctacaca acgaccatac aaactgcctg atttgagcac aacattgaat
121 attcctctgc atgatattcg catcaattgt gtgttttgca aaggggaact gcaagaaaga
181 gaggtatttg aatttgcttt taatgactta tttatagtgt atagagactg tacaccgtat
241 gcagcgtgtc tgaaatgcat ttcattttat gcaagagtaa gagaattaag atattataga
301 gattccgtgt atggagaaac attagaggct gaaaccaaga caccgttaca tgagctgctg
361 atacgctgtt atagatgcct aaaacctcta tgtccaacag ataaattaaa gcatataact
421 gaaaaaagaa gattccataa tatagctgga atatatacag gacagtgtcg tgggtgtcgg
481 acccgagcaa gacacctaag acagcaacga caagcgcgta gtgaaacact ggtgtaaaac
541 aatgcatgga ccaaaagcaa cactttgtga cattgtttta gatttggaac cacaaaatta
601 tgaggaagtt gaccttgtgt gctacgagca attacctgac tccgactccg agaatgaaaa
661 agatgaacca gatggagtta atcatccttt gctactagct agacgagctg aaccacagcg
721 tcacaacatt gtgtgtgtgt gttgtaagtg taataatcaa cttcagctag tagtagaaac
781 ctcgcaagac ggattgcgag ccttacagca gctgtttatg gacacactat cctttgtgtg
841 tcctttgtgt gcagcaaacc agtaacctgc aatggccgat tcggaaggta cagatgggga
901 agggacgggg tgcaatggat ggttttttgt gcaggcaata gtagataaaa aaacaggtga
961 caaaatttca gatgacgagg atgaaaatgc aacagataca ggttcagact tggtagattt
1021 tattgatgat accacaacaa tttgtgtaca ggcagagcgc gagacagcac aggccttgtt
1081 taatgtgcag gaagcccaaa gggatgcacg ggaaatgcat gttttaaaac gaaagtttgg
1141 gtgcagtata gaaaacagta gtgagaaagc ggcggcagga aaaaaagcta agtcaccatt
1201 acaagaaata tcagtaaatg ttaaccaccc aaaagtaaaa agaaggttaa taacagtgcc
1261 agacagcggc tatggctatt ctgaagtgga aatgctcgag actcaggtaa ccgtggagaa
1321 tactggaaat ggggatagca atggcagtgt ttgtagcgac agtcaaatag actgtagcga
1381 cagcagtaac atggatgttg aaaacatagt tccaacatcc cccactaatc aattgttaca
1441 gttattacat agcaaaaata agaaagcagc tatgtatgca aaatttaaag aattgtatgg
1501 gttatcattt caagatttgg ttaggacatt taaaagtgac agaactacct gtagcgattg
1561 ggtaaccgcc atttttggtg ttaatccaac tgtagcagaa ggatttaaaa cattaataca
1621 accctatgtg ctatatgcac atatacaatg cttagattgt gcatggggag tagtaatatt
1681 agcattatta agatataaat gtggaaaaaa tagaataaca gttgcaaaag gacttagcac
1741 attactacat gtaccagata cgtgcatgtt aattgaacca cccaaattgc gtagtggtgt
1801 tgcagcacta tattggtaca gaacaggaat gtccaatatt agtgaagtta taggggaaac
1861 gcccgaatgg atacaaagac taacaattat acaacatgga gttgatgata gcgtgtttga
1921 cctgtcagaa atgatacaat gggcgtttga taatgaccta acagatgaaa gtgatattgc

Fig. 3 (cont.)

1981 atatgaatat gcattaatag cagatagtaa tagtaacgcc gctgcatttt taaaaagcaa
2041 ctgccaggca aaatacctaa aagattgtgc agttatgtgt aggcattata aaagagcaca
2101 aaaaagacaa atgagtatgt cacagtggat aaaatggaga tgtgataaaa tagaagaggg
2161 gggagattgg aaacccatag tacaattttt aagatatcaa ggagtagaat ttataacgtt
2221 tttatgtgca ttaaaagatt ttttaaaagg taccccaaaa agaaattgca ttgtgctgtg
2281 tgggccagca aatacaggca agtcatactt tggaatgagc ctgctacatt ttttacaagg
2341 aactgtaatt tcacatgtaa attcaaatag tcacttttgg ctagaacctt taacagatcg
2401 taaattagct atgctagacg atgcaacaga tagttgttgg acatattttg atacatatat
2461 gcgaaatgct ttggatggca atcctataag tgtagataga aagcataggc acctagtaca
2521 aattaaatgt ccaccaatgc ttattacatc aaatacaaat ccagttacag ataacaggtg
2581 gccatattta aatagcagat taatggtatt taaatttcca aacaaattgc catttgacaa
2641 aaatagaaat ccagtatata caattaatga cagaaactgg aaatgttttt ttgaaaggac
2701 gtggtgcaga ttagatttga acgaggaaga ggaagatgca gacagtgatg gacacccttt
2761 cgcagcgttt aagtgtgtta caggatcaaa tattagaaca ttatgaaaac gatagtaaag
2821 acattaatga acacataaac tattggaaac tggtgcgtat ggaaaatgta attttatttg
2881 cagcaagaga gaacaatata catacattaa accaccaggt ggtgccaacg tttttggtgt
2941 ctaaaaacaa ggcatgtgaa gctattgaac tgcagtcaaa ccgtacttcc actgtaatgc
3001 cctgtttttt aaaacatttt ttaggtgctg tttgccatag ttcttggcat gtttcttgca
3061 ttgtccattg ctcattttta aactcagttt gtgccaaact ctctaacgcc atctgcagca
3121 aggaaaacac aatgcattac acaagctgga catttatata ttatgtaaat gatgtaggac
3181 agtggtgtaa aaccacagga aatgtggact tttggggact atattataaa gtggaagagg
3241 aacaggtgta ctatgtaaaa tttatacatg atgccaaaaa atatgggact acagacaagt
3301 gggaagtgca ttataatggc aaggttattg attgttatga ctctatgtgc agtaccagtg
3361 acgagcaagt atccactgct ggatcttctg agcaactatc atacccctcc gcaacgcccc
3421 ccgaagccac gtacttgggc ccccaaacgt ggaaccgtca gacgaagact ggaaagcgac
3481 caagacagtg tggatacaca cagcaccctc agtctaccag cgtgtcagtg gactactgtg
3541 acaacccagt cgtccgtttg catccaggca acaacccgcg acggcacatc ccttgcagta
3601 acactacgcc tataatacac ttaaaaggtg acaaaaatgg ccttaagtgt ttaaggtata
3661 gattaagaaa agtacactgg ttatttgaaa atatttcctc tacctggcat tggacaggaa
3721 acagaggatc agccaaaaca ggcattttaa cattaacata tacaagcgaa acacaacgca
3781 atgaattttt agatactgta aaaattccta atagtgtaca aatacatgtt gggtatatga
3841 gtgtgtaatg gttgttatgc aaatgtaaca caagccaata ctgctgctat attgtatagc
3901 tgaggaaatg ataacccttg tatttgtgtg ttgtgtttgt gtttgcttgt gtgtgtgttg
3961 caatgtcccg cttctgcaat ctgtctatat gtgtgcatat acatggttac tagtatttgt
4021 gtatattgtg gttatcacct cctcatatga gtgtttttta ctatatatat tgttttttat
4081 aattccactg ttactactat atgcccatgc aatactgtcc atacaataat tgctgtatat
4141 tgtaaattac attgcactgt attgtacagt atattttaaa cacattatta tttttgttag
4201 gtgttggttt tgttacattt ataataaaac atggtttccc atcgtgctgc tcgtcgtaaa
4261 cgtgcctcag caacagactt atataaaact tgcaagcagg caggtacatg cccttctgat

Fig. 3 (cont.)

4321 gttattaata aagttgaagg tacaacttta gctgataaaa tattgcagtg gaccagccta
4381 ggaatatttt taggtggact aggtattggt actggatctg gtaccggtgg cagaacaggg
4441 tacataccttt tagggggggcg tacaaacact atagtagatg tatcgcctgc taaaccacca
4501 gtagttattg aacctgttgg acctacagat ccatctatag ttacattagt tgaggattct
4561 agtgttataa catctggagc cctgccccca acatttacag gtacttcagg atttgaaata
4621 tctacctcta gtacaacaac accagctgtt ttggatataa ccccaacctc ttctgttcaa
4681 attagtagct ctagttttat aaatcctgca tttacagacc cttctgtcat tgaggttccc
4741 caaacaggtg aaatttctgg taatatatta attagtaccc ctacctctgg tgcacatggc
4801 tatgaagaaa ttccaatgca aacgtttgct acggaaggta ctggtttgga acccattagc
4861 agtaccccca atccaacagt acgtcgtgtg gctggaccta gattgtacag tagggctaat
4921 caacaagttc gggtgtctaa cgctgacttt ttaacacgtc catccacatt tgttacatat
4981 gataaccctg cttatgatcc aattgatact acattaactt ttgacccctc atcagaggtt
5041 ccagacccgg actttatgga tatagttcgt ttgcataggc ctgcattaac atccagacgc
5101 agcactgtaa ggtttagtag gctaggacaa cgggcaacca tgtttacccg tagtggtaaa
5161 caaattgggg cccgtgtaca tttttatcat gatataagcc ctataccaca tgctgaagat
5221 attgaattgc aacctcttgt ttcttcccag gctgctactg atgatatata tgatatatat
5281 gcagatatta cagatgaagc acctactagt actgccaaca ctgcatttac aattcctaaa
5341 tcttctttc aaagtttgtc attaacacgg tcggcatcta gcaccttttc aaatgtaact
5401 gttcctttgg ctactgcctg ggatgttcct gtaaatacag gacccgatat agttttacct
5461 aatactaata ttgttgaacc cacttattct actacaccct ttaccaccat acagtctatt
5521 aatatagaag gcacaaatta ttttttatgg cctatatatt attttttacc tcgtaaacgt
5581 aaacgtgttc cctatttttt tacagatggc tctatggcgt tctagtgaca acaaggtgta
5641 tctacctcca ccttcggtag ctaaggttgt cagcactgat gagtatgtca cccgtaccag
5701 tattttctac cacgcaggca gttccagact tcttacagtt ggacatccat attttaaagt
5761 acctaaaggt ggtaatggta gacaggatgt tcctaaggtg tctgcatatc aatacagagt
5821 atttagggtt aagttacctg atcccaataa atttggcctt ccagataaca cagtatatga
5881 tcctaactct caacgcttgg tctgggcctg tgtaggtgtt gaaatcggtc ggggccaacc
5941 tttaggggta ggactcagtg gtcatccatt atataataaa ttggatgaca ctgaaaactc
6001 tcatgtagca tctgctgttg ataccaaaga tacacgtgat aatgtatctg tggattataa
6061 acaaactcag ctgtgtatta ttggctgtgt acctgccatt ggagaacact ggacaaaggg
6121 cactgcttgt aagcctacta ctgtggttca gggcgattgt cctccactag aattaataaa
6181 tacaccaatt gaagatggtg atatggtaga cacaggatat ggggctatgg actttaaatt
6241 gttgcaggat aacaaaagtg aagtaccatt ggatatttgt cagtctattt gtaaatatcc
6301 tgattattta caaatgtcag cagatgctta tggagacagt atgttttttt gtttaaggcg
6361 agaacaggtt tttgccagac atttttggaa tagatctggt actatgggtg atcaacttcc
6421 tgaatcacta tatattaaag gtactgacat acgtgccaac ccaggcagtt atttatattc
6481 cccttcccca agtgggtctg tggttacttc tgattcacaa ttatttaata aaccatattg
6541 gctgcacaag gctcagggtt taaacaatgg tatatgttgg cacaatcaat tgtttttaac
6601 agttgtagat actactcgca gcaccaatct ttctgtgtgt gcttctacta cttcttctat

Fig. 3 (cont.)

6661 tcctaatgta tacacaccta ccagttttaa agaatatgcc agacatgtgg aggaatttga
6721 tttgcagttt atatttcaac tgtgtaaaat aacattaact acagaggtaa tgtcatacat
6781 tcataatatg aataccacta ttttggagga ttggaatttt ggtgttacac cacctcctac
6841 tgctagttta gttgacacat accgttttgt tcaatctgct gctgtaactt gtcaaaagga
6901 caccgcaccg ccagttaaac aggaccctta tgacaaacta aagttttggc ctgtagatct
6961 taaggaaagg ttttctgcag atcttgatca gtttcctttg ggacgtaaat ttttattgca
7021 attaggagct agacctaagc ccactatagg cccacgcaaa cgtgcagcgc ctgcccctac
7081 ctctacccca tcaccaaaac gtgttaagcg tcgcaagtct tccagaaaat agtgttgttt
7141 gttatgtgtt tgtatgtgtg catgttgtat gttttgtatt gtttgcctgt ttgtatgttg
7201 tgtatatgta catgtttgtt tgtctgctgt atgtgtgtat ttgtttttgt acataataaa
7261 gtatgcatga cagtttcatg tgtggttgca cccaatgagt aaggtactgt ccctttattg
7321 tttctttgtc cttattacac attattacac attgccctac ttacataggt gtgtttgttc
7381 cttcatttg tcctgaatgt ccagttttgc atttgcacat tatatggcgt ccattttatc
7441 ctttaaatcc tccattttgc tgtgcaaccg ttttcggtta ccttggttta accttacctt
7501 tttgaacaat taatctgttt aaacatcagc aaaacagtta atccccatct tgtttcctcc
7561 tacacgccta gactactaac acaacttaca aacgccaaat agttagtcat catcctgtcc
7621 aggtgcactc taacaatact tgcataactt tggtggcgcc cttgttaata aaacagcttt
7681 taggcacata ttttcactgt ttttactact ttaattgcat aattggcttg caaaactact
7741 gtgcaatcca agaatgtgtc tataatttat tgtaaaaaac atgactaagg tttttgtcat
7801 tgttaagcaa ccgaaaaagg tcgggcaagt acatgcacac tttctactta ttactttta
7861 caatcatagt aataaaaaag ggtgtaaccg aaaacg

Fig. 3 (cont.)

Human papilloma virus type 59, complete viral genome.

ACCESSION X77858

VERSION X77858.1 GI:557236

3908..4129 gene="ORF putative E5"

atg ataacccttg tatttgtgtg ttgtgtttgt gtttgcttgt gtgtgtgttg 3961 caatgtcccg cttctgcaat ctgtctatat gtgtgcatat acatggttac tagtatttgt 4021 gtatattgtg gttatcacct cctcatatga gtgtttttta ctatatatat tgttttttat 4081 aattccactg ttactactat atgcccatgc aatactgtcc atacaataa 55..537 gene="ORF putative E6"

atggca 61 cgctttgagg atcctacaca acgaccatac aaactgcctg atttgagcac aacattgaat 121 attcctctgc atgatattcg catcaattgt gtgttttgca aaggggaact gcaagaaaga 181 gaggtatttg aatttgcttt taatgactta tttatagtgt atagagactg tacaccgtat 241 gcagcgtgtc tgaaatgcat ttcattttat gcaagagtaa gagaattaag atattataga 301 gattccgtgt atggagaaac attagaggct gaaaccaaga caccgttaca tgagctgctg 361 atacgctgtt atagatgcct aaaacctcta tgtccaacag ataaattaaa gcatataact 421 gaaaaaagaa gattccataa tatagctgga atatatacag gacagtgtcg tgggtgtcgg 481 acccgagcaa gacacctaag acagcaacga caagcgcgta gtgaaacact ggtgtaa 542..865 gene="ORF putative E7"

atgcatgga ccaaaagcaa cactttgtga cattgtttta gatttggaac cacaaaatta 601 tgaggaagtt gaccttgtgt gctacgagca attacctgac tccgactccg agaatgaaaa 661 agatgaacca gatggagtta atcatccttt gctactagct agacgagctg aaccacagcg 721 tcacaacatt gtgtgtgtgt gttgtaagtg taataatcaa cttcagctag tagtagaaac 781 ctcgcaagac ggattgcgag ccttacagca gctgtttatg gacacactat cctttgtgtg 841 tcctttgtgt gcagcaaacc agtaa

Fig. 3 (cont.)

Human papilloma virus type 13 DNA.

ACCESSION X62843 S43933

VERSION X62843.1 GI:60295

TITLE Human papillomavirus type 13 and pygmy chimpanzee papillomavirus type 1: comparison of the genome organizations JOURNAL Virology 190 (2), 587-596 (1992)

1 gtttctaaca atcttaagtt taaaaaatag gtgggaccga aaacggtttt aaccgaaaac
61 ggtgatatat aaaccagccc aaaaattgag caagcggggc ataatggaaa gtgcaaatgc
121 ctccacgcct gcaaaaacta tagaccagtt gtgcaaggag tgcaaccttt ctatgcacag
181 cttgcaaatt ctatgcgtgt tctgcaggaa aaccctgtcc acggcagagg tttatgcatt
241 tcagtataag agtttatata tagtgtggcg aggacagttt ccatttgcgg cttgtgcatg
301 ctgcttagaa atacaaggaa agattaacca gtttaggcat tttgacttcg cgggatttgc
361 tgtaacagtt gaagaagaca caaagcagtc aattttggat gtgctaattc gctgctattt
421 atgccacaaa ccattgtgtg aagtggagaa actaagacat attttgcaga aggcacgatt
481 tattaaatta aacagcagtt ggaaaggccg ctgttttcat tgctggtcat catgcatgga
541 aaatatccta ccttaaaaga cattgtttta gagctgactc ctgaccctgt aggtctacat
601 tgcaatgagc aattagacag ctcagaagac gaggtggacg aacaagccac gcaagccacg
661 caagccacgc aacatagcac actattacaa tgctaccaaa tactaacgtc ctgtagtaaa
721 tgttgtagca acgtccggct ggtggtggag tgtacaggac ctgacattca cgacctacac
781 gacctactgc tgggcacgct gaatatagtg tgccctttgt gtgcaccaaa aagctaacca
841 cgatggcaga ggatacaggt actaataatg aggggacggg atgctcagga tggtttttag
901 tagaggctgt agtagaacga acaactgggc aacaaatatc agatgatgag gatgaaacag
961 tggaagatag tgggttggat atggtggatt tcatagatga cagacctatt acacacaatt
1021 ccgtggaagc acaggcattg ttaaacgagc aggaggcgga tgctcattat gcggctgtgc
1081 aggacctaaa acgaaagtat ttaggcagtc catatgttag tcccctagga catgttgaac
1141 agtcagtgga ctgtgatata agtcctcgat tggacgctat aaaattaagt agaaattcta
1201 aaaaagtaaa gcgacggctg tttcaatcaa gggaaataac ggacagtgga tatggctatt
1261 ctgaagtgga agctgaaacg caggtagaga gaaatggcga accggaaaat gattgtgggg
1321 gtggtggaca cggaagggac aaagaggggg agggacaggt gcacacggaa gtgcacacag
1381 gcagccagat agaagagcac acagggacca cgcgggtgtt agaactcctt aaatgtaagg
1441 atgtaagggc tacattgtat ggtaagttta aagactgtta tgggttatca tttacagatt
1501 taattagacc atttaaaagt gataaaacaa catgtgggga ctgggtggtt gcagcatttg
1561 gtatacatca tagtgtatca gaggcatttg aaaagttaat gcagccatta acaacatata
1621 tgcatataca atggcttaca aatgcatggg ggatggtatt gttagtatta ataagattta
1681 aagtaaataa aagtagatgc acagtggcgc gaacactggc aacctttctt aatattcctg
1741 aggaccacat gttaattgaa cctcccaaaa tacaaagcag tgtggcagca ttatactggt
1801 ttagaacagg tatttctaat gctagtatag taactggtga aacaccagaa tggataaaaa
1861 ggcaaacaat tgtagagcat ggacttgcag ataatcaatt taaattaact gaaatggtgc

Fig. 3 (cont.)

1921 agtgggcata tgataatgat ttttgtgatg aaagcgaaat agcatttgaa tatgcacaac
1981 gaggagattt tgattcaaat gccagggcat ttttaaatag taattgtcag gcaaaatatg
2041 taaaagattg tgcaacaatg tgcaagcatt ataaaaatgc agaaatgaaa aaaatgtcta
2101 tgaaacaatg gataacatat agaagtaaaa aaatagagga agcaggaaat tggaaaccaa
2161 tagtacaatt tttaaggcat caaaatatag aatttattcc atttttaagt aaattaaaat
2221 tgtggcttca tggcacgcca aagaaaaact gtattgcaat agtggggcca ccagatacag
2281 gcaaatcatg tttttgcatg agcttaatta agtttttagg gggcacagta attagttatg
2341 taaattcaag tagccatttt tggctgcagc cattatgtaa tgcaaaggta gctttgctag
2401 atgatgcaac gcagtcatgc tgggtatata tggacacata catgagaaat ttattagatg
2461 gcaatccaat gagcattgat agaaaacata agtctttagc attaataaaa tgtccgccat
2521 tattagtaac atctaatgta gacattacca aagatgacaa atataaatat ttgtatagta
2581 gagtaacaac acttacattt ccaaatccat tcccttttga cagaaatggg aatgcagtat
2641 atgagttgtc tgatgcaaac tggaaatgtt tttttacaag attgtcagca agcctagata
2701 tacaggactc tgaggacgag gacgatggag acaatagcca agcatttaga tgcgtgccag
2761 gaacagttgt tagaactgta tgaagaaaat agtaatgaac ttaaaaaaca tatacaacat
2821 tggaaatgct taaggtacga aagtgtactc ttacacaaag cacgccaaat gggcctaagc
2881 cacattggat tacaagtggt gccaccattg acagtatcac aagctaaggg acatgaggca
2941 attgaaatgc aaatgacttt agagacatta ctagagtctg agtttggtat ggaaccatgg
3001 actttacaag atacaagtcg tgaaatgtgg ctaacacccc caaaacgctg ttttaagaaa
3061 cagggacaaa ctgtggaagt aaaatatgac tgtaatacag acaatagaat ggattatgtg
3121 tcgtggacat acatatatgt gtttgacaca gataaatgga caaaggtgaa aggaatggta
3181 gattataaag ggttgtacta catacatgga aatttgaaaa catattattt agagtttgaa
3241 aaggaggcta aaaaatatgg ggaaacgtta caatgggaag tatgtattgg cagcacagtc
3301 atatgttctc ctgcatctgt atctagtact gtacaagaag tatccattgc tgggcctgct
3361 tcatactcca ccaccacctc cacacaggcc tccaccgcag tgtcctgcag cgcctcggaa
3421 gaatgtgtgc aagcgccgcc ttgtaaacga caacgaggac cttcacgtcc cattggaaac
3481 ccccagaaca cacaaagcat tgtgtgtgtc acagactacg acaccctgga cagtgcaaac
3541 aacaacatca acgttaacca ttacaacaat aacaaaggac gggacaacag ttactgtgca
3601 gctacaccta tagttcaatt acaaggtgac tctaattgtc taaagtgttt tcgatataga
3661 ttacatgaaa aatataaaga tttatttttg ttagcatcat ctacatggca ttggaccgcc
3721 cctaataatt cacaaaaaca tgcactggta accttaacct atgtaaatga acaacaaaga
3781 caagactttt taaaaactgt aaaaatacct ccaaccataa cacataaact aggttttatg
3841 tcattgcaat tgttataaca gcatatattg tatgtaaata tttgttgtgt gtgtgtatat
3901 attgtaaatg gaatttatac ctgtggatgt tagtacacag gcaaccagca agtcattact
3961 gccacttgta attgcactta cagtgtgtgt agttagcatt ataacaatat tgtgcatatc
4021 agagttcttg gtgtacacaa acgttttagt actaacatta attttatatg tacttttgtg
4081 gcttttacta acaactccct tgcaattcta tttactaacc ctgtctcttt gctttcttcc
4141 tgcgttgtgt gtacaccaat atattttaca aacacaagaa taactataca caatgttaac
4201 ctgtactttt gatgatggtg acacatggtt gctattatgg ttaattttat catttattgt

Fig. 3 (cont.)

4261 agccattcta gggttactgt tgctgtatat aagaactgga catatgcatt gccagtgctg
4321 gagtaaataa gtggttttat attttgtgtg tattcattta attatggcac atagtagggc
4381 tcgcagacgc aaacgcgctt cagctacaca actatatcaa acttgtaagg cttctggaac
4441 atgtcctcct gatgttatac caaaggttga acaaaacact cttgcagata aaatattaaa
4501 gtggggcagt ttaggagtat tttttggggg gcttggcatt ggcacaggct ctggtactgg
4561 cggtaggact ggctatgtac cagtaggatc caccccacgc cctgccatat caactgggcc
4621 tactgcacgt cctcctattg ttgttgatac tgttgggcct acagaccctt ctattgtatc
4681 tttggtagag gaatcagcta ttattaattc tggagtacct gaccctttgc ctcccgttca
4741 tgggggtttt gaaatcacca catctcaatc agccactcca gcaatattgg atgtgtctgt
4801 tacaacacaa aacactacgt ccacaagtat atttagaaat cctgtttttt cagaaccttc
4861 tattacacaa tctcaacctt ctattgaaag tggtgcacac gtgtttatat cgccatctac
4921 tatttcccct cattctacag aagacattcc tttagataca tttattgtat cttcctcaga
4981 tagtaatcct gcatcaagca cccctgttcc agcaactgtt gcacgtccac gtctaggcct
5041 ttacagtagg gccttacatc aagtacaggt tactgatcct gcctttttat cgtcgcccca
5101 acgccttata acctttgata accctacata tgaaggtgaa gatataagtt tgcagtttgc
5161 acacaatacc attcatgaac cccctgatga ggcatttatg gatattataa gactacatag
5221 gccagccata acatcacggc gtggtcttgt taggtttagt agaattggtc agaggggggtc
5281 tatgtatact cgaagcggca agcatatagg tggaagggtc catttcttta aggatatttc
5341 tcctatatct gcagctgcag aagaaataga attacacccc cttgtggctg ctgcacagga
5401 tcacagtggt ttgtttgata tttatgcaga acctgaccct gaccctgtgg ctgtaaacac
5461 ctctgggtca ttgtcttctg cctccacacc atttgcacaa tcttctttgt cttccgcccc
5521 atggggtaat actactgttc ctctttcact accaggtgat atatttatac agcctggtcc
5581 tgacataaca ttcccaactg cacctacagt aacgccttat aatcctgtta cgcctgcttt
5641 acctacaggt cctgttttta ttactgcttc tggattttat ttatatccta catggtattt
5701 tacacgcaaa cgccgtaaac gtgtttcctt gttttttaca gatgtggcgg cctagtgaca
5761 acaaactata tgtgcctcct cccgcccctg tatcaaaagt aattactacg gatgcctatg
5821 ttacacgtac caacatattt tatcatgcta gcagttctag actacttgca gtgggaaatc
5881 cttattttcc tattaagaaa caaaacaaaa ctgttgtccc taaggtatct ggttatcagt
5941 ttagggtatt taaagttgta ttacctgacc ctaataaatt tgccctgcct gacacatcta
6001 tatttgactc aactagtcaa cgcttagtgt gggcctgtac aggtttagag gttggtaggg
6061 gtcaaccctt aggtgttggt attagtggtc atccattatt aaataaatat gatgatgtgg
6121 aaaattctgc aagttatgct gccaatcctg gtcaggataa tagggttaat gtggccatgg
6181 actataaaca aacacagtta tgtttagtgg gctgtgcacc tcctttaggt gaacattggg
6241 gacagggcaa gcaatgtact ggtgtaaatg tacaacctgg agattgccct cctttagaat
6301 taattagtag tgtaattcag gatggtgaca tggtggatac aggatttgga gccatgaatt
6361 ttgcggaatt gcaatctaat aaatctgatg tgccactaga catatgcacg tccacatgca
6421 aatatcctga ctatttacaa atggctgcgg atccttatgg agacagatta tttttttatc
6481 tgcgaaagga acaaatgttt gcaaggcatt tctttaacag ggcaggctct gttggtgaac
6541 aaatcccagc agaattatat gttaagggta gtaatacact ttctaatagt atttactata

Fig. 3 (cont.)

6601 atactcccag tggctctctt gtgtcttctg aggcccagtt gtttaataaa ccttattggt
6661 tacaaaaggc ccagggacac aataatggta tatgttgggg caatcacttg ttgttactg
6721 tagttgatac tacacgcagt actaacatga ctgtgtgtgc agccactaca tcatctcttt
6781 cagacacata taaggccaca gaatataaac agtacatgcg acatgtagaa gaatttgatt
6841 tacaatttat ttttcaattg tgcactatta aattaactgc agaggttatg tcatatattc
6901 atactatgaa tcctacaatt ctagaagact ggaactttgg gctatctccc cctcctaatg
6961 gaacattaga agacacatat agatatgtac aatctcaggc cataacgtgt caaaagccta
7021 cacctgataa agaaaaacag gatccgtatg cgggtcttag tttttgggag gttaatctta
7081 aggaaaagtt ttctagtgaa ctagatcagt atccccttgg cagaaagttt ttattacaaa
7141 caggcgttca gtctaggtcc cctattcgtg taggtaggaa acgtgctgca tctacatcta
7201 ctgccacacc tactacacgt aaaaaagcta aaaggaaata atagtttgtt tatgattgtg
7261 tatgtatgtc acgtttgttt gtactgtatg tatgttgtgt actgtatgtg taatgttgta
7321 tgtatgtgca tgttacttat taaagaatgt gtgtgtgtgt ttgtatgcaa taaatctaat
7381 ctgtggtgtc ctgttccacc ctatgagtaa gtggtatgtt gtgtctcgtg tggtgttttg
7441 tatactatac tataacatta gtgcaaccat tttgtaactt ttcttacatt ttacgtctcc
7501 atattaagtg caaccgattt cggttgctat tgtttctgcg accgatttgt tgcagcacgc
7561 tgtttatata atcttaccta ccgcctgcca aaattatcca ccgcttgcca aaatcaccca
7621 cacacctggc gttgctaggg cgcggttata tatatttact aaatcttact aatctttcta
7681 tcactcattt tacctttata acaatacttt tgcttttcaa gtacattttt gtacttacta
7741 gccaatgcct gaaaggtttt ttggctacca gcactacatt tttgtacagt taatgttaca
7801 tgtataaaat gagtaaccta aggtcacaca cctgcaaacc ggtatcggtt aaaacacacc
7861 ctctatagtt ccttataatt

Fig. 3 (cont.)

Human papilloma virus type 13 DNA.

ACCESSION X62843 S43933

VERSION X62843.1 GI:60295

3908..4183 gene="E5"

atg gaatttatac ctgtggatgt tagtacacag gcaaccagca agtcattact 3961 gccacttgta attgcactta cagtgtgtgt agttagcatt ataacaatat tgtgcatatc 4021 agagttcttg gtgtacacaa acgttttagt actaacatta attttatatg tacttttgtg 4081 gcttttacta acaactccct tgcaattcta tttactaacc ctgtctcttt gctttcttcc 4141 tgcgttgtgt gtacaccaat atattttaca aacacaagaa taa 104..556 gene="E6"

atggaaa gtgcaaatgc 121 ctccacgcct gcaaaaacta tagaccagtt gtgcaaggag tgcaaccttt ctatgcacag 181 cttgcaaatt ctatgcgtgt tctgcaggaa aaccctgtcc acggcagagg tttatgcatt 241 tcagtataag agtttatata tagtgtggcg aggacagttt ccatttgcgg cttgtgcatg 301 ctgcttagaa atacaaggaa agattaacca gtttaggcat tttgacttcg cgggatttgc 361 tgtaacagtt gaagaagaca caaagcagtc aatttggat gtgctaattc gctgctattt 421 atgccacaaa ccattgtgtg aagtggagaa actaagacat attttgcaga aggcacgatt 481 tattaaatta aacagcagtt ggaaaggccg ctgttttcat tgctggtcat catgcatgga 541 aaatatccta ccttaa 532..837 gene="E7"

atgcatgga 541 aaatatccta ccttaaaaga cattgtttta gagctgactc ctgaccctgt aggtctacat 601 tgcaatgagc aattagacag ctcagaagac gaggtggacg aacaagccac gcaagccacg 661 caagccacgc aacatagcac actattacaa tgctaccaaa tactaacgtc ctgtagtaaa 721 tgttgtagca acgtccggct ggtggtggag tgtacaggac ctgacattca cgacctacac 781 gacctactgc tgggcacgct gaatatagtg tgccctttgt gtgcaccaaa aagctaa

Fig. 3 (cont.)

Homo sapiens erythropoietin (EPO), mRNA.

ACCESSION NM_000799

VERSION NM_000799.1 GI:4503588

1 cccggagccg gaccggggcc accgcgcccg ctctgctccg acaccgcgcc ccctggacag
61 ccgccctctc ctccaggccc gtggggctgg ccctgcaccg ccgagcttcc cgggatgagg
121 gcccccggtg tggtcacccg gcgcgcccca ggtcgctgag ggaccccggc caggcgcgga
181 gatgggggtg cacgaatgtc ctgcctggct gtggcttctc ctgtccctgc tgtcgctccc
241 tctgggcctc ccagtcctgg gcgccccacc acgcctcatc tgtgacagcc gagtcctgga
301 gaggtacctc ttggaggcca aggaggccga gaatatcacg acgggctgtg ctgaacactg
361 cagcttgaat gagaatatca ctgtcccaga caccaaagtt aatttctatg cctggaagag
421 gatggaggtc gggcagcagg ccgtagaagt ctggcagggc ctggccctgc tgtcggaagc
481 tgtcctgcgg ggccaggccc tgttggtcaa ctcttcccag ccgtgggagc ccctgcagct
541 gcatgtggat aaagccgtca gtggccttcg cagcctcacc actctgcttc gggctctgcg
601 agcccagaag gaagccatct cccctccaga tgcggcctca gctgctccac tccgaacaat
661 cactgctgac actttccgca aactcttccg agtctactcc aatttcctcc ggggaaagct
721 gaagctgtac acaggggagg cctgcaggac aggggacaga tgaccaggtg tgtccacctg
781 ggcatatcca ccacctccct caccaacatt gcttgtgcca caccctcccc cgccactcct
841 gaaccccgtc gaggggctct cagctcagcg ccagcctgtc ccatggacac tccagtgcca
901 gcaatgacat ctcaggggcc agaggaactg tccagagagc aactctgaga tctaaggatg
961 tcacagggcc aacttgaggg cccagagcag gaagcattca gagagcagct ttaaactcag
1021 ggacagagcc atgctgggaa gacgcctgag ctcactcggc accctgcaaa atttgatgcc
1081 aggacacgct ttggaggcga tttacctgtt ttcgcaccta ccatcaggga caggatgacc
1141 tggagaactt aggtggcaag ctgtgacttc tccaggtctc acgggcatgg gcactccctt
1201 ggtggcaaga gcccccttga caccggggtg gtgggaacca tgaagacagg atgggggctg
1261 gcctctggct ctcatggggt ccaagttttg tgtattcttc aacctcattg acaagaactg
1321 aaaccaccaa aaaaaaaaaa aa Mus musculus FMS-like tyrosine kinase 3 ligand (Flt3l), mRNA.

ACCESSION NM_013520

VERSION NM_013520.2 GI:31982427

1 gaattcgcgg ccgcgtcgac attctgggga cgtcggtcgg ggttcttaga agaggagatg
61 acttttcaca gtcactgagg ctcgtgcagg aagcctgggg gagcaggagg cggaaaccga
121 cccacatcaa gggcggcagg gccgggcggc ggggtacagg ggttgggggg gaaggggctg
181 cagggtatga gcccgagacc tgccctcctg tcacttccaa gaacctgtca caggcatgag
241 gggtccccgg cagagatgac agtgctggcg ccagcctgga gcccaaattc ctccctgttg
301 ctgctgttgc tgctgctgag tccttgcctg cgggggacac ctgactgtta cttcagccac
361 agtcccatct cctccaactt caaagtgaag tttagagagt tgactgacca cctgcttaaa
421 gattacccag tcactgtggc cgtcaatctt caggacgaga agcactgcaa ggccttgtgg
481 agcctcttcc tagcccagcg ctggatagag caactgaaga ctgtggcagg gtctaagatg

Fig. 3 (cont.)

541 caaacgcttc tggaggacgt caacaccgag atacattttg tcacctcatg taccttccag
601 cccctaccag aatgtctgcg attcgtccag accaacatct cccacctcct gaaggacacc
661 tgcacacagc tgcttggtct gaagccctgt atcgggaagg cctgccagaa tttctctcgg
721 tgcctggagg tgcagtgcca gccggactcc tccaccctgc tgcccccaag gagtcccata
781 gccctagaag ccacggagct cccagagcct cggcccaggc agctgttgct cctgctgctg
841 ctgctgctgc ctctcacact ggtgctgctg gcagccgcct ggggccttcg ctggcaaagg
901 gcaagaagga gggggagct ccaccctggg gtgcccctcc cctcccatcc ctaggatgcg
961 agccttgtgc atcgttgact cagccagggt cttatctcga tgaggtctca atatgttgcc
1021 caaactgact ttgaaaacct cgatgcacct tcctgcccca caaacttcca aacagctggg
1081 cttacgggca tgctatatac aacaaggctt tcttttcttc tttcttggtg ctagagttgg
1141 gaaccaaaac aa Homo sapiens macrophage colony-stimulating factor (M-CSF1) cDNA to mRNA, complete cds.
ACCESSION M27087
VERSION M27087.1 GI:508985

1 agccgctctc cgcatcccag gacagcggtg cggccctcgg ccggggcgcc cactccgcag
61 cacccagcga gcgagcgagc gagcgagggc ggccgacgcg cccggccggg acccagctgc
121 ccgtatgacc gcgccgggcg ccgccgggcg ctgccctccc acgacatggc tgggctccct
181 gctgttgttg gtctgtctcc tggcgagcag gagtatcacc gaggaggtgt cggagtactg
241 tagccacatg attgggagtg gacacctgca gtctctgcag cggctgattg acagtcagat
301 ggagacctcg tgccaaatta catttgagtt tgtagaccag gaacagttga aagatccagt
361 gtgctacctt aagaaggcat ttctcctggt acaagacata atggaggaca ccatgcgctt
421 cagagataac acccccaatg ccatcgccat tgtgcagctg caggaactct ctttgaggct
481 gaagagctgc ttcaccaagg attatgaaga gcatgacaag gcctgcgtcc gaactttcta
541 tgagacacct ctccagttgc tggagaaggt caagaatgtc tttaatgaaa caaagaatct
601 ccttgacaag gactggaata ttttcagcaa gaactgcaac aacagctttg ctgaatgctc
661 cagccaagat gtggtgacca agcctgattg caactgcctg taccccaaag ccatccctag
721 cagtgacccg gcctctgtct cccctcatca gcccctcgcc ccctccatgg cccctgtggc
781 tggcttgacc tgggaggact ctgagggaac tgagggcagc tccctcttgc ctggtgagca
841 gcccctgcac acagtggatc caggcagtgc caagcagcgg ccacccagga gcacctgcca
901 gagctttgag ccgccagaga ccccagttgt caaggacagc accatcggtg gctcaccaca
961 gcctcgcccc tctgtcgggg ccttcaaccc cgggatggag gatattcttg actctgcaat
1021 gggcactaat tgggtcccag aagaagcctc tggagaggcc agtgagattc ccgtacccca
1081 agggacagag ctttcccccct ccaggccagg agggggcagc atgcagacag agcccgccag
1141 acccagcaac ttcctctcag catcttctcc actccctgca tcagcaaagg gccaacagcc
1201 ggcagatgta actggtaccg ccttgcccag ggtgggcccc gtgaggccca ctggccagga
1261 ctggaatcac accccccaga agacagacca tccatctgcc ctgctcagag accccccgga
1321 gccaggctct cccaggatct catcaccgcg cccccagggc ctcagcaacc cctccaccct

Fig. 3 (cont.)

1381 ctctgctcag ccacagcttt ccagaagcca ctcctcgggc agcgtgctgc cccttgggga
1441 gctggagggc aggaggagca ccagggatcg gaggagcccc gcagagccag aaggaggacc
1501 agcaagtgaa ggggcagcca ggcccctgcc ccgttttaac tccgttcctt tgactgacac
1561 acatgagagg cagtccgagg gatcctccag cccgcagctc caggagtctg tcttccacct
1621 gctggtgccc agtgtcatcc tggtcttgct ggccgtcgga ggcctcttgt tctacaggtg
1681 gaggcggcgg agccatcaag agcctcagag agcggattct cccttggagc aaccagaggg
1741 cagccccctc actcaggatg acagacaggt ggaactgcca gtgtagaggg aattctaaga
1801 cccctcacca tcctggacac tctcgtttgt caatgtccct ctgaaaatgt gacgcccagc
1861 cccggacaca gtactccaga tgttgtctga ccagctcaga gagagtacag tgggactgtt
1921 accttccttg atatggacag tattcttcta tttgtgcaga ttaagattgc attagttttt
1981 ttcttaacaa ctgcatcata ctgttgtcat atgttgagcc tgtggtctat aaaaccccta
2041 gttccatttc ccataaactt ctgtcaagcc agaccatctc taccctgtac ttggacaact
2101 taactttttt aaccaaagtg cagtttatgt tcacctttgt taaagccacc ttgtggtttc
2161 tgcccatcac ctgaacctac tgaagttgtg tgaaatccta attctgtcat ctccgtagcc
2221 ctcccagttg tgcctcctgc acattgatga gtgcctgctg ttgtctttgc ccatgttgtt
2281 gatgtagctg tgaccctatt gttcctcacc cctgcccccc gccaacccca gctggcccac
2341 ctcttccccc tcccacccaa gcccacagcc agcccatcag gaagccttcc tggcttctcc
2401 acaaccttct gactgtcttt tcagtcatgc cccctgctct tttgtatttg gctaatagta
2461 tatcaatttg cactt cDNA encoding Granulocyte-Colony stimulating factor.

ACCESSION E08531

VERSION E08531.1 GI:2176646

1 cggagcctgc agcccagccc cacccagacc catggctgga cctgccaccc agagccccat
61 gaagctgatg gccctgcagc tgctgctgtg gcacagtgca ctctggacag tgcaggaagc
121 cacccccctg ggccctgcca gctccctgcc ccagagcttc ctgctcaagt gcttagagca
181 agtgaggaag atccagggcg atggcgcagc gctccaggag aagctggtga gtgagtgtgc
241 cacctacaag ctgtgccacc ccgaggagct ggtgctgctc ggacactctc tgggcatccc
301 ctgggctccc ctgagcagct gccccagcca ggccctgcag ctggcaggct gcttgagcca
361 actccatagc ggccttttcc tctaccaggg gctcctgcag gccctggaag ggatctcccc
421 cgagttgggt cccaccttgg acacactgca gctggacgtc gccgactttg ccaccaccat
481 ctggcagcag atggaagaac tgggaatggc ccctgccctg cagcccaccc agggtgccat
541 gccggccttc gcctctgctt tccagcgccg ggcaggaggg gtcctggttg cctcccatct
601 gcagagcttc ctggaggtgt cgtaccgcgt tctacgccac cttgcccagc cctgagccaa
661 gccctcccca tcccatgtat ttatctctat ttaatattta tgtctattta agcctcatat
721 ttaaagacag ggaagagcag aacggagccc caggcctctg tgtccttccc tgcatttctg
781 agtttcattc tcctgcctgt agcagtgaga aaaagctcct gtcctcccat cccctggact
841 gggaggtaga taggtaaata ccaagtattt attactatga ctgctcccca gccctggctc
901 tgcaatgggc actgggatga gccgctgtga gcccctggtc ctgagggtcc ccacctggga

Fig. 3 (cont.)

961 cccttgagag tatcaggtct cccacgtggg agacaagaaa tccctgttta atatttaaac
1021 agcagtgttc cccatctggg tccttgcacc cctcactctg gcctcagccg actgcacagc
1081 ggcccctgca tccccttggc tgtgaggccc ctggacaagc agaggtggcc agagctggga
1141 ggcatggccc tggggtccca cgaatttgct ggggaatctc gtttttcttc ttaagacttt
1201 tgggacatgg tttgactccc gaacatcacc gacgcgtctc ctgtttttct gggtggcctc
1261 gggacacctg ccctgccccc acgagggtca ggactgtgac tctttttagg gccaggcagg
1321 tgcctggaca tttgccttgc tggacgggga ctggggatgt gggagggagc agacaggagg
1381 aatcatgtca ggcctgtgtg tgaaaggaag ctccactgtc accctccacc tcttcacccc
1441 ccactcacca gtgtcccctc cactgtcaca ttgtaactga acttcaggat aataaagtgt
1501 ttgcctccaa aaaaaaaaaa aaaaaaaaaa a Granulocyte-Colony stimulating factor gene.
ACCESSION E08530
VERSION E08530.1 GI:2176645
1 ctgccgcttc caggcgtcta tcagcggctc agcctttgtt cagctgttct gttcaaacac
61 tctggggcca ttcaggcctg ggtggggcag cgggaggaag ggagtttgag gggggcaagg
121 cgacgtcaaa ggaggatcag agattccaca atttcacaaa actttcgcaa acagcttttt
181 gttccaaccc ccctgcattg tcttggacac caaatttgca taaatcctgg gaagttatta
241 ctaagcctta gtcgtggccc caggtaattt cctcccaggc ctccatgggg ttatgtataa
301 agggcccccct agagctgggc cccaaaacag cccggagcct gcagcccagc cccacccaga
361 cccatggctg gacctgccac ccagagcccc atgaagctga tgggtgagtg tcttggccca
421 ggatgggaga gccgcctgcc ctggcatggg agggaggctg gtgtgacaga ggggctgggg
481 atccccgttc tgggaatggg gattaaaggc acccagtgtc cccgagaggg cctcaggtgg
541 tagggaacag catgtctcct gagcccgctc tgtccccagc cctgcagctg ctgctgtggc
601 acagtgcact ctggacagtg caggaagcca cccccctggg ccctgccagc tccctgcccc
661 agagcttcct gctcaagtgc ttagagcaag tgaggaagat ccagggcgat ggcgcagcgc
721 tccaggagaa gctggtgagt gaggtgggtg agagggctgt ggagggaagc ccggtgggga
781 gagctaaggg ggatggaact gcagggccaa catcctctgg aagggacatg ggagaatatt
841 aggagcagtg gagctgggga aggctgggaa gggacttggg gaggaggacc ttggtgggga
901 cagtgctcgg gagggctggc tgggatggga gtggaggcat cacattcagg agaaagggca
961 agggcccctg tgagatcaga gagtgggggt gcagggcaga gaggaactga acagcctggc
1021 aggacatgga gggaggggaa agaccagaga gtcggggagg acccgggaag gagcggcgac
1081 ccggccacgg cgagtctcac tcagcatcct tccatcccca gtgtgccacc tacaagctgt
1141 gccaccccga ggagctggtg ctgctcggac actctctggg catcccctgg gctcccctga
1201 gcagctgccc cagccaggcc ctgcagctgg tgagtgtcag gaaaggataa ggctaatgag
1261 gagggggaag gagaggagga acacccatgg gctcccccat gtctccaggt tccaagctgg
1321 gggcctgacg tatctcaggc agcacccct aactcttccg ctctgtctca caggcaggct
1381 gcttgagcca actccatagc ggcctttcc tctaccaggg gctcctgcag gccctggaag
1441 ggatctcccc cgagttgggt cccaccttgg acacactgca gctggacgtc gccgactttg

Fig. 3 (cont.)

1501 ccaccaccat ctggcagcag gtgagccttg ttgggcaggg tggccaaggt cgtgctggca
1561 ttctgggcac cacagccggg cctgtgtatg ggccctgtcc atgctgtcag cccccagcat
1621 ttcctcattt gtaataacgc ccactcagaa gggcccaacc actgatcaca gctttccccc
1681 acagatggaa gaactgggaa tggcccctgc cctgcagccc acccagggtg ccatgccggc
1741 cttcgcctct gctttccagc gccgggcagg aggggtcctg gttgcctccc atctgcagag
1801 cttcctggag gtgtcgtacc gcgttctacg ccaccttgcc cagccctgag ccaagccctc
1861 cccatcccat gtatttatct ctatttaata tttatgtcta tttaagcctc atatttaaag
1921 acagggaaga gcagaacgga gccccaggcc tctgtgtcct tccctgcatt tctgagtttc
1981 attctcctgc ctgtagcagt gagaaaaagc tcctgtcctc ccatcccctg gactgggagg
2041 tagataggta aataccaagt atttattact atgactgctc cccagccctg gctctgcaat
2101 gggcactggg atgagccgct gtgagcccct ggtcctgagg gtccccacct gggacccttg
2161 agagtatcag gtctcccacg tgggagacaa gaaatccctg tttaatattt aaacagcagt
2221 gttccccatc tgggtccttg cacccctcac tctggcctca gccgactgca cagcggcccc
2281 tgcatcccct tggctgtgag gcccctggac aagcagaggt ggccagagct gggaggcatg
2341 gccctggggt cccacgaatt tgctggggaa tctcgttttt cttcttaaga cttttgggac
2401 atggtttgac tcccgaacat caccgacgtg tctcctgttt ttctgggtgg cctcgggaca
2461 cctgccctgc ccccacgagg gtcaggactg tgactctttt tagggccagg caggtgcctg
2521 gacatttgcc ttgctggatg gggactgggg atgtgggagg gagcagacag gaggaatcat
2581 gtcaggcctg tgtgtgaaag gaagctccac tgtcaccctc cacctcttca ccccccactc
2641 accagtgtcc cctccactgt cacattgtaa ctgaacttca ggataataaa gtgtttgcct
2701 ccagtcacgt ccttcctcct tcttgagtcc agctggtgcc tggccagggg ctggggaggt
2761 ggctgaaggg tgggagaggc cagagggagg tcggggagga ggtctgggga ggaggtccag
2821 ggaggaggag gaaagttctc aagttcgtct gacattcatt ccgttagcac atatttatct
2881 gagcacctac tctgtgcaga cgctgggcta agtgctgggg acacagcagg gaacaaggca
2941 gacatggaat ctgcactcga Homo sapiens MCP1 (MCP1) gene, promoter region and partial cds.
ACCESSION AY357296
VERSION AY357296.1 GI:34559719
1 ccgagatgtt cccagcacag ccccatgtga gagctccctg gctccgggcc cagtatctgg
61 aatgcaggct ccagccaaat gcattctctt ctacgggatc tgggaacttc caaagctgcc
121 tcctcagagt gggaatttcc actcacttct ctcacgccag cactgacctc ccagcggggg
181 agggcatctt ttcttgacag agcagaagtg ggaggcagac agctgtcact ttccagaaga
241 ctttcttttc tgattcatac ccttcacctt ccctgtgttt actgtctgat atatgcaaag
301 gccaagtcac tttccagaga tgacaactcc ttcctgaagt agagacatgc ttccaacact
361 cagaagccta tgtgaacact cagccagcaa agctgggaag tttttctctg tgaccatggg
421 ctaattggtc tccttctctg gattgtggct ttatcagata aaaacaagtg gtcatgccac
481 aggatgtcta taagcccatt gattctggga ttctatgagt gatgctgata tgactaagcc
541 aggagagact tatttaaaga tctcagcatc tttcagcttg ttaacctaga gaaaacccga

Fig. 3 (cont.)

601 agcatgactg gattataaag ggaaattgaa tgcggtccac caagttcatg gtaaaggatg
661 cactaacaga ttagagagag gtttcccctg atatgaggaa aacttcttgg aagatgaggt
721 gagatggcct aggaagaaat tcctacacaa aattgcacag tctctagtcc tggaaacatt
781 ttattcattg gataagaatg gattgaggca tgagcagagg actgagacaa acacagagaa
841 gtttcaacac tggttgggga gaaaaggagt aactagtgag attcaggcag aacaagaata
901 aggctcctca agaggcacaa gcaaagcagg gctcgagttg atttgttctc tcttcatcct
961 gctttttgta attccaccag agtctgaaat gaccactcca tagagtctct gctctgggat
1021 tctccaggaa accaatatcc atcatgagac atcaagtcta gtcccaggaa gaagagattc
1081 tggaatggaa acatcctggg tgggagtctc agcacatcta ctattctgtc tgagttactg
1141 gacaaataac ttcagtttta acctaacgaa agctgggttg gttggaggac tgggcaggca
1201 gcgctggaaa gtatgtcagc accatacctg actccctgaa tgcactcaac aatgccatta
1261 ctgaccactt actagaaata aaacagtcat ttgttgaata caacccgttt ctttttacaa
1321 gtgtagtgaa aagtgttttc tttcaagaaa ccccatgcat ttatagacat tgcctcagtg
1381 accctttatg aaagaagtca ctagtctttg tatgcccatt gggcaagggc accgcaaggc
1441 tcagaaggag gaggcagtgg gctaggagaa tggagagatc agaattttaa actcagccca
1501 gccattaaca tgcctcaagt actcctatca tatttgtaag agacaacagt tcactgaaat
1561 gaattctaag gtctttgggt ttttatcagt gtgcttctgt agtttctgag gaaatctaag
1621 gcacaactga ggaatgaagt caggctttcc aattcccgaa atactcctcc actgcttact
1681 catgtccctt ggaaattaag aaggaagcca ggagaatagc tgccataacc agggatgaac
1741 ttcttgtcca ctgctgcctg ctatgctagc aacagcctcc taactcataa tgacttagcc
1801 atgaggaatg tttctagatt ctcctttagc tgtctgccca tttggaagat gctgaggaca
1861 gagagaggac ccaagcaggc aactagttgg aggacttgta cacgtttcct tccagcagta
1921 tgtcagagag gtgagcagcc cactggggac agggctgcct gggttctgtg ctcgagggga
1981 ccttgagcag gctatttaac ccttctgtgc ctcagttgcc tgatctataa catgaaaatt
2041 agcaatccct actagataaa gttggggaat ttacagagtt aatatttgta aaggtctgag
2101 aatattcctg gcagagtaag cactctgtga gtatgacact ggcatttctt ctgcagcact
2161 acatgctgtc tatgcctttg tccaagtctg aaaccctaga actcttagaa ttcagttcaa
2221 tgtttacaca atcctacagt tctgctaggc ttctatgatg ctactattct gcatttgaat
2281 gagcaaatgg atttaatgca ttgtcaggga gccggccaaa gcttgagagc tccttcctgg
2341 ctgggaggcc ccttggaatg tggcctgaag gtaagctggc agcgagcctg acatgctttc
2401 atctagtttc ctcgcttcct tccttttctg cagttttcgc ttcacagaaa gcagaatcct
2461 taaaaataac cctcttagtt cacatctgtg gtcagtctgg gcttaatggc accccatcct
2521 ccccatttgc tcatttggtc tcagcagtga atggaaaaag tgtctcgtcc tgaccccctg
2581 cttccctttc ctacttcctg gaaatccaca ggatgctgca tttgctcagc agatttaaca
2641 gcccacttat cactcatgga agatccctcc tcctgcttga ctccgcccctc tctccctctg
2701 cccgctttca ataagaggca gagacagcag ccagaggaac cgagaggctg agactaaccc
2761 agaaacatcc aattctcaaa ctgaagctcg cactctcgcc tccagcatga aagtctctgc
2821 cgcccttctg tgcctgctgc tcatagcagc caccttcatt ccccaagggc tcgctcagcc
2881 aggtaaggcc ccctcttctt ctccttgaac cacattgtct tctctctgag ttatcatgga

Fig. 3 (cont.)

2941 ccatccaagc agacgtggta cccacagtct tgctttaacg ctacttttcc aagataaggt
3001 gactcagaaa aggacaaggg gtgagcccaa ccacacagct gctgctcggc agagcctgaa
3061 ctagaattcc agctgtgaac cccaaatcca gctccttcca ggattccagc tctgggaaca
3121 cactcagcgc agttactccc ccagctgctt ccagcagagt ttggggatca gggtaatcaa
3181 agagagggtg ggtgtgtagg ctgtttccag acacgctgga g Homo sapiens macrophage migration inhibitory factor (glycosylation-inhibiting factor) (MIF), mRNA.

1 accacagtgg tgtccgagaa gtcaggcacg tagctcagcg gcggccgcgg cgcgtgcgtc
61 tgtgcctctg cgcgggtctc ctggtccttc tgccatcatg ccgatgttca tcgtaaacac
121 caacgtgccc cgcgcctccg tgccggacgg gttcctctcc gagctcaccc agcagctggc
181 gcaggccacc ggcaagcccc cccagtacat cgcggtgcac gtggtcccgg accagctcat
241 ggccttcggc ggctccagcg agccgtgcgc gctctgcagc ctgcacagca tcggcaagat
301 cggcggcgcg cagaaccgct cctacagcaa gctgctgtgc ggcctgctgg ccgagcgcct
361 gcgcatcagc ccggacaggg tctacatcaa ctattacgac atgaacgcgg ccaatgtggg
421 ctggaacaac tccaccttcg cctaagagcc gcagggaccc acgctgtctg cgctggctcc
481 acccgggaac ccgccgcacg ctgtgttcta ggcccgccca ccccaacctt ctggtgggga
541 gaaataaacg gtttagagac t Homo sapiens macrophage inflammatory protein-1-alpha/RANTES receptor mRNA, complete cds.

ACCESSION L10918

VERSION L10918.1 GI:292416

1 ggcacgagcc cagaaacaaa gacttcacgg acaaagtccc ttggaaccag agagaagccg
61 ggatggaaac tccaaacacc acagaggact atgacacgac cacagagttt gactatgggg
121 atgcaactcc gtgccagaag gtgaacgaga gggcctttgg ggcccaactg ctgccccctc
181 tgtactcctt ggtatttgtc attggcctgg ttggaaacat cctggtggtc ctggtccttg
241 tgcaatacaa gaggctaaaa aacatgacca gcatctacct cctgaacctg gccatttctg
301 acctgctctt cctgttcacg cttcccttct ggatcgacta caagttgaag gatgactggg
361 tttttggtga tgccatgtgt aagatcctct ctgggtttta ttacacaggc ttgtacagcg
421 agatcttttt catcatcctg ctgacgattg acaggtacct ggccatcgtc cacgccgtgt
481 ttgccttgcg ggcacggacc gtcacttttg gtgtcatcac cagcatcatc atttgggccc
541 tggccatctt ggcttccatg ccaggcttat actttttccaa gacccaatgg gaattcactc
601 accacacctg cagccttcac tttcctcacg aaagcctacg agagtggaag ctgtttcagg
661 ctctgaaact gaacctcttt gggctggtat tgcctttgtt ggtcatgatc atctgctaca
721 cagggattat aaagattctg ctaagacgac caaatgagaa gaaatccaaa gctgtccgtt
781 tgatttttgt catcatgatc atcttttttc tcttttggac cccctacaat ttgactatac
841 ttatttctgt tttccaagac ttcctgttca cccatgagtg tgagcagagc agacatttgg
901 acctggctgt gcaagtgacg gaggtgatcg cctacacgca ctgctgtgtc aacccagtga
961 tctacgcctt cgttggtgag aggttccgga agtacctgcg gcagttgttc cacaggcgtg

Fig. 3 (cont.)

1021 tggctgtgca cctggttaaa tggctcccct tcctctccgt ggacaggctg gagagggtca
1081 gctccacatc tccctccaca ggggagcatg aactctctgc tgggttctga ctcagaccat
1141 aggaggccaa cccaaaataa gcaggcgtga cctgccaggc acactgagcc agcagcctgg
1201 ctctcccagc caggttctga ctcttggcac agcatggagt cacagccact tgggatagag
1261 agggaatgta atggtggcct ggggcttctg aggcttctgg ggcttcagtc ttttccatga
1321 acttctcccc tggtagaaag aagatgaatg agcaaaacca aatattccag agactgggac
1381 taagtgtacc agagaagggc ttggactcaa gcaagatttc agatttgtga ccattagcat
1441 ttgtcaacaa agtcacccac ttcccactat tgcttgcaca aaccaattaa acccagtagt
1501 ggtgactgtg ggctccattc aaagtgagct cctaagccat gggagacact gatgtatgag
1561 gaatttctgt tcttccatca cctccccccc cccgccaccc tcccactgcc aagaacttgg
1621 aaatagtgat ttccacagtg actccactct gagtcccaga gccaatcagt agccagcatc
1681 tgcctcccct tcactcccac cgcaggattt gggctcttgg aatcctgggg aacatagaac
1741 tcatgacgga agagttgaga cctaacgaga aatagaaatg gggggaactac tgctggcagt
1801 ggaactaaga aagcccttag gaagaatttt tatatccact aaaatcaaac aattcaggga
1861 gtgggctaag cacgggccat atgaataaca tggtgtgctt cttaaaatag ccataaaggg
1921 gagggactca tcatttccat ttacccttct tttctgacta tttttcagaa tctctcttct
1981 tttcaagttg ggtgatatgt tggtagattc taatggcttt attgcagcga ttaataacag
2041 gcaaaaggaa gcagggttgg tttcccttct ttttgttctt catctaagcc ttctggtttt
2101 atgggtcaga gttccgactg ccatcttgga cttgtcagca aaaaaaaaaa aaaaaa Mouse macrophage inflammatory protein 1-beta (MIP-1) mRNA, complete cds.

ACCESSION M35590

VERSION M35590.1 GI:199696

1 gcttctgaag cttctgggcc ctgcagtccc agctctgtgc aaacctaacc ccgagcaaca
61 ccatgaagct ctgcgtgtct gccctctctc tcctcttgct cgtggctgcc ttctgtgctc
121 cagggttctc agcaccaatg ggctctgacc ctcccacttc ctgctgtttc tcttacacct
181 cccggcagct tcacagaagc tttgtgatgg attactatga gaccagcagt ctttgctcca
241 agccagctgt ggtattcctg accaaaagag gcagacagat ctgtgctaac cccagtgagc
301 cctgggtcac tgagtacatg agtgacttgg agttgaactg agcagctcca gcggcagggc
361 aggaggagcc acttcaggag aggcctcctc agccctgatg cttctcactg agaagcgtcc
421 ttgctcctca cgttcagatt tcctgcccct cttcttaatt taaatctctg tgtagacttt
481 gttttgtttt tttgggggag tattatttct attatttatg ttttagttat aggacgcgtg
541 tctcccatgg agatggtcca ccattgctgt ttctctgcta ttgtggatat gactgtgaaa
601 ttgatttcat gcattttcat aataaatctt tctttaag Human macrophage inflammatory protein 3 alpha (MIP-3a) mRNA, complete cds.

ACCESSION U77035

VERSION U77035.1 GI:1790924

Fig. 3 (cont.)

1 atgtgctgta ccaagagttt gctcctggct gctttgatgt cagtgctgct actccacctc
61 tgcggcgaat cagaagcagc aagcaacttt gactgctgtc ttggatacac agaccgtatt
121 cttcatccta aatttattgt gggcttcaca cggcagctgg ccaatgaagg ctgtgacatc
181 aatgctatca tctttcacac aaagaaaaag ttgtctgtgt gcgcaaatcc aaaacagact
241 tgggtgaaat atattgtgcg tctcctcagt aaaaaagtca agaacatgta aaaactgtgg
301 cttttctgga atggaattgg acatagccca agaacagaaa gaaccttgct ggggttggag
361 gtttcacttg cacatcatgg agggtttagt gcttatctaa tttgtgcctc actggacttg
421 tccaattaat gaagttgatt catattgcat catagtttgc tttgtttaag catcacatta
481 aagttaaact gtattttatg ttatttatag ctgtaggttt tctgtgttta gctatttaat
541 actaattttc cataagctat tttggtttag tgcaaagtat aaaattatat ttgggggga
601 ataagattat atggactttt ttgcaagcaa caagctattt tttaaaamma actatttaac
661 attcttttgt ttatattgtt ttgtctccta aattgttgta attgcattat aaaataagaa
721 aaatattaat aagacaaata ttgaaaataa agaaacaaaa agtt Human macrophage inflammatory protein 3 beta (MIP-3beta) mRNA, complete cds.

ACCESSION U77180

1 atggccctgc tactggccct cagcctgctg gttctctgga cttccccagc cccaactctg
61 agtggcacca atgatgctga agactgctgc ctgtctgtga cccagaaacc catccctggg
121 tacatcgtga ggaacttcca ctaccttctc atcaaggatg gctgcagggt gcctgctgta
181 gtgttcacca cactgagggg ccgccagctc tgtgcacccc cagaccagcc ctgggtagaa
241 cgcatcatcc agagactgca gaggacctca gccaagatga agcgccgcag cagttaacct
301 atgaccgtgc agagggagcc cggagtccga gtcaagcatt gtgaattatt acctaacctg
361 gggaaccgag gaccagaagg aaggaccagg cttccagctc ctctgcacca gacctgacca
421 gccaggacag ggcctggggt gtgtgtgagt gtgagtgtga gcgagagggt gagtgtggtc
481 tagagtaaag ctgctccacc cccagattgc aatgctacca ataaagccgc ctggtgttta
541 caact H.sapiens gene for chemokine HCC-1.

ACCESSION Z49269

VERSION Z49269.1 GI:1004266

1 gagctccgtt gggagtccca tgtttcttta tggcataatg ggtgagaaca cagacttgga
61 agccaaacca cctgaatttg aaccccagtt ccatttacca actgtcaaaa gcttaggctt
121 tgattctaag cctgtttcct caactgctgt tctaaagatt aaataggcta atattcataa
181 ggcaactggg acagtggctt gtgtgtatag caaccattat ataagtgaat tatctactga
241 gcaccacagc acttcttcac tccatggtgt ggtgaccaga atggagatga gacagagaac
301 tgcaggttct gcttcgagtt taagttagga tttcccttga ccaatgagac ctgacttgga

Fig. 3 (cont.)

361 ggagtcctgg cctcattcca ttaccccaaa caccctctag tctctagatg aacagatcct
421 gaatgtccag gccccacgtg gcctgttcta aggcctgaga tggaattgga tacaggacac
481 atccagcctt gagatctttt gctaagtgtg acacagtgcc cccagccctg tgctcatgtt
541 catgcctagg gaaaggcttc tatcaaaaga gttgaacttc ttcccactgg ggatggaaga
601 ccatttcctc ccttaaacct tggctctccc tgcttccttc aggccaccaa caacacatgt
661 gcaggatatg aaattgctga ggcatcactg ctttcctact tcccttccaa gtctcagctc
721 ccttatttta aaaaatattt ggcctcaatg atcatttctc aacaattcct caccgcagga
781 gcctctgaag ctcccaccag gccagctctc ctcccacaac agcttcccac agcatgaaga
841 tctccgtggc tgccattccc ttcttcctcc tcatcaccat cgccctaggg accaagactg
901 aatcctcctc acgtgagtgc aatgccttgt cttccttcca acctagagcc tgcagggaaa
961 taagcaggag tgaggttggg gctcagggga agaccaggag cagggactca gaaaggaggg
1021 ctggtatctt cttgaaattg tgtgtatagc aacattatat aaatgaatta tctactgagc
1081 accacagcac ttcaccccat ggtgtggtga gcaggatgga gatgagactt aggactgtag
1141 gttctgctta agagtttaag ttgggatctt ccagccttga ccaatgagac ttgacttggg
1201 agactccagg cttcattcca ctaccccaaa tgccctctag tctccaaata aacagatcct
1261 gaatctccag gcctcacatg gccttgatct cttatcattg ccccccagga ccagtccccc
1321 cttgccctca aggacatgga gtgagaccag cctgcctctc tactccctca atttctctct
1381 ctttgccgct aagcaaaaga gtggcccacc ccatttgggg tatatttcct cagggagatt
1441 aggagcagtg tcttgagccc ctcaagggca tttttctatt ggcctcctga ggtttgggcc
1501 cagcctgctt ccagcgtcac ctgtgcccag tgagtgcagc attgcttggg tatgggctgg
1561 ggggaaacac gacagtgtgg ggtccatcct aggcccccctt ttctcagctg atttcttaga
1621 ataagctgcc tttagagata accaaaacta tttatcactc ttccatttta cctactctcc
1681 ttttcagaaa ctggggggaa accgaaggtt gttaaaatac agctaaagtt ggtgggtatg
1741 tgcacagttt gacttgccct ctccgatgtc atttgtcagc tcagaggaac aaggtgggag
1801 agtataggag ctctgactgg gtctcaggaa acaggggccc cttatgccgt tctttggatc
1861 gtgaggatgc tgcctggaat ggagctggaa aacaggatga gacccttcca cccagacatc
1921 tggccaccct cagtgacctc tgaggccatt gtgatgcaca tccatgattc tatgaagcag
1981 ggtcacataa catgcacaca cctgatttct ccactccata accacaacat gtgcctgttt
2041 gtacagggct cttggcctac aatgtccttc ctgctacctc tataattcaa gcttggggtg
2101 gctgctgtca ccttgcttct cctataaaag ccatgaaact tctcaatcag aaaatagatg
2161 aaaaaatcac ccaatccagt gatttttaaa actttttaga ccacaaaacc ttttcttcaa
2221 gcaatatctt ccacagaggc ccaatatgta aaacagaaaa aatgggttga gtagggtaca
2281 agacaccact ctcaaatgca gcaaggcctc cacaatagtc cctgaggccc ccagagctca
2341 gtgtaaaaac cactgatgca gtccaagggc ctcatttaca gaggagggaa caggggggaaa
2401 gtaaaatggc cacagtacac aggaagcaca ggcaaggtta ggttaggatt tgggtgccct
2461 gactctgtgg cctttgtcct tggggcttgc tgtgggcatc ctgctctctc tgcaggttgt
2521 cggttcaatg ggacatgggg cagggtggag cactaggagg ggctgggttt gcattcccaa
2581 atggcatgtc tccaaatccc tattgggatt tcttccaaat attcctccta tttggagcac
2641 ctttcccgaa taaggcatga aggctgcatg atattggcca agtccctagc cttctctgcc

Fig. 3 (cont.)

2701 agtcggcccc cagagatggt gtaagaagat ctgagtgtgc tgctcttcaa tcctggagtt
2761 gaaagtcatc caccagtctt tccaagaggg gttgaagaaa aggaggaagg gtgattgatg
2821 atgagggagg agaaaaagaa gagcccagga gtaccatgga gaaggagaag agaagatgag
2881 gaaagcctac tctcccctcc aagttctgag ggctgtctc ctccttcctt ccctcctcca
2941 tgccctcagc ttgcaggagc agccaatggt atggccttta acaaggggcc cctcctcagc
3001 atctgatgct ctctcctcag ggggacctta ccacccctca gagtgctgct tcacctacac
3061 tacctacaag atcccgcgtc agcggattat ggattactat gagaccaaca gccagtgctc
3121 caagcccgga attgtgtagg tggtacacac acatcacact gggggagag ggagccagca
3181 gggcctcctg gagggaagca gggagtggtg gtggaatggg gacccccagc gtacctccca
3241 ggtgtgacta catggggaga ggcagctgag gggcaatctg agcgctttct ggctggagcc
3301 tgcaggagcc atggggaaac tgaccccatg gatggggaga tgacagagaa gggagaagaa
3361 ggcaagaggg cacttcctca gggggacaca gagactagat gggtctaggg gtcctaggaa
3421 ccgaagagta tgtctcagag aggagactgg ctctaagctg cctctgtgga agaaaggaaa
3481 agcagtatag gtcaggtggg gaatttagga gggagggaag atggctgtc tcttccggcc
3541 actgggcccc tcggtttgtg atccttctcc ctcttgctcc acagcttcat caccaaaagg
3601 ggccattccg tctgtaccaa ccccagtgac aagtgggtcc aggactatat caaggacatg
3661 aaggagaact gagtgaccca gaaggggtgg cgaaggcaca gctcagagac ataaagagaa
3721 gatgccaagg ccccctcctc cacccaccgc taactctcag ccccagtcac cctcttggag
3781 cttccctgct ttgaattaaa gaccactcat gctcttccct ggcctcattc ctttctacgg
3841 gatttactca ttggccatgc actgaggaca ccagggtgtg gcaccctcgg catcaagcct
3901 cgctctgcag aagttttggt ggagcctggt acaaaaaata ggtcaggcct gcaatgcagg
3961 tagtgagaag cagaaagtga gaaagaaaag cagtgtaaag accgtctcct cctcagcagc
4021 aacagtagca gaccccg H.sapiens mRNA for chemokine HCC-1.
ACCESSION Z49270
VERSION Z49270.1 GI:1004268
1 agcctctgaa gctcccacca ggccagctct cctcccacaa cagcttccca cagcatgaag
61 atctccgtgg ctgccattcc cttcttcctc ctcatcacca tcgccctagg gaccaagact
121 gaatcctcct cacggggacc ttaccacccc tcagagtgct gcttcaccta cactacctac
181 aagatcccgc gtcagcggat tatggattac tatgagacca acagccagtg ctccaagccc
241 ggaattgtct tcatcaccaa aaggggccat tccgtctgta ccaaccccag tgacaagtgg
301 gtccaggact atatcaagga catgaaggag aactgagtga cccagaaggg gtggcgaagg
361 cacagctcag agacataaag agaagatgcc aaggcccccct cctccaccca cccctaactc
421 tcagccccag tcaccctctt ggagcttccc tgctttgaat taaagaccac tcatgctctt
481 c Human myeloid progenitor inhibitory factor-1 MPIF-2 mRNA, complete

Fig. 3 (cont.)

cds.
ACCESSION U85768
VERSION U85768.1 GI:1916251
1 atggcaggcc tgatgaccat agtaaccagc cttctgttcc ttggtgtctg tgcccaccac
61 atcatcccta cgggctctgt ggtcataccc tctccctgct gcatgttctt tgtttccaag
121 agaattcctg agaaccgagt ggtcagctac cagctgtcca gcaggagcac atgcctcaag
181 ggaggagtga tcttcaccac caagaagggc cagcagttct gtggcgaccc caagcaggag
241 tgggtccaga ggtacatgaa gaacctggac gccaagcaga agaaggcttc ccctagggcc
301 agggcagtgg ctgtcaaggg ccctgtccag agatatcctg gcaaccaaac cacctgctaa Mus musculus mRNA for thymus and activation regulated chemokine
(TARC gene).
ACCESSION AJ242587
VERSION AJ242587.1 GI:5102777
1 gaagaccttc acctcagctt ttggtaccat gaggtcactt cagatgctgc tcctggctgc
61 tctgcttctg ggacttttc tgcagcatgc cagagctgct cgagccacca atgtaggccg
121 agagtgctgc ctggattact tcaaaggggc cattcctatc aggaagttgg tgagctggta
181 taagacctca gtggagtgtt ccagggatgc catcgtgttt ctgactgtcc agggcaagct
241 catctgtgca gaccccaaag acaaacatgt gaagaaggcc atcagattgg tgaaaaaccc
301 aaggccgtga ccttcccgct gaggcatttg gagacgccag ggctgctgtc catggtttca
361 acataaagcg gcctgtgacc agcagagccc aagagcagcc acagagcaga agtccctgtt
421 cccttttta tggactctta tgcactacag gcgaacacaa aaaaaagcaa cggaataaag
481 ccttcctccc tc Human line-1 reverse transcriptase gene, partial cds, and
granulocyte chemotactic protein-2 (GCP-2) gene, complete cds.
ACCESSION U83303
VERSION U83303.1 GI:1916228
1 aagaaagtca ttggtagctt gatggggatg gtattgaatc tataagttac cttgggcagt
61 atggccatat tcacgatatt gatttttcct acccatgagc atggaatatt cttccatttg
121 tttgtatcct cttttatttc attgagcagt ggtttgtagt tctccttgaa gaggtccttc
181 atgtcccttg taagttggat tcctaggtat tttattctct ttgaagcaat tgtgaatggg
241 agttcactca tgatttggct ctctgtttgt ttgttattgg tgtataagaa tgcttgtgat
301 ttttgtgcat tgattttgta tcctgagact ttgctgaagt tgcttatcag cttaaggaga
361 ttttgggctg agaccatggg gttttctaga tatacaatta tgtaatttgc aaatagggac
421 aatttgactt cctcttttcc taattgaata ccctttattt ccttctcctg cctaattgtc
481 ctggccattg gagaggagga gcatctccca gacagctgcg tgcctcagag aagccagcct

Fig. 3 (cont.)

541 cgctaacccc tcaagcccag gggatgagac cctcctgaat cgctgctcta ttttggctgg
601 agccacagct ccctccaccg cggggcgggg ctaaaatgtc ctccccctta agggagcagg
661 cagctcctcc cagccaccca ccccaccaat tcccatcctc ccgccccct ccaccaaccc
721 cttctttcca cactgccccc tgagttcagg gaatttcccc agcatcccaa agcttgagtt
781 tcctgccagt cgggagggat gaatgcagat aaagggagtg cagaaggcac gaggaaacca
841 aagtgctctg tatcctccag tctccgcgcc tccacccagc tcaggaaccc gcgaaccctc
901 tcttgaccac tatgagcctc ccgtccagcc gcgcggcccg tgtcccgggt ccttcgggct
961 ccttgtgcgc gctgctcgcg ctgctgctcc tgctgacgcc gccggggccc ctcgccagcg
1021 gtgagagctc ctggcactgg ggtgcatccc agcctctgcg gggccgctgc gttccaggga
1081 actctcccag caacctgccc tataaaaatg tctttcttcc ccagctggtc ctgtctctgc
1141 tgtgctgaca gagctgcgtt gcacttgttt acgcgttacg ctgagagtaa accccaaaac
1201 gattggtaaa ctgcaggtgt tccccgcagg cccgcagtgc tccaaggtgg aagtggtgta
1261 agttctcctg tgttgctgtg tccactgtga cttaggcaag tcctccagcc tgggtcgtca
1321 acctttgtgg ctcatgggtg catcctcttt ttctttactt cagagcctcc ctgaagaacg
1381 ggaagcaagt ttgtctggac ccggaagccc cttttctaaa gaaagtcatc cagaaaattt
1441 tggacaggta tttgtccctt tgatctttgt ggtgttttaa tatcttctat ggaaagcata
1501 tacttcacaa tgtccttatt ctctctgtag gatttagact atgcttagaa ttataaggtt
1561 gttaagaaga ataaggaaac tttttttctg gaatgttctg ggtaaacctt tatcaccaat
1621 cttacatgcc tgaacaatta cacagagctc attactgaca tctatttttt gtctgctctt
1681 tgcttttatt gatttttttc ccccaccaaa cgcttttgaa aaccaaatgt agcatacaag
1741 agtgtgggaa ttggttatac taatataact cttttctcaa cagtggaaac aagaaaaact
1801 gagtaacaaa aaagaccatg catcataaaa ttgcccagtc ttcagcggag cagttttctg
1861 gagatccctg gacccagtaa gaataagaag gaagggttgg tttttttcca ttttctacat
1921 ggattcccta ctttgaagag tgtgggggaa agcctacgct tctccctgaa gtttacagct
1981 cagctaatga agtactaata tagtatttcc actatttact gttattttac ctgataagtt
2041 attgaaccct ttggcaattg accatattgt gagcaaagaa tcactggtta ttagtctttc
2101 aatgaatatt gaattgaaga taactattgt atttctatca tacattcctt aaagtcttac
2161 cgaaaaggct gtggatttcg tatggaaata atgttttatt agtgtgctgt tgagggaggt
2221 atcctgttgt tcttactcac tcttctcata aaataggaaa tattttagtt ctgtttcttg
2281 gggaatatgt tactctttac cctaggatgc tatttaagtt gtactgtatt agaacactgg
2341 gtgtgtcata ccgttatctg tgcagaatat atttccttat tcagaatttc taaaaattta
2401 agttctgtaa gggctaatat attctcttcc tatggtttta gacgtttgat gtcttcttag
2461 tatggcataa tgtcatgatt tactcattaa actttgattt tgtatgctat tttttcacta
2521 taggatgact ataattctgg tcactaaata tacactttag atagatgaag aagcccaaaa
2581 acagataaat tcctgattgc taatttacat agaaatgtat tctcttggtt ttttaaataa
2641 aagcaaaatt aacaatgatc tgtgctctga aagttttgaa aatatatttg aacaatttga
2701 atataaattc atcatttagt cctcaaaata tatacagcat tgctaagatt ttcagatatc
2761 tattgtggat cttttaaagg ttttgaccat tttgttatga ggaattatac atgtatcaca
2821 ttcactatat taaaattgca cttttatttt ttcctgtgtg tcatgttggt ttttggtact

Fig. 3 (cont.)

2881 tgtattgtca tttggagaaa caataaaaga tttctaaacc actgatgttg tttctccttc
2941 ttatacagtt actatttatc tttaattcta cattattcaa aatattacct ctgctcttct
3001 ctggctggca gagaggccct cattacccaa taccattgca ttggttcaac ttttctccat
3061 gttcagcccc cttccagtta ctccttcaca gcaccaatag cctctggggt ctttagaaaa
3121 cacaaatagg ataagatttt cctatctaaa ttcttaaatg gctccctgtt tcctagacat
3181 gaaataaaag ttgctaaaca tgatgaatga ggttctgtct catctcactc ctgatcatcg
3241 gtacttcaac ttcccttgtg cctcacattc actatagtca ggcgttcagt tccctaacta
3301 ggcatgttct ttccccaggc tcatgacttt gtatttgcta gggtctctac ctggaaagca
3361 tttacgtttt cctgcgtata agaggaggct tattcatcct tcagaactca gttcaagcaa
3421 tatctccttc gtgaattttc cttggcacac tcagcaaagc H.sapiens mRNA for granulocyte chemotactic protein.
ACCESSION Y08770
VERSION Y08770.1 GI:1769436
1 ggtcctgtct ctgctgtgct cacggagctg cgttgcactt gtttacgcgt tacgctgaga
61 gtaaacccca aaacgattgg taaactgcag gtgttccccg caggcccgca gtgctccaag
121 gtggaagtgg tagcctccct gaagaacggg aagcaagttt gtctggaccc ggaagcccct
181 tttctaaaga aagtcatcca gaaaattttg gacagtggaa acaagaaaaa ctgagtaaca
241 gtcgacgcgg ccgc Human gro alpha gene 5' end.
ACCESSION M65005
VERSION M65005.1 GI:183624
1 tcccacctct caggtggtat cttcagcgca ggctgccact cagcccccct ccagggatct
61 ggggcagaag gcgaatatcc cagagtctca gagtccacag gagttactct gaagggcgag
121 ccgcgggctg catcagtgga ccccccacacc ccacccgcac cccaagcgct ccaccctggg
181 ggcggggccg tcgccttcct tccggactcg ggatcgatct ggaactccgg gaatttccct
241 ggcccggggg ctccgcccttt tccagcccca accatgcata aaaggggttc gcggatctcg
301 gagagccaca gagcccgggc cgcaggcacc tcctcgccag ctcttccgct cctctcacag
361 ccgccagacc cgcctgctga gccccatggc ccg Human gro beta gene 5' end.
ACCESSION M65006
VERSION M65006.1 GI:183630
1 cgcctcctcg caggcggtta tctcggtatc tctgagagcg gcgggctctc gctcccgctc
61 cagggattcg gggcagaaag agaacatccc acagttggcg ggagttacgc aagacagtca
121 gacccggacg tcactcgtga gtgccccgac ccccctccac cccagaggcg gggccatcgc

Fig. 3 (cont.)

181 cttccttccg aactcgggat cgatctggag ctccgggaat ttccctggcc cgggactccg
241 gctttccagc cccaaccatg cataaaaggg gttcgccgtt ctcggagagc cacagagccc
301 gggccacagg cagctccttg ccagctctcc tcctcgcaca gccgctcgaa ccgcctgctg
361 agccccatgg cccg Human cytokine (GRO-gamma) mRNA, complete cds.
ACCESSION M36821
VERSION M36821.1 GI:183632
1 cacagccggg tcgcaggcac ctccccngcc agctctcccg cattctgcac agcttcccga
61 cgcgtctgct gagccccatg gcccacgcca cgctctccgc cgccccccagc aatccccggc
121 tcctgcgggt ggcgctgctg ctcctgctcc tggtgggcag ccggcgcgca gcaggagcgt
181 ccgtggtcac tgaactgcgc tgccagtgct tgcagacact gcagggaatt cacctcaaga
241 acatccaaag tgtgaatgta aggtcccccg gaccccactg cgcccaaacc gaagtcatag
301 ccacactcaa gaatgggaag aaagcttgtc tcaaccccgc atcccccatg gttcagaaaa
361 tcatcgaaaa gatactgaac aaggggagca ccaactgaca ggagagaagt aagaagctta
421 tcagcgtatc attgacactt cctgcagggt ggtccctgcc cttaccagag ctgaaaatga
481 aaaagagaac agcagctttc tagggacagc tggaaaggga cttaatgtgt ttgactattt
541 cttacgaggg ttctacttat ttatgtattt atttttgaaa gcttgtattt taatatttta
601 catgctgtta tttaaagatg tgagtgtgtt tcatcaaaca tagctcagtc ctgattattt
661 aattggaata tgatgggttt taaatgtgtc attaaactaa tatttagtgg gagaccataa
721 tgtgtcagcc accttgataa atgacagggt ggggaactgg agggtngggg gattgaaatg
781 caagcaatta gtggatcact gttagggtaa gggaatgtat gtacacatct attttttata
841 cttttttttt taaaaaagaa tgtcagttgt tatttattca aattatctca cattatgtgt
901 tcaacatttt tatgctgaag tttcccttag acattttatg tcttgcttgt agggcataat
961 gccttgttta atgtccattc tgcagcgttt ctctttccct tggaaaagag aatttatcat
1021 tactgttaca tttgtacaaa tgacatgata ataaaagttt tatg
//
Homo sapiens neutrophil-activating peptide 78 (ENA-78) gene,
complete cds.
ACCESSION L37036 Z46254
VERSION L37036.1 GI:607030
1 gaattctcag taagcggact taccaaagta ggtgatctgt aggggagtta acaaaattca
61 gtggtccttt caggccactg acttcaagtg gcaagagaca agggtctctt gttatcatgt
121 tatcttggct tccaaagctg gttgaagtcc agagattcat aaagtcattc aagaaaccta
181 gaatgacctg cctgcaagaa gacaggaagg actttcagtt tatagcaatt caaacatgaa
241 taacatttcc tgattaatag taataataat tagaaaggat tgactttcag aaatttttct
301 caaatcaagg ctcctgttac tttggttcca ccttttctct ctagaaggag aggaggagca
361 tctcccagat gctgcgtgct ccagaaaagc cggcatccct agcccgctct ggcacaggcc

Fig. 3 (cont.)

421 atgaggcgct gctgaatcct gctgaatagc tactcccttc tagctggagc cacagctccc
481 tccaccgcgg aacagggtta caacgtccct ctcggtagag gtgcacgcag ctcctcctgg
541 ccaccctccc caccagttcc cattgtctgg ccccccctccc ccaacctctt ctttccacac
601 tgccccatga gttcagggaa tttccccagc atcccaaagc ttgagtttcc tgtcagtggg
661 gagagatgag tgtagataaa aggagtgcag aaggaacgag gaagccacag tgctccggat
721 cctccaatct tcgctcctcc aatctccgct cctccaccca gttcaggaac ccgcgaccgc
781 tcgcagcgct ctcttgacca ctatgagcct cctgtccagc cgcgcggccc gtgtccccgg
841 tccttcgagc tccttgtgcg cgctgttggt gctgctgctg ctgctgacgc agccagggcc
901 catcgccagc ggtgagagcg catggcgcgc gggacgcact cgcactcggg cacagaggtg
961 catcccagcc tctgcggggt cgctgcgttc cagggaactc tcccagcaac ctgccctata
1021 aagggtgtct ctctttcttc cccagctggt cctgccgctg ctgtgttgag agagctgcgt
1081 tgcgtttgtt tacagaccac gcaaggagtt catcccaaaa tgatcagtaa tctgcaagtg
1141 ttcgccatag gcccacagtg ctccaaggtg gaagtggtgt aagttctgtg ctgctgtgtc
1201 cgctgtgacc ttggcaagag agaaatcccg cagcctgggt cttcaacctt ggtatctcat
1261 gagtgtatct tctttttctt tccttcagag cctccctgaa gaacgggaag gaaatttgtc
1321 ttgatccaga agcccctttt ctaaagaaag tcatccagaa aattttggac gggtacttgt
1381 cactttgatc tttgtggttt ctaaatctga tctagggaga ccatagactt cacaaggtct
1441 ttattctctg tacgatttaa gtaacacttt tcatgtttag aattaaaagg ttgttgaatt
1501 gggaaagttt ttctggattg tcctgggaaa atataccaat cttacatgta attacttgag
1561 caattacaca cagcttgtca ctaagttatg ttttttgttt acccattgct tttattgatt
1621 tttgtattct ccttttttac caaacatcat aaacgctgag ttttgacaag ggtggagtag
1681 aaaggagtgt gaaaaatggt taaactaata taacattttt ctcaacagtg gaaacaagga
1741 aaactgatta agagaaatga gcacgcatgg aaaagtttcc cagtcttcag cagagaagtt
1801 ttctggaggt ctctgaaccc agggaagaca agaaggaaag attttgttgt tgtttgttta
1861 tttgtttttc cagtagttag ctttcttcct ggattcctca ctttgaagag tgtgaggaaa
1921 acctatgttt gccgcttaag ctttcagctc agctaatgaa gtgtttagca tagtacctct
1981 gctatttgct gttattttat ctgctatgct attgaagttt tggcaattga ctatagtgtg
2041 agccaggaat cactggctgt taatctttca aagtgtcttg aattgtaggt gactattata
2101 tttccaagaa atattcctta agatattaac tgagaaggct gtggatttaa tgtggaaatg
2161 atgtttcata agaattc Rattus norvegicus monokine induced by gamma interferon (Mig) mRNA, complete cds.

ACCESSION AF537208

VERSION AF537208.1 GI:33331077

1 tttcctaaat aaatatgacc accaagaaca tgttctctga agacattctc agccttgact
61 ccagcacggt gacttaatag agctcggctc tgccatgaag tccgttgctc tattcctcat
121 gggcatcatc ttcctggatc actgtggagt tcgaggaacc ctagtgataa ggaatcagcg
181 atgctcctgc atcagcacca gccaaggcac attccactac aaatccctca aagacctcaa

Fig. 3 (cont.)

241 acagtttgcc ccaagcccta actgcaacaa aactgaaatc atcgctacac tgaagaacgg
301 agatcaaacc tgcctagacc cagattcagc aagggtgaag aagctgatga aagaatggga
361 gaaaaagatc agccaaaaga aaaagcaaaa gaggggggaaa aaccatcaaa ggagcaagaa
421 aacccgaaaa gctaaaacac cccaccatcc ggagtcaaag aagactgcat aagagaccac
481 tttaccaaca agcgctctgc atctaaacgg cttttagatc atactaaaac gccttccctt
541 taatacacaa ctcg Rattus norvegicus interferon-inducible T-cell a chemoattractant
I-TAC mRNA, complete cds.
ACCESSION AY340181
VERSION AY340181.1 GI:33304495
1 atcaccagag ccacagcaga gagctgcagc tgccgctgag atgaacagga cgggcatggc
61 cgtagccctg gctatgatca tctgggccac aacggttcca ggcttcgtta tgttcaaagg
121 ggggcgctgt ctttgcatcg accgcggagt gaaagtggtc aaaatggcag caatcaagga
181 agtttctgta atttacccga gtaacggctg tgacaaagtt gaagtgattg ttaccctgaa
241 ggctcataaa ggacaaaggt gcctggaccc cacatccaag caagctcgcc tcataatgca
301 gacaatacaa aaaaagaatt ttttaaggcg ccagaacatg tgatgggccc tcaaattcga
361 gctctgtgcc aagaagctga ccctctcctg tcttggaata tgcatccgtt ttgccagatt
421 gcagaactcg ctaggaggtc ggatacctct aaactattct gcttggctat gaaaatattt
481 atctcgaaga gtcatgtgtc tctgtgtgtg caca
//
Homo sapiens chemokine (C-X-C motif) ligand 12 (stromal
cell-derived factor 1) (CXCL12), mRNA.
ACCESSION NM_000609
VERSION NM_000609.2 GI:29837664
1 tctccgtcag ccgcattgcc cgctcggcgt ccggcccccg acccgtgctc gtccgcccgc
61 ccgcccgccc gcccgcgcca tgaacgccaa ggtcgtggtc gtgctggtcc tcgtgctgac
121 cgcgctctgc ctcagcgacg ggaagcccgt cagcctgagc tacagatgcc catgccgatt
181 cttcgaaagc catgttgcca gagccaacgt caagcatctc aaaattctca acactccaaa
241 ctgtgccctt cagattgtag cccggctgaa gaacaacaac agacaagtgt gcattgaccc
301 gaagctaaag tggattcagg agtacctgga gaaagcttta aacaagaggt tcaagatgtg
361 agagggtcag acgcctgagg aacccttaca gtaggagccc agctctgaaa ccagtgttag
421 ggaagggcct gccacagcct cccctgccag ggcagggccc caggcattgc caagggcttt
481 gttttgcaca ctttgccata ttttcaccat ttgattatgt agcaaaatac atgacattta
541 tttttcattt agtttgatta ttcagtgtca ctggcgacac gtagcagctt agactaaggc
601 cattattgta cttgccttat tagagtgtct ttccacggag ccactcctct gactcagggc
661 tcctgggttt tgtattctct gagctgtgca ggtggggaga ctgggctgag ggagcctggc
721 cccatggtca gccctagggt ggagagccac caagagggac gcctgggggt gccaggacca
781 gtcaacctgg gcaaagccta gtgaaggctt ctctctgtgg gatgggatgg tggagggcca

Fig. 3 (cont.)

841 catgggaggc tcaccccctt ctccatccac atgggagccg ggtctgcctc ttctgggagg
901 gcagcagggc taccctgagc tgaggcagca gtgtgaggcc agggcagagt gagacccagc
961 cctcatcccg agcacctcca catcctccac gttctgctca tcattctctg tctcatccat
1021 catcatgtgt gtccacgact gtctccatgg ccccgcaaaa ggactctcag gaccaaagct
1081 ttcatgtaaa ctgtgcacca agcaggaaat gaaaatgtct tgtgttacct gaaaacactg
1141 tgcacatctg tgtcttgtgt ggaatattgt ccattgtcca atcctatgtt tttgttcaaa
1201 gccagcgtcc tcctctgtga ccaatgtctt gatgcatgca ctgttccccc tgtgcagccg
1261 ctgagcgagg agatgctcct tgggcccttt gagtgcagtc ctgatcagag ccgtggtcct
1321 ttggggtgaa ctaccttggt tccccccactg atcacaaaaa catggtgggt ccatgggcag
1381 agcccaaggg aattcggtgt gcaccagggt tgaccccaga ggattgctgc cccatcagtg
1441 ctccctcaca tgtcagtacc ttcaaactag ggccaagccc agcactgctt gaggaaaaca
1501 agcattcaca acttgttttt ggtttttaaa acccagtcca caaaataacc aatcctggac
1561 atgaagattc tttcccaatt cacatctaac ctcatcttct tcaccattg gcaatgccat
1621 catctcctgc cttcctcctg ggccctctct gctctgcgtg tcacctgtgc ttcgggccct
1681 tcccacagga catttctcta agagaacaat gtgctatgtg aagagtaagt caacctgcct
1741 gacatttgga gtgttcccct cccactgagg gcagtcgata gagctgtatt aagccactta
1801 aaatgttcac ttttgacaaa ggcaagcact tgtgggtttt tgttttgttt ttcattcagt
1861 cttacgaata cttttgccct ttgattaaag actccagtta aaaaaaattt taatgaagaa
1921 agtggaaaac aaggaagtca aagcaaggaa actatgtaac atgtaggaag taggaagtaa
1981 attatagtga tgtaatcttg aattgtaact gttcgtgaat ttaataatct gtagggtaat
2041 tagtaacatg tgttaagtat tttcataagt atttcaaatt ggagcttcat ggcagaaggc
2101 aaacccatca acaaaaattg tcccttaaac aaaaattaaa atcctcaatc cagctatgtt
2161 atattgaaaa aatagagcct gagggatctt tactagttat aaagatacag aactctttca
2221 aaaccttttg aaattaacct ctcactatac cagtataatt gagttttcag tggggcagtc
2281 attatccagg taatccaaga tattttaaaa tctgtcacgt agaacttgga tgtacctgcc
2341 cccaatccat gaaccaagac cattgaattc ttggttgagg aaacaaacat gaccctaaat
2401 cttgactaca gtcaggaaag gaatcatttc tatttctcct ccatgggaga aaatagataa
2461 gagtagaaac tgcagggaaa attatttgca taacaattcc tctactaaca atcagctcct
2521 tcctggagac tgcccagcta aagcaatatg catttaaata cagtcttcca tttgcaaggg
2581 aaaagtctct tgtaatccga atctcttttt gctttcgaac tgctagtcaa gtgcgtccac
2641 gagctgttta ctagggatcc ctcatctgtc cctccgggac ctggtgctgc ctctacctga
2701 cactcccttg ggctccctgt aacctcttca gaggccctcg ctgccagctc tgtatcagga
2761 cccagaggaa ggggccagag gctcgttgac tggctgtgtg ttgggattga gtctgtgcca
2821 cgtgtatgtg ctgtggtgtg tccccctctg tccaggcact gagataccag cgaggaggct
2881 ccagagggca ctctgcttgt tattagagat tacctcctga gaaaaaagct tccgcttgga
2941 gcagaggggc tgaatagcag aaggttgcac ctccccccaac cttagatgtt ctaagtcttt
3001 ccattggatc tcattggacc cttccatggt gtgatcgtct gactggtgtt atcaccgtgg
3061 gctccctgac tgggagttga tcgcctttcc caggtgctac accctttcc agctggatga
3121 gaatttgagt gctctgatcc ctctacagag cttccctgac tcattctgaa ggagccccat

Fig. 3 (cont.)

3181 tcctgggaaa tattccctag aaacttccaa atcccctaag cagaccactg ataaaaccat
3241 gtagaaaatt tgttattttg caacctcgct ggactctcag tctctgagca gtgaatgatt
3301 cagtgttaaa tgtgatgaat actgtatttt gtattgtttc aagtgcatct cccagataat
3361 gtgaaaatgg tccaggagaa ggccaattcc tatacgcagc gtgctttaaa aaataaataa
3421 gaaacaactc tttgagaaac aacaatttct actttgaagt cataccaatg aaaaaatgta
3481 tatgcactta taattttcct aataaagttc tgtactcaaa tgta

Fig. 3 (cont.)

Human tumor necrosis factor-beta (TNFB) gene, complete cds.

ACCESSION M55913

VERSION M55913.1 GI:339742

1 ccgacctaga acccgcccgc tgcctgccac gctgccactg ccgcttcctc tataaaggga
61 cctgagcgtc cgggcccagg ggctccgcac agcaggtgag gctctcctgc cccatctcct
121 tgggctgccc gtgcttcgtg ctttggacta ccgccccgca gtgtcctgcc ctctgcctgg
181 gcctcggtcc ctcctgcacc tgctgcctgg atccccggcc tgcctgggcc tgggccttgg
241 tgggtttggt tttggtttcc ttctctgtct ctgactctcc atctgtcagt ctcattgtct
301 ctgtcacaca ttctctgttt ctgccatgat tcctctctgt tcccttcctg tctctctctg
361 tctccctctg ctcaccttgg ggtttctctg actgcatctt gtccccttct ctgtcgatct
421 ctctctcggg ggtcgggggg tgctgtctcc cagggcggga ggtctgtctt ccgccgcgtg
481 ccccgccccg ctcactgtct ctctctctct ctctctttct ctgcaggttc tccccatgac
541 accacctgaa cgtctcttcc tcccaagggt gtgtggcacc accctacacc tcctccttct
601 ggggctgctg ctggttctgc tgcctggggc ccaggtgagg cagcaggaga atgggggctg
661 ctggggtggc tcagccaaac cttgagccct agagcccccc tcaactctgt tctcccctag
721 gggctccctg gtgttggcct cacaccttca gctgcccaga ctgcccgtca gcaccccaag
781 atgcatcttg cccacagcac cctcaaacct gctgctcacc tcattggtaa acatccacct
841 gacctcccag acatgtcccc accagctctc ctcctacccc tgcctcagga acccaagcat
901 ccacccctct cccccaactt cccccacgct aaaaaaaaca gagggagccc actcctatgc
961 ctccccctgc catcccccag gaactcagtt gttcagtgcc cacttcctca gggattgaga
1021 cctctgatcc agacccctga tctcccaccc ccatccccta tggctcttcc taggagaccc
1081 cagcaagcag aactcactgc tctggagagc aaacacggac cgtgccttcc tccaggatgg
1141 tttctccttg agcaacaatt ctctcctggt ccccaccagt ggcatctact tcgtctactc
1201 ccaggtggtc ttctctggga aagcctactc tcccaaggcc ccctcctccc cactctacct
1261 ggcccatgag gtccagctct tctcctccca gtaccccttc catgtgcctc tcctcagctc
1321 ccagaagatg gtgtatccag ggctgcagga accctggctg cactcgatgt accacggggc
1381 tgcgttccag ctcacccagg gagaccagct atccacccac acagatggca tcccccacct
1441 agtcctcagc cctagtactg tcttctttgg agccttcgct ctgtagaact tggaaaaatc
1501 cagaaagaaa aaataattga tttcaagacc ttctccccat tctgcctcca ttctgaccat
1561 ttcaggggtc gtcaccacct ctcctttggc cattccaaca gctcaagtct tccctgatca
1621 agtcaccgga gctttcaaag aaggaattct aggcatccca ggggaccaca cctccctgaa
1681 ccatccctga tgtctgtctg gctgaggatt tcaagcctgc ctaggaattc ccagcccaaa
1741 gctgttggtc ttgtccacca gctaggtggg gcctagatcc acacacagag gaagagcagg
1801 cacatggagg agcttggggg atgactagag gcagggaggg gactatttat gaaggcaaaa
1861 aaattaaatt atttatttat ggaggatgga gagaggggaa taatagaaga acatccaagg
1921 agaaacagag acaggcccaa gagatgaaga gtgagagggc atgcgcacaa ggctgaccaa
1981 gagagaaaga agtaggcatg agggatcaca gggccccaga aggcagggaa aggctctgaa
2041 agccagctgc cgaccagagc cccacacgga ggcatctgca ccctcgatga agcccaataa
2101 acctcttttc tctgaaatgc tgtctgcttg tgtgtgtgtg

Fig. 3 (cont.)

Homo sapiens interleukin 1, beta (IL1B), mRNA.

ACCESSION NM_000576

VERSION NM_000576.2 GI:27894305

1 accaaacctc ttcgaggcac aaggcacaac aggctgctct gggattctct tcagccaatc
61 ttcattgctc aagtgtctga agcagccatg gcagaagtac ctgagctcgc cagtgaaatg
121 atggcttatt acagtggcaa tgaggatgac ttgttctttg aagctgatgg ccctaaacag
181 atgaagtgct ccttccagga cctggacctc tgccctctgg atggcggcat ccagctacga
241 atctccgacc accactacag caagggcttc aggcaggccg cgtcagttgt tgtggccatg
301 gacaagctga ggaagatgct ggttccctgc ccacagacct tccaggagaa tgacctgagc
361 accttctttc ccttcatctt tgaagaagaa cctatcttct tcgacacatg ggataacgag
421 gcttatgtgc acgatgcacc tgtacgatca ctgaactgca cgctccggga ctcacagcaa
481 aaaagcttgg tgatgtctgg tccatatgaa ctgaaagctc tccacctcca gggacaggat
541 atggagcaac aagtggtgtt ctccatgtcc tttgtacaag gagaagaaag taatgacaaa
601 atacctgtgg ccttgggcct caaggaaaag aatctgtacc tgtcctgcgt gttgaaagat
661 gataagccca ctctacagct ggagagtgta gatcccaaaa attacccaaa gaagaagatg
721 gaaaagcgat ttgtcttcaa caagatagaa atcaataaca agctggaatt tgagtctgcc
781 cagttcccca actggtacat cagcacctct caagcagaaa acatgcccgt cttcctggga
841 gggaccaaag gcggccagga tataactgac ttcaccatgc aatttgtgtc ttcctaaaga
901 gagctgtacc cagagagtcc tgtgctgaat gtggactcaa tccctagggc tggcagaaag
961 ggaacagaaa ggtttttgag tacggctata gcctggactt tcctgttgtc tacaccaatg
1021 cccaactgcc tgccttaggg tagtgctaag aggatctcct gtccatcagc caggacagtc
1081 agctctctcc tttcagggcc aatccccagc ccttttgttg agccaggcct ctctcacctc
1141 tcctactcac ttaaagcccg cctgacagaa accacggcca catttggttc taagaaaccc
1201 tctgtcattc gctcccacat tctgatgagc aaccgcttcc ctatttattt atttatttgt
1261 ttgtttgttt tattcattgg tctaatttat tcaaaggggg caagaagtag cagtgtctgt
1321 aaaagagcct agtttttaat agctatggaa tcaattcaat ttggactggt gtgctctctt
1381 taaatcaagt cctttaatta agactgaaaa tatataagct cagattattt aaatgggaat
1441 atttataaat gagcaaatat catactgttc aatggttctg aaataaactt cactgaag Homo sapiens interleukin 1, alpha (IL1A), mRNA.

ACCESSION NM_000575

VERSION NM_000575.3 GI:27894329

1 accaggcaac accattgaag gctcatatgt aaaaatccat gccttccttt ctcccaatct
61 ccattcccaa acttagccac tggcttctgg ctgaggcctt acgcatacct cccggggctt
121 gcacacacct tcttctacag aagacacacc ttgggcatat cctacagaag accaggcttc
181 tctctggtcc ttggtagagg gctactttac tgtaacaggg ccagggtgga gagttctctc
241 ctgaagctcc atcccctcta taggaaatgt gttgacaata ttcagaagag taagaggatc
301 aagacttctt tgtgctcaaa taccactgtt ctcttctcta ccctgcccta accaggagct

Fig. 3 (cont.)

361 tgtcacccca aactctgagg tgatttatgc cttaatcaag caaacttccc tcttcagaaa
421 agatggctca ttttccctca aaagttgcca ggagctgcca agtattctgc caattcaccc
481 tggagcacaa tcaacaaatt cagccagaac acaactacag ctactattag aactattatt
541 attaataaat tcctctccaa atctagcccc ttgacttcgg atttcacgat ttctcccttc
601 ctcctagaaa cttgataagt ttcccgcgct tcccttttc taagactaca tgtttgtcat
661 cttataaagc aaaggggtga ataaatgaac caaatcaata acttctggaa tatctgcaaa
721 caacaataat atcagctatg ccatctttca ctattttagc cagtatcgag ttgaatgaac
781 atagaaaaat acaaaactga attcttccct gtaaattccc cgttttgacg acgcacttgt
841 agccacgtag ccacgcctac ttaagacaat tacaaaaggc gaagaagact gactcaggct
901 taagctgcca gccagagagg gagtcatttc attggcgttt gagtcagcaa agaagtcaag
961 atggccaaag ttccagacat gtttgaagac ctgaagaact gttacagtga aaatgaagaa
1021 gacagttcct ccattgatca tctgtctctg aatcagaaat ccttctatca tgtaagctat
1081 ggcccactcc atgaaggctg catggatcaa tctgtgtctc tgagtatctc tgaaacctct
1141 aaaacatcca agcttacctt caaggagagc atggtggtag tagcaaccaa cgggaaggtt
1201 ctgaagaaga gacggttgag tttaagccaa tccatcactg atgatgacct ggaggccatc
1261 gccaatgact cagaggaaga aatcatcaag cctaggtcag caccttttag cttcctgagc
1321 aatgtgaaat acaactttat gaggatcatc aaatacgaat tcatcctgaa tgacgccctc
1381 aatcaaagta taattcgagc caatgatcag tacctcacgg ctgctgcatt acataatctg
1441 gatgaagcag tgaaatttga catgggtgct tataagtcat caaaggatga tgctaaaatt
1501 accgtgattc taagaatctc aaaaactcaa ttgtatgtga ctgcccaaga tgaagaccaa
1561 ccagtgctgc tgaaggagat gcctgagata cccaaaacca tcacaggtag tgagaccaac
1621 ctcctcttct tctgggaaac tcacggcact aagaactatt tcacatcagt tgcccatcca
1681 aacttgttta ttgccacaaa gcaagactac tgggtgtgct tggcaggggg gccaccctct
1741 atcactgact ttcagatact ggaaaaccag gcgtaggtct ggagtctcac ttgtctcact
1801 tgtgcagtgt tgacagttca tatgtaccat gtacatgaag aagctaaatc ctttactgtt
1861 agtcatttgc tgagcatgta ctgagccttg taattctaaa tgaatgttta cactctttgt
1921 aagagtggaa ccaacactaa catataatgt tgttatttaa agaacaccct atattttgca
1981 tagtaccaat cattttaatt attattcttc ataacaattt taggaggacc agagctactg
2041 actatggcta ccaaaaagac tctacccata ttacagatgg gcaaattaag gcataagaaa
2101 actaagaaat atgcacaata gcagttgaaa caagaagcca cagacctagg atttcatgat
2161 ttcatttcaa ctgtttgcct tctactttta agttgctgat gaactcttaa tcaaatagca
2221 taagtttctg ggacctcagt tttatcattt tcaaaatgga gggaataata cctaagcctt
2281 cctgccgcaa cagtttttta tgctaatcag ggaggtcatt ttggtaaaat acttcttgaa
2341 gccgagcctc aagatgaagg caaagcacga aatgttattt tttaattatt atttatatat
2401 gtatttataa atatatttaa gataattata atatactata tttatgggaa ccccttcatc
2461 ctctgagtgt gaccaggcat cctccacaat agcagacagt gttttctggg ataagtaagt
2521 ttgatttcat taatacaggg cattttggtc caagttgtgc ttatcccata gccaggaaac
2581 tctgcattct agtacttggg agacctgtaa tcatataata aatgtacatt aattaccttg
2641 agccagtaat tggtccgatc tttgactctt ttgccattaa acttacctgg gcattcttgt

Fig. 3 (cont.)

2701 ttcaattcca cctgcaatca agtcctacaa gctaaaatta gatgaactca actttgacaa
2761 ccatgagacc actgttatca aaactttctt ttctggaatg taatcaatgt ttcttctagg
2821 ttctaaaaat tgtgatcaga ccataatgtt acattattat caacaatagt gattgataga
2881 gtgttatcag tcataactaa ataaagcttg caacaaaatt ctctgacaaa aaaaaaaaaa
2941 aaa Homo sapiens interleukin 2 (IL2), mRNA.
ACCESSION NM_000586
VERSION NM_000586.2 GI:28178860
1 cgaattcccc tatcacctaa gtgtgggcta atgtaacaaa gagggatttc acctacatcc
61 attcagtcag tctttggggg tttaaagaaa ttccaaagag tcatcagaag aggaaaaatg
121 aaggtaatgt tttttcagac aggtaaagtc tttgaaaata tgtgtaatat gtaaaacatt
181 ttgacacccc cataatattt ttccagaatt aacagtataa attgcatctc ttgttcaaga
241 gttccctatc actctcttta atcactactc acagtaacct caactcctgc cacaatgtac
301 aggatgcaac tcctgtcttg cattgcacta agtcttgcac ttgtcacaaa cagtgcacct
361 acttcaagtt ctacaaagaa aacacagcta caactggagc atttactgct ggatttacag
421 atgattttga atggaattaa taattacaag aatcccaaac tcaccaggat gctcacattt
481 aagttttaca tgcccaagaa ggccacagaa ctgaaacatc ttcagtgtct agaagaagaa
541 ctcaaacctc tggaggaagt gctaaattta gctcaaagca aaaactttca cttaagaccc
601 agggacttaa tcagcaatat caacgtaata gttctggaac taaagggatc tgaaacaaca
661 ttcatgtgtg aatatgctga tgagacagca accattgtag aatttctgaa cagatggatt
721 accttttgtc aaagcatcat ctcaacactg acttgataat taagtgcttc ccacttaaaa
781 catatcaggc cttctattta tttaaatatt taaattttat atttattgtt gaatgtatgg
841 tttgctacct attgtaacta ttattcttaa tcttaaaact ataaatatgg atcttttatg
901 attctttttg taagccctag gggctctaaa atggtttcac ttatttatcc caaaatattt
961 attattatgt tgaatgttaa atatagtatc tatgtagatt ggttagtaaa actatttaat
1021 aaatttgata aatataaaaa aaaaaaa Homo sapiens interleukin 3 (colony-stimulating factor, multiple) (IL3), mRNA.
ACCESSION NM_000588
VERSION NM_000588.3 GI:28416914
1 cagagcccca cgaaggacca gaacaagaca gagtgcctcc tgccgatcca aacatgagcc
61 gcctgcccgt cctgctcctg ctccaactcc tggtccgccc cggactccaa gctcccatga
121 cccagacaac gcccttgaag acaagctggg ttaactgctc taacatgatc gatgaaatta
181 taacacactt aaagcagcca cctttgcctt tgctggactt caacaacctc aatggggaag
241 accaagacat tctgatggaa aataaccttc gaaggccaaa cctggaggca ttcaacaggg
301 ctgtcaagag tttacagaac gcatcagcaa ttgagagcat tcttaaaaat ctcctgccat

Fig. 3 (cont.)

361 gtctgcccct ggccacggcc gcacccacgc gacatccaat ccatatcaag gacggtgact
421 ggaatgaatt ccggaggaaa ctgacgttct atctgaaaac ccttgagaat gcgcaggctc
481 aacagacgac tttgagcctc gcgatctttt gagtccaacg tccagctcgt tctctgggcc
541 ttctcaccac agagcctcgg gacatcaaaa acagcagaac ttctgaaacc tctgggtcat
601 ctctcacaca ttccaggacc agaagcattt caccttttcc tgcggcatca gatgaattgt
661 taattatcta atttctgaaa tgtgcagctc ccatttggcc ttgtgcggtt gtgttctcat
721 ttttatccca ttgagactat ttatttatgt atgtatgtat ttatttattt attgcctgga
781 gtgtgaactg tatttatttt agcagaggag ccatgtcctg ctgcttctgc aaaaaactca
841 gagtggggtg gggagcatgt tcatttgtac ctcgagtttt aaactggttc ctagggatgt
901 gtgagaataa actagactct gaac

//

Homo sapiens interleukin 4 (IL4), transcript variant 2, mRNA.
ACCESSION NM_172348
VERSION NM_172348.1 GI:27477091

1 ttctatgcaa agcaaaaagc cagcagcagc cccaagctga taagattaat ctaaagagca
61 aattatggtg taatttccta tgctgaaact ttgtagttaa tttttaaaaa aggtttcatt
121 ttcctattgg tctgatttca caggaacatt ttacctgttt gtgaggcatt ttttctcctg
181 gaagagaggt gctgattggc cccaagtgac tgacaatctg gtgtaacgaa aatttccaat
241 gtaaactcat tttccctcgg tttcagcaat tttaaatcta tatatagaga tatctttgtc
301 agcattgcat cgttagcttc tcctgataaa ctaattgcct cacattgtca ctgcaaatcg
361 acacctatta atgggtctca cctcccaact gcttccccct ctgttcttcc tgctagcatg
421 tgccggcaac tttgtccacg gacacaagtg cgatatcacc ttacaggaga tcatcaaaac
481 tttgaacagc ctcacagagc agaagaacac aactgagaag gaaaccttct gcagggctgc
541 gactgtgctc cggcagttct acagccacca tgagaaggac actcgctgcc tgggtgcgac
601 tgcacagcag ttccacaggc acaagcagct gatccgattc ctgaaacggc tcgacaggaa
661 cctctggggc ctggcgggct tgaattcctg tcctgtgaag gaagccaacc agagtacgtt
721 ggaaaacttc ttggaaaggc taaagacgat catgagagag aaatattcaa agtgttcgag
781 ctgaatattt taatttatga gtttttgata gctttatttt ttaagtattt atatatttat
841 aactcatcat aaaataaagt atatatagaa tct

//

Homo sapiens interleukin 4 (IL4), transcript variant 1, mRNA.
ACCESSION NM_000589
VERSION NM_000589.2 GI:27477090

1 ttctatgcaa agcaaaaagc cagcagcagc cccaagctga taagattaat ctaaagagca
61 aattatggtg taatttccta tgctgaaact ttgtagttaa tttttaaaaa aggtttcatt
121 ttcctattgg tctgatttca caggaacatt ttacctgttt gtgaggcatt ttttctcctg
181 gaagagaggt gctgattggc cccaagtgac tgacaatctg gtgtaacgaa aatttccaat
241 gtaaactcat tttccctcgg tttcagcaat tttaaatcta tatatagaga tatctttgtc

Fig. 3 (cont.)

301 agcattgcat cgttagcttc tcctgataaa ctaattgcct cacattgtca ctgcaaatcg
361 acacctatta atgggtctca cctcccaact gcttcccct ctgttcttcc tgctagcatg
421 tgccggcaac tttgtccacg gacacaagtg cgatatcacc ttacaggaga tcatcaaaac
481 tttgaacagc ctcacagagc agaagactct gtgcaccgag ttgaccgtaa cagacatctt
541 tgctgcctcc aagaacacaa ctgagaagga aaccttctgc agggctgcga ctgtgctccg
601 gcagttctac agccaccatg agaaggacac tcgctgcctg ggtgcgactg cacagcagtt
661 ccacaggcac aagcagctga tccgattcct gaaacggctc gacaggaacc tctggggcct
721 ggcgggcttg aattcctgtc ctgtgaagga agccaaccag agtacgttgg aaaacttctt
781 ggaaaggcta aagacgatca tgagagagaa atattcaaag tgttcgagct gaatatttta
841 atttatgagt ttttgatagc tttatttttt aagtatttat atatttataa ctcatcataa
901 aataaagtat atatagaatc t Human interleukin 5 (IL-5) gene, complete cds.
ACCESSION J03478
VERSION J03478.1 GI:186338

1 atcctaatca agacccccagt gaacagaact cgaccctgcc aaggcttggc atttccattt
61 caatcactgt cttcccacca gtattttcaa tttcttttaa gacagattaa tctagccaca
121 gtcatagtag aacatagccg atcttgaaaa aaaacattcc caatatttat gtattttagc
181 ataaaattct gtttagtggt ctaccttata ctttgttttg cacacatctt ttaagaggaa
241 gttaattttc tgattttaag aaatgcaaat gtggggcaat gatgtattaa cccaaagatt
301 ccttccgtaa tagaaaatgt ttttaaaggg gggaaacagg gatttttatt attaaaagat
361 aaaagtaaat ttatttttta agatataagg cattggaaac atttagtttc acgatatgcc
421 attattaggc attctctatc tgattgttag aaattattca tttcctcaaa gacagacaat
481 aaattgactg ggacgcagt cttgtactat gcactttctt tgccaaaggc aaacgcagaa
541 cgtttcagag ccatgaggat gcttctgcat ttgagtttgc tagctcttgg agctgcctac
601 gtgtatgcca tccccacaga aattcccaca agtgcattgg tgaaagagac cttggcactg
661 ctttctactc atcgaactct gctgatagcc aatgaggtaa ttttctttat gattcctaca
721 gtctgtaaag tgcataggta atcatttgtg atggttcctt tactatatat agagatctgt
781 tataaataat aagattctga gcacattagt acatgggtga taactacatc accagcaaac
841 attctgttaa aagttatgaa tgctggtgtg ctgtaaaaat gattgtattt cctttcctct
901 ccagactctg aggattcctg ttcctgtaca taaaaatgta agttaaatta tgattcagta
961 aaatgatggc atgaataagt aaatttcctg ttttaagctg taaatcatta gttatcattg
1021 gaactattta attttctata ttttgttttc atatgggtgg ctgtgaatgt ctgtacttat
1081 aaatatgagg aatgactttt tatcaagtag aatcctttaa acaagtggat taggctcttt
1141 ggtgatgttg ttagtttgcc ttcccaaaga gcatcgtgtc aggattcttt ccagaaggat
1201 tccacactga gtgagaggtg cgtgctagtc tccgtgcagt tctgactctt tctcactcta
1261 acgtgtttct gaaagtatta gcaactcaga attatatttt tagaaccatg atcagtagac
1321 attaaaatat ataacaaatg ccctatatta ataattctgc atacttaaat aattatgact

Fig. 3 (cont.)

1381 atatgatggt gtgtatgcat tgaatatgcc tggtcatatt aaaatgtaaa atatatagtt
1441 tattagtcta aatagaataa aactaccagc tagaactgta gaaacacatt gatatgagtt
1501 taatgtataa tgcattacac ttccaaaaca tttttttcca gttacataat taagttatat
1561 cctttataaa actcctcagt aatcatataa gcttcatcta ctttttgaaa attttatctt
1621 aatatgtggt ggtttgttgc ctagaaaaca aacaaaaaac tctttggaga agggaactca
1681 tgtaaatacc acaaaacaaa gcctaacttt gtggaccaaa attgttttaa taattatttt
1741 ttaattgatg aattaaaaag tatatatatt tattgtgtac aatatgatgt tttgaagtat
1801 gtatacattg cagaatggac aatggaccaa atttttatac cttgtcttga ttatttgcat
1861 tttaaaaatt ttcctcattt agcaccaact gtgcactgaa gaaatctttc agggaatagg
1921 cacactggag agtcaaactg tgcaaggggg tactgtggaa agactattca aaaacttgtc
1981 cttaataaag aaatacattg acggccaaaa agtaagttac acacattcaa tggaagctat
2041 atttgtcctg gctgtgccta tttctatgga attgacagtt tcctgtaata cctattgtca
2101 tttttctttt ttcacagaaa aagtgtggag aagaaagacg gagagtaaac caattcctag
2161 actacctgca agagtttctt ggtgtaatga acaccgagtg gataatagaa agttgagact
2221 aaactggttt gttgcagcca aagattttgg aggagaagga cattttactg cagtgagaat
2281 gagggccaag aaagagtcag gccttaattt tcaatataat ttaacttcag agggaaagta
2341 aatatttcag gcatactgac actttgccag aaagcataaa attcttaaaa tatatttcag
2401 atatcagaat cattgaagta ttttcctcca ggcaaaattg atatactttt ttcttattta
2461 acttaacatt ctgtaaaatg tctgttaact taatagtatt tatgaaatgg ttaagaattt
2521 ggtaaattag tatttattta atgttatgtt gtgttctaat aaaacaaaaa tagacaactg
2581 ttcaatttgc tgctggcctc tgtccttagc aatttgaagt tagcacagtc cattgagtac
2641 atgcccagtt tggaggaagg gtctgagcac atgtggctga gcatccccat ttctctggag
2701 aagtctcaag gttgcaaggc acaccagagg tggaagtgat ctagcaggac ttagtgggga
2761 tgtggggagc agggacacag gcaggaggtg aacctggttt tctctctaca gtatatccag
2821 aacctgggat ggtcgaaggg taaatggtag ggaataaatg aatgaatgtc gtttccaaga
2881 tgattgtaga actaaaatga gttgtaagct cccctggaag aagggatgtg gaacctgtaa
2941 ctaggttcct gcccagcctg tgagaagaat ttggcagatc atctcattgc cagtatagag
3001 aggaagccag aaaccctctc tgccaaggcc tgcaggggtt cttaccacct gaccctgcac
3061 cataacaaaa ggacagagag acatggtagg gcagtcccat tagaaagact gagttccgta
3121 ttcccggggc agggcagcac caggccgcac aacatccatt ctgcctgctt atggctatca
3181 gtagcatcac tagagattct tctgtttgag aaaacttctc tcaaggatcc

//

Homo sapiens interleukin 6 (interferon, beta 2) (IL6), mRNA.

ACCESSION NM_000600

VERSION NM_000600.1 GI:10834983

1 ttctgccctc gagcccaccg ggaacgaaag agaagctcta tctcgcctcc aggagcccag
61 ctatgaactc cttctccaca agcgccttcg gtccagttgc cttctccctg gggctgctcc
121 tggtgttgcc tgctgccttc cctgccccag taccccccagg agaagattcc aaagatgtag
181 ccgccccaca cagacagcca ctcacctctt cagaacgaat tgacaaacaa attcggtaca

Fig. 3 (cont.)

241 tcctcgacgg catctcagcc ctgagaaagg agacatgtaa caagagtaac atgtgtgaaa
301 gcagcaaaga ggcactggca gaaaacaacc tgaaccttcc aaagatggct gaaaaagatg
361 gatgcttcca atctggattc aatgaggaga cttgcctggt gaaaatcatc actggtcttt
421 tggagtttga ggtataccta gagtacctcc agaacagatt tgagagtagt gaggaacaag
481 ccagagctgt gcagatgagt acaaaagtcc tgatccagtt cctgcagaaa aaggcaaaga
541 atctagatgc aataaccacc cctgacccaa ccacaaatgc cagcctgctg acgaagctgc
601 aggcacagaa ccagtggctg caggacatga caactcatct cattctgcgc agctttaagg
661 agttcctgca gtccagcctg agggctcttc ggcaaatgta gcatgggcac ctcagattgt
721 tgttgttaat gggcattcct tcttctggtc agaaacctgt ccactgggca cagaacttat
781 gttgttctct atggagaact aaaagtatga gcgttaggac actattttaa ttatttttaa
841 tttattaata tttaaatatg tgaagctgag ttaatttatg taagtcatat ttatattttt
901 aagaagtacc acttgaaaca ttttatgtat tagttttgaa ataataatgg aaagtggcta
961 tgcagtttga atatcctttg tttcagagcc agatcatttc ttggaaagtg taggcttacc
1021 tcaaataaat ggctaactta tacatatttt taaagaaata tttatattgt atttatataa
1081 tgtataaatg gtttttatac caataaatgg cattttaaaa aattc Homo sapiens interleukin 7 (IL7), mRNA.

NM_000880

VERSION NM_000880.2 GI:28610152

1 acatccgcgg caacgcctcc ttggtgtcgt ccgcttccaa taacccagct tgcgtcctgc
61 acacttgtgg cttccgtgca cacattaaca actcatggtt ctagctccca gtcgccaagc
121 gttgccaagg cgttgagaga tcatctggga agtcttttac ccagaattgc tttgattcag
181 gccagctggt ttttcctgcg gtgattcgga aattcgcgaa ttcctctggt cctcatccag
241 gtgcgcggga agcaggtgcc caggagagag gggataatga agattccatg ctgatgatcc
301 caaagattga acctgcagac caagcgcaaa gtagaaactg aaagtacact gctggcggat
361 cctacggaag ttatggaaaa ggcaaagcgc agagccacgc cgtagtgtgt gccgcccccc
421 ttgggatgga tgaaactgca gtcgcggcgt gggtaagagg aaccagctgc agagatcacc
481 ctgcccaaca cagactcggc aactccgcgg aagaccaggg tcctgggagt gactatgggc
541 ggtgagagct tgctcctgct ccagttgcgg tcatcatgac tacgcccgcc tcccgcagac
601 catgttccat gtttctttta ggtatatctt tggacttcct cccctgatcc ttgttctgtt
661 gccagtagca tcatctgatt gtgatattga aggtaaagat ggcaaacaat atgagagtgt
721 tctaatggtc agcatcgatc aattattgga cagcatgaaa gaaattggta gcaattgcct
781 gaataatgaa tttaactttt ttaaaagaca tatctgtgat gctaataagg aaggtatgtt
841 tttattccgt gctgctcgca agttgaggca atttcttaaa atgaatagca ctggtgattt
901 tgatctccac ttattaaaag tttcagaagg cacaacaata ctgttgaact gcactggcca
961 ggttaaagga agaaaaccag ctgccctggg tgaagcccaa ccaacaaaga gtttggaaga
1021 aaataaatct ttaaaggaac agaaaaaact gaatgacttg tgtttcctaa agagactatt
1081 acaagagata aaaacttgtt ggaataaaat tttgatgggc actaaagaac actgaaaaat
1141 atggagtggc aatatagaaa cacgaacttt agctgcatcc tccaagaatc tatctgctta

Fig. 3 (cont.)

1201 tgcagttttt cagagtggaa tgcttcctag aagttactga atgcaccatg gtcaaaacgg
1261 attagggcat ttgagaaatg catattgtat tactagaaga tgaatacaaa caatggaaac
1321 tgaatgctcc agtcaacaaa ctatttctta tatatgtgaa catttatcaa tcagtataat
1381 tctgtactga ttttgtaag acaatccatg taaggtatca gttgcaataa tacttctcaa
1441 acctgtttaa atatttcaag acattaaatc tatgaagtat ataatggttt caaagattca
1501 aaattgacat tgctttactg tcaaaataat tttatggctc actatgaatc tattatactg
1561 tattaagagt gaaaattgtc ttcttctgtg ctggagatgt tttagagtta acaatgatat
1621 atggataatg ccggtgagaa taagagagtc ataaacctta agtaagcaac agcataacaa
1681 ggtccaagat acctaaaaga gatttcaaga gatttaatta atcatgaatg tgtaacacag
1741 tgccttcaat aaatggtata gcaaatgttt tgacatgaaa aaaggacaat ttcaaaaaaa
1801 taaaataaaa taaaaataaa ttcacctagt ctaaggatgc taaaccttag tactgagtta
1861 cattgtcatt tatatagatt ataacttgtc taaataagtt tgcaatttgg gagatatatt
1921 tttaagataa taatatatgt ttacctttta attaatgaaa tatctgtatt taattttgac
1981 actatatctg tatataaaat attttcatac agcattacaa attgcttact ttggaataca
2041 tttctccttt gataaaataa atgagctatg tattaacaaa aaaaaaaaaa aaaaaaaaaa
2101 aaaaaaaaaa aaaaaa Homo sapiens interleukin 8 (IL8), mRNA.
ACCESSION NM_000584
VERSION NM_000584.2 GI:28610153
1 ctccataagg cacaaacttt cagagacagc agagcacaca agcttctagg acaagagcca
61 ggaagaaacc accggaagga accatctcac tgtgtgtaaa catgacttcc aagctggccg
121 tggctctctt ggcagccttc ctgatttctg cagctctgtg tgaaggtgca gttttgccaa
181 ggagtgctaa agaacttaga tgtcagtgca taaagacata ctccaaacct ttccacccca
241 aatttatcaa agaactgaga gtgattgaga gtggaccaca ctgcgccaac acagaaatta
301 ttgtaaagct ttctgatgga agagagctct gtctggaccc caaggaaaac tgggtgcaga
361 gggttgtgga gaagtttttg aagagggctg agaattcata aaaaaattca ttctctgtgg
421 tatccaagaa tcagtgaaga tgccagtgaa acttcaagca aatctacttc aacacttcat
481 gtattgtgtg ggtctgttgt agggttgcca gatgcaatac aagattcctg gttaaatttg
541 aatttcagta aacaatgaat agtttttcat tgtaccatga aatatccaga acatacttat
601 atgtaaagta ttatttattt gaatctacaa aaaacaacaa ataattttta aatataagga
661 ttttcctaga tattgcacgg gagaatatac aaatagcaaa attgaggcca agggccaaga
721 gaatatccga actttaattt caggaattga atgggtttgc tagaatgtga tatttgaagc
781 atcacataaa aatgatggga caataaattt tgccataaag tcaaatttag ctggaaatcc
841 tggatttttt tctgttaaat ctggcaaccc tagtctgcta gccaggatcc acaagtcctt
901 gttccactgt gccttggttt ctcctttatt tctaagtgga aaaagtatta gccaccatct
961 tacctcacag tgatgttgtg aggacatgtg gaagcacttt aagtttttc atcataacat
1021 aaattatttt caagtgtaac ttattaacct atttattatt tatgtattta tttaagcatc
1081 aaatatttgt gcaagaattt ggaaaaatag aagatgaatc attgattgaa tagttataaa

Fig. 3 (cont.)

1141 gatgttatag taaatttatt ttattttaga tattaaatga tgttttatta gataaatttc
1201 aatcagggtt tttagattaa acaaacaaac aattgggtac ccagttaaat tttcatttca
1261 gataaacaac aaataatttt ttagtataag tacattattg tttatctgaa attttaattg
1321 aactaacaat cctagtttga tactcccagt cttgtcattg ccagctgtgt tggtagtgct
1381 gtgttgaatt acggaataat gagttagaac tattaaaaca gccaaaactc cacagtcaat
1441 attagtaatt tcttgctggt tgaaacttgt ttattatgta caaatagatt cttataatat
1501 tatttaaatg actgcatttt taaatacaag gctttatatt tttaacttta agatgttttt
1561 atgtgctctc caaatttttt ttactgtttc tgattgtatg gaaatataaa agtaaatatg
1621 aaacatttaa aatataattt gttgtcaaag taaaaaaaaa aaaaaa Homo sapiens interleukin 9 (IL9), mRNA.
ACCESSION NM_000590
VERSION NM_000590.1 GI:10834979
1 ccgctgtcaa gatgcttctg gccatggtcc ttacctctgc cctgctcctg tgctccgtgg
61 caggccaggg gtgtccaacc ttggcgggga tcctggacat caacttcctc atcaacaaga
121 tgcaggaaga tccagcttcc aagtgccact gcagtgctaa tgtgaccagt tgtctctgtt
181 tgggcattcc ctctgacaac tgcaccagac catgcttcag tgagagactg tctcagatga
241 ccaataccac catgcaaaca agatacccac tgattttcag tcgggtgaaa aaatcagttg
301 aagtactaaa gaacaacaag tgtccatatt tttcctgtga acagccatgc aaccaaacca
361 cggcaggcaa cgcgctgaca tttctgaaga gtcttctgga aattttccag aaagaaaaga
421 tgagagggat gagaggcaag atatgaagat gaaatattat ttatcctatt tattaaattt
481 aaaaagcttt ctctttaagt tgctacaatt taaaaatcaa gtaagctact ctaaatcagt
541 atcagttgtg attatttgtt taacattgta tgtctttatt ttgaaataaa t Homo sapiens interleukin 10 (IL10), mRNA.
ACCESSION NM_000572
VERSION NM_000572.2 GI:24430216
1 acacatcagg ggcttgctct tgcaaaacca aaccacaaga cagacttgca aaagaaggca
61 tgcacagctc agcactgctc tgttgcctgg tcctcctgac tggggtgagg gccagcccag
121 gccagggcac ccagtctgag aacagctgca cccacttccc aggcaacctg cctaacatgc
181 ttcgagatct ccgagatgcc ttcagcagag tgaagacttt ctttcaaatg aaggatcagc
241 tggacaactt gttgttaaag gagtccttgc tggaggactt taagggttac ctgggttgcc
301 aagccttgtc tgagatgatc cagttttacc tggaggaggt gatgccccaa gctgagaacc
361 aagacccaga catcaaggcg catgtgaact ccctgggga gaacctgaag accctcaggc
421 tgaggctacg gcgctgtcat cgatttcttc cctgtgaaaa caagagcaag gccgtggagc
481 aggtgaagaa tgcctttaat aagctccaag agaaaggcat ctacaaagcc atgagtgagt
541 ttgacatctt catcaactac atagaagcct acatgacaat gaagatacga aactgagaca
601 tcagggtggc gactctatag actctaggac ataaattaga ggtctccaaa atcggatctg

Fig. 3 (cont.)

661 gggctctggg atagctgacc cagccccttg agaaacctta ttgtacctct cttatagaat
721 atttattacc tctgatacct caaccccat ttctatttat ttactgagct tctctgtgaa
781 cgatttagaa agaagcccaa tattataatt tttttcaata tttattattt tcacctgttt
841 ttaagctgtt tccatagggt gacacactat ggtatttgag tgttttaaga taaattataa
901 gttacataag ggaggaaaaa aaatgttctt tggggagcca acagaagctt ccattccaag
961 cctgaccacg ctttctagct gttgagctgt tttccctgac ctccctctaa tttatcttgt
1021 ctctgggctt ggggcttcct aactgctaca aatactctta ggaagagaaa ccagggagcc
1081 cctttgatga ttaattcacc ttccagtgtc tcggagggat tcccctaacc tcattcccca
1141 accacttcat tcttgaaagc tgtggccagc ttgttattta taacaaccta aatttggttc
1201 taggccgggc gcggtggctc acgcctgtaa tcccagcact ttgggaggct gaggcgggtg
1261 gatcacttga ggtcaggagt tcctaaccag cctggtcaac atggtgaaac cccgtctcta
1321 ctaaaaatac aaaaattagc cgggcatggt ggcgcgcacc tgtaatccca gctacttggg
1381 aggctgaggc aagagaattg cttgaaccca ggagatggaa gttgcagtga gctgatatca
1441 tgcccctgta ctccagcctg ggtgacagag caagactctg tctcaaaaaa taaaaataaa
1501 aataaatttg gttctaatag aactcagttt taactagaat ttattcaatt cctctgggaa
1561 tgttacattg tttgtctgtc ttcatagcag attttaattt tgaataaata aatgtatctt
1621 attcacatc Homo sapiens interleukin 12A (natural killer cell stimulatory factor 1, cytotoxic lymphocyte maturation factor 1, p35) (IL12A), mRNA.

1 tttcattttg ggccgagctg gaggcggcgg ggccgtcccg gaacggctgc ggccgggcac
61 cccgggagtt aatccgaaag cgccgcaagc cccgcgggcc ggccgcaccg cacgtgtcac
121 cgagaagctg atgtagagag agacacagaa ggagacagaa agcaagagac cagagtcccg
181 ggaaagtcct gccgcgcctc gggacaatta taaaaatgtg gccccctggg tcagcctccc
241 agccaccgcc ctcacctgcc gcggccacag gtctgcatcc agcggctcgc cctgtgtccc
301 tgcagtgccg gctcagcatg tgtccagcgc gcagcctcct ccttgtggct accctggtcc
361 tcctggacca cctcagtttg gccagaaacc tccccgtggc cactccagac ccaggaatgt
421 tcccatgcct tcaccactcc caaaacctgc tgagggccgt cagcaacatg ctccagaagg
481 ccagacaaac tctagaattt tacccttgca cttctgaaga gattgatcat gaagatatca
541 caaaagataa aaccagcaca gtggaggcct gtttaccatt ggaattaacc aagaatgaga
601 gttgcctaaa ttccagagag acctctttca taactaatgg gagttgcctg gcctccagaa
661 agacctcttt tatgatggcc ctgtgcctta gtagtattta tgaagacttg aagatgtacc
721 aggtggagtt caagaccatg aatgcaaagc ttctgatgga tcctaagagg cagatctttc
781 tagatcaaaa catgctggca gttattgatg agctgatgca ggccctgaat ttcaacagtg
841 agactgtgcc acaaaaatcc tcccttgaag aaccggattt ttataaaact aaaatcaagc
901 tctgcatact tcttcatgct ttcagaattc gggcagtgac tattgataga gtgatgagct
961 atctgaatgc ttcctaaaaa gcgaggtccc tccaaaccgt tgtcattttt ataaaacttt

Fig. 3 (cont.)

1021 gaaatgagga aactttgata ggatgtggat taagaactag ggagggggaa agaaggatgg
1081 gactattaca tccacatgat acctctgatc aagtattttt gacatttact gtggataaat
1141 tgtttttaag ttttcatgaa tgaattgcta agaagggaaa atatccatcc tgaaggtgtt
1201 tttcattcac tttaatagaa gggcaaatat ttataagcta tttctgtacc aaagtgtttg
1261 tggaaacaaa catgtaagca taacttattt taaaatattt atttatataa cttggtaatc
1321 atgaaagcat ctgagctaac ttatatttat ttatgttata tttattaaat tatttatcaa
1381 gtgtatttga aaaatatttt taagtgttct aaaaataaaa gtattgaatt aaagtgaaaa
1441 aaaa Homo sapiens interleukin 20 (IL20), mRNA.

ACCESSION NM_018724

VERSION NM_018724.2 GI:31083165

1 ctttgaattc ctagctcctg tggtctccag atttcaggcc taagatgaaa gcctctagtc
61 ttgccttcag ccttctctct gctgcgtttt atctcctatg gactccttcc actggactga
121 agacactcaa tttgggaagc tgtgtgatcg ccacaaacct tcaggaaata cgaaatggat
181 tttctgagat acggggcagt gtgcaagcca aagatggaaa cattgacatc agaatcttaa
241 ggaggactga gtctttgcaa gacacaaagc ctgcgaatcg atgctgcctc ctgcgccatt
301 tgctaagact ctatctggac agggtattta aaaactacca gacccctgac cattatactc
361 tccggaagat cagcagcctc gccaattcct ttcttaccat caagaaggac ctccggctct
421 gtcatgccca catgacatgc cattgtgggg aggaagcaat gaagaaatac agccagattc
481 tgagtcactt tgaaaagctg gaacctcagg cagcagttgt gaaggctttg gggggaactag
541 acattcttct gcaatggatg gaggagacag aataggagga aagtgatgct gctgctaaga
601 atattcgagg tcaagagctc cagtcttcaa tacctgcaga ggaggcatga ccccaaacca
661 ccatctcttt actgtactag tcttgtgctg gtcacagtgt atcttattta tgcattactt
721 gcttccttgc atgattgtct ttatgcatcc ccaatcttaa ttgagaccat acttgtataa
781 gatttttgta atatctttct gctattggat atatttatta gttaatatat ttatttattt
841 tttgctattt aatgtattta tttttttact tggacatgaa actttaaaaa aattcacaga
901 ttatatttat aacctgacta gagca

Fig. 3 (cont.)

DEFINITION Kaposi's sarcoma-associated herpesvirus latent nuclear antigen gene, partial cds.

ACCESSION AF305694

VERSION AF305694.1 GI:11037007

1 agaccagatt tcccgaggat ggcgcccccg ggaatgcgcc tgaggtcggg acggagcacc
61 ggcgcgccct taacgagagg aagttgtagg aaacgaaaca ggtctccgga aagatgtgac
121 cttggcgatg acctacatct acaaccgcga aggaagcatg tcgccgactc cgtcgacggc
181 cgggaatgtg gaccccacac cttgcctata ccaggaagtc ccacagtgtt cacatccggg
241 ctgccagcat ttgtgtctag tcctacttta ccggtggctt ccattccttc acccgctccc
301 gcaacacctt tacctccacc ggcactctta ccccccgtaa ccacgtcttc ctccccaatc
361 cctccatccc atcctgtgtc tccggggacc acggatactc attctccatc tcctgcattg
421 ccacccacgc agtctccaga gtcttctcaa aggccaccgc tttcaagtcc tacaggaagg
481 ccagactctt caacacctat gcgtccgcca ccctcgcagc agactacacc tccacactca
541 cccacgactc ctccacccga gcctccctcc aagtcgtcac cagactcttt agctccgtct
601 accctgcgta gcctgagaaa aagaaggcta tcgtcccccc aaggtccctc tacactaaac
661 ccaatatgtc agtcgccccc agtctctccc cctagatgtg acttcgccaa ccgtagtgtg
721 tacccccccat gggccacaga gtccccgatc tacgtgggat catccagcga tggcgatact
781 ccgccacgcc aaccgcctac atctcccatc tccataggat catcatcccc gtctgaggga
841 tcctcgggtg atgacacagc catgttggtg ctccttgcgg agattgcaga agaagcatcc
901 aagaatgaaa aagaatgttc cgaaaataat caggctggcg aggataatgg ggacaacgag
961 attagcaagg aaagtcaggt tgacaaggat gacaatgaca ataaggatga tgaggaggag
1021 caggagacag atgaggagga cgaggaggat gacgaggagg atgacgagga ggatgacgag
1081 gaggatgacg aggaggatga cgaggaggat gacgaggagg atgacgagga ggatgacgag
1141 gaggatgacg aggaggatga cgaggaggat gacgaggagg atgacgagga ggaggacgag
1201 gaggaggacg aggaggagga cgaggaggag gaggacgagg aggaggagga ggacgaggag
1261 gatgacgatg atgaggacaa tgaggacgag gaggatgacg aggaggagga caagaaggag
1321 gacgaggagg acgggggcga tggaaacaaa acgttgagca tccaaagttc acaacagcag
1381 caggagccac aacagcagga gccacagcag caggagccac aacagcagga gccacagcag
1441 caggagccac agcagcagga gcccctgcag gagccacaac agcaggagcc acagcagcag
1501 gagccacaac agcaggagcc acagcagcag gagcccctgc aggagccaca gcagcaggag
1561 ccacagcagc aggagccaca gcagcaggag ccacaacagc aggagccaca gcagcaggat
1621 gagcagcagc aggatgagca gcagcaggat gagcagcagc aggatgagca gcagcagcag
1681 gatgagcagc agcaggatga gcagcagcag gatgagcagc agcaggatga gcaggagcag
1741 caggatgagc agcagcagga tgagcagcag cagcaggatg aacaggagca gcaggaggag
1801 caggagcagc aggaggagca ggagcaggag ttagaggagc aggagcagga gttagaggag
1861 caggagcagg agttagagga gcaggagcag gagttagagg agcaggagca ggagttagag
1921 gagcaggagc aggagttaga ggagcaggag caggagttag aggagcagga gcaggagtta
1981 gaggagcagg agcaggagtt agatgagcag gagcaggagt tagaggagca ggagcaggag
2041 ttagaggagc aggagcagga gttagaggag caggagcagg agttagagga gcaggagcag
2101 gagttagagg agcaggagca ggagttagag gagcaggagc aggagttaga ggagcaggag

Fig. 3 (cont.)

2161 caggagttag aggagcagga gcaggagtta gaggagcagg agcaggagca ggagttagag
2221 gaggtggaag agcaagagca ggagcaggaa gagcaggaat tagaggaggt ggaggagcaa
2281 gagcaggagc aggaggagca ggaggagcag gagttagagg aggtggaaga gcaggaagag
2341 caggagttag aggaggtgga agagcaggaa gagcaggagt tagaggaggt ggaagagcag
2401 gagcagcagg gggtggaaca gcaggagcag gagacggtgg aagagcccat aatcttgcac
2461 gggtcgtcat ccgaggacga aatggaagtg gattaccctg ttgttagcac acatgaacaa
2521 attgccagta gcccaccagg agataataca ccagacgatg acccacaacc tggcccatct
2581 cgcgaatacc gctatgtact cagaacatca ccaccccaca gacctggagt tcgtatgagg
2641 cgcgttccag ttacccaccc aaaaaagcca catccaagat accaacaacc accggtccct
2701 tacagacaga tagatgattg tcctgcgaaa gctaggccac aacacatctt ttatagacgc
2761 tttttgggaa aggatggaag acgagatcca aagtgtcaat ggaagtttgc agtgattttt
2821 tggggcaatg acccatacgg acttaaaaaa ttatctcagg ccttccagtt tggaggagta
2881 aaggcaggcc ccgtgtcctg cttgccccac cctggaccag accagtcgcc cataacttat
2941 tgtgtatatg tgtattgtca gaacaaagac acaagtaaga aagtacaaat ggcccgccta
3001 gcctgggaag ctagtcaccc cctggcagga aacctacaat cttccatagt taagtttaaa
3061 aagcccctgc cattaaccca gccaggggaa aaccaaggtc ctggggactc tccacaggaa
3121 atgacat Human herpesvirus 8 ORF73 gene, complete cds.
ACCESSION AF360120
VERSION AF360120.1 GI:13936995

1 atggcgcccc cgggaatgcg cctgaggtcg ggacggagca ccggcgcgcc cttaacgaga
61 ggaagttgta ggaaacgaaa caggtctccg gaaagatgtc accttggcga tgacctacat
121 ctacaaccgc gaaggaagca tgtcgccgac tccgtcgacg gccgggaatg tggaccccac
181 accttgccta taccaggaag tcccacagtg ttcacatccg ggctgccagc atttgtgtct
241 agtcctactt taccggtggc tcccattcct tcacccgctc ccgcaacacc tttacctcca
301 ccggcactct tacccccgt aaccacgtct tcctccccaa tccctccatc ccatcctgtg
361 tctccgggga ccacggatac tcattctcca tctcctgcat tgccacccac gcagtctcca
421 gagtcttctc aaaggccacc gctttcaagt cctacaggaa ggccagactc ttcaacacct
481 atgcgtccgc caccctcgca gcagactaca cctccacact cacccacgac tcctccaccc
541 gagcctccct ccaagtcgtc accagactct ttagctccgt ctaccctgcg tagcctgaga
601 aaaagaaggc tatcgtcccc ccaaggtccc tctacactaa acccaatatg tcagtcgccc
661 ccagtctctc cccctagatg tgacttcgcc aaccgtagtg tgtacccccc atgggccaca
721 gagtccccga tctacgtggg atcatccagc gatggcgata ctccgccacg ccaaccgcct
781 acatctccca tctccatagg atcatcatcc ccgtctgagg gatcctgggg tgatgacaca
841 gccatgttgg tgctccttgc ggagattgca gaagaagcat ccaagaatga aaaagaatgt
901 tccgaaaata atcaggctgg cgaggataat ggggacaacg agattagcaa ggaaagtcag
961 gttgacaagg atgacaatga caataaggat gatgaggagg agcaggagac agatgaggag
1021 gacgaggagg atgacgagga ggatgacgag gaggatgacg aggaggatga cgaggaggat

Fig. 3 (cont.)

1081 gacgaggagg atgacgagga ggatgacgag gaggatgacg aggaggagga cgaggaggag
1141 gacgaggagg aggaggacga ggaggaggag gaggaggacg aggaggatga cgatgatgag
1201 gacaatgagg acgaggagga ggacaagaag gaggacgagg aggacggggg cgatggaaac
1261 aaaacgttga gcatccaaag ttcacaacag cagcaggagc cacagcagca ggagccacaa
1321 cagcaggagc cacagcagca ggagccacag cagcaggagc ccctgcagga gccacagcag
1381 caggagccac aacagcagga gccacaacag caggagccac aacagcagga gccacaacag
1441 caggagccac aacagcagga gccacagcag caggatgagc agcagcagga tgagcagcag
1501 caggatgagc agcagcagga tgagcagcag caggatgagc aggagcagca ggatgagcag
1561 cagcaggatg agcagcagca ggatgagcag cagcagcagg atgaacagga gcagcaggag
1621 gagcaggagc agcaggagga gcaggagcag caggaggagc aggagcagga gttagaggag
1681 caggagcagg agttagagga gcaggagcag gagttagagg agcaggagca ggagttagag
1741 gagcaggagc aggagttaga ggagcaggag caggagttag aggagcagga gcaggagtta
1801 gaggagcagg agcaggagtt agaggagcag gagcaggagt tagaggagca ggagcaggag
1861 ttagaggagc aggagcagga gttagaggag caggagcagg agttagagga gcaggagcag
1921 gagttagagg agcaggagca ggagttagag gagcaggagc aggagttaga ggagcaggag
1981 caggagttag aggagcagga gcaggagtta gaggagcagg agcaggagtt agaggagcag
2041 gagcaggagt tagaggagca ggagcaggag ttagaggagc aggagcagga gcaggagtta
2101 gaggaggtgg aagagcaaga gcaggagcag gaagagcagg aattagagga ggtggaggag
2161 caagagcagg agcaggagga gcaggaggag caggagttag aggaggtgga agagcaggaa
2221 gagcaggagt tagaggaggt ggaagagcag gaagagcagg agttagagga ggtggaagag
2281 caggagcagc agggggtgga acagcaggag caggagacgg tggaagagcc cataatcttg
2341 cacgggtcgt catccgagga cgaaatggaa gtggattacc ctgttgttag cacacatgaa
2401 caaattgcca gtagcccacc aggagataat acaccagacg atgacccaca acctggccca
2461 tctcgcgaat accgctatgt actcagaaca tcaccacccc acagacctgg agttcgtatg
2521 aggcgcgttc cagttaccca cccaaaaaag ccacatccaa gataccaaca accaccggtc
2581 ccttacagac agatagatga ttgtcctgcg aaagctaggc cacaacacat cttttataga
2641 cgctttttgg gaaaggatgg aagacgagat ccaaagtgtc aatggaagtt tgcagtgatt
2701 ttttggggca atgacccata cggacttaaa aaattatctc aggccttcca gtttggagga
2761 gtaaaggcag gccccgtgtc ctgcttgccc caccctggac cagaccagtc gcccataact
2821 tattgtgtat atgtgtattg tcagaacaaa gacacaagta agaaagtaca aatggcccgc
2881 ctagcctggg aagctagtca ccccctggca ggaaacctac aatcttccat agttaagttt
2941 aaaaagcccc tgccattaac ccagccaggg gaaaaccaag gtcctgggga ctctccacag
3001 gaaatgacat aa Kaposi's sarcoma-associated herpesvirus v-cyclin gene, complete cds.

ACCESSION U79416

VERSION U79416.1 GI:1711134

1 atggcaactg ccaataaccc gccctcggga cttctggatc ccacgctatg tgaggatcgg
61 atcttttaca atattcttga aattgagccg cgctttttaa cttctgactc tgtatttggg
121 tcctttcaac aatctcttac ttcgcatatg cgtaagttac tgggcacatg gatgttttca

Fig. 3 (cont.)

181 gtttgccagg aatacaacct agaacctaac gtggtcgcgt tggcccttaa tcttttggac
241 agactcctac ttataaagca ggtgtccaaa gaacactttc aaaagacagg gagcgcctgc
301 ctgttagtgg ccagtaagct cagaagcctc acgcctattt ctaccagttc actttgctat
361 gccgcggcag actccttttc ccgccaagaa cttatagacc aggagaaaga actccttgag
421 aagttggcgt ggcgaacaga ggcagtctta gcgacggacg taacttcctt cttgttactt
481 aaattgctgg ggggctccca acacctggac ttttggcacc acgaggtcga caccctgatt
541 acaaaagcct tagttgaccc aaagactggc tcattgcccg cctctattat cagcgctgca
601 ggctgtgcgc tgttggttcc tgccaacgtc attccgcagg atacccactc gggtggggta
661 gttcctcagc tggcaagcat attgggatgc gatgtttccg ttctacaggc ggcagtggaa
721 cagatcctaa catctgtttc ggactttgat ctgcgcattc tggacagcta ttaa

Fig. 3 (cont.)

Epstein-Barr virus nuclear antigen (EBNA1) mRNA, 5' end.

ACCESSION M13941

VERSION M13941.1 GI:330399

1 ttagagagtg gctgctacgc attagagacc actttgagcc acccacagta accacccagc
61 gccaatctgt ctacatagaa gaagaagagg atgaagacta agtcacaggc ttagccagta
121 acccagcact ggcgtgtgac gtggtgtaaa gttttgcctg aacctgtggt tgggcaggta
181 acttaggaag cgtttcttga gcttccctgg gatgagcgtt tgggagagct gattctgcag
241 cccagagagt agtctcaggg catcctctgg agcctgacct gtgatcgtcg catcatagac
301 cgccagtaga cctgggagca gattcaccgc cgcggccgtc tcctttaagt gtgaatcatg
361 tctgacgagg ggccaggtac aggacctgga aatggcctag gagagaaggg agacacatct
421 ggaccagaag gctccggcgg cagtggacct caaagaagag ggggtgataa ccatggacga
481 ggacggggaa gaggacgagg acgaggaggc ggaagaccag gagccccggg cggctcagga
541 tcagggccaa gacatag Epstein-Barr Virus LMP1 gene.

ACCESSION X66863 S48740

VERSION X66863.1 GI:59181

1 aatccgccac ctcattctga aattcccata tcccccgtct gctgcttcgt cacccgccga
61 cccttagccc tctatccgcc tcacccgcct cccctacggt taccccacag ccttgcctca
121 cctgaacccc cctaaagcac agcctcccgc ctgccgacaa cgacctccca acgttgcgcg
181 ccctacgcct ctttgtgtgg attacactgc cgcttcccac aacactgctc actccccctt
241 gtgattgccg cactgccttt ccatttccct gtacgcttta ccaccgcatt cccacagctt
301 gcccctcggg gactcgcttt tctaacacaa acacacgctt tctacttcct cttttaacgc
361 ttacatgcac acacactacg cgctttcggg aaagcggcgc ccgtaccctg tccggcagac
421 cccgcaaatc cccccgggcc tccatcccca gaaacacgcg ttactctctc gtaggcggcc
481 tacataagcc tctgtcactg ctctgtcagc ttctttcctc agttgccttg ctcctgccac
541 actaccctga ccatggaacg cgaccttgag aggggcccac cgggcccgcc acggccccct
601 ctaggacccc ccctctcctc ttccataggc cttgctctcc ttctcctgct cttggcgcta
661 ctgttctggc tgtatatcgt tatgagtaac tggactggag gagcgctcct tgtcctctat
721 tcctttgctc tcatgcttat tattatcatt ctcatcatct ttatcaacag aagagacctt
781 ctctgtccac ttggaggcct tggtctactc ctactgatga gtaagtatta caccctttgc
841 cccccacccc ctttccctta cgcttccttc tctaacgcac tttctcctct ttccccagtc
901 accctcctac tcatcgctct ctggaatttg cacggacagg cattgtacct tggaattgtg
961 ctgttcatct ttggctgctt acttggtaag atctaacatt ccctaggact tatttaccac
1021 accctcacct ttccagccct aacactcttt tttcaacgca gtcttaggtc tctggatcta
1081 cttggagatt ctctggcggc ttggtgccac catctggcag cttttggcct tcatcctagc
1141 cttcttccta gccatcatcc tgcttattat tgctctctat ctacaacaaa actggtggac
1201 tctattggtt gatctccttt ggctcctcct gtttatggcc attttaatct ggatgtatta
1261 tcatggacca cgacacactg atgaacacca ccacgatgac tccctcccgc accctcaaca

Fig. 3 (cont.)

1321 agctaccgtc gattctagcc atgaatctga ctctaactcc aacgagggca gacaccacct
1381 gctcgtgagt ggggccggcg acggaccccc actctgctct caaaacctag gcgcacctgg
1441 aggtggtcct gacaatggcc cacaggaccc tgacaacact gatgacaatg gcccacagga
1501 ccctgacaac actgatgaca atggcccaca ggaccctgac aacactgatg acaatggccc
1561 acaggaccct gacaacactg atgacaatgg cccacaggac cctgacaaca ctgatgacaa
1621 tggcccacat gacccgctgc ctcataaccc tagcgactct gctggaaatg atggaggccc
1681 tccaaaattg acggaagagg ttgaaaacaa aggaggtgac cggggcccgc cttcgatgac
1741 agacggtggc ggcggtcatc cacaccttcc tacactgctt ttgggtactt ctggttccgg
1801 tggagatgat gacgaccccc acggcccagt tcagctaagc tactatgact aacctttctt
1861 tacttctagg cattaccatg tcataggctt gcctgactga ctctccctcc atttactggg
1921 aatgccttag ctaatcacct taactggcac acactccctt agccacactg tctgtctagg
1981 ctgaaaagcc acattcatat tctatttcaa aacaagggga aggaggacat a Epstein-Barr virus latent membrane protein 2A (LMP 2A) mRNA, complete cds.
ACCESSION M87778
VERSION M87778.1 GI:330384

1 ccaatgggcg cgggtccccc tagccccggc ggggatccgg atggggacga tggcggaaac
61 aactcccaat atccatctgc ttctggctct tctgggaaca cccccacccc accgaacgat
121 gaggaacgtg aatctaatga agagccccca ccgccttatg aggacctaga ttggggcaat
181 ggcgaccgtc actcggacta tcaaccacta ggaaaccaag atccaagttt gtacttggga
241 ttgcaacacg acgggaatga cgggctccct ccccctccct actctccacg ggatgactca
301 tctcaacaca tatacgaaga agcgggcaga ggaagtatga atccagtatg c

//

Epstein-Barr virus latent membrane protein 2A (LMP 2A) mRNA, complete cds.
ACCESSION M87777
VERSION M87777.1 GI:330382

1 actatggggt ccctagaagt gatgccaatg ggcgcgggtc cccctagccc cggcggggat
61 ccggatgggg acgatggcgg aaacaactcc caatatccat ctgcttctgg ctcttctggg
121 aacaccccca ccccaccgaa cgatgaggaa cgtgaatcta atgaagagcc cccaccgcct
181 tatgaggact cagattgggg caatggcgac cgtcactcgg actatcaacc actaggaaac
241 caagatccaa gtttgtactt gggattgcaa cacgacggga atgacgggct ccctccccct
301 ccctactctc cacgggatga ctcatctcaa cacatatacg aagaagcggg cagaggaagt
361 atgaatccag tatgcctgct tgtaattgtt gcgccctacc tgttttggct ggcggctatt
421 gccgcctcgt gtttcacggc ctcagttagt accgttgtga ccgccaccgg cttggccctc
481 tcacttttac tcttggcagc agtggccagc tcatatgccg ctgcacaaag gaaactgctg
541 acaccggtga cag

Fig. 3 (cont.)

Epstein-Barr virus (EBV) genome, strain B95-8.

ACCESSION V01555 J02070 K01729 K01730 V01554 X00498 X00499 X00784

VERSION V01555.1 GI:59074

1 agaattcgtc ttgctctatt cacccttact tttcttcttg cccgttctct ttcttagtat
61 gaatccagta tgcctgcctg taattgttgc gccctacctc ttttggctgg cggctattgc
121 cgcctcgtgt ttcacggcct cagttagtac cgttgtgacc gccaccggct tggccctctc
181 acttctactc ttggcagcag tggccagctc atatgccgct gcacaaagga aactgctgac
241 accggtgaca gtgcttactg cggttgtcac ttgtgagtac acacgcacca tttacaatgc
301 atgatgttcg tgagattgat ctgtctctaa cagttcactt cctctgcttt tctcctcagt
361 ctttgcaatt tgcctaacat ggaggattga ggacccacct tttaattctc ttctgtttgc
421 attgctggcc gcagctggcg gactacaagg catttacggt tagtgtgcct ctgttatgaa
481 atgcaggttt gacttcatat gtatgccttg gcatgacgtc aactttactt ttatttcagt
541 tctggtgatg cttgtgctcc tgatactagc gtacagaagg agatggcgcc gtttgactgt
601 ttgtggcggc atcatgtttt tggcatgtgt acttgtcctc atcgtcgacg ctgttttgca
661 gctgagtccc ctccttggag ctgtaactgt ggtttccatg acgctgctgc tactggcttt
721 cgtcctctgg ctctcttcgc caggggggcct aggtactctt ggtgcagccc ttttaacatt
781 ggcagcaggt aagccacacg tgtgacattg cttgcctttt tgccacatgt tttctggaca
841 caggactaac catgccatct ctgattatag ctctggcact gctagcgtca ctgattttgg
901 gcacacttaa cttgactaca atgttccttc tcatgctcct atggacactt ggtaagtttt
961 cccttccttt aactcattac ttgttctttt gtaatcgcag ctctaacttg gcatctcttt
1021 tacagtggtt ctcctgattt gctcttcgtg ctcttcatgt ccactgagca agatccttct
1081 ggcacgactg ttcctatatg ctctcgcact cttgttgcta gcctccgcgc taatcgctgg
1141 tggcagtatt ttgcaaacaa acttcaagag tttaagcagc actgaattta tacccagtga
1201 gtatctattt gttactcctg tttagttgaa gaaaacaagc tattggattg taacacacat
1261 tttacgcttt gttccttaga tttgttctgc atgttattac tgattgtcgc tggcatactc
1321 ttcattcttg ctatcctgac cgaatggggc agtggaaata gaacatacgg tccagttttt
1381 atgtgcctcg gtggcctgct caccatggta gccggcgctg tgtggctgac ggtgatgtct
1441 aacacgcttt tgtctgcctg gattcttaca gcaggattcc tgattttcct cattggtaag
1501 tgtgacacca acaggtgttg ccttgttatg tcaccgttct gacacatgac ttacatgggt
1561 ttggcttttg taggctttgc cctctttggg gtcattagat gctgccgcta ctgctgctac
1621 tactgcctta cactggaaag tgaggagcgc ccaccgaccc catatcgcaa cactgtataa
1681 aggtaagtat tattaaattt tagagacact atcacgtgta acttgacgtg caaggatgga
1741 agagagggggc agggaaacgc aaatgccggt tgcccggtat gggggcccgt ttattatggt
1801 aaggctcttc gggcaagatg gagaggcaaa catacaggag gaaaggctat atgagctact
1861 ctctgaccca cgctccgcgc tcggcctaga cccggggccc ctgattgctg agaacctgct

Fig. 3 (cont.)

1921 gctagtggcg ctgcgtggca ccaacaacga tcccaggcct cagcgtcagg agagggccag
1981 agaactggcc ctcgttggca ttctactagg aaacggcgag cagggtgaac acttgggcac
2041 ggagagtgcc ctggaggcct caggcaacaa ctatgtgtat gcctacggac cagactggat
2101 ggcaaggcct tccacatggt ccgcggaaat ccagcaattc ctgcgactcc tgggcgccac
2161 gtacgtgctt cgcgtggaga tgggcaggca gtttggcttc gaggtgcata gaagccggcc
2221 ctccttccgt cagttccagg ccatcaatca ccttgtcctg tttgacaacg cccttcgcaa
2281 gtacgattcc ggccaggtgg cggcgggctt ccagagggcc cttctggtgg ccgggccaga
2341 gaccgctgac acgaggccgg acctccgcaa gctgaatgag tgggtgtttg gtggcagggc
2401 tgctggtggc agacagctgg ccgacgagct aaagatcgtg tccgcgctgc gagacactta
2461 ctcgggccac ttggtccttc agcccacgga gaccettgac acatggaagg tgttgagcag
2521 ggacacacga accgctcata gtttggagca cggattcatt catgccgcgg ggaccatcca
2581 ggccaactgc ccacagctgt ttatgagacg ccagcacccc ggcctctttc ccttcgttaa
2641 tgcaatagca tcatcgctgg gctggtacta ccagaccgcc accggccccg gagcagatgc
2701 cagggcggcg gcccggcgcc aacaggcctt tcagaccagg gcggcggctg aatgccatgc
2761 caaaagcggg gtgccggtcg tggccggctt ctacaggacc atcaacgcca cgctcaaggg
2821 aggagagggc ctacagccca ctatgtttaa cggggagctg ggggccatca agcaccaggc
2881 acttgacact gtgaggtatg actacggcca ctatctcata atgttggggc cattccagcc
2941 atggagcgga ctgacggccc ctccgtgccc ctacgccgaa agttcatggg cacaggcggc
3001 cgtgcagacg gccctcgagc tgttctcggc cctgtacccg gccccgtgca tctcgggcta
3061 cgcgcgcccc ccgggcccca gtgctgtgat cgagcatctg ggtccctag ttccaaaggg
3121 gggtctgctg ttgtttctgt ctcacctacc ggatgatgtt aaggacgggc tcggagaaat
3181 ggggccggcc agggccacgg gacctggaat gcagcagttt gtcagcagct acttcctcaa
3241 ccccgcctgt tccaacgtct tcattacagt gaggcagcga ggggagaaga tcaacggccg
3301 taccgtcctc caagcgctcg gacgcgcatg cgatatggca ggctgccagc actatgtgct
3361 gggctccacg gttcccctcg gtggactcaa ctttgtcaac gacctggcgt ccccggtttc
3421 caccgccgag atgatggatg atttctctcc cttcttcacc gtggagtttc cccgattca
3481 agaggagggc gcaagttctc cggtaccctt agatgtggac gagagcatgg acatctctcc
3541 gtcttacgag ttgccctggc tctcgctgga gtcatgcctc acaagcatcc tgtcacaccc
3601 caccgtggga agcaaggagc acttggtcag gcacacggac agggtcagcg gaggacgcgt
3661 ggcacagcag cccggggtag gtcccctgga cctgccgctg gcggactacg ccttcgttgc
3721 ccacagtcag gtctggacca ggcccggtgg ggctcctccc ttgccctatc gtacctggga
3781 tcgaatgaca gagaagctgc ttgtctccgc aaaacccggc ggagagaacg ttaaggtttc
3841 aggtaccgtg attacattgg gagaacaggg gtacaaagtg tcgttggatc tgagggaggg
3901 aaccaggctg gcaatggctg aggcgctgct gaacgcagca tgtgccccaa tcttggatcc
3961 ggaagacgtc ttgctcaccc tgcatctaca cctggatccg cgccgggcag acaactcggc
4021 cgtgatggag gctatgacgg cggcgagtga ctacgcgcgt ggcctgggcg tgaagctgac
4081 ctttggctcg gcctcctgcc ccgagaccgg ctcgtccgcc tccaacttca tgaccgtggt
4141 ggcctctgtc tccgccccag gggaattctc gggtcctctg atcacgccag tgcttcagaa
4201 gacgggcagt ctcctgattg cggtgcgttg cggggatggc aagatccagg gagggtcgct

Fig. 3 (cont.)

4261 gtttgagcag ctctttagcg acgtggccac gaccccacgg gcacccgagg cgttgtctct
4321 gaagaatctc ttccgggcag tccagcagct ggtcaagagc ggcatcgtgc tgtcagggca
4381 tgacatcagc gacgggggcc tggtgacctg cctggtggag atggccctgg ccgggcagcg
4441 gggagtgacc atcactatgc cggtggcctc cgactacctc ccggagatgt ttgcagagca
4501 ccccggcctg gtgtttgagg tggaggagcg cagcgtgggt gaggtgctgc agaccctgcg
4561 ctccatgaac atgtacccgg cagtcctcgg tcgagtgggc gagcaaggtc cagatcaaat
4621 gtttgaggtg cagcacggcc cagagacggt gttgcgccag tcgctgcgcc tgctgctggg
4681 aacctggtca tcctttgcca gcgagcagta cgagtgcctg cgaccagatc ggattaaccg
4741 gtccatgcac gtgtccgact acggctataa cgaagcactg gcagtctccc cgttgacagg
4801 aaagaatctc agcccacgcc ggttggtgac agagcctgac ccacgatgtc aggtggccgt
4861 gctatgcgcc ccgggcacca ggggccatga aagcctcctg gcggccttca cgaatgccgg
4921 atgcctgtgc cgacgggtgt tctttcgcga ggttagggac aacacgttcc tcgacaagta
4981 cgtgggtctg gccatcggag gagttcatgg ggccagggac tctgccctgg caggccgtgc
5041 caccgtggcg ctgattaatc gtttccccgc cctgcgtgac gctattctaa agttcctcaa
5101 caggccagat acgttctcgg tggccttggg ggagctgggg gtgcaagttt tggctggcct
5161 gggggccgtg ggtcaacag ataatccacc cgcccctggc gtggaagtta atgtccagag
5221 atcacctctg attctggccc ccaacgcctc tggcatgttt gagtcccgct ggctgaacat
5281 tagcatcccg gcgaccacca gctctgtcat gctgcgtggc ctccggggct gcgtcctgcc
5341 ttgttgggtg caaggctcgt gcctgggcct gcaatttact aacctcggga tgccatatgt
5401 tttgcagaat gcccaccaga tcgcctgcca cttccacagc aatggcacgg atgcctggcg
5461 ctttgctatg aattatccaa gaaaccccac ggagcagggc aacattgcag ggctctgttc
5521 acgcgatggt cgtcatctgg ctctcctgtg tgacccctca ctttgtacag acttttggca
5581 atgggagcac attccccccg cctttgggca ccccacgggg tgctcccccct ggacacttat
5641 gtttcaagca gctcacctat ggtcactcag gcacggtcgc ccctccgagt gaccagtcac
5701 cttccagact atgcatacac tgaatttagc ctgatattgt ccccctagcc ccgggcccag
5761 ccctcctcag aaaactctgc atggagaagc tggacgtgaa cctccccccc agacctgtgt
5821 gctgtattta caaacactac aataaaccca atgtgcaaat gtggtttgta tggctacttt
5881 gtgttcctaa aaaatgcaac aatagaagtg gaaaccctca gtcacgggac attaacctca
5941 accacaaaat gggggttgga gaaagtaacc acatatactg gagatgattc atgggctggg
6001 ggttcccgga caatacaccc atctggagtt caacctaatt acatggtaga taaattaaga
6061 gtccctcctc accactcgaa actatggcag acattctata agataacgag gagagatgag
6121 gtgagggcag aggacattgg gcaggtgtgg gccacggggc agctggccat atcccccgca
6181 ctacagaagt gtaagcaaag tgaagggctc ggaaggcagg cggggcctag caatgtcaca
6241 gctaaatgcc caccagggca cacactcaag cggggtctcg gagctcctag gtcagaccac
6301 gaaaggtcag cctgcaaggt ggatggcgtg ttttctgagg ttatccccgc tacgtgcagt
6361 gctgggtgat agagacccta gaatgtgtcg aaatgaccaa gcgtccccgc agcggggctc
6421 ccaacacggg ttcccagaga gggtaaaaga gggggccata aagcccaggg tgtaaaacac
6481 cgaccgcgcc accagatggc acacgtgggg gaaatgaggg ttagcatagg caaccccgc
6541 ctacacacca actatagcaa accccgcccc gtcacggtga cgtagtctgt cttgaggaga

Fig. 3 (cont.)

6601 tgtagacttg tagacactgc aaaacctcag gacctacgct gccctagagg ttttgctagg
6661 gaggagacgt gtgtggctgt agccacccgt cccgggtaca agtcccgggt ggtgaggacg
6721 gtgtctgtgg ttgtcttccc agactctgct ttctgccgtc ttcggtcaag taccagctgg
6781 tggtccgcat gttttgatcc aaacttttgt tttaggattt atgcatccat tatcccgcag
6841 ttccacctaa acggggctta acgttgcatc ccagaagatg cacgcttaac cccgcctaca
6901 accgtgacgt agctgtttac cagcatgtat agagttacgg ttcgctacat caaacaggac
6961 agccgttgcc ctagtggttt cggacacacc gccaacgctc agtgcggtgc taccgacccg
7021 aggtcaagtc ccggggggagg agaagagagg cttcccgcct agagcatttg caagtcagga
7081 ttctctaatc cctctgggag aagggtattc ggcttgtccg ctattttttt gtggctagtt
7141 ttgcacccac aacatgtaag ggcccgctac ccctacaaca caaaacaaac tatctcccct
7201 aaccatcctt ttgccaatca attctgtgac agggtttcct ggacacccag tcttagttca
7261 ggtagacacc cagttatgca gtgccaccaa ttccaaccat ttttaaacct cctggaattc
7321 tatcattaaa cggcatgcag gaaaaggaca agcagcgaaa attcacgccc ccttgggagg
7381 tggcggcata tgcaaaggat agcactccca ctctactact gggtatcata tgctgactgt
7441 atatgcatga ggatagcata tgctacccgg atacagatta ggatagcata tactacccag
7501 atatagatta ggatagcata tgctacccag atatagatta ggatagccta tgctacccag
7561 atataaatta ggatagcata tactacccag atatagatta ggatagcata tgctacccag
7621 atatagatta ggatagccta tgctacccag atatagatta ggatagcata tgctacccag
7681 atatagatta ggatagcata tgctatccag atatttgggt agtatatgct acccagatat
7741 aaattaggat agcatatact accctaatct ctattaggat agcatatgct acccggatac
7801 agattaggat agcatatact acccagatat agattaggat agcatatgct acccagatat
7861 agattaggat agcctatgct acccagatat aaattaggat agcatatact acccagatat
7921 agattaggat agcatatgct acccagatat agattaggat agcctatgct acccagatat
7981 agattaggat agcatatgct atccagatat ttgggtagta tatgctaccc atggcaacat
8041 tagcccaccg tgctctcagc gacctcgtga atatgaggac caacaaccct gtgcttggcg
8101 ctcaggcgca agtgtgtgta atttgtcctc cagatcgcag caatcgcgcc cctatcttgg
8161 cccgcccacc tacttatgca ggtattcccc ggggtgccat tagtggtttt gtgggcaagt
8221 ggtttgaccg cagtggttag cggggttaca atcagccaag ttattacacc cttattttac
8281 agtccaaaac cgcagggcgg cgtgtggggg ctgacgcgtg cccccactcc acaatttcaa
8341 aaaaaagagt ggccacttgt ctttgtttat gggccccatt ggcgtggagc cccgtttaat
8401 tttcgggggt gttagagaca accagtggag tccgctgctg tcggcgtcca ctctctttcc
8461 ccttgttaca aatagagtgt aacaacatgg ttcacctgtc ttggtccctg cctgggacac
8521 atcttaataa ccccagtatc atattgcact aggattatgt gttgcccata gccataaatt
8581 cgtgtgagat ggacatccag tctttacggc ttgtccccac cccatggatt tctattgtta
8641 aagatattca gaatgtttca ttcctacact agtatttatt gcccaagggg tttgtgaggg
8701 ttatattggt gtcatagcac aatgccacca ctgaaccccc cgtccaaatt ttattctggg
8761 ggcgtcacct gaaaccttgt tttcgagcac ctcacataca ccttactgtt cacaactcag
8821 cagttattct attagctaaa cgaaggagaa tgaagaagca ggcgaagatt caggagagtt
8881 cactgcccgc tccttgatct tcagccactg cccttgtgac taaaatggtt cactaccctc

Fig. 3 (cont.)

8941 gtggaatcct gaccccatgt aaataaaacc gtgacagctc atggggtggg agatatcgct
9001 gttccttagg accctttac taaccctaat tcgatagcat atgcttcccg ttgggtaaca
9061 tatgctattg aattagggtt agtctggata gtatatacta ctacccggga agcatatgct
9121 acccgtttag ggttaacaag gggccttat aaacactatt gctaatgccc tcttgagggt
9181 ccgcttatcg gtagctacac aggcccctct gattgacgtt ggtgtagcct cccgtagtct
9241 tcctgggccc ctgggaggta catgtccccc agcattggtg taagagcttc agccaagagt
9301 tacacataaa ggcaatgttg tgttgcagtc cacagactgc aaagtctgct ccaggatgaa
9361 agccactcag tgttggcaaa tgtgcacatc catttataag gatgtcaact acagtcagag
9421 aacccctttg tgtttggtcc cccccgtgt cacatgtgga acagggccca gttggcaagt
9481 tgtaccaacc aactgaaggg attacatgca ctgccccgcg ggaaatacgt cctacccagg
9541 aacccgaaac agtgtttccc agaagctgta aaaatagaac gccctggaac tgccccactg
9601 tgcaatgcag cttttagcca tgccatgctc tataaatcac ttccctatct caggtaggcc
9661 tgcacacctt aggtatggag cgaaggttag tggtcactct gcagtgcctg gtgctgcttt
9721 acctggcacc tgagtgtgga ggtacagacc aatgtgacaa ttttccccaa atgttgaggg
9781 acctaagaga tgccttcagt cgtgttaaaa ccttttcca gacaaaggac gaggtagata
9841 accttttgct caaggagtct ctgctagagg actttaaggg ctaccttgga tgccaggccc
9901 tgtcagaaat gatccaattc tacctggagg aagtcatgcc acaggctgaa aaccaggacc
9961 ctgaagccaa agaccatgtc aattctttgg gtgaaaatct aaagacccta cggctccgcc
10021 tgcgcaggtg ccacaggttc ctgccgtgtg agaacaagag taaagctgtg gaacagataa
10081 aaaatgcctt taacaagctg caggaaaaag gaatttacaa agccatgagt gaatttgaca
10141 tttttattaa ctacatagaa gcatacatga caattaaagc caggtgataa ttccataccc
10201 tggaagcagg agatgggtgc atttcacccc aaccccccct ttcgactgtc atttacaata
10261 aaatgaaacc ttttattctt gattgcctct tgtgttcttg ccgcccaggt accttcctgt
10321 gttctcccca cgggaaaaag aatagcttct gcagaaggcc attgacgcaa gttttgcccg
10381 tggggattac ccgacccagc cacttacagc acattttgtt ctaggtccat cttaggagcc
10441 cgggccagca ttctatcagc ttaacgggaa gagaagtggg gagggcactc gcccactaac
10501 cttaacacct gcagcctaca aaagtacact agctgtttgc tctattcgcc actagagacc
10561 gccaagatgc gaaactacag gcccgggccc aggccttgca gggcagacgg ttaggctgac
10621 aaggggacaa gtgtggcagg tgggcgggaa ggggcacaag aatgccggcg aaactggacc
10681 acggtccacc ccgccctcaa gcgtccggga gccgggcggc tcggctaagg agggcggcct
10741 tgcgaacaat tattagtagc taccaacaag ggcccccaga tgccccccac cagtcacccg
10801 gccgtgtcca ctcacatatt ccactcttat ttttaaatta atgtgtccca attagaaacc
10861 caagcgcaga aattagttga gaggctagtg ttttaaacat gcaccctagg ccagccagag
10921 ataatgtcac aagattatca agttggtgta aacacgccgt gggaaaaaat ttatggttca
10981 gtgcgtcgag tgctatcttt ggaacagtag aaaattgaac cttgttggcg ggagaaggaa
11041 taacgcctta tctgggagga gcgacggatt atagccaata agagagctca agacgcaggg
11101 ctcgcaaagt atagtggccc cgtgggacct tagaggtgga gcaacgtcta aagtggtaat
11161 aacaccaggc ggggctgggc aaaggggtcc tacgggcggg attaattacg ccttgcttac
11221 gcaagctcag ttaattcgcc cacgacttga aaaatgtagc ccttaaccaa ttggcggccc

Fig. 3 (cont.)

11281 ctaaggggggg gactaaggtc ccactacaaa aactctgtgt tctgctgcaa attttagatc
11341 agatggcata gagacaagga caccgaagac ccccagagcc ctcatcgcag ggttcttacc
11401 atgcggccat gtaggcccac ttaacactac aagacctacg cctctccatt catcatgtaa
11461 cccacaaatc atctaaaccg taagtctaag ggcctcctga ggttttctca ggaggcccta
11521 atgtataatt aatcatgcat ttgattttaa aaaagtaggt tacactcatt ttaggccaga
11581 ctttatttgc agattaataa tttatgtgat tctccttccc tctaggactg aagaaacagc
11641 ctcctgcacg tgagcatgta tctgaaataa ttattatgtc ataagtgtaa tgattagaaa
11701 gtcataaacc cacttccctt tacatgaatc tgggcactga attttggggt acttctaaag
11761 actaacgtgt tcgatttcgg ggtcacttcc ccttttataa gtgtgtgaac agtgatttca
11821 gtaaaaccta agagatattt ggtgtcactt ccgcatttta agtttcagaa aattttaaaa
11881 ttaaaattga aatttctctc aaaataattc caatgaaaac ttcaaagaat cttatgtatg
11941 taattctttt gccccaaact gggcttcaga tgccttctat tgcactctca caaaaacatt
12001 ctggacacat gtgccagacg cctgggcctc taaggccctc gggtccccct ggaccccggc
12061 ctcagcaacc ctgctgctcc cctcctgcca ccccagcctc ccccctcccc cgtccccctt
12121 cgctcctgtt cctcccccgg tccccagtag ggccgcctgc cccctgcac ccagtacctg
12181 cccctcttgg ccacgcaccc cgggccaggc caccttagac ccggccaagc cccatccctg
12241 aagacccagc ggccattctc tctggtaacg agcagagaag aagtagaggc ccgcggccat
12301 tgggcccaga ttgagagacc agtccagggg cccgaggttg gagccagcgg gcacccgagg
12361 tcccagcacc cggtccctcc ggggggcaga gacaggcagg gccccccggc agctggcccc
12421 gaggaggcgc ccggagtggg gccggtcggc tggctggcc gagcccgggt ctgggaggtc
12481 tggggtggcg agcctgctgt ctcaggaggg gcctggctcc gccgggtggc cctggggtaa
12541 gtctgggagg cagagggtcg gcctaggccc ggggaagtgg agggggatcg cccgggtctc
12601 tgttggcaga gtccgggcga tcctctgaga ccctccgggc ccggacggtc gccctcagcc
12661 ccccagacag accccagggt ctccaggcag ggtccggcat cttcaggggc agcaggctca
12721 ccaccacagg ccccccagac ccgggtctcg gccagccgag ccgaccggcc ccgcgcctgg
12781 cgcctcctcg gggccagccg ccggggttgg ttctgcccct ctctctgtcc ttcagaggaa
12841 ccagggacct cgggcacccc agagcccctc gggcccgcct ccaggcgccc tcctggtctc
12901 cgctcccctc tgagccccgt taaacccaaa gaatgtctga ggggagccac cctcggggcc
12961 caggccccag agtccagagg tcaggggcac ctcagggtgc ctccccgggt cccaggccag
13021 ccggagggac cccggcagcc cggcggcccc cagaggccgg ttcctcgccc cttccccggg
13081 cttcagagcc caggatgtcc cccagaaggg accctaggcg tcccctctcc tcccctccag
13141 gcccgagcct ctccctcgcg gagaggggcc tctttgggcc ctcaagtcca gccccaccga
13201 gacccgagtg gcccggatcc ccccaccggc ccttctctct gtccccctgc tcctctccaa
13261 ccttcgctcc accctagacc ccagcttctg gcctccccgg gtccaccagg ccagccggag
13321 ggaccccggc agcccgggcg agtcgccttc cctctcccct ggcctctcct tcccgcctcc
13381 cacccgagcc ccctcagctt gcctccccac cgggtccatc aggccggccg gagggacccc
13441 ggcggcccgg tgtcagtccc ccctgcagcc gcccagtctc tgcctccagg caagggcgcc
13501 agcttttctc cccccagcct gaggcccagt ctcctgtgca ctgtctgtaa agtccagcct
13561 cccacgcccg tccacggctc ccgggcccag cctcgtccac ccctccccac ggtggacagg

Fig. 3 (cont.)

13621 ccctctgtcc acccgggcca tccccgcccc cctgtgtcca ccccagtccc gtccaggggg
13681 gactttatgt gacccttggg cctggctccc catagactcc catgtaagcc tgcctcgagt
13741 aggtgcctcc agagcccctt ttgcccccct ggcggcccag cccgaccccc gggcgccccc
13801 aaactttgtc cagatgtcca ggggtccccg agggtgaggc ccagccccct cccgccccctg
13861 tccactgccc cggtcccccc agaagccccc aaaagtagag gctcaggcca tgcgcgccct
13921 gtcaccaggc ctgccaaaga gccagatcta aggccgggag aggcagcccc aaagcgggtg
13981 cagtaacagg taatctctgg tagtgatttg gacccgaaat ctgacacttt agagctctgg
14041 aggactttaa aactctaaaa atcaaaactt tagaggcgaa tgggcgccat tttgtcccca
14101 cgcgcgcata atggcggacc taggcctaaa acccccagga agcgggtcta tggttggctg
14161 cgctgctgct atctttagag gggaaaagag gaataagccc ccagacaggg gagtgggctt
14221 gtttgtgact tcaccaaagg tcagggccca agggggttcg cgttgctagg ccaccttctc
14281 agtccagcgc gtttacgtaa gccagacagc agccaattgt cagttctagg gaggggggacc
14341 actgcccctg gtataaagtg gtcctgcagc tatttctggt cgcatcagag cgccaggagt
14401 ccacacaaat gtaagagggg gtcttctacc tctccctagc cctccgcccc ctccaaggac
14461 tcgggcccag tttctaactt ttccccttcc ctccctcgtc ttgccctgcg cccggggcca
14521 ccttcatcac cgtcgctgac tccgccatcc aagcctaggg gagaccgaag tgaaggccct
14581 ggaccaaccc ggcccgggcc ccccggtatc gggccagagg taagtggact ttaatttttt
14641 ctgctaagcc caacactcca ccacacccag gcacacacta cacacaccca cccgtctcag
14701 ggtcccctcg gacagctcct aagaaggcac cggtcgccca gtcctaccag agggggccaa
14761 gaacccagac gagtccgtag aagggtcctc gtccagcaag aagaggaggt ggtaagcggt
14821 tcaccttcag gggtaagtaa cctgacctct ccagggctca cataaaggga ggcttagtat
14881 acatgcttct tgcttttcac aggaacctgg gggctagtct gggtgggatt aggctgcctc
14941 aagttgcatc agccagggct tcatgccctc ctcagttccc tagtccccgg gcttcaggcc
15001 ccctccgtcc ccgtcctcca gagacccggg cttcaggccc tgcctctcct gttacccttt
15061 tagaaccaca gcctggacac atgtgccaga cgccttggcc tctaaggccc tcgggtcccc
15121 ctggaccccg gcctcagcaa ccctgctgct cccctcctgc caccccagcc tcccccccctc
15181 cccgtccccc ttcgctcctg atcctccccc ggtccccagt agggccgcct gccccccctgc
15241 acccagtacc tgcccctctt ggccacgcac cccgggccag gccaccttag acccggccaa
15301 gccccatccc tgaagaccca gcggccattc tctctggtaa cgagcagaga agaagtagag
15361 gcccgcggcc attgggccca gattgagaga ccagtccagg ggcccgaggt tggagccagc
15421 gggcacccga ggtcccagca cccggtccct ccggggggca gagacaggca gggcccccccg
15481 gcagctggcc ccgaggaggc gcccggagtg gggccggtcg gctgggctgg ccgagcccgg
15541 gtctgggagg tctggggtgg cgagcctgct gtctcaggag gggcctggct ccgccgggtg
15601 gccctggggt aagtctggga ggcagagggt cggcctaggc ccggggaagt ggagggggat
15661 cgcccgggtc tctgttggca gagtccgggc gatcctctga gaccctccgg gcccggacgg
15721 tcgccctcag ccccccagac agaccccagg gtctccaggc agggtccggc atcttcaggg
15781 gcagcaggct caccaccaca ggcccccccag acccgggtct cggccagccg agccgaccgg
15841 ccccgcgcct ggcgcctcct cggggccagc cgccggggtt ggttctgccc ctctctctgt
15901 ccttcagagg aaccagggac ctcgggcacc ccagagcccc tcgggcccgc ctccaggcgc

Fig. 3 (cont.)

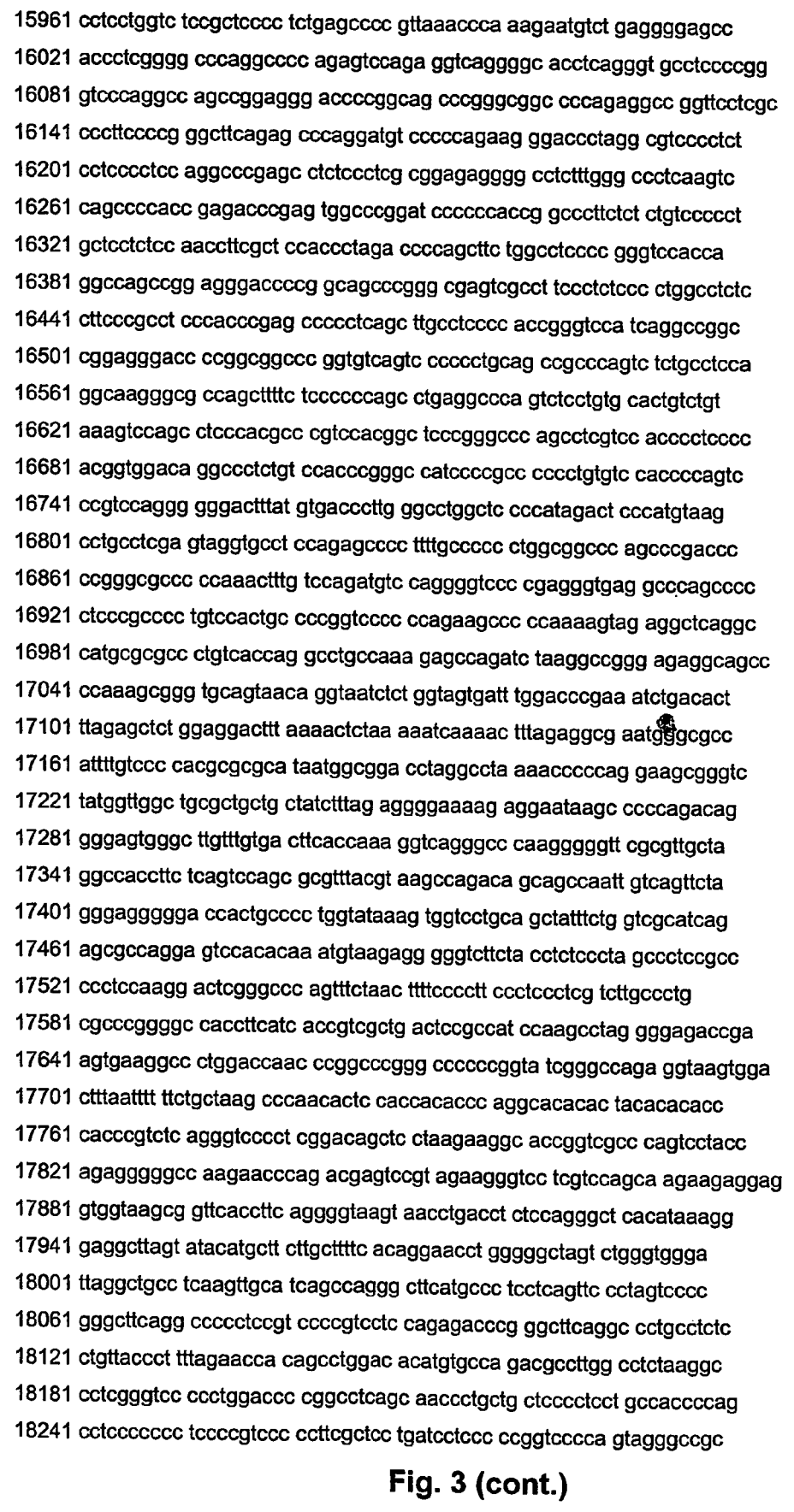

15961 cctcctggtc tccgctcccc tctgagcccc gttaaaccca aagaatgtct gaggggagcc
16021 accctcgggg cccaggcccc agagtccaga ggtcaggggc acctcagggt gcctccccgg
16081 gtcccaggcc agccggaggg accccggcag cccgggcggc cccagaggcc ggttcctcgc
16141 cccttccccg ggcttcagag cccaggatgt cccccagaag ggaccctagg cgtcccctct
16201 cctcccctcc aggcccgagc ctctccctcg cggagagggg cctctttggg ccctcaagtc
16261 cagccccacc gagacccgag tggcccggat ccccccaccg gcccttctct ctgtcccccct
16321 gctcctctcc aaccttcgct ccaccctaga ccccagcttc tggcctcccc gggtccacca
16381 ggccagccgg agggaccccg gcagcccggg cgagtcgcct tccctctccc ctggcctctc
16441 cttcccgcct cccacccgag ccccctcagc ttgcctcccc accgggtcca tcaggccggc
16501 cggagggacc ccggcggccc ggtgtcagtc ccccctgcag ccgcccagtc tctgcctcca
16561 ggcaagggcg ccagcttttc tccccccagc ctgaggccca gtctcctgtg cactgtctgt
16621 aaagtccagc ctcccacgcc cgtccacggc tcccgggccc agcctcgtcc acccctcccc
16681 acggtggaca ggccctctgt ccacccgggc catccccgcc cccctgtgtc caccccagtc
16741 ccgtccaggg gggactttat gtgacccttg ggcctggctc cccatagact cccatgtaag
16801 cctgcctcga gtaggtgcct ccagagcccc ttttgccccc ctggcggccc agcccgaccc
16861 ccgggcgccc ccaaactttg tccagatgtc caggggtccc cgagggtgag gcccagcccc
16921 ctcccgcccc tgtccactgc cccggtcccc ccagaagccc ccaaaagtag aggctcaggc
16981 catgcgcgcc ctgtcaccag gcctgccaaa gagccagatc taaggccggg agaggcagcc
17041 ccaaagcggg tgcagtaaca ggtaatctct ggtagtgatt tggacccgaa atctgacact
17101 ttagagctct ggaggacttt aaaactctaa aaatcaaaac tttagaggcg aatgggcgcc
17161 attttgtccc cacgcgcgca taatggcgga cctaggccta aaacccccag gaagcgggtc
17221 tatggttggc tgcgctgctg ctatctttag aggggaaaag aggaataagc cccccagacag
17281 gggagtgggc ttgtttgtga cttcaccaaa ggtcagggcc caagggggtt cgcgttgcta
17341 ggccaccttc tcagtccagc gcgtttacgt aagccagaca gcagccaatt gtcagttcta
17401 gggaggggga ccactgcccc tggtataaag tggtcctgca gctatttctg gtcgcatcag
17461 agcgccagga gtccacacaa atgtaagagg gggtcttcta cctctcccta gccctccgcc
17521 ccctccaagg actcgggccc agtttctaac ttttcccctt ccctccctcg tcttgccctg
17581 cgcccggggc caccttcatc accgtcgctg actccgccat ccaagcctag gggagaccga
17641 agtgaaggcc ctggaccaac ccggcccggg cccccccggta tcgggccaga ggtaagtgga
17701 ctttaatttt ttctgctaag cccaacactc caccacaccc aggcacacac tacacacacc
17761 cacccgtctc agggtcccct cggacagctc ctaagaaggc accggtcgcc cagtcctacc
17821 agaggggggcc aagaacccag acgagtccgt agaagggtcc tcgtccagca agaagaggag
17881 gtggtaagcg gttcaccttc aggggtaagt aacctgacct ctccagggct cacataaagg
17941 gaggcttagt atacatgctt cttgcttttc acaggaacct gggggctagt ctgggtggga
18001 ttaggctgcc tcaagttgca tcagccaggg cttcatgccc tcctcagttc cctagtcccc
18061 gggcttcagg ccccctccgt ccccgtcctc cagagacccg ggcttcaggc cctgcctctc
18121 ctgttaccct tttagaacca cagcctggac acatgtgcca gacgccttgg cctctaaggc
18181 cctcgggtcc ccctggaccc cggcctcagc aaccctgctg ctcccctcct gccaccccag
18241 cctccccccc tccccgtccc ccttcgctcc tgatcctccc ccggtcccca gtagggccgc

Fig. 3 (cont.)

18301 ctgccccct gcacccagta cctgcccctc ttggccacgc accccgggcc aggccacctt
18361 agacccggcc aagccccatc cctgaagacc cagcggccat tctctctggt aacgagcaga
18421 gaagaagtag aggcccgcgg ccattgggcc cagattgaga gaccagtcca ggggcccgag
18481 gttggagcca gcgggcaccc gaggtcccag cacccggtcc ctccgggggg cagagacagg
18541 cagggccccc cggcagctgg ccccgaggag gcgcccggag tggggccggt cggctgggct
18601 ggccgagccc gggtctggga ggtctggggt ggcgagcctg ctgtctcagg aggggcctgg
18661 ctccgccggg tggccctggg gtaagtctgg gaggcagagg gtcggcctag gcccggggaa
18721 gtggaggggg atcgcccggg tctctgttgg cagagtccgg gcgatcctct gagaccctcc
18781 gggcccggac ggtcgccctc agccccccag acagacccca gggtctccag gcagggtccg
18841 gcatcttcag gggcagcagg ctcaccacca caggcccccc agacccgggt ctcggccagc
18901 cgagccgacc ggccccgcgc ctggcgcctc ctcggggcca gccgccgggg ttggttctgc
18961 ccctctctct gtccttcaga ggaaccaggg acctcgggca ccccagagcc cctcgggccc
19021 gcctccaggc gccctcctgg tctccgctcc cctctgagcc ccgttaaacc caaagaatgt
19081 ctgaggggag ccaccctcgg ggcccaggcc ccagagtcca gaggtcaggg gcacctcagg
19141 gtgcctcccc gggtcccagg ccagccggag ggaccccggc agcccgggcg gccccagagg
19201 ccggttcctc gcccctttccc cgggcttcag agcccaggat gtcccccaga agggacccta
19261 ggcgtcccct ctcctcccct ccaggcccga gcctctccct cgcggagagg ggcctctttg
19321 ggccctcaag tccagcccca ccgagacccg agtggcccgg atccccccac cggcccttct
19381 ctctgtcccc ctgctcctct ccaaccttcg ctccacccta gaccccagct tctggcctcc
19441 ccgggtccac caggccagcc ggagggaccc cggcagcccg ggcgagtcgc cttccctctc
19501 ccctggcctc tccttcccgc ctcccacccg agccccctca gcttgcctcc ccaccgggtc
19561 catcaggccg gccggaggga ccccggcggc ccggtgtcag tccccccctgc agccgcccag
19621 tctctgcctc caggcaaggg cgccagcttt tctcccccca gcctgaggcc cagtctcctg
19681 tgcactgtct gtaaagtcca gcctcccacg cccgtccacg gctcccgggc ccagcctcgt
19741 ccacccctcc ccacggtgga caggccctct gtccacccgg gccatccccg cccccctgtg
19801 tccaccccag tcccgtccag gggggacttt atgtgaccct tgggcctggc tccccataga
19861 ctcccatgta agcctgcctc gagtaggtgc ctccagagcc ccttttgccc ccctggcggc
19921 ccagcccgac ccccgggcgc ccccaaactt tgtccagatg tccaggggtc cccgagggtg
19981 aggcccagcc ccctcccgcc cctgtccact gccccggtcc ccccagaagc ccccaaaagt
20041 agaggctcag gccatgcgcg ccctgtcacc aggcctgcca aagagccaga tctaaggccg
20101 ggagaggcag ccccaaagcg ggtgcagtaa caggtaatct ctggtagtga tttggacccg
20161 aaatctgaca ctttagagct ctggaggact ttaaaactct aaaaatcaaa actttagagg
20221 cgaatgggcg ccatttgtc cccacgcgcg cataatggcg gacctaggcc taaaccccc
20281 aggaagcggg tctatggttg gctgcgctgc tgctatcttt agaggggaaa agaggaataa
20341 gcccccagac aggggagtgg gcttgtttgt gacttcacca aaggtcaggg cccaaggggg
20401 ttcgcgttgc taggccacct tctcagtcca gcgcgtttac gtaagccaga cagcagccaa
20461 ttgtcagttc tagggagggg gaccactgcc cctggtataa agtggtcctg cagctatttc
20521 tggtcgcatc agagcgccag gagtccacac aaatgtaaga gggggtcttc tacctctccc
20581 tagccctccg ccccctccaa ggactcgggc ccagtttcta actttcccc ttccctccct

Fig. 3 (cont.)

20641 cgtcttgccc tgcgcccggg gccaccttca tcaccgtcgc tgactccgcc atccaagcct
20701 aggggagacc gaagtgaagg ccctggacca acccggcccg ggcccccggg tatcgggcca
20761 gaggtaagtg gactttaatt ttttctgcta agcccaacac tccaccacac ccaggcacac
20821 actacacaca cccacccgtc tcagggtccc ctcggacagc tcctaagaag gcaccggtcg
20881 cccagtccta ccagaggggg ccaagaaccc agacgagtcc gtagaagggt cctcgtccag
20941 caagaagagg aggtggtaag cggttcacct tcaggggtaa gtaacctgac ctctccaggg
21001 ctcacataaa gggaggctta gtatacatgc ttcttgcttt tcacaggaac ctgggggcta
21061 gtctgggtgg gattaggctg cctcaagttg catcagccag ggcttcatgc cctcctcagt
21121 tccctagtcc ccgggcttca ggccccctcc gtccccgtcc tccagagacc cgggcttcag
21181 gccctgcctc tcctgttacc cttttagaac cacagcctgg acacatgtgc cagacgcctt
21241 ggcctctaag gccctcgggt ccccctggac cccggcctca gcaaccctgc tgctcccctc
21301 ctgccacccc agcctccccc cctccccgtc cccctcgct cctgatcctc ccccggtccc
21361 cagtagggcc gcctgccccc ctgcacccag tacctgcccc tcttggccac gcaccccggg
21421 ccaggccacc ttagacccgg ccaagcccca tccctgaaga cccagcggcc attctctctg
21481 gtaacgagca gagaagaagt agaggcccgc ggccattggg cccagattga gagaccagtc
21541 caggggcccg aggttggagc cagcgggcac ccgaggtccc agcacccggt ccctccgggg
21601 ggcagagaca ggcagggccc cccggcagct ggccccgagg aggcgcccgg agtggggccg
21661 gtcggctggg ctggccgagc ccgggtctgg gaggtctggg gtggcgagcc tgctgtctca
21721 ggaggggcct ggctccgccg ggtggccctg gggtaagtct gggaggcaga gggtcggcct
21781 aggcccgggg aagtggaggg ggatcgcccg ggtctctgtt ggcagagtcc gggcgatcct
21841 ctgagaccct ccgggcccgg acggtcgccc tcagcccccc agacagaccc cagggtctcc
21901 aggcagggtc cggcatcttc aggggcagca ggctcaccac cacaggcccc ccagacccgg
21961 gtctcggcca gccgagccga ccggccccgc gcctggcgcc tcctcggggc cagccgccgg
22021 ggttggttct gcccctctct ctgtccttca gaggaaccag ggacctcggg caccccagag
22081 cccctcgggc ccgcctccag gcgccctcct ggtctccgct cccctctgag ccccgttaaa
22141 cccaaagaat gtctgagggg agccaccctc ggggcccagg ccccagagtc cagaggtcag
22201 gggcacctca gggtgcctcc ccgggtccca ggccagccgg agggaccccg gcagcccggg
22261 cggccccaga ggccggttcc tcgccccttc cccgggcttc agagcccagg atgtccccca
22321 gaagggaccc taggcgtccc ctctcctccc ctccaggccc gagcctctcc ctcgcggaga
22381 ggggcctctt tgggccctca agtccagccc caccgagacc cgagtggccc ggatcccccc
22441 accggccctt ctctctgtcc ccctgctcct ctccaacctt cgctccaccc tagaccccag
22501 cttctggcct ccccgggtcc accaggccag ccggagggac cccggcagcc cgggcgagtc
22561 gccttccctc tcccctggcc tctccttccc gcctcccacc cgagccccct cagcttgcct
22621 ccccaccggg tccatcaggc cggccggagg gaccccggcg gcccggtgtc agtcccccct
22681 gcagccgccc agtctctgcc tccaggcaag ggcgccagct tttctccccc cagcctgagg
22741 cccagtctcc tgtgcactgt ctgtaaagtc cagcctccca cgcccgtcca cggctcccgg
22801 gcccagcctc gtccacccct ccccacggtg gacaggccct ctgtccaccc gggccatccc
22861 cgcccccctg tgtccacccc agtcccgtcc aggggggact ttatgtgacc cttgggcctg
22921 gctccccata gactcccatg taagcctgcc tcgagtaggt gcctccagag ccccttttgc

Fig. 3 (cont.)

22981 cccoctggcg gcccagcccg accccogggc gcccccaaac tttgtccaga tgtccagggg
23041 tccccgaggg tgaggcccag ccccctcccg cccctgtcca ctgccccggt ccccccagaa
23101 gcccccaaaa gtagaggctc aggccatgcg cgccctgtca ccaggcctgc caaagagcca
23161 gatctaaggc cgggagaggc agccccaaag cgggtgcagt aacaggtaat ctctggtagt
23221 gatttggacc cgaaatctga cactttagag ctctggagga ctttaaaact ctaaaaatca
23281 aaactttaga ggcgaatggg cgccattttg tccccacgcg cgcataatgg cggacctagg
23341 cctaaaaccc ccaggaagcg ggtctatggt tggctgcgct gctgctatct ttagagggga
23401 aaagaggaat aagcccccag acaggggagt gggcttgttt gtgacttcac caaaggtcag
23461 ggcccaaggg ggttcgcgtt gctaggccac cttctcagtc cagcgcgttt acgtaagcca
23521 gacagcagcc aattgtcagt tctagggagg gggaccactg cccctggtat aaagtggtcc
23581 tgcagctatt tctggtcgca tcagagcgcc aggagtccac acaaatgtaa gagggggtct
23641 tctacctctc cctagccctc cgccccctcc aaggactcgg gcccagtttc taacttttcc
23701 ccttccctcc ctcgtcttgc cctgcgcccg gggccacctt catcaccgtc gctgactccg
23761 ccatccaagc ctaggggaga ccgaagtgaa ggccctggac caacccggcc cgggcccccc
23821 ggtatcgggc cagaggtaag tggactttaa ttttttctgc taagcccaac actccaccac
23881 acccaggcac acactacaca cacccacccg tctcagggtc ccctcggaca gctcctaaga
23941 aggcaccggt cgcccagtcc taccagaggg ggccaagaac ccagacgagt ccgtagaagg
24001 gtcctcgtcc agcaagaaga ggaggtggta agcggttcac cttcaggggt aagtaacctg
24061 acctctccag ggctcacata aagggaggct tagtatacat gcttcttgct tttcacagga
24121 acctgggggc tagtctgggt gggattaggc tgcctcaagt tgcatcagcc agggcttcat
24181 gccctcctca gttccctagt ccccgggctt caggccccct ccgtccccgt cctccagaga
24241 cccgggcttc aggccctgcc tctcctgtta cccttttaga accacagcct ggacacatgt
24301 gccagacgcc ttggcctcta aggccctcgg gtccccctgg accccggcct cagcaaccct
24361 gctgctcccc tcctgccacc ccagcctccc cccctccccg tcccccttcg ctcctgatcc
24421 tcccccggtc cccagtaggg ccgcctgccc ccctgcaccc agtacctgcc cctcttggcc
24481 acgcaccccg ggccaggcca ccttagaccc ggccaagccc catccctgaa gacccagcgg
24541 ccattctctc tggtaacgag cagagaagaa gtagaggccc gcggccattg ggcccagatt
24601 gagagaccag tccaggggcc cgaggttgga gccagcgggc acccgaggtc ccagcacccg
24661 gtccctccgg ggggcagaga caggcagggc cccccggcag ctggccccga ggaggcgccc
24721 ggagtggggc cggtcggctg ggctggccga gcccgggtct gggaggtctg gggtggcgag
24781 cctgctgtct caggaggggc ctggctccgc cgggtggccc tggggtaagt ctgggaggca
24841 gagggtcggc ctaggcccgg ggaagtggag ggggatcgcc cgggtctctg ttggcagagt
24901 ccgggcgatc ctctgagacc ctccgggccc ggacggtcgc cctcagcccc ccagacagac
24961 cccagggtct ccaggcaggg tccggcatct tcaggggcag caggctcacc accacaggcc
25021 ccccagaccc gggtctcggc cagccgagcc gaccggcccc gcgcctggcg cctcctcggg
25081 gccagccgcc ggggttggtt ctgcccctct ctctgtcctt cagaggaacc agggacctcg
25141 ggcaccccag agcccctcgg gcccgcctcc aggcgccctc ctggtctccg ctcccctctg
25201 agccccgtta aacccaaaga atgtctgagg ggagccaccc tcggggccca ggccccagag
25261 tccagaggtc aggggcacct cagggtgcct ccccgggtcc caggccagcc ggagggaccc

Fig. 3 (cont.)

25321 cggcagcccg ggcggcccca gaggccggtt cctcgcccct tccccgggct tcagagccca
25381 ggatgtcccc cagaagggac cctaggcgtc ccctctcctc ccctccaggc ccgagcctct
25441 ccctcgcgga gaggggcctc tttgggccct caagtccagc cccaccgaga cccgagtggc
25501 ccggatcccc ccaccggccc ttctctctgt ccccctgctc ctctccaacc ttcgctccac
25561 cctagacccc agcttctggc ctccccgggt ccaccaggcc agccggaggg accccggcag
25621 cccgggcgag tcgccttccc tctcccctgg cctctccttc ccgcctccca cccgagcccc
25681 ctcagcttgc ctccccaccg ggtccatcag gccggccgga gggaccccgg cggcccggtg
25741 tcagtccccc ctgcagccgc ccagtctctg cctccaggca agggcgccag cttttctccc
25801 cccagcctga ggcccagtct cctgtgcact gtctgtaaag tccagcctcc cacgcccgtc
25861 cacggctccc gggcccagcc tcgtccaccc ctccccacgg tggacaggcc ctctgtccac
25921 ccgggccatc cccgcccccc tgtgtccacc ccagtcccgt ccagggggga ctttatgtga
25981 cccttgggcc tggctcccca tagactccca tgtaagcctg cctcgagtag gtgcctccag
26041 agccccttt gcccccctgg cggcccagcc cgacccccgg gcgcccccaa actttgtcca
26101 gatgtccagg ggtccccgag ggtgaggccc agcccctcc cgcccctgtc cactgccccg
26161 gtccccccag aagcccccaa aagtagaggc tcaggccatg cgcgccctgt caccaggcct
26221 gccaaagagc cagatctaag gccgggagag gcagccccaa agcgggtgca gtaacaggta
26281 atctctggta gtgatttgga cccgaaatct gacactttag agctctggag gactttaaaa
26341 ctctaaaaat caaaacttta gaggcgaatg ggcgccattt tgtccccacg cgcgcataat
26401 ggcggaccta ggcctaaaac ccccaggaag cgggtctatg gttggctgcg ctgctgctat
26461 ctttagaggg gaaaagagga ataagccccc agacagggga gtgggcttgt ttgtgacttc
26521 accaaaggtc agggcccaag gggttcgcg ttgctaggcc accttctcag tccagcgcgt
26581 ttacgtaagc cagacagcag ccaattgtca gttctaggga gggggaccac tgcccctggt
26641 ataaagtggt cctgcagcta tttctggtcg catcagagcg ccaggagtcc acacaaatgt
26701 aagagggggt cttctacctc tccctagccc tccgcccccct ccaaggactc gggcccagtt
26761 tctaactttt ccccttccct ccctcgtctt gccctgcgcc cggggccacc ttcatcaccg
26821 tcgctgactc cgccatccaa gcctagggga gaccgaagtg aaggccctgg accaacccgg
26881 cccgggcccc ccggtatcgg gccagaggta agtggacttt aattttttct gctaagccca
26941 acactccacc acacccaggc acacactaca cacacccacc cgtctcaggg tcccctcgga
27001 cagctcctaa gaaggcaccg gtcgcccagt cctaccagag ggggccaaga acccagacga
27061 gtccgtagaa gggtcctcgt ccagcaagaa gaggaggtgg taagcggttc accttcaggg
27121 gtaagtaacc tgacctctcc agggctcaca taaagggagg cttagtatac atgcttcttg
27181 cttttcacag gaacctgggg gctagtctgg gtgggattag gctgcctcaa gttgcatcag
27241 ccagggcttc atgccctcct cagttcccta gtccccgggc ttcaggcccc ctccgtcccc
27301 gtcctccaga gacccgggct tcaggccctg cctctcctgt taccctttta gaaccacagc
27361 ctggacacat gtgccagacg ccttggcctc taaggccctc gggtcccccct ggaccccggc
27421 ctcagcaacc ctgctgctcc cctcctgcca ccccagcctc ccccctccc cgtcccccctt
27481 cgctcctgat cctccccccgg tccccagtag ggccgcctgc ccccctgcac ccagtacctg
27541 cccctcttgg ccacgcaccc cgggccaggc caccttagac ccggccaagc cccatccctg
27601 aagacccagc ggccattctc tctggtaacg agcagagaag aagtagaggc ccgcggccat

Fig. 3 (cont.)

27661 tgggcccaga ttgagagacc agtccagggg cccgaggttg gagccagcgg gcacccgagg
27721 tcccagcacc cggtccctcc ggggggcaga gacaggcagg gccccccggc agctggcccc
27781 gaggaggcgc ccggagtggg gccggtcggc tgggctggcc gagcccgggt ctgggaggtc
27841 tggggtggcg agcctgctgt ctcaggaggg gcctggctcc gccgggtggc cctggggtaa
27901 gtctgggagg cagagggtcg gcctaggccc ggggaagtgg agggggatcg cccgggtctc
27961 tgttggcaga gtccgggcga tcctctgaga ccctccgggc ccggacggtc gccctcagcc
28021 ccccagacag accccagggt ctccaggcag ggtccggcat cttcaggggc agcaggctca
28081 ccaccacagg ccccccagac ccgggtctcg gccagccgag ccgaccggcc ccgcgcctgg
28141 cgcctcctcg gggccagccg ccggggttgg ttctgcccct ctctctgtcc ttcagaggaa
28201 ccagggacct cgggcacccc agagcccctc gggcccgcct ccaggcgccc tcctggtctc
28261 cgctcccctc tgagccccgt taaacccaaa gaatgtctga ggggagccac cctcggggcc
28321 caggccccag agtccagagg tcaggggcac ctcagggtgc ctccccgggt cccaggccag
28381 ccggagggac cccggcagcc cggcggcccc cagaggccgg ttcctcgccc cttccccggg
28441 cttcagagcc caggatgtcc cccagaaggg accctaggcg tcccctctcc tcccctccag
28501 gcccgagcct ctccctcgcg gagaggggcc tctttgggcc ctcaagtcca gccccaccga
28561 gacccgagtg gcccggatcc ccccaccggc ccttctctct gtccccctgc tcctctccaa
28621 ccttcgctcc accctagacc ccagcttctg gcctccccgg gtccaccagg ccagccggag
28681 ggaccccggc agcccgggcg agtcgccttc cctctcccct ggcctctcct tcccgcctcc
28741 cacccgagcc ccctcagctt gcctccccac cgggtccatc aggccggccg gagggacccc
28801 ggcggcccgg tgtcagtccc ccctgcagcc gcccagtctc tgcctccagg caagggcgcc
28861 agcttttctc cccccagcct gaggcccagt ctcctgtgca ctgtctgtaa agtccagcct
28921 cccacgcccg tccacggctc ccgggcccag cctcgtccac ccctccccac ggtggacagg
28981 ccctctgtcc acccgggcca tccccgcccc cctgtgtcca ccccagtccc gtccaggggg
29041 gactttatgt gaccccttggg cctggctccc catagactcc catgtaagcc tgcctcgagt
29101 aggtgcctcc agagcccctt ttgcccccct ggcggcccag cccgaccccc gggcgccccc
29161 aaactttgtc cagatgtcca ggggtccccg agggtgaggc ccagccccct cccgcccctg
29221 tccactgccc cggtcccccc agaagccccc aaaagtagag gctcaggcca tgcgcgccct
29281 gtcaccaggc ctgccaaaga gccagatcta aggccgggag aggcagcccc aaagcgggtg
29341 cagtaacagg taatctctgg tagtgatttg gacccgaaat ctgacacttt agagctctgg
29401 aggactttaa aactctaaaa atcaaaactt tagaggcgaa tgggcgccat tttgtcccca
29461 cgcgcgcata atggcggacc taggcctaaa acccccagga agcgggtcta tggttggctg
29521 cgctgctgct atctttagag gggaaaagag gaataagccc ccagacaggg gagtgggctt
29581 gtttgtgact tcaccaaagg tcagggccca agggggttcg cgttgctagg ccaccttctc
29641 agtccagcgc gtttacgtaa gccagacagc agccaattgt cagttctagg gagggggacc
29701 actgcccctg gtataaagtg gtcctgcagc tatttctggt cgcatcagag cgccaggagt
29761 ccacacaaat gtaagagggg gtcttctacc tctccctagc cctccgcccc ctccaaggac
29821 tcgggcccag tttctaactt ttccccttcc ctccctcgtc ttgccctgcg cccggggcca
29881 ccttcatcac cgtcgctgac tccgccatcc aagcctaggg gagaccgaag tgaaggccct
29941 ggaccaaccc ggcccgggcc ccccggtatc gggccagagg taagtggact ttaatttttt

Fig. 3 (cont.)

30001 ctgctaagcc caacactcca ccacacccag gcacacacta cacacaccca cccgtctcag
30061 ggtcccctcg gacagctcct aagaaggcac cggtcgccca gtcctaccag agggggccaa
30121 gaacccagac gagtccgtag aagggtcctc gtccagcaag aagaggaggt ggtaagcggt
30181 tcaccttcag gggtaagtaa cctgacctct ccagggctca cataaaggga ggcttagtat
30241 acatgcttct tgcttttcac aggaacctgg gggctagtct gggtgggatt aggctgcctc
30301 aagttgcatc agccagggct tcatgccctc ctcagttccc tagtccccgg gcttcaggcc
30361 ccctccgtcc ccgtcctcca gagacccggg cttcaggccc tgcctctcct gttacccttt
30421 tagaaccaca gcctggacac atgtgccaga cgccttggcc tctaaggccc tcgggtcccc
30481 ctggaccccg gcctcagcaa ccctgctgct cccctcctgc caccccagcc tcccccccctc
30541 cccgtccccc ttcgctcctg atcctccccc ggtccccagt agggccgcct gcccccctgc
30601 acccagtacc tgcccctctt ggccacgcac cccgggccag gccaccttag acccggccaa
30661 gccccatccc tgaagaccca gcggccattc tctctggtaa cgagcagaga agaagtagag
30721 gcccgcggcc attgggccca gattgagaga ccagtccagg ggcccgaggt tggagccagc
30781 gggcacccga ggtcccagca cccggtccct ccgggggggca gagacaggca gggcccccg
30841 gcagctggcc ccgaggaggc gcccggagtg gggccggtcg gctgggctgg ccgagcccgg
30901 gtctgggagg tctggggtgg cgagcctgct gtctcaggag gggcctggct ccgccgggtg
30961 gccctggggt aagtctggga ggcagagggt cggcctaggc ccggggaagt ggaggggggat
31021 cgcccgggtc tctgttggca gagtccgggc gatcctctga gaccctccgg gcccggacgg
31081 tcgccctcag ccccccagac agaccccagg gtctccaggc agggtccggc atcttcaggg
31141 gcagcaggct caccaccaca ggccccccag acccgggtct cggccagccg agccgaccgg
31201 ccccgcgcct ggcgcctcct cggggccagc cgccggggtt ggttctgccc ctctctctgt
31261 ccttcagagg aaccagggac ctcgggcacc ccagagcccc tcgggcccgc ctccaggcgc
31321 cctcctggtc tccgctcccc tctgagcccc gttaaaccca aagaatgtct gaggggagcc
31381 accctcgggg cccaggcccc agagtccaga ggtcaggggc acctcagggt gcctccccgg
31441 gtcccaggcc agccggaggg accccggcag cccgggcggc cccagaggcc ggttcctcgc
31501 cccttccccg ggcttcagag cccaggatgt cccccagaag ggaccctagg cgtcccctct
31561 cctcccctcc aggcccgagc ctctccctcg cggagagggg cctctttggg ccctcaagtc
31621 cagccccacc gagacccgag tggcccggat ccccccaccg gcccttctct ctgtcccccct
31681 gctcctctcc aaccttcgct ccaccctaga ccccagcttc tggcctcccc gggtccacca
31741 ggccagccgg agggaccccg gcagcccggg cgagtcgcct tccctctccc ctggcctctc
31801 cttcccgcct cccacccgag ccccctcagc ttgcctcccc accgggtcca tcaggccggc
31861 cggagggacc ccggcggccc ggtgtcagtc ccccctgcag ccgcccagtc tctgcctcca
31921 ggcaagggcg ccagcttttc tccccccagc ctgaggccca gtctcctgtg cactgtctgt
31981 aaagtccagc ctcccacgcc cgtccacggc tcccgggccc agcctcgtcc acccctcccc
32041 acggtggaca ggccctctgt ccacccgggc catccccgcc cccctgtgtc caccccagtc
32101 ccgtccaggg gggactttat gtgacccttg ggcctggctc cccatagact cccatgtaag
32161 cctgcctcga gtaggtgcct ccagagcccc ttttgccccc ctggcggccc agcccgaccc
32221 ccgggcgccc ccaaactttg tccagatgtc caggggtccc cgagggtgag gcccagcccc
32281 ctcccgcccc tgtccactgc cccggtcccc ccagaagccc ccaaaagtag aggctcaggc

Fig. 3 (cont.)

32341 catgcgcgcc ctgtcaccag gcctgccaaa gagccagatc taaggccggg agaggcagcc
32401 ccaaagcggg tgcagtaaca ggtaatctct ggtagtgatt tggacccgaa atctgacact
32461 ttagagctct ggaggacttt aaaactctaa aaatcaaaac tttagaggcg aatgggcgcc
32521 attttgtccc cacgcgcgca taatggcgga cctaggccta aaaccccccag gaagcgggtc
32581 tatggttggc tgcgctgctg ctatctttag aggggaaaag aggaataagc ccccagacag
32641 gggagtgggc ttgtttgtga cttcaccaaa ggtcagggcc caaggggggtt cgcgttgcta
32701 ggccaccttc tcagtccagc gcgtttacgt aagccagaca gcagccaatt gtcagttcta
32761 gggagggggga ccactgcccc tggtataaag tggtcctgca gctatttctg gtcgcatcag
32821 agcgccagga gtccacacaa atgtaagagg gggtcttcta cctctcccta gccctccgcc
32881 ccctccaagg actcgggccc agtttctaac ttttcccctt ccctccctcg tcttgccctg
32941 cgcccggggc caccttcatc accgtcgctg actccgccat ccaagcctag gggagaccga
33001 agtgaaggcc ctggaccaac ccggcccggg ccccccggta tcgggccaga ggtaagtgga
33061 ctttaatttt ttctgctaag cccaacactc caccacaccc aggcacacac tacacacacc
33121 cacccgtctc agggtcccct cggacagctc ctaagaaggc accggtcgcc cagtcctacc
33181 agagggggcc aagaacccag acgagtccgt agaagggtcc tcgtccagca agaagaggag
33241 gtggtaagcg gttcaccttc aggggtaagt aacctgacct ctccagggct cacataaagg
33301 gaggcttagt atacatgctt cttgcttttc acaggaacct gggggctagt ctgggtggga
33361 ttaggctgcc tcaagttgca tcagccaggg cttcatgccc tcctcagttc cctagtcccc
33421 gggcttcagg ccccctccgt ccccgtcctc cagagacccg ggcttcaggc cctgcctctc
33481 ctgttaccct tttagaacca cagcctggac acatgtgcca gacgccttgg cctctaaggc
33541 cctcgggtcc ccctggaccc cggcctcagc aaccctgctg ctcccctcct gccaccccag
33601 cctccccccc tccccgtccc ccttcgctcc tgatcctccc ccggtcccca gtagggccgc
33661 ctgccccccct gcacccagta cctgcccctc ttggccacgc accccgggcc aggccacctt
33721 agacccggcc aagccccatc cctgaagacc cagcggccat tctctctggt aacgagcaga
33781 gaagaagtag aggcccgcgg ccattgggcc cagattgaga gaccagtcca ggggcccgag
33841 gttggagcca gcgggcaccc gaggtcccag cacccggtcc ctccgggggg cagagacagg
33901 cagggccccc cggcagctgg ccccgaggag gcgcccggag tggggccggt cggctgggct
33961 ggccgagccc gggtctggga ggtctggggt ggcgagcctg ctgtctcagg aggggcctgg
34021 ctccgccggg tggccctggg gtaagtctgg gaggcagagg gtcggcctag gcccggggaa
34081 gtggaggggg atcgcccggg tctctgttgg cagagtccgg gcgatcctct gagaccctcc
34141 gggcccggac ggtcgccctc agcccccccag acagacccca gggtctccag gcagggtccg
34201 gcatcttcag gggcagcagg ctcaccacca caggccccccc agacccgggt ctcggccagc
34261 cgagccgacc ggccccgcgc ctggcgcctc ctcggggcca gccgccgggg ttggttctgc
34321 ccctctctct gtccttcaga ggaaccaggg acctcgggca ccccagagcc cctcgggccc
34381 gcctccaggc gccctcctgg tctccgctcc cctctgagcc ccgttaaacc caaagaatgt
34441 ctgaggggag ccaccctcgg ggcccaggcc ccagagtcca gaggtcaggg gcacctcagg
34501 gtgcctcccc gggtcccagg ccagccggag ggaccccggc agcccgggcg gccccagagg
34561 ccggttcctc gcccccttccc cgggcttcag agcccaggat gtcccccaga agggacccta
34621 ggcgtcccct ctcctcccct ccaggcccga gcctctccct cgcggagagg ggcctctttg

Fig. 3 (cont.)

34681 ggccctcaag tccagcccca ccgagacccg agtggcccgg atccccccac cggcccttct
34741 ctctgtcccc ctgctcctct ccaaccttcg ctccacccta gaccccagct tctggcctcc
34801 ccgggtccac caggccagcc ggagggaccc cggcagcccg ggcgagtcgc cttccctctc
34861 ccctggcctc tccttcccgc ctcccacccg agccccctca gcttgcctcc ccaccgggtc
34921 catcaggccg gccggaggga ccccggcggc ccggtgtcag tccccccctgc agccgcccag
34981 tctctgcctc caggcaaggg cgccagcttt tctcccccca gcctgaggcc cagtctcctg
35041 tgcactgtct gtaaagtcca gcctcccacg cccgtccacg gctcccgggc ccagcctcgt
35101 ccacccctcc ccacggtgga caggccctct gtccacccgg gccatccccg ccccccctgtg
35161 tccaccccag tcccgtccag gggggacttt atgtgaccct tgggcctggc tccccataga
35221 ctcccatgta agcctgcctc gagtaggtgc ctccagagcc ccttttgccc ccctggcggc
35281 ccagcccgac ccccgggcgc ccccaaactt tgtccagatg tccaggggtc cccgagggtg
35341 aggcccagcc ccctcccgcc cctgtccact gccccggtcc ccccagaagc ccccaaaagt
35401 agaggctcag gccatgcgcg ccctgtcacc aggcctgcca aagagccaga tctaaggccg
35461 ggagaggcag ccccaaagcg ggtgcagtaa caggtaatct ctggtagtga tttggacccg
35521 aaatctgaca ctttagagct ctggaggact ttaaaactct aaaaatcaaa actttagagg
35581 cgaatgggcg ccattttgtc cccacgcgcg cataatggcg gacctaggcc taaaaccccc
35641 aggaagcggg tctatggttg gctgcgctgc tgctatcttt agaggggaaa agaggaataa
35701 gcccccagac aggggagtgg gcttgtttgt gacttcacca aaggtcaggg cccaaggggg
35761 ttcgcgttgc taggccacct tctcagtcca gcgcgtttac gtaagccaga cagcagccaa
35821 ttgtcagttc tagggagggg gaccactgcc cctggtataa agtggtcctg cagctatttc
35881 tggtcgcatc agagcgccag gagtccacac aaatgtaaga gggggtcttc tacctctccc
35941 tagccctccg ccccctccaa ggactcgggc ccagtttcta acttttcccc ttccctccct
36001 cgtcttgccc tgcgcccggg gccaccttca tcaccgtcgc tgactccgcc atccaagcct
36061 aggggagacc gaagtgaagg ccctggacca acccggcccg ggccccccgg tatcgggcca
36121 gaggtaagtg gactttaatt ttttctgcta agcccaacac tccaccacac ccaggcacac
36181 actacacaca cccacccgtc tcagggtccc ctcggacagc tcctaagaag gcaccggtcg
36241 cccagtccta ccagaggggg ccaagaaccc agacgagtcc gtagaagggt cctcgtccag
36301 caagaagagg aggtggtaag cggttcacct tcaggggtaa gtaacctgac ctctccaggg
36361 ctcacataaa gggaggctta gtatacatgc ttcttgcttt tcacaggaac ctgggggcta
36421 gtctgggtgg gattaggctg cctcaagttg catcagccag ggcttcatgc cctcctcagt
36481 tccctagtcc ccgggcttca ggccccctcc gtccccgtcc tccagagacc cgggcttcag
36541 gccctgcctc tcctgttacc cttttagaac cacagcctgg acacatgtgc cagacgcctt
36601 ggcctctaag gccctcgggt ccccctggac cccggcctca gcaaccctgc tgctcccctc
36661 ctgccacccc agcctccccc cctccccgtc ccccttcgct cctgatcctc ccccggtccc
36721 cagtagggcc gcctgccccc ctgcacccag tacctgcccc tcttggccac gcaccccggg
36781 ccaggccacc ttagacccgg ccaagcccca tccctgaaga cccagcggcc attctctctg
36841 gtaacgagca gagaagaagt agaggcccgc ggccattggg cccagattga gagaccagtc
36901 caggggcccg aggttggagc cagcgggcac ccgaggtccc agcacccggt ccctccgggg
36961 ggcagagaca ggcagggccc cccggcagct ggccccgagg aggcgcccgg agtggggccg

Fig. 3 (cont.)

37021 gtcggctggg ctggccgagc ccgggtctgg gaggtctggg gtggcgagcc tgctgtctca
37081 ggaggggcct ggctccgccg ggtggccctg gggtaagtct gggaggcaga gggtcggcct
37141 aggcccgggg aagtggaggg ggatcgcccg ggtctctgtt ggcagagtcc gggcgatcct
37201 ctgagaccct ccgggcccgg acggtcgccc tcagcccccc agacagaccc cagggtctcc
37261 aggcagggtc cggcatcttc aggggcagca ggctcaccac cacaggcccc ccagacccgg
37321 gtctcggcca gccgagccga ccggccccgc gcctggcgcc tcctcggggc cagccgccgg
37381 ggttggttct gcccctctct ctgtccttca gaggaaccag ggacctcggg caccccagag
37441 cccctcgggc ccgcctccag gcgccctcct ggtctccgct cccctctgag ccccgttaaa
37501 cccaaagaat gtctgagggg agccaccctc ggggcccagg ccccagagtc cagaggtcag
37561 gggcacctca gggtgcctcc ccgggtccca ggccagccgg agggaccccg gcagcccggg
37621 cggccccaga ggccggttcc tcgccccttc cccgggcttc agagcccagg atgtccccca
37681 gaagggaccc taggcgtccc ctctcctccc ctccaggccc gagcctctcc ctcgcggaga
37741 ggggcctctt tgggccctca agtccagccc caccgagacc cgagtggccc ggatcccccc
37801 accggccctt ctctctgtcc ccctgctcct ctccaacctt cgctccaccc tagaccccag
37861 cttctggcct ccccgggtcc accaggccag ccggagggac cccggcagcc cgggcgagtc
37921 gccttccctc tcccctggcc tctccttccc gcctcccacc cgagccccct cagcttgcct
37981 ccccaccggg tccatcaggc cggccggagg gaccccggcg gcccggtgtc agtccccccct
38041 gcagccgccc agtctctgcc tccaggcaag ggcgccagct tttctccccc cagcctgagg
38101 cccagtctcc tgtgcactgt ctgtaaagtc cagcctccca cgcccgtcca cggctcccgg
38161 gcccagcctc gtccacccct ccccacggtg gacaggccct ctgtccaccc gggccatccc
38221 cgcccccctg tgtccacccc agtcccgtcc aggggggact ttatgtgacc cttgggcctg
38281 gctccccata gactcccatg taagcctgcc tcgagtaggt gcctccagag cccctttgc
38341 ccccctggcg gcccagcccg acccccgggc gcccccaaac tttgtccaga tgtccagggg
38401 tccccgaggg tgaggcccag ccccctcccg cccctgtcca ctgccccggt ccccccagaa
38461 gcccccaaaa gtagaggctc aggccatgcg cgccctgtca ccaggcctgc caaagagcca
38521 gatctaaggc cgggagaggc agccccaaag cgggtgcagt aacaggtaat ctctggtagt
38581 gatttggacc cgaaatctga cactttagag ctctggagga ctttaaaact ctaaaaatca
38641 aaactttaga ggcgaatggg cgccattttg tccccacgcg cgcataatgg cggacctagg
38701 cctaaaaccc ccaggaagcg ggtctatggt tggctgcgct gctgctatct ttagagggga
38761 aaagaggaat aagcccccag acaggggagt gggcttgttt gtgacttcac caaaggtcag
38821 ggcccaaggg ggttcgcgtt gctaggccac cttctcagtc cagcgcgttt acgtaagcca
38881 gacagcagcc aattgtcagt tctagggagg gggaccactg cccctggtat aaagtggtcc
38941 tgcagctatt tctggtcgca tcagagcgcc aggagtccac acaaatgtaa gagggggtct
39001 tctacctctc cctagccctc cgccccctcc aaggactcgg gcccagtttc taacttttcc
39061 ccttccctcc ctcgtcttgc cctgcgcccg gggccacctt catcaccgtc gctgactccg
39121 ccatccaagc ctaggggaga ccgaagtgaa ggccctggac caacccggcc cgggcccccc
39181 ggtatcgggc cagaggtaag tggactttaa ttttttctgc taagcccaac actccaccac
39241 acccaggcac acactacaca cacccacccg tctcagggtc ccctcggaca gctcctaaga
39301 aggcaccggt cgcccagtcc taccagaggg ggccaagaac ccagacgagt ccgtagaagg

Fig. 3 (cont.)

39361 gtcctcgtcc agcaagaaga ggaggtggta agcggttcac cttcaggggt aagtaacctg
39421 acctctccag ggctcacata aagggaggct tagtatacat gcttcttgct tttcacagga
39481 acctgggggc tagtctgggt gggattaggc tgcctcaagt tgcatcagcc agggcttcat
39541 gccctcctca gttccctagt ccccgggctt caggccccct ccgtccccgt cctccagaga
39601 cccgggcttc aggccctgcc tctcctgtta cccttttaga accacagcct ggacacatgt
39661 gccagacgcc ttggcctcta aggccctcgg gtccccctgg accccggcct cagcaaccct
39721 gctgctcccc tcctgccacc ccagcctccc cccctccccg tccccccttcg ctcctgatcc
39781 tcccccggtc cccagtaggg ccgcctgccc ccctgcaccc agtacctgcc cctcttggcc
39841 acgcaccccg ggccaggcca ccttagaccc ggccaagccc catccctgaa gacccagcgg
39901 ccattctctc tggtaacgag cagagaagaa gtagaggccc gcggccattg ggcccagatt
39961 gagagaccag tccaggggcc cgaggttgga gccagcgggc acccgaggtc ccagcacccg
40021 gtccctccgg ggggcagaga caggcagggc cccccggcag ctggccccga ggaggcgccc
40081 ggagtggggc cggtcggctg ggctggccga gcccgggtct gggaggtctg gggtggcgag
40141 cctgctgtct caggaggggc ctggctccgc cgggtggccc tggggtaagt ctgggaggca
40201 gagggtcggc ctaggcccgg ggaagtggag ggggatcgcc cgggtctctg ttggcagagt
40261 ccgggcgatc ctctgagacc ctccgggccc ggacggtcgc cctcagcccc ccagacagac
40321 cccagggtct ccaggcaggg tccggcatct tcaggggcag caggctcacc accacaggcc
40381 ccccagaccc gggtctcggc cagccgagcc gaccggcccc gcgcctggcg cctcctcggg
40441 gccagccgcc ggggttggtt ctgcccctct ctctgtcctt cagaggaacc agggacctcg
40501 ggcaccccag agcccctcgg gcccgcctcc aggcgccctc ctggtctccg ctcccctctg
40561 agccccgtta aacccaaaga atgtctgagg ggagccaccc tcggggccca ggccccagag
40621 tccagaggtc aggggcacct cagggtgcct ccccgggtcc caggccagcc ggagggaccc
40681 cggcagcccg ggcggcccca gaggccggtt cctcgcccct tccccgggct tcagagccca
40741 ggatgtcccc cagaagggac cctaggcgtc ccctctcctc ccctccaggc ccgagcctct
40801 ccctcgcgga gaggggcctc tttgggccct caagtccagc cccaccgaga cccgagtggc
40861 ccggatcccc ccaccggccc ttctctctgt ccccctgctc ctctccaacc ttcgctccac
40921 cctagacccc agcttctggc ctccccgggt ccaccaggcc agccggaggg accccggcag
40981 cccgggcgag tcgccttccc tctcccctgg cctctccttc ccgcctccca cccgagcccc
41041 ctcagcttgc ctccccaccg ggtccatcag gccggccgga gggaccccgg cggcccggtg
41101 tcagtccccc ctgcagccgc ccagtctctg cctccaggca agggcgccag cttttctccc
41161 cccagcctga ggcccagtct cctgtgcact gtctgtaaag tccagcctcc cacgcccgtc
41221 cacggctccc gggcccagcc tcgtccaccc ctccccacgg tggacaggcc ctctgtccac
41281 ccgggccatc cccgcccccc tgtgtccacc ccagtcccgt ccaggggggga ctttatgtga
41341 cccttgggcc tggctcccca tagactccca tgtaagcctg cctcgagtag gtgcctccag
41401 agcccctttt gcccccctgg cggcccagcc cgacccccgg gcgcccccaa actttgtcca
41461 gatgtccagg ggtccccgag ggtgaggccc agccccctcc cgcccctgtc cactgccccg
41521 gtccccccag aagcccccaa aagtagaggc tcaggccatg cgcgccctgt caccaggcct
41581 gccaaagagc cagatctaag gccgggagag gcagccccaa agcgggtgca gtaacaggta
41641 atctctggta gtgatttgga cccgaaatct gacactttag agctctggag gactttaaaa

Fig. 3 (cont.)

41701 ctctaaaaat caaaacttta gaggcgaatg ggcgccattt tgtccccacg cgcgcataat
41761 ggcggaccta ggcctaaaac ccccaggaag cgggtctatg gttggctgcg ctgctgctat
41821 ctttagaggg gaaaagagga ataagccccc agacagggga gtgggcttgt ttgtgacttc
41881 accaaaggtc agggcccaag gggttcgcg ttgctaggcc accttctcag tccagcgcgt
41941 ttacgtaagc cagacagcag ccaattgtca gttctaggga gggggaccac tgcccctggt
42001 ataaagtggt cctgcagcta tttctggtcg catcagagcg ccaggagtcc acacaaatgt
42061 aagagggggt cttctacctc tccctagccc tccgccccct ccaaggactc gggcccagtt
42121 tctaactttt ccccttccct ccctcgtctt gccctgcgcc cggggccacc ttcatcaccg
42181 tcgctgactc cgccatccaa gcctagggga gaccgaagtg aaggccctgg accaacccgg
42241 cccgggcccc ccggtatcgg gccagaggta agtggacttt aattttttct gctaagccca
42301 acactccacc acacccaggc acacactaca cacacccacc cgtctcaggg tcccctcgga
42361 cagctcctaa gaaggcaccg gtcgcccagt cctaccagag gggccaaga acccagacga
42421 gtccgtagaa gggtcctcgt ccagcaagaa gaggaggtgg taagcggttc accttcaggg
42481 gtaagtaacc tgacctctcc agggctcaca taaagggagg cttagtatac atgcttcttg
42541 cttttcacag gaacctgggg gctagtctgg gtgggattag gctgcctcaa gttgcatcag
42601 ccagggcttc atgccctcct cagttcccta gtccccgggc ttcaggcccc ctccgtcccc
42661 gtcctccaga gacccgggct tcaggccctg cctctcctgt taccctttta gaaccacagc
42721 ctggacacat gtgccagacg ccttggcctc taaggccctc gggtccccct ggaccccggc
42781 ctcagcaacc ctgctgctcc cctcctgcca ccccagcctc ccccccctccc cgtccccctt
42841 cgctcctgat cctcccccgg tccccagtag ggccgcctgc ccccctgcac ccagtacctg
42901 cccctcttgg ccacgcaccc cgggccaggc caccttagac ccggccaagc cccatccctg
42961 aagacccagc ggccattctc tctggtaacg agcagagaag aagtagaggc ccgcggccat
43021 tgggcccaga ttgagagacc agtccagggg cccgaggttg gagccagcgg gcacccgagg
43081 tcccagcacc cggtccctcc ggggggcaga gacaggcagg gccccccggc agctggcccc
43141 gaggaggcgc ccggagtggg gccggtcggc tgggctggcc gagcccgggt ctgggaggtc
43201 tggggtggcg agcctgctgt ctcaggaggg gcctggctcc gccgggtggc cctggggtaa
43261 gtctgggagg cagagggtcg gcctaggccc ggggaagtgg agggggatcg cccgggtctc
43321 tgttggcaga gtccgggcga tcctctgaga ccctccgggc ccggacggtc gccctcagcc
43381 ccccagacag accccagggt ctccaggcag ggtccggcat cttcaggggc agcaggctca
43441 ccaccacagg ccccccagac ccgggtctcg gccagccgag ccgaccggcc ccgcgcctgg
43501 cgcctcctcg gggccagccg ccggggttgg ttctgcccct ctctctgtcc ttcagaggaa
43561 ccagggacct cgggcacccc agagcccctc gggcccgcct ccaggcgccc tcctggtctc
43621 cgctcccctc tgagccccgt taaacccaaa gaatgtctga ggggagccac cctcggggcc
43681 caggccccag agtccagagg tcaggggcac ctcagggtgc ctccccgggt cccaggccag
43741 ccggagggac cccggcagcc cgggcggccc cagaggccgg ttcctcgccc cttccccggg
43801 cttcagagcc caggatgtcc cccagaaggg accctaggcg tcccctctcc tcccctccag
43861 gcccgagcct ctccctcgcg gagaggggcc tctttgggcc ctcaagtcca gccccaccga
43921 gacccgagtg gcccggatcc ccccaccggc ccttctctct gtccccctgc tcctctccaa
43981 ccttcgctcc accctagacc ccagcttctg gcctccccgg gtccaccagg ccagccggag

Fig. 3 (cont.)

44041 ggaccccggc agcccgggcg agtcgccttc cctctcccct ggcctctcct tcccgcctcc
44101 cacccgagcc ccctcagctt gcctccccac cgggtccatc aggccggccg gagggacccc
44161 ggcggcccgg tgtcagtccc ccctgcagcc gcccagtctc tgcctccagg caagggcgcc
44221 agcttttctc cccccagcct gaggcccagt ctcctgtgca ctgtctgtaa agtccagcct
44281 cccacgcccg tccacggctc ccgggcccag cctcgtccac ccctccccac ggtggacagg
44341 ccctctgtcc acccgggcca tccccgcccc cctgtgtcca ccccagtccc gtccaggggg
44401 gactttatgt gacccttggg cctggctccc catagactcc catgtaagcc tgcctcgagt
44461 aggtgcctcc agagcccctt ttgccccct ggcggcccag cccgaccccc gggcgccccc
44521 aaactttgtc cagatgtcca ggggtccccg agggtgaggc ccagcccccct cccgcccctg
44581 tccactgccc cggtcccccc agaagccccc aaaagtagag gctcaggcca tgcgcgccct
44641 gtcaccaggc ctgccaaaga gccagatcta aggccgggag aggcagcccc aaagcgggtg
44701 cagtaacagg taatctctgg tagtgatttg gacccgaaat ctgacacttt agagctctgg
44761 aggactttaa aactctaaaa atcaaaactt tagaggcgaa tgggcgccat tttgtcccca
44821 cgcgcgcata atggcggacc taggcctaaa acccccagga agcgggtcta tggttggctg
44881 cgctgctgct atctttagag gggaaaagag gaataagccc ccagacaggg gagtgggctt
44941 gtttgtgact tcaccaaagg tcagggccca agggggttcg cgttgctagg ccaccttctc
45001 agtccagcgc gtttacgtaa gccagacagc agccaattgt cagttctagg gagggggacc
45061 actgcccctg gtataaagtg gtcctgcagc tatttctggt cgcatcagag cgccaggagt
45121 ccacacaaat gtaagagggg gtcttctacc tctccctagc cctccgcccc ctccaaggac
45181 tcgggcccag tttctaactt ttccccttcc ctccctcgtc ttgccctgcg cccggggcca
45241 ccttcatcac cgtcgctgac tccgccatcc aagcctaggg gagaccgaag tgaaggccct
45301 ggaccaaccc ggcccgggcc ccccggtatc gggccagagg taagtggact ttaatttttt
45361 ctgctaagcc caacactcca ccacacccag gcacacacta cacacaccca cccgtctcag
45421 ggtcccctcg gacagctcct aagaaggcac cggtcgccca gtcctaccag agggggccaa
45481 gaacccagac gagtccgtag aagggtcctc gtccagcaag aagaggaggt ggtaagcggt
45541 tcaccttcag gggtaagtaa cctgacctct ccagggctca cataaaggga ggcttagtat
45601 acatgcttct tgcttttcac aggaacctgg gggctagtct gggtgggatt aggctgcctc
45661 aagttgcatc agccagggct tcatgccctc ctcagttccc tagtccccgg gcttcaggcc
45721 ccctccgtcc ccgtcctcca gagacccggg cttcaggccc tgcctctcct gttacccttt
45781 tagaaccaca gcctggacac atgtgccaga cgccttggcc tctaaggccc tcgggtcccc
45841 ctggaccccg gcctcagcaa ccctgctgct cccctcctgc caccccagcc tcccccccctc
45901 cccgtccccc ttcgctcctg atcctccccc ggtccccagt agggccgcct gcccccctgc
45961 acccagtacc tgcccctctt ggccacgcac cccgggccag gccaccttag acccggccaa
46021 gccccatccc tgaagaccca gcggccattc tctctggtaa cgagcagaga agaagtagag
46081 gcccgcggcc attgggccca gattgagaga ccagtccagg ggcccgaggt tggagccagc
46141 gggcacccga ggtcccagca cccggtccct ccggggggca gagacaggca gggcccccg
46201 gcagctggcc ccgaggaggc gcccggagtg gggccggtcg gctgggctgg ccgagcccgg
46261 gtctgggagg tctggggtgg cgagcctgct gtctcaggag gggcctggct ccgccgggtg
46321 gccctggggt aagtctggga ggcagagggt cggcctaggc ccggggaagt ggagggggat

Fig. 3 (cont.)

46381 cgcccgggtc tctgttggca gagtccgggc gatcctctga gaccctccgg gcccggacgg
46441 tcgccctcag ccccccagac agaccccagg gtctccaggc agggtccggc atcttcaggg
46501 gcagcaggct caccaccaca ggccccccag acccgggtct cggccagccg agccgaccgg
46561 ccccgcgcct ggcgcctcct cggggccagc cgccggggtt ggttctgccc ctctctctgt
46621 ccttcagagg aaccagggac ctcgggcacc ccagagcccc tcgggcccgc ctccaggcgc
46681 cctcctggtc tccgctcccc tctgagcccc gttaaaccca aagaatgtct gaggggagcc
46741 accctcgggg cccaggcccc agagtccaga ggtcaggggc acctcagggt gcctccccgg
46801 gtcccaggcc agccggaggg accccggcag cccgggcggc cccagaggcc ggttcctcgc
46861 cccttccccg ggcttcagag cccaggatgt cccccagaag ggaccctagg cgtcccctct
46921 cctcccctcc aggcccgagc ctctccctcg cggagagggg cctctttggg ccctcaagtc
46981 cagccccacc gagacccgag tggcccggat ccccccaccg gcccttctct ctgtcccccct
47041 gctcctctcc aaccttcgct ccaccctaga ccccagcttc tggcctcccc gggtccacca
47101 ggccagccgg agggaccccg gcagcccggg cgagtcgcct tccctctccc ctggcctctc
47161 cttcccgcct cccacccgag ccccctcagc ttgcctcccc accgggtcca tcaggccggc
47221 cggagggacc ccggcggccc ggtgtcagtc ccccctgcag ccgcccagtc tctgcctcca
47281 ggcaagggcg ccagcttttc tccccccagc ctgaggccca gtctcctgtg cactgtctgt
47341 aaagtccagc ctcccacgcc cgtccacggc tcccgggccc agcctcgtcc acccctcccc
47401 acggtggaca ggccctctgt ccacccgggc catccccgcc cccctgtgtc caccccagtc
47461 ccgtccaggg gggactttat gtgacccttg ggcctggctc cccatagact cccatgtaag
47521 cctgcctcga gtaggtgcct ccagagcccc ttttgccccc ctggcggccc agcccgaccc
47581 ccgggcgccc ccaaactttg tccagatgtc caggggtccc cgagggtgag gcccagcccc
47641 ctctcgccca agctgctttg attcctggga tatttttggg aatggtgtta actttctccc
47701 cttgtatttg ctattcaatc aacctgattc cccctgctca tacctccact tacaaccaag
47761 ccactacggc cacgtccccg gcctcccgct cgggtaagtg ctttttcatt tttagcccca
47821 gcccctcctc tataagttct aggcaaacct ccaatcacca gccaccttcc aatgtagtct
47881 cttagagagt ggctgctacg cattagagac cactttgagc cacccacagt aaccacccag
47941 cgccaatctg tctacataga agaagaagag gatgaagact aagtcacagg cttagccagg
48001 tgatttgtga atttcagttt atttactttc ttccaatcaa gctttcccag cctccgcttg
48061 ttaggtccta gttatgggtt ttccatgggg gacttagtat ccgttctatt agattaacgt
48121 gcaagacgct aaacttaacc aaggtcagcc aagggacgcg tgttatccca ggctgcccac
48181 cctgaggatt tccccccaaa atcctcctac cctctcttta tgccatgtgt gttgttggct
48241 tgtgttagtg ctatgtaatg cgttgccgcc aggtggcagc ctgtttatag atgtgcagta
48301 ccccttaatg ttaggtctgc tttagggctg ccaggtggcg caatctagga ttaattcacc
48361 tgtatccctt tccctccacc cgcagtaacc cagcactggc gtgtgacgtg gtgtaaagtt
48421 ttgcctgaac ctgtggttgg gcaggtacat gccaacaacc ttctaagcac ccgcgcttgt
48481 gttttgcttt atctgccgcc atcatgccta cattctatct tgcgttacat gggggacaaa
48541 catatcatct aattgttgac acggatagtc ttggaaaccc gtcactctca gtaattccct
48601 cgaatcccta ccaggaacaa ctgtcagaca ctccattaat tccactaaca atctttgttg
48661 gggaaaacac gggggtgccc ccaccactcc caccaccccc cccaccacca cccccaccac

Fig. 3 (cont.)

48721 ccccaccacc cccaccaccc ccaccacccc caccacctcc accaccttca ccaccacccc
48781 cgcccccacc acccccacca cctcagcgca gggatgcctg gacacaagag ccatcacctc
48841 ttgataggga tccgctagga tatgacgtcg ggcatggacc tctagcatct gctatgcgaa
48901 tgctttggat ggctaattat attgtaagac aatcacgggg tgaccggggc cttattttgc
48961 cacaaggccc acaaacagcc cctcaggcca ggttggtcca gccacatgtc ccccctctac
49021 gcccgacagc acccaccatt ttgtcacctc tgtcacaacc gaggcttacc cctccacaac
49081 cactcatgat gccaccaagg cctacccctc ctacccctct gccacctgca acactaacgg
49141 tgccaccaag gcctacccgt cctaccactc tgccacccac accactactc acggtactac
49201 aaaggcctac cgaacttcaa cccacaccat caccaccacg catgcatctc cctgtcttgc
49261 atgtgccaga ccaatcaatg caccctctta ctcatcaaag caccccaaat gatccagata
49321 gtccagaacc acggtccccg actgtatttt ataacattcc acctatgcca ttaccccccct
49381 cacaattgcc accaccagca gcaccagcac agccacctcc aggggtcatc aacgaccaac
49441 aattacatca tctaccctcg gggccaccat ggtggccacc catctgcgac cccccgcaac
49501 cctctaagac tcaaggccag agccggggac agagcagggg gaggggcagg ggcaggggca
49561 ggggcagggg caagggcaag tccagggaca agcaacgcaa gcccggtgga ccttggagac
49621 cagagccaaa cacctccagt cctagcatgc ctgaactaag tccagtcctc ggtcttcatc
49681 agggacaagg ggctggggac tcaccaactc ctggcccatc caatgccgcc cccgtttgta
49741 gaaattcaca cacggcaacc cctaacgttt caccaataca tgaaccggag tcccataata
49801 gcccagaggc tcccattctc ttccccgatg attggtatcc tccatctata gaccccgcag
49861 acttagacga aagttgggat tacatttttg agacaacaga atctcctagc tcagatgaag
49921 attatgtgga gggacccagt aaaagacctc gcccctccat ccagtaaaaa cccttgccct
49981 ctccagcaac caatgtatcc caaataaatg ttacttcttt tgctcttaac cattgacacg
50041 cctgtcattc tatcaattaa acaagggaaa aaggtttagc tattccacca acacgacccc
50101 aaggaaggct tgccaaaatt ggtgccttgc tctcagcact ttgccagcaa cttatagcat
50161 ggtaggcagc tcaactcggc ccgtcttact gcccagccta ctctccactc ccagtccatg
50221 ttcgcactcc tatgcatttc ctgccctccc acttttaccc cagtcccaac ccaaaaccac
50281 acacaacaca tagaattgtt agtttaaaca gtttattgat aggtggctgc ttttagccta
50341 attgtgtatt gctctcgttg ccaaaacctg ttgtaagggc cggcacccgc aacatgggga
50401 aaacataacc gccgccatcc catggggagg gtagaggcgg ttgacatgta ggtgagtagt
50461 gtaagaagca tggcgaagta gacaggttac ttttagagtg tagtgtacag ggccgggcgc
50521 aacagtgcca ccaacccggg gtctgagcat tccatgggca gcagggacac tgcactaccg
50581 ccaggtcctg ggcagccggg ggttcctggc gctccggggg cagccgggcg gccgccggtg
50641 ggtccgctgg gccgctgccc cgctccgggt ggggggtggc cccgctgggc accgctgcgc
50701 cgccgccagg tcctggggca gccggggttc ctggcgctcc gggggcagcc gggcggccgc
50761 cggtgggtcc gctgggccgc tgccccgctc cgggtggggg gtggccccgc tgggcaccgc
50821 tgcgccgccg ccaggtcctg ggcagccggg ggttcctggc gctccggggg cagccgggcg
50881 gccgccggtg ggtccgctgg gccgctgccc cgctccgggt ggggggtggc cccgctgggc
50941 accgctgcgc cgccgccagg tcctggggca gccggggttc ctggcgctcc gggggcagcc
51001 gggcggccgc cggtgggtcc gctgggccgc tgccccgctc cgggtggggg gtggccccgc

Fig. 3 (cont.)

51061 tgggcaccgc tgcgccgccg ccaggtcctg gggcagccgg ggttcctggc gctccggggg
51121 cagccgggcg gccgccggtg ggtccgctgg gccgctgccc cgctccgggt ggggggtggc
51181 cccgctgggc accgctgcgc cgccgccagg tcctggggca gccggggttc ctggcgctcc
51241 gggggcagcc gggcggccgc cggtgggtcc gctgggccgc tgccccgctc cgggtggggg
51301 gtggccccgc tgggcaccgc tgcgccgccg ccaggtcctg gggcagccgg ggttcctggc
51361 gctccggggg cagccgggcg gccgccggtg ggtccgctgg gccgctgccc cgctccgggt
51421 ggggggtggc cccgctgggc accgctgcgc cgccgccagg tcctggggca gccggggttc
51481 ctggcgctcc gggggcagcc gggcggccgc cggtgggtcc gctgggccgc tgccccgctc
51541 cgggtggggg gtggccccgc tgggcaccgc tgcgccgccg ccaggtcctg gggcagccgg
51601 ggttcctggc gctccggggg cagccgggcg gccgccggtg ggtccgctgg gccgctgccc
51661 cgctccgggt ggggggtggc cccgctgggc accgctgcgc cgccgccagg tcctggggca
51721 gccggggttc ctggcgctcc gggggcagcc gggcggccgc cggtgggtcc gctgggccgc
51781 tgccccgctc cgggtggggg gtggccccgc tgggcaccgc tgcgccgccg ccaggtcctg
51841 gggcagccgg ggttcctggc gctccggggg cagccgggcg gccgccggtg ggtccgctgg
51901 gccgctgccc cgctccgggt ggggggtggc cccgctgggc accgctgcgc cgccgccagg
51961 tcctggggca gccggggttc ctggcgctcc gggggcagcc gggcggccgc cggtgggtcc
52021 gctgggccgc tgccccgctc cgggtggggg gtggccccgc tgggcaccgc tgcgccgccg
52081 ccaggtcctg gggcagccgg ggttcctggc gctccactgc acctggaatg cagggtgggg
52141 gcgtggtccc ctggacccca gccccgccga tccctccccc agggcgtacc cggcttgcct
52201 ggttctgggg ctcctctggg ggtcgctgca tccgccggta gggttcgaat gggcgtggtc
52261 cgcttgctct gctggcccgg tacgcctgga ttgccggctg ggggctgggg tcccgggacg
52321 cccctccct gctcccaccc ggttccctcc cccagggcgt gccccgcttg cctggtcctg
52381 gagctcatcc ggggatgctg catccgctag tccgacctgg gtgggtgcgg tccgctggcc
52441 ccaccctggg ggtagccgcc gggtctgctg gtccggtgca cctggaaggc aggggggggg
52501 gcagtgaggg aggggcgtgg tcctgggacc ccgcgccgac tggcaggggg tccccatggc
52561 acaggcctag gggtccaggg ggcagccgcg gcccagcgcg ccccgttcac gggggaggac
52621 cgcggccgag ccaccagggg cccggcgggg gtggggggtg cgctcccagg ccggaccctg
52681 gtgccaggca gggaccccgc gccaccccgct tcatgggggg ggaggccgcc gcaaggacgc
52741 cgggccggct gggaggtgtg cacccccccga gcgtctggac gacgctggcg agccgggccg
52801 gctcgccttc ttttatcctc tttttggggt ctctgtgtaa tactttaagg tttgctcagg
52861 agtgggggct tcttattggt taattcaggt gtgtcatttt agcccgttgg gtttcattaa
52921 ggtgtgtcac caggtgggtg gtacctggag gttattctat tgggataacg agaggaggag
52981 gggctagagg tccgcgagat ttggggtagg cggagcctca ggagggtccc ctccataggg
53041 ttgaaccagg agggggagga ttgggctccg ccccgatata cctagtgggt ggagcctaga
53101 ggtaggtatc catagggttc cattatcctg gaggtatcct aagctccgcc cctatatacc
53161 aggtgggtgg agctaggtag gattcagcta ggttcctact ggggtacccc cctaccctac
53221 cttaaggtgc gccacccttc ctccttccgt tttaatggta gaataaccta taggttatta
53281 acctagtggt ggaatagggt attgcagctg ggtatatacc tataggtata tagaacctag
53341 aggaagggaa ccctatagtg taatccctcc cccccctacc ccccctccc ttacggttgc

Fig. 3 (cont.)

53401 ctgagcccat cccccacccc agcaccccgg ggtgacgtgg caccccgcgt gccttactga
53461 cttgtcacct ttgcacattt ggtcagctga ccgatgctcg ccacttcctg ggtcatgacc
53521 tggcctgtgc cttgtcccgt ggacaatgtc cctccagcgt ggtggctgcc tttgggatgc
53581 atcactttga gccactaagc ccccgttgct cgccttgcct gcctcaccat gacacactaa
53641 gcccctgcta atccatgagc cccgccttta ggaagcacca cgtcccgggg acggaagggg
53701 acttggggtg attttctatg tgggggtgga aatatgagca agaataagga cggctcctta
53761 ttaacctgat cagccccgga gttgcctgtt tcatcactaa ccccgggcct gaagaggttg
53821 acaagaaggg tcaaggtttc gtctgtgtgt tgaagggcag gggctgttgg gtgcatctgg
53881 aacggcttac ctcgggtaac tgtttgccat taaaaggttg gggattaggt ttagcccctt
53941 tagctgccat ttcgaaccgg ggtgtgcaga tgcaggtctc cgggtgggca ggcagtacga
54001 gatgtcacgt tgtgttgtct ttcctcccac ccctgtcctg gctgtggcaa atgcgaccct
54061 catagagttg tgtttcaggt ctgtgtcctg ttttgcggtg ggttatttct tccctcagtg
54121 tttgccagct tatttcccca gttttcacgt actggggcct gtggacacct gagggagcgg
54181 ccgttggtgg gtatgtgttg gaattgctcc caccctcaat tttcgcttgc cttcttccct
54241 tgttaacctg atagcatagc ctctaggttt ccttgtaggt ctgtttgggt ttgttggttc
54301 acgtggtgct aacttgaatt ttttggtttt ctagttccct cttaattaca tttgtgccag
54361 atcttgtaga gcaagatggc ctattcaaca agggagatac tgttagccct gtgtatacgg
54421 gacagtcgtg tgcatggaaa tggtaccctg catcctgtgt tggagctagc agcaagagaa
54481 acacctctcc gcctttcgcc agaggacact gtagttctgc gttatcatgt gttgcttgag
54541 gagataattg aacgaaattc agagacattt acagaaactt ggaacagatt tataacacac
54601 accgaacatg tggatctgga ttttaactca gtatttttag agatatttca ccgtggagac
54661 ccaagccttg ggcgcgcgtt ggcctggatg gcctggtgca tgcatgcctg caggacattg
54721 tgttgtaacc agtctactcc ttactatgtt gtggacctgt cagttcgtgg gatgttagaa
54781 gccagcgaag gcctggatgg ttggattcat caacagggcg gctggtctac attaattgaa
54841 gacaacattc ctggatccag aaggtttagc tggactttgt ttcttgctgg actgactttg
54901 agtctgttag ttatatgtag ttatttattt atctccagag gaagacacta atctatacat
54961 tttctcagca ctttatatga atcagggtca ttgggcctgc ggggaactga gccagtagga
55021 tattaggcaa gggtgacaca gtgcccatgc attataattt aaccaaacag tggtcgtgag
55081 ttttaggccg gccatggggg cttacaagaa taacatgcca atgacccggc ccccactttt
55141 aaattctgtt gcagcagata gctgataccc aatgttatct tttgcggcag aaattgaaag
55201 tgctggccat atctacaatt gggtgtccta ggtgggatat acgcctgtgg tgttctaacg
55261 ggaagtgtgt aagcacacac gtaatttgca agcggtgctt cacgctcttc gttaaaataa
55321 cacaaggaca agatactaaa gaaataactg aggtgagtgt gggaagatgg gaatactatg
55381 tgttatgtta acgggtgaga gcctatactg cagcccagac tcggggggag gaggaaatgg
55441 taagagttat actctactta tcttttttga cactacattt aactgttatg taacaatgtt
55501 tgcttatttt catgttcaat aaacgctatg ttaatgatga agaacctgtg ttctttggaa
55561 gtgggcccaa tggggtagta ggttttggga gggtgccgtg ctagatattt caactgccac
55621 agaccccatt ttgtcccacc tgttaccaca ttctaggtcc tgcatccagt gggccaggtg
55681 tctcaccatg gctctttcta ggtggatacc acagtccagg cccccaaggc taccgtgcta

Fig. 3 (cont.)

55741 attacctcct catgtccacc cccaccctgt gttactgtcg cctgattatc ctggcttagc
55801 agcctccaag ttttacaaga cgtcccattg ccctgccctt ggtccaagtc tcgccggttt
55861 tcagcagcct gttgtagcct gcccccaagt ttcgcaggtt tcccccatgc ttccacccgt
55921 taacccaata gcatgacagc caatccaaca cgaggcaagt tttaagagtt aaaagcaact
55981 actgtttatt ttccaaaatg agctgggtat agttgatgat ctgtaggcgc agctcatccc
56041 cacattccag gtccttgatg gcctcgtaga tggcatcttc gtcgacattg acagccttct
56101 catataccgt gtctctgggg ctgaccttta tacagaaggc gtcccctact aggtccacgg
56161 ccagctcgta ggtggggcct atgttttcac ataacagttt caagcaggtc tctgggatgt
56221 gaagggaggt gccctggagc aggagatgca tgattaggcg cccttttcca tttgtgctga
56281 agatggggca gatggtgcca caaaagtgtc cggtgaccag gtaagcgtag agaaggctgg
56341 gttgggaaag tccagccttt actgcactgg gagagctgct gagcagagac acatagaagg
56401 tcttgttggg tattatcttg tggacattgt tgaagaagga gagctgggtg gagctaaact
56461 cctgaggcac atgaacctgg gacctattga tgcagatctc gcagtgagac cccagagtca
56521 ggctgtggcc gaagggagac aggcgaaggc agcgcccggg ggagagagtg cacagtgaca
56581 gtgggagaaa cacggcctct gagacatgta tgggggtgtt catctcacgc agaaaatctt
56641 tgcccagctc aaagttggca gagattcccc tgaagaagtc ccgtagtgaa aaatgggatc
56701 tgtctacacc atgtctggtg tgccgggaac atattgatcg ggccacactg ccaacccttt
56761 ccattcttcc cagctctgag cgagattttc cacacctgga caccgacttc acgctatgcg
56821 ccgaggcctt tgaggccgtg tagtttctgt ggtgcggatg cattaggcgg cgcaatgcgg
56881 gatctgccgg tcgctgttgg cgtgcattca cggcatctgg ggtgaccggg gccatcgggt
56941 ttacttttca cacgtagacc tgggaagttt gataggactg taccaggtca aggccgtgga
57001 tgcgcaggac cacgtccagt tccttagtga catccacgag gattgttttg cccactctgg
57061 ccacttgtgt ggatttaaat atgtacacaa gcgtaattaa cgagtcacag accccctgtt
57121 ccagattctg accggctgca agcgctgcct taaaggcctg gaagctgggt gggtaaatct
57181 gaccaaacag cacgctcgga ttcgtgatgc tgtggttgat ggcacacagg gggtcgcaga
57241 acaggtgctt gtggaagtct tgcggggtgc acatctgcag ccaggcccctt agcctggggc
57301 atggcacatc cagcagcgtg ttttgggtct tgatgaggaa cacgatcctg tctaggattt
57361 tgatgttgtt gccgaacgag tcaagaatca ggctcttgaa gcggtcaagg gtgtccttgg
57421 cgtccgggtg ggccccgagg ctctcgcaga gtgggcagat ggtccgtgag gcattcttgt
57481 gccttagtcc aaacatgggg gccaggaggc aggggccctg cgaatggtcg ccagcctccg
57541 gtctggtgat ggccagggcc aactccgcca gctcatcgcc gctgtattcc gcgtttaaac
57601 cgatagcatg gtggcctggc cccccgagca ggtccgtccc ctgccacgta cctaatagta
57661 gtccacagta gtcggccttg gttgtaattt caggagagag tcctcccttt tcggccctga
57721 gaaatggatg ctgaactcgg tttctggtag gcaggtggca gcacagggcg gtgtacaggc
57781 ccctgccgac gtcccctggg acatcctggg aatctttgca ggttctgggt ccagggaggg
57841 taagaaaagt gggggtggtt ctgggccaca tggacttgaa gcagaagttg gccggggact
57901 ggccggtgag gatggatttc agaaactcca atttgtagta gccgaggttg gcatttctaa
57961 tcatgtcaga agaggacaca gggaggaagc accggcaaat gtaaaagtga agctggatgt
58021 caatggcaag aatcctggag ggcatgaaga gggaatccaa ccccccggcc atggggaagt

Fig. 3 (cont.)

58081 attttatcag gatgtgtaaa aagtccatgc ctgtgatgag gctagagatc caggctcgtg
58141 gggcatttag acagtagtag cagagcaggg catagtcctc aaagaaggcc acgggggcat
58201 ctgagtgatt gaccagggtg tcgagcagat cacaaactcg gcaggtgctg gctggagaga
58261 gggactcgta ggtgtggacg agtggtgggt aggctatgcc ttcttccgcg ttggctggaa
58321 gataggagtg ggccatcaaa aggccgactg cctcgaactg gcttttcaga ttgtccacgg
58381 tccagggcac aaagtcctcc atctttggag ttctgcccgc gatctgtgcc acctctgtta
58441 cgccactcct cgtgaggggg cagctggaca gtctttttcc ggtcaggggg tttggctcgt
58501 ttgcgctcgt gactttgtga gccatgacac atctgggtgg caaggtgagg tcttctgggt
58561 ttttaatacc ggggtcggca ccagtttctg ggacaccgcc acaaggacaa ggtgggctag
58621 caagttctcg agtctacgaa gactccgggg gcagtctttt gagtttctcg cctatgatcc
58681 accccaatct cgccccccta attgcgccat ctgcctacgc gaggctgaac ctcctgaatc
58741 actgcatctt tcttgaggcg tttaaagaag agaatagtgg ccagggcctc ggtggggtcc
58801 agcgtgaggt cttatttttg aaaagggata ttataaaaca ggtcattgct cggattgtgg
58861 cagccgatag caccctagat ctagtgaatc atggcgagcc cggaagagag gctcctagac
58921 gagctcaata acgtaattgt gtcatttctg tgtgactctg ggtctctgga agtggagaga
58981 tgctccgggg cgcatgtgtt ctccaggggc agctcccaac ccctctgcac cgtgaagctg
59041 cgccacggac agatttacca cctggagttt gtctacaagt tcctggcctt taagctgaag
59101 aactgcaact acccctcctc gcccgtgttt gtgatatcca acaacggcct ggccaccacc
59161 ctgaggtgct ttttgcacga gccgtcgggt ctcagatcgg gccagagcgg cccttgcctg
59221 ggtctctcaa cggatgttga cctaccaaag aactccatca ttatgctggg ccaggatgac
59281 ttcattaagt tcaaaagccc cctggtcttc cctgctgagc ttgatctcct gaaatctatg
59341 gtggtctgcc gggcctacat cacggaacac cggacgacga tgcagtttct ggtgtttcag
59401 gccgccaacg cccagaaggc ctcgcgggtc atggatatga ttagtgatat gtctcagcaa
59461 ctgtctcggt ctggtcaagt cgaggatacg ggcgccagag tcacaggtgg aggaggtccc
59521 aggcctggcg tcacgcactc ggggtgtctt ggggactcac acgttagggg gcgcggtggt
59581 tgggacttgg ataacttttc agaagctgag accgaagacg aggcgagtta cgctccttgg
59641 agggacaaag actcgtggtc ggaatccgag gcggcgccgt ggaagaagga actcgtgagg
59701 cacccccatcc gcaggcaccg gacacgcgag actcgccgta tgcgcgggag ccattcacgg
59761 gtggaacacg tgcccccccga gacccgggag acggtggtgg ggggagcatg gcgttattct
59821 tggcgcgcca caccttatct ggcacgggtg ctggctgtca cggccgtggc cctgctcctg
59881 atgtttctga ggtggacctg acgttgcagg cccttgggga gcgggggttc tccaggctcc
59941 tggatctggg gctggcctgc ctggatctga gctatgtgga aatgagggaa tttgtggttt
60001 ggggcaggcc cccagcttct gaggcggctg tggcctctac gccaggctcg cttttccgaa
60061 gccactcgtc cgcctactgg ttgtcggagg tggagaggcc cgggggcctt gtccgctggg
60121 ccaggtcaca gaccagcccc tcatccctga ccctcgcgcc ccatcttggc ccgtccctct
60181 tgtccctttc agtggtcacc ggtggtgggt gtggagccgt ggccttttgc aacgcctttt
60241 tcctagctta ttttttggtt gtgcggtctg ttttccccgc gttttccgat agaatagctg
60301 cctggatctg cgaccggtcc cctttctgcg aaaacacccg ggccgtggcc aggggttacc
60361 gaggcctcgt gaagaggttc ttggcattcg tgtttgagcg tagtagctat gacccccccct

Fig. 3 (cont.)

60421 tgttgaggca aaactctagg cctgtggagc gctgctttgc catcaagaat tatgtcccgg
60481 gcctggactc acaaagctgt gtgacggtcc cgagcttctc ccgctgggcc cagtctcacg
60541 ccagcgagct cgatccccgg gagattcgcg acagagttac accagcgact gcaccttcgt
60601 tcgtggctga tcatgcctcg gctctattgg cctccctcca gaagaaggcc tccgacaccc
60661 cctgtgggaa tcccattcag tggatgtggt accgcctgtt ggtaaactcg tgcctgagga
60721 gtgcccactg tcttctgcct atacctgccg tctctgaggg ggggagaaag acgggcgggg
60781 gcgtagggga ggagctcgtg gggggccgggg ggccctgcct gagccgggat gttttcgtgg
60841 cgatcgtaag ccgcaatgtt ctctcgtgtc tgctgaacgt gcctgccgcg ggtccccggg
60901 cctacaagtg tttcagatcc cacgcctcca gaccggtgtc tggcccggat taccctccct
60961 tggccgtgtt ttgcatggac tgcggttact gcttgaactt tggaaagcag acaggtgtag
61021 gaggcaggct caattccttt agacccactc tccagtttta tccccgtgac cagaaggaga
61081 agcatgtgct gacctgccat gccagcggcc gtgtgtactg ctccaactgc ggctctgcgg
61141 cggtgggctg ccagaggctg gctgagccac cgagcgcccg ctcgggctgg cggcccccgaa
61201 tccgggcagt gctgccgcac aacgcggcct acgagctcga ccgtggctcc cgcctcttgg
61261 atgccatcat cccctgcttg ggacccgacc gcacttgcat gcggccggtg gtcctgcggg
61321 gggtgacggt caggcagctc ctgtatttaa ctttgcggac agaggccaga gccgtttgct
61381 ccatctgtca gcaacgccaa gctccagagg acgcccgcga cgagcctcac ctgttctcct
61441 cctgtttaga ggtagaattg ccacctggtg agcggtgtgc gggctgccgt ctctatcaga
61501 cgcgttatgg cacgccggct gcccaagccc accctccagg ggaggctgga ggcggatttt
61561 ccagacagtc ccctgcttcc taaatttcaa gagctgaacc agaataatct ccccaatgat
61621 gtttttcggg aggctcaaag aagttacctg gtatttctga catcccagtt ctgctacgaa
61681 gagtacgtgc agaggacttt tggggtgcct cggcgccaac gcgccataga caagaggcag
61741 agagccagtg tggctggggc tggtgctcat gcacaccttg gcgggtcatc cgccaccccc
61801 gtccagcagg ctcaggccgc cgcatccgct gggaccgggg ccttggcatc atcagcgccg
61861 tccacggccg tagcccagtc cgcgaccccc tctgtttctt catctattag cagcctccgg
61921 gccgcgactt cgggggcgac tgccgccgcc tccgccgccg cagccgtcga taccgggtca
61981 ggtggcgggg gacaacccca cgacaccgcc ccacgcgggg cacgtaagaa acagtagagg
62041 gcacgaaaca tggtgtatgc actttattaa taaacaatta cagatacaaa aacttgagtc
62101 tctcgaggtc tgcgatgagg cggtgggtgg aacgctccag cttgcggcga agctggctca
62161 cgaagcgaga cagtactcgg ctagcctgac taagggtgag gctataacgc aggtcctgtt
62221 ccggggcggc ggtggataga gaggaggggg atccggaggg gaccactagg tcgccggagg
62281 tcgaccctcc tgtcaccacc tccctgataa tgtcttcaat agacagaaat tgggtgacca
62341 ctgagggagt gttccacagt aatgttgtct ggtcgctaga tggcgcgggt gaggccacgc
62401 tttgcgaaaa cgaaagtgct tgaaaaggcg cgggatagcg tgcgctaccg gatggcgggt
62461 aatacatgct atccttacat tttggcattt tgggcagctg ggaggcggcg gatgggggtg
62521 cttcttttcg cacggtgtat gtttggggac ccgcatgccg gtactgggat aggcgcacct
62581 cgggccgcgc gccaggctcc gagccggaat gcattggggg caatgggatt gcgggggatt
62641 gttgctgtct gctcctgaca gggagagaca cgcgcggcgg agatgcagcc gacggcgggg
62701 ccgcggtggg ctgcccccga ggacgggcgc cggccgccag cgcccccgtg gcctttggca

Fig. 3 (cont.)

62761 cgggcctggc acccaccgct ttaattgtgg gggtgggcag ggcagctgca tcttggggcc
62821 tttgtgcttg cgttttttgg gggcgcggtg ccaatgcacc aactggggtg tgcgccgggg
62881 cggccaagcc ggaccccagg gcgggtgcct gggggatggg aaagccggac ggcgcttctc
62941 ccgggtcgaa cgctggagta gcggaggctg ctgcgccggc ggccaccacg ggcgcacggg
63001 gtcgcagccc gacggccgtg gggaggcggg tggcggaggg ccgaatctcc gcggcttctt
63061 cccggccccc ctgctgtttc ttctcccgtt gcatgataga atggccatag ggtgggtcct
63121 gagaggaggc ttgtgtgtcc tggggctgga gcccaaaagt cgttaaagat gccgctgatg
63181 gtgtgggagc tatgcctccc gtcgactggc cgggcttgta gggggctgag ggtggataac
63241 tgggcttctg tgaaggcacc aaccctggaa tctggatggt atgtttcttc tgtgaccccg
63301 aggcagtcga tggtgtagag tgtggagaca atgtgtagac gatgggccct tgttcagaag
63361 cccagggact tgagggggc tgttgtggtg ctggttgggg aaggagctcc agggaatctt
63421 tgggccatgg ccttggggag cttcccggag accggtctgg gctctcggaa gccctcgttt
63481 cggccccgaa atagggcctt gccatcaatc gggggcctgg gagagtgatg ggggcggcca
63541 atcccggggt aactgtcacg tcccgggggg aggaggtagg agacagccag tccctgggcc
63601 tgccaggggc caccttctct aagaggggc tctgtgggct gggagggcca gaggcctcag
63661 attcagcagt agtgctcccc ttttccccct ggtccgtctc ccctcctccc aactgctgga
63721 gccggtcgga ggaggccggg gtgttatctg ctgactgaaa cccgtccccg ctgaccagtc
63781 cgtgccccac ccttgggggg aaaccggaga acagctcctg gacgttgcgt ggattcgggg
63841 gaagctggta tccaaccggc agtggaggat cttcgtgctc gtagaaggag ggttgagta
63901 catcggtcgg ccatcgtgag gccccggccg cgttaaagta gaactgcacg tccggcagat
63961 tgtgccgata ggtgaaacac ttccagatga tgttttttct gttggccagg atggccacgg
64021 tggggggcct ggcctcctta ggtttggcgg ccctggcctc ggtgagaagc tcgcgtagcc
64081 acacggcctg gcgtgcaaag atggacatct ctggctcgaa agactcggag tagccgtcca
64141 ggtcctgcag aaaattcagc gagatggtct ccaccaggga ccggaagggc tcagagtgcc
64201 cgtcgcagta gaggagggga gcaacgaccc tgacctgtcc cagggtcttc aggttaaaca
64261 gatattgaga ggagacaaag agagttaggg gccgaccgag gaaggccgcc gccacggccg
64321 cctcaaaaac ggagacgggg atggtgtcac cggagcccct cttaggaccg gtaatgggag
64381 tgccataagg cataagattt ctcagggccc ggccggtaac ggtgccgtag gaagacgggg
64441 tttcgcgggg gacctcgagt ccctccgccc tggggagctc ttctccgcgt gtataggcct
64501 gcttcacaaa gtcgcgcagg tagtcctgaa atgcgaccgg gccctccagc gggcgcaatg
64561 agtgccagag ctgctgaagg gcctcggggg cgaagcaccg gcgtgcgagg agcagcatgc
64621 aggctcgggc gcgggccgta ctttggttgt ggaccaggcc caagaactcg gggtgcggcc
64681 agagggcggc tcgggtatcc atctcctccc aggcgtcctg gaagaagatg aagccggtgg
64741 gtggaccggc gatgcggtgg cgggtgaggc ggcgcgcgtc ttccccgtcg ttgctgccgc
64801 gggtggttga gggcatgccc cccctcccgg aggctggact cctgaccagc ctgtaggtga
64861 ggaccgagtc cgacaggagg tctcccaaac ccccatctct cgctagagcc gagaccaggc
64921 cgagtcctgc gtagaacgat ggggcgccca ggaaggcggc agcgtaggcc ggatgtgtgc
64981 cgaccagcag cgccatcatc tcccgttgtt ccaatagaat aacttcccgg tctgtggccg
65041 gggctggata agggggtga ttcctagagg cgatgagact ggcgtgcgct aaaagtgtca

Fig. 3 (cont.)

65101 tggccacaat ggggttgtct gccaggtctt ccatcagggc tttgggcgca gagacgtatt
65161 cccgaagcag ctccccggcg ttggactcca cgtcgggcca ggtgtcccag taggagtcgg
65221 cggcggcggc gctgaggcgg gcggaagcta cactggccag ggttcttctc ctcctctctt
65281 ggtcatcctg cgggggacca atagcttggg ggcgtccggc tggggtcagg gaaaaggcct
65341 ctgggttctc cagcacggtg ggcatgacat attccagaaa gttgtggtag acggggatgt
65401 agttgagcgg ctcctgggtg tctgcggaga cgtaggccgg gttaaggggg tcgcagggag
65461 actctgtttc cagccagagg gtgccggcgt atttcgccgg ccctgccgcc gccagaaatt
65521 gtgcccgccg ggtcggggct ccattgcccc atccagttgg tggtgccgaa atcgtgatga
65581 ggaggggcag gttgttggtc aagggatgct taacgaaaac ggtaggctgg gcggtctcgt
65641 aaaaagccag gaaactctgc ttggccgagg catagcgcag cagcttgtcc ttgaggaggg
65701 catactggga gccagccgag gccccaagcg ccaggcccct ggcagcctcc accacgatct
65761 tgagctggcg cgggtcggtg tggcccctgg cctgggtgac cagatcctgc agcgttccct
65821 gcagctggga ctcttcctgg gcctcctgga tgatggcctc cagtcgggag aggcgccttt
65881 tccagtctgc gacggtctcc ttgccccccg cgacccgctt ggggtccaac gtggccagag
65941 ccaacctcag ctcctccatg ccatccatgg agttctgggc catgccctcg acttccagga
66001 gccgtgttag ctcatgaatt tcaccgtcag ccgcagcggc taggttcagc caggcacccg
66061 cgcccccagc taaggccagg gctccttcgg aaagaccccg cacggcctcg cagatgcccc
66121 ggatccactt ggcggctgcc agggatttcc ggtagggcca tgagccgttc ccggccgctg
66181 cccgggccag ggcggcctcg aggggagcct ggacaggggc tttgggcggg gagggaagca
66241 ggctccggag ttcatcgtcg gggcttcgt cgcgtgacct ggagaggacg gcctccagag
66301 ccgtgtgaaa gccccgccga gtgcttgccg ccatctcgtg ggccttcgcc atcagggtct
66361 ggctctcccg gacctgctct tccagcgccc ggacctcggc cgcctcggcc tcggtcagca
66421 gctccgagaa gaagtccccc gtggcctgga ggagatcgtc ccgctctcgc cttgtcagca
66481 gctggggctt cttaggccag agcgccgagt ccgaggccag cctgggcggg gcggttgcct
66541 gggggatagt tggaggagga ggcaggttag cctggcctgg gtcattagtg gcttcgggta
66601 gcgtccgatc cacgtactcg ctcacgatgg ccgtcagggc agcctcggct gctcgtcttt
66661 tttccagaag cccggccagc ccccgctcgt actccgcgta gggggcctcc agatccgtgt
66721 tgaccaccgc tgatttcatg tccggggact gcagggcctg gcgcgtctgc gcgagggccg
66781 aacggatggc atcggccgcc gtcctggcgc gaaagagggc cccggccgct tcctccgctc
66841 ctcgccctcc tcctccttct ttggcggtag ccgcgggggt ggcgggccaa gcgtccagtc
66901 tggccagagg gccggtctcg atatccgtga accagccggg ttccgcggcc tccattctct
66961 ccgccgcacc accatcgtcc acgagcaggg atcgcagtct ctccctcctc accctcgtta
67021 ttcccaatag catagcggca aggatctgtg tgagggagtc caagatgtcc gtgtttctgg
67081 ctactgccgc cgctgctgcc gcggctgagt ccgtattgtc tggcagcagg gaggccagca
67141 gggtgttcca gtcatcgggc gaagtgggag cgggctctgg gcgtgccccc agcgccttcc
67201 taattctggc ccaggcctca ttcgcctctc gcgctcgccg ctcctgcctc tccttgtctt
67261 cctgttctcg gagcttctcc ttttccttgc gcccggtctc cataagctgc cgcagcttct
67321 tctcatactg tcgcttgagc tctttgttgg gggcagtgtc cagaaaggcc tcgagctgtt
67381 cctcggtggc gggcttaaag ccttcggcct ccaggcgcca ggcctgcacc tccttctgtc

Fig. 3 (cont.)

67441 tgagctgatc gttgttgtta ttcttcaatt tctgcaggta acttaggaag cgtttcttga
67501 gcttccctgg gatgagcgtt tgggagagct gattctgcag cccagagagt agtctcaggg
67561 catcctctgg agcctgacct gtgatcgtcg catcatagac cgccagtaga cctgggagca
67621 gattcaccgc cgcggccgtc tcctttaagg tgctgtgagt agcaaaattc tgcaaggcca
67681 ctaggcgcgc tggctccagc gtcagccggt tgcccatctc gaatgtgtgc agggcctctg
67741 agaccatggg gtccaggatg cggtcaatgc catcctgcac ctcagggtca aggaccggca
67801 agtcacgata gaggtggtct atgctctcct cgaaggaggc aatgtagtta tcgatggtgt
67861 agaaggtgat ggatttcagg atgttcatca ggtacttttt ggagcgaaca atctgctgta
67921 tagtgtcacg taggcggatg tacgtggggt tctttgcggc cccgactatc gaccctgcat
67981 ttgcgatgta cttttctatg acggggatgg tgagggccgc ggtgtcggcc agcggtggcg
68041 tggcttcggg gttgtcgtgg ttggcgggtg tcgcagaggg agaggcggga gagatggggg
68101 cgcctggggc cgaggccaca ccggccaggc ccaacattgc ctcgatgtcg tccaggatgg
68161 tgcggaggcg cttttcgttt tctctggtgg tctcgagctc cttctgtttt ttcgcgactg
68221 tctcaaactc tggaaggggg gcaatgctgg ggtcgtcctc ctcaactcgc tccaggggcc
68281 aggggatacc gctcatatca ctaagggcgg tgcccaggta gaggagctcg cgatagtccc
68341 attcaatgga cgtgtaccgg atgtttagga gaggcaggga ggcgatgatc tggcatgtgt
68401 gccgcaggtg tgtcaggagg tcgtcaaaat ccatcactgt tgggaggctt gggtcctcaa
68461 ggtaggagag ataatcggag gccgccgagg ccaccttgtc cctgatgtcc gccgtacacc
68521 tgcgcacgtg cagggccgca ttcttggacc ggacggccac gttgtggaca aagggggggca
68581 ctgaggcggc gggagggggcc ccatactcta tcgctgtcaa cagcgccaaa aagcggacgt
68641 cctcctcatc taccccagcc tgttgtctgg ccacggccgt tcgggcggcc tccgccaggg
68701 ataggaggcg cttccagctt tcgtcgtcca ggaccaaggg gacgtccacg tgcgggcccc
68761 tgtagatgga attatcctcg ggttctcctc ctccttcccc cgcctcctga tctccgcccg
68821 agagcaggtc ggtcaggcgt ctgcgggccg cctccaggtc aaattttcca tcgtcgctct
68881 cggccagctg ggaatttca gccagcatct tagcaccggc atctacacgg accgcgtcct
68941 tcgtggccag ggacggcagg caggcctcca gctttgcggc caggtgctta tggaactctc
69001 ccgctcttcc cttgttttct gatagcatgt ttgcgaggtt ttggatgtta agttcggaag
69061 tgagcagttg ctccaggtcc agcgtgggga cctgcagatg tcccgaccag tcctttaaga
69121 attccagcag atttagcaca gacgatcggt ccctactcct tattagcccc tgctcgagga
69181 ccactgtcac aagaagatag tctatcatgc tcaaggcatc tgcctctggc acttcccggt
69241 tagaggccgg gtcgtagacg atggcctgtt cctggtaggt atgtccggct attctcgcaa
69301 tgttgctctc gaggggcaca aagtccatct caggagtctc tatgtcaaag gtggtctgat
69361 agtattggct cctggcggtg tccagtgtga tgggggacgt gggggcactg gatcccgatt
69421 ccaggctgtt ggagaacact tcatcttcga acatgtcttc atcctctgtg gtggggatat
69481 cggaggctaa gtcgctctcc gcttcttcag agtcggacat ggataggaaa ggctcctcta
69541 ggtcagacag gtagcggacg aggccagaac ccccagatgc atcatcccca aaggagggct
69601 gctgcccgaa gggaggtgat ggggatatct ccgttccagc cctgtcagcg gccgggggat
69661 ggtttttttc tggttcgagt gtcgtggctg atggtgggag ctgctgagca ggaggaggag
69721 ccggggtagc tgatggcagg ggctgctgct gaggaggaag aggagaagga gcccgggcgg

Fig. 3 (cont.)

69781 ctgatggcgg gggctgctgc tgaggaagaa gtggagaagg agccggggcg gctgatggcg
69841 tgggctgctg ctgaggaaga agtggagaag gagccggggc ggctgattgc gggggctgct
69901 gctgagttgg aggaggagaa agagtcgtgg tggtgggggc tgctgctgca gtcggggaag
69961 gggatggggt ggtcagaggg atttttgggt tcgagggagc tgcctgtggc agagggatgg
70021 gtatttgcaa agggaggcga ggagatggag tgactgaagg agcgatagtt gagactggcg
70081 cggggtgggg tgtcggggag gcgggtggtg attggtgagg gatggggatt actggagggg
70141 gaaggcgagc tgctgaaggg gggcgatggg gcggaacgtg ggtgcgtggc agctgatcat
70201 cctctgtgtc agtggtggag gacagaggga ggcggcggcc ggaggtgggc ttcttgtggg
70261 ggctatcttt gcccaatccc tttttcctct tgggagtctg aggcgctgcg ccgctcgacg
70321 cccttggtgg cgtggaggga gcggggaccc cgggggtgtg acctaggccg gggatgggga
70381 tgaagagggg agggctggag gccggggccg cggaggccgg ggccgcggag gccggggccg
70441 cggaggccgg ggccgcggag gccggggccg cggaggccgg ggccgcagag gccggggccg
70501 cagaggccgg ggccgcagag gccggagacg acggcgggga gttggtcttt gcaggactat
70561 acctggcggc agggaatgag tcggatgtga aagatcgaga gggcagtggc ctgaggttat
70621 acggtattat tcgccgttca aacggtagca tgacgggagg gctgctatca gcaccgggcg
70681 tccccgccgc ctccccatca ctggacacaa gctcgggccc caccaggtca aagccgctgc
70741 cgttggcctc ataaaagtca tacacgccat agtgttccag cataaagatg cgggggtcct
70801 ctgtctcaaa ggcctcgggt agaaaataga gatgcacgca agtgtactgg gcccctggtg
70861 cccccacgta ctgcaggatg tcgtgcgcat aggtgctgac tctgacatgg gcgggggtgc
70921 ccggggccgc atccttctgg cagtgggggt caaacaagta gaaggagcca tctgtctcga
70981 tgatgatggc ccccgcgtag atgtcgcaga tgtagaggat gaactgggcc accccgttgt
71041 aactgccgtg caggacctcg gccagggact gaacaactgc cgagtttgcg atctgggcag
71101 ggaataggac gaggccaaag atctccgccg agcggtatat gtgcacgcgc ccaccgcccc
71161 tcaggaccac ggagctgggc acgtccgtca actgggccat ctcgtgcccc ttgaggatgc
71221 cgctctggcg catgagggca tccagccgcg ccccctcgtc caggacctcg tccagctcag
71281 ggcgggaggt caggggcgg ccggccagga agctcttgac caggtagagg acgcagttgc
71341 tgacgcactg gatgccggca aagcggccaa acttgcagtg ggcctggttg cacgaggccg
71401 tgcctaggat gcggagggcc gagcctccac tcccgccccc gggggcattc acatccatgg
71461 tcctgattcc gcgcacgggg ccggttcccc gggtgcgctg gctttgcccc cagtcgccgt
71521 tactcatctt cggcggtggg gcggggagga cgccttgtcg cccccccttct ggtccggggt
71581 cttacgcggc tggcggcggc agccgccgag agataagggg ggtacgtgtg tgcctccgcc
71641 tctcctctgt ctgggccgcc gccgccgctt gcccgccttg aaggagaggg ggtagtccgc
71701 ggactgcgtc tgcgggggca ggaggtctca accttctggg ctcgggccgc ggtgtcgata
71761 tccgatggcc tttccctgtc ttcctcgtat gctccttctc ctcctcctcc cggcacgccc
71821 ctgagatctg cctcccctcc ctctccctcg tcctggtcgg aaaagtctga ggaggagaag
71881 gagaatgggg aggagtccaa aacggcacgc cacctgccgt ggggcggtgg tgacaggtcc
71941 cggctggccc ggcgcttgct cgcgttcctg ccgttaccca ggagaatggc cgcgagtttt
72001 ttggcgggga ggatgcggaa tggcgggggc gtttgtccca cgggtgaggg ggaatcgtcg
72061 gttagggccg gcacgaggtg gtgggtctgg acccgggccg tgcgagcaaa ggcggcgaga

Fig. 3 (cont.)

72121 accgaggggc ttctgggggt gactgtgatc tgttccggat ttaggtccat ggcgggtgtg
72181 tatgttttaa taggggtggt ctctggcgcg gcaggatgat ggtcgaggac gtccaccagg
72241 gccttgcaga tgctcttgcc tagatacagg atgtcgtcca tgctgagggg aggtggggtg
72301 tctgctcccc cctgcggaag ccgcctgggt gcggggatga agacaggtgg tgggcgggcg
72361 tctcgccgga ctatggcctc ggcacgctcg gcgtcgatgg cgggtggctg gaacaggcgg
72421 gcgaatgtgt aatcccggaa ccggtaggcg acgctgcgcc tgagggcgcc cgtcaggctg
72481 tatcccagct ccagggcgtg ctccacccgc tcgttgagct cctcgagatc cggacgcagg
72541 ggctcgctgg tgtgggccca gaggggggtga tccgcgatgc cccggctctc cctgagggcc
72601 ggcaccagga ggcgccttct gagggtggcc gtgtcggccg tggccagggc ccacctggcg
72661 gcggcgtccc ggcacacatc ctggatgccc tccacgacgc tctttagcgt ctggaggtcc
72721 gtggagtagt ggcgggggga ggatgaaacg ctcttttcct tcaccgctac caccgcctcc
72781 tcctcctctt ccgtcgccag agggatctgc accctcccgg tctctgcgtc gtacaggagc
72841 gggcgggagc acagcctcca agctgccccc gtcaagcgcg agatgtcctc cgagagggtc
72901 tcacccgaga ccagaaagcg gcgggtggcc aggcccaacg actccgccgt cgtgctgtat
72961 ctcagggtga agaggagtga aaagagggag gtgggccagg caagcggtgg tgcttccgcc
73021 gcccgctctg aagctgagat agtctcggag atgatgcctg agacctctcg gacggcgtcc
73081 atgatcctaa ggactgcgtc gtgggacgac agcccccagg ggcccccgcc ctcttcgtct
73141 tctgcaccct cggctcctgc gtccccggcc ttgccttccc cctctaagtt gaggggggcgc
73201 agtccgaccg cctgggggga ctccccaggc atcggagggg ccccgtcata gatctcccag
73261 acggtggcgt atatgagctc gagaggacgg cgggcccggg tcagctcggg ggaagggagg
73321 gccaggtcgc tgccgaagga gaccagccag cgcagggcgg ccagagagcg ggttttgggc
73381 agctcgttgg agaggacccg gcgaagggcg ggccagattt ggaactcgat gaaggcggcc
73441 gggaagaagg ggctgtggac ataggccgga tccgcgcgcg ccgtttggcc ggccctcagg
73501 gaccggcagt atgcctcgac gtctgtccgc ggggccgccg ccaccgctgc cgtccactgc
73561 cttcttccct gctcgccggg gagtaggggg ggcttacagg ggagggccgg agccggggcc
73621 ggggcctgcc acaggcggct gtagcggacc catagcagag acctgaggag ttcggatgaa
73681 aggtcccccg ccacctgctc atactcggcc gcgggagggg ggacgatgaa gatgcgcaga
73741 ggggttacgg cgtcccaagg gtccgccgcc gccccccacac ccacagccgt cgcggcgggg
73801 gcggcggcgg gcgtagaggg gccgctggtg cgccgggctc gtctgtccac ggcctcggcc
73861 tccgcccgca ggtaggccgc ccgggccaca cgggcgaagc ggctcgtggg gctcgcggtg
73921 ggcagcagtc ggaaaaagtg cagggcaaag cccgatagac tctctaggag ggcggcggtg
73981 gcctcgagcc acctccaccg cgagcgggac acccggggca cagaggccag catcatggcg
74041 tagtcccccg ccacggtctc gttgagcccg gccgagagca gaaccgtggc cacctgctcg
74101 atggcggctg gagagaagga tgcccggctc cccgccgcct cctgcacacg agcggccagg
74161 gcctccatct ctgccgccat cccggccagg aaggcctcga tgaccgagtc tgggacgccg
74221 taagtctggt cccagagcag ggcctcgtac acatagtcgt aaaagagggc ccctgagggc
74281 tccaaaagcc ggagccgggc ggcgtcaaag gccaggacgg gcacagccgc gacggggggc
74341 gtttgtcccc cgctggcctc cgcgtacacg cccaggatct ctaccgcccg ccgccgggcc
74401 aggggcagcg aggccaccac gctggaaagt gactcggggc ggtgaaagag accaccaccg

Fig. 3 (cont.)

74461 ctttcttcac cctctccccc gccggccccg cccccactgt gctccaccag ctccacggcc
74521 atggccttga tgtccgcggc cgtgggctga ccctgccctg cagccgccca ggggtagcgg
74581 ttggtctccg cgtatacggt gaccagccat ctccccagcg tcgttttcgc cgcgttaaaa
74641 gcgtagaatg acagcccctc ccgcgggaag gcgtcccacc gggccagata agtgtcggcc
74701 accagctctt ccacgaaggc aaaggtggcc gttgggccag agaccgcgag cacctccccg
74761 ctgccctctt cgatgatgcg ccggtacgcg gccgccaggg cccgggtctc tgcgatgagc
74821 cgagagccgt ccagcggatc gtcggtggcc ggagaggctg tcgtgggggg cagtgaggat
74881 gccagcacgt ccagggccgc ctccagatgg ccgaggccga agctgcgcct ggaaaaggag
74941 gccgcccgga gtaggtagta ggcgtggtgg cggaggaccg ccgccgggta agcgtggccg
75001 ctcatgaggg tgagagtatt taaaaaatcg cgcaccagca ccggctgggc caaatccccc
75061 agtccaaaga tccccagctc cagaggcatc agcgcgcgca ggcgggcagc ggggtcgtcc
75121 ccagacagca gcaactgacg cgtcacgcgg gcgagccccc cgtccacctc tgccaggggt
75181 ggctgggcgt ctgcccctcc gctaccgccg ctgctgtcac tctccatagc ggacgccatg
75241 aaggtccagg ggtccgtcga tcgccgccgt ctgcaacgcc gaatcgcggg gctgctgccc
75301 cctccggccc ggcgtctaaa tatttcccgg gggtccgaat tcacgcggga cgttcgtggg
75361 ctggttgagg aacacgcgca ggcctcctcg ctgagtgcgg cggccgtctg gcgcgcaggg
75421 ctgctggccc cgggggaggt ggcggtcgcc gggggtggca gtggaggggg gagcttcagc
75481 tggtctgggt ggcggccgcc agtctttggg gactttctga tacacgccag ctccttcaac
75541 aacgccgagg ccactggaac gccccttttc caattcaagc agagtgaccc gttctcgggc
75601 gtcgacgcgg tattcactcc tctctccctg tttatcctaa tgaatcacgg ccggggtgta
75661 gccgcccggg tcgaggcagg tgggggcctg acgcggatgg ccaacctgct gtacgacagc
75721 cccgcaaccc tggctgacct ggtcccggac tttgggcggc tggtggccga ccgccgcttc
75781 cacaacttca tcacccctgt gggccccctg gtggagaata taaagagcac ctatctgaat
75841 aaaatcacca cggtggtcca cgggcctgtg gtcagcaagg ccatccctcg cagcaccgtc
75901 aaggtgacgg tgccccagga ggcctttgtg gatctggacg cgtggctctc cggcggcgcc
75961 gggggtggcg gtggagtatg cttcgtcggg gggctgggcc tgcagccgtg ccccgccgat
76021 gcgcgcctct atgtcgctct gacctatgag gaagccgggc cgcggtttac gtttttccag
76081 tcgtcccgcg gccactgtca gatcatgaat atcttaagaa tttattactc accatccatc
76141 atgcaccgct atgctgtggt ccagccccta catatagagg agctaacctt cggggcggtt
76201 gcctgtctgg ggacatttag tgctactgac ggttggagga ggtctgcctt caattaccgt
76261 ggctctagcc tccccgtggt ggagattgac agcttttatt ccaacgtctc tgactgggag
76321 gtgattctct agacttaacg ggaggaaaca ggaggaggag ggggacaaga gcacaaaagt
76381 ggttcagtgg acacccacca cacagcatgg caacgaccag tcatgtcgag catgagctcc
76441 tctccaaatt gattgatgag ttaaaggtca aggccaactc agaccccgag gctgatgtcc
76501 tggccgggcg cctgctccac cgccttaagg ccgagtcagt tacacacaca gtagccgaat
76561 atctggaggt cttctctgac aaattctacg atgaggaatt cttccagatg caccgggatg
76621 agctggagac ccgagtctct gctttcgcgc agagcccggc ctacgagcgc atcgtctcca
76681 gcggctacct gtcggccctg cgctactatg acacctatct gtatgtgggg cgcagcggga
76741 agcaggagag tgtgcagcac ttttacatgc ggttagccgg cttctgtgcc tcaaccacct

Fig. 3 (cont.)

76801 gcctctacgc gggtctcagg gcagccctgc agcgggccag gccggagatt gagagtgaca
76861 tggaggtgtt tgattactac tttgagcacc taacctccca gacggtgtgc tgctccacgc
76921 cctttatgcg ctttgccggg gtggaaaact ccactctggc cagctgcatc ctcaccaccc
76981 ccgacctcag ctccgagtgg gacgtgaccc aggccctcta taggcacctg gggcgctacc
77041 tctttcagcg agccggggtg ggtgtagggg tgacgggggc tggccaggat gggaaacaca
77101 tcagcctcct gatgaggatg atcaacagcc acgtggagta ccacaactat ggctgcaaga
77161 ggccggtcag tgtggcggcc tacatggagc cctggcacag ccagattttc aagtttttgg
77221 aaacgaagct gccggagaac cacgagaggt gcccgggcat ctttacgggg ctctttgtcc
77281 ccgagctctt cttcaagctt tttagggaca cgccctggtc ggactggtac ctgtttgacc
77341 ccaaggacgc cggggacctg gagaggctct acggggagga gtttgagcgc gagtactatc
77401 ggctggtgac agcgggcaag ttttgtgggc gggtctccat caagtccctg atgttctcta
77461 tcgtcaactg cgccgtcaag gccggcagcc ccttcatcct tttgaaggag gcctgcaacg
77521 cccacttttg gcgcgacctg cagggcgagg ccatgaacgc cgccaacctg tgcgccgagg
77581 tgctgcagcc ctcgaggaag tctgtggcca cctgcaatct ggccaacatc tgcctcccgc
77641 gctgcctggt gaatgcgcct ctggcggtgc gggcacagcg ggccgacacg caggggggatg
77701 aactcctgct ggccctccct cgactctcag tcaccctacc tggagagggg gcagtcggtg
77761 atggattctc gctagcccgc ctcagagatg ccacccagtg tgccaccttt gtggtggcct
77821 gctccattct tcagggatcc cccacttatg attccaggga tatggcctcc atgggcctcg
77881 gggtgcaggg cctggccgat gtctttgcgg acctgggctg gcagtacact gaccctccct
77941 ctcgctcgtt aaacaaggaa atattcgaac atatgtactt tacggccctc tgcaccagta
78001 gtctgattgg acttcacacc aggaagattt ttccgggttt caaacagagc aagtatgccg
78061 gggggtggtt tcactggcac gattgggcag gaacagacct ttctattccc agggaaattt
78121 ggtctcgcct ctctgaacgc attgtgaggg atgggctttt caattcacag tttatcgccc
78181 tgatgcccac ctcaggctgt gcccaggtga cgggctgttc ggacgccttc tacccccttct
78241 atgccaatgc gtccaccaag gtcaccaaca aggaggaggc ccttaggcca aaccggtctt
78301 tttggcgtca tgtgcgtctg gatgacaggg aagctttgaa tcttgtcggg ggccgtgtct
78361 cctgcctccc ggaggctctg cggcagcgct acctgcgttt ccaaacggcc tttgattaca
78421 accaggagga cctgattcag atgtcccggg acagggcccc ctttgtggac cagagccaat
78481 ctcacagcct gtttttgcgt gaggaagatg ccgcgcgggc cagcacgcta gccaacctac
78541 tggtgcgcag ctacgagctg ggcctgaaga ctatcatgta ctattgtcgc attgagaagg
78601 ccgccgatct gggggtgatg gagtgtaagg ccagcgcggc tctgtcggtg ccgcgggagg
78661 aacagaatga gcggagtccc gctgagcaga tgccgcctcg tcccatggaa ccggcgcagg
78721 ttgcggggcc ggttgacatc atgagcaagg gcccagggga gggaccaggt gggtggtgtg
78781 tgcccggggg attggaagtg tgctataagt accgtcagct cttctcagag gatgatctgt
78841 tggagactga cggttttact gaacgagcct gtgaatcttg ccaataaacg tttattgcca
78901 tgtccaagtt gttgtacgtg cgtgatcatg agggctttgc ctgcctaacg gtcgaaaccc
78961 accgcaaccg ctggttcgcg gctcacattg tcctcaccaa ggactgcggg tgtctcaagc
79021 tactcaatga gagggacttg gagttttaca agttcctctt tacgttcctg gccatggccg
79081 agaagcttgt gaactttaac attgatgaac tggtcaccag cttcgagagc cacgacattg

Fig. 3 (cont.)

79141 atcactacta caccgagcag aaggccatgg agaacgtcca cggggagact tatgctaaca
79201 ttttaaacat gctctttgat ggggacaggg cggcgatgaa cgcctacgca gaggccatca
79261 tggccgacga ggccctgcaa gccaagattt cctggctccg tgacaaggtg gcggccgccg
79321 tcaccctgcc ggagaagatt cttgtgttcc tgctgattga aggcatcttc ttcattagct
79381 ccttctacag catagccctg ctgcgggtcc ggggcctaat gcctggcatc tgcctggcca
79441 ataactacat aagtagggat gagctgctcc acacccgcgc tgcctccctg ttatacaata
79501 gcatgacagc caaggctgac cgaccaaggg ccacctggat ccaggagctg tttcgcactg
79561 cggtggaggt agagactgcc ttcatcgagg ctcgtggaga gggggttacc ttggtggatg
79621 tgcgagccat aaagcagttt ctggaggcca cggccgatcg catcctgggt gacattggtc
79681 aggctccctt gtatggcaca ccacccccca aggactgccc gctcacctac atgactagca
79741 tcaagcaaac taatttcttt gagcaagaga gttccgatta caccatgctg gtggtagatg
79801 acctttgagt cagggtggct acttgctcag gtttctgggc ataaattctc ctgcctgcct
79861 ctgctctggt acgttggctt ctgctgctgc ttgtgatcat ggaaaccact cagactctcc
79921 gctttaagac caaggcccta gccgtcctgt ccaagtgcta tgaccatgcc cagactcatc
79981 tcaagggagg agtgctgcag gtaaaccttc tgtctgtaaa ctatggaggc ccccggctgg
80041 ccgccgtggc caacgcaggc acggccgggc taatcagctt cgaggtctcc cctgacgctg
80101 tggccgagtg gcagaatcac cagagcccag aggaggcccc ggccgccgtg tcatttagaa
80161 accttgccta cgggcgcacc tgtgtcctgg gcaaggagct gtttggctcg gctgtggagc
80221 aggcttccct gcaattttac aagcggccac aagggggttc ccggcctgaa tttgttaagc
80281 tcactatgga atatgatgat aaggtgtcca agagccacca cacctgcgcc ctgatgccct
80341 atatgccccc ggccagcgac aggctgagga acgagcagat gattgggcag gtgctgttga
80401 tgcccaagac ggcttcctcg ttgcagaagt gggcacgcca gcaaggctca ggcggcgtta
80461 aggtgacact caatccggat ctctacgtca ccacgtatac ttctggggag gcctgcctca
80521 ccctagacta caagcctctg agtgtggggc catacgaggc cttcactggc cctgtggcca
80581 aggctcagga cgtgggggcc gttgaggccc acgttgtctg ctcggtagca gcggactcgc
80641 tggcggcggc gcttagcctc tgccgcattc cggccgttag cgtgccaatc ttgaggtttt
80701 acaggtctgg catcatagct gtggtggccg gcctgctgac gtcagcgggg gacctgccgt
80761 tggatcttag tgttatttta tttaaccacg cctccgaaga ggcggccgcc agtacggcct
80821 ctgagccaga agataaaagt ccccgggtgc aaccactggg cacaggactc caacaacgcc
80881 ccagacatac ggtcagtcca tctccttcac ctccgccacc tcctaggacc cctacttggg
80941 agagtccggc aaggccagag acaccctcgc ctgccattcc cagccactcc agcaacaccg
81001 cactggagag gcctctggct gttcagctcg cgaggaaaag gacatcgtcg gaggccaggc
81061 agaagcagaa gcaccccaag aaagtgaagc aggcctttaa ccccctcatt taacaccatg
81121 ttctcgtgca agcagcacct gtccctgggg gcctgtgtct tctgtctcgg cctcctggcc
81181 agcacccccct tcatttggtg ctttgtcttt gccaacctgc tctctctgga gatcttctca
81241 ccgtggcaga cacacgtgta caggcttgga ttcccgacgg catgcctaat ggccgtcctc
81301 tggacgctgg tacccgccaa gcacgcggtg agggccgtca ctccagccat catgctgaat
81361 attgccagcg ccttgatctt cttctccctc agagtctact cgaccagcac gtgggtttct
81421 gccccctgtc tctttctggc caacctgcct ctcttatgcc tgtggccccg gctggccatc

Fig. 3 (cont.)

81481 gagattgttt acatctgccc ggctatacac caaaggttct ttgaacttgg gttgctcttg
81541 gcctgcacca tctttgccct gtccgtggtc tccagggccc tggaggtgtc ggctgtcttc
81601 atgtctccat ttttcatctt tctggctttg ggctctggaa gcctggccgg tgctcggcgt
81661 aaccagattt acacctcggg tctcgagcgg agacgcagca ttttctgcgc ccggggagat
81721 cattcggtgg catccctgaa ggagaccctc cataaatgcc cgtgggatct gctggccatc
81781 tctgccttga ccgttcttgt cgtctgtgtg atgattgtgt tgcatgtgca cgcagaggtg
81841 ttctttggac tctctagata cctgcccctc tttctctgtg gggcgatggc ctccgggggg
81901 ctgtacctgg gccattccag catcattgca tgtgtcatgg ccaccctctg caccctgaca
81961 tctgttgtgg tatatttcct ccatgaaacc cttggacccc tgggcaagac cgtgctgttt
82021 atctcaatct ttgtctatta ctttagcggg gtagcggccc tgagcgcagc tatgcgctac
82081 aagcttaaga agtttgtgaa cggacccctg gtccatctcc gtgtggtata catgtgctgt
82141 tttgtcttta ctttttgtga atatctgttg gtgacattca ttaaatccta acgaccggag
82201 tcctgtctct ttgtgttctt gggggacttg agttagctgt ctttcctctt attacattgg
82261 gctaacggga ggaaatgaac ccaggggtgg cagtggatgg ggtcatttat gggcaaaact
82321 cacaggacat gtttggggag ttagcattgg cgtcgggaaa cacagctctg gcagttataa
82381 ccgcaccagc taacaggaca tgtttggggg agttggcatt ggcgtcagga gacacggctc
82441 tgtcagttat caccgtacca tgagtgccat gtgtgtccag tgcctaatca ccgttcctca
82501 ttttgtgtgc ctcctcaaat gttccagaag tcggccacag gggaggtggc tgaattaggg
82561 ccttttccct cattccccca tgagacccac gtggcaggcc taggggctac attcgcctcc
82621 cacgtttccc ttcgcgtgag gcatccgata tgactgaatt ttcgcagtct cttttccctc
82681 ttcccttgtt attcccatag aattacagtg aggttacaca ggtggagatt cagtttaacc
82741 atttattgat ttaatccagg aacaaaaaac agtcctagtg acccagtgcc cggagagaga
82801 atggccctga caagtcggct gcatgatgca cttcggcagt cacgtgtgtg agtctccacg
82861 gcctctgtca aaagggagct tagcgtgcca gggttgtaat tcttgatgta gtggcccagg
82921 aattcaactt catcgtgtct ccgtctgcag ttggcgttaa tgtaggctgg ggctactgcc
82981 gcatatgctg ccaagagaca gaggggctgc ttcacatatg agctgctcag ggtctccacc
83041 accttgtttt gacgggccgt ggcacaggtg atgtagaaga gttgcttcac aaagttgtag
83101 tctcgcgtgt taggaaggaa gcagggtgcc agctctttga gcttggtcag gatcaccttg
83161 ctaagactca tggcgcaggc caggaggatg tcttccgcgg gagctagggg caggtcgccg
83221 tggtaggtga tctcctggag ccaaaagatg gtctcttcta gcatggccac cagggtgcag
83281 agccccgcgt tctggatcgc ctgcatgcgt gcatccagcc atgtgtcctt gttggttgac
83341 ttggtgaaaa actcacgtag tgtcttgtag ctcctgcgca gctcgtgtct gggttgcact
83401 ttctgccagg ctccaatctc tggatgggcg gccaccgcca gcatcgactg taggaacggg
83461 tcttggatgg gctctagggt cagagaggcc agggggctgg gcaaggtgac aaatgtaatc
83521 ttggagacag gcttaaccag actcatgtca aaccacggtt tgttcggcag gggcctctgg
83581 ctgcgttctt gcctcgcctg cttccttgtg ctcctgccgg cccctcgaga ttctgaccgg
83641 ggacctctgg ttgctctgtt gcttcgggga gctcttggag acctcggtgc tctaggcacc
83701 ctgggggccc ttggggctct gggcgctctt gctcccgggg gcaggtgtcg gcgcttgcca
83761 taactttcat cggtgcagcc atggacctct ccgcgtcgcc ttttgtggcc tctggtgtaa

Fig. 3 (cont.)

83821 gaggagttgc cagtctcctc cttctcgtcc tcgtccctgc acaggggtga gcgatgcaat
83881 gtgactgtct tgtcctgtag gtcccacttc tttctgggaa tcacaaacga tgccgaggta
83941 ggggttatga ccacgctgga gggccgtgca ggtatggcgt gggccggagt tggatcttca
84001 tcctcctcct ctgaggatga aatctctcca tctgtggagt gttcttcgct gccctccata
84061 gggtccagat cgcagtctgt gttggtgtct gagaccgctt cgagttccag aatgtggctc
84121 tctgcagagg ggagacaaaa ggtggagact gccttgagca cctctgtctc aggcaccgga
84181 tgccccggc tccacggccc cggccactgg ccggtgtagc ttcttacctg cgggatcctc
84241 gttggaggaa atgctgctag ttcgggagag tctctgagaa ggaaccatct tgtctgtctc
84301 tacgacgggc tagctgggat gtagtgctgt cttgactggc ctcagcccta tttatgattc
84361 tggaggcggg cacgctgatg gagaaatggg cggtcggttg attggcccca cagcgaccgg
84421 cgaagcactg actcatgaag gtgaccgtga tggcctgtga tgtgtagtag agtaccagaa
84481 acaccctcac attcttggag ctggccctgt gggtatgcct caggcacgca aagttcctgc
84541 cccgggcatg gcacacctga actaagtttg gcccggtttg ctcaaacgtg acatggagaa
84601 actgggggaa tttgtcttct ggcacagctg ttgccagggt gctcatgagc gagggccaga
84661 tgcaggagct gacccaggcg acgagatcca ggcccagatg tccctctatc atggcgcaga
84721 cattctccac ggtgggggc agggtctcgc gggtcctctg gattagatag tcacgcccat
84781 catccgcgat gtggtagcag aaggttttgg gggccggcca gcccacgtgc agtgagtgat
84841 gtaagaggtt ttgaatgttg agggcattct taacatagct gtgcttgtct tcctcttccg
84901 gatgacagac aaagaggcgc agctgccggc taagaccacc gcccctgtcc accttgtagg
84961 tatgcggcag ccggatgcac cgcccggcgt gatacacgcc gctgtcaaaa agcggggccc
85021 caatctcttt gatcttgtga cgcatgcggc gcaggcaggc cgttaggccc atgagcttct
85081 gcagcacaga cacaaaccct tgtactgcgc ttgttcccac aatagcatgg cctctaggta
85141 ggggggtgat gacgcgaaag cccagttttc ccgtgcatat gcaaaagggg agcacatctt
85201 ccatattatc cgggtcggcg ggtggacaag ctgatttgaa aaaatagact gggtgggccc
85261 tggacactgg acccaggcgg cgcatgaggc gcagtacctc acgccgcacg gtccggcaca
85321 ggtcatagat ttcctccagc gaccaggggg ccccccttgat ctttagatcc aggtccaaga
85381 ccaggttgca gaccggaagc cggggattaa agtattcatg ccgggagaca aagagctgct
85441 cgctcaggct gttctgtgaa tagtacactg gggtgtagga gagggccctg gtgagacacg
85501 tgtctgggag gcggcagttg gtcggggtgg agacgacctc cgccaggtgg gatgagaagg
85561 ggtcagcggc tgtcattaca aagtagtgcc tgtctgcaaa atggcagagg aagaccggta
85621 gccgctgcac ccttcgaagg acggtgggtg ggaggaattg ttccttggga ttccactggc
85681 cccggcaggt ggcctggccg gccaagcata gaaacccttg aagcgtgggg gggtatgtgg
85741 gaccctcatc cgcgtgccag cgcgcgagct ccaccagctc ccgggccacg tccacactga
85801 gcccggccca ggcccgcatg agtccgtcat cggggtcggg gtcccacgtg tatggggccg
85861 ggggctccat gcggattttc agctgctgga cacgcacatg ctcagccagg taagtctccc
85921 gggtgaagta ggtgcgcatg tgctccgcaa agcccctgtc caggagcgag gggagcacga
85981 cgccccccga aggcagacac ccaatttctc ccatgctcgt taactgagag tatcgcttaa
86041 aggttccctc gttgaagcac tgtgcgtggg ccaaatagac gtagcgcacg agatcggccg
86101 aggccagggg aaggcgcccc ctgtaggcgt ctatcgtcct tgccacagcg cggatctctc

Fig. 3 (cont.)

86161 gcgagtcccg ccgcagtttc tcgtgtgcaa agtgggcaaa agcctcggtc tgctccgccc
86221 atgccgagga gccaaagacc tcccccagct cggccaggga cgtgacggcg gccaggctct
86281 gaccagactc ggaagtaaat agctccgtga ggtgcgccag ggtctcaatc gtacaaggaa
86341 tgccccaaaa atagtaagca gccgtgacta gcacgaactg ggcctcgtgg gagccaaagg
86401 tgctaatgaa ccacctggcc gagatgttaa cgcggtagat gcggcgcaga cagcccacga
86461 tcttgggacg cagccacgcc acgcggcctc tggcatcccc ctgtggctgt ttcttagcgc
86521 tcagtgtgag cagttccacg aggggcgtga gcgagcgcag ggcccccgcg cgatctaggt
86581 aggtggatag acggtccgcg gtgagcggcg tgaggccgcg caggaagggg aaggcctcct
86641 ccgccggcag gtgcagcgtc agaaccaggc cgcagcggct ctgtgaggtc agccgcttct
86701 tgggcaggtg aagctgcagt tccacgagag aacccgccac gtggtggagg ggcgaggcgt
86761 tgtggcacaa acaaaacagg cggaagccct cgtcaggccg cgagaggatg gcatcgagga
86821 tggcctccgc aatgtcagtg tttgaggcca caagggcctt gatgacgacg ggggcggaca
86881 ttatttaaga ccgggaggcc ccaacggcgg gctaaacaga acgatggcct tctatctccc
86941 agactggtcg tgctgcgggc tctggctctt tggccggccc aggaatagat acagccagct
87001 ccctgaggag ccggagacct ttgagtgccc ggaccgctgg cgagccgaga tagatctggg
87061 cctgcccccct ggtgtgcagg tgggagattt gctaagaaat gagcagacga tgggctcact
87121 gagacaggtt tatttgctcg ctgttcaagc caatagcatc acggatcacc tgaagcgctt
87181 tgacgccgtc cgcgtccctg agagctgtcg tggggtggtg gaggcccagg tggccaagct
87241 tgaggccgtg cgctcagtca tctggaatac catgatctct ctggctgtaa gcggcatcga
87301 gatggacgag aatgggctca aggccctgct ggacaaacag gctggcgaca gcctggccct
87361 gatggagatg gagaaggtgg ccacggcgct caagatggac gagaccggtg cctgggcgca
87421 agagatctcg gccgttgtct catcggtgac cgccccctca gcctcggccc ctttcatcaa
87481 ctccgccttt gagcccgagg tgcccacccc cgtccttgca ccgcctcccg tggtgcggca
87541 gccggagcac tctgggccca cggagctcgc gttaacgtag caaccagact ccacaccaaa
87601 taaacatttt attggtaaaa caagggatat gaaggtgtca ttgacccgag gatccaaacc
87661 ccctcccctg tctcccctcg agcgcctcgc tcagcccact atcacccatg gccaggctcg
87721 gcacctcctc gaaggtgcag ctggcccacc taaagagaga tctggggcca aggacccccg
87781 cgtcactgtg gggggctgtag aaggaggtga ggtggtgctt gtgaaggtaa acaagctgac
87841 agaagcgccg gtacttgtta aggaacacgg tctggtcact aaagttggtc aggctgacgt
87901 ccaccccacc ccggcgccac ctgcagggct tcactagaat accctgcatg gccaggcccg
87961 acctgccaaa gattgtcggc ctgtggtgag ggatagaagg ggggggcacg gtgagtgtca
88021 ctgagacggt ctgatggggg aagagggcca ggtcctttgg caaagagacg tccaggccca
88081 cgtccccggg gtactggggg tggttgatgg gacccttgtc ctcctccatc tggggggtgg
88141 catatctgaa ggcagccagg tggattttga gctccgatgg acgcagcgtg gagttgtagc
88201 gccgctgatt ctggaggatt agccggagtt cccccgtgta gccgggatcg atgatgccaa
88261 catgagacgt gaccggacgg gaggtgctgc cccacagcat gagcccatga ccctcgggtg
88321 ggcgggcata gaggcctagg tccacagttg tggtcttcat cgggcgcagc aggatggtgg
88381 tcttgttgac caaggtgagc cgccctacac tagcctgctg gagcaacagc ttgtcattct
88441 ggaaggcgta gcgtatgtgt ggacaggcct ccatggtgat gatctaacag acagggacgg

Fig. 3 (cont.)

88501 cggcgctata tataagagcc caagacccgg ctctctttac tgcgaaatgg ggaaggtcct
88561 aagaaagccg tttgcaaagg ctgtgccact gctcttcctc gccgccacct ggcttctgac
88621 cggggtgctg ccggccggcg cttccagtcc cacaaacgcg gcggcggctt ccctgactga
88681 agcccaggac cagttctact cctacacatg taatgcggac acattctcgc cttctttgac
88741 cagctttgcc tccatctggg cacttctgac gcttgtctta gtcattatag cctcagccat
88801 ctacctgatg tacgtctgct ttaacaagtt tgtgaacacg ctgctgacgg attagatggg
88861 gatatttaaa aggggcagca atctcggctg tttgtacttc ttctctgctc gttaaaccaa
88921 tagcatgtca gctccacgca aagtcagatt gccttctgtt aaggctgttg acatgagcat
88981 ggaagacatg gccgcccgcc tggctcgcct ggagtctgag aataaggctc tgaagcaaca
89041 ggtcctcaga gggggtgcct gtgcctcgtc tacctctgtt ccttctgctc cagtgcctcc
89101 gcctgagccg cttacagctc gacagcgaga ggtaatgatt acgcaggcca cgggccgttt
89161 ggcgtctcag gctatgaaga agattgaaga caaggttcgg aaatctgttg acggtgtaac
89221 tacccgcaat gaaatggaaa atatattgca aaatctgacc ctccgcattc aagtatctat
89281 gttgggtgca aaaggccaac ccagccctgg tgagggaaca cgaccacgag aatcaaacga
89341 ccccaacgcc acccgacgtg cccgctcccg ctcccgggga cgtgaagcaa agaaagtgca
89401 aatttctgat taataaattt ttattgactt tatacatagg tctcggcgtc atcatatggt
89461 ggggtggtgt aggtatggga tgtagacaag ttacgcctaa aggcgcagtc cgccatgacc
89521 agcagcagca gaagggtcag cacagccaga gaggccccact gcagtactag catggagagg
89581 tttgagaatc tgggctggga cgttggcggg actggcacgg tggcttgggc tgtggtaacc
89641 ggtgggctcg taaaagtcca gcggggccgc agtttgctag aagtgctggg aggtagatag
89701 gtggtcgcat tgtatctcgg tcttggcgta gttgaatcac cgccgtaatc tgtggtgggc
89761 tctgtacttg tccgggctcc atgtcctgtg gtgtgctttc caccggtggt agaattggcc
89821 tttccacctg ttgaggtgac cgtgggaacc gccgtctttt ggccactggg ggcctggggc
89881 gacgttgcat tttggggggg cgtgcctttg gtgacattaa cctcccccgg ttttgtggat
89941 gtggaactgt ttccagggcc tgacgcttgg ctggtggtgc ctgggcgggg tgctggcgaa
90001 ctggtggaca catgatgtgt gctgatagag gctggtgtca cctgtgttat attttcacca
90061 cctgttgggt gagcggaggt tagtaaaggc atatgtgacg ttgaattgtc actggtggag
90121 gggctgagtg tctctgggtt tgaactgggt ctcagtgaca tggaagaggt tgaacttgaa
90181 gttatgttat gttggcctgt ggtaacagca ctggttgcat tttttggttg gctggtaact
90241 actggggtgg gacttgttcc tcctaaggtg tggttggtgg catttgcctg tggacttgtt
90301 tctcccacag tagggccggt ggcatttggg gttggggtag tcactgctga ggtggggctt
90361 gtttttccca aggtggggct ggtggcattt ggggttgggg tagtcactgc tgaggtgggg
90421 cttgtttttc ccaaggtggg gctggtggca tttggggttg gggtagtcac tgctgaggta
90481 ggacttgttt ttcccaaggt ggggctggtg gcatttgggg ttggggtagt cactgctggg
90541 gtggggctgg tggcatttgg ggttggggta gtcactgctg gggtggggct ggtggcattt
90601 ggggttgggg tagtcactgg tgaggtggag ctggtcatgt cgggggcctt actttctgtg
90661 ccgttgtccc atggagatgg acttggtgtc accggtgatg cgcctgacgt tgtgccggct
90721 ggtgttgggc tggtgacatc cgcggtggat acagtggggc ctgtgcttgc aggtgcggtg
90781 aggttggtag gcacgtgagt agagctgggt agacctgtcg ttgtattggg atcagcaaat

Fig. 3 (cont.)

90841 ccagttgtat tcaaggtagg ggaggtggtg gtgctctcgg gtgccttgga gaatataacc
90901 ttgtgggttg ttgtggtggc attggtagcc gttcgtgtga taatgagtgt cttgggggcc
90961 gtgccaagac ccgagacagt aatgtcaaat gtccgattgc tcgcaaatgc accagaaata
91021 ttttcacaac ccgaaggtgt ccccgaggtg agagtccatt tgcacttaaa gtcagtttca
91081 gtgttgtttg gccaggccca aaaggcagtc actgtaacat ttggcgagtt tgcgtcctca
91141 gaagtgacca ttggcactga ataggtagca ttgtcaccca catatgtgat gtctgtggtg
91201 tttgtcggca tgtcctgtga agctggaatc tcatcagaga acacaatgtt ggactgaatg
91261 cagtaatctc ccccgctcgc cttcggtcca ttcccagagt aaaacacgta caggatactg
91321 ttattgccaa gaaatcgtga cactggacgt ggtgtcagac gcaggctgta tgcataccct
91381 gtaccaggta ttggggtggc cacgggactc gttgatgtga gaattccgcc gctgggaaca
91441 tggctctcgt atccactgca ggtgatgtta aatttgttgt ctccgggcag aacttgtgaa
91501 atttcgccat cctccataat acactcaata tctatctcat taccgagcat ttctgttttt
91561 acgctgaaat tcgagtcttg agctgacgtt ggcaaactta agggtagcgt gacatccagc
91621 ccctgtgccc tcactactgc cgttatattg gtagaattac agttatccca ctttatgtat
91681 ggcactgttt ctggtatcag gtacacgggg ttttgcattt ctgcatggtg gcaccacatg
91741 gttccaaaca catcttgaaa gtagacatct acagattcca ggcttacttg ttgctcctct
91801 ccggtggtga cgttaattgg aagcttctta gaccgcatag ttagagccaa ttctcctgca
91861 ccaaggagct ccagtagaaa gagattggtg gcattttctg agccaccaaa tgcacctcga
91921 ggttggtaga cagccttcgt atggggtgtc agctggccaa agtcaagatc aagttgatgc
91981 tttttgcccc cgacatcgaa attgatagtt acattgacat ctgccgtgca aacattgcat
92041 gtggggtaaa atgggaattc cggaatctca acattgaaaa aaccaggatc ttcacccgtg
92101 agatggatca ggctctggat ggtgtactga cacacaagca aggctgcctc cattgtctcg
92161 gcaccgattt ctaggcagca tcctctttaa taggtacaag gggggtgcgg tgttggtgag
92221 tcacactttt gttgcagaca aaatggacaa ggacaggccg ggtcccccgg ccctggatga
92281 caacatggaa gaagaagtcc catctacctc ggttgtgcag gaacaggtat cggcgggaga
92341 ttgggaaaat gtcctcatag agttatcaga tagcagctca gaaaaggaag cagaagatgc
92401 ccacctggag ccggcccaga agggtacgaa gagaaagcgg gtcgatcatg atgccggtgg
92461 gtcagctcca gcacgaccca tgctcccacc ccagccggat ctccctgggc gagaagccat
92521 tctccgcagg tttccactag atctaagaac acttcttcaa gcgattggag ccgcggctac
92581 ggtgagcatc cctatggcct aagtgtgtga tgtgtgtttt tacccatcac acaacaacaa
92641 ggtaagtaat ttgttgccgt tggtttcagc gcatcgacac acgagccata gaccagtttt
92701 tcggatccca gatttcaaat accgagatgt acataatgta tgccatggcc attcgacagg
92761 ccattagaga tcgtcggaga aatccagctt ctcgtagaga tcaggccaaa tggagactgc
92821 aaaccctggc cgccggatgg cctatgggtt accaggcata cagcagctgg atgtacagct
92881 acaccgatca ccagacgact cccacattcg tacatctcca ggcgacactt gggtgcacag
92941 gtggccgtag gtgtcacgtg accttttccg ccggcacctt taagctgccg cgatgtaccc
93001 ccggggatcg ccagtggttg tatgttcaga gctccgtggg taacattgta cagagctgta
93061 atccccgcta cagtattttc tttgactata tggctataca caggagcctc acgaaaatct
93121 gggaggaagt tttaacacct gaccagcgtg tttcatttat ggaattccta ggatttttgc

Fig. 3 (cont.)

93181 agagaacgga tttgtcctat atcaagagct ttgtcagcga tgccctgggc accactagta
93241 tccaaacacc gtggatcgat gacaatccta gcacggagac ggcacaggct tggaatgccg
93301 gctttctccg gggtcgtgcg tatgggatag acttgcttag aactgaaggg gaacatgtcg
93361 aaggtgctac cggtgaaacg cgagaagaaa gtgaggacac ggagagcgat ggagatgatg
93421 aagatcttcc ttgtatagtg tccagaggtg gacctaaggt caaacgaccc cctatattta
93481 taagacgtct gcacaggttg ctgctgatga gagcgggcaa acgaacagaa cagggcaagg
93541 aggtactgga aaaggcccgt gggagcactt atggcacacc taggccgcct gttccgaaac
93601 caagaccaga ggtcccacaa agcgacgaga cagctaccag tcacgggtcg gcgcaagtcc
93661 cagaaccccc aaccattcac ctagcagctc agggaatggc atacccatta catgaacaac
93721 acggcatggc cccgtgtccg gtagcacagg ccccacctac gcccttgccc cctgtatctc
93781 caggggatca actcccaggt gtttttagcg acgggcgagt ggcgtgtgca ccagtacccg
93841 ccccggctgg gcctattgtc cggccctggg agccatccct gacacaggct gcggggcagg
93901 cctttgcacc cgttagacca caacacatgc cagtagaacc cgtccctgtc ccgacagtgg
93961 cacttgagcg accagtttac cccaagccag ttcgtccggc acctcctaag attgctatgc
94021 agggccccgg ggaaacttct ggcattagac gcgcgcggga gcgttggagg cccgcacctt
94081 ggacgccaaa tccaccccgt tctcccagtc agatgtccgt gcgtgaccgt ctggctcgtt
94141 tgcgtgctga ggcacaggtc aaacaggcta gtgttgaggt gcagcccccc cagttgaccc
94201 aagtatcccc tcagcaacca atggaggggc cgttggtacc agagcagcag atgttccctg
94261 gtgcccccct tagccaggtt gctgatgtgg tccgggcacc tggggtaccg gcgatgcagc
94321 cacagtactt tgacctcccc ttaattcaac ccattagcca gggggcaccc gtggccccgt
94381 tgagggctag tatgggcccg gtacctccgg taccggcaac acagccacag tattttgaca
94441 tcccccttaac tgaacccatt aaccaggggg catccgcggc ccattttctc cctcagcaac
94501 cgatggaggg gccgttggta cctgagcagt ggatgttccc aggtgccgcc ctgagccaga
94561 gtgttaggcc aggggtagcg cagtcacaat attttgacct ccccttaact caacccatta
94621 accatggggc acccgcagcc catttcctcc atcagccacc aatggagggg ccgtgggtac
94681 ccgagcagtg gatgttccaa ggtgcccccc ctagccaagg cactgacgtg gtccaacatc
94741 agctggatgc tttggggtat acactccatg gtcttaacca tcccggggtt cccgtgtctc
94801 ctgccgttaa ccaatatcat ctcagccagg ctgcctttgg gttacctatt gatgaggatg
94861 agagtggcga ggggtccgat acctccgagc cgtgtgaagc tcttgatttg tcaatccatg
94921 gcaggccctg ccctcaggcc cccgagtggc ctgttcaaga ggagggtggc caggatgcca
94981 ccgaggttct tgatttgtca atccatggca ggccccgccc tcggaccccc gagtggcctg
95041 ttcaaggggga aggtggccaa aatgtcacag gccctgaaac tagaagggtg gtggtgtcag
95101 ctgttgttca catgtgtcag gatgacgagt ttccggatct acaagatcct ccagatgagg
95161 cctaagcaaa ggtgtagaag tgtgtccccc tccattccac ccactgataa tacgcccgac
95221 aataaagttg atgatattga attccacacc tgcttgtgtt tgtgatttta tttcatattc
95281 catgagagag acctcgcata tttgcagaag ggtcactgaa acatcttatc ttaaaacagt
95341 tacacctgaa taatgaagaa agcgtggctc agcagagcac agcaagccga tgccgggggg
95401 gcatctggct ccgaggaccc accagattat ggagatcaag gtaatgtgac acaggtggga
95461 tctgagccta tttcacctga gattggcccc tttgaactct ctgcggccag tgaggatgat

Fig. 3 (cont.)

95521 cctcaatctg ggccagtgga agagaattta gatgccgctg caagagagga agaggaacct
95581 catgagcagg agcacaatgg tggtgacgat cccttggatg tccatactcg ccagcctaga
95641 tttgtggatg tgaacccaac gcaggctcca gtgatccaac tagtccacgc tgtctatgat
95701 tccatgttgg taagaggcac ctagaacatt tccagatgtt tcgcttggat tttttggcca
95761 gtcttaattg attgtcattg gtttcagcaa tcggacctcc ggcccctagg cagtttattc
95821 cttgagcaaa acctgaacat cgaagaattt atatggatgt gcatgaccgt gcgtcacaga
95881 tgtcaggcca tcagaaaaaa accattacca attgttaagc agaggcgttg gaagctcctg
95941 tcatcttgca gatcctggcg tatgggttac cgcacgcata acctcaaagt aaacagtttt
96001 gagtcagggg gggacaatgt ccacccggtc cttgtgactg ctacgctagg atgtgatgag
96061 ggcacgcggc atgcaacaac gtacagtgct ggcattgtac agataccacg aatatcagac
96121 caaaaccaaa agatcgaaac agccttcctg atggcacgtc gtgctaggtc actttcggca
96181 gaaagatata ctttgttctt tgatttagta tcctccggaa acaccctgta tgctatatgg
96241 attgggctgg gcacgaaaaa ccgagtttca tttattgagt ttgtaggatg gttatgcaag
96301 aaggaccaca ctcatatacg cgaatggttc cgccagtgca ccgggagacc caaagcagcc
96361 aagccatggt taagagcgca tcctgtcgcc attccttatg atgatccgtt aacaaacgag
96421 gagattgatc tggcctatgc ccgcgggcag gccatgaata ttgaggctcc tagactgcca
96481 gatgatccta taattgttga ggatgacgac gaaagtgagg aaattgaagc tgaaagcgac
96541 gaggaggaag acaagagtgg aatggaatct cttaaaaata taccgcaaac actgccgtac
96601 aatccaacag tatacggcag gcccgcggtg tttgaccgaa agtcagatgc aaaatcaacc
96661 aaaaaatgca gggccatagt aactgacttt agtgtaatca aggccattga agaggaacac
96721 agaaagaaga aggcagccag aacagagcag ccaagagcca cgcctgaatc ccaggccccc
96781 acagtggtcc tccagcgacc acccacgcag caagagcctg gccccgtcgg cccactgagt
96841 gtccaggctc ggctggagcc atggcaacct ttgcctgggc cccaagtgac agcagttcta
96901 cttcacgaag aatccatgca gggtgtccaa gtacatggtt cgatgctaga ccttcttgaa
96961 aaagacgatg aagtcatgga gcagagggtt atggcaaccc tactgccacc agtaccacaa
97021 cagccccggg ctggcagaag aggcccttgt gtcttcaccg gtgacctagg catagagagt
97081 gatgagcccg cttcgacaga gccggttcat gatcagctac tgcctgcccc aggacctgac
97141 cctcttgaaa tccaaccact aacgtccccc accacgtctc aacttagcag ttcggcacca
97201 agctgcgcac aaactccatg gccggtggtt cagccaagtc agactccaga tgacccaacg
97261 aaacagtccc ggccaccgga aacagctgcc ccacgccagt ggccaatgcc cctgcgacct
97321 atccctatgc gccccttgcg gatgcagcca atcccattta atcatccagt gggacccact
97381 ccccatcaga cacctcaagt ggaaataaca ccatataagc ccacttgggc tcagataggg
97441 cacattccat atcagcctac accaacgggt cctgctacca tgctgttgcg ccagtgggca
97501 cccgccacca tgcagacacc accgagagcg cccactccca tgtcaccacc tgaggtgcca
97561 cccgttcccc ggcagaggcc tcgggggcg cccactccca cgccacctcc tcaggtgccg
97621 cccgttcccc ggcagaggcc tcgggggcg cccactccca cgccacctcc tcaggtgctg
97681 cccactccca tgcagctggc actaagggct cctgctggtc agcaggggcc gacaaagcaa
97741 attttgcgcc aattgttaac gggggcgtc aagaaaggga gaccatcact taagttacag
97801 gccgcccttg agcgtcaagc cgctgcgggc tggcagcctt caccagggtc cggcaccagt

Fig. 3 (cont.)

97861 gacaagattg tgcaggcgcc tattttctac ccacccgttt tgcagcccat acaggttatg
97921 gggcaagggg gttccccaac ggccatggcc gcctcagcgg tgacacaggc acccacggaa
97981 tataccaggg aaaggagggg agtggggcct atgcctccca ccgatattcc gccgtctaaa
98041 cgagcgaaga tcgaggccta tacagagccc gagatgccgc acggggggc ctcgcactct
98101 cccgtcgtta tcttggagaa tgtcggccag gggcaacagc agactctgga gtgcggagga
98161 actgctaaac aggaaaggga catgttgggg ctgggggaca ttgcagtttc ttccccttcc
98221 tcttctgaaa catcgaacga tgagtgattt cgcccatgta acaagaactg ggatgaaccc
98281 tggggcaaca gactgcgggg aggagggggg cagtgataag tcatgacaat tttagatgag
98341 gtagaaattt tgcatatttt cagacccacc atggaatcat ttgaaggaca gggggactct
98401 agacagtcac ccgacaatga gcggggagat aatgtacaga ctaccggcga gcatgatcag
98461 gaccctgggc cggggcctcc atccagtggg gcttctgaga gattggtacc agaagagtca
98521 tactcaagag atcagcaacc ttgggggcaa agcaggggtg atgaaaacag aggctggatg
98581 cagcgcatca ggcgaaggcg gagaagacgg gctgccttgt ccggccatct tttagacacg
98641 gaagacaatg tgccgccatg gttgcctcca cacgacatca caccatatac cgcaaggaat
98701 atcagggatg ctgcctgccg ggctgtcaag gtgagtatgc ctctaactgg gttcatgggg
98761 gccatctaag gcccacgtgt gacccatgtt tccattaatt ttagcaatcg cacctgcaag
98821 cgctatcaaa cctgatactc gatagtgggt tagacacaca acacatcttg tgcttcgtga
98881 tggcagccag gcagcgtctt caggacattc gacgtggacc cttggttgcg gagggcggtg
98941 tgggttggcg acattggctt ctaacatctc ccagccaatc ctggcccatg ggatatcgta
99001 cagcaacact acgcacatta actcccgtgc ctaacagggt tggggctgac agcatcatgt
99061 taactgccac atttggatgc caaaatgcgg cacgaactct aaacaccttc tctgccaccg
99121 tgtggacacc accccatgct ggaccaagag agcaagaaag atacgctcgg gaagccgagg
99181 tacgcttcct tcgtggtaaa tggcagaggc ggtaccgaag aatctatgat ttgatagaac
99241 tgtgtggctc tctgcaccac atctggcaaa acttgctcca gaccgaggag aaccttttag
99301 atttcgtgcg tttcatgggt gtcatgtcca gctgcaataa tccagctgtg aattactggt
99361 ttcacaagac aatcggaaac tttaagccat attacccgtg gaatgcacca cctaatgaaa
99421 atccatatca cgcgcggaga ggcataaaag aacacgtaat ccagaacgca tttcgaaagg
99481 cacaaataca gggtttatca atgttagcaa cgggaggtga acccagaggt gatgctacta
99541 gtgaaacgag cagtgatgag gacaccggta gacagggttc ggacgtggag ctagagtcct
99601 cggacgatga gctgccatat atcgatccca atatggagcc ggttcagcag aggcccgtca
99661 tgtttgtgag ccgtgtgcct gcaaagaaac cgaggaaact gccttggccc acgcccaaga
99721 cgcacccagt gaagcgcaca aatgttaaga cctctgatag atctgataag gcagaagcac
99781 aaagcacccc tgaaaggccg ggcccttccg aacaatcatc agtgaccgtg gagcccgccc
99841 acccgacccc ggtggagatg ccaatggtga ttctccatca accacctcca gtgcccaaac
99901 cggttccagt caagcctacg ccaccgcctt cccgtaggag aaggggagcg tgtgttgtgt
99961 acgacgatga tgtcatagag gtgattgatg ttgaaaccac cgaagattca tcgtcagtgt
100021 cacagccaaa taagccacat cggaaacatc aagacggctt tcaacgttca ggccgacgtc
100081 aaaaacgagc cgcgcctccc accgtgagtc cttcggatac tgggcctcct gccgtggggc
100141 ctcctgccgc ggggcctcct gccgcggggc ctcctgccgc ggggcctcct gccgcggggc

Fig. 3 (cont.)

100201 ctcctgccgc ggggcctcct gccgcggggc ctcgcatact ggcgcctctt tccgctgggc
100261 ctcctgccgc ggggcctcac atagtgacgc ctccttccgc ccggcctcgt ataatggcgc
100321 ctcccgtcgt acgtatgttt atgagggagc gacagctccc ccagtccacc ggccgtaaac
100381 ctcagtgctt ctgggaaatg cgggctggtc gtgaaattac acaaatgcaa caagaaccaa
100441 gttcacacct gcagtccgcc actcagccta caacgcctcg cccatcatgg gccccatcag
100501 tctgcgccct ctcggtgatg gatgctggta aggcccagcc catagaaagt tcacacttga
100561 gttccatgtc gcccacacag ccgatatcgc acgaagaaca accccggtat gaggatcctg
100621 acgctcctct ggatttaagt ttacatccag acgttgctgc tcaaccagct ccccaggctc
100681 cataccaggg ataccaggag ccgccggccc cccaggctcc ataccaggga taccaggagc
100741 cgccgccccc ccaggctcca taccagggat accaggagcc gccggcccac gggctccaat
100801 catcttcata tccaggatat gcgggtccct ggaccccaag gtctcaacat ccatgttata
100861 ggcacccctg ggcaccatgg tctcaagatc ctgtgcatgg gcacacccag ggtccatggg
100921 atcccagggc accacatctc ccacctcagt gggatggatc tgcaggacat ggccaggatc
100981 aggtctccca gttcccacat ctgcaatcgg agacaggccc accacgtctt caactttcat
101041 tggtgccact ggtctcatcc tctgcaccat catggtcatc tccccagccc cgagccccca
101101 tacgccccat tccaacaaga ttccccctc cccctatgcc gttacaagat agcatggccg
101161 tggggtgtga ctcatcaggt acagcatgcc caagcatgcc ctttgccagt gattacagtc
101221 aaggtgcatt taccccactg gacattaatg ccaccacgcc aaaaaggcct cgagtagaag
101281 aaagttctca cggacctgcc cggtgttccc aagctactgc tgaagcacag gagattctca
101341 gtgacaattc tgagatctcc gtgttcccaa aggacgcgaa gcagactgac tacgatgcat
101401 ccactgaaag tgagctagat taaggggatc caaggtgacc cctgttagct atttgatctt
101461 tgactgacac ataaacatgg tttaaggaat gaacactcat ggtgtgagac tggaactgta
101521 ctaaatttgc tgacatatgt acaatgagag ccaaaaattt gataaacctt aaaagtcccc
101581 ccatctaatg atgtccagtt cccttctccc accctgtaca ccccgaccca aagggactca
101641 atggcattca gatttctagt taccacaggt agaatatcgg gcgttggccc ataaaaataa
101701 gtgcatggat atagctctgc acaggcttgg aaacacccat tccaggtgtg cttcttttg
101761 gtgaaataaa aacagcatcc tttatatgaa aatgtgtatt ctctggtgtt gcagtatgta
101821 cagttagctt tggtatagtt ttggggtacc tgaaatgtgt gcagggtggg tgtccaatgt
101881 ggcagtttta cctctttgtc cccatactcc tgctcggccg tcttgttaaa gttaaccggc
101941 ggtggaggat ccaccggcca gacctctaca tttggtttgg gtacccaggt gatggccgcg
102001 gctgccaccc gccctcctcc tcttaccctg ggtggcaaaa agtatgccag gagtagaaca
102061 ataacaagtg cgatggcggt aaacaatggc accctcacct gcttaaatga aaccatggca
102121 accacttcaa agagagccga caggaagata tttattaata ttccattagt aaacgaggcg
102181 tgaagcaggc gtggtttcaa taacgggagt tagaaattta agagatcctc gtgtaaaaca
102241 tctggtgtcc gggggataat ggagtcaaca tccaggcttg ggcacatctg cttcaacagg
102301 aggcgcagcc tgtcattttc agatgatttg gcagcagcca cctgcggaca aaaatcaggc
102361 gtttagatgg ggcatttatg tttgggacgc tagccgcctg ggcattcgtg ttagtatata
102421 ctgacctcac ggtagtgctg cagcagttgc ttaaacttgg cccggcattt tctggaagcc
102481 acccgattct tgtatcgctt tatttctagt tcagaatcgc attcctccag ctgcgagcaa

Fig. 3 (cont.)

102541 gggaatgcgt tactacaagt ggtgcctagt cagttgaaac aagccccacc atccgctgcc
102601 gcccctccat gagccccacc gtccgctgcc gcccctcctt gagcccctcc ttaccgattc
102661 tggctgttgt ggtttccgtg tgcgtcgtgc cggggcagcc actggtgcag gctgtggaac
102721 accaatgtct gctagctgtt gtccttggtt agccccgggg caagcaaaca ccactgctgc
102781 tgctgtttga acagtagaat tgtctccagg ttgaggtgct tctcccccgg cttggttagt
102841 ctgttgattc tgggttatgt cggagactgg gaacagctga ggtgctgcat aagcttgata
102901 agcattctca ggagcaggct gaggggcaga aaaccacgac ccagtcggag cggttgaaac
102961 atgataggca gttagctggc cttgtggcag aggctctggc agcaccggcc acagcacaca
103021 aggcaaagga gcttgcgatg gccctcccag gtcctgatag actctggtag cttggtcaaa
103081 agcttgtaca aaaggcacct ggtatgggtc aggtgtaaat tttacatctt cagaagtcga
103141 gtttgggtcc atcatcttca gcaaagatag caaaggtggc cggcaaggtg caatgtttag
103201 tgagttacct gtctaacatc tcccctttaa agccaaggca ccagcctcct ctgtgatgtc
103261 atggtttggg acgtgctaaa tttaggtgtg tctatgaggt acattagcaa tgcctgtggc
103321 tcatgcatag tttctaaaag aggaggaggc agttttcaga agtgtctaaa ataagctggt
103381 gtcaaaaata gacagcccag ttgaaatatg catggcatgc agcagacatt catcatttag
103441 aaatgtatcc aagatttcat taagttcggg ggtcaggggg gagtccagat tcaaatcctc
103501 tgtcatggac tctagtgttg tggtcagttc gtccaaatgg ccacgagggg gcgggtggct
103561 caggtccatc tgtccacata tggctgcttc ctccttctgg ggaataacag tgtcagccat
103621 ctcccttagg gccttcacgg cctgactggt ttcttcatca gggtcctcca acagatgact
103681 tgcctcgggg gttactgcgg gggccgggtc aagtggctgg ggcaccgggg ctggcgttag
103741 ggatccgacc ggttcatgga caggtcctgt gggggtggga gccaaagagg caggcagggg
103801 ccggttggcc cacggggatc cgggtggatg gaagggcctg atcctctttg gctgacacac
103861 ctctcgcccc tcgaacacgt cagatatggc actgcccgct tccggctttg gcaggaacat
103921 accttcccgg ctatccctga ggcccttctt ccttttaacg ggaggaagaa aggtgggctt
103981 tgaggggtgg gggaatatgg gtctctcatc gctctcttgg tggaccgctg ctatccaagg
104041 ctgttcaggt tccgccgcgt tggaaggaca tggagtttga ccacggttgg gcctggatgt
104101 ccggcgcgac tttggggccc gcaggcgcgg ggcctcggcc ctggcctctt cccgctcgct
104161 ctgctcggtg tcactgttgc ccgagtcact gctgctggaa ctgctgtcac cgcagtcggc
104221 gctttgggca ccgggcttca ggggcatggt cgggctcggg agactttcga gttcatctgt
104281 aaaagcatga aactgtccgg actccgagta gcgggcctcg gtgtgagagg cacccccatc
104341 attccccatg agctcctcgt ccatcctgtc ggctccggac acgaggatag gagtttccac
104401 tgccttggac ttggttgaca gcaggcacgc gggaagcacg ccgctcacgt agctcctctg
104461 tccggcgtgg ctggagtagg aggcccgggg cagtgtctta atcagagccc tgacatcctt
104521 aacatcgtcc gtcagatggc ctgtcttgga cgagaccata gtctggaaca tctcctcgag
104581 gacgggatag gtgaacaccc acttgcaaaa ggccttgaac ttggagctta ggaggccttc
104641 cttctccatc ctgttcaggt gttccactac ctgcttgccg gaggccatga tggccgcgcg
104701 gtccacgccc agcaccttgc tgtaggtgta ggcccgcacc cgactgtgtt ttaggagctt
104761 gtacatagcg gtgcctatgg tggcaggaat catcacccgg ttgctggggg cctggatgaa
104821 gaatctgtca gtgaccacta tcaggtggtc taacacgtag cgcatcacta tagggcacgc

Fig. 3 (cont.)

104881 gatggaacat gcgtcgttgc cggcattctc agcccgtctt cttaccctgt tgtttcggag
104941 aatggcccaa aaattgcaga tgttgagcgt ggccattagc ccgccccatt ctcgcccgtg
105001 ggccttggcc tcatttataa atgccttgca tattttgtag gatctcagag taatctccac
105061 actcccggct gtaaattcct tgttgaggac gttgcagtag tcagagacca gagagcccag
105121 ctgcttttg atttcaggag ttagcctcag aaagtcttcc aagccatcct ttttaggcct
105181 catggctagt agtaacagag gaaatgcccg accattaaaa tctttcctcc atgagcttta
105241 cctgaaacac tatcccgaag tgggggatgt ggtgcatcta ctgaacacca tcggggtcga
105301 ctgcgacctc ccacctagcc acccactcct gacagcccag agggggctgt tcctggcaag
105361 agtcttgcag gctgtacagc agcacaagct gctggaagac accatcgtcc ccaagatctt
105421 aaagaagctg gcttatttct tagagctgct aagctactac tccccccaagg atgaacagcg
105481 tgacatcgcc gaggttcttg accacctcaa gacgaatcgg gacctggggc tggacgacag
105541 actctgggcc ctgattagga aactgcgcca agacagacac catgcctctg taaatgtcct
105601 catgccagga agcgactaca cagccgtgtc gctgcagtac tacgacggca tctccatagg
105661 tatgaggaag gtaatcgcgg atgtctgccg cagtggctat gcctccatgc cctccatgac
105721 ggccacgcac aacctctccc accagctctt gatggcgtcc gggcccagtg aggaaccgtg
105781 cgcctggcgc gggttcttta accaggtcct cctctggact gtggccctct gcaagtttcg
105841 cagatgcatt tactataact acattcaggg atctatagcc accatctccc agcttctgca
105901 cctcgagatc aaggccctct gcagctggat aatatcccag gatggcatgc gcctctttca
105961 acacagcagg cctctcctca ccctctggga gagcgtggcc gcaaatcagg aggtcacgga
106021 tgccattacc ctgcctgact gcgctgaata catagaccta ctaaagcaca caaaacatgt
106081 cttagaaaac tgttctgcca tgcaatacaa ataaatttct cttacctgcg tctgtttgtg
106141 tagtgaggtg ttgtgtcctg tatggtattc tactttaaaa aggccggctg acatggatta
106201 ctggtctttt atgagccatt ggcatgggcg ggacaatcgc aatataaaac cctgaccatc
106261 acatggggca ttaggcgact ctgcatcagc atcgcttaag tatgagtggg cagcagagag
106321 gctcggttat tttggttcct gaacatctgg ctggggcatt aactaagctt atgagcgatt
106381 ttatcacagg acaagatgtc actctttctg gaggaaatat tgcagtcaaa attcgcgatg
106441 ctataaacca gaccccccggg ggtggtgatg tagctatact ttcttccctg tttgctttat
106501 ggaatgccct cccaacatct ggtagacaat cctccaggga cgatttaatc ccagccgccg
106561 tgcaggcctt aaccacggcc cacaacttat gtctgggtgt tattccaggt gagacctcac
106621 acaaggacac acccgagtca ttgctccggg ctatcgtgac gggtctccaa aaattgtggg
106681 tggattcgtg cggatgtcca gagtgcctac aatgtcttaa gggattgaag gcaattaagc
106741 ccggccttta tgaaatccct aggataatac cacacactaa gcagtgtagt cctgtcaatc
106801 tcctgaacat gttggtccac aagcttgtgg ctttacgtgg tcatgtgcag cttgcatacg
106861 acgcccgtgt cctgacgcct gactttcacg aaatccctga cctcgatgac tccgatgctg
106921 ttttcgcacg caccttattg gcagccttat ttcacctcaa tatgttcttt attctcaaag
106981 attacataac acaagactcc atgagcttga agcaggccct cagtggtcat tggatgtctg
107041 ccacgggcaa ccccctgcct gcagcaccgg aaaccctgcg agactacttg gaagctttcc
107101 gaaattcgga taatcacttt tatctcccga cgacagggcc tttaaacacc ttccaatttc
107161 ccgaagagct tctggggcgc gttgttgtta ttgattcctc tttgtgtgcc gccagtcacg

Fig. 3 (cont.)

107221 ttcaggacgt tatcacccat ggtgttgggg cgggtgttcc tcgtcctcgg ttttcggccc
107281 tgcctccggc cccatcccgc gagccccagc agacatgctc tcagttaacg agcagaggga
107341 atgaaagctc acggcgaaac ttgggccagc ccggggggac ctcccctgct gttcccccag
107401 tttgccccat cgtttccctg acggcctcag gggccaagca aaaccgcggg ggcatgggat
107461 ccttgcactt agccaagcct gaggaaacct cccccgccgt ctccccagta tgccccatcg
107521 cttccccagc ggcctccagg tccaagcagc actgcggggt cactggatcc tcacaggccg
107581 cacccagctt ttcttccgtt gccccagtag catctctgtc tggtgacctt gaagaggaag
107641 aggaggggtc ccgagaatcc ccatccctac cgtccagcaa aaagggggac gaggaatttg
107701 aggcctggct tgaggctcag gacgcaaatc ttgaggatgt tcagcgggag ttttccgggc
107761 tgcgagtaat tggtgatgag gacgaggatg gttcggagga tggggaattt tcagacctgg
107821 atctgtctga cagcgaccat gaagggggatg agggtggggg ggctgttgga gggggcagga
107881 gtctgcactc cctgtattca ctgagcgtcg tctaataaag atgtctattg atctctttta
107941 gtgtgaatca tgtctgacga ggggccaggt acaggacctg gaaatggcct aggagagaag
108001 ggagacacat ctggaccaga aggctccggc ggcagtggac ctcaaagaag agggggtgat
108061 aaccatggac gaggacgggg aagaggacga ggacgaggag gcggaagacc aggagccccg
108121 ggcggctcag gatcagggcc aagacataga gatggtgtcc ggagacccca aaaacgtcca
108181 agttgcattg gctgcaaagg gacccacggt ggaacaggag caggagcagg agcgggaggg
108241 gcaggagcag gaggggcagg agcaggagga ggggcaggag caggaggagg ggcaggaggg
108301 gcaggagggg caggaggggc aggagcagga ggaggggcag gagcaggagg aggggcagga
108361 ggggcaggag gggcaggagc aggaggaggg gcaggagcag gaggaggggc aggaggggca
108421 ggagcaggag gaggggcagg aggggcagga ggggcaggag caggaggagg ggcaggagca
108481 ggaggagggg caggaggggc aggagcagga ggaggggcag gaggggcagg aggggcagga
108541 gcaggaggag gggcaggagc aggaggggca ggaggggcag gaggggcagg agcaggaggg
108601 gcaggagcag gaggaggggc aggaggggca ggaggggcag gagcaggagg ggcaggagca
108661 ggaggggcag gagcaggagg ggcaggagca ggaggggcag gaggggcagg agcaggaggg
108721 gcaggagggg caggagcagg aggggcagga ggggcaggag caggaggagg ggcaggaggg
108781 gcaggagcag gaggaggggc aggaggggca ggagcaggag gggcaggagg ggcaggagca
108841 ggaggggcag gaggggcagg agcaggaggg gcaggagggg caggagcagg aggaggggca
108901 ggagcaggag gggcaggagc aggaggtgga ggccggggtc gaggaggcag tggaggccgg
108961 ggtcgaggag gtagtggagg ccggggtcga ggaggtagtg gaggccgccg gggtagagga
109021 cgtgaaagag ccaggggggg aagtcgtgaa agagccaggg ggagaggtcg tggacgtgga
109081 gaaaagaggc ccaggagtcc cagtagtcag tcatcatcat ccgggtctcc accgcgcagg
109141 ccccctccag gtagaaggcc atttttccac cctgtagggg aagccgatta ttttgaatac
109201 caccaagaag gtggcccaga tggtgagcct gacgtgcccc cgggagcgat agagcagggc
109261 cccgcagatg acccaggaga aggcccaagc actggacccc ggggtcaggg tgatggaggc
109321 aggcgcaaaa aaggagggtg gtttggaaag catcgtggtc aaggaggttc caacccgaaa
109381 tttgagaaca ttgcagaagg tttaagagct ctcctggcta ggagtcacgt agaaaggact
109441 accgacgaag gaacttgggt cgccggtgtg ttcgtatatg gaggtagtaa gacctcccctt
109501 tacaacctaa ggcgaggaac tgcccttgct attccacaat gtcgtcttac accattgagt

Fig. 3 (cont.)

109561 cgtctcccct ttggaatggc ccctggaccc ggcccacaac ctggcccgct aagggagtcc
109621 attgtctgtt atttcatggt ctttttacaa actcatatat ttgctgaggt tttgaaggat
109681 gcgattaagg accttgttat gacaaagccc gctcctacct gcaatatcag ggtgactgtg
109741 tgcagctttg acgatggagt agatttgcct ccctggtttc cacctatggt ggaaggggct
109801 gccgcggagg gtgatgacgg agatgacgga gatgaaggag gtgatggaga tgagggtgag
109861 gaagggcagg agtgatgtaa cttgttagga gacgccctca atcgtattaa aagccgtgta
109921 ttcccccgca ctaaagaata aatccccagt agacatcatg cgtgctgttg gtgtatttct
109981 ggccatctgt cttgtcacca ttttcgtcct cccaacatgg ggcaattggg catacccatg
110041 ttgtcacgtc actcagctcc gcgctcaaca ccttctcgcg ttggaaaaca ttagcgacat
110101 ttacctggtg agcaatcaga catgcgacgg ctttagcctg gcctccttaa attcacctaa
110161 gaatgggagc aaccagctgg tcatcagccg ctgcgcaaac ggactcaacg tggtctcctt
110221 ctttatctcc atcctgaagc gaagcagctc cgccctcacg ggccatctcc gtgagttgtt
110281 aaccaccctg gagactcttt acggttcatt ctcagtggaa gacctgtttg gtgccaactt
110341 aaacagatac gcatggcatc gcgggggcta gacctctggc tggatgagca cgtgtggaag
110401 aggaaacagg agattggtgt gaaaggagaa aatctgcttc tccccgactt atggctagat
110461 ttcctacaac tcagccccat cttccagcgc aagcttgctg ccgttattgc ctgtgtccga
110521 cgcctgcgga ctcaggccac cgtctaccca gaggaggaca tgtgcatggc ctgggcccgc
110581 ttttgcgacc cctctgatat taaggtggtt attttgggcc aggaccccta tcacgggggt
110641 caagcaaacg gcctggcatt cagcgtcgca tacggctttc cagttccccc cagcctgagg
110701 aacatctacg cggagctgca ccggagcctg ccggagtttt ctcccccaga tcacggctgt
110761 ctagacgcgt gggcctccca gggggtgttg ctactcaaca ccatcctgac cgtgcaaaag
110821 ggcaagcccg gctcgcacgc agacattggc tgggcgtggt ttactgacca cgtaatttca
110881 ttgctctctg agcggttaaa agcgtgcgtg tttatgctgt ggggtgcgaa ggcgggagac
110941 aaagcttcac taatcaactc caagaagcat ctggttctga cctctcagca tccctctccc
111001 ctggcccaga acagcacccg aaagagtgcc cagcagaagt tcctgggcaa caaccacttt
111061 gtcctcgcta acaacttttt gcgtgagaag ggctcggtg agatagattg gaggctgtag
111121 aggggtcatc actatggcca tgtttctgaa gtcgcgtggg gtccggtctt gcagggaccg
111181 gcgcctcttg tcggacgagg aggaagagac ttcacagagc agcagctaca ctctggggtc
111241 tcaggcctcc cagtctatcc aggaggagga cgtgagtgac actgatgagt ctgactactc
111301 agatgaagac gaggagattg atttggagga agagtacccc agtgacgaag acccatctga
111361 gggcagtgat agcgacccct cgtggcatcc ttcagattca gacgagtctg actacagcga
111421 gagcgacgag gatgaagcaa cccccggctc tcaggcctca cgatcttcaa gagtctcgcc
111481 atctacccaa cagtcttcag gtctgacacc cacgccttcg ttctcccgac cacgcacccg
111541 ggcacctccg aggccgccgg ctcccgcgcc ggtcagggga cgggcctcag cacctcccag
111601 gccaccagcc ccagttcagc aatccaccaa agacaagggt ccccatagac ctacgcgacc
111661 tgtacttaga ggcccagctc cacgccgccc ccctccacct tcaagtccca atacatacaa
111721 taaacacatg atggaaacca cccccccat taagggcaat aacaactaca attggccatg
111781 gctgtaaata aaatgtcata acctggagtc tgcatgtctg ttgttttatt cagtaaacca
111841 gtagtgcgcg tgagttcttt agggcatcca cgatgtagcc gctcgcgggg ttcccctccc

Fig. 3 (cont.)

111901 cagtgatcat ctcggatagg ggattcctgt ccatgaccac gcaattagag tgccgggccc
111961 gggacagcgc cacatacaca tggccgggtt tgatgtttct gtggctgccg aagcagatgg
112021 cgactttgtt tagggacaga ccctgggcct tggctatggt catggccagc tttgagctaa
112081 tgccatagtc acggatgctg cagaggttca gggacttgtc ctctatcgtc tcatacagtt
112141 tgttagtatt gtgttccagg cagcacacga agcctgcctc atccttgacc attagcctgg
112201 gcatgcgtga actgccagcg tcctgaggct gctgctttcc tcggatgcca aagaagacgt
112261 tgagatgcgt gtagcccaga agcgtgtagt tctcggtggt ggaggcgtag tccaggaggc
112321 cgtgaaggag aggctcgtct gaggtgaact ctatgttgtc gcgaatcagc atgttgttgg
112381 taaatgtgca gaaggggagg tccctgaact cccttccgcc atagcggacg gccacatcca
112441 ggcattgcct gaaataggcc ctgaggtcat tatatatgtt taacagggag cagagggggg
112501 cagaatttgc ggccggggga gccagtactc gggcatagaa gacagcggcg gggctccgct
112561 ccccatccca ggcaacctcc agcggcagtt cgcccagctc catcccagca gtcacctccg
112621 gatcccacgt acgcccgggc aggggcacag caccaagctc cgccacgtat tccccgtttt
112681 cacagagaga atgtcctccg tggctaaaag cgtagatgcc tccgtagatg agtcgggcca
112741 ggaagctgta gacatactcg ggctgctcat gcccgtgggc ctccacgaag ctgtccgcct
112801 cgagcgtgtc cataaagtcc ccgaaggtgc cggtatagcc acagatggac tttttggtct
112861 tgcagttgac cgacaccgag ctgtgcttga cgtaggtgac attgtaggtg accttgaccc
112921 gttcttcgtc ctgctcggtg cccaccggga ccatgtcttg gtcggcgaac tgcgagtagt
112981 taccgaggcg tgcataattc ttttggagcc aggtgtgggc cgtgaggccc ggaagcccga
113041 ccagggtctt gtactgggcc aggggatcga ggaagacctc gcactccacc gggcaggtaa
113101 acatggtcac cccgcccccca tctcccccgg ttccccgcgc ggcacgcccc tgcccggcag
113161 tcttgagcgt ggcatggagg gtggtgagga aggtcttgac ctcggcgtgg gagaggaaga
113221 gccgggtcca gcccacgtac tgcgcggggt ccattatggc cgccctgggg acgacgaagc
113281 ggtcgacgta ggccaggatg tccggcgaga gctcgaggcc gtactcgagg gtcttcatga
113341 ggtgtccaaa ctggacgtcg gtgcagcgct tgttgttgat gaagagggcc cagttgcggg
113401 ccacgtccac gtaggtcgcg gccctggggt tgcccaccag gaaggtgagg atgttgtcgc
113461 actcgcgaat cttgtttacc tgggtctcgt ggctaaagga ggactgaaag gcgtctgtct
113521 gggtgggaga gcccacgcag acgatgcagg gaatgcggcc ccggcggtag agtggggtac
113581 gcagccaggc gttgaagaac cagtagcaaa agaccacggc tgttagaatg tgcacggaaa
113641 gcgttccagc ttcgtccacc acgatcacat tggtggtcca tagctgcccc tggtgcatgt
113701 ctctcaggac ctcaaaggcg gggccagaga ctcccgagta gagccccctg ggcttggttc
113761 gcctgaactc ggcggcaatg tcggagagta ccggccagta tttggccagg tcccgccgct
113821 ggagttcctc tagggcggcg tccgtagagc gaccatgact gctgacccgc tgcgtcatat
113881 ttatgtggcg gctcttgaac ccaaaggcgc tatagacggt tgggcagtag gctcggagtg
113941 tctgggagag gttctgtgcg gccacggttg tggctcccgt gaccaggcag tccatcgtgt
114001 ggtggaggca gctaacgctg gtgctcttgc cagccccccgc cgttcccgta attacatagg
114061 ctgaaaaggg caggaagggg ggctccgaga gctccgggtc aaactcgggg gagaacgtct
114121 ccatatccgg gagttgttgg acgcggcgcc tagccagggt ccctatcctc ctgactatac
114181 gcctcacgga ggcgtctgag gtcatgttca acatgaacgt ggacgagagc gcctctggcg

Fig. 3 (cont.)

114241 ccctcggctc ctcggccatt cctgttcacc ccacgccggc ctcggtccga ctttttgaga
114301 tcctgcaggg aaagtacgcc tacgtccagg gacagaccat ctacgccaac ctccgcaacc
114361 ccggagtctt ctcgaggcag gtgtttaccc atttgtttaa acgagccatc tctcattgca
114421 cgtacgatga cgtgctacat gactggaaca agttcgaggc ctgcatccag aagcgatggc
114481 cgagcgatga ctcgtgtgcg agccggtttc gtgagtccac cttcgagtcg tggtccacga
114541 ccatgaagct gaccgtgcgt gacctgctga ccaccaacat ctaccgagtg ctacacagcc
114601 gctccgtgct ctcctatgag cgttatgtgg actggatctg cgccaccggc atggtgcccg
114661 ccgttaagaa gcccataacc caagagctcc actccaagat aaagagcctg agggacaggt
114721 gcgtctgtcg ggaattgggg cacgagagga ccatcaggag tatcgggacg gaattatatg
114781 aggcaacgaa ggaaataata gagtcgctca actccacgtt catccccccag tttacggagg
114841 tgaccatcga gtaccttccg aggagcgacg agtatgtggc ctactactgt ggccgccgca
114901 tcaggctgca tgtgctcttc cccccggcca tctttgccgg aacggtgacc ttcgacagcc
114961 cggtgcagcg cctctaccag aacattttca tgtgctaccg cacgctggag catgccaaga
115021 tctgccagct cctgaacacg gcccctctca aggccatcgt gggccacggg gggcgagaca
115081 tgtacaagga catcctggcc catctggagc agaactcaca gcgcaaggac cccaagaagg
115141 agctgctgaa cctgctggtc aagctctcgg agaacaagac catcagcggg gtcacggacg
115201 tggtggagga gttcataacg gatgcctcca acaacctggt ggaccgcaac cgtctatttg
115261 gccagcccgg ggagacagct gcacagggcc taaagaaaaa ggtctccaac acggtggtca
115321 agtgtctgac tgatcagata aacgagcaat ttgaccagat taatggccta gagaaggaga
115381 gggagctcta tctaaagaag atccgctcca tggagtctca gctgcaggcc tccctgggtc
115441 ccggcggcaa caacccagcg gcgtcagccc ccgccgcagt tgcggcagaa gccgcgtctg
115501 tagatatact gacgggcagc accgcctccg caatcgaaaa gctgttcaac tccccgtccg
115561 ccagcctggg tgccagggtg tctggtcaca atgaaagcat cctaaacagt ttcgtttctc
115621 aatacatccc cccttcgcgg gaaatgacta aggatctgac tgaactttgg gaaagcgagc
115681 tgtttaacac cttcaagtta acacccgtgg ttgataatca ggggcagcgt ctctacgtca
115741 gatactcgtc agacacgatc tctatattat tgggcccctt cacctatctg gtggcagagc
115801 tttcaccggt ggaactcgtg acagatgtct acgccaccct aggcatcgtg gagatcatcg
115861 acgagctcta ccggagcagt cgcctggcca tctacatcga ggacctcggt cgaaaatact
115921 gccccgcgag cgcgaccggg ggagatcatg gcatccggca agcaccatca gcccgggggg
115981 acacggagcc tgaccatgca aaaagtaagc ctgcgcgtga cccccccgcct ggtgctggaa
116041 gttaaccgcc ataacgccat ctgcgtggcc accaacgtcc ctgagttcta caatgccagg
116101 ggggacctta acatccgaga cctccgggcc cacgtcaagg cccggatgat ctcgtcccag
116161 ttttgcggct acgtcctcgt gagtctgctg gactccgagg accaggtcga ccacctcaac
116221 atattccccc acgtgttctc cgagaggatg atcctgtaca aacccaacaa tgtgaacctt
116281 atggagatgt gcgccctgct ctcgatgatt gagaatgcca agagcccctc cataggcctc
116341 tgccgggagg tgctgggtcg cctgaccctc ttgcactcca agtgcaacaa tctggactct
116401 ctgtttctgt acaatggggc caggacgctg ctgtccaccc tggtcaagta ccacgacctg
116461 gaggaggggg ctgccacccc cgggccgtgg aatgagggcc tgagtctctt taagctgcac
116521 aaggagctga agcgcgcccc atccgaagcc cgggacctca tgcagagcct ctttctgacc

Fig. 3 (cont.)

116581 tcggggaaga tggggtgcct ggccaggtca cccaaggatt actgcgcgga tctaaacaag
116641 gaggaagatg ccaactcggg cttcacattt aacctgtttt atcaagattc tttattgacc
116701 aagcatttcc agtgccagac cgtcctccag accttgagac gcaagtgcct cgggagtgac
116761 acggtctcaa aaataattcc ctagaataaa ctgagaacag tcatcagtaa atctgtctct
116821 cgcgtgattt ccataggaat ggtgtagccg gggtggaggg ccgatatcac atcaagcaga
116881 aaggccataa tctctcgaaa gtaggcggtg gggctgagac catgctcagt ggccgtctgg
116941 cagggggccg ggcgcgctcc gtccttgtcc aggagacaca cgtggcttcc agagaggcgc
117001 agcccagccc tccgcagccg ctgaagccag gctcgcggaa gagcccaaaa cctgtttcgg
117061 cgccgcccgg gggccagtct ccgggtcagg tcgcggacca gggtcaacag gtggtcgtgg
117121 gatggcgggg ccttgtctgc ctcgggtctc gccgctagtt ggtccagggt ccaggagaag
117181 gcttcgtgcc aaaccaaaaa gggccccgag tgctccctac atccacccac gtaaagatcc
117241 ccctgaaaga tggccatcag taggcacccg ggcccgcgtc gagccttcac ccgaatgtgt
117301 ctgcgggcca cggtggcctc tccacccatc acatcccggt cgagccggct ggcatcctcc
117361 gagtctttca cgccttgcag gaaagcctag gagatacagc aacagaaagc tattagccgg
117421 tggttccccc accatcattc ttcctgttaa cgggaagaat aagagttggg caaaccccgg
117481 gggccgcgct ctcccaccca gccccgcttc tcacctgtgc tagtggctcc tctgaaggat
117541 gggcggaggt tggtgccaca aagcccagga tgaactcgtc tgcataagcc caggtcagtc
117601 ctaggtcagc ggccgcgtgt aggagaaccc gggtgacggc ggtgtagagg cccccgagtg
117661 cccgtcgcgt gtctgaggtg ccatagcggt gaagggcccg cagccaggtt tgcgcgtccc
117721 gcgcctgccc tccgccatca ggcgttccca cgggggcgcc cctggcagag aggtggcagc
117781 gggccaattc gtagagccac caagtggcat cagcctcaag gatggctgtg gcctccgcgc
117841 gcccgaccac cgtcgtctcg tcctcccccc ctccctcgcc gccttcccgc gtgcaaacgt
117901 ggcgagggtt aatctccttt cgggtcgggg gccagatttg ttgtaggagc agcgagccgc
117961 gtcgttgccc tgaccgcgcg tcgaggccca ggagggcgtc tgccaggggc gtcccagaga
118021 ctcccaggtt caggtccagt agcaggagac cctcgctgtg tggcgcccgg tgccagaagg
118081 ccggcctcgc ccgtcccaca taatggatgg gcaggaaggg aaagcccggg acatagggct
118141 ggaaatctga gccccctggg cagagttcgg ggtccaggag gtagaagatg ggcttggtgc
118201 ctctgtggtt ggcgtagcag gaggcataga tactgcggag gaaggcgtag agcccgcccc
118261 cggccatact ccaagagttg acaagccagg actcgaatcc cccagccggc tcaagaattt
118321 tcaggctgac gcggtgccgt cgggcgtccc caccacggcc ggtggccccg tcggacgaca
118381 ccagatctac ttcataagtg accggtcgca ggatgtccct aaaggggacg ggagaggggt
118441 cgtcgggagt ctcggtggaa taggtgaaaa catccccacg cggtgtcctg atgtatacgt
118501 ccaactgtcc gggagactca gagtgcctct gagcatgggg gcatgtctgt tccccctcca
118561 tctcggaccc gaagccatca acaggtgggg gttgttggtc ccgcccatca tcccccgagc
118621 agctttggca gaccacctgt gctggaaaga gaggctggaa gatgaggccc tgctcatcct
118681 ccaccctggc ggcggacaag agtctgcggt ctcgggttct aaatgaaagg tcaaataggt
118741 ccttctcggc ggcatcggcg agcatagcaa tgagcccccc gctgcgcctg agctcccgct
118801 cccatcgcaa aaagttgagt tcggtagtcg agggcgcgtt gaccacgggg ggctccaggg
118861 agcctccaag cggcggctgg caggcctgca ccacgatcag agtctcaacg tcctcccttt

Fig. 3 (cont.)

118921 tgatgggcac gatgcccacg acccaaatcg cccaccaccg ccctgcggtc tgggtaacat
118981 tataaaaggt aaccgagctg acgcgggccc tgacgctctc cgcgggtgtt tccatcattg
119041 tttgagatct gaggaggact ggacccttta aaacatccgg tcacgccctt tgcaaattat
119101 ttaaaaggtg aatgctcaac tgagaccatc gcaatcatga agtcctccaa gaatgacacg
119161 ttcgtctata gaacgtgggt caaaacgctt gttgtgtact ttgtgatgtt tgtcatgtcg
119221 gcggtggtcc ccatcaccgc catgttcccc aacctggggt accccctgcta ctttaacgca
119281 ctggttgatt acggggcact taacctgacc aattacaacc tggcccacca cctgaccccc
119341 acgctctatc tggagccgcc ggagatgttt gtctacatca cactggtctt tatcgcggac
119401 tgcgtggctt tcatctacta cgcctgcggc gaggtggcgc taatcaaggc ccgaaaaaag
119461 gtctcgggtc ttacagacct ctcggcctgg gtctcggcag tgggctcccc aaccgtgctg
119521 tttttggcca tcctcaagct ctggtccata caggtcttca tccaggtcct ttcctacaag
119581 cacgtctttc tctcggcctt tgtgtacttt ttgcactttc tggcctcagt tctacacgcc
119641 tgcgcatgtg tgacccgctt ctccccggtc tgggtggtca aggcccagga caactctatt
119701 ccccaggaca ccttcttgtg gtgggtggtc ttctacctga agcccgtagt tacaaacctg
119761 tacctggggt gccttgccct ggagacgctg gtcttctcgc tcagcgtgtt cctggccctg
119821 ggcaacagct tttactttat ggtgggggac atggtgctgg gagccgtgaa cctcttcctc
119881 atcctgccca tcttctggta cattctgacg gaggtgtggc tggcctcctt cctgcggcac
119941 aactttggct tctactgcgg catgttcatc gcctccatca tcctgatcct gcccttggtc
120001 aggtacgagg ccgtctttgt ctccgccaag ctgcacacca ctgtggccat caatgtggcc
120061 atcataccta tcctgtgctc ggtggccatg ctcatcagga tatgccggat tttcaaaagc
120121 atgcgccagg gcactgacta tgtccctgtc tcggagacgg tggaactgga gctagagtca
120181 gagccgaggc ctaggccctc gcgcacgcca tcacccgggc gcaaccgccg ccgctcttct
120241 acgtcctcat cttcctccag gtcaaccagg agacagaggc ccgtctctac ccaagccctc
120301 gtctcctccg ttttaccgat gacgacggac agcgaggagg agatcttccc ctaatgcaat
120361 aaaaacttaa aacactgagg ttactttccc gtcattcttt cgggggaacg aggggaggcg
120421 ggaattgggt taagataggg gcgaagggtg ggggtgggtg caagaattgg ggctgggaat
120481 ggagagggga gtgggctagg tgccgacacc ggggtgccaa gataatggat tgagtaagca
120541 tggggctctg atcgggtccg ccgggtctc aggggtgtag tgggtgggca ttgcatattt
120601 ttgccgcggt gctgttgggc cttggactcg gggtgatcat ccgtaccatc acccgcaccc
120661 gcaccccagt ccacagccac cggccaaggt cctgggcctc ccaccaccgt tatgcctccc
120721 cctttaccca ttaattacaa gagatgttag tttggttttt tatttggcaa aaacagcaat
120781 tcatcatttt cagagtcctc atcatattcg agcccctcgt tggtttcccc gcaggccctc
120841 ccttcttcgg ccgctattag cttagtagtc tccaggttaa actcctcata gtcattatac
120901 aggttgatta ttccccccgtc cacgtcgcct atggagttga ctcgtcgtcg gcaaagagac
120961 cagagggcac ccatggcgcg gtgtcaaaag tattgtctgc gtacgctttc caggagccag
121021 ccgcggtgct caaggtctta cggatgacag agtccggcag gaccacgggt gtcaccagca
121081 ccgccacggg aatctccacc gaggcgtcca gaagcaggtc tgagccgagc gtgcaggtcg
121141 ccgggtctag aggcgaccgt tttcgaaaga aggccgtcac aatgttcacc cggggtgagc
121201 agtctctccc gggcttgcca cccccactgt ggcggacgta gtctccaaca attttgtatt

Fig. 3 (cont.)

121261 ggaggagcac ctggtagaag tagttgtgcc gtggattgat gaagatgttg actgggaccc
121321 ggtctttaat accaatgcgc cccgcatttt cgcttgggtc cgtcattacg tagagcatag
121381 actccacccc cctgttggca gctaggctgt ctgccaccag gtcatgaccg gggcccagtt
121441 tgcgcttacg gacatcttta agattccagg cctcatcctg cgtcaacaga tagtcaccct
121501 ccgagggcaa ccgcccatcc gggacgtact ccacggtagg acgagctata gaattgataa
121561 atctgataaa tgacctcttg catggcctct tgtaaagcgc agtgtaggat gggtagatgg
121621 ggtcaaattc tgacttggaa aagaggtact tgaagcggca cttaatctca taaatgcagc
121681 tccggtcggt gaacagtata aagtctccct gtgactccac attgacgcaa agatccagag
121741 acaccccaaa aatgccatcc gtgggactaa tcataaagcc aaattgacgg ttggcggatg
121801 cgtccccgca gatgagctta cagacaatgt ccttgaccgt gtcctcacac cgcaggccaa
121861 aggccacagg tcccccaaag tagtgatttg tggagatggg agctggctca aacaccttgg
121921 tgggtccatt cttaatggtg gagagcagct tggaagagga aattatgcca tttcgcaata
121981 tgtcccacat caggttctca gactgccccc tggtcatgga ctccacgtac gagcagagaa
122041 cagtcctctg ctcgtcggtg gcctcctgta gcccccagta aatggatttc agggagggac
122101 cgtccttgct gtcattctct tggactaacg aggagacaaa gtcacagaag ccagtttcac
122161 cagagaactc ttgtatttgt ttacagaggc aatagagata gacaaagcgc atggccggca
122221 tctgaggtgg acggtcaagg ttacggacaa aggcctcagt ctccggactg cggaggaagc
122281 gggcaaacgt gtaggaggtc atctcctcca tgggatcctc gagctcatcc acgtcggcca
122341 tctggaccaa agaagtcgtc tgccaagagt tcagctacca gacctggaag atgagggtgc
122401 tcaaaccgtg ggcgacagtt gaagaagtag ctctccttga acctcttttt aaggctccgg
122461 caccactgca agaattgact catatgctcc gccgtgacat ccacgcacgg actctcgcca
122521 cacgaggtca ggcccatgtc taagttcagg ttccacatct gcgacagcac ctccaacagc
122581 accacctttg gggctgcaaa ttgcaaaaag tagagcgggt cggatcggtc aaatcccatg
122641 tcagggttgg ggtaggggat tttgtgggtg gagtcagcga ggtgcatgat accatagagc
122701 agcgagtagc cgagcgactg cagatccagg cgaagggccg tctgcgcccc cacggggcca
122761 cacgccgagg ggtcagggat gtgcccagcc cccctcaaga tgtagcactt gctcaaaagg
122821 cagaggggct tataggtgtc cttggctata gaaaatggtt ccctctggca atagaggcga
122881 tagagctgcc ggcccttaga agactttagc cgcacatcca gcatcttgtt gcggtcgtgg
122941 agggaagcag tcccataatc agtcaggacc agcctaccca tgccccacat ggtgtctgtg
123001 aaatccacca ggatgttgct ggggctaatg tccgaatgga agaggccgca gtgccgattc
123061 agaaagtaaa cggcatcttt gaggccctga aagccccgca ccaggggctc aatactacca
123121 tcatgccagt ggccataatc ctggagactg catctgaact ggggcataaa cagggcgtgg
123181 caggacgtgc aggccgacag gtagtccacc agggccttgt cctgcccatc ctcggccgtg
123241 gccttcccaa tctgaatcat gtcacacacc atgagctcgt gatacagctc cgtcacagag
123301 tcatagagtt tgaccgtggc attatctgca tgtgcataca cggcccccgta gctcccccgc
123361 cccagcagat actcgcaggt aatggggagg tgatcacagc gcgtcatgtt ctccggcagc
123421 tttacataga gggtctccgt catgtcatca atgttggtca ccttcaggtg tttgtgctga
123481 aaggtgaagt aatcaatgac agtcaccttc cccaaaaagg cctgggtctc tcgagggggt
123541 tctggggaga cactcaactc gccactgctg gaggagttcg tcgggctcaa ctccgcagcc

Fig. 3 (cont.)

123601 atattcacat ccatgttcct caaatggctc gagggcctgt cgcagctcgt ctctggcctc
123661 aagctcctgc tcacggagct cctccacccg ctctagctgc ttgtagttga ttttggaaa
123721 ttgagtcttg gtcgcggtga ccaccctctg ataggtagaa attagctgtt tggactcaaa
123781 cgtctccctt gcgtggcgca gggactctaa ggcaccccga gcagatgtaa actgtgtttc
123841 aaacagagcg tggtccctcc caaatctgtc acgtgcgctc acagccgctc tcttttctac
123901 cgaggctctt agttgctggg ccaccagatc tcgcttagaa ctactcatct tcataagtca
123961 ccatgtccgc aactatggag cccagatcat acgtggggta gagtacggta gttccagtgg
124021 aggcttcccg gtaatttccc acagcgtcca ccatatatct ttctgcctct cccgttagaa
124081 ttaggcaagg atcatacgtg tccaccggcc ttttatactg agcgtttagg ttttgtttat
124141 gtagcaagca caaaaggcac acacgagtga tgcaaaaggg ttcctgaggc agcaggcaga
124201 gctgttttgc cattttattc aggcggctaa cgtcaaaggg aggagctata tcctcaccct
124261 tccagtcacg cacgtccaag tacagggcat acacacacct ggtgaggtgt gccaggaatg
124321 cctctatgtt ggcacatggt gtataaaccg cagtgggtag cagaataggg ccccttttgc
124381 cccgtgccgc agcgtaaacg cagtgacgct cttcgcagtg ggacctgggg ccgtagaaga
124441 gggcccacat ccaagggagt gggtcttcag gcaccaggga ggtccaggtt tgggagtggg
124501 ccaatatttg caaggcctga cctataacct catctttgtt ccaggccagc gcaattcgca
124561 taaggtcccc atcaaacacc tcaaaacaca gacccatgcc catttcaggc tgagagggct
124621 ccatccggct cgaccaacct tgtccaccaa actgccattc ttctggtaaa cgggggttga
124681 ggggcaagag ctccaaagcc aggctcgaga agtcatagtc atcctcggcc acacggccgg
124741 agctccgggc ctcgtgccag ggcctgttgt cctgggggag gatattggac acgagcagga
124801 agctcttgag tggcgtctcc accagcttaa attgctcggg cgtgtcctgg caggcctcca
124861 gtgccagttc cagacactgc ccatacctgc gggcgagcat cgggtcatcg ggcatatcgg
124921 ccttgaccgc gttgaacatg ctgtatgcct cgcagcgcgg ccgtctgacc gagaacctaa
124981 gaaacgccct tcagcaggac agcaccacgc aaggctgcct gggtgccgag accccgagta
125041 ttatgtacac aggggccaag tcagacaggt gggctcaccc tctggtgggc acaattcacg
125101 ccagtaattt atattgccca atgcttcgag catactgccg ccactatggc cccaggcccg
125161 tgtttgtagc ttctgatgaa tcattaccca tgttcggtgc gagccctgcc cttcacaccc
125221 cagtccaggt ccagatgtgc ctactaccag agctacgcga cacgttacag cgcctgctgc
125281 caccacccaa tcttgaagac tccgaggcct tgacggaatt caagaccagc gtgtcctctg
125341 cccgtgccat ccttgaggac cccaactttt tggagatgag agagtttgtc accagcctgg
125401 ccagcttcct gagtggtcag tacaagcaca agcccgcccg cctagaagca ttccagaaac
125461 aagtagtgtt acattctttt tattttctga tctcaatcaa atctttagag attacagaca
125521 ccatgtttga catctttcaa agtgctttcg gattggaaga aatgacgctg gagaagctgc
125581 acatttttaa gcaaaaagcc agcgtgtttc ttatccccag gcgccacggc aagacctgga
125641 tagtcgtggc catcatcagc ctcatcctct cgaatctctc caacgtgcaa ataggctacg
125701 tggctcacca gaaacatgtc gcgtccgccg ttttcactga aattattgac accttgacca
125761 agagcttcga ctccaagcgt gtagaggtca acaaggagac cagcaccatc acgtttaggc
125821 acagtgggaa aatctccagc accgtaatgt gtgccacctg cttcaataag aatgtaagac
125881 ctgacgtttc agtacttggc aattgtagag catagcccgg ctgtaaaggt cagaaaatcg

Fig. 3 (cont.)

125941 cagcagggtc caaggttgtg ctgtacatgg gacctctttc ccattagcaa gaaccccctg
126001 caggacacgt gacatgtccg ggtgcatttt gggtgggtta aatctcagtc ccaccacaaa
126061 gggggcatcc tccggtttga acatcagacc caacaaagcc cgatgcccag ttatgggtac
126121 gtagtcgttg ttcagggccg tgcatggcag cagacaagga caggtgccag atgtgcctgg
126181 gctatcgtcc tccgtccagc cacgcaggat gttcacgtgg gccccggcac catagcatgt
126241 cacacattcc ccgttatcac atctggttag caggttgata aaatgggtca gtgatggaaa
126301 ggttggcata ttggggcagc acatcagcat gtccatgtta acgaaaaaca tgtacagggc
126361 cccttctgca taccaggcac caccccgtcc cagtgggatg atctccgagg gtgtgatatc
126421 ttgcagttct tctactgttt taacggcggt tgaggtggta aagacgtggg ccgtggtcag
126481 atctgtgcag gtgactacag ggttacccct aatctccaca ggcaccgcct cacccactgc
126541 atctgagaat accccaaagt acatgagagt caggctgtgt ggcccctgga ctgccttagt
126601 gaagagaacc tcgggcctgg ccacggtggc tagggttcca ttgatgtaga cggtcacata
126661 ggtgggcttc ttcttgggct tcagcacaat gagggtaaca ttcatgtagg ttttaggagg
126721 tccggctatc tgaggcacgt acacagctga cacggcggtt gtggccgtat agactttcat
126781 ctggggcgta gaggcatcgc tcagcaccca gaggcactcc ttgttgagga acttgcgaag
126841 ctgttcccgg ctactgttcg cggcggatgc catgacgtgc cagaatatat cccctctcct
126901 cgggggtgag tgccaattgg cctttaataa caaagccccc aggcagcacc aaaaatgcct
126961 gcccgtccga tgtggtggcc aggtggacgc agtgcccgtc agttccaagg gctactagct
127021 gggaagcagc cccaaccagc ccaccccggg gcctggagtc gatcacctta ccccaggccg
127081 aggccccttc ctcatacagc gggtggctat ctatccatag gcaggcatcc ggcgtctttg
127141 gtgcattgga gatagtagct ttcacccaac aactttccca actaacccgt gtctggacag
127201 tgaagaacgc ttccctgatc aggtctgaat ttttatagat acgggagtag gaggtgggaa
127261 taacaactgg gatttcttgt tgtgctgtcc aggcctgcat ggccagtttt tccctgaagc
127321 tagcagaaat tctgagggcc actgaaatga ggaagcgaaa ctccctctct ggagctccca
127381 aaattgaaac ctcagcaaga tctgttgctg gggaggcatg ggtgacagct gtcatcctgt
127441 gcagtctgcc ctgggcactc agctctggat atgtgacaac atagagagcg tgggggctaa
127501 aaatatgagc aattcccctg accagggccc tggactcacg aatggcccga cgggtcttag
127561 agaaagaaac aggcaccctc gagagtgccc ccgacccgac ccccacagtg ccgccagtcc
127621 ctgctcggcc tccgccgcct tccccaccgg cgctgccccg gatgttgctg gggttctcga
127681 gggctgggtg gtgcttggac acagaggtct cagcagccgc cttggtctcg gccccggccc
127741 taagtctgag ccccaggcaa agggccggac tcccagcgtg gcccaacctc tgctcccctc
127801 tattctcctc ttgcgttatc tccaatagaa tttgcttgag gtcatacgtt ttagggtgct
127861 cgacctgggc cgcggccacc ggcatatgct ctatacccgc ccctccgggg ggcccaggat
127921 ctataggtat gggctgcata gccgcagcag actcctggac cccagaggcc tctctgataa
127981 gatgcccgtc ggtcagagcc cttttggccc cctcaaagag agacaggtaa taaatctgta
128041 gctccccaac cagccctcct tcatcgtaaa atcgaagggc ggccacgtgg aaggggttgt
128101 agagctctgg aaggccctca tcgcagtaca ctggcacact ggtaaacgtg ccccgatggc
128161 taggccgtcc gggcagcatg ccccgagcag caaacacgcg gcagaccctc gtgagacccg
128221 tccggtcact gaagagagtc tggcaccagg ccccctcgca gtttggcacg cgattggggc

Fig. 3 (cont.)

128281 aaagctctgc cataaccgtg tcgggaacaa ataggtgcac gaggaggggg gtcccgaggc
128341 cactcaacac ttggttgtca atgtggacat ccatagctct ctcatgcgtt tggctacagc
128401 atcatagcgc ttgtttctgg tggatttaaa taacagggcc ccgtagacag tcttttgtga
128461 gtaaatagag atgatgacat ggatgtagag actgaggacc acatccacca ccttctcgga
128521 ggaggccccc ctaaacagca tcaggcagca agggaacaca aaggaaacca gggccgggat
128581 gtgaggcctc agcgcccct cctgatcaaa gagggcctcg ctgaccccgg agatgacatt
128641 ctcattcaga aagtagtgat agaggtgatt gaccacagtc ttaaccaggc cctggacttg
128701 ttcaggctcc cacttgtccc gctggtcctg tgtgtcttgt cggatctcgg tccagggcct
128761 cagcgccggc tggaaatgcg gccccatgta gttgcctgta agggcgcaca ccactccctc
128821 atgggtctca atcagggtgc actcgctgga tccatcacat acgtggtact cgccacagcc
128881 ccagcaggca aacacggagg ccatgctctc aggtaacggg agatggaact ccagcttact
128941 atacgagcac aggtggcgag gattgggctc atccgtgccc ccctccccc gcgggaggct
129001 caatcggcct tggtctgaca ttccaccccg gccaggtcca ggagggtgca aatattctcc
129061 aggcgctgca cctcagagac ctcctgctca aagagacctc ccaccgccac gtagacgcgg
129121 gccaccgtcc ggggaaggtc agtggggtcc cagctcagca attctccaaa ttctctctcc
129181 ccaatagtgc ctcgcttctt atcctgtctt tcagagcatc cgggggcaga catttcacct
129241 cttgtttgtg gacgaggcta actttatcaa gaaggaggcc ctgccggcga tcctgggctt
129301 tatgcttcag aaggatgcca agattatctt catctcgtct gtgaactcgg ctgaccaggc
129361 caccagcttt ctttataagc tgaaggatgc tcaggagcgg ctgctgaacg tggtaagtta
129421 tgtgtgtcag gagcatcggc aagattttga catgcaggac agcatggtct catgcccctg
129481 ctttcgcctg cacatcccgt cctacatcac catggacagc aacatccgag caaccaccaa
129541 cctctttctg gacggggcct ttagcaccga gctgatgggt gacacctcct cgctgagcca
129601 gggtagcctg agccgcactg tgcgtgacga tgccatcaac cagctggagc tctgccgggt
129661 tgacaccctc aaccccgag tagccggacg cctagcctcc tccctctacg tgtacgttga
129721 tccggcctat accaacaaca catccgcatc aggcaccgga atcgccgccg tgactcacga
129781 cagggcggac cctaacaggg tcatcgtcct gggcctggaa cacttcttcc tcaaggacct
129841 aacaggggac gctgccctcc agatcgccac ctgcgtcgtg gccctcgtct cctcgatcgt
129901 caccctgcac ccccacttgg aggaggtgaa ggtagccgtg gagggcaaca gcagtcagga
129961 ctctgcggtg gccattgcct caatcattgg ggaatcctgc cccctcccct gcgccttcgt
130021 gcacaccaag gacaagacgt ccagcctgca gtggcccatg tacctcctga ctaatgagaa
130081 gtccaaggcc tttgagaggc tcatctacgc agtgaacacg gccagccttt ctgccagtca
130141 ggtcaccgtc tccaacacca tccagctctc cttcgatccg gtcctctatc tcatctccca
130201 gatcagggcc atcaagccca tccctctccg cgacggtacc tacacctaca ccggcaagca
130261 gcgcaacctc tctgacgacg tgctggttgc gctagtcatg gctcattttc tcgcaacaac
130321 acagaagcac acgttcaaga aagttcatta aactttattg actacaccag tcccttgtaa
130381 agcgacgggt ctcgcgtgac ggcattcgtg agcagggctt cgtccagggg cttgttcttg
130441 gcggacatca ttagcccagc cgcaaatatc agaattagca tcagaaaagt gagccccaca
130501 aacaccagtg tccagagagg aagaccgtaa gataaagatg gctgcctctc atctggaacg
130561 gtgggaagct cagcagttgt ttttgtggca ttggacgtcc ctttggagga cagcgtgggg

Fig. 3 (cont.)

130621 gccaaggtgg tagcgttggt aatacgggta gtagcactgg tggtggagga ggacctggtg
130681 gtgacattgc tagtcacacc cgtggaggtt cctgttccgg cctcggtggc agtgatgttc
130741 tgtgcagtaa ccttagtggt gacattgatg gtggatgcgt tggaagttgt tgggactggt
130801 gtgacagttg tcccagtgaa tgtcaccgtg gttgtgttgg tgctcagaat agcagttgtg
130861 gttatagggg cgctagtcgt ggtcaaggtc gtagactggt ttgtgctagg acccgatgcc
130921 gacggtgatg gtgtagtcac agccgttgtg cctgtcacgt tccccgccga ggccgtcgaa
130981 ctgccactag atgtccaaat aaggcttgtc tcacagatga gtatcatggc cataacagcg
131041 cctgccttgt ctctggcgtg tgccatcgcg tctggacgca gaaggcctcc cggcctcttt
131101 tatagctagt ctccacaccc aatactctac tgaaccatca catacatgac ctcctcgagg
131161 tatgcaggga atgagcggtc cgtgagccgg tcaacacgac attgcttccg tttcatgcct
131221 ccagctgccc ctgaccagtt aggacccttg acggatgtct ttaacggcgc ggtgcagttg
131281 gtcaccaatg acggcctaaa ggccaacaca tccttgaagc agggcgtagg aatggtacca
131341 aactcggggc ccacccccatc aaagacataa tatgtctcat agtggcagtg atgatgcatc
131401 accaccacag cactcgccag gaccctctgc atatcttgta caaggcgcct ttcaactcgg
131461 ccactggctc tggtgacgtt aaatgtcctg ttcctattag tcacagcctg tagatttggg
131521 cacccagact caaaaagtgc agctacatga agggcagccg cctcaaatcc accatgaccc
131581 ccatggctgt ccgtgttgtt ggggtaataa gtcacattgt taatgaccac ggccgggata
131641 agggtgtaaa ccttgcagaa tggattggtc ggacacccat aagacagggg caccccaaaa
131701 tcacgcccct taccccgaag caccttggcc cccaccggca taaagctggg caaaaagagt
131761 gggttaaaac caaaggcgag tagggccagg aacgccaaat agcagcagta atagatgaaa
131821 acaaagctca gcatgaaaca gcgtggaggc tcagctaggg tctctgcctc tccatcatag
131881 acatcttcct tgaatctcat tctctcaccg catacctcgc tcttcatcca ggaggggggcc
131941 atggctgcca ttctaccagt taacgaggag agagagagta ggtccgcgga aattggtgcc
132001 cctctctgcc ctcctgacga ggccatggtg tcatccatct ccgcagtccg ttcttcagct
132061 ttggcattgg tccgggtccg ggtggtctga ttttgattct gatcctgggt attggtcttg
132121 gtctctcctc ccccattggc atggattggc ataggtgggt gtggctcagg ctcaggttcc
132181 ggccctggga cggcagcagc cgccgggacg gtgaagtcgt ggaaggtaga ggcccgtccc
132241 tcccgaggtc gtggggccgg agccttataa aagacttcca ccctctcccc gctggccaag
132301 acacgccgct cgtggaccac gccatcttcc tcccggctga ttgtgtggct gacggtgccg
132361 tgttccaccg ccacttgttc atcgaccatg gtaccccctt tatcttaacc agcaagtggc
132421 cgtcagggtc tcttgagagt atgccgctgt ggccaagcga ggccccaaat taaatagtga
132481 tgccaaagac tgtaggtagg tcatcatcac acgcatgcgt gataaatcat ccgccactga
132541 caggtcatcc aggtctatcc gggctatctc atccggcacc atttcctgga agagattcaa
132601 gaggtcgtga tgctcatgcc ggataaggcc tcggaccagg cgcatactgg ccctgggcag
132661 cagggtcacc atgatgcaaa agtagagact cagattgtcc agcagggcca agccaagggg
132721 ccctggcacc tccgggaggg ccaactcgta gtggtgcccc aggtatgaaa cagagccaag
132781 atgcatgtgt acatcgagca tgtctgcgtt cccgggagcc tgcatgacaa cccgggagta
132841 cacgttaaac aggagaatct tctgcagcac ctcctctgct atgggcgtag gcagcaccat
132901 ggggaaaaca atgtccacat cattggactc taacttcacg gtggcatgct ctcgtccaaa

Fig. 3 (cont.)

132961 taccgggggc ataacactga ggctcccggt cccatgccac tggaaaaagg gctggtactt
133021 gttcttaatg gcgtaggtct gacctggaac aatcttggtg agtatcaaac tgtccacgct
133081 aacctcatcc agcacggcca gggtgcaatc agacaggtag ttgtacatgg acacgtagtc
133141 cgggaccgtc tctagagagt acacctgacc caagcccaat ccctgcacat tctgcgtccc
133201 gtgagtggaa gccaggggta agatgcagcc aatcctctgt tgcatcttgg caatctcatc
133261 ggtatacaga cgagaggaga gagacactac cactttcaaa tccatcttta ttgacaatta
133321 tcaaaaaacc accttatttc caaactttaa tattcttcgt accggcgcca cctcttcaat
133381 tatatagtgt ccgtaatgga tgggggcgtg ggtctgtttg acagacataa actcatcgat
133441 gagtgcccgg gaggaggctg agagtgcggg gaatgcctcc tgcagaaagc tgcagggctg
133501 ctccagaaac acgtcagtgc cagcaatcac tacaaactgc acctctgtgt tgctggtggc
133561 tgggtgccct ccaagtcgct ggctgtactc gttgaccatg ttgtagagtc ccctgttgtt
133621 gcgcagaagc tcctccttgt tgaaaaatgc ccggcagggg ctgtagaggc ccgggacggc
133681 cgtctggcga taggaggagt tgtacatgat gtcacccaga gaacccagct gagatgccca
133741 gggattcaca gtgctccggt attcataggc ggcatccggg cgagaatggt catagatgag
133801 cccctcggca acctcctgat tgtagttttc acaggagacc acacaggcgg cccgtcccct
133861 tggagagttg gacttttgaa aataagccac gtctgccgtg accggtgtta cgataatctc
133921 acaggtggcc tgctggccgt ggcagagtcc tggagctcca ttaacattag tcatacctgc
133981 caggtatgtc ctggggtccc gaagcagcgt cccattgcgc tgagcgccca ccttggcctt
134041 gatgtagtca ttgacttgct ggttgccaaa ggcctcggcc ggaaagacgc taaagaagtc
134101 ttgggtgtgg atacccatgt cagtagtgat ggccgccacc ctggccggag tcatggtcga
134161 gctataacta agcccggtgt cgatggaggc catctcgtga tgcacctcaa aggttaccgc
134221 gtccaccctg gcctcccggc ggctaacatt tggggtccca atgaacatgg atgttgaggc
134281 cctggagcta aacaatatgt tttcagagag gatctcatcg gtcctgacca cggtcatggc
134341 cacccctggg tggatcttga gcttggcctg ggcaatatag gccatggggg acatcttgat
134401 gtgcatggcg gtcattccac tgattgaaac gagggaagga agacattcgg ccgcgtattt
134461 gcccatgggc gagcggtgcc actcccggta ctctgcaaag agctgctctg gccggttgaa
134521 ggcttccacg gcccgctgct gaggattgcg cataacaaag gtggcaacat cctggtgcat
134581 ggtggcagcc actcgcgggt ccccgtaaaa catatggaaa ggaatggcgt gaaagagaca
134641 ctgggtgacg gcccgggtcc tctcggagaa ggcaaaggcc accagcccgt tcaccaaaac
134701 agtctgctct gtccgcttgt cggcgggatt cggggccagc tgctgcgtaa cgtcattgtc
134761 caccgacaca cgcacggcac gggtgaaagt ggggcaggtc atgaatgagg cgctgaggtc
134821 cctgatcatg cccacggtgg ggcggaggtc ggagatctcc agcagatccc tgagcgtccc
134881 attctccaaa ttgtcgagga tgtcctcgtc cctggtaaaa tggtggctga aggctggccc
134941 gttgtaggcc agggtctggg ccacgtgctg aaagtccacc ccgaggccgc acatgtgggc
135001 attggtgcag gttgggagga aaacgtagta aaagatcttt tccagcacat ccgcatgccc
135061 ctcatctaca taagggccta ggtgcagacg gaaatcgtgg tcgtggtctc cgttaacccg
135121 gtagccgtac aaggccacaa attgggcagc catctcatcc atgtttccaa ccctctcaat
135181 aaactggggc gcggccaggg tgtcagcgta aacctcattt ccgataataa tctgggggc
135241 ccggtcacta acggtgagaa gatgggtgaa aatgtctgtg taggccaccg gggggagcag

Fig. 3 (cont.)

135301 gttagggtcc aggagagcgc agacatactg acccacgctc tcatccccca caacatctga
135361 cccggccagg cgcatcaggg cctgctctag ggctataagt tccccataga ttttctata
135421 catggaatag gcctccttgg agatggcgtt atttcccagg tggcggcaga tgaacttgat
135481 catggaaaag ctgttcacaa aggcaagcct ccctgaccgt tcccagtagg tgttgatgca
135541 cagggacacc aaaggcacgt tcatgacaaa cttttcctca aacccgtgga tcatagcctc
135601 gactacgtag aagaaggctg gataggcagt gtcataggca gtatcctgca cagtctcaat
135661 aacggcctga tccaccacgt gggccagaga tgtggcggtc tcaaactgct gcccccgggc
135721 ctcttggaat gcagctgggg ccaggggagt cggcaggtta cccaccatta gccggtgcac
135781 agccctgtgc ctggccctct ccccggcatc cctgccaatg taaatatcat aaagggggtg
135841 cagctccagc cgcagcaggt cataattgga cgggtggagg aagtcttcgg tggcagcccc
135901 gcacttgaga gctatatctg tcacgggggc tgcatacttg ttatcataga actcgtccac
135961 aataacaagc acattcatgt gattgggcct cctgtgttgc agggagtagg tctcgcgcct
136021 gtctcgcggg gccggggccg cgttgaggct gtttagggta tgggcgggtg tgtggagtcg
136081 ggggtgacag agaaccttga gagcattctg taggttaaac gcgaggagaa ggttattctt
136141 gtttacgatc catgcctcca ccggtagctg ctgtgtgggg ttgtccagca ttttgatggc
136201 ggcggaggtc gtgtacttgg gattgggcat aaacaggccc actgggaaat agtagctgta
136261 ctgcattctt ctgttgaggg ggtatgggga ctgagtgtca ttgtacatct tttgcaggct
136321 ttccacggcc accgcgtggt tgcccagctt gatgacggcg gctgagatcg gcacccgggg
136381 ctgatcctcg acccctgcgg ccacagccgg caggtcagac ttggtgcttc cggctttttc
136441 cggtgagtcc acgatcctag ccatgaaatg ctcaaacgta cgcatcacgc gcccgtagct
136501 cacggcagtg accaggttct ccccccgtac cacaaaagaa gcatagctcg agggccccat
136561 aatctggttg tcggcctcct cacccaggaa ggtcaagagc tggcgcagaa cgttgtcggt
136621 gacaataaac accccccca ctggctctcc ccccttggcg gtcgtgtagg tactgacccc
136681 cttgagcacg ctctccccgg acacggccgc taccatctca gagagacggc ttcgcacgta
136741 ctgagaaaac ccggagccca tgttctcggc ccggtccagg aagaaggagt gctccagcag
136801 atgcctcttg aacatggcaa tgaggtcaga cttgacagtc ttggagaacc ccctctcagt
136861 gaaggtggga tccgccaggg tctgcaggat aaacatggga ggggcatggc gaagcttcac
136921 actcaggacg gtgttaatga ggcccctctc cagggcatcg accccaaact gtagggccga
136981 ggccacggtc ttgacagccc ccacgtactc tgcgtactcg accggggtct cggggatact
137041 atgcaggatc tccagatcca gcatggacag ttccatttcc gtactaatgt ggtgtttgtg
137101 gcaatttttg accacaatga atgtccgctg cttgctgggt ctccttccgt ccccgtgagc
137161 aatggtgggg acggagattc gaaattgaat cttgccatcc gtcatacgac tcaggtcttt
137221 gaattccgtg ttcacacagg acacggccag tgccgtctcc aggaagcgaa catattggat
137281 ggcgttcgtg tagaccccga gtagcacctc aaacttgatg cccgcctctc tggcatcctt
137341 gcccaccagc aggtcaaagc tatgaaacaa cccctcagcc gctgactgcc gcaggttcga
137401 gagcaggtcg gcatccaccg tcagataggg gaagggtctg ttttccacac cctcatttga
137461 ggccatgaca caaggtaaga gggagatggg gggaggtctc gagggcttct cttcacagct
137521 gggtctcttt tacgccctgg cctgcaaccg cagcccaccc acacttcccg aggatgctac
137581 ccttctaatc aaatggttgg acacggccct gggcagggag gccacctttt acgcgtgtcg

Fig. 3 (cont.)

137641 ggctatgcgt cggcttctac tcggcgttat ccgaatgaat gactgccagg agctgccacc
137701 cggtttaata attctgagtc cgggcaccgt ccctggcccc cttggagtcc agagtctgga
137761 gcatacagac tgcgaaatat ggtcctctgc ccaccctgac cacgctgccc acctcccggt
137821 gcccagggtc atcacataca ccgactgccc gggttccata aacacgagct caatgtttcg
137881 ccttatcatc cgctacttgt ctcatcacca atttgagcgc tgcttcgagc agttctgccg
137941 cgtggtcccg cgtcggcttc ctagggacct gtaagcgaaa ctctgcaaag atgctggctc
138001 atctgaatca ggttaccagg atcccccct gtccgccctt cagcgggcgg gaggccagac
138061 tcaagttcca cttcttctcc tggagcacat tcatgctgtc atggccaaac aatgccacac
138121 tccgggagat caggacgagg gccgccacca acctcaccca ccacccacat ctagtggata
138181 ctctgtacca cgcctctccg cagaccccat ttctgacacg cagcggtgct ctataccgct
138241 tcgtcacctg ttgcaactgc accctgccca atatctccat ccagcagtgc aaggccgggg
138301 acagaccggg ggacctggag atcattctac agagtaacgg cggagggagg cccgcgagct
138361 tccagttccc ctcctcccca actggctccc tattgcgatg catagttgct gcgtccctgc
138421 tgccggaggt gtccgtgggg caccaggagc tgtctccgct gcggtccaga agccagggag
138481 ggcagacgga tgtcaggtcg ggcccggacc cggcccggag actggtggcc ctcctgcgaa
138541 gggaagatgg ggcacctaaa gaccccctc tgggaccgtt tggacacccc cgggggcccg
138601 gcccggccaa gagcgaagac gaggagtctg agcgtcgaga cgcccctcca cccccgctcg
138661 attccagctt ccaagcttcc cggttggtgc ccgtggggcc tgggtttcgc ctgctcgtgt
138721 tcaacaccaa tcgggtgatc aacactaaat tggtgtgctc agagcccctg gtgaagatgc
138781 gagtttgcaa tgtcccccgc ctcatcaaca actttgtagc ccgcaagtac gtggtgaaag
138841 agacggcgtt caccgtcagt ctattcttta cggacggggt gggggccaac ctagccatca
138901 atgtcaatat cagtggcacc tatctgagct tcctattggc catgacgtca ctgcggtgct
138961 tcctgcctgt ggaggctatt tatcccgcgg ccgtgtcaaa ctggaactcg actctagatc
139021 tccatgggct ggaaaatcag agcctagtca gagagaaccg aagcggggtc ttttggacta
139081 ccaactttcc ctcggtggtg tcctgccggg acggtctcaa cgtgtcctgg tttaaggccg
139141 caactgccac catatctcga gtgcacgggc agacattgga gcagcacctg atccgtgaaa
139201 tcacccccat cgtgacgcat cgagaggcaa aaatctcccg gattaaaaac cggctcttta
139261 ccctgctaga gctacgcaat cggagtcaga ttcaagtgct gcacaagcgt ttcctggaag
139321 gcctgctaga ctgcgcctcc ctcctgcgcc tggatcccag ctgtatcaac cgaatcgcct
139381 ccgagggcct gtttgatttc tccaagagaa gcatcgccca ctccaaaaac cgacacgagt
139441 gcgcgcttct gggtcacaga cattcggcga acgtgacaaa gctggtggta aacgagcgca
139501 agacccgcct ggacatactg ggccgtaacg ctaacttttt aacgaggtgt aagcatcagg
139561 ttaatctaag acagtcacct attttcctga ccctcctgag gcacatccgc cgacgtctgg
139621 gcctgggccg tgcttccgta aaacgagaga ttacccttct cctggcccac ctgcgcaaaa
139681 agacagcccc catccactgc cgtgatgctc aagtgtaagc agcccggggc ccgcttcatt
139741 cacggggccg tgcacctgcc atcgggacag attgtcttcc acaccatcca cagccccact
139801 cttgcctcgg cgctgggact gcctggggaa aatgtaccca tcccggccct cttccgtgcc
139861 tcgggcctca acgtccgtga gagcctaccc atgaccaaca tgagggcacc gatcatctcg
139921 ctggctcgcc tcatcctggc ccccaacccc tatatcctag agggacagct gacggtgggc

Fig. 3 (cont.)

139981 atgacacagg acaacggcat tcccgtgctt tttgccaggc ctgtcattga ggtaaaaagc
140041 gggcctgagt ccaacattaa agcctcctcg caacttatga tagcagaaga ctcctgcctg
140101 aatcagatcg ccccctttc cgcatcagag caccccgcct tctccatggt tgagtccgta
140161 aaacgagtcc gggtcgatga gggagcaaac acccggcgca ccatccggga tattctggag
140221 atccccgtga ctgtgctctc atccctgcaa ctgtctccca ccaagtccat cctgaaaaag
140281 gcaccggagc ccccacctcc ggagccccaa gccaccttcg atgccacccc ctatgcccgc
140341 atcttttacg acatcgggcg acaggtgccc aagctgggca atgccccgc cgcgcaggtc
140401 agcaacgtgc tcatcgccaa ccgctcccac aactctctaa ggctggtgcc caatccggac
140461 ttgctgcctc tccagcattt gtacctcaag cacgtagtgc taaagagtct gaatctggag
140521 aatatagtgc aggactttga ggccatcttc acctccccgt ctgataccat cagtgaggct
140581 gaaaccaagg cctttgagaa gctggtggag caagccaaaa acaccgtaga gaacatagtc
140641 ttttgcctca acagcatctg ttccacctct acactcccag atgtcgtccc cgatgtcaat
140701 aacccaaaca ttagcctggc tctagagaag tattttctca tgttccctcc ctcaggcacc
140761 attatgagaa atgtcagatt cgccaccccc atcgtccggc tcttgtgcca aggggctgag
140821 cttggcacca tggcacagtt tctaggaaag tacatcaagg tcaagaagga aactggaatg
140881 tacacactgg tcaagcttta ttacctgctg cgcatctaaa ggaaaaacat aacaatcttg
140941 tgaaccagaa agatacccag agcaaaagca ataaagtaca ggattattgc caaaacaacg
141001 tgtgctcttt cttcatacag gcccgcaatt tccatgacag tcccgttggt ggtcagcagc
141061 agatagtgaa cgtggaggtt gtcaaaatca aagtagttgg agctcaagat ggagttttgg
141121 acttcctggg aggtgatgta ggttgtagtt tccaggcctt ccttttcatc ataactgagc
141181 agggcaaagc cacaaaaaat gcaggatttc tgcgtcctgg taaaattctg gatctttgga
141241 atctggcggg gctccccagc cacagcaccc tgcgaacatt tattcattat aacgggggag
141301 agaaagagag agctgctgag ataggtggtg ctggcctcgt atagcgccga gcctcggacc
141361 tcacggtcac tagagattat gaatgtcaca ttgatgagcg ggataatcat cagaactttg
141421 tcgagcctgt ccacgcattt gtaggcgggg agatgccacg catccctgtc ttctcgctcc
141481 aaagagagcc gcccaagaaa cccatccaca gcatttgaaa cggccgcctg gtccagcgtt
141541 gcctcctggg gggccatgct cagcagcttg tctcgtgtga ggtcaaatcg taggctgagg
141601 tagcacggtg agaagagccc gctctctgtc cccagggcta gcccccgcaa aacctcccca
141661 atctctaggg ccgagcacag ggcggtggac agcagttggt atagggcaag gttgggcccc
141721 tgggtagtca cgttcagccg caactcgcgt agcaccacgt ggctgccgat aaacagggtc
141781 tctctcatca cggtatgcag gggctggaaa agggggtggc ggttgtaggc cgagagaagc
141841 acagatgtgg cgcctccaat gaggccactg taaaccccgg ccttggggta gccgacggtg
141901 gctaacctca gcgcgtactc ctgtttctca gtagtcaggt gacccagctc ctccatcttg
141961 accgtggcca tcagcatggc ggccaagcgc tccagcccgt aggattgcat gcccttgaca
142021 gtggccccat aacatatgcc gatgatgtct ttcaggacag tcagctcaaa gaagctcttg
142081 gccaaccagc ggaggtccac gcagccattg ccagtctcac ccacagcatg acccacctta
142141 aagaaggcca cagaaacctc aaacatggta gtcagcgttt ccgtgtccag ttccggctcc
142201 cggcagcctc ccttcatctc cagcaggacc agtttctgga gaacgtagcg agcgtagctg
142261 gcggctgtca tggtgacggc tcgggaaaac atatccttca ggttgggtac aaagtagttg

Fig. 3 (cont.)

142321 tgaaagttgg cataatgcac aaaggttgta acaatcacca gggaatagtc cccgctttgg
142381 gcactggtta aggatgggta actaaaaggc cccctcagat ccggcaggtc cttcgtcttg
142441 ccaaagacca ggctcaacac atgctcatct cccttctcgg tcactcgctt gtaggtgccc
142501 atcagaaatt tagaagtcat ggcccccgtg tactgaaact tgtccccgtt gatggacagg
142561 gccacataag acaagtgaca gcgcagctga taaaagacat agctgtgtgg ccgcgtgttg
142621 ggcagcatgg tgccaatata gtagaagagc tgcttctcaa ggggggcact aagcatgcag
142681 gcaggggaat tcaggccgct aatgactccg ggatggacct tagatgcatc cacttgcatg
142741 gatccttcag agacagcagg gatatcgaca ggctcggcca gcgcaatacc aagggtacca
142801 gacgtcttgt aaattaactt gtagcggtta agcatagacg ccaaatcttc ggtgacattt
142861 gcctctctcc acagcgcctc tgggctaagg cctgggacct ttgccatcag ttcggtccat
142921 gggatggtgt aatgcgaagc atgcccctct atgtccaggt gcagcttaac ctcgctgagg
142981 ctggcagccc ccacctccca tagcaacacc aggcaaaaaa cacagagcaa ctgcatccta
143041 gtcccgattt cccctctcaa aatcagagat caccttgctc agaccagccc aatcgaaaaa
143101 ctgagatcgt attgccggat tcttcaatgc ctgcatgtaa atctccgtcc agcatccagg
143161 taaatcgtcc tgaaactctg agaggtccac aagcacaaac tgaaggtagg ctagcgttcg
143221 ggtgaacgca agacaaactt ccaacaacac cgcgtcggct cggaaaggct gtatgacttc
143281 cttaagtaca ctaaagatgc tgttcttata cagcttctcg gccacaccac ttcgaattat
143341 gggggtgtgg ctttgatgac atactgtcgt gattgttgtt agaccggcac ataccttcac
143401 aatgtcctcg gggggcaaaat actgtgttag gagccaggca cagtaaacgg cgtgatatgc
143461 atcgttgaca ctcttcaggt agccagcatc cagtcctgac tcatgtttcc tccctcgctt
143521 cttcaggcgg cgcatgttct cctccacgtt taacttcatc cagactatgg tgtcccccgg
143581 gtctgcggta aacgtggcca aaacttgaat aaagtcacta taggagagaa gctggctccg
143641 gagcagcatt agagggaaaa ccacggaggc cgacagcaaa tggcgatcat gcaaaatcca
143701 acaatccagg ggcgcgactg acctggcacc agactcggta accagcaagc tccgcttcct
143761 agaggccaag actctgaaag gggtggtaaa tttcatctgg catgctaaaa cctcagccga
143821 cgtgtcttcc cttccatgcc tcgcccgagt cacattcttg tgcatggcct taatggcatt
143881 ttcatacaca tgagtccagt accgcatcgg ttcagggact acaatggtca ggtccccaaa
143941 gacagccttc aaatgattca gcatagtagt ctttcccaca ccaggggcac cttccaaaaa
144001 tagggaacag gcaggtttga ttactggtac atgatttgtt aggtgggtca caattggaac
144061 ccgcatgctc tccttcctct gagccttggc ctggcgggtg tcttgggcat catccagatt
144121 cagaacattc atcacactcc cacttagccg cttcagctgg gcagcatgct tggataactt
144181 actaaactcg cgcccatggg cggccaggtg ttcgaagaga ccagaaggct taccccttgcc
144241 accattcttt tgttttaacg cggaatgaga agagggcctg cggaaattag actcatcctc
144301 agactcacag tcagatttgt catcgagccc aaggccggcc aggccctcct caaagccttt
144361 ctggtacatg aagctccggc tcgtggagtc cgcacctcct tctgtgcacg aagttttgcg
144421 gaaccaggag aaggggtctg gcgtcttgct ggggccacac tcccggctac ggggcttcgg
144481 ggtaggggca gtaggctttt ggtgtgcggg tgctggtggc tgggctcccc tgggcagggt
144541 aaaggggcac gatgtgtgcc ggctacccgg agagtttcca gtattagatg tcacggcagc
144601 ctgggtccgg cacggcaccc tctccccaga cagtccggtc ggagccatca agggggggcca

Fig. 3 (cont.)

144661 gtgggtgggc acctggtaga ggccgtcgtc atcttcctca cctgcccctg agtcactacc
144721 ggttggggta agaactgagg gggcaaagtc atcaatctca gcgtaaaagt tttcgtgtct
144781 ttcgttttca ggggactcat cctcctgaca ttttcgccag ccgccgggcg ggccggcctc
144841 ctttcctgga aatccagcca tggatcccac ccggggtctg tgtgccctct ccacacacga
144901 cctggcaaaa tttcacagtc ttcccccggc tagaaaggcg gcaggtaagc gagcgcacct
144961 tcggtgttac tccaagctgc tctctcttaa gagctgggag caactggcct cttttttgtc
145021 tctgcccccg ggacccacgt ttacagactt tagactattt ttcgaagtca ccctgggtcg
145081 gagaatcgca gattgcgttg tggtagctct gcagccttat ccccggtgtt atattgtaga
145141 atttaagacg gccatgagca acacggccaa cccgcaaagc gttactcgca aggcacagag
145201 gctagagggc accgcccagt tgtgtgactg tgccaatttt cttcgcacgt cctgcccccc
145261 cgtgctgggc agtcagggcc tggaagtctt ggcggcgttg gtatttaaaa accagcgatc
145321 cctgagaacg ctccaggtag agtttccagc cctgggccaa aagaccctcc ccacctccac
145381 caccggcctg ctaaacctcc tctcccgctg gcaggatggc gctctccggg cacgtcttga
145441 tagaccccgc ccgactgccc agggacacag gccccgaact catgtgggcc ccaagccttc
145501 gcaactcact gcgcgtgtcc cccgaagcgc tcgagctggc agagcgggag gccgaaaggg
145561 ccaggtcgga gcggtgggac aggtgtgccc aggtgctcaa aaataggctg ctccgcgtgg
145621 agctggacgg catcatgcgt gaccacctgg ccagggcgga ggagatccgc caggacctgg
145681 atgctgtagt ggccttctct gatggcctgg agagcatgca ggtcaggtcc ccctccacgg
145741 gagggcgctc tgcgccagcc ccgccctccc catccccagc ccagccgttc actcggctca
145801 ccgggaacgc ccagtatgca gtctcaatct ctcccacgga cccccctctg atggtggccg
145861 gcagcctggc tcaaacgctg cttggtaatc tgtacgggaa catcaaccag tgggtaccgt
145921 ccttcggacc ctggtacagg accatgtcgg ctaatgccat gcagcggcgc gtgttcccta
145981 agcagctgag ggcaacctg aactttacca actccgtctc cctaaagctg atgacagaag
146041 tggtggcggt gcttgagggc accacccagg actttttctc agacgtcagg cacctgccag
146101 acctccaggc tgccctgatc ctctcggtgg cctacctgct actccagggg ggctcctcac
146161 accagcagcg ccccctccct gcctcacggg aagagctgct ggagctgggc ccggagagcc
146221 tagagaaaat catcgccgac ctcaaggcca agtcacccgg cggaaatttt atgattttaa
146281 caagcggaaa caaggaagcg cgccagtcaa tagcccctct caaccgacag gcggcatatc
146341 cacccggcac attcgcggac aataagattt acaacctgtt tgtgggagcg ggactactgc
146401 ccacgacggc cgcgctgaac gtgcccgggg cggcgggtcg ggaccgggac ctggtgtacc
146461 ggatcgccaa ccagatcttt ggggaggatg tgcccccctt ctcatctcac cagtggaacc
146521 tgcgcgtagg tttagccgca ctcgaggccc tgatgctcgt ctacacgctc tgcgagaccg
146581 ccaacctggc cgaggcggcc acccggcgtc tacacctatc gtccctgctc ccccaggcaa
146641 tgcagcggcg caagcctgcc atggcgtcag ctggtatgcc gggcgcctat ccagtccaga
146701 cgcttttccg ccacggggag ctcttccgct tcatctgggc ccactacgtg aggcccacgg
146761 tggcggcaga cccccaggcc tccatcagct ctcttttccc cgggctggtt ttgctggccc
146821 tggagctgaa gttgatggat gggcaggctc cctcccatta tgccataaac ctgaccggac
146881 aaaagtttga caccctcttt gagattatca accagaagct tttatttcac gacccggctg
146941 ccatgctggc ggcgcgcaca cagctgcgtc tagccttcga ggacggcgtc ggtgttgccc

Fig. 3 (cont.)

147001 tggggcgccc ctcgcccatg cttgcggcgc gggagatcct ggagcgtcag ttctcagcct
147061 cggatgacta cgaccggctg tacttcctga cgctgggcta cctggcctcc ccggtggccc
147121 caagctgagc cagttcctcg cactggagtg ggtcattggc aaaaaggtaa ataaactcat
147181 cgcacggggg ttttgcctcc ttctcgtctc ttgtttcggg taggggagta aggccgctgc
147241 caggccgcca tgctcagggc cacggcgtgc cagaggccct cgtagtcgtg cgcatccgag
147301 aggatggcac ggtccagaag cagatagccg gccaggcaga ggaaggccac aaagaggggg
147361 cgaaggcgtg cccgaacccg ggtttcatgc tcgtctgcac cccagtggac aaggcagtag
147421 aggacaccca ccaccaggcg gttagggagg acactgccaa ggttgaagag cagatttccg
147481 tcagccaggg tgacctggct caggtccggc gccctgcgag tccaagctgc gcccacacac
147541 atgcacagac ggcccctgtg acatcaggcc ggtcatgcaa aaacagacaa agagaccgtg
147601 agcggttacc ggggcgcagg gcctctgccg ggaagcccac ccgggccagg gcccggtaaa
147661 gcaggtacca gtattcatcc ggcaccttgc gtgccaacac acgattcgtg cggtttccag
147721 tatttatcac ggcttcccgc cacaggtaaa agttaacact tagggtcagc agcttggtca
147781 gggataggtg caaaaacctg agctcgtcct cgcgcagagc gcaaagcggc cagttcttta
147841 gcatcttcag gaggagcccg tgaatcccag gtgtcattcg cgcgtcatcc ccgcgcaccc
147901 ccagtcccat taacatagcg ggcacaatgg tgcaggcacc gtctgtatac gtctgcggct
147961 tcgtggagcg cccggacgcc ccacccaagg acgcctgcct tcacctggat cccctcaccg
148021 tcaagagcca gctccctctg aagaagccct tgccactcac ggtggaacac ctgccggatg
148081 ctccggtcgg ctcagtcttt ggcctttacc agagccgagc gggtctcttt agcgcagcct
148141 cgattacctc tggggacttc ctgtccctgc tggactcaat ttaccacgat tgcgatattg
148201 cacagagtca gcgcctgccc ctccctcgag aacccaaggt ggaggctctg cacgcctggc
148261 tcccctcact gtcactggcc tccctccacc cagacatacc ccaaaccacc gcagatggag
148321 gcaagctgtc cttctttgac cacgtgtcta tctgtgccct gggtcgtcgg cgcggcacca
148381 cggcagtcta cggtacagac cttgcgtggg tcctgaagca ctttagtgac ctggaaccgt
148441 ctatcgccgc ccagattgag aatgacgcca atgccgcaaa gcgtgaatcc ggatgcccgg
148501 aagaccaccc tctgcccctc acgaagctca tagctaaggc aatcgatgct ggatttctga
148561 gaaaccgcgt ggagactctg aggcaggaca ggggtgtggc caatatccca gccgagtcgt
148621 atttaaaggc cagcgacgcc ccggacctac aaaagccgga caaggcactt cagagcccac
148681 caccggcctc cacagaccca gccaccatgc tatcaggtaa cgcaggagaa ggagcaacag
148741 cctgcggagg ttcggccgcc gcgggccagg acctcatcag cgtcccccgc aacacccttta
148801 tgacactgct tcagaccaac ctggacaaca aaccgccgag gcagaccccg ctaccctacg
148861 cggccccgct gcccccccttt tcccaccagg caatagccac cgcgccttcc tacggtcctg
148921 gggccggagc ggtcgccccg gccggcggct actttacctc cccaggaggt tactacgccg
148981 ggcccgcggg cggggacccg ggtgccttct tggcgatgga cgctcacacc taccaccccc
149041 acccacaccc ccctccggcc tactttggct tgccgggcct ctttggcccc cctccacccg
149101 tgcctcctta ctacggatcc cacttgcggg cagactacgt ccccgctccc tcgcgatcca
149161 acaagcggaa aagagacccc gaggaggatg aagaaggcgg ggggctattc ccgggggagg
149221 acgccaccct ctaccgcaag gacatagcgg gcctctccaa gagtgtgaat gagttacagc
149281 acacgctaca ggccctgcgc cgggagacgc tgtcctacgg ccacaccgga gtcggatact

Fig. 3 (cont.)

149341 gcccccagca gggcccctgc tacacccact cggggcctta cggatttcag cctcatcaaa
149401 gctacgaagt gcccagatac gtccctcatc cgccccccacc accaacttct caccaggcag
149461 ctcaggcgca gcctccaccc ccgggcacac aggcccccga agcccactgt gtggccgagt
149521 ccacgatccc tgaggcggga gcagccggga actctggacc ccgggaggac accaaccctc
149581 agcagcccac caccgagggc caccaccgcg gaaagaaact ggtgcaggcc tctgcgtccg
149641 gagtggctca gtctaaggag cccaccaccc ccaaggccaa gtctgtgtca gcccacctca
149701 agtccatctt ttgcgaggaa ttgctgaata aacgcgtggc ttgaaagtaa actttattgc
149761 gtgttagtac ctgtccattc acaggggtat ccagcccttg cgccgcctcc cccagcccgc
149821 cagccacccc agacaggaga tgataatgat gaggagcacc ggagccacca cagcacaagt
149881 gattaggagc agggcccagt gcacccaggt ggtcttaggg cgccagggat cgattggaaa
149941 agggcccagg gtcactggct tatgcgtggg acgtttagaa acaggccgcc tatggggcct
150001 gtgactggtg cttgtggtgt gggagactaa tgtggtgggg gctatggtag tggctgggat
150061 aacagtaaga tgcatacgct gagtgagggt ccggttggca tggtattggt cgtcttcttc
150121 ccctgcagag taattgcagt ggaccccgga ggccacactg caatttctca gtgtcacatt
150181 gcacgtgtag taacctgcat gcgcaagggt cacattgggg attatcagag agacggaggt
150241 gttggagtca tttacccatt ctagggtaag gctataattg taaccccccgt tagttatatg
150301 agttccgttg ttggaagtag ctacggccaa gggcagttgt ccatccccgg gagtgtatcc
150361 ccggcccaac tcgatccgag agaccgactc attgctagga acgctgcagg tgagattcac
150421 tctagcacct gcatgggcgg tgacattttc aaatttaacc agatctgaga aaaatgcaca
150481 aacagacccc acacagcagc acaatagaag cactaaatga gtcattccta aactgtcagt
150541 tttaaaactc cctgcttctc aggcctaaat atgtggtggg gtgtgcttag gatcactttc
150601 atattctgca acaacagcca tacccggaag aggagctgcc ggttgccatt tttcaagctg
150661 ctaaaccacg agtggcagca ggcctaagaa gctcctcagc aacatggaga cctcgaaggg
150721 aaactggcag gagcagggag tcacgtaggc actagcctct tcatgtgagg taagagatcg
150781 ctaaaaatgg gatcagggta tgtaaaccga gttttgcggg ggatggtgag ccagacacgg
150841 cgggtggggg aaggagctga cacgattgag tagaaagggc caaaaataca ccagctataa
150901 ggaattgctc aggccaaagt tgttcctcag gtggctttag gcctaatgta ggcaattgcg
150961 tgcctagaac attgctaatg tgccctgggt ttcctgcctt catgcaaata ttctacctcc
151021 cccggcctgg tgcaaaatgt ctgcctcaga atactaacag ctaatccaag ctaacattct
151081 atcagtaaac gggcagaaaa ctgataagga ccgcggagtt tggccctccg cggtgtccgg
151141 tggtcctcac acgtgccctc cccccgggcc gatggctgag gcccggaata tgcaagtgca
151201 tctttctaac cagtaggggc ctccacctag gtgctttgtt aatctttagt gggaactagt
151261 gggagtgctg tgcctcgggt acccctatcc tataggtcct accggagctc cttgtcttga
151321 taatccctgt aaacacacac cacctaagaa caaggcattg ttaacctttg gtggaaccta
151381 gtgttagtgt tgtgctgtaa ataagtgtcc agcgcaccac tagtcaccag gtgtcaccgg
151441 aggctacttg cctcagtgcc acttttacct tctcaaatct atacgggggg gggggggggct
151501 ctgtaacatt tggtgggacc tgatgctgct ggtgtgctgt aaataagtgc ctagcacatc
151561 acgtaggcac caggtgtcac cagggctact tgcctcggca tctcctcacc ggagaagggg
151621 ttaacaaacc cgtggggggt cttagtggaa gtgacgtgct gtgaatacag gtccatagca

Fig. 3 (cont.)

151681 ccgctatcca ctatgtctcg cccgggctat atgtcgcctt acctccccta tatagtcacg
151741 accccaccga accaggcatg atgtagaata aaattttatg catcatcttc taatctgtgc
151801 cgcttggagg gaaacatgac cacctgaagt ctgttaacca ggtcagtggt tttgtttcct
151861 tgatagagac acaaggactg ccagccccat tggggagggg gggtgggtac gggagagttt
151921 gggctcgttt aaacaaagtc tcatctgatg ctctgtggca cctcaaggtg aatatagctg
151981 cccatcgacg tatcgctgga aaccggtggg ccagggcctc gtaggccgag acgggcagcc
152041 ggagcttgtg gtactgtccc tccggcaggt ggagtgggac acagttagag aacattagtc
152101 ctctggtccc tatctccacc cgccaggcct gtgtgtcagt ttgcagggcc atcctcgcac
152161 tcaggtggac tggctaggca cccttctgaa gtatctggcg gtgactgtca cctggttctt
152221 gagagagtcc ataaaatggc tgaagctcca ggcgtatagt ataatgagca acagggccaa
152281 acaggcggcg gggcctgggt agtagcgggc aacgagagac tctgtgcaat caaaccccag
152341 gctcccggcc tcacccagga agagcagcgg cagggacagc ataaaccagg agaaggcgca
152401 aatgagtccg gtgaaggtga cgttgcatat caggcgcggc ttccttccga attttgtgcg
152461 caaaagtttc cagatgatga taactgtgag gaggacgatc aggactgccg ccagtaggta
152521 gcagccggct ttcagtcctt ggacggccgt gtgcatgcct ttggtggggc cttccctgca
152581 catgttgggg cctctgttga gattggcgtc ggggcccatg gtaatgagga ggatgataat
152641 cagcaggagt accagacaaa acacgcccat caggtacagg cacacatttc tgtgggaggt
152701 tctcttgggc gttcggctga acaatgctag ggtcttctcc aacgccatac ccaagtgagt
152761 ccatacggag cacatcaggc ccaagaacat catgttctgg gtcaaaaggc agagaccggt
152821 agacgagaac tcctgaatca tttttcccag cacccagagc agcagttcta tgagaagagc
152881 tatcagccag acatccattc ggtgaaccaa ttttcttaca aagatgataa acaagatgcc
152941 agccagtgtt agcagaatca gcaggacgag cagcaggctt gtcatgccgc tgaggaaggc
153001 gctgtaggat ttagtgcacg catcttccgt tgcattgacg gaagtcatgt tggccaccag
153061 ggtccccacg gtggacccgg gggccatggt ggagagcatc ttgctggtca gagccagact
153121 gggtggtgtc tgcagcaaaa gaggaacttg cccaggcagt cagttatttt gcatgccacc
153181 tccctgcctg gtggacttcc agactatttt ctgcattcgc ccttgcgtgt ccattgttgc
153241 aaggagcgat ttggagaaaa taaactgtga gtttcacaga tccacgggcc acgctcccct
153301 gggggcttca tgatcccacc gcctttcccg atgatgatga caaccgcggc tgtctgaagc
153361 ggctgacgaa atcggttgag attctgatga gaggcttggg ggggtctttg ccctcaaggc
153421 gaggctcctt ctcctaggaa tgccgagccc cctgcactag cttcgctcca ctggggatct
153481 ttgccagcct tcatactaga ttcagcgatc ccccggttgg gaatcttcgc cagccccccg
153541 tcctgctatc ccgctcgtcg ccgcgcctcc catgctaagg gccccttcc tttcccttga
153601 ctttggggat attcggagtc tgctctcgcc gctctcttct ctcgtttaaa cgagagaata
153661 gtagtagggt ccagtctcag gccccctcac tttgggtctt agaatggtgg ccgggctgta
153721 aaattctgga ggacggagag ggcggccccg gagttgttat caaagaggca ctggaggatg
153781 ttggccgctc cttggagcag cttgtcgaaa taatgatcca cggccacggg aacgccgtgc
153841 cgctcggcgt aggccgggtc ctcggccatc tccgtctttc tcgccccctt cactcccccc
153901 ttgggctcca caaagacgta ctggatgcgg tcgtggatct ggggcagttc ctcgttgcgc
153961 tcgacgaact tctggtagac ggccaggtga ggcatctggg tgctcttgta ggctgagagc

Fig. 3 (cont.)

154021 ttgcggctga gctccgttga aaagcagagc tcccccatgg ggaccctgcc ttcacggagg
154081 tctgtgtagg cctggtttag gatgtcaatg acgggcaaaa agcccacagg tagcccttgt
154141 gtaaatgact cttggaaggg ccggtgggag aggaggctgg ccgcctcctt tacccgggca
154201 tccgccagca ccaggtcgag cacgcgccgg cagcgtgtct gcacaaactt gcaggccgtc
154261 ttccggacga gctccacccc cttcatcagg gtcttgccgt ccgtcagcac ccccacatat
154321 ctcttctttg taatcagcat caggcaggag aaggtcttct cggcctccag ggagatgggg
154381 gccacaaaca ggctccgggt ggtgtgggcg gccagggcat cggcaaagcg cagggtctcg
154441 ctctctgaaa acccccggca ctcgataaac agcgagtccg tgtccccgta gatgactcga
154501 agctggccct cggggttgag gggcgcccag gcgtccgggg agggggccag ggcctgcagg
154561 ttggcggggc tcagggcctc cacgaaggcc ttggcccgct ccaacatcgt gcggccctgc
154621 agcgtcaccg tctcggcgat ggagaggcag ggaaagaggc cgttggccac cccggtgaag
154681 ccgtagacgg cgttgcacgt gcacttgatg gccagctgct gcttgtcgag gatggtcctt
154741 tggcgcggat cctcgcaggc cgccagcagc ttcttgatgg ccttgcgctt ggccagccag
154801 gaggtcaaca gactagccaa gaaggactcg tgcacgtgct tctttacaaa gtggtagacg
154861 ccccccgtga gcctgaagga ctcatagtct tctcccgggc gcaggccggc tagcctgtgc
154921 tcttctcccg gcgttatcat ggtagaataa cagagattat gagcctgaat gatgctcggg
154981 tagaggctgg caaagtccac caccagaacc ggggagttgt agaatccgga caggggctgg
155041 atgacggtgg ccccctggta gccgtcccgg tcagaggccg agggcatggg caggataaag
155101 ttttcctttt gggcggccgc caggaggcag gagaacacgc ggatctgctg cccatcgtcc
155161 agcacccgcc tgcaggggat gtgagcgatc ttggcaatct ctgccacctc cacgtggatc
155221 acgaaatggt ttagcagatc catgaccagg gccgagtcct gcacgcagta catgccgagc
155281 cgcctgcgcc cctcggggcc cgctgcaaag aggcgaggaa tctccttgta atgcacatcc
155341 tccttcttgg cccccagtag gtgcctggct actgtgtcca gcttgtagtc tgagaggctg
155401 agcttgtccc ggcacacggc gtacatgtcg atggggatga ggccggtgat gcggaccttg
155461 gtgttggccc gcaagaagcc cttgcccgca tcatggggtc gcctgacctc gcagacgccc
155521 ccagccctaa ttttgcccag agaggctggg ttgatgctgt agatgtgcct ggctctgtcc
155581 agaatgtagg gccagtcaaa gttggccacg ttgtagccgg tcacaatctc cacgctgagg
155641 tctctgatga gctggaagaa ggcgtagagc atgtccagct ccgatgggaa ctcgtagacc
155701 tcaacccccct ctatgtcttc gcaggtgccc agcgtcagca ggatgcgcct atagcgcccg
155761 gcctcctccc ctgtcgacca gaggacgcag gatatctgca ggatcaggtc agcctcgttg
155821 gtggccgtgg ggaagccctc ctcccccaga cactcgatat cgaaggccag ggcctggtag
155881 gagggccagg agctgtcttc acgccggacc gagaggtcgc ccacctcaca gtcgtactcg
155941 agctcggcgt acgagtcccg gtgctggagg cgggggatgg cgcggcggca gctgtaccag
156001 ccaaaggtga caaagtcatt gtccaggaca aagcggcgcg tggcatccac gttggcctca
156061 aagatccgac acccgtgctt gtcttgcagc cacgtggcca cgtgacacac actgttggga
156121 tgggagaggg tgatcttgtg gtagtcgccg gcatggttgc cgtagcccat aatggaacgg
156181 cgcgtgacct tctccaccga gacccggcag gggtcctgc ggtcgaaggt gctggccttg
156241 agggcgctga ggactgcaaa ctccacgtcc agaccctgag gcgcgctggc gtagaagtag
156301 gcctgctgcc caaacacgtt cacacacacg ctggccccat cggccttgcg ccggcccagt

Fig. 3 (cont.)

156361 agcttgatga cgatgccaca tggcaccaca tacccctgtt tatccgatgg aatgacggcg
156421 catttctcgt gcgtgtacac cgtctcgagt atgtcgtaga catggaagtc cagagggctt
156481 ccgtgggtgt ctgcctccgg ccttgccgtg ccctcttggg cacgctggcg ccaccacatg
156541 ccctttccat cctcgtcacc ccccaccacc gtcagggagt cttggtagaa gcacaggggg
156601 ggctgaggcc cccgcacatc caccacccct gcggcgcctg gtgtctggaa acacttggga
156661 atgagacgca ggtactcctt gtcaggcttt ttcagaaggc ctttattagg tcttaggaaa
156721 gggttataga agagtccccc agacatggtt aaaactcagt ctctgcctcc ccaagcagtg
156781 cggcggcggt ctctggatcg tgatagcgtc ttctgcgtag gcctggaaaa cggtccctgg
156841 ctgcctgcaa tgctctgctg gccactgagg gtccggccgc cctctgagct gctctctttt
156901 gctcctggtt ttgctcatgc agcgctaaca tgatggcttg taattctgtc ttactaatgg
156961 gattaatgcc tggaccctca ccagaggcat gttgctgagc gagctcgtcg atcccggggt
157021 agagcatctg caccggctgc tgcgacatct ggcgcgtgcg cctcgtgagg gaaataacca
157081 ggatcaccac ccccgccacc aggaccagaa tgagcatgcc gccgaagggg tttttgaaga
157141 aggagatgaa accagagacc aggctgctaa acaaaccccc caccgtgctg actaggttgg
157201 tgatggactg acccacgcta cccagactgt ccataagttc ccccaggccg tccacgaatt
157261 gatttcttcc gtttgacact gcattgtcca aatccttccg caggccggcg atgttttgcg
157321 cctggaagtt gtactcccgg aagatgccct ccaggtcaaa gacgttggag gcacgctgtt
157381 cgtcccgtga gtacagctcc agggaggcaa agtcaatgtt ctcgatgagg gaggtgttta
157441 gtgagatgaa ggtctgcagg gtggcaatgc cgtccagctc gatggtttta aagtggtggt
157501 agtcgttgta gacgtggatc tcgttgccgg actggaagta gtactggctg gtcgcctggc
157561 acacctccgt catctttttt gtgaggaaga tctcgttgtc ggtgcccagc tgtccctcgt
157621 aggtcttggt gtcgttgata aagctgaagg acaccagggg gcgcgagtag cacatggtct
157681 cggagccagg gaccctcatg ctcttgcgca gggtgacggt ggcctggtta acgggcacgc
157741 actgggagac tgagatgaca tcccccaggc gcttggccgc caccgcctta ccgtagatgc
157801 tggacatgac ggtggttgga ttaatcttgg ttagttctct cagcaccatg ttctgcctct
157861 tctgctccag gcaccaggcc cgcgcaaggt ctcccagcat gcggttgatc tggcggcgca
157921 gggagtcgta ggcaaattgg atctggacgg tggcgggatt gttgagggtg cccagggact
157981 tcccgggggc cgtgggggc accggtgtgg tggcgttccc cgcatcccgc ctccgacgcc
158041 tcagaacggc ggcgggggtg ctcccgcggg ccgcggatgg ggctgggggc gatggactgc
158101 tggggggtga ggaagtcgga gtggtaagct ccgtcaggtt cttgacggtg gccaacgagc
158161 gcggggtcag aggtagccaa gctaataaca atcctccgct cgttataaaa tatgtaatgg
158221 cttcctggcc cttcgtgtaa cgatcctgga cggcctcgta cttctcatgc atggtcttgt
158281 tcacctgctc ttcgatgcac ttgaaggcgt ccgggagctc tatgcccacg gttgtgttgg
158341 tcacgaagct agaggtgccc tcgtcagtca caaaatgtat tgacttccct gtttctgtgg
158401 cgatggtcga gtcaaaggtt tgccagtgtt gaagcgggca gtaggctgtc ctgttctcga
158461 gcttccaaga tagcgtgtaa gtgcccttgt ccaggaaggc tcggcgttcg ccttgcgggt
158521 tcgtccctcg gttgtcgtag tccactatct tgtagttagt tctcacgtgg aaggagtctg
158581 cccgctcatg gaaggtttcc ttatttttcc cgtcatagaa aggggacatt tccacagtct
158641 gcccggtggt ggtcacaaag aagtcgaagg ggctgttgga cttggccatc atgtcagtta

Fig. 3 (cont.)

158701 tcaggcagtt gacggtagtt cttgttctgt aagtccatat caaccacccg ggggcgtcat
158761 agagctccgt ctggctggcg tagcggcgca ccccgttggc caggcccccg gtgggcttta
158821 ggttgacggt gatgttaact ccgtcgcggt ctacatacac gcgcgtcagc ccatcttttg
158881 tcatcttgac cgcgttgtag cactggtaga tggtatccat ctggtcagtt tcgtagctgt
158941 caacggagaa cttctcctcg tgccggttgg tcacggagtc cgcgtaccag ccattgtaga
159001 tgagaatgtt ggtcactatc ttggtgtagg agcggacctt aaacgagtag ggaataatgt
159061 tgtctttaaa caccatcaac aggccctccg tgtgattctc ccgcgtgcca aacgagggac
159121 actggatgtc cgaggagaag cggaacaggt cgccgtggct ggagagctcg cagactcgga
159181 aaggaaagct ggtttgctga cgcgtggcgg taggctgcac cgtggtggcg gggggtgcgg
159241 gctgctctgg ggtctgcgca ccgagacggc acgccagggc ggctagcagc acgaccacgc
159301 ttagcacccct acgccgagtc atctctcatt tggaggtgca ggtagagaag ggcatataga
159361 tccttaaata cccaccccct gcccttatac agaagaatta gggggcggtc agagtcgtac
159421 gtgaggtaaa gcccatccgg gggcagggcc tggccggggc tgaccgcgtc cgcccggcgc
159481 aggatcaagg accgccccca ggtcttgttg tagagggaca cggttaggac ggcctcgcgc
159541 agcgcccggc acagaatttg ctggctagat gccagtgagc ccccgggtac gctgtagaag
159601 ctgttgaagg aggtctctat ccagtcgctc ggctcgatgc ctggccatat cagggaagtc
159661 aggaatgcct tctggtgggg cagcgtacct gcggcgtcac agcagcgagc cagggccacg
159721 ttgctgggtg ggggaaagag cccgctctcc tccgccaggg gccccgtgat gaaggtgtac
159781 aggctgtgcg tcagcgcgtg caggtgctcc gagctcaggg tctgggtaaa caggtgtgtt
159841 ttgatgtact tggaattctc aaaggcggca ccctcgccgg cgcgcctgtc ctcccaggga
159901 cccgagacga aggcccgtct gtagaggaag tggttgcgca tgcgggccag ctcccagtag
159961 accacgtccc cccagacgcg caggcacagg gtctcggtca gggtctcgct ctgttgcgcc
160021 aggcaggact gcagcttggc cagaccctcg gtggccacct ggcgcaggta ctgctccttg
160081 cgcttgagcg cgtccgagag ggcgccggac gggccgggct ctcgtgcccc agccggccgg
160141 ggcacctccg ggctctcccg ggacgcctcc tcctcgcctc ggcccaaccg ctgcatggct
160201 cggttgagcc gcgtgtacag ctcgttcctc ttttgcagga tggcccggta ctgggggtgc
160261 gccgtgaagg cggcggcgca gtccgccttc agcgcctcca ccgcgtcgcc cgaggagctg
160321 tagaccccgc cgcagaagag ccgctccgtg gccccgggag ccacggcgtc aaacaggtga
160381 gtcagccttg cccccgccag cgcctcctcg caggcccccc gcaccagggc caggcgacgc
160441 tcccggcaa acagggcaga gaggcgggaa tggccgccac cctccccctg ccccgttgca
160501 ccgatagcat ggccgccaga gttccaatag aggagctccg agagctccgc cacctccggg
160561 ggcactgtcg agaagacgtt gtaggtgtcc agcgctctgg tcgccccctc tgcctccggc
160621 cgccccgggc ccgggaccgc gccctcctct gggccgcccg gcctcgcctt ctcctcagcc
160681 tccaacaggt gcccgagccc cgcctggcgg acttcattct caaacagtcc cgagaccggc
160741 tccggattca ccggcaccgc caggtggtta caggagacgt gggtcccctc tgccgtggaa
160801 gggttgccgt ggttgggcag aaccatcagc tcgcccacac agcgccagca gggcacagag
160861 gtgatgtaga ggcgcgggtc tgggatggga cttacgcccc gaaagcggcc cagcagatcc
160921 agggcccgtt ccaggctctc cagccccatg gtgtgagaca tgcaataaaa cacgctattg
160981 attctcttca ttaaaatctc tatgtcattt attaggcaca aacttacatc gactttatgc

Fig. 3 (cont.)

161041 cccccgtaaa actccacaga gtacgcgact gagggggtac ggagaggcgg gacccgggta
161101 ccctttctac caggggcgag cagcgcggca gaggcctctc tcgagttctc tagcaggtgc
161161 accagctcca gggacagggc gctgcatgca cggtcattct gccgtctcaa acggggaagg
161221 aggatggcct ccagctcggc cagcaggccg gcgttgcgca ccaccgcagc cacgtccaga
161281 ctccgggggt ccagccgggt gcacacgctc agctcaaccg ccagggcgta cacctggctg
161341 tacgccgccg ccagcagccc cgacatcgcc gccccagggg tctctagacc tcgagtccgg
161401 ggagaacggt ggccagacgg cgcttgcgtc tgcccccgga gccctgccct cctccaccca
161461 gcagcagccc ggccgaggcc tgcgacgcgg tgctgaccgg ctcggccacg ctgataaagt
161521 tgtcctgggc tgccccgggc ccaccccaca ctccctccag aaagtcccga gcggcctccg
161581 ccgtccactc tatcccgctg gaggcaatgg tcgccagggt ttctaggacg ctgtccgcca
161641 ggacggagaa gcggcccaat aagtactccg cgtcgtccct agtcagcgag gcgcatgcct
161701 cgcccatggc atccacaagg ttgcacacca catcaaacac acagtcttcc tcctgttttt
161761 gtgatataat ggcctccagg ccagccctga tgttctcaat ctcatatgtg gtcgcggctt
161821 gggtccggcg cttcacggtc aaccctaggg tgggggtggc aaagacaaac ttcttccgca
161881 tggaagagcc cccggcctgc ttgcgcagcc cagccccggg ggcctgcagc aggttcctgt
161941 ccacgccccg gcccataaag tatcccaggt tcccggcctg gaatatctgg ttgttgccgt
162001 tgacccccgt gtacttgttg atggtcactg gcagcgtgac aaccggacgg gccttgcaga
162061 cctggctaag acagtctgtg gccgcgcaga ccaccgtggt cgcagtaagg gaggaggtgg
162121 cctccgcgta ggccgctgcc gactccaccg cccgcgtgcc cagtacgtgg gggtagtcac
162181 gggcgggcac cgactgcgtc ctcggcacca gtccctgaat caggctgatg tagaactggg
162241 tctggccgca cgccttcagg atggcgttgt tgagcctctg cttggcgtaa gtgaccaggt
162301 tgccaggcac cacatctatg acgttgctct cttcgtgggc ccgggagccc ccgtccacaa
162361 agagggccag gtcagagtac tcctccgcgc tggccccgct ggggacaggg accgagcgcc
162421 gcctggaaaa gttgtgccac aggtacaggc ttgagagctt agtgtccggg aatagggtct
162481 tgtggtaggt gttgaggaat ttcatgtagg gcccgttgat gatgtagttc tccctcctgg
162541 tagtggactt gatgaagctg ttctggaggg cggcattctc ccccgtgaag accaccctgt
162601 tcttgatctt gatgttcctg gggcacagca tcagcacctt ggacatgcgc acaggcagcc
162661 gccggccgta cacccggccc tgcagggccg cgtccaggtc tggcaggtcg caggtgggct
162721 ccccatgcac caccttggcc tccttggccg tgaggacccc cttgtcgatg gccaggctcc
162781 taaagttggt gcacagcgtc tggtagtgac cctttagcca ctctgggggg ctctggccaa
162841 gcccggggtt gtcattctca tagcacatac agatgggcag ggagatgtcc tgcaggatgg
162901 tcagcagtga gcggtaaaac agctgggtga agatggggca ggcgggctgc gcaaaggggt
162961 tgcacgagta ctgcatcacg tggtagcagc tcttgaccag gtccttgtag gtgatgttgt
163021 tcttggccat gctgttcata aactggacca cttcggcgtc caccgccgca tccacgtcct
163081 tgaacatctt gacaaagtca cgcgggccat ggggctcctt ctctagcttt ccttcagcgt
163141 ctatgcccag ccgagacagc cgctccagca ggttctggtt cagctgccag taggtgtagc
163201 ggggctcgtc gtccggccgc tgcccgtcgt cctccttatc gatgaagttg agaaagttgc
163261 ccaaaaagtc cgtctcgttg taggagcccg aggcccccga gatcacatag gggtccctcc
163321 gctgcgtgga catgacgggg gggaagcggt ccctcagcct aaagaagagc gtgttcaggc

Fig. 3 (cont.)

163381 acacggccgg ggcccggccc tcgcagagcg agcacatggg actggcggcc gccccgcca
163441 cgtagctgcc cgtctccggc accggggtca gagagctctt ctgtccctgg caaaactgca
163501 ggtagtaggc atagcgggca agaaggttgg gcgagaagga ggccgcatag accaggtgct
163561 ccacagcgta gtttcccgga ccgttggttc cggtcacgtc tggcccaccc cagcccgaga
163621 agcagggtcg gcggcagggg tcccaggtcc cctcctgcag ggtccccagg ccgtgggtca
163681 tgtagaaact gttaaagaga ctctccttgc cctgaccggt tgacttcgag acccccgaga
163741 cgtagaggac ggaattggtg gcaaagatct gcgtggacac gtggggggcc aggctggcat
163801 tatatcggtg taacgcagcc acacgggcct ctggaccctc acagtcggca aacaggggcc
163861 acgagtcgta gttgaggctg gccggggtct cgtgcgaggc ctccagcatg gcgggtgcgt
163921 agctcaccgc cagctcgcat gccgcgctgt ccacaatcat taaggctccc gagtccgggt
163981 gactgatggt tgaggctggg aactccttga ggggggccac cttggccacc ttggcctggt
164041 cctgcaggct ctgcttctcc agcagctcca ccagcttgcc cacccgtcgg acgcgcagcg
164101 cctgcgccag cccggtgtac agcgcctcgt gcatgcagcg gctgaggtcc gagttgtaaa
164161 actggcggag ctggggcacg ccctctggga acacctcctt gtcgtagagc gggaccctaa
164221 cgctcgcaga ctgccccacc gctacctcct gttttaacga tggaatggcc accaggtttc
164281 cgctgtagag tcgctccttg aaggcctcgg ttattgccac cgcccccagg taggcagagg
164341 gatctagccc ttcggggaag aagtccccg gcttggagct ttccctcggt agggcgctgt
164401 aggcgtcgta cccaaacacc tccctggtct cgccacagag ggcctcgaga cccggcccct
164461 caaagatggg gggaaccata tgggcattgt ggaacacgta gatgtccctg tgataggagg
164521 tagcgcgtag gagcccgcag ttggggtcgg gcctcctgtg cagagccttg acattgatgc
164581 tgaagcccgg ctccacggtg atgccgcaaa ggagcggcac cgtcaggcac ctgtggcccg
164641 cgtagccggt ccccagtgtg gccacctccc taagagggta ggtggccagg gggtaaaagt
164701 agatgtagcc gcacggaccc ggctggctct ggctgcccag attatcctcg ctagtctgtg
164761 caccctgcat gatgcccaag gtatcgcccc ggcctcccag tcccacatta aatgttacac
164821 tttactcatc acgcaacacc cactgtttat tcatttacaa agatttcagg aagtcagtca
164881 ggctggccag ggcccacgtc acggggaact gacgtctcag cgatcttggc atgccgccca
164941 gcctcgcaaa ccagagtctg cgatagaggg ccaggtagtg ggcgattgcc cccagcacga
165001 aggcggcgct cttgtggtca tccaggtagt ttcgcaccgc aaacaccact gtgtagcaca
165061 gcaccaccct gagccgcgac cagtagtcgt agtggtcgtt gtacactgcg cgcaggacgc
165121 tgatgatgag ccgtacgtgc gtgtctttgc ccccgatgtc ggctgtcctg caggccagct
165181 ccgcgtacag cttcctatcc ttcctcaggg aggccttgat gagccggcag aggaccaggg
165241 ctggcaaagg caggtctttc tcatcccggg tgaacaccgc gtacatggcc ctgaacatga
165301 ggtagctgga ctcagccacc ttgtcgtccg gcggcgaggg cgcgacccac gcctcgaccg
165361 gggtcctcac aaacacagaa tctgtagact tggctggcct catggtctcg tcaggccagc
165421 tcacgggctt caggcttata tgataaaatg ggcgtggcag aatagtataa gacgcgaggc
165481 ctgggtgagg agagtccaga gcaatggcca ggttcatcgc tcagctcctc ctgttggcct
165541 cctgtgtggc cgccggccag gctgtcaccg ctttcttggg tgagcgagtc accctgacct
165601 cctactggag gagggtgagc ctcggtccag agattgaggt cagctggttt aaactgggcc
165661 caggagagga gcaggtgctt attgggcgca tgcaccacga tgtcatcttt atagagtggc

Fig. 3 (cont.)

165721 ctttcagggg cttctttgat atccacagaa gtgccaacac cttcttttta gtagtcaccg
165781 ctgccaacat ctcccatgac ggcaactacc tgtgccgcat gaaactgggc gagaccgagg
165841 tcaccaagca ggaacacctg agcgtggtga agcctctaac gctgtctgtc cactccgaaa
165901 ggtctcagtt cccagacttc tctgtcctta ctgtgacatg caccgtgaat gcatttcccc
165961 atccccacgt ccagtggctc atgcccgagg gcgtggagcc cgcaccaact gcggcaaatg
166021 gcggtgttat gaaggaaaag gatgggagcc tctctgttgc tgttgacctg tcacttccca
166081 agccctggca cctgccagtg acctgcgttg ggaaaaatga caaggaggaa gcccacgggg
166141 tttatgtttc tggatacttg tcgcaataaa cgcacttgcc tatttcacct tgttttagtg
166201 tggcattggg ggggtggcat tgcgggtgga tagcctcgcg actcgtggga aaatgggcgg
166261 aagggcaccg tgggaaaata gttccaggtg acagcagcag tgtgtgaaga ttgtcacagc
166321 tgctggtttg gagaaaacgg gggtgggcgg tgatcaggga gaacaattcc ccggggacac
166381 ctgcacgaga cccctgggct ctcaggaact ccgcccaggt cttgccaatt ggggtgatcc
166441 tgtagcgccg cggtttcagc atcacaggtt attttgcctg aagcttgctg ggcgtaaat
166501 ccctctcgcc ttgtttctca gagagcattt caggccggtt ttgcagtcgc tgctgcagct
166561 atggggtccc tagaaatggt gccaatgggc gcgggtcccc ctagccccgg cggggatccg
166621 gatgggtacg atggcggaaa caactcccaa tatccatctg cttctggctc ttctgggaac
166681 acccccaccc caccgaacga tgaggaacgt gaatctaatg aagagccccc accgccttat
166741 gaggacccat attggggcaa tggcgaccgt cactcggact atcaaccact aggaacccaa
166801 gatcaaagtc tgtacttggg attgcaacac gacgggaatg acgggctccc tccccctccc
166861 tactctccac gggatgactc atctcaacac atatacgaag aagcgggcag aggaaggtaa
166921 gagtgccatc tatctgtact tttatttatt gcatcacaag tcacatcaat aataagggcg
166981 ccatctagcg ggagatgtta tccacaccat cccaattcac atctcaggga caacaggtca
167041 aagttctttg ttgacacccc cagcgctggc tccagggggt ggaagcgttg gatgcagtcc
167101 tccgcatcgg ggcggacgcc tcctcccaac gcgtttctgc ggatcagtcg ctggctggtg
167161 ggcatcggag tcggtgggcg gtcctccacg gggacacgct ccttcttggc cttgttcttt
167221 gaccttttgg acattcttct gaaggaacgg cggagagtag cgtagaatcc agccagtggt
167281 ctacccggtc gcatggtggc ttcttagatg aggagcaggc ataaaagtcc aaacaggaca
167341 cagagtacca ccaggagtag tcttagtctg ctgacgtctg ggtcctcggg gcaggggtgg
167401 ctaggcctgg tctccgtaga agagccgggc aggccgcagg cagaggactg ctgctctagc
167461 aaagcacgct ccaggacgtg taccatctcg agagtgaggc acagctgttt tcgtggactt
167521 ttatacagta aggacaagga aagaaggcca gaggaatgtg gaaagatgag cgaggacagg
167581 tgtggaggtt ttgggctagc tcttagtttc tgggtgtgag agagggatta aagtgcttat
167641 gcgcaaagaa tgtgtcaaca acaggtgttc ctgcctctgc tggcatgagt taggtgtggc
167701 ttgggctgaa tccaaatgtg tattggcaca agatggaaag caaagttgct ggagttactg
167761 ggtgggagac agggatgtat gtggtccccc gctggtatgc cagtaccctg tggaagtaag
167821 gggcctcatc tgcctggtag ttgtgttgtg cagaggtctg atgtgtgtag gaggggtggg
167881 ttcaacgcag gggcgttggt ggcggagtct ggcaacgccc gggtccttgc tacctgtgtg
167941 gtgtgttaag ggctgggtaa aggtgtctgc caattctcgc atgtcctcct ttccccttgt
168001 tttgaaatag aatatgaatg tggcttttca gcctagacag acagtgtggc taagggagtg

Fig. 3 (cont.)

168061 tgtgccagtt aaggtgatta gctaaggcat tcccagtaaa tggagggaga gtcagtcagg
168121 caagcctatg acatggtaat gcctagaagt aaagaaaggt tagtcatagt agcttagctg
168181 aactgggccg tgggggtcgt catcatctcc accggaacca gaagaaccca aaagcagcgt
168241 aggaaggtgt ggatcaccgc cgccatggcc ggaatcatga ctatgaccgc cgcctccgtc
168301 tgtcatcaaa ggcgggccct ggtcacctcc tttgttttca acctcttccg tcaattgtgg
168361 agggcctcca tcatttccag cagagtcgct agggctatga ggcagcgggt catgtgggcc
168421 attgtcatca gtgttgtcag ggtcctgtgg gccattgtca tcagtgttgt cagggtcctg
168481 aggcagcggg tcatgtgggc cattgtcatc agtgttgtca gggtcctgtg ggccattgtc
168541 atcagtgttg tcagggtcct gtgggccatt gtcaggacca cctccaggtg cgcctaggtt
168601 ttgagagcag agtgggggtc cgtcgccggc tccactcacg agcaggtggt gtctgccctc
168661 gttggagtta gagtcagatt catggccaga atcatcggta gcttgttgag ggtgcgggag
168721 ggagtcatcg tggtggtgtt catcactgtg tcgttgtcca tggtaataca tccagattaa
168781 aatcgccaga aacaggagga gccaaaggag atcaaccaat agagtccacc agttttgttg
168841 tagatagaga gcaataatga gcaggatgag gtctaggaag aaggctagga agaaggccaa
168901 aagctgccag atggtggcac caagtcgcca gagcatctcc aataagtaga tccagatacc
168961 taagactgcg ttgaaaaaag agtgttaggg ttggaaaagt gggggtgtgg taaataattc
169021 ctagggaatg ttagatctta ccaagtaagc acccgaagat gaacagcaca attccaagga
169081 acaatgcctg tccgtgcaaa ttccagagag cgatgagcag gagggtgact ggggaaagag
169141 gagaaagtgc gttagagaag gaagagtaag ggaaaggggg tgtggggcaa agggtgtaat
169201 acttactcat cagtaggagt atacaaaggg ctccaagtgg acagagaagg tctcttctga
169261 agataaagat gatcaaaatt ataattataa gcatgagagc aaaggaatag aggacaagga
169321 gggctcctcc agtccagtca ctcataacga tgtacagcca aaacagtagc gccaagagga
169381 ggagaaggag agcaaggcct agggaagagg agaggggggg tcctcgaggg ggccgtcgcg
169441 ggcccggtgg gcccctctca aggtcgtgtt ccatcctcag ggcagtgtgt caggagcaag
169501 gcagttgagg aaagaagggg gcagagcagt gtgagaggct tatgtagggc ggctacgtca
169561 gagtaacgcg tgtttcttgg gatgtaggcc cggggggatt tgcggggtct gccggaggca
169621 gtacgggtac agatttcccg aaagcggcgg tgtgtgtgtg catgtaagcg tagaaagggg
169681 aagtagaaag cgtgtgtttg tgttagaaaa gcgggtcccc ggggggcaag ctgtgggaat
169741 gcggtggcca agtgcaacag gaaatggaaa ggcagtgcgg caatcagaag ggggagtgcg
169801 tagtgttgtg ggaagcggca gtgtaatctg cacaaagagg cgcggggcgc gcaacgttgg
169861 gaggtcgttg gcggcaggcg ggaggccgtg ctttaggggg gttcaggtga ggcaaggctg
169921 tggggtaacc gtaggggagg cgggtgaggc ggctaagagg gctaagggtc ggcgggtgac
169981 gaagcagcag acggcggata tgggaatttc agaatgaggt ggcggattca ggcgaaaagg
170041 gtgtgggctg tgcgagtgtc atgaggcagg cgcggaaagt cgctgcggct tgctggggca
170101 tggggggccg cgcattcctg gaaaaagtgg agggggcgtg gccttccccc gcggcccccc
170161 agcccccccg cacagagcgg cgctacggcg ggcgggcggc ggggggtcgg ggtccgcggg
170221 ctccgggggc tgcgggcggt ggatggcggc ggacgttccg gggatcgggg gggtcggggg
170281 gcgccgcgcg ggcgcagcca tgcgtgaccg tgatgagggg gcagggtcgc agggggtgtg
170341 tctggtgggg gcgggagcgg ggggcggcgc gggagcctgc acgccgttgg agggtagaat

Fig. 3 (cont.)

170401 gacagggggc ggggacagag aggcggtcgc gccccggcc gcgccagcca agcccccaag
170461 gggggcgggg agcgggcaat ggagcgtgac gaagggcccc agggctgacc ccggcaaacg
170521 tgacccgggg ctccggggtg acccagccaa gcgtgaccaa ggggcccgtg ggtgacacag
170581 gcaaccctga caaaggcccc ccaggaaaga cccccggggg gcatcggggg gtggggcatg
170641 gggggccgcg cattcctgga aaaagtggag ggggcgtggc cttcccccgc ggcccccag
170701 cccccccgca cagagcggcg ctacggcggg cgggcggcgg ggggtcgggg tccgcgggct
170761 ccgggggctg cgggcggtgg atggcggcgg acgttccggg gatcgggggg gtcgggggc
170821 gccgcgcggg cgcagccatg cgtgaccgtg atgagggggc agggtcgcag ggggtgtgtc
170881 tggtgggggc gggagcgggg ggcggcgcgg gagcctgcac gccgttggag ggtagaatga
170941 cagggggcgg ggacagagag gcggtcgcgc ccccggccgc gccagccaag cccccaaggg
171001 gggcggggag cgggcaatgg agcgtgacga agggccccag ggctgacccc ggcaaacgtg
171061 acccggggct ccggggtgac ccagccaagc gtgaccaagg ggcccgtggg tgacacaggc
171121 aaccctgaca aaggcccccc aggaaagacc cccgtggggc atgggggcc gcgcattcct
171181 ggaaaaagtg gagggggcgt ggccttcccc cgcggccccc cagccccccc gcacagagcg
171241 gcgctacggc gggcgggcgg cggggggtcg gggtccgcgg gctccggggg ctgcgggcgg
171301 tggatggcgg cggacgttcc ggggatcggg ggggtcgggg ggcgccgcgc gggcgcagcc
171361 atgcgtgacc gtgatgaggg ggcagggtcg cagggggtgt gtctggtggg ggcgggagcg
171421 gggggcggcg cgggagcctg cacgccgttg gagggtagaa tgacaggggg cggggacaga
171481 gaggcggtcg cgcccccggc cgcgccagcc aagcccccaa ggggggcggg gagcgggcaa
171541 tggagcgtga cgaagggccc cagggctgac cccggcaaac gtgacccggg gctccggggt
171601 gacccagcca agcgtgacca aggggcccgt gggtgacaca ggcaaccctg acaaaggccc
171661 cccaggaaag acccccgggg ggcatcgggg ggtggggcat gggggccgc gcattcctgg
171721 aaaaagtgga gggggcgtgg ccttcccccg cggcccccca gcccccccgc acagagcggc
171781 gctacggcgg gcgggcggcg gggggtcggg gtccgcgggc tccgggggct gcgggcggtg
171841 gatggcggcg gacgttccgg ggatcggggg ggtcgggggg cgccgcgcgg gcgcagccat
171901 gcgtgaccgt gatgaggggg cagggtcgca gggggtgtgt ctggtggggg cgggagcggg
171961 gggcggcgcg ggagcctgca cgccgttgga gggtagaatg acagggggcg gggacagaga
172021 ggcggtcgcg cccccggccg cgccagccaa gcccccaagg ggggcgggga gcgggcaatg
172081 gagcgtgacg aagggcccca gggctgaccc cggcaaacgt gacccggggc tccggggtga
172141 cccagccaag cgtgaccaag gggcccgtgg gtgacacagg caaccctgac aaaggccccc
172201 caggaaagac cccgggggg catcgggggg ggtgttggcg ggggcatggg ggggtcggat
172261 ttcgccctta ttgccctgtt t

Fig. 3 (cont.)

Human herpesvirus 8, genome

Accession: NC_003409

1 tactaatttt caaaggcggg gttctgccag gcatagtctt ttttctggc ggcccttgtg
61 taaacctgtc tttcagacct tgttggacat cctgtacaat caagatgttc ctgtatgttg
121 tctgcagtct ggcggtttgc tttcgaggac tattaagcct ttctctgcta tcgtctccaa
181 atttgtgccc tggagtgatt tcaacgcctt acacgttgac ctgtctgtct aatgcatcct
241 tgccaatatc ctggtattgc aacaatactc ggcttttgcg actgacggag agaagagtca
301 ttcttgacac cattgcctgc aattttactt gtgtggaaca atctgggcat cgacagagca
361 tttggattac atggcgtgca caacctgtct tacaaacctt gtgtgcacag ccatcaaaca
421 cagtcacttg tggtcagcat gttactttgt attgttctac ctctggaaat aatgttaccg
481 tttggcatct accaaacgga cgaaatgaaa ccgtgtcaca aactaaatac tataatttta
541 cgctgatgag ccaaactgag ggtgttata cttgttctaa cgggctgtcg tctcgcctgt
601 caaatcgtat atgtttttgg gcgcgttgtg ccaatataac tccagaaact catactgtat
661 ctgtcagcag tactacaggc tttagaacat tgagtactaa tagcttagtg aagataatcc
721 atgcaaccac acgtgatgta gttgtagtga aagaagcaaa atctacacat tttcatattg
781 aagtgcattt tcttgtattt atgacactcg tagctctgat aggaaccatg tgtggtatct
841 taggaactat tatctttgcc cattgtcaaa aacaacgtga ctcaaacaaa acagtgccac
901 aacaattgca ggattattat tccctacacg atttgtgcac ggaagactat acgcaaccag
961 tggattggta ctgacattca ggtaagataa tctaaatatt ctctataaca taattgtaat
1021 gtgttttatg tttatagcta caaatgtttt atgcaaaata cattttatga ggtcggatac
1081 ttattaaaag cattgtctta agtacattaa aaggacattg tataaccgtg ctacttacag
1141 catggccttt ttaagacaaa cactgtggat tttatggaca tttaccatgg ttattggcca
1201 ggacaatgaa aagtgttccc aaaaaacctt aattggatat agacttaaaa tgtctcgtga
1261 cggtgacatt gcagttggag aaacagtgga attacgttgt agatctggat acactactta
1321 tgcccgcaat ataacagcaa catgtttaca aggtgggacg tggtctgaac caacggcaac
1381 atgtaacaaa aagtcctgtc caaacccagg tgaaatacaa aatggaaagg ttatatttca
1441 tggtggacaa gatgccttaa aatatggggc aaacatttca tatgtttgta atgaaggata
1501 ttttttggtt ggtcgagaat acgtgcgata ttgtatgatt ggagcatctg gccaaatggc
1561 gtggtcatct tctcctcctt tttgtgaaaa agaaaagtgt cacagaccga aaatcaaaaa
1621 tggagatttt aagcctgata aagattatta tgagtataat gatgcagttc attttgaatg
1681 taatgaagga tatactctag ttggaccaca ttccattgca tgtgcagtta ataacacgtg
1741 gacatctaac atgccaacct gtgaactcgc aggctgtaaa tttccatcgg tgactcatgg
1801 ttatccaatc caaggttttt ctcttactta taaacataag caaagtgtta cttttgcatg
1861 caatgatgga tttgttctca gaggatcccc cacaattacg tgtaacgtta ctgaatggga
1921 cccaccactt cctaagtgtg ttttggaaga tatagatgat ccaaacacaatt caaatcctgg
1981 acgtttgcat ccaacaccca atgaaaaacc aaatggtaat gtctttcaac gctcaaacta
2041 tacagaacct ccaacaaagc ctgaagacac ccatacagca gctacttgtg ataccaactg
2101 tgaacagcca cctaaaatcc tgccaacatc cgaaggtttt aatgagacta ccacatctaa

Fig. 3 (cont.)

2161 tacaattaca aaacaattag aggatgagaa aactatatcc cagccaaata cacatattac
2221 atctgcctta acatccatga aagcgaaagg taactttacc aacaagacca ataactctac
2281 tgatctacat atagcgtcta cacccacttc ccaagatgat gctacgcctt caatacctag
2341 tgtacagaca cccaattata atactaacgc accgacacgt acactaacgt ctctccatat
2401 tgaagaaggc ccatccaatt ctactacttc agaaaaggcc acttcctcta ctctctcaca
2461 caactcacac aaaaatgaca ccggaggcat atacacaaca ttaaacaaaa caacacagtt
2521 gccatccact aataaaccta caaacagtca agccaagagt tccactaagc cacgcgttga
2581 gacacacaat aaaacaacca gtaatcctgc catttcttta acagattctg cagatgtgcc
2641 tcagagaccg cgagaaccaa cactccctcc cattttcagg ccaccggcgt ctaaaaatcg
2701 ctatctggaa aagcaactag ttattggact actaaccgct gtcgccctaa cgtgtggact
2761 gattacctta tttcactatc tgttctttcg ttagcctaga acttgctcca gtgttagaca
2821 gggctatgat tgcttctcca cgctgtccac cttaacactt cccaataaca aatccggtat
2881 gcagcagcgt gacactacta atgtaaccta aaaaatgtgc atgtggtatg tattgtacta
2941 aagataccga ccaatacaag acaactaata ttaaccatag tgtgcgtttc tttgtataaa
3001 atacgcgtgt gggaaagcga cagaaggggg cggcgtttcc atatgaggcc aagtgcattg
3061 gctattttag ggcggtgac cacgcactat agtgcgcggt gtggcagaaa attcacaccg
3121 tatataaaca aggaaagggg actctgcgcg cttaagcgcc aagccattat acacacgggt
3181 tttttgttgt cttggccaat cgtgtctcca tggcgctaaa gggaccacaa accctcgagg
3241 aaaatattgg gtctgcggcc cccactggtc cctgcgggta cctctatgcc tatctgacac
3301 acaacttccc catagggga gcctccctgc tggcaatgg ctacccggag gcaaaagtat
3361 tttcactacc tcttttgcac gggctcacag tggaatccga tttcccctta aacgtaaagg
3421 cggtgcacaa gaaaatcgat gcaaccacag cttctgtgaa attaacttca taccacaggg
3481 aggccatcgt ctttcataat actcacttat ttcagccaat ctttcaagga aagggactgg
3541 aaaagttatg tcgagagagc cgagagctgt ttggattttc aacgtttgtt gagcaacaac
3601 acaaagggac gctctggagc ccagaggcat gccctcagct accctgcgcg aatgagattt
3661 ttatggcggt catagttaca gagggattca aggagagact gtacggcggc aaactggtgc
3721 ccgtgccctc tcagacaacg cccgtacaca ttggggaaca ccaggcgttc aagataccct
3781 tgtatgacga ggatctgttt ggtccaagtc gcgcccaaga actatgtagg ttttacaacc
3841 ccgatatcag tagataccta catgactcca tattcactgg aatagcacag gctctaaggg
3901 taaaggacgt tagcacggtc atccaagcct cagaaaggca atttgtgcac gaccaataca
3961 agataccaaa gctggtccaa gccaaggact tcccccagtg tgcttccagg ggaaccgacg
4021 ggtctaccct aatggtgata gacagtctgg tggctgaact tggtatgagt tatggtctgt
4081 cctttattga gggaccccag gatagctgcg aggttctaaa ttatgacacg tggcccatct
4141 ttgaaaactg cgagacgcca gatgcccgcc ttcgtgcact agaagtttgg cacgcagagc
4201 aggccttgca tattggcgcc cagctgtttg cggccaactc tgtgctctac ctgaccagag
4261 tggcaaagct gcctcagaag aatcagagag gagacgccaa catgtacaac tcattctacc
4321 tacagcatgg cctgggatac ctctcagagg caacagtaaa ggaaaatgga gcctctgcct
4381 tcaagggcgt gccagtgtct gcactggatg ggtcatctta caccctccag cacctggcct
4441 acgcgtcctc tttctcccca catctcctgg caaggatgtg ttactatctg cagttcttgc

Fig. 3 (cont.)

4501 cccaccataa aaacaccaac agtcagtcat acaatgtggt ggactacgtg ggcaccgcgg
4561 cacctagtca aatgtgtgac ctgtgtcagg ggcaatgtcc agctgtatgc atcaacacgc
4621 tgttttacag gatgaaggac aggttcccac ctgttctgtc aaacgttaag agagacccat
4681 atgtgatcac gggcacagcg ggaacgtaca atgacctaga gattctcgga aactttgcca
4741 ccttcaggga gagagaggag gaggggaatc ctgtggaaga tgctccaaag tatacatatt
4801 ggcaactatg ccagaatata accgagaagc tagcgtccat gggcatctcg gagggcggcg
4861 atgccctaag aaccctcatt gtggacatcc ccagcttcgt caaagtgttc aaggggatag
4921 acagcacggt agaggcagag ctcctaaagt ttattaactg catgatcaaa aacaattaca
4981 acttcagaga gaacatcaaa tccgtccatc acatccttca gtttgcatgc aacgtatact
5041 ggcaggcgcc gtgcccggtt tttctgaccc tttactacaa gtcactgctg acggtcatac
5101 aggacatatg tctgacgtca tgtatgatgt acgagcagga caacccggcc gtgggaattg
5161 taccatccga gtggcttaaa atgcactttc agacaatgtg gaccaacttc aagggtgcct
5221 gcttcgacaa aggagcaatc acgggcgggg aactaaaaat agtccaccag tccatgttct
5281 gtgacctctt tgacaccgac gctgccatag gagggatgtt tgcacccgct cggatgcagg
5341 tcaggatagc cagagcaatg ctcatggttc caaaaaccat aaaaataaaa aacaggatca
5401 tctttccaa ctccaccgga gcagagtcga tccaggcagg ttttatgaag ccggccagcc
5461 aaagggattc atacatcgtc ggaggaccct acatgaaatt cctaaacgcc ctgcacaaaa
5521 cactttttcc ttccacaaaa acttctgccc tgtacttgtg gcataagatt ggccagacca
5581 caaaaaatcc catactacca ggtgtctcgg gggaacacct aacggagtta tgtaattatg
5641 taaaggcaag tagccaggct ttcgaagaga taaatgtttt ggaccttgtg ccagacaccc
5701 tgacatcata tgcgaaaata aaactaaaca gttccattct ccgggcttgc ggacagacac
5761 agttttatgc aactactctc tcttgccttt cgccagtgac tcagctggtt ccggccgagg
5821 agtaccccca cgtactgggg ccagtggggt tgtcatctcc agatgaatac agggcaaaag
5881 tcgccggcag gtctgtaacc attgtacagt caacactgaa gcaagctgtt tccaccaacg
5941 gacgactccg gcctatcatt accgtgccac tggtggtcaa caaatataca gggagcaacg
6001 ggaacacaaa cgtctttcac tgtgcaaacc tgggatactt ctcggggaga ggggtggaca
6061 gaaatctcag gccagaaagc gtcccctta aaaagaataa tgtcagctct atgctaagaa
6121 aacgccacgt gattatgacc cccctggtag acaggctggt aaagagaata gttggcatca
6181 actctgggga attcgaggca gaagcggtta agagaagtgt gcagaatgtc ctggaagaca
6241 gagataaccc aaacctgccg aagacagttg tattagagtt ggttaagcca cctcggtgga
6301 gctcctgtgc aagtctcaca gaggaggacg tgatttacta cctgggccct tatgccgtac
6361 ttggggacga ggtcctgtca ttactgagca cagtgggcca ggcgggggtg ccatggacgg
6421 ccgagggtgt ggcctcggtc atccaggaca taatagatga ttgcgagtta cagtttgtgg
6481 gcccagaaga gccttgcctt atccaaggac agtcggtagt ggaggagctt tttccgtccc
6541 cgggcgtccc aagcctgaca gtgggtaaaa aacgaaaaat cgcatccctg ctctctgacc
6601 tggatttgta gttgtgtacc cgtaacgatg gcaaaggaac tggcggcggt ctatgccgat
6661 gtgtcagccc tagccatgga cctctgtctt cttagttacg cagacccggc aacactggac
6721 actaaaagtc tggccctcac tacagggaag tttcagagcc ttcacggcac actactcccc
6781 ctcctcagac gacaaaacgc acacgaatgc tcaggtctgt cactagaatt ggagcacttt

Fig. 3 (cont.)

6841 tggaaaacgt ggctgatgct ctggccacgt tgggagtgtg cactagcaga aaactgtctc
6901 cagaagagca tttttccctc ctgcatttgg acacaacatg caacaagcaa ccggagcgtt
6961 aggtttaatt tttacggaaa ttgggccttg gagttaaagc tgtcactaat aaacgacgtt
7021 gaaattttct ttaaacgtct tagtagcgtt ttttattgta taggatcggg cagtgctctg
7081 gagggtttag gggaggtatt gcgtttcgtt gggaagctga ggggtatctc acccgtacct
7141 gggccggacc tatatgtctc aaatctgccc tgcctagaat gccttcagga agtgtgtctg
7201 actcccaacc agggcaccag tctgcaggcc atgctcccag acacggcctg cagtcacata
7261 tgtacccccg catgcggtga gcctgtccgg ggcctctttg agaacgagct aaaacagctc
7321 gggcttcaaa cccctgagtc catacctact accccctgtc agtcccgggt aaggcaagat
7381 gatgaaatca gacagagctc tctaatggcg gtaggagatc accacatttt cggagaggtg
7441 accagatctg tcctggaaat ctcaaacctg atctattgga gctctggcca ctcggatgcc
7501 acctgcgacg gagacagaga ctgctctcac ctggcctcgc tgtttactca cgaggctgac
7561 atgcataaaa ggcgcgtcga cctggccgga tgcttgggcg aacgcggcac gcccaaacac
7621 tttttgact gctttcgccc agactcccta gaaacccttt tctgtggtgg tctttttagc
7681 tccgtggagg acaccataga aagtctccaa aaggactgct cttctgcctt ctaccaacag
7741 gtaaactaca ctactgcact gcaaaaacag aacgagtttt acgtccgact cagcaaactg
7801 ctggcagctg gtcagctaaa tttgggcaaa tgttccactg aaagttgcca atccgaggcc
7861 cgtaggcagc tggtaggtgg gggcaaacca gaggaagtgc tgagggatgc aaaacaccgg
7921 caagaactat accttcagaa agtggcacgc gacggtttta aaaaactctc tgattgtata
7981 agacaccagg gccacatcct gtctcagacc ctgggtctaa gactgtgggg gtctgtcatc
8041 tacaacgagg catctgccct acaaaaccac tttttacaca gagcacagtt catatccctc
8101 ccctggcagg acctgacggt cgactgtcca acgcggtttg aaaattctaa atatatcaaa
8161 aattctctgt actgccagcg tctggggcgg gaacacgtag agatcctgac actggagttc
8221 tacaaactta tcacgggccc gctgtcaaag cgacatactt tatttcccag tcctccaaat
8281 gtgacgctgg ctcagtgctt cgaggctgcg ggcatgcttc cccatcaaaa gatgatggta
8341 tcagagatga tctggcccag catagagccg aaggactgga tagagcccaa cttcaaccag
8401 ttctatagct ttgagaatca agacataaac catctgcaaa agagagcttg ggaatatatc
8461 agagagctgg tattatcggt ttctctgtac aacagaactt gggagaggga gctaaaaata
8521 cttctcacgc ctcagggctc accggggttt gaggaaccga aacccgcagg actcacaacg
8581 gggctgtacc taacatttga gacatctgcg cccttggtgt tggtggataa aaaatatggc
8641 tggatattta aagacctgta cgcccttctg taccaccacc tgcaactgag caaccacaat
8701 gactcccagg tctagattgg ccaccctggg gactgtcatc ctgttggtct gcttttgcgc
8761 aggcgcggcg cactcgaggg gtgacacctt tcagacgtcc agttccccca cacccccagg
8821 atcttcctct aaggccccca ccaaacctgg tgaggaagca tctggtccta agagtgtgga
8881 cttttaccag ttcagagtgt gtagtgcatc gatcaccggg gagctttttc ggttcaacct
8941 ggagcagacg tgcccagaca ccaaagacaa gtaccaccaa gaaggaattt tactggtgta
9001 caaaaaaaac atagtgcctc atatctttaa ggtgcggcgc tataggaaaa ttgccacctc
9061 tgtcacggtc tacaggggct tgacagagtc cgccatcacc aacaagtatg aactcccgag
9121 acccgtgcca ctctatgaga taagccacat ggacagcacc tatcagtgct ttagttccat

Fig. 3 (cont.)

9181 gaaggtaaat gtcaacgggg tagaaaacac atttactgac agagacgatg ttaacaccac
9241 agtattcctc caaccagtag aggggcttac ggataacatt caaaggtact ttagccagcc
9301 ggtcatctac gcggaacccg gctggtttcc cggcatatac agagttagga ccactgtcaa
9361 ttgcgagata gtggacatga tagccaggtc tgctgaacca tacaattact ttgtcacgtc
9421 actgggtgac acggtggaag tctcccctt ttgctataac gaatcctcat gcagcacaac
9481 ccccagcaac aaaaatggcc ttagcgtcca agtagttctc aaccacactg tggtcacgta
9541 ctctgacaga ggaaccagtc ccactcccca aaacaggatc tttgtggaaa cgggagcgta
9601 cacgctttcg tgggcctccg agagcaagac cacggccgtg tgtccgctgg cactgtggaa
9661 aaccttcccg cgctccatcc agactaccca cgaggacagc ttccactttg tggccaacga
9721 gatcacggcc accttcacgg ctcctctaac gccagtggcc aactttaccg acacgtactc
9781 ttgtctgacc tcggatatca acaccacgct aaacgccagc aaggccaaac tggcgagcac
9841 tcacgtccct aacgggacgg tccagtactt ccacacaaca ggcggactct atttggtctg
9901 gcagccccatg tccgcgatta acctgactca cgctcagggc gacagcggga accccacgtc
9961 atcgccgccc ccctccgcat cccccatgac cacctctgcc agccgcagaa agagacggtc
10021 agccagtacc gctgctgccg gcggcggggg gtccacggac aacctgtctt acacgcagct
10081 gcagtttgcc tacgacaaac tgcgggatgg cattaatcag gtgttagaag aactctccag
10141 ggcatggtgt cgcgagcagg tcagggacaa cctaatgtgg tacgagctca gtaaaatcaa
10201 ccccaccagc gttatgacag ccatctacgg tcgacctgta tccgccaagt tcgtaggaga
10261 cgccatttcc gtgaccgagt gcattaacgt ggaccagagc tccgtaaaca tccacaagag
10321 cctcagaacc aatagtaagg acgtgtgtta cgcgcgcccc ctggtgacgt ttaagttttt
10381 gaacagttcc aacctattca ccggccagct gggcgcgcgc aatgagataa tactgaccaa
10441 caaccaggtg gaaacctgca aagacacctg cgaacactac ttcatcaccc gcaacgagac
10501 tctggtgtat aaggactacg cgtacctgcg cactataaac accactgaca tatccaccct
10561 gaacactttt atcgccctga atctatcctt tattcaaaac atagacttca aggccatcga
10621 gctgtacagc agtgcagaga aacgactcgc gagtagcgtg tttgacctgg agacgatgtt
10681 cagggagtac aactactaca cacatcgtct cgcgggtttg cgcgaggatc tggacaacac
10741 catagatatg aacaaggagc gcttcgtaag ggacttgtcg gagatagtgg cggacctggg
10801 tggcatcgga aaaacggtgg tgaacgtggc cagcagcgtg gtcactctat gtggctcatt
10861 ggttaccgga ttcataaatt ttattaaaca ccccctaggt ggcatgctga tgatcattat
10921 cgttatagca atcatcctga tcatttttat gctcagtcgc cgcaccaata ccatagccca
10981 ggcgccggtg aagatgatct accccgacgt agatcgcagg gcacctccta gcggcggagc
11041 cccaacacgg gaggaaatca aaaacatcct gctgggaatg caccagctac aacaagagga
11101 gaggcagaag gcggatgatc tgaaaaaaag tacaccctcg gtgtttcagc gtaccgcaaa
11161 cggccttcgt cagcgtctga gaggatataa acctctgact caatcgctag acatcagtcc
11221 ggaaacgggg gagtgacagt ggattcgagg ttattgtttg atgtaaattt aggaaacacg
11281 gcccgcctct gaagcaccac atacagactg cagttatcaa ccctactcgt tgcacacaga
11341 cacaaattac cgtccgcaga tcatggattt tttcaatcca tttatcgacc caactcgcgg
11401 aggcccgaga aacactgtga ggcaacccac gccgtcacag tcgccaactg tcccctcgga
11461 gacaagagta tgcaggctta taccggcctg tttccaaacc ccggggcgac ccggcgtggt

Fig. 3 (cont.)

11521 tgccgtggac accacatttc cacccaccta cttccagggc cccaagcggg gagaagtatt
11581 cgcgggagag actgggtcta tctggaaaac aaggcgcgga caggcacgca atgctcctat
11641 gtcgcacctc atattccacg tatacgacat cgtggagacc acctacacgg ccgaccgctg
11701 cgaggacgtg ccatttagct tccagactga tatcattccc agcggcaccg tcctcaagct
11761 gctcggcaga acactagatg gcgccagtgt ctgcgtgaac gttttcaggc agcgctgcta
11821 cttctacaca ctagcacccc agggggtaaa cctgacccac gtcctccagc aggccctcca
11881 ggctggcttc ggtcgcgcat cctgcggctt ctccaccgag ccggtcagaa aaaaaatctt
11941 gcgcgcgtac gacacacaac aatatgctgt gcaaaaaata accctgtcat ccagtccgat
12001 gatgcgaacg cttagcgacc gcctaacaac ctgtgggtgc gaggtgtttg agtccaatgt
12061 ggacgccatt aggcgcttcg tgctggacca cgggttctcg acattcgggt ggtacgagtg
12121 cagcaatccg gcccccgca cccaggccag agactcttgg acggaactgg agtttgactg
12181 cagctgggag gacctaaagt ttatcccgga gaggacggag tggcccccat actcaatcct
12241 atcctttgat atagaatgta tgggcgagaa gggttttccc aacgcgactc aagacgagga
12301 catgattata caaatctcgt gtgttttaca cacagtcggc aacgataaac cgtacacccg
12361 catgctactg ggcctgggga catgcgaccc ccttcctggg gtggaggtct ttgagtttcc
12421 ttcggagtac gacatgctgg ccgccttcct cagcatgctc cgcgattaca atgtggagtt
12481 tataacgggg tacaacatag caaactttga ccttccatac atcatagccc gggcaactca
12541 ggtgtacgac ttcaagctgc aggacttcac caaaataaaa actgggtccg tgtttgaggt
12601 ccaccaaccc agaggcggtt ccgatggggg caacttcatg aggtcccagt caaaggtcaa
12661 aatatcgggg atcgtcccca tagacatgta ccaggtttgc agggaaaagc tgagtctgtc
12721 agactacaag ctggacacag tggctaagca atgcctcggt cgacaaaaag atgacatctc
12781 atacaaggac ataccccgc tttttaaatc tgggcctgat ggtcgcgcaa aggtgggaaa
12841 ctactgtgtt attgactcgg tcctggttat ggatcttctg ctacggtttc agacccatgt
12901 tgagatctcg gaaatagcca agctggccaa gatccccacc cgtagggtac tgacggacgg
12961 ccaacagatc agggtatttt cctgcctctt ggaggctgct gccacggaag gttacattct
13021 ccccgtccca aaaggagacg cggttagcgg gtatcagggg gccactgtaa taagcccctc
13081 tccgggattc tatgacgacc ccgtactcgt ggtggatttt gccagcttgt accccagtat
13141 catccaagcg cacaacttgt gctactccac actgataccc ggcgattcgc tccacctgca
13201 cccacacctc tccccggacg actacgaaac ctttgtcctc agcggaggtc cggtccactt
13261 tgtaaaaaaa cacaaaaggg agtcccttct tgccaagctt ctgacggtat ggctcgcgaa
13321 gagaaaagaa ataagaaaga ccctggcatc atgcacggac cccgcactga aaactattct
13381 agacaaacaa caactggcca tcaaggttac ctgcaacgcc gtttacggct tcacgggcgt
13441 tgcctctggc atactgcctt gcctaaacat agcggagacc gtgacactac aagggcgaaa
13501 gatgctggag agatctcagg cctttgtaga ggccatctcg ccggaacgcc tagcgggtct
13561 cctgcggagg ccaatagacg tctcacccga cgccccgattc aaggtcatat acggcgacac
13621 tgactctctt ttcatatgct gcatgggttt caacatggac agcgtgtcag acttcgcgga
13681 ggagctagcg tcaatcacca ccaacacgct gtttcgtagc cccatcaagc tggaggctga
13741 aaagatcttc aagtgccttc tgctcctgac taaaaagaga tacgtggggg tactcagtga
13801 cgacaaggtt ctgatgaagg gcgtagacct cattaggaaa acagcctgtc gtttgtcca

Fig. 3 (cont.)

13861 ggaaaagagc agtcaggtcc tggacctcat actgcgggag ccgagcgtca aggccgcggc
13921 caagcttatt tcggggcagg cgacagactg ggtgtacagg gaagggctcc cagaggggtt
13981 cgtcaagata attcaagtgc tcaacgcgag ccaccgggaa ctgtgcgaac gcagcgtacc
14041 agtagacaaa ctgacgttta ccaccgagct aagccgcccg ctggcggact acaagacgca
14101 aaacctcccg cacctgaccg tgtaccaaaa gctacaagct agacaggagg agcttccaca
14161 gatacacgac agaatcccct acgtgttcgt cgacgcccca ggtagcctgc gctccgagct
14221 ggcagagcac cccgagtacg ttaagcagca cggactgcgc gtggcggtgg acctgtactt
14281 cgacaagctg gtacacgcgg tagccaacat catccaatgc ctcttccaga acaacacgtc
14341 ggcaaccgta gctatgttgt ataacttttt agacattccc gtgacttttc ccacgcccta
14401 gtgactcaga cgcggaaaca gcgcctagaa agtttcctct tgcgctatgt gggacaacta
14461 gagtccaacc tggcaagcag tggagcaaga cgccagacag ccgatctcga aaaaaataat
14521 gcagacagag gcaacgttca tcctaggtga ctgggagata acggtgtcta actgccggtt
14581 tacttgcagc agcctaacat gtggcccccct ttacagatct agcggcgact acacgcggct
14641 aagaatcccc ttctctctgg atcgactaat acgtgaccat gccatctttg ggctagtgcc
14701 aaatattgag gatctgttaa cccatgggtc atgcgtcgcc gtagtggccg acgcaaacgc
14761 cacaggcggc aacgcgcgac gcatcgtcgc gcctggcgtg ataaacaatt tttcagaacc
14821 catcggcatt tgggtacgcg gccctccgcc gcaaacgcgc aaggaagcta ttaagttctg
14881 catatttttt gtcagtcccc tgccccccgcg ggagatgacc acatatgtgt tcaagggcgg
14941 cgatttgcct cccggagcag aggaacccga aacactacac tccgccgagg cacccctacc
15001 gtcgcgcgag acgctggtaa ctggacagct gcgatccacc tcgccgcgaa cgtatacggg
15061 atactttcac agtcctgtcc cgctctcttt tttggacctc ctgacattcg agtccattgg
15121 gtgtgacaac gtggaaggtg accccgagca attgacaccc aagtacttga cgttcacgca
15181 gacgggagaa agactttgca aagtaaccgt ttacaacacc cattcgacag catgcaagaa
15241 ggcccgtgtt cgtttcgtct acagaccgac gccgtccgcc cgtcagcttg tcatgggtca
15301 ggcttcaccc ctcataacaa cccctctggg agccagggta ttcgcagtct atccagactg
15361 tgagaaaact atcccacctc aggaaaccac caccctgagg attcaattgc tgttcgagca
15421 gcatggtgcc aacgccggag actgcgcctt tgtcatcatg ggctcgcccc gtgaaacaaa
15481 gtttgtctca tttcccgcag tactccttcc gggcaagcac gaacacctta ttgtattcaa
15541 cccacagaca catcctctga ccattcaacg ggacacaata gtgggcgtgg caatggcttg
15601 ctatatccac cccggtaagg cagccagcca ggcaccatac agcttctacg actgcaagga
15661 agagagctgg cacgtggggc tcttccagat caaacgcgga ccgggagggg tctgtacacc
15721 accttgccac gtagcgatta gggccgaccg ccacgaggaa cccatgcaat cgtgactgtc
15781 cgagcacata tggcgcagga gtcagagcag tgctcccgtg cgtttgcagt gtgcagtagt
15841 aaacgacagc tcgggcgcgg cgagcccgtg tgggattccg tcattcaccc gagccacatc
15901 gtcatctcta atcgagtacc cctcttacta agagaacagc acatatgtct cccttcgtgc
15961 cccagcgtcg gccagatcct ccacagagcc taccccaact ttacatttga caacacgcac
16021 cgcaagcagc aaacggagac ctacactgca ttctacgctt ttggggacca aaataacaag
16081 gttaggatct tgcccactgt tgtggaaagc tcctcgagcg tgctgatttt tagactgcgt
16141 gcatcggtct ctgcgaacat cgccgtggga gggctcaaaa taataatact tgctctcacc

Fig. 3 (cont.)

16201 ctggtgcatg cccaaggagt gtacctgcgt tgcggtaagg acctttctac accacactgc
16261 gcaccggcta ttgttcagcg tgaggtgctg agcagcgggt ttgagccgca gtttaccgta
16321 actggcattc cagtgacatc ctcgaactta aaccaatgct actttctggt aagaaagcca
16381 aaaagccggc tggcaaagcc gtttgcacgc ctgtccgcgg agacgactga ggagtgtcgc
16441 gtcaggtcta tccgccttgg gaagacacac ctgcggatat cggtgactgc gcctgcgcag
16501 gaaacgcccg tctgggggct cgtgaccacg agcttcagcc ttacccccac cgcaccgctg
16561 gcctttgatc gtaacccgta caatcacgag acatttgcct gtaatgccaa gcactacatc
16621 ccagtcatct acagcggacc aaaaattacg ctggccccgc gcggccgcca ggtagtctgg
16681 cacaacaaca gctacacgtc ctccctgcca tgcaaagtca cagccatcgt gtcaaaccac
16741 tgctgtaact gtgacatatt tttagaggac tcggaatggc gcccaaacaa gccagcaccc
16801 ctgaaactgg tgaacacgag tgatcatccc gtcatattgg agccggacac acacattgga
16861 aacgccctct tcatcatcgc acccaaggcc cgaggtttac gcagactgac tcgcttaacc
16921 acaaaaacca ttgaacttcc tggcggggta aagatagaca gcaggaaatt acaaacattc
16981 agaaaaatgt atgttgccac cggacgcagt taggtgtccg gttcccaccc acacatttgt
17041 ctttattgct ttcaaataaa acggtgttct gtcaacctcc tccgggctca ctagtattgt
17101 gttcccatac gcgcctgtcg ccccaggatc aacacttcgt cccctatcca ccctaataca
17161 taacacacac aaagacatag tgactgtaga cagttaatct ttattgtcta gacacgcaaa
17221 gtatattagt gttataagaa attttatgtc acgtcgctct ttacttatcg tggacgtcag
17281 gagtcacgtc tgggatagag tccaaaacac gcaccgcttg acctgcaaac ttttccattg
17341 cactcagaac ataaaacgaa gcaaagtgtc tcacccaata cttaagtccc tgaagcctcc
17401 ctaatagacc gcggtcaaat ttgggtggac tgtagtgcgt cttagtcagc ttattgagct
17461 cttcctgtat gtcccatcct aaggtcttcg tcagaagctc catgacgtcc acgtttatca
17521 ctgattttcc aaactccgtc gttaaaaact taaacaacac ctcgaattca aaaaagccat
17581 cggcgagctt tttaaggcag ctagtctcat taaatcctat taacccgcag tgatcagtat
17641 cgttgatggc tggtagtttc agatgaaaaa tagcagcggg ctctagaata cccttgcaga
17701 tgccggtacg gtaacagagg tcgcggaagc attcatcgat cacccatagc atccaattga
17761 gtctctgaat gagaagatcc ttttcaaact cgggggcgtc cggcaacttg ccccgcgttc
17821 cagataccag cagtgaaccg accagcaaga gagaccacaa cttgaaccag cacatggctg
17881 ctaacgcggc atacactagc cggtggtgcc cgagcgggag ttacgaagtc tcactgaagg
17941 gcggggtcgc gggtcggggc cgctccaaat caggcaacgc cgtatccgaa ctctgagtca
18001 cttttatgta ggtctcaaac atgtaaaaga taccacgttc ttgaaaaacc ctctcttgct
18061 cgccaggctt ggggttcacg cgggcatacg cagccaagct atcatgcgag agaaacacgt
18121 cacacgcaaa gtcatgtaaa acccgggtta aaaatagcct aactggccag gggccagtga
18181 gcgcctcccg gtacaagtcc ccaccccga tgacccaaac cttgtcaatt tgctgtgcta
18241 gctctgggct tctcgccaac ccaagcgcgg catcgagcga actcgccaaa aagtgagcac
18301 cagggggcgg ggtttctaac gtgcgactta gaaccacatt gattctaccc gccaatggtc
18361 gacagcccgc gggaatcgaa agccatgtgc gccgccccat aacaaccatg ttttgttttc
18421 caggggcaca gtcggtagtc agctgtcgaa aacgcctcat gtctccccgc aatgcaggcc
18481 acgggagaca tctgtttttt ccgatcccga gtttggtatc aaccgcaact acacagtaaa

Fig. 3 (cont.)

18541 gtgtaggatc catgccgcga gggtataggt aaacaccacc aaccacacag tgtgctctta
18601 tatactttta atgaaacata agggcagacg aaacagccga acgtttccta atcacgccca
18661 tggaaccata gccacccccca ggcaaaccct gtggaaggat atcaactaga gaggagggtc
18721 cagccttatt atggcaggag acactataag ccccatcgcc cgactgggca ccaacataac
18781 cgccacagta agtggcccta taccgctcag cgcccaagtt gttacagtca cacccaaccg
18841 cggttggctc tacattgtca tcacgtccat cattatgtgt tggttctccc gcttccttgt
18901 accctgcagc ttcatccacg gattcttctg agtcgcgatg cacaggagcg ccatccgcgg
18961 ggccatcttg gtcgcctgga gctgcccccg cggggccatt ttggtcgcct ggagctgccc
19021 ccgcgggccc ctcctcgtcc tggttatccc cacggggaag aatttcctga agctcgatct
19081 cctctactgc acactctggt gatgtcggcc gaggtctata tggaaacact tcaacccgcg
19141 tgtttacagc agcgtatgcc cgccccacgt ggcgcatcat gtggaaaaac gcacccaacc
19201 caaaaacgac aaacaattgg taaaacacga aaaaaacgta gtacgcggct gcagcgacgt
19261 gatctatctc tgggtcatga ccgcccacta tatatagcca aacccacgtc gcagcggcaa
19321 ggccagcggc ccccaatgtc ataatgaaaa taaaaacaat cagttccaga ccctcctggt
19381 aagtcagccg aggcaatagc gtcatttcgc gcaagggtcg ccagaccacg cgcgtgttgt
19441 atacgacgcc acatatctga caggccgtgt ttctagagat agtgagccag gtgcttaaac
19501 aacttctatg gacgttctcg agctctcctg tgcatccaca ggctctaaat ctctcatttc
19561 cgagctcctc gttgcaaatc cagcagacag gaacatcctc atcttccata tcctgagaga
19621 gaacccacaa taaaacatgg cattaacccc tgcaacaagt gaccgtacca gggcacgcgt
19681 ccaggcaacc ggggtccccc tcgttggtct atacaattcc atgactacct actggtaatg
19741 ctacagccac tcactgtaca agccggttaa ctgggaggcg acgctggcgt ggtatcggcc
19801 aactgaaaca caccactcca ctccaaacac ttatgtactt tgtggctcgg ctttattgta
19861 acagccaaga ggggcgtttg tggctcagct ttattgtaac agccaagagg gacgtatgtg
19921 gctatctcac aaaaagtcac cgattcatgt agacaacccg ctcccacgaa ttcggttttt
19981 aaaaagccct cacgtataca gacgggccac taaatacgca catgagcggg catcctgttt
20041 ccgccttgac gcccaccact ctgaccgcac gctaaacatc gccctacctg ctatactgcc
20101 atttccatac gaatggtagg atgcgggcag tagtccacca gtctaaaatc atcaggtgta
20161 aactcttcca tggaagaaac agaccggagt atctccaggc gcggaaaggg acgtggagtg
20221 cgcgtcagct gcagccgtag tggctctata tgcgttttgt agatgtgggc atctcccaac
20281 gtgtgaataa actccccggg tctaagacca gtaacatgag caagcatata agttaagagg
20341 gaatagctgg caatgttaaa aggaactccc aaacccatgt ctcccgacct ctgatacagc
20401 tgacaggaaa gctcaccgtc agctacataa aattgacata acaagtgaca gggcggaagc
20461 gccatcaacg acaagtccgc cgggttccac gcacacataa tgattcttct atcgtgcgga
20521 ttatttttta ttaaatccac aatgtacgac aattggtcaa acccctggcc tgtatagtca
20581 gcatccgcgt ccacgtacgc cgccccaaag tgcctccact ggaaaccgta aacaggtccc
20641 aaatccccct cccttctgtg cgccaggccg cgcccggcca ggaactccct ggagccattt
20701 ttgtcccata tcttgactcc tgttcttgaa agctccctgg agtcagtact ccccttcaga
20761 aaccaaagca gctcttgcac tacgcctcgc caaaacaccc gctttgtggt tagtaaggga
20821 aagtggtccc gcagactata cctggcctgc atgccaaata gagagagggt gcctatgccg

Fig. 3 (cont.)

20881 gtgcggtcga gtcgatcgct gccacggcac aaaatttccc tcaactgcct gagatactga
20941 agttcctcgt ggggcgtctc agccccagtt acctcatgct gaatcgaaca agggtcaacc
21001 tcgggggcca aagccaagac gccaggcttt tgacagaagc gaaacccccct ggcacggaat
21061 aactttttgg cgacatacaa gcttaaaggt acaaacggaa acatgataga tcctggaagt
21121 ttgtgaagcc ctgtgcccgg agagacaccc ctcaactcgc agtgctcgga gacctacatg
21181 tatactcagg ctcttctata aaccctcccc aaaagtttat aaaacaccgt acgtaataca
21241 cattactcac agttcccacg gtgacgccca aacccatgca cacgggcgtg atcgatacca
21301 gaaaacatca caagaacaaa aagtgtgtgt ctgacattca catttatttt tacaagacaa
21361 ttttgtgcag tagagttgtg ccttccgaca ccccgcgccg ttcgctgttc tcctgtaatt
21421 gggagatccc actccttggc aggcacgttt cacgaaacgc tcttgtctcg ctggccttag
21481 acttgtggac ccaacatggg tatcgttaga gatccgtcgc gtaaatgcgc agctggcaaa
21541 gcattcttca gcgagcagtg actggtaatt gctgcatcag cttcttcacc cagtctttcg
21601 atttgtcggc acacacctgg cgaccacgct ttgtcaaaaa tatcacaccc ggcttgctgc
21661 acagttggga ggtggggtac cagctggaca gaagcacctg tggtaatggt cttttctggt
21721 aaccgagaca gcacttgtcc ggtctatgcc aggacgctcc cagcgtgtcc ccagattgca
21781 aacaaagcaa ggcagtcagc acagcgacga gcaggatgcc cttggtgtcc ataactcccc
21841 tcgtgtgtcc tcgtgtaaat gcgaaacggc gatgttaggt caggcgcggt aaacagctca
21901 actcggttca aaacacgtac gtgatgtagt gctggttcta cgacgcctac ctgtaaactc
21961 caggatcctg ggcttttatt acgaaggcca acaccccaaa aaatccacgc ccccgtgacc
22021 gcaggggcgg ttactaacga cggttacagg tccctcccga gccacgcacc tgccatgtaa
22081 cctgcaaggt aaccagacaa acatctagga agcgtaaata tccccaggta ggagaagtat
22141 tgcatatgtc acagactcaa cacacacggg ccgttacgca acggctaggg gcataaccct
22201 ttaccggcgc gaagcgctac gcgcttcgcg agaggtatct ccgtgtgctt ctccatcaga
22261 agacgcgtgc gccgcttcgc aggcgacccg catactttcc gccccgagtg cgttacaaaa
22321 atgactgcct tctggcgaca atacacggtg gacgtccagt accacccgca tatcagctta
22381 tccggtggca atctggcact ggacagggaa ttctcgcaac aatccgaggc catgatggtg
22441 gcaggaccgc tggccgcaca tagctcaatc acggccaccc agaagagcag ccccaaatgt
22501 gcgcgcaaca cccagcacat gctccacata cagttctggc gccacaacga tgatgcgcaa
22561 aggggtgcat taccctaaat cccagcctag ttataaatta ttgaagccca ggcgaccagg
22621 ggtcgccgcg cttttcctcc ccaaacgcga cgataaagac cagcgttgcc aaatgtaact
22681 tatgtataac ccaaaatatt gcgcatcgat aaggtttgcc aaaacacccg aaagtacaca
22741 cacaaaaaaa cagcaacaag acgctcacta gacattcacc ccttccccca cccccgaaaa
22801 caaaacaact tgacacaggg gaaacaccag gggcggcgga ggttgtcaat agtgtccagt
22861 atttcgttag acgcgggttc ttggacccga tgtcccaggt cattaaagtc tcaaatggga
22921 ttaaaggatc atagttccca ggtttaatac tccaagctat cccagaacag gaccccggca
22981 gaaccccgct taacagcacc aaatccactt gcggtcccag aaaaggtcgc cgaggtggca
23041 aggtgactga aaaggtcata gagaggacac cggtcccatt tcccacggtc caaaaatcca
23101 gcgcgcccca ccggctttcc gagaacttcg gcaaagctaa tttgcatgcg ctaatccttt
23161 tatgtgcata aattatgtag atgaggagtc gcgcatgcgc agaaaaattc agagcgcccg

Fig. 3 (cont.)

23221 ggtgcacggg gtcacctcca ggtcacgccg ctaggtggga ccgtgagcga ctcgaaaaat
23281 tataattttt ggccatttca tgggcgccgc catcttgaat ttgctaatcc cccataatcc
23341 tctgccccgc tcccattggt ccgccggccc gtcaatcaaa gttttccgag ccgccattgg
23401 cccatccggc cgaccaatcc cgttcgagct aggcgaccgc gccattccat tggacgcccc
23461 agccgtcaat caaattcgga ggcctcccat tggcccctat ccctagaact cccaagctga
23521 ttggcccaga gcgggaacca atcagcgatt agagttttgt tttgattttt cctatatata
23581 tatatataat cctttaatcc tagcgcagct gagtcatcgc agcccctatt ccagtaggta
23641 tacccagctg ggtaatccag taggtatacc caggtgggtg aacccagctg ggtataccca
23701 gctgcaattc tataattaaa caaggtagaa accaacgggg tcctcaggtg gtatttccgg
23761 aagcattacc aaataaggca acctcagctg ggaataccag cggactaccc ccaactgtat
23821 tcaaccctcc tttgttttcc ggaagtatat ccatttatgg aaatcagctg ggtcactcta
23881 ctgggttatt ctttataata gggcccgatg agtcatgggg ttgggatttt tctactaggt
23941 cgtttcggtg gatgggtgcc aggattatag gggccctgtc cacggggttg ttcggtggcg
24001 gggggggggc tagtgagtca cgggcctgga atctcgcctc tgggtggttt cggtagatgg
24061 gggccgggag gatggggccc cgcccaccgc tggcgcgccc cagaacatgg gtggctaacg
24121 cctacatggg cagcttgtcc tacggttacg cccatttgag acgggttaac caactgttac
24181 accccttcgc cgggaacgct ataaaaacga gggacagcag cccccccctcg cgcactgcgc
24241 gcgcggcggc acgtgggacg gatctcttgg atttacccgt aacgaggagc cccggcagca
24301 ccccaggagc cccggcagca ccccaggagc cccggcagca ccccaggagc cccggcagca
24361 ccccaggagc cccggcagca ccccaggagc cccggcagca ccccaggagc cccggcagca
24421 ccccaggagc cccggcagca ccccaggagc cccggcagca ccccaggagc cccggcagca
24481 ccccaggagc cccggcagca ccccaggagc cccggcagca ccccaggagc cccggcagca
24541 ccccaggagc cccggcagca ccccaggagc cccggcagca ccccaggagc cccggcagca
24601 ccccaggagc cccggcgcgc caccctcccc ggagggggat cccggcgcgc caccctcccc
24661 ggagggggat cccggcgcgc caccctcccc ggagggggat cccggcgcgc caccctcccc
24721 ggagggggat cccggcgcgc caccctcccc ggagggggat cccggcgcgc caccctcccc
24781 ggagggggat cccggcgcgc caccctcccc ggagggggat cccggcgcgc caccctcccc
24841 ggagggggat cccggcgcgc caccctcccc ggagggggat cccggcgcgc caccctcccc
24901 ggcaacaacc tgttgccatg tatggcgatt tgtatcagtc acaagcacac aacccctgct
24961 agtattaatg gtgtttaaaa cgttctacac gtacggcgga ccgcatccgt cgcaagcacg
25021 cgcatataac ccccaaatgc accatgatga gaagcacagc cacgcgtcaa aaaactttaa
25081 aaacatcgtt atccaatatc attaaaaacc acaccgaaat ttacacaggt agcacgtcac
25141 cgtgttagtg tcacccactg tacacaaggc gtgtcgtata tgtagtatag gtatttgatg
25201 aggcggaagc atatcccgct tccagcgaac ggaaataaga atcatccgtt ccagcattta
25261 ttcaaagagg gcacagagga ttcacattgt ttagagagag tttttcttag tcaccattcc
25321 atacttgggc agtattggcc tacgatttgg gcgacgtttc aggctggtct attctccgtc
25381 cacttttccc cggctattct gtcccagcat aggctcttga aataaacaat gtttaccgag
25441 taaaaggttc cactcaccct catttgtcgt tgcacccatc cccccttttgc ttaatcaccc
25501 gaaaactaga ggacacggat ggaaaacata tcgcacgcgg gttgtttgaa agtcaacagc

Fig. 3 (cont.)

25561 tacttgtttt taatgaggac agatttgggc acaggccaga gggtaaagcc ctacgtgtgc
25621 gcgggggggg gggtgtatac gctgcgaaaa cctgcacggt gcataacacc cagggcgtca
25681 cgtcacatat ctctgtgcac ccaagtggtt gttcaaccgt tgttttttgg atgatttttc
25741 cgcaccggct tttttgtggg cgcgcatagg tcggtacgcg ctgtcccccct aagtcccgca
25801 cggtcgttcg ggcccccgtc cggctcgtct ccggatgaac cgtcacgttc tttgtctcca
25861 gaggcgacgt ctccttcaga tgactcgtcc gtgggctcct cgtccgtccc gcccgcgggt
25921 ccgacaagga ccgtcaattc gatgttatct tcgttcgcgg ttggccggcg cggccgtcgg
25981 tatggcagta cggtcacccg ggtgttattt gccgcgtata atgccctcac agtgccactt
26041 acgcggcata tgccgccaaa tgcaaacaca ataaatattt ggtaaaaccc aaagaagcag
26101 agaaaaccga gcacggcccc gggggagaat gttcccgcag gagcagttag gatgaccagg
26161 agcgtccagg tgcacaacgc cacgccgaca agcccagcca ccaccacaga catcagcaga
26221 aacagttcaa aaatttcttg gcgctccatc tccggccaca ggttaaggcg actacgccac
26281 tgcgtgcgcg tgcggtatat aacgcgacac atttgacagg ccgtgtttcg agacactgtt
26341 agccaagtgc ttaaacactg cgggtggacg acatccagct ctccggtaca ggcgcagggg
26401 tgtatgccct cgttccccac ctcttcccta catatccagc agatgggtcc ctctacaccc
26461 tcttctacgt ccttagacgc catctctgca gctggggtgg aagtctgaaa aagggaaagg
26521 ggaggtgagc agagtgccca gttagtctcc gacccgccgt ccgccctact gtcgctatcc
26581 cgccttgaca gatgtctaac gtattcacgg acgccacatg tgtgtctatt ttcctacatc
26641 caggctttcc ctggaaaact gtcacaaccc accctgcttt agctctacat ctgtattttt
26701 gtttacgcac aggatcaacg cttcgtgccc gtccaccccc gcgctctccg cctgtgtttg
26761 gaggttttat gagtggttag ttctaggcag ctccggacaa gttgtccaaa acacggcgcg
26821 ccccgccctt ccttccctcc ggatccgccc acaccggacc tatgaaataa gggacacgcg
26881 tcatcactag ttatgagaga aaaaccacaa cagctttatt ggaaaacacc tgagtggatc
26941 ccccaccccc cgcgtacgac aggcgtttct gtggtgcgct tctgggaaaa acgtttttcc
27001 cccatttctt cctcgacagg tcttctaagg tagataaatc cccccccttt gcgcgtctcc
27061 tagaatggcc taggcgcacg atggcgttgt cgcctcgagc agttgggccg cagtgatatc
27121 ttcaactttc gaccgtctaa gctatggcag gcagccgctg catcagctgc ctaacccagt
27181 ttttggaagg gtctgcgcag atctgacgcc ctcgcttggt cagcaaaata actccgggtt
27241 ttgggcacgc tggggacgtg ggataccact cttttagaat ttggacgggc ggtgggtgct
27301 gctggaaccc gtagcagcag ctattaggcg tgtacgacac gagtgacccc gcgctttctg
27361 tgggcgtcag gtaaaacgtg gcaagcagta cgctaacgca gcataaaacg tggacggggg
27421 ccatctggag gtgccaagtt cgcaacagtc taaagaaaac cgtaaaggct atttggggtt
27481 tctgttctgt cagatgtaac gccgagttcc ttatatgctt acctgattct ggtctcacct
27541 gtttatttat agtggcgtat gctaaccgcc agcttacatg cgggataagt tggcctaact
27601 caccaaaaac gggttgcaga caaaagtgat tgttggggcg cttacttaga aggtgtgagg
27661 gtttctaaga aaccccgcca acgcccggaa accgcatgcg ttccagtcgg tgcggcctgc
27721 gccggcgtcg ctgtggcgcc tttgtgggct ttgagttctg tcattaagcc aggtttccat
27781 tgccacccgg gcgaaaacaa gccgggtagt ttcaggggtc atctggcgat cagtgtacca
27841 tattcccacg acccatcaac accgctgctt gaggcgtgtc tctgtatgtg tcaccggaga

Fig. 3 (cont.)

27901 ctgcatgtat cgtgcatatc tgtattgtgc gcttgcgcgg agacaacata ccgacgacca
27961 agtcaggggt cacctccagt gcacgccgct aggtgggacc gtgggcgagc cgaaataatt
28021 atatattttt ttggcacggt tgtgagcaac gccatcgtga gttggttaat accctctaaa
28081 cgcatagtct ttttttattt gtcaaccaac cagtcaatca cctgtcatcg ccgctcagaa
28141 gcacacgtct tcggccaatg ccgtgttggc gggtttgacc acggttactg ataggtagac
28201 gagtccgaca atcacacacg tccgccagcg atttgcagcg cagctaaaat cgcgtggccg
28261 ggttggtaga agcaaattat ccaatggtcg tgtttgggtt tgttttgggg ttatctacat
28321 attatattcc ttatcccgac tggttgcgga agtattcgca gcttggctac tctgctcgat
28381 taccccgtga ataactgggc ggggggtgac ccaacatagt gattcggtag atttggggga
28441 ctggatgaac attaatgaaa gtttattaat gttcatccgt attgtgtata tgtaatttgg
28501 tttccatatt tggtaggagt atggagtttt cttatggatt attaagggtc agcttgaagg
28561 atgatgttaa tgacataaag gggcgtggct tccaaaaatg ggtggctaac ctgtccaaaa
28621 tatgggaaca ctggagataa aaggggccag cttgagtcag tttagcactg ggactgccca
28681 gtcaccttgg ctgccgcttc acctatggat tttgtgctcg ctgcttgcct tcttgccgct
28741 tctggttttc attggtgccg ccgattgtgg gttgattgcg tcgcttttgg caatataccc
28801 atcctggctt tcggctaggt tttccgtcct actttccca cattggcctg agagctgtag
28861 tacaaaaaac accgcgcggt ctggagctct ccataagccc gcagaacaaa agctgcgatt
28921 tgcccaaaaa ccttgccatg gcaactatac agtcacccct tgcgggttat tgcattggat
28981 tcaatctcca ggccagttgt agcccccttt tatgatatgc gaggatactt aacgtgtctg
29041 aatgtggaat ataatgtgaa aggaaagcag cgcccactgg tgtatcagaa cagtggtgca
29101 ctacctatct gctcattcgt tgtttcggtt ctgtgtttgt ctgattctta gatagtgttg
29161 aggtaattct agaaagcgga ttgagtgtaa atcgggccac tttgccctaa atgtgacaat
29221 ctggatgtgt atcttattgg tgcgttgtga agcattttaa aatgcgtttt agattgtatc
29281 aggctagtgc tgtaatggtg tgtttatttt tccagtgtaa gcaagtcgat ttgaatgaca
29341 taggcgacaa agtgaggtgg catttgtcag aagtttcaaa gtcgtgtaag aacattggac
29401 taaagtggtg tgcggcagct gggagcgctc tttcaatgtt aatgttttaa tgtgtatgtt
29461 gtgttggaag ttccaggcta atatttgatg ttttgctagg ttgactaacg atgttttctt
29521 gtaggtgaaa gcgttgtgta acaatgataa cggtgttttg gctgggtttt tccttgttcg
29581 caccggacac ctccagtgac cagacggcaa ggtttttatc ccagtgtata ttggaaaaac
29641 atgttatact tttgacaatt taacgtgcct agagctcaaa ttaaactaat accataacgt
29701 aatgcaactt acaacataaa taaaggtcaa tgtttaatcc atatttcctg acttgtgtct
29761 tgacttgcgt cgattgggat gggggtgtgg gatgggggtg tgggatgggg gtgtgggatg
29821 ggggtgtggg atgggggtgt gggatggggg tgtgggatgg gggtgtggga tgggggtgtg
29881 ggatgggggt gtgggatggg ggtgtgggat gggggtgtgg gatgggggtg tgggatgggg
29941 gtaaatgaca atgggggtaa atgacaatgg ggcgcttggt gacacatttg ccccaccgtc
30001 gcctgcccgg aaccagcttg gtgatgtgct gtctggctct caggtgcact ttatgcaaag
30061 cagttgaggc gcattagata tataaaactt gggtacacac ccttggtgct gtgcgcgtgc
30121 tatgtgccct ggtgaccgtc cacaatggac gaggacgttt tgcctggaga ggtgttggcc
30181 attgaaggga tattcatggc ctgtggatta aacgaacctg agtacctgta ccatcctttg

Fig. 3 (cont.)

30241 ctcagcccta ttaagctata catcacaggc ttaatgcgag acaaggagtc tttattcgag
30301 gccatgttgg ctaatgtgag atttcacagc accaccggta taaaccagct tgggttgagc
30361 atgctgcagg ttagcggcga tggaaacatg aactgggggc gagccctggc tatactgacc
30421 tttggcagtt ttgtggccca gaagttatcc aacgaacctc acctgcgaga ctttgctttg
30481 gccgttttac ctgtatatgc gtatgaagca atcggacccc agtggtttcg cgctcgcgga
30541 ggctggcgag gcctgaaggc gtattgtaca caggtgctta ccagaagaag ggacggaga
30601 atgacagcgc tattgggaag cattgcatta ttggccacta tattggcagc ggtcgcgatg
30661 agcaggagat aacgcgtaat tcgaggtccc cggaagagta gagggttgca tgttatacaa
30721 acaacataaa cattaaatga acattgttca aaacgtatgt ttattttttt tcaaacaggg
30781 gagtagggta ggaagggtac gtctaatacg taactgttcg ctactgcttg ttcaggagct
30841 cctcgcagaa catcttgcga attttagatt ttggactaga gcgactgctg gcttcaacgc
30901 ggttcgatgt agggttcggc gtaggagcgt ctttctccac cgccgcgcat ggtgtatgcg
30961 tggtctccgg tgcctgttgt tggatgctct gcgtgctgga ggcgggggtg ggttcagcgg
31021 gtggtgcgcc aactaccgcg agtcctgtag agactggcgg gtggctcaca tgtggctgag
31081 caaaaaggat gggcgccgct tgctggaact gaccgtgtgg cgcctgcacg taaatgggtg
31141 ggtgtacgta ggttcctccg tgctccttca ttgtcgggaa ttgacacggg accgctgaat
31201 tggcgtgggg cctgtagtgt ggatctactg cggctgctgc tgcagaggag gacggcggtg
31261 gccctgcgtg ccaaccgttc agtttcatct ctttgagttc agactgtatt tccgctatgt
31321 tctttgacat ggacaagata tccttgtgat acgccggctc ctctcctgga aagaggtgtc
31381 cttcgtcgtc ctctgcgccg cgcttgcgct tccccgtcct atatccaggc agctgtggcg
31441 agtaatacca tggatcgtat gggttcttgt aagcgtagcc gtatggtggc gctgggtttg
31501 aaacatacga aggtaggtga tggtcggtgg ggaacatctg gccccccacac cccattaggc
31561 ctggccctga aagtgtatgt gacattttg ccgctgtggt cttcattcca tcgatgctgc
31621 tttgtagcat gctcaggaag gcggatttgg ggatggatat gatatcctct tgaccagagc
31681 tgttcatggc tggtctgggt ggtgtgacgg cttggatgcc gaccgggaat tggctggcct
31741 ttaaatacgc cggctcaat atgctggcca cacctctgtc agttttcaat aggtcgaggc
31801 ggtcccgtat gaagctggca tctatagctt ttgccattaa ggtctccagg ggactgacga
31861 aatttggtgt ggaaaggtcc tccagcctgc agctacttac gtgctggagg atgtgggcgc
31921 gctccgactt agatactgat gagaatctgg aaaccaccca ctcggcgtcg tgtccgtaca
31981 cggccactgt gccgcgtcgg cgcccccaggg cgcatagtga tacgtgttga aacacgggac
32041 cgctgggagt ctgggataac tcgcggggat gtatagacga taaagacagc cccgggagcc
32101 acgtgtggag tatctccaac agtggttcct tagggagatt tttcacgggg gctctggcca
32161 cgtgggaggt gtccgccagc ctggatgcca gctctaggaa ggctggcgac gtgatggctc
32221 cggtgcagaa aataccgtgg gacacttgaa atagacccag tgtccagccc acttctgtct
32281 ctggtaggtg ttcgattgtt attggaaggg gttctgtgac tgggagataa tccgtcacct
32341 gatccggatc gagatagagc tcttgctcca gcttggggca ggacacaaca tctacaaacc
32401 ctccgacgta caggccctgt gccatgctcg gaaaatacgt gtgtgagacc gagccgctga
32461 gcccggggct taggaggctc atgtggcgct ttttgcaaaa taagaattta aatacattcc
32521 acgcccaaga gctgcgtttt attcatttgg ttctctgcag gatgtacaat ttcggtctaa

Fig. 3 (cont.)

32581 atgtgtacct gttaagggag gctactgcca atgccgggac ctacgacgag gtggtcctgg
32641 gacgcaaggt tcctgcggag gtgtggaagc tcgtgtacga tgggctcgag gagatgggcg
32701 tgtcaagtga gatgctgctg tgtgaggcat accgggacag cctctggatg cacttgaacg
32761 ataaggtggg gctcttgagg ggcctggcga attatctgtt tcaccggcta ggggtcaccc
32821 acgacgttcg catcgccccg gaaaacctgg tggacggaaa ctttttgttt aatctgggaa
32881 gtgtgctccc ctgcaggctg ctccttgcgg cgggctactg cctcgccttt tggggcagcg
32941 atgaacacga acgctgggtg cgcttcttcg cccagaagct tttcatttgc tacctgatag
33001 tctccgggcg tcttatgcca cagaggtctc tgctagtttg ggccagcgaa acgggctatc
33061 ccggtccggt ggaggcagtc tgtcgcgaca tccgctccat gtacggcata cgaacgtatg
33121 cggtctcggg ttatcttccg gctccgtccg aagcgcagct ggcctacctt ggtgcgttta
33181 acaacaacgc ggtttaaacg accgcgagga ccaccggcag gcagccaaga accataaagt
33241 acgctctatc gtagtcatcg ccgccgccaa actgggactt gataatctcc tggagaaggg
33301 tgggtgggga tgggtgtgaa agcaggacgt ccaggcccctc ttctgttgcc aggcggaggg
33361 ctgttctcgc ctggagcagc gccagtggat ctcggaatgt aagctgctgg ttcaggattt
33421 cgaatatctc attaaaccta ctgcctgtca gatttacaaa tggtccgggt tgtttgtggg
33481 acacggtcga tcgcgcctcg agggcggcca gtattatgcc agggaagatg aaggacacgg
33541 gggcgtttgg attagcctgc agtgtgggga ttatgtagtg ctccgatatg aacgaaaata
33601 gctggcccct tttcagcatg ggggcgtttg gatccggtag ggcaccgggc tgaaatttgg
33661 gtcccagcag ggataccagg ttcaagcggc ggtttgggtg ccctcgcgcg acttgcccaa
33721 actccagcaa tccatacgcg aggataaaca cctccagcgc aacaatcccc gctcgcaggt
33781 tccactggta tgcggaaaat ggtggtatat cggacccaaa catggcgctc gtaatggcga
33841 ataccaagtc catggcgggc gctgtccctg gcgcgcccgt acccttgttg tggggaaata
33901 atccagcctt agccatcatt gcgtgaagct tgtggcgctg gaagaaggct gtcggatagc
33961 ggctctcctt attgagaggc gccagcgagg cgcgctcctg gggggtttgag tatgtgaagc
34021 tgaagtcccc aggaccgctt tcctgtttta gctgagtgat tagcaggtct agcttttgag
34081 gcaggtctgc taacaggtca tcgggagtag cgggcagttg cctggatgtc ttttgacaaa
34141 agtacgcgtt gacgaggcaa agcgcggcct gggtgtccgt gagatgcctg gcgtcggcga
34201 aaaagtcagc ggtggtcgag gcgaccgtcg tcagggtgtg agagatgagt ttgagcgatg
34261 tggaattctg aaagttaaca gtccccttta gttctttagg gaagacgcgc cgctgcatgg
34321 cgttgtccgt gaggctgatg aaccacggcc caaaggatgg caaccactga ttctggttca
34381 tgtacagggt gggcatgagc tcgccgcgca ggtccctgtc aacggagaag tgagggtccc
34441 cggggacgat cgccacggtg aagttacggt ggctggcctg cgggggggat gtcactaagg
34501 gaggctcatg ggaacggctt tggggcatgt ctatgttgtc agaccatgtc atgttgccta
34561 tcatctgttt caccgcgtcg atatctgcgt taatgacgcg gacgcgtgag tcatggacct
34621 gaacaagccg gtccagctct agggaaagca ggtgtgcctt tgtctttcgt tctcgatttc
34681 gcacgagttg gctgcgcagt ccaagggcga cccttcttgt ttcttccatg gtgggcttgt
34741 gaataaacag cacgttttcc gggtgtgggg cccagaatct tcccgcctct gtccatcttc
34801 ggttttttgg gtaccttaga taggaccttt ctgatgtcag cattttctct agcagtgaga
34861 aaggcgcaca attttccttc ggtggtgtgc accggcgtgg gaaacgcccc gggtgattca

Fig. 3 (cont.)

34921 gagtatactg tctttagtgt tttctgattc ttaaatatca gcaggggcgt gatagtccac
34981 gcctcggtac ccggaggggc cgagtgagcg atgtaatgga tcgagtcgga gagttggcac
35041 aggccttgag ctcgctgtga cgttctcacg gtgttggttg ggatcagctg gtgactcaga
35101 caagtcttga gctctacaac gtaacatacg ggctgatgcc cacccgatac cagaattacg
35161 cagtcggcaa ttctgtgccc tagagtcacc tcaaagaata atctgtggtg tccaagggga
35221 gggttctggg gccggctact tagaaaccgc catagatcgg gcagggtgga gtacttgagg
35281 agccggcggt aggtggccag gtgggcccgg ttacctgctc ttttgcgtgc tgctggaagc
35341 ctgctcaggg atttcttaac ctcggcctcg gttggacgta ccatggcaga aggcggtttt
35401 ggagcggact cggtggggcg cggcggagaa aaggcctctg tgactagggg aggcaggtgg
35461 gacttgggga gctcggacga cgaatcaagc acctccacaa ccagcacgga tatggacgac
35521 ctccctgagg agaggaaacc actaacggga aagtctgtaa aaacctcgta catatacgac
35581 gtgcccaccg tcccgactag caagccgtgg catttaatgc acgacaactc cctctacgca
35641 acgcctaggt ttccgcccag acctctcata cggcaccctt ccgaaaaagg cagcattttt
35701 gccagtcggt tgtcagcgac tgacgacgac tcgggagact acgcgccaat ggatcgcttc
35761 gccttccaga gccccagggt gtgtggtcgc cctccccttc cgcctccaaa tcacccacct
35821 ccggcaacta ggccggcaga cgcgtcaatg ggggacgtgg gctgggcgga tctgcaggga
35881 ctcaagagga ccccaaaggg atttttaaaa acatctacca aggggggcag tctcaaagcc
35941 cgtggacgcg atgtaggtga ccgtctcagg gacggcggct ttgcctttag tcctaggggc
36001 gtgaaatctg ccatagggca aaacattaaa tcatggttgg ggatcggaga atcatcggcg
36061 actgctgtcc ccgtcaccac gcagcttatg gtaccggtgc acctcattag aacgcctgtg
36121 accgtggact acaggaatgt ttatttgctt tacttagagg gggtaatggg tgtgggcaaa
36181 tcaacgctgg tcaacgccgt gtgcgggatc ttgccccagg agagagtgac aagttttccc
36241 gagcccatgg tgtactggac gagggcattt acagattgtt acaaggaaat ttcccacctg
36301 atgaagtctg gtaaggcggg agacccgctg acgtctgcca aaatatactc atgccaaaac
36361 aagttttcgc tcccccttccg gacgaacgcc accgctatcc tgcgaatgat gcagccctgg
36421 aacgttgggg gtgggtctgg gaggggcact cactggtgcg tctttgatag gcatctcctc
36481 tccccagcag tggtgttccc tctcatgcac ctgaagcacg gccgcctatc ttttgatcac
36541 ttctttcaat tactttccat ctttagagcc acagaaggcg acgtggtcgc cattctcacc
36601 ctctccagcg ccgagtcgtt gcggcgggtc agggcgaggg gaagaaagaa cgacgggacg
36661 gtggagcaaa actacatcag agaattggcg tgggcttatc acgccgtgta ctgttcatgg
36721 atcatgttgc agtacatcac tgtggagcag atggtacaac tatgcgtaca aaccacaaat
36781 attccggaaa tctgcttccg cagcgtgcgc ctggcacaca aggaggaaac tttgaaaaac
36841 cttcacgagc agagcatgct acctatgatc accggtgtac tggatcccgt gagacatcat
36901 cccgtcgtga tcgagctttg cttttgtttc ttcacagagc tgagaaaatt acaatttatc
36961 gtagccgacg cggataagtt ccacgacgac gtatgcggcc tgtggaccga aatctacagg
37021 cagatcctgt ccaatccggc tattaaaccc agggccatca actggccagc attagagagc
37081 cagtctaaag cagttaatca cctagaggag acatgcaggg tctagccttc ttggcggccc
37141 ttgcatgctg gcgatgcata tcgttgacat gtggagccac tggcgcgttg ccgacaacgg
37201 cgacgacaat aacccgctcc gccacgcagc tcatcaatgg gagaaccaac ctctccatag

Fig. 3 (cont.)

37261 aactggaatt caacggcact agttttttc taaattggca aaatctgttg aatgtgatca
37321 cggagccggc cctgacagag ttgtggacct ccgccgaagt cgccgaggac ctcagggtaa
37381 ctctgaaaaa gaggcaaagt cttttttcc ccaacaagac agttgtgatc tctggagacg
37441 gccatcgcta tacgtgcgag gtgccgacgt cgtcgcaaac ttataacatc accaagggct
37501 ttaactatag cgctctgccc gggcaccttg gcggatttgg gatcaacgcg cgtctggtac
37561 tgggtgatat cttcgcatca aaatggtcgc tattcgcgag ggacacccca gagtatcggg
37621 tgttttaccc aatgattgtc atggccgtca agttttccat atccattggc aacaacgagt
37681 ccggcgtagc gctctatgga gtggtgtcgg aagatttcgt ggtcgtcacg ctccacaaca
37741 ggtccaaaga ggctaacgag acggcgtccc atcttctgtt cggtctcccg gattcactgc
37801 catctctgaa gggccatgcc acctatgatg aactcacgtt cgcccgaaac gcaaaatatg
37861 cgctagtggc gatcctgcct aaagattctt accagacact ccttacagag aattacactc
37921 gcatatttct gaacatgacg gagtcgacgc ccctcgagtt cacgcggacg atccagacta
37981 ggatcgtatc aatcgaggcc aggcgcgcct gcgcagctca agaggcggcg ccggacatat
38041 tcttggtgtt gtttcagatg ttggtggcac actttcttgt tgcgcggggc attaccgagc
38101 accgatttgt ggaggtggac tgcgtgtgtc ggcagtatgc ggaactgtat tttctccgcc
38161 gcatctcgcg tctgtgcatg cccacgttca ccactgtcgg gtataaccac accacccttg
38221 gcgctgtggc cgccacacaa atagctcgcg tgtccgccac gaagttggcc agtttgcccc
38281 gctcttccca ggaaacagtg ctggccatgg tccagcttgg cgcccgtgat ggcgccgtcc
38341 cttcctccat tctggagggc attgctatgg tcgtcgaaca tatgtatacc gcctacactt
38401 atgtgtacac actcggcgat actgaagaa aattaatgtt ggacatacac acggtcctca
38461 ccgacagctg cccgcccaaa gactccggag tatcagaaaa gctactgaga acatatttga
38521 tgttcacatc aatgtgtacc aacatagagc tgggcgaaat gatcgcccgc ttttccaaac
38581 cggacagcct taacatctat agggcattct ccccctgctt tctaggacta aggtacgatt
38641 tgcatccagc caagttgcgc gccgaggcgc cgcagtcgtc cgctctgacg cggactgccg
38701 ttgccagagg aacatcggga ttcgcagaat tgctccacgc gctgcacctc gatagcttaa
38761 atttaattcc ggcgattaac tgttcaaaga ttacagccga caagataata gctacggtac
38821 ccttgcctca cgtcacgtat atcatcagtt ccgaagcact ctcgaacgct gttgtctacg
38881 aggtgtcgga gatcttcctc aagagtgcca tgtttatatc tgctatcaaa cccgattgct
38941 ccggctttaa cttttctcag attgataggc acattcccat agtctacaac atcagcacac
39001 caagaagagg ttgccccctt tgtgactctg taatcatgag ctacgatgag agcgatggcc
39061 tgcagtctct catgtatgtc actaatgaaa gggtgcagac caacctcttt ttagataagt
39121 cacctttctt tgataataac aacctacaca ttcattattt gtggctgagg gacaacggga
39181 ccgtagtgga gataaggggc atgtatagaa gacgcgcagc cagtgctttg tttctaattc
39241 tctcttttat tgggttctcg ggggttatct actttcttta cagactgttt tccatccttt
39301 attagacggt caataaagcg tagattttta aaaggtttcc tgtgcattct ttttgtatgg
39361 gcatatactt ggcaagaaat ccgagcacct cagaaagtgg attgccgtca catatcagtt
39421 cgaccacccc tgcacctagc catgcggcgc tttgacggtc tttggggcta cacatcataa
39481 agtacttttc catggcttct ataagcacct tggaacaatc tgggggttgg cgaatgggtt
39541 ccctaaacgg gaaatcctct atggtattca ggcagaagac cgcgtcctcc acccgacgtt

Fig. 3 (cont.)

39601 tgagtctttc tagcagagcg ccgaagaact cccgctcgtg tgttttcgca ggggcaagtt
39661 ctgcgccgta cagcgatgag aaacacgaca cgatgttttc cagccccatg ctgcgcagca
39721 acacgtgctt caggaacagg tgttgtagcc ggttcagttt tagcttgggt agaaaagtta
39781 tcgagttgtt agcacgctcc atgatggtaa cggtgttgaa gtcacagacc gggctttctc
39841 cgagtctcgg ccgcctgagt ccaatcatgt agaacataga cgcggcctcg ttgtctgtgt
39901 taagtgacac gatatcccgt tcgcaaacct gtgcgatgtt gtgtttcagt atagatctgg
39961 tctgaccggc acggggtgtt atggggtgac gcggtaaagg cgactctggg tcaaacacct
40021 ttatgcggtt ggcggcctcg tcgatgacga cacgcttgtt cgcggcgtgt atggggacgc
40081 gacggcatcc cgctggcaga tctataatct taaagttggt ataagactgg tcgctcgtta
40141 tggccagccg gcactccggt agtatctgcg tgtcctcgaa ttcgtggccg cgtacgactg
40201 gcttggagtg caggtaaacg ccaagagatg cggtctcttc gcctacgcac aagtggcttc
40261 ttaacgcgta ggggtgcggt gagagcatga tccgtagcaa cgatagttcc gggtgcctag
40321 ccgcgtagag tggcagggta gacgagtccg gagtcccaaa cttttcgaac aacagtggca
40381 tcgggacttc aggattagag actcccacca tggccgccac cgccggagag gtcaagacgt
40441 gaaacacgcg ctcgcctgtc gacaggcgcg ccgcgccctc tactagacta gccttcacgt
40501 ccggaactcg taacatagct tagaccagcg gacggacgca acgtacgtgg ggatcggctg
40561 gcggtgtctg ctcgttggac gcggccgttc ggtggcgcca gtgcaggcct agtttgcgaa
40621 tggcgtgacg gacaatttgt ggctttagag cggcgaaccg atgacccgtg gtggcgacga
40681 acgaaatgaa gtttgcattg cggcccaact cgtctagcct ggtcttcttg tttcgggcat
40741 agattttcgg gattaggtta cactttttat atcccagtac tgcgcactcg tgtttgcttt
40801 tagtgtgact gattatcttc tttgagaagt caaacaggcc ccgggcggcg gctcgcctaa
40861 tgcaagccac gtcaagcctg agaaacgaac agcattccac cagacactcc aggaaccttt
40921 tgtgtagcgt ctgtatttgg gaacggtttc tgtgctcaag tagggagaat attctatttt
40981 tgtttccgtc gatgcgcgcg tgctggtccg tgagaatggg cgccagctcg tggcgaatct
41041 gttccacaag aggctgcccg tacactttag aaatcgtggc tgtcgcggcc ttaaaccagg
41101 acacgtttag cccatccttg ctggagacca cagatggaaa gtttgtggtc caaaatacgt
41161 tttttcgccc cattctcacc atgtactggt tttccagtcc gtgcaggtcc aacgtggagt
41221 tccaatttgc tatcgataca ggaaatatgt gcctgattgg cagaaagcat ttcagcgtac
41281 ccattgcgaa gagaaagtgc agcatgtccc cactgatgtt gatgtttatt gcggtgcctt
41341 gacacatgtt gtcggaaaaa aacacgctta tggtaaaaga aggttccttt acggagtact
41401 ttcgtataac aaaattgttg gtcaatctgg ggatgtttaa aatagtcttt tgcagggtgt
41461 taggaacgtg gcagcttatc ttagtgttaa tcaccatgtt ggtgttgaat atggtgatct
41521 tgaagttttc caaactgacg tgttttgtgg gttccagcat gtctgacact gtagagctgc
41581 ccagagtccg cgcgtccgtg gccgcgtatc gttggaagca cgcctgcaaa tttcctttca
41641 tggctgctcg ccggtctttc ggcgcgtacc ggattcttga aagcgtcgcc gccaggagac
41701 gcggtgtctc gtgggtgcct aaaaagtttg cgcaggggtg cagtccgctg cacgagtggc
41761 cgatgcagtc tgccactgcc atacacatga cgagtctgta gatggccggt gtgcccggat
41821 acactagata gtaggtacaa tctggggtac tgacgaccac cctgtatggc tttggtccgg
41881 ggtccttgcg ttggattttt acgtgcagac gggacacgag ctggtttaga gccagctgaa

Fig. 3 (cont.)

41941 agcccaccag atcccgtccg ttaaccttga cgtcctggtg cttactctgt ttcgacaggt
42001 tcttcagcac ggtgggcagt cgctctacgt tgtgagcgat ggcacggcgc agcgagacca
42061 gctctccgtg ccaccccac gtggccatga agctgctgat gttaaacttt aaaaaatgta
42121 gctgtgcgtc tggggatgcg ggtggcatta ttgaaaacga gagatgcttc aggctctcca
42181 ggagtgcaaa ataattttga tagattgtgg gttgtagact atggggcaac accgccagaa
42241 acgcatgaaa acactgttcg aactcccaga actccaggta cctgcacact atcctgaaca
42301 tggctttgta acatatggtg cacgttagta gcgcgggaag atacagcgag cgtagctccc
42361 tgaattcgca gggtttatca caatcatcgg taagttccca tgatcccacc gcaggtaggt
42421 agttgtcggt gtctatctgt ccgcgcgtaa acactccacc accgtcaatt attaaacctt
42481 cgccgctgta ccgtcgaccc acttttccca aaagagtccc ttcttgatgt ataaaagggt
42541 ggaggcgttc ccccaggagt agtctgcgta tcgctctgca ggcgaaaaag gtgggctcgg
42601 gctgcatcat cttatcaaga ccttctaagg tcagctctgc ctgcaggtgc gagttggtgg
42661 ccagacagca gaatatttcc agctgtgatt cccaagtcgc ttgataacac gtggtctgcg
42721 gactcgtcgt cagggaggcg ctcggtggca gtagtagggg gccctcgagc gctgccatgg
42781 aggcgacctt ggagcaacga cctttcccgt acctcgccac ggaggccaac ctcctaacgc
42841 agattaagga gtcggctgcc gacggactct tcaagagctt tcagctattg ctcggcaagg
42901 acgccagaga aggcagtgtc cgtttcgaag cgctactggg cgtatatacc aatgtggtgg
42961 agtttgttaa gtttctggag accgccctcg ccgccgcttg cgtcaatacc gagttcaagg
43021 acctgcggag aatgatagat ggaaaaatac agtttaaaat ttcaatgccc actattgccc
43081 acggagacgg gaggaggccc aacaagcaga gacagtatat cgtcatgaag gcttgcaata
43141 agcaccacat cggtgcggag attgagcttg cggccgcaga catcgagctt ctcttcgccg
43201 agaaagagac gcccttggac ttcacagagt acgcgggtgc catcaagacg attacgtcgg
43261 ctttgcagtt tggtatggac gccctagaac gggggttagt ggacacggtt ctcgcagtta
43321 aacttcggca cgctccaccc gtctttattt taaagacgct gggcgatccc gtctactctg
43381 agaggggcct caaaaaggcc gtcaagtctg acatggtatc catgttcaag gcacacctca
43441 tagaacattc attttttcta gataaggccg agctcatgac aagggggaag cagtatgtcc
43501 taaccatgct ctccgacatg ctggccgcgg tgtgcgagga taccgtcttt aagggtgtca
43561 gcacgtacac cacggcctct gggcagcagg tggccggcgt cctggagacg acggacagcg
43621 tcatgagacg gctgatgaac ctgctggggc aagtggaaag tgccatgtcc gggcccgcgg
43681 cctacgccag ctacgttgtc aggggtgcca acctcgtcac cgccgttagc tacggaaggg
43741 cgatgagaaa ctttgaacag tttatggcac gcatagtgga ccatcccaac gctctgccgt
43801 ctgtggaagg tgacaaggcc gctctggcgg acggacacga cgagattcag agaacccgca
43861 tcgccgcctc tctcgtcaag ataggggata agtttgtggc cattgaaagt ttgcagcgca
43921 tgtacaacga gactcagttt ccctgcccac tgaaccggcg catccagtac acctatttct
43981 tccctgttgg ccttcacctt cccgtgcccc gctactcgac atccgtctca gtcaggggcg
44041 tagaatcccc ggccatccag tcgaccgaga cgtgggtggt taataaaaac aacgtgcctc
44101 tttgcttcgg ttaccaaaac gccctcaaaa gcatatgcca ccctcgaatg cacaacccca
44161 cccagtcagc ccaggcacta aaccaagctt ttcccgatcc cgacgggggga catgggtacg
44221 gtctcaggta tgagcagacg ccaaacatga acctattcag aacgttccac cagtattaca

Fig. 3 (cont.)

44281 tggggaaaaa cgtggcattt gttcccgatg tggcccaaaa agcgctcgta accacggagg
44341 atctactgca cccaacctct caccgtctcc tcagattgga ggtccacccc ttctttgatt
44401 tttttgtgca cccctgtcct ggagcgagag gatcgtaccg cgccacccac agaacaatgg
44461 ttggaaatat accacaaccg ctcgctccaa gggagtttca ggaaagtaga ggggcgcagt
44521 tcgacgctgt gacgaatatg acacacgtca tagaccagct aactattgac gtcatacagg
44581 agacggcatt tgaccccgcg tatcccctgt tctgctatgt aatcgaagca atgattcacg
44641 gacaggaaga aaaattcgtg atgaacatgc ccctcattgc cctggtcatt caaacctact
44701 gggtcaactc gggaaaactg gcgtttgtga acagttatca catggttaga ttcatctgta
44761 cgcatatggg gaatggaagc atccctaagg aggcgcacgg ccactaccgg aaaatcttag
44821 gcgagctcat cgcccttgag caggcgcttc tcaagctcgc gggacacgag acggtgggtc
44881 ggacgccgat cacacatctg gtttcggctc tcctcgaccc gcatctgctg cctccctttg
44941 cctaccacga tgtctttacg gatcttatgc agaagtcatc cagacaaccc ataatcaaga
45001 tcggggatca aaactacgac aaccctcaaa atagggcgac attcatcaac ctcaggggtc
45061 gcatggagga cctagtcaat aaccttgtta acatttacca gacaagggtc aatgaggacc
45121 atgacgagag acacgtcctg gacgtggcgc ccctggacga gaatgactac aacccggtcc
45181 tcgagaagct attctactat gttttaatgc cggtgtgcag taacggccac atgtgcggta
45241 tgggggtcga ctatcaaaac gtggccctga cgctgactta caacggcccc gtctttgcgg
45301 acgtcgtgaa cgcacaggat gatattctac tgcacctgga gaacggaacc ttgaaggaca
45361 ttctgcaggc aggcgacata cgcccgacgg tggacatgat cagggtgctg tgcacctcgt
45421 ttctgacgtg ccctttcgtc acccaggccg ctcgcgtgat cacaaagcgg gacccggccc
45481 agagttttgc cacgcacgaa tacgggaagg atgtggcgca gaccgtgctt gttaatggct
45541 ttggtgcgtt cgcggtggcg gaccgctctc gcgaggcggc ggagactatg ttttatccgg
45601 taccctttaa caagctctac gctgacccgt tggtggctgc cacactgcat ccgctcctgg
45661 caaactatgt caccaggctc cccaaccaga gaaacgcggt ggtctttaac gtgccatcca
45721 atctcatggc agaatatgag gaatggcaca agtcgcccgt cgcggcgtat gccgcgtctt
45781 gtcaggccac cccgggcgcc attagcgcca tggtgagcat gcaccaaaaa ctatctgccc
45841 ccagtttcat ttgccaggca aaacaccgca tgcaccctgg ttttgccatg acagtcgtca
45901 ggacggacga ggttctagca gagcacatcc tatactgctc cagggcgtcg acatccatgt
45961 ttgtgggctt gccttcggtg gtacggcgcg aggtacgttc ggacgcggtg acttttgaaa
46021 ttacccacga gatcgcttcc ctgcacaccg cacttggcta ctcatcagtc atcgccccgg
46081 cccacgtggc cgccataact acagacatgg gagtacattg tcaggacctc tttatgattt
46141 tcccagggga cgcgtatcag gaccgccagc tgcatgacta tatcaaaatg aaagcgggcg
46201 tgcaaaccgg ctcaccggga aacagaatgg atcacgtggg atacactgct ggggttcctc
46261 gctgcgagaa cctgcccggt ttgagtcatg gtcagctggc aacctgcgag ataattccca
46321 cgccggtcac atctgacgtt gcctatttcc agacccccag caacccccgg gggcgtgcgg
46381 cgtgcgtggt gtcgtgtgat gcttacagta acgaaagcgc agagcgtttg ctctacgacc
46441 attcaatacc agaccccgcg tacgaatgcc ggtccaccaa caacccgtgg gcttcgcagc
46501 gtggctccct cggcgacgtg ctatacaata tcacctttcg ccagactgcg ctgccgggca
46561 tgtacagtcc ttgtcggcag ttcttccaca aggaagacat tatgcggtac aatagggggt

Fig. 3 (cont.)

46621 tgtacacttt ggttaatgag tattctgcca ggcttgctgg ggccccgcc accagcacta
46681 cagacctcca gtacgtcgtg gtcaacggta cagacgtgtt tttggaccag ccttgccata
46741 tgctgcagga ggcctatccc acgctcgccg ccagccacag agttatgctt gacgagtaca
46801 tgtcaaacaa gcagacacac gccccagtac acatgggcca gtatctcatt gaagaggtgg
46861 cgccgatgaa gagactatta aagctcggaa acaaggtggt gtattagcta acccttctag
46921 cgttggctag tcatggcact cgacaagagt atagtggtta acttcacctc cagactcttc
46981 gctgatgaac tggccgccct tcagtcaaaa atagggagcg tactgccgct cggagattgc
47041 caccgtttac aaaatataca ggcattgggc ctggggtgcg tatgctcacg tgagacatct
47101 ccggactaca tccaaattat gcagtatcta tccaagtgca cactcgctgt cctggaggag
47161 gttcgcccgg acagcctgcg cctaacgcgg atggatccct ctgacaacct tcagataaaa
47221 aacgtatatg ccccctttt tcagtgggac agcaacaccc agctagcagt gctaccccca
47281 ttttttagcc gaaaggattc caccattgtg ctcgaatcca acggatttga cctcgtgttc
47341 cccatggtcg tgccgcagca actggggcac gctattctgc agcagctgtt ggtgtaccac
47401 atctactcca aaatatcggc cggggccccg gatgatgtaa atatggcgga acttgatcta
47461 tataccacca atgtgtcatt tatggggcgc acatatcgtc tggacgtaga caacacggat
47521 ccacgtactg ccctgcgagt gcttgacgat ctgtccatgt acctttgtat cctatcagcc
47581 ttggttccca gggggtgtct ccgtctgctc acggcgctcg tgcggcacga caggcatcct
47641 ctgacagagg tgtttgaggg ggtggtgcca gatgaggtga ccaggataga tctcgaccag
47701 ttgagcgtcc cagatgacat caccaggatg cgcgtcatgt tctcctatct tcagagtctc
47761 agttctatat ttaatcttgg ccccagactg cacgtgtatg cctactcggc agagactttg
47821 gcggcctcct gttggtattc cccacgctaa cgatttgaag cgggggggg gtatggcgtc
47881 atctgatatt ctgtcggttg caaggacgga tgacggctcc gtctgtgaag tctccctgcg
47941 tggaggtagg aaaaaaacta ccgtctacct gccggacact gaaccctggg tggtagagac
48001 cgacgccatc aaagacgcct tcctcagcga cgggatcgtg gatatggctc gaaagcttca
48061 tcgtggtgcc ctgccctcaa attctcacaa cggcttgagg atggtgcttt tttgttattg
48121 ttacttgcaa aattgtgtgt acctagccct gtttctgtgc ccccttaatc cttacttggt
48181 aactccctca agcattgagt ttgccgagcc cgttgtggca cctgaggtgc tcttcccaca
48241 cccggctgag atgtctcgcg gttgcgatga cgcgattttc tgtaaactgc cctataccgt
48301 gcctataatc aacaccacgt ttggacgcat ttacccgaac tctacacgcg agccggacgg
48361 caggcctacg gattactcca tggcccttag aagggctttt gcagttatgg ttaacacgtc
48421 atgtgcagga gtgacattgt gccgcggaga aactcagacc gcatcccgta accacactga
48481 gtgggaaaat ctgctggcta tgttttctgt gattatctat gccttagatc acaactgtca
48541 cccggaagca ctgtctatcg cgagcggcat ctttgacgag cgtgactatg gattattcat
48601 ctctcagccc cggagcgtgc cctcgcctac cccttgcgac gtgtcgtggg aagatatcta
48661 caacggact tacctagctc ggcctggaaa ctgtgacccc tggcccaatc tatccacccc
48721 tcccttgatt ctaaatttta aataaaggtg tgtcactggt tacaccacga ttaaaaacca
48781 ctcactgaga tgtcttttta accgctaagg gattataccg ggatttaaaa ccgcccactg
48841 attttttac gctaagagtt gggtgcttgg ggggttttgc attgctctgt tgtaaactat
48901 atataagtta aaccaaaatt cgcagggaga caaggtgacg gtggtgagaa ctcagttgag

Fig. 3 (cont.)

48961 agtcagagaa tacagtgcta atcagggtag atgagcatga cttccccgtc tccagtcacc
49021 ggaggaatgg tggacggctc cgtcctggtg cgaatggcca ccaagcctcc cgtgattggt
49081 cttataacag tgctcttcct cctagtcata ggcgcctgcg tctactgctg cattcgcgtg
49141 ttcctggcgg ctcgactgtg gcgcgccacc ccactaggca gggccaccgt ggcgtatcag
49201 gtccttcgca ccctgggacc gcaggccggg tcacatgcac cgccgacggt gggcatagct
49261 acccaggagc cctaccgtac aatatacatg ccagattaga acggggtgtg tgctataatg
49321 gatggctatg ggggggctgt agataattga gcgctgtgct tttattgtgg ggatatgggc
49381 ttgtacatgt gtctatcatc ggtagccata aaatgggcca tgacaactgc cacaagtaag
49441 tcgtccgaca tgtgcttttg cttggcgctg tatgactgcc ctccatccct aagcgggacg
49501 cacttgatcg cgcggacctg ttctaccagg taggtcaccg ggtcaaatga tatttgatg
49561 gtgttggaca ccaccgtctg gctggcgctc agggtgccgg agttcagagc gtagatgaat
49621 gtctcaaacg cggaggattt ctcgcctccc aacatgtaaa ttggccactg cagggcgctg
49681 ctcttgtcag tatagtgtag aaaatgtatg gggagcgggc atatttcgtt aaggacggtt
49741 gcaatggcca ccccagaatc ttggctgctg ttgccttcga ccgccgcgtt cacgcgctca
49801 attgtggggt ggagcacagc gatcgcctta atcatcgtgc atgcgcagga cgctatctcg
49861 taagcagctg cgccagtgag gtcgcgcagg aagaaatgct ccatgcccaa tatgaggctt
49921 ctggtgggag tctgagtact cgtgacaacg gcgcccacgc cagtaccgga cgcctccgtg
49981 ttgttcgtat acgcggggtc gatgtaaaca aacagctgtt ttccaaggca cttctgaacc
50041 tgctgggcgg tggtgtctac ccgacacatg tcaaactgtg tcagcgctgc gtcacccacc
50101 acgcggtaaa gcgtagcatt tgacgacgct gctccctcgc ccattagttc ggtgtcgaat
50161 gccccctcca taaagaggtt ggtggtggtt ttgatggatt cgtcgatggt gatgtacgtc
50221 ggaatgtgca gtctgtaaca aggacaggac actagtgcgt cttgcaggtg gaaatcttcg
50281 cggtggtccg cacacacgta actgaccaca ttcagcatct tttcctgggc gttcctgagg
50341 ttaagcagga aactcgtgga gcggtctgac gagttcacgg atgatataaa tataagcttg
50401 gcgtctttct gaagcatgaa acccagaata gccggcagtg catccttttt aataaaattc
50461 gcctcgtcta cgtagagcag gttaaaggtc tgtccccgaa tgctctgcag acacggaaag
50521 acacaaaaga ggggctcata agcggctaac agtaaaggag aggaggcgaa cagtgcgtgg
50581 ctcttgttct tgggaataaa agggggcgtg tgtgccgatc gtatgggtga gccagtggat
50641 cctggacatg tggtgaatga gaaagatttt gaggagtgtg aacaattttt cagtcaaccc
50701 cttagggagc aagtggtcgc gggggtcagg gcactcgacg gcctcggtct cgctgactct
50761 ctatgtcaca aaacagaaag actctgcctg ctgatggacc tggtgggcac ggagtgcttt
50821 gcgagggtgt gccgcctaga caccggtgcg aaatgaagag tgtggcgagt cccttatgtc
50881 agttccacgg cgtgttttgc ctgtaccagt gtcgccagtg cctggcatac cacgtgtgtg
50941 atgggggcgc cgaatgcgtt ctcctgcata cgccggagag cgtcatctgc gaactaacgg
51001 gtaactgcat gctcggcaac attcaagagg gccagttttt agggccggta ccgtatcgga
51061 ctttggataa ccaggttgac agggacgcat atcacgggat gctagcgtgt ctgaaacggg
51121 acattgtgcg gtatttgcag acatggccgg acaccaccgt aatcgtgcag gaaatagccc
51181 tgggggacgg cgtcaccgac accatctcgg ccattataga tgaaacattc ggtgagtgtc
51241 ttcccgtact gggggaggcc caaggcgggt acgccatggt ctgtagcatg tatctgcacg

Fig. 3 (cont.)

51301 ttatcgtctc catctattcg acaaaaacgg tgtacaacag tatgctattt aaatgcacaa
51361 agaataaaaa gtacgactgc attgccaagc gggtgcggac aaaatggatg cgcatgctat
51421 caacgaaaga tacgtaggtc ctcgctgcca ccgtttggcc cacgtggtgc tgcctaggac
51481 ctttctgctg catcacgcca tacccctgga gcccgagatc atcttttcca cctacacccg
51541 gttcagccgg tcgccagggt catcccgccg gttggtggtg tgtgggaaac gtgtcctgcc
51601 aggggaggaa aaccaacttg cgtcttcacc ttctggcttg gcgcttagcc tgcctctgtt
51661 ttcccacgat gggaactttc atccatttga catctcggta ctgcgcattt cctgccctgg
51721 ttctaatctt agtcttactg tcagatttct ctatctatct ctggtggtgg ctatgggggc
51781 gggacggaat aatgcgcgga gtccgaccgt tgacggggta tcgccgccag agggcgccgt
51841 agcccaccct ttggaggaac tgcagaggct ggcgcgtgct acgccggacc cggcactcac
51901 ccgtggaccg ttgcaggtcc tgaccggcct tctccgcgca gggtcagacg gagaccgcgc
51961 cactcaccac atggcgctcg aggctccggg aaccgtgcgt ggagaaagcc tagacccgcc
52021 tgtttcacag aaggggccag cgcgcacacg ccacaggcca ccccccgtgc gactgagctt
52081 caaccccgtc aatgccgatg tacccgctac ctggcgagac gccactaacg tgtactcggg
52141 tgctccctac tatgtgtgtg tttacgaacg cggtggccgt caggaagacg actggctgcc
52201 gataccactg agcttcccag aagagcccgt gcccccgcca ccgggcttag tgttcatgga
52261 cgacttgttc attaacacga agcagtgcga ctttgtggac acgctagagg ccgcctgtcg
52321 cacgcaaggc tacacgttga gacagcgcgt gcctgtcgcc attcctcgcg acgcggaaat
52381 cgcagacgca gttaaatcgc actttttaga ggcgtgccta gtgttacggg ggctggcttc
52441 ggaggctagt gcctggataa gagctgccac gtccccgccc cttggccgcc acgcctgctg
52501 gatggacgtg ttaggattat gggaaagccg cccccacact ctaggtttgg agttacgcgg
52561 cgtaaactgt ggcggcacgg acggtgactg gttagagatt ttaaaacagc ccgatgtgca
52621 aaagacagtc agcgggagtc ttgtggcatg cgtgatcgtc acacccgcat tggaagcctg
52681 gcttgtgtta cctgggggtt ttgctattaa aggccgctat agggcgtcga aggaggatct
52741 ggtgttcatt cgaggccgct atggctagcc ggaggcgcaa acttcggaat ttcctaaaca
52801 aggaatgcat atggactgtt aacccaatgt caggggacca tatcaaggtc tttaacgcct
52861 gcacctctat ctcgccggtg tatgaccctg agctggtaac cagctacgca ctgagcgtgc
52921 ctgcttacaa tgtgtctgtg gctatcttgc tgcataaagt catgggaccg tgtgtggctg
52981 tgggaattaa cggagaaatg atcatgtacg tcgtaagcca gtgtgtttct gtgcggcccg
53041 tcccggggcg cgatggtatg gcgctcatct actttggaca gtttctggag gaagcatccg
53101 gactgagatt tccctacatt gctccgccgc cgtcgcgcga acacgtacct gacctgacca
53161 gacaagaatt agttcatacc tcccaggtgg tgcgccgcgg cgacctgacc aattgcacta
53221 tgggtctcga attcaggaat gtgaaccctt ttgtttggct cgggggcgga tcggtgtggc
53281 tgctgttctt gggcgtggac tacatggcgt tctgtccggg tgtcgacgga atgccgtcgt
53341 tggcaagagt ggccgccctg cttaccaggt gcgaccaccc agactgtgtc cactgccatg
53401 gactccgtgg acacgttaat gtatttcgtg ggtactgttc tgcgcagtcg ccgggtctat
53461 ctaacatctg tccctgtatc aaatcatgtg ggaccgggaa tggagtgact agggtcactg
53521 gaaacagaaa ttttctgggt cttctgttcg atcccattgt ccagagcagg gtaacagctc
53581 tgaagataac tagccaccca acccccacgc acgtcgagaa tgtgctaaca ggagtgctcg

Fig. 3 (cont.)

53641 acgacggcac cttggtgccg tccgtccaag gcaccctggg tcctcttacg aatgtctgac
53701 tacttcagcc gcttgctgat atatgagtgt aaaaaactta aggccctggg cttacgttct
53761 tattgaagca tgttgcgcac atcagcgagc tggaccgtcc tccgggtcgc gtgtagatta
53821 tggttccgtt ctccttcttg atgtttaaat ttttgggggg gaaccaccga caaagcgtct
53881 ttatgatttc cgcgaacacg gagttggcta cgtgcttttg gtgggctacg tacccaatgt
53941 taatgttctc tacggatgcc agtagcatgc tgatgatcgc caccactatc catgtctttc
54001 cgtgtctcct tggtattagg aatacgcttg ccttttgctt aaacgtctgt aaaacactgt
54061 ttggagtttc aaataaaccg aagtactgct taaacaatcc aaacaactgg tgcgtctttt
54121 gtggggcctt gattgaaacc aaaaagaaaa aagtgtgcat tactagctgc tgttggaagg
54181 gctccagcca gtgcaccccg ggaacgtaac agccgttcag aaaggacgaa aggttaacca
54241 gaaaagcctg aagttcgcgg tagacagagc aggcgtgcag ggagtcgtgt gtttttctgg
54301 ccgcctggta ctcgaccagt tgatcggccg tggagacgtg cgcgtcctcg cgcacacacc
54361 gcatctgcaa gtatgttgat agggactcca ataggcgcgg ctttgcgggg acgttgtcct
54421 cggacggtct gggggttccc acgtcgggat ttgctgacgt gggcgtggcg ggatggtgcc
54481 gtgtgcagta tgtttccagg accgaactgt atgagtttat tctgtgcacc acgccaataa
54541 aagggtgcgc catccgtgcc gttttgggac agtgtcgcgt gaatgtcggg gcactcagtt
54601 cccacctctc tccggcgtct ttggcggtct cctgcaggtt ggcggcaagg cgctccctgt
54661 gacggctgag cagcatgttt gctttgagct cgctcgtgtc cgagggtgac ccggaggtga
54721 ccagtaggta cgtcaagggc gtacaacttg ccctggacct tagcgagaac acacctggac
54781 aatttaagtt gatagaaact cccctgaaca gcttcctctt ggtttccaac gtgatgcccg
54841 aggtccagcc aatctgcagt ggccggccgg ccttgcggcc agactttagt aatctccact
54901 tgcctagact ggagaagctc cagagagtcc tcgggcaggg tttcggggcg gcgggtgagg
54961 aaatcgcact ggacccgtct cacgtagaaa cacacgaaaa gggccaggtg ttctacaacc
55021 actatgctac cgaggagtgg acgtgggctt tgactctgaa taaggatgcg ctccttcggg
55081 aggctgtaga tggcctgtgt gaccccggaa cttggaaggg tcttcttcct gacgaccccc
55141 ttccgttgct atggctgctg ttcaacggac ccgcctcttt ttgtcgggcc gactgttgcc
55201 tgtacaagca gcactgcggt tacccgggcc cggtgctact tccaggtcac atgtacgctc
55261 ccaaacggga tcttttgtcg ttcgttaatc atgccctgaa gtacaccaag tttctatacg
55321 gagatttttc cgggacatgg gcggcggctt gccgcccgcc attcgctact tctcggatac
55381 aaagggtagt gagtcagatg aaaatcatag atgcttccga cacttacatt tcccacacct
55441 gcctcttgtg tcacatatat cagcaaaata gcataattgc gggtcagggg acccacgtgg
55501 gtggaatcct actgttgagt ggaaaaggga cccagtatat aacaggcaat gttcagaccc
55561 aaaggtgtcc aactacgggc gactatctaa tcatcccatc gtatgacata ccggcgatca
55621 tcaccatgat caaggagaat ggactcaacc aactctaaaa gagagtttat taagtcggct
55681 ctggaggcca acatcaacag gagggcagct gtatcgctat ttgatcgttt tgggggtagc
55741 agcgccgtgt ttgagaagca gtttcaggac gcacagcatg ccgtcagggc ccacggtgca
55801 ctgaagcgcg aagccgagct cgggactctg gtacgcaagg cgggccagag gtttgaggcg
55861 ctgaaaaggg aacggtcaat tttgcgccag ccgcgcgacc tcccacgggt cgccgacatt
55921 gacgccctgg tcgacgccgt cgcggacctc aaagaagagg tggccgtgcg cctagatgcg

Fig. 3 (cont.)

55981 ctggaagaga atggagagga gaccccccact cactcctctt cggagatcaa ggacacaatc
56041 gtcaggtgga ggcttgacga tttgcccccg gtgtgccctg aaactcccta aggctacccg
56101 gatttcagag agaccctggg cgtccacatg gcagctgaat cagcatatac aggtgtccaa
56161 gactaaaaag gccaccgcgt atcttaaagc gccccgtgaa tgggggcagt gcacgcacca
56221 ggatccagac tggtccaagc gtctgggtcg tggcgccttt ggcataatcg tccctatctc
56281 cgaggatctg tgtgtgaagc agtttgatag ccgccgggag tttttctacg aggcaattgc
56341 caacgacctg atgcaggcca cccgagagag gtaccccatg cattctggtg gatctagact
56401 gctaggattc gtgcagcctt gcataccctg tagatcgatt gtgtatccta gaatgaagtg
56461 caacctgctg cagctggact ggagtcaggt caacctgagt gtcatggcgg cggagttcac
56521 cggcctaatg gcggcggtgt cctttctaaa cagatactgt ggcatggtgc actgcgacgt
56581 tagtccagac aatattttgg ccacaggaga cctaacgccc atgaaccccg ggaggctggt
56641 ccttaccgat ttcggttccg ttgcgctaca ctctgggagc aagtggacta accttgtggt
56701 gacctctaac ctggggttta agcaacactg ctacgacttc agggtgccac ccaaactcat
56761 ttgtaagcat ctctataagc cgtcttgcgt cctcttccag tgttacctat ccagtctcgg
56821 taagatgcac gcgcaggtat tggaccaacc gtaccctatc agccctaaca tgggactgac
56881 catcgacatg tcctcgttgg gctacactct gctgacatgc ctggaactct atctcgatct
56941 gccgctaaac aaccctctga agttcttggg ttcagccacc agagacggac gccccgaacc
57001 catgtactac ttgggcttca tgattcccag ggtggtgatg actcagatcc tgtccgctgt
57061 gtggaccatg acgcttgacc tgggactaga ttgcaccggc aaagcccagg cgattcccat
57121 gcgacaggag caccagctgg cgtttcagaa gcagtgctat ttatataaag ccaaccaaaa
57181 ggcagagtcg ttagcgaact gctccgataa gctaaactgc cccatgttaa agtctctcgt
57241 tagaaagcta ctagagcgag actttttcaa ccatggaggc cacccccaca cccgcggact
57301 tgttttctga agactatctg gttgacaccc tggatgggtt aacagtggat gaccaacagg
57361 ctgtcctcgc aagcttgagc ttttcaaagt ttctaaagca cgccaaggtt cgagactggt
57421 gcgcacaggc caagatccaa cccagcatgc ctgcgctgcg catggcttac aactatttcc
57481 ttttttcaaa agtgggcgag tttattggta gtgaggatgt gtgtaacttt ttcgtggacc
57541 gtgtgtttgg tggtgtcagg ttactggacg tggccagcgt gtacgccgcc tgttcgcaaa
57601 tgaacgcaca tcagcggcac cacatctgct gtctagtgga gagggccact agtagtcaga
57661 gtctgaaccc cgtgtgggac gccctgcgag acggaattat atcttcatcc aagtttcact
57721 gggcagttaa acaacagaac acttcaaaaa agatattcag cccatggcct ataacgaaca
57781 accactttgt cgcgggcccg cttgcctttg ggctgcggtg cgaggaggtg gtgaaaacgt
57841 tgctggccac ccttttgcac ccggacgaga caaattgtct cgattatggg tttatgcaga
57901 gtccgcaaaa tggaatattt ggcgtgtcgc tggatttcgc ggcgaacgtc aaaactgaca
57961 ccgagggtcg tctacagttt gaccctaact gtaaagtgta tgaaataaaa tgcaggttca
58021 agtacacctt tgcgaaaatg gagtgtgacc ccatatacgc cgcgtatcag cggctgtacg
58081 aggcacccgg aaagctggca ctgaaggact tcttctatag catttccaag cctgcggttg
58141 agtacgtggg acttggaaaa ctgcccagtg aatctgatta cttggtggct tatgatcagg
58201 aatgggaggc gtgtcctcgc aaaaagagga aattaacgcc ccttcacaat cttattaggg
58261 agtgtatttt gcacaactcg accacggagt ctgacgtcta cgtacttact gatcctcaag

Fig. 3 (cont.)

58321 atactcgggg tcaaatcagt attaaagccc gcttcaaagc caacctcttc gtgaacgtcc
58381 gtcacagcta cttttatcag gtattgctgc agagttcgat cgtcgaggag tacattggcc
58441 tagatagcgg cattcctcgc ctcggatcac cgaaatacta catcgccacc ggcttcttca
58501 gaaagcgggg ctatcaggat cctgtcaact gtaccatcgg tggcgatgct ttagacccgc
58561 acgtggagat tcctacgctg ctaatcgtaa cccccgtcta ctttccccga ggcgcaaagc
58621 atcgtctgct tcaccaagct gccaactttt ggtcaagaag tgcgaaggac acctttccat
58681 atatcaaatg ggatttctcc tatctatctg caaacgtccc tcacagcccg tagacgtgga
58741 cggggaaccg ctcgacgtag tcgtggacta tgaccccatt cgcgtttcag aaaagggcat
58801 gttgcttgag caatcgcaat ccccatatcc cgcattaaaa aagaagaaaa aaaataaaga
58861 agcaatttat taagcaaaca gtatggtttt ctgtacgtat tttattccgt ggtgggtgaa
58921 aaataacggg ggatggagga agagggatgg gtttataatg ccaatatatc agctaaatga
58981 atatcatttg cgtttcgtcg atttcactgt cactttcatg gtcggactgg tattgggtcc
59041 tcggggcggg cgtcgatatg tccttcactt tggcgcgggc tctggtcttt gctgggaggg
59101 gcggcggttt ctggtgaaca gtcggagttc tatcgaccgt cggcgccgac gtcgccagag
59161 gcatgtatgc cgcactcggc gtacagagtc cccagtcgct ccttataacg cgtataacga
59221 tggctaggat gcacagtata gggatacagg agatattgat agccactatg tagtggagat
59281 tagcctgcac gaacgcgttt tcatacctga tgacaggcag cagtagaatc agataaccca
59341 ccaatactcc cacgtaaaag cctacctgcc gtctcataaa ctttaccagg aaaaattccg
59401 tgtttatgta ccacacgacc gtcaaggcta ggaacatgtt caccgcacca aaaatggcgt
59461 ctgacacgag cacgtaaaag ctgttgccaa cggccatcat ggtgctcaat gaaaacagca
59521 gcatttccaa ggcggttgtt gataggtaca ggttgacgca gaccggtttc caccgagtca
59581 gcagtgactc catcatggta ttatcaggta cgtgctgttc caggagaggt atttcccact
59641 gggcggagtt acatgttatc agtgactgga tgtgggcaaa ggatatgcaa aaatgaatgc
59701 agtagacaaa ggctgccata agtacgtgtt tatatgacag aacatggata aacagttgca
59761 tgctccacat ccttaagatg gcgacataaa gcacgctatg tgatccaagt agcgctatcc
59821 aggattgcat gctcatcatg gtagtggcgt gaacatgctt ggcccgatat acggccaccg
59881 ccgcgagaca gtagtatact atggcaatgc cgtccacgat aaaagtccaa aatatgtaca
59941 ccagcatctc tggtttctct aaaaacaggg tcggggtgag gtgcttcgct gagttgcgca
60001 ccgtgaggtt tagcgcgctg tagtttacca gattgttgaa gtagcagggg aaaccaaggc
60061 cctcgtacgt ggcggccatg ggcacgactg cagagcaaat gtacataatt acagccacaa
60121 acaacagctt gacccaggag gacatgagaa aacggtcgct ctttgaagcg cgcatgtttc
60181 tcggtctttt taactttcgc caggcggcgc tgcggcggga gagccaatct gatgccactg
60241 cctatcgcgg ttgactttta aatacgcgcc ccgggcagaa gccagaggta gtcgactcat
60301 tgactcaatg gcaacgagcg aagaaacggc ggccggttat gtcatcggtg tctactttca
60361 cagcgttcac gtccactgcc gcattattgt ctggcaggtt aattttctac ccctggaccc
60421 aaacgacggg gagactgaat gctactttgt ggtggacacg ctgacgaaag aggcgatgga
60481 gcgcatgccc gaaatccagg aatgcgtccc gtctattact gaacacgccc gtgacctggc
60541 gatctgggag ttggcgctgc gactgcagaa tcagacgatc gtcaaggccg tccggacagc
60601 gtcgcttccg gtggttctaa ttatgactgt gggtcgcata gtgaatgatg tgattccctg

Fig. 3 (cont.)

60661 ccccaacgtc agaacaccca gaccactagc ctgtgcttac ctacactgtg aggcgacggt
60721 gacctttgag gtcccactaa ccgggcccgc ggcgtccacc ggaacgtggc acagctctat
60781 ctatagggaa tgtgcgatct cggctatcga gatatgcttg aagaccagtc gaggcatata
60841 ctcctgccag tcgaacgagg ccccctgaggc caagagggaa aagcgaggtt tagacatatc
60901 agatgtgttt gtctgtctca cgtatgatat ccctatcgca gggcgggtcc tttctctgct
60961 ggtgccccac gcgcccgctt ttcacgtctt atggatcaat gaggacagca agtggaacgg
61021 ggcagccgtc gaatttttca gagccctaca ccataagctg ttcagtgaac gcaatggtat
61081 accccctctg tggttgtacg tgttcccggg agctgtggaa gagggcacag cctttgcgcc
61141 attacttccc gcattccctt gcataccttt gcggtatggg tcgcctacct ctctggacag
61201 ggcgtccgtg cagtgggacc tatttgaacc gcacatcctg acccactttg acgggataaa
61261 gcgaacttct ttggcagata cagtgtttgg gtacgactcc ctggccattt caagggaatg
61321 tgaagatcag tatgtgtggc ccacgcctgt cactgacatt aatattaatt tgtgcacgga
61381 tagtgacact atggccatcg ttagagaacc atccggtctg gtggccgtga atctagaagc
61441 cctgttgcgc accgactccg tattatcgcg ggtctcgtcc attgtctcac tcgatacgct
61501 cttggacctt tccaccccgg agtgccgtag gagcgtggag cttagataca actcactttt
61561 gtcgactgta ttatcatggt ccacctctag ggtcacaaa tgggccgcaa tcgtgaagtg
61621 gaagttattt ttcctcgtcc aagctttgga gcctgaggtg agacctactg tccctgcttg
61681 aagcggagag ggggtggtgc gagttggcag ttgacgggtt tgtgatagct ggagtgctga
61741 ccacggcaca ggacccatta actttcctat gtgtttattt ttagcaatgg tctccagaat
61801 tcaaggatct caaaagggcc tgccagatgg ccgggtttac tctgaagggg gggacttcgg
61861 gggatcttgt attctcatcg catgcgaact tgctctttc aacctcgatg ggatatttcc
61921 tccatgcagg cagtccaagg tcgacagcgg ggacgggggg tgagcctaac ccacgtcaca
61981 tcaccggacc agacactgag ggaaatgggg aacacagaaa ctcccccaac ctctgcggct
62041 ttgttacctg gctgcaaagc ttaaccacat gcattgaacg agccctaaac atgcctcccg
62101 acacttcctg gctgcagctg atagaggaag tgatacccct gtattttcat aggcgaagac
62161 aaacatcatt ctggctcatc cccctatcgc actgtgaagg gatcccagta tgcccccctt
62221 taccatttga ctgcctagca ccaaggctgt ttatagtaac aaagtccgga cccatgtgtt
62281 accgggcagg cttttcgctt cctgtggatg ttaattacct gttctattta gagcagactc
62341 tgaaagctgt ccggcaagtt agcccacagg aacacaaccc ccaagacgca aaggaaatga
62401 ctctacagct agaggcctgg accaggcttt tatctttatt ttgaaaaaag ggaaacaatg
62461 gggggtttga aaagggtgca cattttcaga tattttaaaa cttcattgtt ctccaggtgc
62521 ttggtaaaga tggtatcaca ataaaaaatg tttactgggt ccgcgcaggt ttgtttgtca
62581 tcttcattct ctccactaga ctccagttta aaagactcta gataaatggg tttcattagt
62641 ccccccatgg gggttgaagc gtcgcctatc gccttatgaa gcttaaacat aacgagtggg
62701 gtggccctga aatgatcgtc cacggacagc tcgtaaacaa aggcggccgt ggcagtcaac
62761 gtctctatac cgtgcatgac gaaggccgcg tccatccccg gcgtcctctc atgtgtcttt
62821 ctggcgcgac aaataataga tctcaaaaac gttggtgaca tgtctcgaca gttctcgagc
62881 atcgataaca ggcagcagag ctcggttatg ccgggagatg taggtctaag gaggcacact
62941 cgctcttgga acacgtgagg gtgtaggtct atgtgggtca ccatgtcttc gtgctccacc

Fig. 3 (cont.)

63001 aggcacacca ccgtaaatcc cacaaagttg ggcgaggaca ggcgagattt cacgtgctcc
63061 ctgagacacg ctatatctaa gtggcccatc acggacattt tgggggtatt gcttccaacc
63121 agtgcgttgt ttttcctatg cacttccagg acaaggcggg gcaccacagg gtgggggtat
63181 acgggacagg cctcttctga ctcgcgagtc ttcggggcat gagtactcat tggcactcca
63241 gtcagtctcg ccagggccct ttccagggac attctcgaag ggtggtgtaa ctagacagta
63301 tttctgtccc acgtcggtta tatacacaaa gagtctgcta gtctgatata aataggccgc
63361 gatgtcctgc aagctggagg atacgaagga gtgactaatg agctccatct gaagcaggtc
63421 cgcgatcaca tacgtgaatg gaccaagcag gatggatatg gtgtcctgag aataggtgac
63481 gctgagccgc tgcccttggt tgtcaacaac gggagccagc ttgtaggttt gaaacatctc
63541 gctttcccac aggttcgtga gatctttcat gctttctctc actgggggta tgtaagaaga
63601 gaaaaagcta tttagcacgg cactgcccga tgggatatgg gaagacgtta gctgcagaga
63661 ggggtcctgt aaacgtccca gagattgaaa tgtgttggcg gtcagcagat tcacactccc
63721 gggacccttt gcgtcaccgg gctgttggtg tgacagctgt gtctcaatac attttagcct
63781 cttcatgcag agctccctct ccttttcaag ttgagttatt gtgtcaaatt gttcgtttat
63841 ctggttggtg agacacttga aaacgctgtt ggacacctgg cgcctgagcc cctgagtggt
63901 cgtctcttgg cctgtgccga atagtttatt cttgtctact atgttttggg acacgtcggt
63961 gacaaagtcc tccacgacgt cggtgacacc gctcactgtc ttgttttctg ccagtttcat
64021 gagcaggttg aggagctctc gcttggggtc tgttctctga gaggcctgct ccaggtgggt
64081 catgatgtct ttgtacacat tgttacaggc gcttccaacg agggccttgg tgggggctgt
64141 gttcaggagc tggcaaagtt ttgcgtgctc tgccgtccgg tgacagctca taatgctggt
64201 atacatcctc tgaatggggc tgtcaaagat cacccgccca gccaagatgg cgggcatagt
64261 aatcacctcc acatgaaccc ttttctgctt atacaatccc acgaaagtgt ttttaacaca
64321 gtcatagtct atgctcacct ctgagtagcc cggaatatag agggcgctta aactagacac
64381 caggttgcta atctcctgag tcacgctggt gagtatccgg cctatggttt tttcaccaga
64441 ggccagacgc tggcaatctt tcatcagctg ttcctggata gagttaacca gcttgtggtc
64501 gggtgtgtgc ttgacgactg gtaccattcc taccgtgacc acccagtcta cgtatctctc
64561 atacgagagc tgtgtcttgg cgtagaggac ccggttgatg gcattgagaa gcaggtggtc
64621 taatgtcatg cgcatagtct gggcccagga gtcgaaggtt gaccttctgt aagaccccca
64681 ctgtgcttcc ttttctggcc acctggtttt tgctgaggac tcgtatgtcc tccagtcgga
64741 caagacgtgg tcgtagctac agttggccaa tgcattcttg tacaggtgga taaatagctg
64801 tctgaaaaaa acacccgggt ttcgcaggct gcagtgtaga gtctgacctc tgacataaga
64861 atacttgcct tgcaggatct caaagaggga gatggacagc tcggaagggt gcactgatat
64921 ggacgagccc agccccgggt tcatcctcaa catgacatcg gatgccaaag tcaggagcgt
64981 agtggaacag attgacaggt tgtcaaatat cactacctcg ccccccggaga tgggctggta
65041 tgacctagag ttcgatccac tggaagacga aggccccttt ctgccgtttt cggcatacgt
65101 aataacgggg actgcaggag cggggaaaag caccagcgta tccgccctac atcagaatct
65161 caactgccta attacggggg ctacagtggt agcggcacag aatctttcca gggctttaaa
65221 gtcctactgt cccactatat accacgcctt cggattcaag agcagacaca ttaatatctg
65281 ccagaggaaa gtgcccaagg taactcagtc ctccatcgag caactccaga gatacgagct

Fig. 3 (cont.)

65341 ggctaggtac tggccaactg tcaccgatat tattcgagaa tttatgcgca agaaacaaaa
65401 ggggcagtat agctccctct ctcaaagcgc tttcagactc ctttgccgta tgggtggagc
65461 caatttgtgg acgagtaaca ttatcgtgat agacgaagct ggaaccctct cgtcccatat
65521 tttgacggcc gtggtgttct tctattggtt ttacaacagt tggctggaca ccccgctata
65581 cagaaatggt gccgtgcctt gcatagtctg cgtggggtct cccacccaga cggacgcctt
65641 tcagtcggtc ttcaaccaca cgcagcagag aaacgagata tctgcctgtg ataatgtgct
65701 caccttccta ttgggaaaac gtgaggttgc agattatatt aggctggacg agaattgggc
65761 cctatttata aacaataagc gctgtacgga tccccagttt ggtcacttgc tgaagacctt
65821 agaatataat ctagacatat caccagagtt aatggactat atagataggt ttgtggttcc
65881 gaagagtaag attctggacc cgctcgagta tgcagggtgg acaagactct tcatctcaca
65941 ccaggaggtg aagtcttttc tggcaacgct gcacacctgc ctgtcgagta ataaggatgc
66001 tgtgtccaca aagcttttca cctgcccagt ggtctgtgag gtgtttacag agccatttga
66061 ggagtacaaa cgggcggtag gcctcacaca catgactccc atagaatggg taacaaaaaa
66121 tcttttcagg ctaagtaact actcgcagtt tgctgatcag gacatggctg tggttgggac
66181 ctatatcaca gacgcgtcca cacagatcac cttcgccact aaatttgtca aaaacagcta
66241 tgctaccctt actggaaaga ccaaaaaatg tatatgcggg tttcacgggt cataccaaag
66301 attcaagtcc atcctagacg gggagctatt tatcgaaagt cattcgcacg ataaccccgc
66361 ttatgtgtac agtttcctta gtaccctgct atataatgcc atgtactcat tttacgcgca
66421 cggggtgaag caggggcatg aagaattcct cagggacctc agggaactgc cggtgtctca
66481 agagctgatc tctgagatga gctccgagga cgttctgggg caggaggggg acacagatgc
66541 cttctacctc accgccagcc tcccaccatc cccacccac gcggctcttc caacactggt
66601 ggcctattac tccggggcca aggaactatt ctgcaacagg ctggccctgg cacgccgaca
66661 ctttggtgac gagttcctcc actccgattt ttcaacgttt acggtgaaca tcgtggtgcg
66721 agatggcgtg gactttgtgt ccacttcccc cgggctccac ggtctagtgg catacgcatc
66781 cactatagac acctatataa tccagggata tacgttcctc ccagtgagat tcggccgtcc
66841 aggaggacag cgcctcagcg aggacctgcg cagaaagatg ccctccatag ttgtccagga
66901 ctcatcgggg ttcattgcct gcctggaaaa taacgtcacc aagatgacag agaccctcga
66961 aggtggcgac gtgtttaaca tatgttgtgc aggggactac ggtatcagtt ctaatctggc
67021 tatgaccata gtgaaggcac agggggtttc actaagtagg gtggccatat cgttcggcaa
67081 ccaccgcaat atcagagcca gtctagtgta tgtgggtgta tccagggcca tcgacgctcg
67141 ttacctggta atggacagta atccccttaa gctaatggac cgcggtgacg cccagtcccc
67201 atcctcaaag tacatcatca aagccctatg caaccccaag actactctga tctactgacc
67261 cgtacccctc tcttaggaca ctgatgtgtt tgggaataaa gcatgagact tgacacctat
67321 aatggtctgt attgacacca ttcttttatt tatcagtcca gccacggcca gttatatgca
67381 ccgtttccac acaggggtgg cgtggaggcc aggatgcggg ttgggtcgct gcacctggac
67441 cccgcggtag ttgtgcttcc tgatgaaatc gagtgggcgg aagtactggg agattgggtt
67501 gggaggtgac cctttgtgct cgacggagac acgatcacgc tcacggcgga cgagggctcc
67561 tcgtctgtgt cactccccga ggatataatt atcacggacg ccactgcttt gcggcttaag
67621 tttggttgtc tctggcagcg caccacatcc tcgctaccag aggaggcggt agactgcctt

Fig. 3 (cont.)

67681 ttgcgcttct ggcccacgtc catgagcccg attctctgac tcaatacttc cccttggtct
67741 tctccgtcct cctcggacga gggtggctgg tgggaaaaat ggcgcgcgtc ggtaaacgcg
67801 gcctcattgt tcacgtccgg agagttggaa ctgtcatcgc tatcagagtc cgatgtcagg
67861 tcgacgatcg cggtgggtgc ggcgcgcagg gggcgccacg agggcccttc atcagggtcg
67921 ctgtatggtg aactttgtgt tccaggtaca ctatttctgg aagcaggtga aagtccgtat
67981 gccccggtcc cagtgtatgc cgccatcggt tccaggatag caaccccctc gtcgtctgaa
68041 ggtgagagcc cagcagggga aaatccgtca tcctgactaa cccatcccat ggacgcctcg
68101 gactccgccg tgtccgttga actgcgcacg cggcccgcta ccactgctac cggtttgggc
68161 gtatgggccc gtctggccag aggcctcggg cgcaagtgag ataaaggttg aaaaaagtct
68221 gcagggtacc cctctggctc gtcttcctcc tgaacatcgt cattttcttc ttcatcttca
68281 tcttcctcat cctcgtcata ttcagattcg ccgctcgact gatccgggga tatctgtaga
68341 tccagagggg ttgctggcgg cgatggcgtg tcctcggcga agacgtcgtc tggggcagac
68401 atatctatca ccgtgggtcc agcatagccg cgcggcctgc caaatcctgg aagtgatgaa
68461 agaggtggag gtgggaatat gaacttcacg gggggtcgtc tgcgaggcgc tccttcaatt
68521 ggaagcattc tctcttcatc gtgtgtgcta gacgaggtcc tcacaaacat cgccatggcc
68581 ttgtacgggg ttgaccgcta ggggcggaaa tttacaaagc acacgagtta ttgcctttac
68641 tgctccaaca ggccccagtc cacagtctca cgccggtggc gagtcaaata gtcgttggct
68701 aggttaaagt gattacagcc ctggaaccga ggccatcgcg agtgtcggcc accaagagag
68761 gccagcggag atggatgctg ggccgtaagc accaggtgtt tctgtgcgtt tatgagcgga
68821 gttctgtcaa tggccttgcg cccccacagg agaaaaacgc aatgttctaa ctttgaggat
68881 atgctactga tgatgaaact cgtgaaccaa tcccagccaa gtccctcgtg tgagccggcc
68941 ctccccttct ccaccgtcaa aactgtgttt agtagcaaca caccctggcg agcccagctg
69001 tcgaggcacc cgtgggaagg agtactgaaa ttggggacgg aagcctctag ctctctaaag
69061 atgcttctca aactgggtgg aacctgacat tgcggatcca cactaaacgc caggccagta
69121 gcttggccct tgtggtacgg gtcctggcct aagatcacca ctttaatatc ctctggatcg
69181 cagcagtggg accaccacat cagcttgtcc tgtgggggat acactgtggt ggttagccta
69241 agttcccgaa tctgtctgag cagcgagagc agtttctgtt tcagaaatga tgagaggctc
69301 agaaaggaaa tccacttagg tgccagtaac agatcccggt cgtccacccc ctgactgatg
69361 gatagggtgc ccctaaagac cgtctgttgc aaccatgcgt ccatgttgaa cttattttcc
69421 cttttgacct gcgtgcgctc tccggctgct gcttttagcc cgagtctgac ttccgctaac
69481 agaacctgtc cggttcatgg cctttcccac gcttattata attatgttta cgttgtgaat
69541 agagctatct gcagtggtcg cgttaaaacc tacagtatag gccgtcaaac ttcgttgtaa
69601 ataccacaac aacctcaggt tttcctgcga cgcccaggac cccaatcttc gaacgaccgc
69661 gactaaaaat gacctcagat taaacccatt cacgcatgtt tccacggtaa tgtcgcctgt
69721 tttgcttcgc agcttggcta tacagacccc gttgcagtga ttcggatcgg cgaagtggat
69781 agagtggacc gcaaagaaca acggcagggt agaggctgcc gatgcctgaa ttgcgcaaca
69841 tggtaaggcg acgtatgcgt gagatgtgac caatagggtg gtccacagga cggcaaatag
69901 cgcaaagatc cccatggggc aaatccgggt ttcacccttg tgttgcctgg ttcggtgctc
69961 cccagggagc ccccttccgt aatatctgtt ttatatagtg agggttcacg catgcgcgag

Fig. 3 (cont.)

70021 tcccgactaa tgaggacaat tactgaaatt gaccttttcg cgacacgggg gtgaggtcta
70081 tttcccacga catacttccg cggaaaaata cccacgctcc ttaatttccg tgggaagacg
70141 atgggggaaa tgtggcatta cctgacacgg tttcaatcat actcatcgtc ggagctgtca
70201 cacgtctggc tgagattttc taaaaagtca tccaatgaat catcggaatc atcagcacac
70261 tctagaacta ctccatatgc cggggtgcgc gggggtcccg agtagtgcac gtcgccatcg
70321 ggagacacag atgatgggtt tgaaatgtcc atacgggccg tgtgcacaag ggtcacgtcc
70381 ccatccccaa cacaaggacc tttagatacc ctctcccggc atgtgcgcgt atccgggcaa
70441 gcaagctggt gttctggatt ccaaacgtgc ccagcggtac ccaaaatcgc cagggcgtgt
70501 tttattattt ccacaggaac cggtttctct aattgcatca ccagggtatc caaaagccgg
70561 gcttccacgt tgatccggct taccgacagt tctttccagg gtttcctggt ggggcgcggc
70621 agctgactca aaaaggtcac tgcctctgcc catgggcggg tgggtgacag tccgccatac
70681 tcttccagga cactggccat gcatgactcc aaccgtctca cgtccgaggt aatgtgctct
70741 atgaagatgt ggtagagcca gcagacgttc aaacacgatg aaatcaagct aagctcccgc
70801 cggaactcca catccacaaa ggggtattgc tccggtgtct gtattaggtc tggaatagaa
70861 aactcagaaa aagacactga cccaccaagg agaacctggc gtcttgcaaa gttgatgagc
70921 cccgcagaaa gaatgtgtct cccgtgggac aaagagcttg ggggggcaga gatggcgcta
70981 cagtgggtga tttcttctac cacggtcata cattggtggc acccacaggc ctgttccagt
71041 atcagcataa atctatcttt gcagtcatcc cagatcaaag tcatgtcaga tgctgttgcc
71101 tggcattttg cccgcatgta catttcctgt cccacatatt ttaacatctg taatactgga
71161 agtagattca gtctggtgtt gagccccccc ggggaagcca gcgtatgctt caggaccacc
71221 agggacgcta agaaccccgg gtgtccgcgc tccggaaaca gacctctgag aatacgctcg
71281 gtcttgacga aacccgatgt ggtaccgaat gccacaatct gtgccctcca gctctcacaa
71341 ttttcatctc caatacccgg aattgggata cacacctcca tgttcagtca catgtacgct
71401 agggtctccc cacccaaccc ccataggacc cagctacagc ttatcctcca ctaaatacca
71461 ggcagctacc ggcgactcat taagccccgc ccagaaacca gtagctgggt ggcaatgaca
71521 cgtccccttt aaaaagtcaa ccttactccg caagggggtag tctgttgtga gaatactgtc
71581 caggcagcca caaaaatggc gcaagatgac aaggtaaaga tcgacctttt tattgtatac
71641 tgaacaatgc gtgtttacaa tggtgtaggt gggagcagag ttcgccaagc tctacgtccg
71701 aacagtcggg tgtcagggct cttattaagt gttcggtgta cttgaccaaa gccgcggaac
71761 ctaggttggg tctgtacagg tcgtaccagg caaaaaagga tcgggcggtg cttttcagga
71821 gagttaggga cgtgctgatt atgtggacaa gcttctgctc gtaaatgcac cgctggtaca
71881 tctgaacgac agctgtccaa aaaaaacaaa ggttcagctg cacgttaaaa tctgtatcct
71941 gaaagtcctc gtaaatgaca gtttctacca agaaaaactt ttttaccacg ctggccatcc
72001 actgaaagga gggagcacac gtcccgttgt gcgttgttag gatatcccta acttcggagc
72061 ggagacggcc ggacgctccc acaaaatggg agaggcacca ctctgtgcag tccgcggtct
72121 ggggttctga ttccaggggc gccgtgtggg ggtattggag agtcaaaact ctgggcagtc
72181 ccttaatgag ctctctctca aaacctatgc agccagcgtc cactagtggc agcatgccgt
72241 taataacacc ccttatcttg tcgttgccaa gtttgtacaa ctgctgcagg gaataagcca
72301 aattcgccct agccgcggga accaggtacg gctcgctttg tcggtgctgg accaatatct

Fig. 3 (cont.)

72361 gaatggtctt tgcaaggtat agggtcttct caacgtttag agcgggtacg tggcagtctg
72421 gattgagggt ggcgacggac agggtatcta actcctgaag tatctgatcc caggacgggt
72481 aatgatacct aaacagatgg ttgaacaggt gatctttaag gggccttctc gatgtcattg
72541 taaaaactat gacacgccac tctctcctta gggtaagaag cttcggcggt cctgtgtgga
72601 aagcttcgtc ggcctctcgg acgaactgaa ggcccaactc taccagtgtg tgctccttat
72661 aaatgacgca tacgaaacaa tctacgatcc cagtgaccta aatagagtgg tggaagatgt
72721 gtgcattcgg attatgaaag aatgttccaa gcttggtgcg ctatgtggtc tgtttacaga
72781 cattaacatg tttaaccttt tctgcttttt tcgtgcctct cgaatgagga ccaaaggcgc
72841 ggccgggtac aacgtgccat gcgcagaggc atcccaaggc attattcgga tcctcacgga
72901 gaggatctta ttctgcacag aaaaggcatt tctgacagcc gcatgcagcg gggtgagcct
72961 gcctccagcc atatgtaagc tactacacga aatatacact gaaatgaagg ccaaatgcct
73021 gggggcctgg aggcgactcg tctgcaatcg gaggcccatt atgatattaa cctcttccct
73081 actgaagctc tacaacacgt acgataccgc cgggctgctc tctgagcagt ccagggccct
73141 ctgccttttg gttttccaac cggtctacct tccgaggatt atggcgccgc tggagatcat
73201 gaccaagggt cagctcgccc ctgaaaactt ttacagcatc accggttctg ctgagaaacg
73261 ccggccaatt accaccggca aggtcactgg actgtcctat ccaggaagcg gtctcatgcc
73321 agaatcttta attttgccaa tcctggagcc aggactgttg ccggcttcca tggtagacct
73381 cagcgatgtg ctggcaaaac ccgccgttat tctgagcgcc cctgccctga gccagtttgt
73441 cattagcaaa ccccatccca acatgccgca caccgtcagc atcatcccct ttaacccatc
73501 gggtacagac ccggcgttta ttagtacgtg gcaggccgcg tcacagaata tggtgtacaa
73561 cacatccacc gcgcccttaa aaccggccac cggtagttca cagacggtgt cagtcaaggc
73621 ggttgctcaa ggggccgtga ttactgcgac aacggtgccg caggcaatgc cagcgcgggg
73681 taccggaggg gagttgcctg taatgtcagc gtccactcct gcaagagatc aggtcgctgc
73741 atgttttgtc gcagagaaca ccggagattc tcccgacaac ccgagctctt tcctgacgtc
73801 atgtcaccct tgcgatccga acacggttat agtggcccag caatttcaac caccgcaatg
73861 cgttacgttg ttgcaggtta cctgtgcccc ctcttcgaca ccaccccccg attcaacagt
73921 ccgggccccg gtggtgcagt tgccaacagt agtccctctg ccggccagcg cgttcctccc
73981 ggcgctcgcc caaccagaag cctcgggcga agagcttccg ggcggtcatg acggagacca
74041 aggtgtgccg tgtagagatt caacggcggc ggctacggcg gcagaggcga caacacccaa
74101 acgaaagcag agaagcaaag agaggagctc aaagaagcgt aaggctttga ccgtgccaga
74161 agccgacacc acgccatcga ccacgacacc tggtacctct ttgggatcaa ttaccacccc
74221 ccaggatgtg cacgccacgg atgtcgccac gtctgaggga ccatcggagg cacaaccccc
74281 gctactgtcg ttaccccgc cactggacgt agatcagagt ctattcgccc tgttagacga
74341 agcgggccct gaaacatggg atgtcgggtc gcctctctcc cccactgacg acgcgctgtt
74401 gtccagtatt ctgcaaggac tgtaccagct ggacacgcca ccgcctctgc ggtcaccctc
74461 ccccgcttcc ttcggcccgg agtctccggc ggatataccg tcaccttctg gtggagagta
74521 tacgcaactg caaccggtca gggcgacctc ggcgacgccc gctaacgagg tacaggagtc
74581 cggcacactg taccagctgc accaatggcg taattacttc cgagactgaa gtgttcgcaa
74641 gggcgtctgt gcctgcgtta acttcccagg cagtttattt ttaacagttt ggtgcaaagt

Fig. 3 (cont.)

74701 ggagttaacc tacagattct acttaaaata gctcattttc tcacgaatct ggttgattgt
74761 gactatttgt gaaacaataa tgattaaagg gggtggtatt tcctccgttg tcgactataa
74821 cctggcgtgt aaacgtgtaa ccctgccaaa tgcccagaat gaaggacata cctactaaga
74881 gttccccggg aacggacaat tctgagaaag atgaagctgt cattgaggaa gatctaagcc
74941 tcaacgggca accatttttt acggacaata ctgacggtgg ggaaaacgaa gtctcttgga
75001 caagctcgct gttgtcaacc tacgtaggtt gccagccccc ggccataccg gtctgtgaaa
75061 cggtcattga ccttacagcg ccttcccaaa gtggcgcgcc cggtgacgaa catctgccat
75121 gctcactgaa tgcagaaact aaattccaca tccccgatcc ttcctggacg ctctctcaca
75181 caccaccaag aggaccacac atttcgcaac agcttccaac tcgcagatcc aagaggcgac
75241 tacatagaaa gtttgaagag gaacgcttat gcactaaggc caaacagggc gcaggtcgcc
75301 ccgtgcctgc gtctgtagtt aaggtaggga acatcacccc ccattatggg gaagaactga
75361 caaggggtga cgccgtccca gccgccccta taacaccccc ctccccgcgc gttcaacgcc
75421 cagcacagcc cacacatgtc ctgttttctc ctgtttttgt ctctttaaag gccgaagtat
75481 gtgatcagtc acattctccc acgcgaaagc aaggcagata cggccgcgtg tcatcgaaag
75541 catacacaag acagctgcag caggtataga cgggaaacag gtgtctatct tggccggctg
75601 gttactcaaa tgggaacaat ggcgccacct tgctgtcttt gtaggcatta gaagaaaagg
75661 atgcacaact atgtttccta gcggcgagat tggaggcaca taaggaacag attattttcc
75721 ttcgcgacat gctgatgcga atgtgccagc agccagcgtc gccaacggac gcgccactcc
75781 caccatgttg aagcttggtt gtgccgtcgt ccgggagaac catgccagac tttgtgtggt
75841 aagaaggaat tgttatccgg cagcaatatt aaagggaccc aagttaatcc cttaatcctc
75901 tgggattaat aaccatgagt tccacacaga ttcgcacaga aatccctgtg gcgctcctaa
75961 tcctatgcct ttgtctggtg gcgtgccatg ccaattgtcc cacgtatcgt tcgcatttgg
76021 gattctggca agagggttgg agtggacagg tttatcagga ctggctaggc aggatgaact
76081 gttcctacga gaatatgacg gccctagagg ccgtctccct aaacgggacc agactagcag
76141 ctggatctcc gtcgagtgag tatccaaatg tctccgtatc tgttgaagat acgtctgcct
76201 ctgggtctgg agaagatgca atagatgaat cggggtcggg ggaggaagag cgtcccgtga
76261 cctcccacgt gacttttatg acacaaagcg tccaggccac cacagaactg accgatgcct
76321 taatatcagc cttttcaggt gtattacacg tttcaactgt aatccctcgc aattgggtaa
76381 accgtcggtg tgtagggata aagcgtaacc ttacgttctg tctcatctac aggatcatat
76441 tcatctgggg aaccatccag gaccacgcga attcgcgtat caccggtcgc agaaaacggc
76501 agaaatagtg gtgctagtaa ccgtgtgcca ttttctgcca ccactacaac gactagagga
76561 agagacgcgc actacaatgc agaaatacgg acccatcttt acatactatg ggctgtgggt
76621 ttattgctgg gacttgtcct tatactttac ctgtgcgttc cacgatgccg gcgtaagaaa
76681 ccctacatag tgtaacacaa aaccataaaa gtaaataaac gtgtttattg ttcacatgat
76741 aaagagtggt actctttact ggtttggggg ttgggttgtg gcgtggtggc tggtccgcgg
76801 ttcagtcatc aaccccccgcc cgtgttgtcg aggctcctct tcgtcgcctg ttattggcac
76861 caggaggcgg tttagcggtg cccccgtctg acatgcagac gtcgattcta agcgaaagtc
76921 ccttcagggc atcgtccact tgcttttgtg ttacaacctt gctgaatatt gtcctgaccc
76981 tggcttcgat tttcttagcg gccgccgcac tcagtgcacc cacagtagcg gtaagctgcg

Fig. 3 (cont.)

77041 cttccttctc ggtggccgtc agaggccgat ctctcggatc ggcagtggat cccagtgctt
77101 tccgaagctc ccgattctcc acagtcaatt ggcttatctt tgcggttagg tcttccatcg
77161 taaggtcctt tttgggtctg cccctgggcg cggccatgtc aggtacgcgt agatgtacgt
77221 gttggtgatg ctcacaacaa aagcccaaat ccctccttta tacccagctt taaatacttt
77281 attgaaaaac catagctttc gtcagcgctt gtgcgagtaa tcacatgcca gtctatgcat
77341 ggaccacctc gtccacaaac ttgaaaaaac aaagatatac cagatagaaa aatgtggcca
77401 cgacgactag taacgcgtta atcaaggccc agacgctaga aaagctagaa agggaggggc
77461 taaaactatc cgcggaacaa gcaacgtcat agaatcctgg ggtagtgact gatgtgggac
77521 cgggcgaagg cctggcgctg agcccagccg tactgggact agaacgctct gtagatgatg
77581 cgacacctgt cgagttggcc gtaacccagc agtgacctag tatcgaggcc acaaataaag
77641 ccagggccac cgtggacgct gtcattatga acaaccgccg aggctccaag ccgtctatcc
77701 aacgttccgc gttcgcctct tatatacact ctgcaatgca gtccgactct gcccctctac
77761 ccagggtgga atatgtgttc gaaacaagca aatttagaat gacgtcgaga gcaaatgaag
77821 ccagactcag actgacaaat gagtgtccga tactggtgag accccacgag ccgttcatca
77881 tgcccaccgg aatacacttc acgcgaaccc ctagctgcgc tttcatcctg accggagaga
77941 ccgacaagga tgtattttgc cacacgggcc taatcgacgg aggctaccgc ggggagatac
78001 aggttatttt actcaacaag aggaagtacc ctgtgacgct gtatcgcggg gagctcaaca
78061 tctgcctgtc tgctttcaat tacgtgctac ctccgttgag ggacgtatca ttcttaaccc
78121 cccctatgta tgcaaacgac gccggatttg acgtgatggt gatgcactct atggttatcc
78181 ctcctactac tgaccaaccg ttcatgatat atctaggagt ggagacccca ggcccccctg
78241 aaccccacgt ggctctagca ttggggcgat ccggtctagc atctaggggt atagttatag
78301 acgttagtga gtggggaccg cgaggattgc agctgaagtt ttataactac tcggggcagc
78361 cgtggctggc gcagcccggt agccgcatat gccagattgt gtttgtggaa cgcagacaca
78421 tcctcaaggg cttcaaaaag tgcttgcgcc ataggaagct agctcctggc gtccgtttcc
78481 gggaggctcg agtgcatttt cgcgaggata caaatagcgt ccgaaaacat acccacgaag
78541 acaaccccgt ccacgaaccc aacgtagcca ccgcttccgc tgacattcgt ggaaccaagg
78601 ggctggggtc gtctgggttt tagagccgcc gccaaatgcg gccagtttat tagggcgatt
78661 cgatcccgca acccacagca tccccaaat aaaaaaacga gtgtacacag ccaatgtttt
78721 tattattgtt cgattcatta ctggtaccag agaataaagc caacctatgt cgaacctatc
78781 gcgctttctg tcgtctcttc cagggttgac gaaggccggg gagggattga cgaatgcatc
78841 gcggaaacgg acgggtcttc ggtgggtggc ttgggtaaag ttgcctccgg ctggcgcgta
78901 acggcaggcg tgagaggcaa tacagaagtg ggttccgaca aggagtggct gatctcagag
78961 gcccatatta ccgagtcgtc tgacgccata gcagtcgcca gtttttccat ctccatgagc
79021 gaaacgcatt ccccggccct tttgtttaag agggactgga gcgcactgtc gtccacggta
79081 atctcgccga ccgccaaggc cagcattgtg ttccacacga cgttctgaat agactgcagt
79141 tttttcacct gggttttcac ggtctcctgg cagcccgccg gaattttagc cacgtcaaaa
79201 cgcttcaggt agtctgtgat cttgtttgac tgtacagcca gaaggtaggt ctggtgcagc
79261 gccgtcgtgc caaggttcga ctggacaacg tcacccagac acactccggg ggggaggccc
79321 aaatctatct cttgccgcca gcgctctgga cagccttcca gagggtcacc gaggcgcttg

Fig. 3 (cont.)

79381 taagcgtggt tgccgcgtcc aaaaaggttt ataccgcaac acgtccaggt gtaccatgga
79441 gacgacatac cgccgcgagg cgctgacagt aagggttatt ttttgtacga gtggcgacag
79501 cgccgagacg atcgccgacg tccttacggg ggccccaacg tcagcgtcct tcttttctgt
79561 actccacgac cttttttatt cccagatact cgccccccagg gtaaccctaa aattgtgcct
79621 ccccgcacgg cgtcctggca acggcacaag gtgttcgccc gtgttggtcc tacgtactga
79681 cgcatcagtg gcctcggggt tccttggcgg ccggccactg gaggcgtccg acattaaata
79741 tatgctgctc agcgaccaga ccgcggggtt gttcaagccg ctgttggaga taatcggtgg
79801 cgcgcgcgca ccaccaaatc aggacgcgtg cactttccag agccaggtgg cctggctcag
79861 aacgaaattt gttaccgcat tgagaaaact ttacaagatg actccctcac cctactggat
79921 gctgtctgca tttggcgctc aggaagccca gttcgtcctg accagctcat tctatttttt
79981 tgaacacact gtggtctgta ccacagagac agtttctcac ctgtctagac tgttttcgcc
80041 tcaacaggga cagacgctgg tttccgttac cagccacgag gagctggggc agctatacgg
80101 cacttcccct ttcaggcggc gcgtccccgc gttcgtcgct tatgtaaaag agaaattagc
80161 gagagacagt ctggagacgg aggccatcga ccgcaccata gaccagatca ggggcaaact
80221 catgctgtct aaccaggacc tggtccattt catatatatc tccttttatc agtgcctcaa
80281 caaacgggcg ttcctgcgct actctagaca gacgtcctct tcaagtgctc taagggagct
80341 gggggaagac cctcaattgt gtggcgccct acacggggag tttcgtgacc acgtccagtc
80401 ctactaccac aaaaaaacct acctatccac ttacatagac attcggtacg tgggtggcgt
80461 attaccagac ggctattttg gcgggagtct tgtaggcgag cggtgcgttt attggtgcgg
80521 gcagtcaaag gacacggcca gcctgttggc caccattagc caacaggtgc cgcacctgag
80581 gttgcaaaac gagttcgctg gcatgctaga cgtggccgca ctgcgaggtt ccgatgacgg
80641 tcagtttaaa gagggccttt tctcccacag tcaagcccta cccctgtaca ggtgcgagtt
80701 tctgggcaag cagtttttca caatgcttca ggaagacggc ctagagcgat actgggagca
80761 aagtgtgata tttccaggcg accaggactg ggatatgtta tctgacaaag acctcaccta
80821 ccgaattttt taccatgacc tcagcctatc gctgccaaca ctgaaggaac agctccttgt
80881 ttcaagacac gaatacttca accctcgctt gccagtgtat agatgggtat tagactttga
80941 cctgcccgtc tgccgcgaca ttgacaggac attcgaggag gtgcactctc tctgttgttc
81001 cctgcgtgag gccatactcg acatcattca actccttgga ccagtggatc ctcgaacaca
81061 cccagtatat tttttcaaat cagcctgtcc accggacgag tggcgcggcg aagacgtcgc
81121 cagcaccagc ttctgtcggt gtcatgacaa actgggtatg cgtattatcg tcccgttccc
81181 agaaggagta tgcgtcgttg ggtcggagcc catggtggca ctcactggca ttctaaacag
81241 gacgataaag cttgatccgg agctggtcca cagattcccg tcaatacaaa aaaagggggg
81301 ccctttcgac tgtggcatat acggccgagg acgaagcgtc cggcttcccc actgttacaa
81361 ggtgggctta gtgggggaac tctgccgcct actgaagata ctagtctgtc accccgcccc
81421 caacggcaag gcgcagtacg tgcggcgcgc ctttacgctt cgcgaactgc tccatcactc
81481 cccgggccac agcgccggtc atgtcggccg aatcatctat agcatcatgg atcgcaatga
81541 gaatttttta gaaaacaaga ccattagcta tctgccggcc aaaatacctc acatctttca
81601 gcggatagag accctatccg gtcgttcaat agaggactgg ctacactcgg ccgtttggga
81661 taaagcatac gacactatat gtaaattttt cccagatgaa aaagcacaac agttttctca

Fig. 3 (cont.)

81721 cgttgcattt acgcaacaag gggaaaacat catccagtta agaccccgtc agggaagaca
81781 cttcctctgc atcaaccata atcataaaaa caagtcaaaa acagtccgtg tattccttac
81841 ccttcattcc attagggtga gcgaagtcac ggtaacactt atgagtcagt gttttgccag
81901 caagtgtaac aataatgttc ccacggccca tttttcgttt gtggtaccag tgggactggc
81961 cagttaatcc cactatataa cctggctgcc aggttcccaa aatagcccgc ggcatacggc
82021 tcacttcccc ccacattccc cccgtgcaca atataagaac caaaggacat ggtacaagca
82081 atgatagaca tggacattat gaagggcatc ctagagggta agtcctcgtc tacaacagac
82141 ttttcccatt tctaacgtat cgtgctatct tcgtcgcccg gcggaccatc cccccacccc
82201 tcatttatcg cgtttgatat tacagactct gtgtcctcct ctgagtttga cgaatcgagg
82261 gacgacgaga cggacgcacc gacactggaa gacgagcaat tgtccgaacc cgccgagcct
82321 ccggcagacg agcgcatccg tggtacccag tcggcccagg gaatcccacc ccccctgggc
82381 cgcatcccaa aaaaatctca aggtcgttct caactgcgca gtgagatcca gttttgctcc
82441 ccactgtctc gacccaggtc cccctcacca gtaaacaggt acggtaaaaa aatcaagttt
82501 ggaaccgccg gtcaaaacac acgtcctccc cctgaaaagc gtcctcggcg cagaccacgc
82561 gaccgcctac aatacggcag aacaacacgg ggcggacagt gtcgcgctgc accgaagcga
82621 gcgacccgcc gtccgcaggt caattgccag cggcaggatg acgacgtcag acagggtgtg
82681 tctgacgccg taaagaaact cagactccct gcgagcatga taattgacgg tgagagcccc
82741 cgcttcgacg actcgatcat cccccgccac catggcgcat gtttcaatgt cttcattccc
82801 gccccaccat cccacgtccc ggaggtgttt acggacaggg atatcaccgc tctcataaga
82861 gcagggggca aagacgacga actcataaac aaaaaaatca gcgcaaaaaa gattgaccac
82921 ctccacagac agatgctgtc ttttgtgacc agccgccata atcaagcgta ctgggtgagt
82981 tgccgtcgag aaaccgcagc cgcccggaggc ctgcaaacgc ttggggcttt cgtggaggaa
83041 caaatgacgt gggcccagac ggttgtgcgc cacgggggt ggtttgatga gaaggacata
83101 gatataattt tggacaccgc aatatttgtc tgcaatgcgt ttgttaccag atttagatta
83161 cttcatcttt cctgcgtttt tgacaagcag agcgagctag cactgatcaa acaggtggca
83221 tatttggtag cgatgggaaa ccgcttagta gaggcatgta accttcttgg cgaggtcaag
83281 cttaacttca ggggagggct gctcttggcc tttgtcctaa ctatcccagg catgcagagt
83341 cgcagaagta tttctgcgcg cggacaggag ctgtttagaa cacttctgga atactacagg
83401 ccaggggatg tgatggggct actaaacgtg atagtaatgg aacatcacag cttgtgcaga
83461 aacagtgaat gtgcagcggc aacccgggcc gcaatggggt cggccaaatt taacaagggt
83521 ttattctttt atccactttc ttaaggattg ccaaacccca tggcagagtg tctcccgtat
83581 tccatgtaac tcacgtagcc tttctctaat aaacaagcta cctgcaaact atacacaaat
83641 gaaatgagtc aggcgtggtc tcttctctac cgtgaatcgc accttaaaca caacaccaga
83701 ccgccaccag gtggcaccca acatccatta tggaaaaacc ccgcgccacc ttccgccacg
83761 tggagccaac aaacaagaca cacccgccaa tgttttggtc tctttattga tatgatatac
83821 tccctcccat aacaatacgg tgtaggcatt ttgtattatt tattgcatgg catcccataa
83881 cggcttcggc attatttcga gtacgacgca ggcgtctgag aaattactgc acctcgccgc
83941 aaagtctcgc ggggacgggg cgtggggctc taacttgcca accgccaccg gtttccccag
84001 ccacagcttc accaaaggac acgtcacgtg agagggtgct ggtaacggtg aatttgccaa

Fig. 3 (cont.)

84061 ccccaccaga aatgtattcg ggttaaatat cctcgtcggt tttccctggg gcagcaagag
84121 ggggccggag tcaggcggaa cggtatttcc aataaagtgc acgggcccgt tatgataaca
84181 tacgcaaaat atgccattac aagagctagt cagcagaatg ccttttgcac atgcgtccag
84241 cgtatcgcat agctcccgct tggctatctc gcaggccagg tttggcacat tgggtagcca
84301 tacctggccc ggagacccca ctgcacagta atgaactgcg gggtccctac gcaaggccga
84361 tgagattcga cagcccgact ggcttgtcgt cagtaactca tgaacctgtt cgccattata
84421 atacatcctg ataaacaacc gaccccagtc aatgacggcc tcctgaccct ctgccgtcgt
84481 acaagatggc acgggcgtta caatctcgcc tggcaagcac tgccccgggg aaaaaaatcc
84541 ctcttgcaag agacgtgcca tattgttaaa atcgtggacg gctccggcca cgactccaca
84601 ttccacgcat tgttcttcct ccggtttacg tactctaaag accagaaaat ggtgtccatc
84661 ctgagaaatg cctttgccaa tctcttgtaa accccgcgtc ctgcgtagcg cggcaagcat
84721 tcgcctgcgc cccctggtgc ctttaaacga ggcgtccacg ggcatgttac ccctttcgcg
84781 gatatacaca acacccaatt ccccgtctct gcgccattca aaacaggggt ccgcgagggg
84841 cgtaactggt atacggaagc gggtgcgctc ttcgtcttcc cactctactc cgggaaattt
84901 tccactgttg acttgacata ctatccaatc cttgattgac gctttcccct cactggcacc
84961 ggtagatatt cttagttgtc gtgtccggct ccactccgtt atcgcagcca ccacagcctg
85021 ccgtgtaata tcgcctgcgg ctgcagaacc cccggtcccg gagggtcctt ctcccggtga
85081 ctccgacctg gatggttcat cgcaaggagc cccggagcca gatgttcccg gtgacccttg
85141 tgacaaacaa ggttttttgg gtatcgcccc aggcgcccca aaagggttcg gtctttggcc
85201 tgggtccatt gtcccgcaac cagactagct cgcgccgcaa tgtccagtgg taagcacagc
85261 tatgccgggg agccaccggc catcagatat agagaggcga caggctctct atatatcacg
85321 gctaggtggc tgacatatta gtgggcctag ccgcagaatt gcctgggtag tcaaaaacca
85381 gcgtttctca aattaaccga aactacattt ttctatttta agtacgggat acaaagcagg
85441 gtctgaggca atctgccgcc ctccaccccc acccaccata cccaaaaaag atatgtcaga
85501 aagagcactc tacctattaa ctcgtggaga aacatcatac aaaatctgta cattattttt
85561 aatactttaa tttgtgcagg tttcttcacc ccacacctgc tttttgtctg gtacaaaaaa
85621 ccactgcagg gtcccgccta tagccaactc ctaagcgggt tttttgctaa agcacttttt
85681 tagactgtcc cagaaaccac atagcttcct tttcactcat ttgaaaaaca gccccgccca
85741 actgcctgga gaattttcca ccccctctac catttcgcgc ctttaccgct ggtgcgaaat
85801 ctagccatcc tatcaccgcg gatccgctgg accaatatac cacgcccact tttcgtaatc
85861 agcaaccctc tacgcctaca cccctatgac tgaatataac ccccaacaag gctatgaaat
85921 catgaatggt aactgtctgg acaccaatct tccgcggggt ggcggcagtg cgacgcaagt
85981 atccacaata aatggtgcaa taattggcga aatgtcgtgt ctggtttatt tggactacaa
86041 gattacatcc ggttttataa ttcacatata tgatcaatgt agactatccc aaatggagcc
86101 tataaaaatt ttaacagtca agggtacatt ttggaaattt tctgtagatg ccggggatgc
86161 gccgaaaaat accgtcccgc acgtcactgg gttgacgctc agcggtgtct gtgggattgc
86221 ggctgtggtt gccaggtatc gcgcggtgtt gaacagctgc tgcggaactc tggggctaaa
86281 gcttcggagg atgcgttcat agcgggaatt tggattacca aaccaccagc cttccacttg
86341 agtggcgttt ctggagtata ttccagacat cgagcaaaat attgggaatc cgtggccaag

Fig. 3 (cont.)

86401 gccttcaaaa actcggttca aaatctccat ttgctcgggt gaggggactg taagacgcgg
86461 tatgcgaagc agttctggta cgaaactctg acataggtgc cccaacgtat ccccaacagg
86521 ccagctacat aacattgcct cgcccgcgtc accttcgcgt ctcagagttc cacgaaggtt
86581 cccatacaca aagatttcca caacaaaaga cacccgctga ctatcagggg gatcaaaaaa
86641 catctttgaa ggtggctttt cgggaccgga gtggctaacg ggcgtacgcc gcccgtgcgg
86701 ggacctggac ctcgggcgcc gcctatccgt ggcctgtctg gttgaggagc tcggttcctc
86761 ctgcagctca gacaaaatgt tacccaaccc ttcttcccac gtacatatat cctctccttg
86821 aaggttcgag agcgtaagag ggagacccaa aggcggcggc actaaagatt gttctggtcc
86881 ataacccccc actgcatatc tatctccagc atatgtacta acaagtggaa ctctgggcct
86941 ttcgccacta cccgggcaca cacactcccg ccgctccagc tctgtcggta aatgcgaaac
87001 ctcggggttc acagcgggct ccggtgcaga ataaagcacc gtaggttgga aaacgcgcgg
87061 cccactgaca ggtaggggcg tggatgctac agtggtagat ggggtatcgg aatccccagt
87121 gaggtcaata atctccactt cgagggcacc agaactagtt gtcacgcgtc tgtatccagt
87181 cgccatgttg tccccctggc agacgtacgg tattccagac gaggatggct cctgtcgctc
87241 tgccacctct ggggtgggtg gtgcgccggc ggagggcgtg gccgacgcgc caccctgcgt
87301 gtgggaaaga ccctggtttg gagcgcctcc actagaccac ggaatccaaa gcggtgtgcg
87361 aacttccggc accacggcgt gaccaactgg tgggtgccaa acaggcgcgc gtatgggtcg
87421 cgtagctggc ggttctgcca atggactcca attgtaacat gatggtttcg catacccggg
87481 cgcggggggcg ctgggcggtt gaggttcgaa gggatacacc cgctcactcg cagcaccctg
87541 aggagcccgg ccttctgtag atgccccgca agcgccttcg gcaccggttt cccggcgggg
87601 aagccacgcg cgagcacatt ggccgctttg ggggagcaat ccctgtggcg ccagaggtgc
87661 accctggctg aactcaccga caaatgttcc cgcttgggcg tgcggcggaa tccaactggg
87721 ggcagcagga ttcagctggc tgctaggaat ccccgtatat gtccaacggg gggaaagggg
87781 atcaaattgg cccgtggttg gcggatgcac tttctccggg agaccagacg cgccctgagg
87841 ccaccatccc gtgacaggaa gatctcccca tggaaaacac gcaggtatcc acggggacgt
87901 agatggcagc ctagacccat cgcgcatggg aggggctagt tgccccgtat cccccggcgt
87961 ctgtgcgacg ccggagaccc ctgacacagt accggcaagc cgtgtttcgt gctgcggctt
88021 gggcggcgcc gtgcccggta ggcctgcacc agatgagtga gggtctgaag ggccggtcag
88081 cgttgatgga gcaggcggat ctccgggaac ccgccacgta aaggacgagg cctgcgtaac
88141 ttgtcgcgtc ccagaggacc ccatacctga ggtagatgcg ccctcattca ctggtatcca
88201 cacggagcag gcagccttct gttcagtcgt tatatcgcca acattgtaat agcggttcga
88261 tttccgaggg cgacccctca gccccgatgg cgccttaggg ggagcaggtg ctgcagcccc
88321 tgcctcctcg tagctttgtt ctctaagtaa aaggcacgag agttaacgtg gttagggtac
88381 ctaaagtatt tcccgccgac accaacgcat caaacctcac acccccttcc ccgagttaca
88441 tacctagtgt cactgcgtcg cgtagccgtg gtttgcattg ggggggacaa cagacactga
88501 ataaatcgct gcagtttttc aggaccatac gcggccccat agcaatacgt acagtttta
88561 aacggcgttc gcaccaactg ccatactacg tagctaccac caaatgtgtc gctgtaccgt
88621 aaatcgttcc gcacgacggc cctcctggtt ccacgcaaca gtctcccaaa acgtccatac
88681 accgtctgtc ccacgacagg cgatggtccg tagactctat cacactcctc atcaaatgca

Fig. 3 (cont.)

88741 tggtacaccg aataccagcc aggcgggata tcgctgccgg caggcagggg cgcgggggct
88801 gcaaaaagaa ggttgttcct atcaaaccag gaaaaatagg gaaacttatt gttttcaagg
88861 gcatcaataa tccataacgt ggcccattct gagccaccgg ctttaggcat ggtccgacac
88921 agaaaccgat cggcgttcgt ctttgaggca cagtcccgac tgagccttat agtgcccccc
88981 ttcttgctat gaaaaaaacc cacgaccgtt acgcaaattt gaggagctac tcacctaaaa
89041 gtagctcctt tgacaaatgt cctggtttta taccaattgt tcacaatgac atattgtgct
89101 ggcggaaaca ggtgtcccga tgtatcctcg gcaagtaagc accattacca tgtgccatca
89161 tattgtgtgg cacaaaaaaa gcaacttttc acgcacgcag cataagaccc gagccagtcg
89221 cgccctccat cgcgcctgcg aattttccca ccacccaata ttgtggcaga tctttcttat
89281 gtatatgtgg ttacaaacac cacgcccctt aagctgtcct ctctcccaag ggactagat
89341 tataacagtg acatacgaaa ccgagacgct ctcaaatgct ttctatttta tttatcgatt
89401 ccgggttaac ataatcacag gtagctataa aatccccatc ctcttgacct ggtaaccctg
89461 gcttgaggtt tcctctgtta tcaaacaaac ctgaccacaa ctgtacagag aaaagtgggt
89521 gaaatgtagt gtttatttta tcctcacact ttcacttaac cacagcccgt caaaccacag
89581 ggaccctgtt ggctgactat tagtcatcac atgtaactga acgcaatctg agcttgatga
89641 cgagggggac catatcgaac tgttctgccg acgttgggtc acctccgatg aacacagttg
89701 tttttttaat gtgctcatgt ccctgtatgc gatattgtgc cacattaaaa acatccagaa
89761 cagccctaga tgacagtccg cagatcacac caaacttctt tggaggatta tttccatgat
89821 ataatacggt agacttgcac aaattcttaa cataaatgcc agatcggaga gaaactatca
89881 caagacccga agcaaacgag cgcagcacgg ccgccagcag gttaacgtct cctggccctg
89941 tgttattgtc gtcaggtttg ggcaacaaaa ctcttaaccc tttgcgcgaa tgcaagcaag
90001 agtggctaat gtctgccagt gggttctggg aacatagaat aaacaccttt cgttccactt
90061 ccaaagacat tgcagggcgg ccaaaataaa acacttccac accaagccta tcggttatca
90121 ttactggcgg ccgtgccact ctataatatg cggatctaag cttcctgtgg cgaatgcgcc
90181 tcgtggtagg cctctcgtgt ctccgtggcc catcatccca taaaaattcg ccaacaactg
90241 gccggcgtct ggacgccggc ggcagtccag caccatcatc gacttcttcg tcacttatct
90301 ccaacacata ttcccctgct acattctggg cctcgagtgc cccagctaag tacacatcct
90361 ctacacccgc cccgacagcc gaggcggcga ttgagccctc tgttaccacg ccgcttgcat
90421 ccgtgtcgcc tccgggctgt gatgttgcga taacatcctc tgggatgcca agcagatcaa
90481 agaggtcttc atcgcacatc gccctcatta gcatgtccat ctcctgtccc acgtggtaca
90541 tcaatgcaca tgcagattct ttatcaagca gtgtgaggtc atcttcaacg ttgtctgtgt
90601 gcaccgttgt ttcatcggcc gggggggggct gcgagtcgct atgacgcgtc gagggtcctt
90661 cgtctccaga gccaggagag tcggcattgg catcatcaac tggctgaacc ccagacgcac
90721 tatggcgcgt cgatggtccc tcgtctccag agtcctcaga ttccgcgccc gtctgcgtga
90781 ccggcacatc gcaaaaggct gggtgatcct cctcactgga atccgagttt tcacccacaa
90841 atggcctaca gaaaaaaaaa caaatatgtc aaccggacta gggtggccaa accatttgcc
90901 ccacccctcc ccactctttc cccaggggac acatcttacc ttggtcttct ccgatgcttc
90961 tcgagccgta cactgtgttg atacaaaatt tcccatagtg atgacccact gtgtaggtga
91021 gtcctggcat gaacgcacca ccagcattcc tttacctcgg cacacaggag gcgccacctt

Fig. 3 (cont.)

91081 ctacaattaa ttccctgtac gacctcgtac tcttcacctg gcaagcgtct aaggcgccgc
91141 gacgtggtac atattttccc aaaagccgta atcggcgagc ccagtaaatc tctgggatgc
91201 aggcccttcg ataggcattc cctcttaaaa tcaatgaaaa actgtaggct atccagagga
91261 attacgtcat tacgggcagc cggagcaaga aatgttccag tagatctatc tagccacttg
91321 accaaaggat atttatcaga gtccaaagca cctacaataa actcagaaat ccaggtaagc
91381 ctgcgtcccg ccatgttgac ctgtcagaat ggtctgcctc cgagcattac cccacctcaa
91441 cagaagtaat ctactacgca aaccacaaca tgcttcctgc agctttaacc ttcagtcacg
91501 ggtcaaaaag cattgcctgt attagacaca tgtgtttctc actatgaatc gtgctctcca
91561 gcgctggcaa gaacatctgg ggtgatgctg ccccggacca gctttgaaac agggtattgc
91621 atgcataatg aagcccacat gtttgtctta ctttactaac ctcattacct tgcattgcag
91681 gggacacccc cttgccttgg cagctgagtg aatcccaacc gcctaggaaa aaaataacca
91741 ctcagacttt attttgcagc cacacggtgg cgctaacctt taatgatgtc ccactcagtg
91801 agtttggcca ctcccaagcc cacatgggcc tactataaca ggaaacatag aagttgcgga
91861 tagagcctgg tttctaacgg caatgatatt tatagtgcaa aacggagggc ggtaagacaa
91921 agggaggtac ccggacagag tgacaagaag acttgtcaaa attttagtct ctgtggtaaa
91981 atggggcaag gtaaatgtgc aaaatgactg gatagtgatc cgagtcatat tcaggcgacg
92041 gccggcggcc cagaaacagg gacgcgtacc gggacccttc aggttctcga ttatgtcgct
92101 ccacgtcaaa agcttgttgg atctcgtggc ggtgggacag gggcctacat ttgcctattc
92161 ttcttcgcga tgcatttcca acaaagtatg ctgggtattc caataatccc ttcagaaaaa
92221 tgcccatgtt tgtaccgatg gccacaactc ccatggaaaa cctgtccagc gtctgttcca
92281 aagttcggtt tgcgtccaca ctacagtggg ccgttctggg aagtaagcat ttatacgggg
92341 gtaccgtctg acatatgtgt tcaggggagg cctctgggac ttgggagcaa ataacgatgc
92401 cccccgttaa atcaaagtgg gtcttcacct tttctccgaa ataatacact tccaccacta
92461 ggggcacaag cttgtcaccc actttgtaaa tagcctgttt cttactcagg tatgctgcca
92521 cggattgggt ggcggttaag accttgggcc tcatgtcgct tccataccag taaaatgtct
92581 ggtcagcttt ctcttggtcc tcgacgtccc ggtcatcacg acacaacggt ggaatacaat
92641 caataaaatc atccacattg tcggaagctt ggaaagatga acccatgaca gaggccccag
92701 gtgccgaact ctcaagggga tgcgtggcgg gaagtactga gacactctcc gtggacccct
92761 cctcacctcc ctccgactgc atcgggccct gagggctcgc agtttcacac agaagttcac
92821 tcaggtcgcc taagtcagga agctcctggc ctgaacccat gacagaggcc ccaggtgccg
92881 aactctcaag gggatgcgtg gcgggaagta ctgagacact ctccgtggac ccctcctcac
92941 ctccctccga ctgcatcggg ccctgagggc tcgcagtttc acacagaagt tcacccaggt
93001 cgcctaagtc aggaagctcc tggccaacat ctgacaagag atctaacaaa cacccctcaa
93061 tgtgatccac catcggtagg caatcatcca gcccactgac atgactgggg acggggcctt
93121 ctggggaaaa tggggtttgc gactgtccag caggcggcgc taataagcct tgtgtctcat
93181 gtggaaaaat aacaggagaa ggtaaacccc ccgttggcaa acatagatcc gtcggggtgt
93241 gcacgtgtaa tgggccctgc acctggctcg tggagggacg cggggaatcc ggagctaata
93301 agctcgatga ctgaccagat gacccaaacc ccgacggttc tggctcttca aaaaacaaac
93361 tgtgcatatc cctccctaca aaaccctgag cccccaccca aagttcgttt tcgctgtcac

Fig. 3 (cont.)

93421 tcgattccgt atcttcgctc tgtgaccgtg atgaaacttc agctgcggag gatgttgtgg
93481 gcgtggcgac tgccgccgcc tgtttcctgg cggcctccct aaacaaaagt taattacaca
93541 aaggtaagtc tgagtgacat ctccaatttc ccgtgatgcc cgctgcacgt acatcccgcc
93601 gcccacacaa cccaccgccc agtacatcaa ccatcctacc tctgggcttt ttttctaagg
93661 ctccttctaa gtgccttttc tctgtgtttg tcatcatggg gatagatccc aaacaatgct
93721 tttagcatgt ttttcatggc tggttcctgc gtcaagtaca caagacatcc ttcacatccc
93781 ttgtatggcc taggtgtcat aatccagcgg ttgagtttca tttttccctt atagatggta
93841 aagggcctct cctgtctggc tcgattggcg gtccttaata gccgtccaaa gcagcccagg
93901 ccagtctcag tctccgggat ttctggcagc ccgtgcctac gtcgctcctc caaaaatgcc
93961 tcatagaagt catcgaagcc ttctggcatt ctctcccgcc ggtttcgacc cggcacggtg
94021 aatattctct tttgttcatc caaccaccct acccccccaga agcgtccact gtctaaagca
94081 tctataataa agtccgtgag ccattccgac tccgtgtagc gaggcatctt tttaggcaaa
94141 agccacgaca caaaacacct tttccgtggg cgactttctc gccacaacta gctggacccc
94201 aaccccactg gcacgtagac tctgtgccat ctaacaacaa aactcaatat atgcagctca
94261 acaccgcccc ccccagccgg ttgtcgggct gcggaaactt gtggttagaa ctcactacgg
94321 aaaagggaac caatgcagtt gaactactgg cacacaccca taacccggga cagcacccag
94381 gcactgtcca ccctctaata caagcggcct ttggacgcga gggaggggtg tcatggtcaa
94441 caaaccaaga aaaacacatg tattattcaa ttagccaaca actttattta ttaccgacag
94501 gagacatgag atacataaat ttccaaccgt gcatagggcc aataccatct gtggagcgtt
94561 aagtgccctg tggagttttc gcctaattag ctgaatctcg acccccattg cggccagcat
94621 gctcacgagg aataggcagc agaggcagga cctaactagg agcatatccg gacctgatcc
94681 aagtatgtgc accaaggtga gcaacactgc cgccaaaggc aggagaacaa atagcgctcg
94741 tcgggaggcg acggatacgc ccacgcatga cagtaaccca acataaaata gcgtcatata
94801 cttatccagg ccaatcagga ccggagtcag caggccgatc gaggccgtcg atatcagggt
94861 ggccagcagt aaggtcacaa acacgacaac ctcgcgccta cagtaggccc aggcctggaa
94921 cactgaatag gtgatgtact tcccgggcat gatgaatatg gccctcctcc tttgcattcc
94981 ggccctgatg tacacatgct gttccaggtg cctaaatgcc aaaagtcccc cgaccaagaa
95041 gacaatgaag ggcagccaga aaacgccgga cacaaagacc ttcttaaaca acagaaggta
95101 gtacaccata aatgctccgc agaagcccag ctcatagtac ctgtgtacta ttggcggcgc
95161 ctgatacacc gccgttgcgg tggctagcgg ataaggtaac agcagtaaac agttaagtac
95221 gcacagaccc ggtatgaagg gcacacgaga aaatgtaaac ccagaaaagg ccgcgcaaac
95281 tacagcagca aacactgctg acgcgcagat ccattccagc ctccggtcca gctgtttttg
95341 cgccgcaggg cacagacaca tgcatatcag ggccaagtgc gtgactggca gcgaccagaa
95401 aaacacggcc gtgatctctg tggtaaagag tgtgaacgag tacagggcct tgaagataaa
95461 acaccacaga aagggggtcg ccgccaacgt cccgctcaga taactgaaga gcgacagagc
95521 gcgctcactg tccaggcggc acatggtgtc aaatcagggg gttaaatgtg gttttgggca
95581 ccttcccacg atccctggac tggctcgagt ctgagcgcct cttgtgaggc ctctttgtgc
95641 tgtccttagt tggcgccgct ggggggcagc tggtgacaga ggcagcgtcc tcagaggcgt
95701 cctccagcgg cccaaaggga ccaactggtg tgagaggggg agaatccgga gactccaatt

Fig. 3 (cont.)

95761 ccggctgcct cctggagtcc ggtatagaat cgggaacctt ttgcgaagac tcgcctccct
95821 cggcagacac agatcggttt acctctaaaa gtaggacact taactttacg tcacctgatt
95881 ggcagccagt gggcacacct tccacttcta atatttcgtt ggagtgccaa atcagcccgg
95941 gggtaaacca acccgggact ttacacagtc tcagggcggc gattaaggac tccaggctaa
96001 cccggctcag ggcgtcggtg tgcaccacgc ccacatccac cgacttcttc cccttcagac
96061 catcccagcc agaaacgggt ttggtttctg gcttgaaatc aatgatcttg ctcacgccac
96121 caagagaaaa tgtcacgatc gacagcgtct cgctgacaga cacagtcacc gtttggtcct
96181 cttttgtttt ttgctgcctt agccacttaa gtaggaatgc acccgttttg ccacagagga
96241 gaagcctggt ggtcctacca ccggcttcca tccgatcgtg gaaaggtagg atacccttt
96301 ggtccaccac gcttttgtgc acggtggagg tgaggttgtc cccgtaggaa atggtggtcc
96361 tgacgaactg cggttgggcc cccgtatcgc atgcctcccc ctttcgataa aaggctatgc
96421 cagcgtcgag tacattcgca ccgaatagct cacgcgtgtg cgtgaagccg ctaccgacgg
96481 acgtattcct gaagctgaag ctaacgtctc cactgccttc cgtgtgtccc accaggggcg
96541 taagggcatt ctttattctt aaccccagaa cgccagctgt ccccacgctg gacagcacac
96601 tgagggttgg cgtgcaagcc gatccgtgca cttgcactac tccggtttta gtggcactct
96661 taatgtgttc attgaccctc ctgattttag acaggagggt cacgtccacc ctgaccccat
96721 agtgaaaatc cacaggcatg attgcggccg tagacgcaca gagaaatcac aggaaagctg
96781 cgcgcacact gggtgatctg gagacgatag actgccttaa atagaacttt taggggaggt
96841 ggaagtgtgc gacatggaca ggttaacctt cacaaatcgt cagtcacaca cgtggtgtaa
96901 tcagaattgt ctcgctcaaa aaaattcaca gccttgaaac tgccggtgta tgagaggggg
96961 cacgcttctg gcggaggcgt gccaaatatg ggaggaacga aaatatcacg cagaatcctg
97021 tcagcggtgg cttccaggaa cctccggatg tccaccacgt taacaagcgt caccccggcc
97081 gccttggcct ggataaaccg aatctcaata ttcactgcct ccctgaacag cgcctggacc
97141 tctgcgtgac tgggttttc ctgtatctcc accatagtgt tgtacaacat actggcggcc
97201 ttggtgtgca gcagctcgtc cctggaaatg taatcgttgg caaggcacac cccgggcatg
97261 atgcctcgca ccctgcacaa actgatagag tagaaggagc taataaagta tatcccctcc
97321 acaatcaaaa acatcagaat cttctgagct ttggtggtcg ccttacgcac cctggagtga
97381 agccactcca gcttctcgca aagggcgggg tccaaaatga tcttggcagc atatgctaga
97441 agttcgcctc gactgttgtt gaaaaatatc ttcaagatat tggcatacac gacaccgtgg
97501 atattctcca tggcaacctg ttcggcataa tagtgggcca cgtcgtggct gttaaaattt
97561 gtgacaaggt cctcaatgtt aaagttaact aggcgttcgg ccattcccaa aaacgtaaac
97621 aaaaatctat aaaagtcctt gtcggcatcg ctgagctggt gcacgtggga aacatcaagg
97681 tgcaggggta tctggctagg aaaccatcgg ttctgccaag tctcgcgcgt tagcgccaaa
97741 aatccgtcgt gatcgcttgt atacagaaat cgatcaactg aatccattgg cctcacccgg
97801 cttgcagaga cctacctact gacagaccag gcactcgggg tctgccgcgc aggactcctc
97861 ctccgggttt ttaggtccgg gtaaccacgc cccatcttgt ttcatcccag agtgaggcgg
97921 tgaccctgga tctgccaggc actgaagagc cgtcagacta gattgcttct gaaccctaca
97981 gtagtacatg agggttttta gaccaagcct gtatccatgt agcagcaggt ccctaagata
98041 gctcgcattc ctgactctgt cctccttgag gaagaagctc atggactggc tctggtctac

Fig. 3 (cont.)

98101 aaacggcgcc ctggcacgag ccctgtccag tagcttaaat ggacagtaat caaaggctgt
98161 taggaatacc ctatatcttt ccctgtgatg cttggggaac gtggaaacgt ccccaccata
98221 ctgtctaacc acccgaaggt cgtcggggag aaccttctta aaaaaagtca cattgggcct
98281 caacacctct tctttattgg tgaccttgga agatatatta gcaaaaaagg ggtacacaga
98341 ctcggcatag ccagttactt gcgaggtccc agccgtcggc atcaccgcca gaaactgaga
98401 attgaatatg ccatgctcgg caatgctctt tcccaacgcg tcccagcgat ggcgtggtac
98461 aaacgaagca tcctccccct cccatgtttg ccaatgaaac ctgcccttgg cgaagttact
98521 gacctcccag ccatgaaatg ggacaccctg tccctccaaa acaaggttgt gactagtctc
98581 caccgcggtg tagtacatag actggaatat attcttgtct aactcagcgc tctcagcatc
98641 gaggtacccg taccccaatt ccgcaaacac atccgccaac ccctgaacac caatccccat
98701 agacctctcc ttttgacctc gctcgacccc cggtgttgga tgggaaccac ccagaatgca
98761 ggcgttgatg acgaggactg ccacccttac tgcgtcgccc aaggcctcaa aacaaaaaaa
98821 cggcctgttg gcgtccgtgg tgccaaccct cgcgctttca acagttctca gacactttgg
98881 aaggcagata tttgccaggt tgcacaccga agtgtttctt cctggcagtt ggactatctc
98941 tgcacacaag tttgagcagt taatggccat gccctgagtg tcggtccagt ggtgttcatt
99001 gagcgcttct tttaaaagca cgtacggtga gcctgtcttt atgatggtgt ggataagagt
99061 gaacatcata gacttcaacg gcatgcaact aacgtacttt ccagcccgca ccaggcgctc
99121 gtattcgtta tcgaacgcag caccgtatag cttaatcaaa ttgggggcgg tggctggatc
99181 gaacaaatac cataacttgg atgggtcctt ttcatacatc ctgaaaaaca atgttgggat
99241 gcacacgccc tgaaagagac tgtgacatct gtcgggattc tccggtagtt tggcgttcaa
99301 aaaatcacag atttgactgt gccagagttc catgtatgcg ctcgcgccaa cgggcctgat
99361 gttattgtca ttgaaataat gaacctgggc atccaccagt ttgaggcaac tggctatgtt
99421 cttttggtgg gagaatgacg taacatccag acccacgcct gacttactgg ccagcaacgg
99481 actcatatcg tggtacaggg cgtccaaagt acccgactca ttcatcatgg agggctgcag
99541 aataaaacag ctggcgagtt gtccgccttc gactccagct gagcgcagta ttggcgtggc
99601 gcagcacacg tgctgcgcag cgaggtagcc aaaaacgtac tccactatag ccatctcaga
99661 tacagactta gcgtcctcaa taaggtcccg cgccaaccaa tacaggcatt catgctctaa
99721 gcactgacag gcaacaaaca cggaaaccct cataaacatt tgcgccacgc tttcatagac
99781 aggctctgtc cccatggtcc ttaggacgta agtatcatac aacctcacgg ccgataggta
99841 gccacagtta agtgtgtcct cgtaagcttt ggaccgtctg taggcgcaca acatatcttc
99901 caaggcatca atgttctttt gaataaacga ttccacccga tgtcccaaca cgcctcgaaa
99961 aatcccaaga tactgcttga gagtcgctgg gcacctagcc tccataattt ggtgccacag
100021 ccgccccgcc atggcattgg cccgcacgtc ccacccgacc ctaaccttta gaaagtctat
100081 gagagattgg gcacacatat caaaatccga caattgtccc gcagacacct gagacccgcg
100141 tcgctctggt gggacagctc ccaagtgaac ctgacaaaat gtccggacag acatgacctt
100201 acagaaacac agtccagggg ccacacgcgg cctcaaagtt cgcaaacacc agtacaggca
100261 aggacgtgcc cttcacgttc agactttggt gcaccggatg agaatcaaag ggaactgtgc
100321 ccagcgtaca aaccgcccca aaaacaagcc gatttatata cagctcgtgc ctcagctgaa
100381 tatacttggt ccggattaca tccgtaaagt gatcctttat catggccaca acctccgcaa

Fig. 3 (cont.)

100441 agcccttccc agactggaaa aacgtcagcg ccatagatgg tctctggttc acacggagat
100501 aaaccaacga ggcataaata gtaacgttta ggcctgccgg ttcccggcgc tggaccatgg
100561 gacatgactc atccaaatca actagcatat cacaagggag ggtcaagcct acgtgtgcac
100621 ggggctcgtc ccgggccaac ccaactccct tcatggcgga ggtgaccttg gtcacgaagg
100681 tactgtggac actctggacc attggaccta ctggggtaag gagggtatga aactccccag
100741 tgtccatgag ttcactcaag ttagggatga aatccgccag gccggatcca cttccgtacc
100801 acacaccggc cactttgtga gtctgtggcg cttttgccgc ttccattcca gagagcataa
100861 acagggacgt gggtgttagc agcatatcca tagacgagcc gttgtcctcc tgcttgaatg
100921 aaaataaaaa ggttcccaga ggctcctggg gactaaaggt ctgtgaatac acgaggaaat
100981 ctccataggt cggctgccta aacggcgcct gccgcaaggc ctcatgcagc gagccaaccg
101041 tgggtcgtgt ggacgccgca tatttagaga gtaaatcccg caccccccctg gcaaactccg
101101 gtcctctagt gagggatacc cggtgagttg gtggaggtaa aagacccaac acttgcctac
101161 ccaggcgagc cgcattttca gcctgcacct tcatatccac gccggcaatg gacggcacag
101221 acgctcttga aaagcttacc aaaggcctga gtgggggagg cgggagcctt caccagacaa
101281 agctgttgat ggaatttcaa ctccgaggac tgccggtgcc tgccctctta aacagcagca
101341 caacagagca gtttttaaat actgttgccc aactgccgac ggacctatca aaatttatac
101401 gcgactatcg cgtgttcgca ctggttcgcg cggcgtattt tttagaaccc ccttctagca
101461 tcgacccccct tgaggcagcg cgcgctcttg gacgcctggt tgatatatta tcatcacaac
101521 caccgcagaa caccgcaccg gcgcagccac ccacctccga cgacaccctg aataactgta
101581 cattgctcaa actactagcc cactacgcgg atcagatagc aggtttcaaa acccccgctc
101641 tccctcccgt gccacctgga atcatcggcc tgttcacatg cgtggaacag atgtaccacg
101701 catgttttca gaaatactgg gcagctgcac taccccccaat gtggatactg acatacgacc
101761 ctcccacttc tccgttacag gactggctta tagtcgccta tggtaacaag gaaggactgc
101821 tactcccctc tggcataccc tcggaggagg tgttagccaa aacattagta acagaacacc
101881 acgagttgtt cgtatcgcgg tcgaattcga ccgagaccgc cgtcaccatg cccgtatcca
101941 aagaacgcgc cctcgccatc taccgggtgt tcgccaaggg tgaggtggtg gcggaaaata
102001 ctcccattct tgccttcacc gacgtggaac tatccacact caaaccccac tatctgttca
102061 tctatgattt tatcatagag gcattatgca agagctacac atactcatgc acccaggccc
102121 gcctggaatc ctttttgagc cgaggtatag acttcatgac tgacctaggt cagtacctag
102181 ataccgctac tagcggcaag cagcagctga cgcacagcca aataaaggaa atcaaataca
102241 ggctgctaag ctgcggtctc tcggcttccg cgtgtgatgt tttcagaact gtgatcatga
102301 ccctcccata tcgaccgacc cccaacctcg ctaacctgtc cacgtttatg ggatggttc
102361 accaactgac catgttcgga cactatttct accggtgcct gggcagctac agtcccaccg
102421 gcttggcctt cacagaattg caaaagatac tgacacgcgc cagcgcggag caaacggaac
102481 gtaacccgtg gagacatccg ggtatctcgg acattccact gcgttggaaa atatcgcgtg
102541 ctctagcatt cttcgtccct ccggccccca taaacacttt gcagcgcgtg tacgccgcgc
102601 tgccctcgca actcatgcgg gccatcttcg agatctcggt caagaccaca tggggaggcg
102661 ccgtaccggc aaacctggcg cgcgacattg acacaggacc gaacacacaa catatctcct
102721 ccacaccacc gcccaccctc aaggatgttg agacatactg tcaaggtctg cgggtgggag

Fig. 3 (cont.)

102781 acacggagta cgatgaggac attgtgagaa gcccgctctt tgcagacgcg tttaccaaga
102841 gtcacttgtt gcctatactg cgcgaggttc tggaaaaccg cctgcagaaa aacagagctc
102901 tgtttcagat aagatggctg ataatatttg ctgccgaggc ggcaaccggg ctcatccctg
102961 ccaggcgccc gctagccaga gcctacttcc acatcatgga cattctggag gagagacatt
103021 cccaagacgc cctatacaac cttttggact gtatccagga gctcttcacc cacatcaggc
103081 aggctgttcc agacgcacag tgtccgcacg cctttctaca gtccctgttc gtctttcaat
103141 tccgcccttt cgtactcaaa caccagcagg gtgtaacctt gtttctagat ggcttgcaga
103201 catccctccc cccggtgata agtctggcca accttggaga caagctgtgt cgtctcgagt
103261 tcgagtacga cagcgagggc gacttcgtgc gcgtgccagt tgcaccgcca gaacaaccac
103321 cgcacgtaca tctgtcgcat ttcaagaaga caatacagac catcgaacag gccaccaggg
103381 aggccaccgt agccatgaca acaatcgcaa agccaatata ccccgcctac atccggttac
103441 tgcagcggct agaatatctt aacagactca accaccacat tctcaggatt cccttcccac
103501 aggacgccct ttctgaactc caggaaacct acctggcggc gtttgcacgg ttgacaaaat
103561 tggcagcgga cgcagcaaac acttgtagct actccctcac caagtacttt ggagttttat
103621 tccaacacca gctggtcccc acggccatcg ttaaaaaact gctacatttc gacgaggcta
103681 aagataccac agaagccttt ttacagagcc tggcacaacc cgtagtgcag ggacaacggc
103741 agggggcggc tggcgggtcg ggtgtcctga cgcagaaaga acttgagctc ttgaacaaaa
103801 taaacccaca gtttacagac gctcaggcta acattcctcc atctattaaa cgttcatatt
103861 caaataaata tgacgtccct gaggtctcag tcgactggga aacgtactcc cggtctgcct
103921 tcgaggcacc ggacgacgaa ctccgttttg tcccactgac gctggcaggc ctccggaaac
103981 tgtttgtcga atagaggcca tggcagccca gcctctgtac atggagggaa tggcctccac
104041 ccaccaagct aactgtatat tcggagaaca tgctggatcc cagtgcctca gcaactgcgt
104101 catgtacctg gcgtccagct attataacag cgaaaccccc ctcgtcgaca gagccagcct
104161 ggacgatgta cttgaacagg gcatgaggct ggacctcctc ctacgaaaat ctggcatgct
104221 gggatttaga caatatgccc aacttcatca catccccgga ttcctccgca cagacgactg
104281 ggccaccaag atcttccagt ctccagagtt ttatgggctc atcggacagg acgcggccat
104341 ccgcgagcca ttcatcgagt ccttgaggtc ggttttgagt cgaaactacg cgggcacggt
104401 acagtacctg atcattatct gccagtccaa agccggagca atcgtcgtca aggacaaaac
104461 gtattacatg tttgaccccc actgcatacc aaacatcccc aacagtcctg cacacgtcat
104521 aaagactaac gacgttggcg ttttattacc gtacatagcc acacatgaca ctgaatacac
104581 cgggtgcttc ctttacttta tcccacatga ctacatcagc ccagagcact acatcgcaaa
104641 ccactaccgc accattgtgt tcgaagaact ccacgggccc agaatggata tctcccgcgg
104701 ggtggaatca tgctccatca ccgaaatcac gtccccttct gtatccccg cgcctagtga
104761 ggcaccattg cgcagggact ccacccaatc acaagacgaa acgcgcccgc gcagacctcg
104821 cgtcgtcatt cctccttacg atccgacaga ccgcccacga ccgcctcacc aagaccgccc
104881 gccagagcag gcagcgggat acggtggaaa caaaggacgc ggcggtaaca aaggacgcgg
104941 cggaaagacg ggacgtggcg gaaatgaagg acgcggtggc caccagccac cagacgagca
105001 ccagcccccca cacatcaccg cggaacacat ggaccagtcc gacggacaag gcgccgatgg
105061 agacatggat agtacacccg caaatggtga gacatccgtt acggaaaccc cgggccccga

Fig. 3 (cont.)

105121 acccaatccc ccagcacggc ctgacagaga gccaccgccc actccccgg cgaccccagg
105181 cgccacagcg ctgctctctg acctaactgc cacaagaggg cagaaacgca aattttcctc
105241 gcttaaagaa tcttatccca tcgacagccc accctctgac gacgatgatg tgtcccagcc
105301 ctcccaacaa acggctccgg atactgaaga tatttggatt gacgacccac tcacaccctt
105361 gtacccacta acggatacac catctttcga cataacggcg gacgtcacac ccgacaacac
105421 ccaccccgag aaagcagcgg acggggactt taccaacaag accacaagca cggatgcgga
105481 caggtatgcc agcgccagtc aggaatcgct gggcaccctg gtctcgccat acgattttac
105541 aaacttggat acactgctgg cagagctggg ccggttggga acggcacagc ctatccctgt
105601 aatcgtggac agactaacat cgcgaccttt tcgagaagcc agcgctctac aggctatgga
105661 taggatacta acacacgtgg tcctagaata cggtctggtt tcgggttaca gcacagctgc
105721 cccatccaaa tgcacccacg tcctccagtt tttcattttg tggggcgaaa aactcggcat
105781 accaacggag gacgcaaaga cgctcctgga aagcgcactg gagatccccg caatgtgcga
105841 gatcgtccaa cagggccggt tgaaggagcc cacgttctcc cgccacatta taagcaagct
105901 aaacccctgc ttggaatccc tacacgccac tagtcgtcag gacttcaagt ccctgataca
105961 ggcattcaac gccgaaggga ttaggatcgc ctcgcgtgag agggagacgt ccatggccga
106021 actgatagaa acgataaccg cccgccttaa accaaatttt aacattgtct gtgcccgcca
106081 ggacgcacaa accattcaag acggcgtcgg tctcctcagg gccgaggtta acaagagaaa
106141 cgcacagata gcccaggagg ctgcgtattt tgagaatata atcacggccc tctccacatt
106201 ccaaccacct ccccaatcgc aacagacgtt cgaagtgctg ccggacctca aactgcgcac
106261 gctcgtggag cacctgaccc tggttgaggc gcaggtgaca acgcaaacgg tggaaagtct
106321 acaggcatac ctacagagcg ctgccactgc tgagcatcac cttaccaacg tgcccaacgt
106381 ccacagtata ctgtctaaca tatccaacac tctaaaagtt atagattatg taattccaaa
106441 atttataata aacaccgata cactggcccc atataaacag cagttttcat atctgggggg
106501 tgaactggca tctatgttct ccctgactg gcctcacgca cctgcagagg cggtagagcc
106561 actacccgtg ctgacttctc tgcgaggtaa aatcgcagag gcgctgacgc gtcaagaaaa
106621 caaaaacgct gtagatcaaa ttctaaccga cgccgaaggc ctccttaaga acattaccga
106681 tccaaacggc gcacacttcc acgcccaggc cgtatcaatt ccagtgttag aaaactacgt
106741 acataacgcg gggggtccttc tcaagggcga aaagagcgag aggttctccc ggctgaagac
106801 cgccatccaa aacctggtat cctccgaatc atttatcacc gtgaccctac acagtacaaa
106861 ccttggaaac ctagttacca acgtaccaaa acttggtgag gcgttcaccg ggggcccgca
106921 cctcctgaca agcccgtccg tgagacagtc cctttccacc ctgtgcacaa ccctgctgcg
106981 agatgccctg gacgccctgg aaaaaaagga tccggccctt cttggtgagg ggaccacgtt
107041 ggcgctggag acactcctag gatacgggtc ggtgcaggac tacaaggaga cggtacagat
107101 aatatccagc cttgtgggca tccaaaaatt agtcagggac cagggcgcgg acaagtgggc
107161 cactgccgtg acaaggctaa ctgacctcaa atcaactctg gccacgaccg ccatcgagac
107221 ggctacgaaa cggaaactat acagattgat ccaaagggac ctcaaagagg ctcaaaaaca
107281 cgagaccaat cgggccatgg aggaatggaa gcagaaagta ctggctcttg acaatgcgtc
107341 tccggaacgt gtcgccaccc tcctgcaaca ggctcccacc gcgaaggcta gagagtttgc
107401 agagaagcac ttcaaaatac tactccccgt acccgcggac gcccccgtcc aagcgtctcc

Fig. 3 (cont.)

107461 aacgccgatg gaatacagcg ccagccccct cccggaccca aaggatatag acagagctac
107521 atccatccac ggggaacagg cgtggaagaa gatacagcag gcgttcaagg atttcaactt
107581 cgccgtcctg cggcccgctg actgggatgc cctggcagcg gagtaccaac gccgtggttc
107641 gccccttccg gcggccgtgg gtccagcgct ctcagggttc ctggagacga tcctagggac
107701 gctgaacgac atctacatgg ataagctccg ctcctttctg cccgacgcgc agcctttttca
107761 ggcgccgccc ttcgactggc taacgccgta tcaggaccaa gtcagctttt tcttgcgcac
107821 catagggctg ccgctggtgc gagcgctggc cgacaagatc agcgtgcagg cactgaggct
107881 tagccacgcg ctccagtccg gcgatttgca gcaggccacg gtgggcacgc ccctggagct
107941 ccctgccaca gagtacgcgc gcatcgcctc caacatgaag tccgtgttca acgaccacgg
108001 acttcaggtg cgatcagagg tcgcggatta tgtggaggcc caacgagccg acgcacacac
108061 gccacacgtc ccacgtccaa agatacaggc accaaagact ctgattccac atccggacgc
108121 aatcgtcgcg gacggactac ccgcctttct taagacgtcc ctactgcagc aagaggccaa
108181 acttctggcg ctacagcggg cggacttcga gtcgctcgag agcgacatgc gcgccgcaga
108241 ggcccagaga aaagcatcgc gcgaggaaac ccagcgcaaa atggcacacg ccatcactca
108301 gctcttacag caggcaccca gtgcgatctc ggggcgcccg ctatccttac aggacccggt
108361 gggcttcctc gagggcatca tatacgacaa ggtcctggag cgcgaatcct acgagacggg
108421 tctcgaggga ctgtcctggc tcgagcagac catcaagtcc atcaccgtat acgctcccgt
108481 agaggagaag caaagaatgc acgtgctgct ggacgaggtg aaaaagcagc gagcaaacac
108541 tgagaccgct ctcgagctag aggccgcggc tacgcacggc gacgacgcta gactcctgca
108601 gcgagcggtc gatgagctgt caccgttgcg cgttaagggg gggaaggccg cggtggaatc
108661 ctggcggcag aaaatccaaa ccctgaaatc cctggtacag gaagcggagc aggccggcct
108721 cctgttggcc accatagaca cggtggccgg ccaggcccag gagaccatat caccatccac
108781 actccaggga ctgtaccaac agggacagga ggccatggcg gccattaagc ggtttaggga
108841 ctcgccccag ctagctggcc tgcaggaaaa gctggccgag ctacagcagt acgtcaagta
108901 caagaagcag tatctggaac actttgaggc cacccaaagc gtagtgttta cagcctttcc
108961 gctcacacag gaggttacga tcccagccct gcattacgcg ggacctttcg acaacttgga
109021 gcggctctca cgatacctac acatcggcca gacgcagccg gctccgggac agtggctcct
109081 gacacttccc acattcgacc ccacgcgccc ggcctgcgtc ccagccggcg gccacgaacc
109141 cccgttgcac agacaggtgg tgttctccag ctttttggag gcccagatcc gattagcgtt
109201 gtccgtagcg ggccccgtgc ctggacgggg tctgcccgga acaccgcaga tccgaagggg
109261 cgtggaggct gccgcttgtt tcctccacca gtgggacgag atatctcgcc tccttccaga
109321 ggtactggac accttttcc acaacgcgcc ccttcccgca gagtcttcct ccaatgcttt
109381 cctggccatg tgcgtattga cgcaccttgt ctacctagct gggcgcgccg tcttgggccc
109441 acgggagccg gagcacgccg ccccggacgc gtacccaagg gaggtggcgc tggccccgcg
109501 cgacctgacc taccttctac tggccatgtg gccatcttgg atctcggcaa ttttgaaaca
109561 gccttcgcac gcggaggcgg cgcacgcatg tcttgtcacg ctgccaacaa tgctcaaggc
109621 tgtgccgtac ctcacgctgg aagcctcagc tggaccactg ccggcggaca tgcgccactt
109681 cgccacgcca gaagcgcgtc tgtttttccc cgcgcgatgg caccacgtca acgtgcagga
109741 gaaactgtgg ctgcgtaatg attttatgtc gctgtgtcac cgttccccgg ggcgcgcgcg

Fig. 3 (cont.)

109801 catagccgtc ttggtgtggg ccgtcacttg cctagatcct gaggtaataa ggcagctgtg
109861 gtccaccttg cggcccctta ctgcggatga atccgacacg gcttctggac tgctgcgggt
109921 gctagtagaa atggagtttg gtccgccgcc caagacgccg cggcgggagg cggtggcgcc
109981 cggcgcaaca ctgccaccgt acccctacgg ccttgccacc ggcgagcgcc tggtcggcca
110041 ggcgcaggaa cgctctggcg gcgctggcaa gatgccggtg tccgggtttg agatagtttt
110101 aggcgcactg ctgttccgcg ccccctacg cattttcagc accgcatcaa cccacaggat
110161 ctcagatttc gagggcggtt tccagatact gactcctctc ctggactgtt gcccagatcg
110221 cgagccattc gcctccctgg ccgccgcacc acgaaggacg gtgccactgg gagacccgtg
110281 cgccaacatt cacaccccg aagagataca gatctttgcg cgtcaagccg cctggcttca
110341 atataccttc gcaaattacc agatccccag caccgacaac ccgataccga tcgttgtgct
110401 aaacgctaac aataaccttg aaaacagcta catccctcgc gatcgcaaag cggacccgct
110461 acgaccattc tatgtagtcc ctctgaagcc gcagggtaga tggcctgaaa taatgaccac
110521 agcaacaacc ccctgccgcc taccgacatc gccagaagag gcgggatcac agttcgccag
110581 actccttcag agccaggtga gcgccacatg gtctgacatc ttctccaggg ttcccgagcg
110641 cctcgctccc aatgcgcctc agaagagttc ccagacaatg tcagaaatcc acgaggtcgc
110701 cgccacgccg ccactcacaa tcaccccaaa taaaccgacc ggaacccctc acgtctcccc
110761 ggaggctgat ccaataacag aacgcaaacg cggacagcag ccgaagattg tcgcggacaa
110821 catgcctagt cgtattctcc cgtcgctacc gaccccgaaa cccagagagc ctagaatcac
110881 gctaccccac gcactgcccg ttatatcacc cccagcacat cgcccgtcgc ctataccgca
110941 tctgccagca ccgcaggtaa cggagcccaa aggggttctc caaagcaaac gtggaactct
111001 cgtgctgcgg cccgccgcgg tcattgaccc acggaagccc gtctcggcac cgatcacgcg
111061 atatgagagg acggcgctcc agcccccccg gactgagggc gaaggccggc gccctcccga
111121 cacgcaaccc gtcactttaa cctttcgtct cccacctacc gcacccactc ccgcaactgc
111181 agccctagaa accaaaacaa ctccccatc cacgccccca cacgccatag acattagccc
111241 accacagaca cctcccatgt ccacctcacc tcacgcgaga gacacaagcc cccccgcaga
111301 aaagcgggcc gcacccgtca ttcgagtaat ggcgcccacg caaccgtcgg gagaggcaag
111361 agtcaagcga gtggagatcg aacagggcct ttccacacgc aatgaagccc ctccccttga
111421 acgctcgaat cacgccgtgc ccgccgttac cccaaggcgc accgtagccc gcgaaatcag
111481 gatcccgccg gagataaagg cgggttggga cactgcaccg gacattcctc tgccccacag
111541 ctccccggag tcatccccac cgacttcccc ccagcctatc cgcgtggatg ataaatcgcc
111601 tcttcccaac ctcgtagaga gatacgcgcg gggtttcctg gacacgccct ctgtagaggt
111661 gatgtccctg gaaaatcagg acatcgccgt ggaccccgga ctgctaaccc gccggattcc
111721 atccgtggtg cccatgcccc atccaattat gtggtcaccc atagtaccca tcagtttaca
111781 aaacacagac atagacactg caaagataac actgattagt tttattagac gcatcaaaca
111841 aaaagtggcc gccctatcgg cgtccctggc ggagacggtt gacagaataa agaagtggta
111901 cttgtgactc cacggttgtc caatcgttgc ctatttcttt ttgccagagg ggggtttcct
111961 cgcgtcggcc accgcggggg cggccgtttc cgtcgtggat gagagggttg tgagaatgtc
112021 tgacgccggc gacaatgaat ggggaccaga ggacagggtg gttatactgc ttcccgagac
112081 ccccagtgag tcctggcccc cgggcgtggt gccggatgca gggcctggcc tcgaaggcac

Fig. 3 (cont.)

112141 ggtgaacgtc cccgcgtcgt aagccgacgc cgcggaaact cggtcagcgc gctcgcgcgg
112201 tttctgatcc ctaagggtct gcagatgatc ccgcctttga attccaccca tcctcctcag
112261 ataggcctca taataatgat gggcaattaa gaacacgaga tagtgtctct tttgcacgag
112321 gtattcggcc tgcgacatat ttccctgatc cagggtattc atgcgagcca ccaggggatg
112381 gtgagcgtag tcatgatcca gtcgctcctg gatcacgggg tctctcacct taaagttgga
112441 catcttccac acaggcgggc gaaatagcct caggaggaac acttcccgca acagaactcc
112501 agcagctgtg aggtgagctg aagcagtccg cgcacgtcac ggtgctttaa tagggcagcc
112561 tcgcagtcgg gcgtcccaag gcaaggcact acaaaactga cagtttgatc taggtctcga
112621 atggcaaggg ccgcgttgtt agctagaaca gccctgatta cgacgcgtgc tagggtcccg
112681 cgtccggtaa tatcgcacag gggatacacc ctcatatgtt cgctgccaca gtaagaacag
112741 tagatcctcc ccgtggtcgc acagatggtg aactgcttct ctttcctgtc cctgctgaaa
112801 aacacgttgg tgggaggaaa attgacagta tgaaacttgc ccctgccaaa gttaagacag
112861 tgtccacact ccatgcacac aaccgcccga gcgcaacgcg cccgcttggc aagggccgcg
112921 cgggccacgc gagaacagat gacgggtatg gacacgcagg gggagagaac attgtatgcc
112981 agaagcctcc tgccaaggtt ccgcacgaga ccaggtccct cctgctcgca ggcgggcagc
113041 actacgtggc gggacttaat aaggctcaaa aaacacagtg acccaagcat ggcgtcgaac
113101 gggttaccgc agggaaccgt aggggcgacg cgctccaagg cctcccggag gccggtatct
113161 gccgccccta tcccgagccc gttaccgtct tcggtcgcag ccacaccgcg acgggtgtgc
113221 gagggcacct ccaggagggg acgacgcggc aacggcccat gccacttctt ccttagccag
113281 ggtagcgacg gtgggggctt cgaacagcag gtcactaacg gaaagcgaga gcaaagcgcc
113341 aacagcttgc agagttgggc acaggccttg gaaaatggaa gcgacaggta ttttgcccat
113401 acgtggcgcg gtatcgccct agcatggtcg gcggcctggg cacgggacag cgtcaccaca
113461 acccatacgt gggcgccaag cagctgctgc gccgcacaaa tctgcgcctg tttggcgacg
113521 gtgtctgagc cagcgcgcaa cacggcgatc gcctgcgcca gcgacgggcg gtccaacagg
113581 tgcctggccc aggagggcat gtttccctgg aaaccccgct ccccgaatat gacaaaagcc
113641 acatattcct ccactggcac gccattctcg ccctcgaaca cgcggtgggc cgtcagctgg
113701 gcctcatcca aaccaaacca agacacaaga aagcgatccc agcgctgatc cagggccatg
113761 accttctcac cagcgcgacc gcacggccta agctccactg aaaggcgccc agaatccgca
113821 ccgtcctacc cccctggccc gcccaatata ccgctgtgac gtctgatgta caggcccgcg
113881 cgtcgcggcc gttggtggga aaaccggcac caccctgtgc ggccgaatcc gccacggggg
113941 ctgccagaca gtacactgtc tccagcagcg acttcagtct cttgtgactt ttgggcgtca
114001 ccaccaaaaa ttgcaaaacc tgcctgtagt ccgtgaagta ggtacggcat attaccatgg
114061 agttgtacac gcccaggttc tttgagaaca ccaggctcgc cttgaacttt gtaaagtcat
114121 cctgccccag cacgacagac gtatttttgg caaggtatac gtccgactcc acgggaagga
114181 cgtgcccaaa ctgggacacg gcgtcgcttg gtcggcacag aaagcacttc agggttgtgg
114241 aaaggccatt attcgatata acaaagcagg gagagaacgg gtagtgcatc tcctccagga
114301 ggtgcgccca aaacttatac acaaactcta agtggtacac gcaaccgtgc tgcattctaa
114361 ccgtacatat ggcggtagca ccgcccttag cataaactgg ggccccgtcg atgcaccgtt
114421 ccaaatccag ggactgacca gactgtccca agtatgagga taccacccga cacagttcgt

Fig. 3 (cont.)

114481 ccactacacg cttaccaacg acactcatgg cgacagcggg gtggggctgg caaggccccc
114541 aaagcgcgac acccgcagtc aatcagggcc gtgcccgcgc ctcggagaat acggcgtccg
114601 tgctcacgat cttgcgcagg acctgcctta ccgtgtccac cttgctctcc aacaccagag
114661 tatgatcgca ggctgcaggc tgtgcccgct ggacgagaaa ggtttttaaa tactgacagt
114721 agttgatggc gttcaatcta caatagatcg tgggaaataa aatttgcatg tcacgaggca
114781 gaagctggtc agacgcgtac tccatgttgg gttccacggg gaggggaaca cacgccccaa
114841 gacacgacgg cgcacatagg gagcggagca aacaattgat tcaaatattt gactccgcag
114901 cgagccggtt tgcagagtgg tcacctgccc tgctccacac ccaccccgc gtctcttcca
114961 actctcaact cacgatccag ggaaaccacc gtccagtggc catgtttgtt ccctggcaac
115021 tcggtacaat tacccgtcac cgagatgagc tccaaaaact actggcagcc tccctgctcc
115081 cggagcaccc ggaggagagc ctcggtaacc ccataatgac acagattcac cagtcgctcc
115141 aaccatcttc cccctgcagg gtctgtcagc tcctattttc tctggtccgc gattcgtcca
115201 cccccatggg tttcttcgag gactatgcct gcctctgctt cttctgtcta tacgccccac
115261 actgctggac ctcgaccatg gcggcagcgg cagacctgtg cgagatcatg catctgcact
115321 ttccagaaga ggaggcgaca tacgggctat tcggaccggg tcgccttatg ggtatcgact
115381 tgcagctgca cttctttgtt caaaagtgct ttaagaccac cgccgccgaa aaaatactgg
115441 gaatatccaa cctgcaattt ttaaaatcag aattcatccg gggcatgctc acaggcacca
115501 tcacctgcaa cttctgcttc aaaacgtcct ggcccaggac agacaaggag gaggccaccg
115561 gccccacccc atgctgccag attacagaca ccaccaccgc acccgcgagc ggcataccgg
115621 aactagcccg ggccacattc tgcggcgcaa gtcgccccac aaagcccagc ctacttcccg
115681 cgctaataga tatctggtcc acgagctcag agctccttga cgagccgcgc cctcgactga
115741 tcgcaagcga catgagtgaa ctcaaatccg tggtcgcatc ccacgatccg ttcttctctc
115801 ccccgcttca ggcagacacc tcacagggtc catgtctgat gcacccaacc ctggggctac
115861 gatacaaaaa cgggactgca tccgtctgcc tcctctgcga gtgccttgcg gcacacccag
115921 aggcacccaa ggcgctgcag acccttcagt gcgaggtaat gggccatata gaaaacaacg
115981 taaagctggt agacagaatt gcctttgtgt tggacaaccc attcgccatg ccatatgtat
116041 cagatccgct acttagagag ctgatccggg gctgtacccc acaggaaatt cacaagcacc
116101 tgttctgcga cccgctgtgc gccctcaatg ctaaggtggt gtcagaggac gtactattcc
116161 gcctgcccag ggagcaggag tataaaaagc tcagggcatc cgcggccgcc ggacagctcc
116221 tcgatgccaa caccctgttc gactgcgagg tcgtgcagac tttggtcttt ctctttaagg
116281 gtctccaaaa cgccagggtg gggaaaacca cctcactaga cattattcgg gagctaaccg
116341 cacaactaaa aagacaccgc ctagacctgg cccacccctc acagacgtca cacttgtacg
116401 cttgagctgg tcccgggcct tcgcacccca tccaccgatg ccgaaatcag tgtccagcca
116461 catcagcttg gcgacctcaa ccggtcgcag tggaccgcga gacatcagaa gatgcttgtc
116521 atcccgcctg cggtcggtcc cgcccggggc gcgaagcgcc agcgtcagca gcaagcacag
116581 aaacggcctt cgcaagttta tctcagacaa ggtatttttt agcatcctat cgcacagaca
116641 cgagctagga gtggactttc tccgtgagat ggagaccccg atatgcacct ccaaaacagt
116701 aatgctgccc ctagacctgt ctaccgtcgc acccggccgc tgcgtctccc tctctccgtt
116761 tggacactcc tcaaacatgg ggttccagtg cgctctgtgc ccatccacag aaaatcccac

Fig. 3 (cont.)

116821 cgttgcccaa ggctcccggc ctcagacaat ggtgggcgat gcgctcaaaa aaaataacga
116881 gctatgctcg gtagcgctgg ccttttatca ccacgcagac aaagtgatcc aacacaagac
116941 gttttaccta tcactcctca gtcactccat ggatgtggtt cggcagagct tcctgcagcc
117001 tggtctactg tacgctaacc tggtcctaaa aacctttggg cacgatcccc tacccatctt
117061 cactaccaac aacggcatgc taacaatgtg catccttttt aaaacccggg cactacatct
117121 gggagaaact gcgcttaggc tgcttatgga taacctcccc aactacaaga tatcggcgga
117181 ctgctgcaga cagtcctacg tggtcaagtt tgtcccaacg cacccggaca ccgcaagcat
117241 tgcagtgcag gtacacacca tatgcgaagc ggttgcggcg ctagactgca ccgacgagat
117301 gcgggatgac attcaaaagg gaaccgcact tgtcaacgcc ctataacctc acatgtagcc
117361 tgtcacccca gctcctattg caactgacca tgttcaggtg gtaataaagt cattaaacga
117421 caaagtgatt cttttaatct gtttattgtt tttgaacatg tggcacacgc tgcaatgtac
117481 tgccatgaaa ggtggttcta tatccaccac ttggcgtctg ccgaagtcag tgccacaatt
117541 tcattaacaa acaaggtcaa tacattgtga gggagtgttt tttgccatgg taccattcgt
117601 gtggtttggg agagcggacg ccatttgcgt gcaaaatgtg ctttgctgga ggccaacttc
117661 cgtcgcgctg gttgatgcgc ggcacattgt gtcaaccagg gcaccctccc ccaccgagtg
117721 ctttaatgcg gagaggaatg gtggcctggt tgacaccgcg tgccggccat ctgaactgtg
117781 actgtgttat gagccacggg tatgccctcg atacgcctgc tcttcagcat tgtatgtgtt
117841 taatgttgtg cttggtgcaa ccgtgattgt gtttttgtat tttattttac tgacactctt
117901 tgggagggca cgctagcttc agtgcgcgcc cgttgcaact cgtgtcctga atgctacggg
117961 gccacgctgg ccactcgggg ggacaacact aatcgccaac agacaaacga gtggtggtat
118021 cgcccccaagc ctccagcgcc acccatttag taacacatcc gggacatgaa ctgccacaaa
118081 caccgttaag cctctatcca tgcattggga ttggagtgag gagggaggag ggcaccaggt
118141 tcccggggag gagggcacca ggttcccggg gaggagggca ccaggttccc ggggaggagg
118201 gcaccaggtt cccggggagg agggcaccag gttcccgggg aggagggcac caggttcccg
118261 gggaggaggg caccaggttc ccggggagga gggcaccagg ttcccgggga ggagggcacc
118321 aggttcccgg ggaggagggc accaggttcc cggggaggag ggcaccaggt tcccggggag
118381 gagggcacca ggttcccggg gaggagggca ccaggttccc ggggaggagg ctggggtgcg
118441 ccgcgccggg ttcctggggt gcgccgcgcc gggttcctgg ggtgcgccgc gccgggttcc
118501 tggggtgcgc cgcgccgggt tcctggggtg cgccgcgccg ggttcctggg gtgcgccgcg
118561 ccgggttcct ggggtgcgcc gcgccgggtt cctggggtgc ggggtgcggg ggaccgcgcc
118621 ggggtactgc agggttcgca gggttcgggg gtactacctg gtttcctggg gtgtgccagg
118681 acgggttcct ggggtgccac cgctcctcga tacgtgtaaa tccaagagat ccgtcctccg
118741 tgccgccgcg cgcgtaatgc gcgagggggg tcggtctccc ctcttcttta tagcgtttcc
118801 tgcgaagggg gcgtaaccgt aggacaaact gcttatgtag gggttagcca cccatttccc
118861 ggggccgcgc cagaggtgag cgtggaccta gcatcccgct cccatttacc gaaaccaccc
118921 agaggcgaga ttccagggcc gtgactcact agctcccctc ccatcgaaca accacgcttg
118981 gctaacacgg ctggagtggc ggtgggcggg gcccctataa tcctggcccc catctactga
119041 aacgacccag tagaaaaatc ccaaccccat gactcatcag gccctattat atagaatatc
119101 ccagtagagt gacccagctg gtttccataa atggatatac ttccggaaaa cgaaggaggg

Fig. 3 (cont.)

119161 ttgaatacag ttgggggtag tccgctggta ttcccagctg aggttgcctt atttggtaat
119221 gcttccggaa ataccacctg agtaccccat tggtttatac cttgtttaat tgtagaatta
119281 cagctggatt tacccagccg ggtttacgca gctgcgtata cccagctgtg tttacgcagc
119341 ggggtttacg cagctgggta gacccagctg ggtataccta ctggaatagg ggctgcgatg
119401 actcagctgc gctaggatta aaggattata tatatatata taggaaaaat caaaacaaaa
119461 ctctaatcgc tgattggttc ccgctctggg ccaatcagct tgggagttct agggataggg
119521 gccaatggga ggcctccgaa tttgattgac ggctggggcg tccaatggaa tggcgcggtc
119581 gcctagctcg aacgggattg gtcggccgga tgggccaatg gcggctcgga aaactttgat
119641 tgacgggccg gcggaccaat gggagcgggg cagaggatta tgggggatta gcaaattcaa
119701 gatggcggcg cccatgaaat ggccaaaaat tataattttt cgagtcgctc acggtcccac
119761 ctagcggcgt gacctggagg tgaccccgtg cacccgggcg ctctgaattt ttctgcgcat
119821 gcgcgactcc tcatctacat aatttatgca cataaaagga ttagcgcatg caaattagtc
119881 agatagcagg gccatccaca ctttatgttg gccgcgtgcc aggcgccggc gtgggcgccg
119941 cgcgcgtgct ctctcagtcg cgcctagctg cttccaacag acaaaagcgg ggcgttagtg
120001 agggagtgcg cgcgctgcgc tgacttggcc gatttccagt gcatgctttg tcaccccagc
120061 gcgagaatgg aattttcatt attgagcaat ttgggcaccc tgggcacgat aaccatacat
120121 ggatacacgg gttccaaata tgcaaagtag acactaaggt accatttggc atatttggac
120181 gtcctgggca ggttagctac ccaccagaat atatgggact ctgggcagga tagccaccca
120241 caattgtttt gcgcccctct ttggccaggg gaccaaggtc gtatggttcg cgctacacta
120301 agcccgaacg ttcagctttg cgtgctttcg acgtccaggc ggctggcaca cgggccgtga
120361 gcgccagcaa catgggatca tggtagtaag atacagcata aatccccgtc cggtggcgct
120421 caacgccaat atgcgcggct gcgtggtatc tcatcggtgg gcacgcgtac ggtggtctca
120481 tgggtattgg acttgtaggc gaggggaggc gcatacgaca aaaattgccg ccgtgaaggt
120541 cgggaacccg cccgcgcttc cgcaaggcac ggggccgcat cggacacagg ctaagcatta
120601 aggatcataa caccgcccta gaaatgttta agctgtgacc aaagcgaacc tcgcatgagg
120661 catacgcgag cgtggaggta ggattcccaa ggctattgag agacggtggg tgaaatgatg
120721 aagaacacac agaacaataa cgggcgacta gataaaaaga ctcgctcaac agcccgaaaa
120781 ccatcagccc gaccgccgat ggattaggtg ctgctggaca agtctttcta aacccgcgca
120841 gggtttgtgt cgatccagac gcttacgaac gcccgcttta aaaacactat tcataattaa
120901 cagaagttga caccagcccg cagttaccca accttctatt tttttggagt gttgacaagt
120961 ttccatcgcc cgtttggcgt ttcccgcatg gtgtcaaatt agtgacgcac cctccccccg
121021 tcactatggg tttaccctga tttagtaagt aaaactgccg cccccgccca ctcatttttt
121081 taccctgtta tttgctgtat ttacatctac ggaccccctt ttggtgagat tgccgtggtt
121141 ctaaataacg ttgtggtttt cggacccttt cagggaccaa atcttttacg tgttgccaag
121201 gtagcatttg ctggacccgc ataggttttt gtggcaccag gttatggtct tatgagcggg
121261 cttgaccggc aagttccagg catcctaagt gcttgatgta gacccttagg gcaccaggga
121321 ctacctaggt caaactcccc cttagtcatg acgccgtgcc cacgaggttt gagaggcgta
121381 gacatccgtg tcgactgctg gacggaggta gtataatcag ctaggcctca gtattctatg
121441 taacaaatga atgccctaga gtactgcggt ttagctagtt atactgcccg gttccaccag

Fig. 3 (cont.)

121501 gcggcgttgt ggccacgggc ggttcgtcgc ttggacctgg aggggtgtca cattctgtga
121561 ccgcgacgtt gacgttagac acacgtcgct gccgtcctca gaatgtgata gcccatcaca
121621 ggcattgtag ctgttgcgtt ggttgggagt ttggggacca aatttctata attggtgtca
121681 ccgcggcagc tctagccctg gaagatctgg aagcttgctt caatggctca gatcgacccg
121741 gactacagtt agcgaagtag acccattata atcttaatct taaatctggt tgacggactt
121801 tcgcgccggg aacacgcagg tggcagcgga tgtgttttgc ccaaacacga gggttgcagg
121861 aaacaggtgc tgccggggat tatgtacagc ttacacccag tttcctgtaa tcgcccgcat
121921 ccggccgtcc tgggcagcac cgcaccctgc gtaaacaacc gcgtactttt tcctcctccc
121981 cccacccccca catccttcct cccaccctgc cagtccaacc cgcttcctgt tttattcgcc
122041 ttcaaacaga agcacgcatt ctaatgattc ttacaaaact tgttagtgtt tattaaatca
122101 gatacataca ttctacggac caaaaattag caacagcttg ttatctatgg tgtatggcga
122161 tagtgttggg agtgtgatgg gccggaaagg tgaaggccca ttagggtttg cacttggcgc
122221 tgtaggtcta ctcttgacaa agatctaagc attgacatta gggcatccac gtcagtggga
122281 cccagtaggt ctaagttttc catacagtac acccagtgta agaatgtctg tggtgtgctg
122341 cgagacccta tagtgtcctt gcttaaaaat atcaaagacc taatatccct cgcacacagc
122401 tccccgtcta cgtggagaac agtgagctga taagggctga aataactcat tgtgcccgct
122461 aggtggcgct ctaaaaaacg cgggtctaag tgaagcaggt cgcgcaagag gtctctgcga
122521 cctgcacgaa acagacattc cgctaacagg ggaaacgtta acctgccctc ctcctttaaa
122581 gctctaagag ctccaattaa ttgggccagt gtgggttgag gtatgaacac gtttaggagg
122641 aacaatacca cttccctgtc atccgtgccc agtttccgcg ccacctcaca gagaacctcg
122701 taagtggcca tggtgccggc ttgtatatgt gaaggcaccg atgtggaaaa acaaaggaaa
122761 atttattttt ccgccctaaa caaaatcaca agcttaatag ctgtccagaa tgcgcagatc
122821 aaagtccgaa acagatgtta ggatctgttc cactgccgcc tgtagaacgg aaacatcgca
122881 tcccaatatg cttgccagct gaggaactac ccccacccgag tgggtatcct gcggaatgac
122941 gttggcagga accaacagcg cacagcctgc agcgctgata atagaggcgg gcaatgagcc
123001 agtctttggg tcaactaagg cttttgtaat cagggtgttg acctcgtggt gccaaaagtc
123061 caggtgttgg gagccccccca gcaatttaag taacaagaag gaagtgacgt ccgtcgctaa
123121 gactgcctct gttcgccacg ccaacttctc aaggagttct ttctcctggt ctataagttc
123181 ttggcgggaa aaggagtctg ccgcggcata gcaaagtgaa ctggtagaaa taggcgtgag
123241 gcttctgagc ttactggcca ctaacaggca ggcgctccct gtcttttgaa agtgttcttt
123301 ggacacctgc tttataagta ggagtctgtc caaaagatta agggccaacg cgaccacgtt
123361 aggttctagg ttgtattcct ggcaaactga aaacatccat gtgcccagta acttacgcat
123421 atgcgaagta agagattgtt gaaaggtccc aaatacagag tcagaagtta aaaagcgcgg
123481 ctcaatttca agaatattgt aaaagatccg atcctcacat agcgtgggat ccagaagtcc
123541 cgagggcggg ttattggcag ttgccatata gagtggcgag cgtatgtggc ctacctgtag
123601 agcctggagt ttcagggtgc tctgtcaggt tctcccatcg acgacgctgg gccgcgagag
123661 tacgctagcc gttgtccgtg tgttcagttg aggtagatgg gtcgtgagaa cactgccccc
123721 cacacacacc agcacccatg gcgccaaatg caagtgcgga gcggcgacgg tggcttctag
123781 ggaggaaaaa gggggagagg tgtggctttt atgtcatttc ctgtggagag tccccaggac

Fig. 3 (cont.)

123841 cttggttttc ccctggctgg gttaatggca ggggcttttt aaacttaact atggaagatt
123901 gtaggtttcc tgccaggggg tgactagctt cccaggctag gcgggccatt tgtactttct
123961 tacttgtgtc tttgttctga caatacacat atacacaata agttatgggc gactggtctg
124021 gtccagggtg gggcaagcag gacacggggc ctgcctttac tcctccaaac tggaaggcct
124081 gagataattt tttaagtccg tatgggtcat tgccccaaaa aatcactgca aacttccatt
124141 gacactttgg atctcgtctt ccatcctttc ccaaaaagcg tctataaaag atgtgttgtg
124201 gcctagcttt cgcaggacaa tcatctatct gtctgtaagg gaccggtggt tgttggtatc
124261 ttggatgtgg ctttttgggg tgggtaactg gaacgcgcct catacgaact ccaggtctgt
124321 ggggtggtga tgttctgagt acatagcggt attcgcgaga tgggccaggt tgtgggtcat
124381 cgtctggtgt attatctcct ggtgggctac tggcaatttg ttcatgtgtg ctaacaacag
124441 ggtaatccac ttccatttcg tcctcggatg acgacccgtg caagattatg ggctcttcca
124501 ccgtctcctg ctcctgctgt tccaccccct gctgctcctg ctcttccacc tcctctaact
124561 cctgctgctc ctgctcttcc acctcctcta actcctgctc ttcctgctct tccacctcct
124621 ctaactcctg ctcttcctgc tcttccacct cctctaactc ctgctcctcc tgctcctcct
124681 gctcctgctc ttgctcctcc acctcctcta attcctgctc ttcctgctcc tgctcttgct
124741 cttccacctc ctgctcttgc tcttccacct cctgctcctc taactcctgc tcctgctcct
124801 ctaactcctg ctcctgctcc tctaactcct gctcctgctc ctctaactcc tgctcctgct
124861 cctctaactc ctgctcctgc tcctctaact cctgctcctg ctcctctaac tcctgctcct
124921 gctcctctaa ctcctgctcc tgctcctcta actcctgctc ctgatcctct aactcctgct
124981 cctgctcctc taactcctgc tcctgctcct cctgctgctc ctgctcctcc tgctgctcct
125041 gttcatcctg ctgctgctgc tcatcctgct gctgctgctc atcctgctgc tgctgctcat
125101 cctgctgctg ctgctcatcc tgctgctgct gctcatcctg ctgctgctca tcctgctgct
125161 cctgctcatc ctgctgctcc tgctcatcct gctgctcctg ctcatcctgc tgctgctcat
125221 cctgctgctg ctcatcctgc tgctgctcat cctgctgctg ctcatcctgc tgctgctcat
125281 cctgctgctg ctcatcctgc tgctgctcat cctgctgctg ctcatcctgc tgctgctcat
125341 cctgctgctg ctcatcctgc tgctgctcat cctgctgctg ctcatcctgc tgctgctcat
125401 cctgctgctg ctcatcctgc tgctgctcat cctgctgctg ctcatcctgc tgctgctcat
125461 cctgctgctg ctcatcctgc tgctgctcat cctgctgctg ctcatcctgc tgctgtggct
125521 cccgctgctg tggctcccgc tgctgtggct cccgctgctg tggctcccgc tgctgtggct
125581 cccgctgctg tggctcccgc tgctgtggct cccgctgctg gggctcccgc tgctgtggct
125641 cccgctgctg tggctcctgc tgctgtggct cctgctgctg tggctcctgc tgctgtggct
125701 cctgctgctg tggctcctgc tgctgtggct cctgctgctg tggctcctgc tgctgtggct
125761 cctgctgctg tggctcctgc tgttgtggct cctgctgttg tggctcctgc aggggctcct
125821 gctgctgtgg ctcctgctgt tgtggctcct gcaggggctc ctgctgctgt ggctcctgct
125881 gctgtggctc ctgctgttgt ggctcctgca ggggctcctg ctgctgtggc tcctgctgct
125941 gtggctcctg ctgttgtggc tcctgctgct gttgtgaact ttggatgctc aacgttttgt
126001 ttccatcgcc cccgtcctcc tcgtcctcct tcttgtcctc ctcctcgtca tcctcctcgt
126061 cctcattgtc ctcatcatcg tcatcctcct cgtcctcctc ctcctcgtcc tcctcctcgt
126121 cctcctcctc gtcctcctcc tcgtcatcct cctcgtcatc ctcctcgtca tcctcctcgt

Fig. 3 (cont.)

126181 catcctcctc gtcatcctcc tcgtcatcct cctcgtcatc ctcctcgtca tcctcctcgt
126241 catcctcctc gtcatcctcc tcgtcatcct cctcgtcctc ctcatctgtc tcctgctcct
126301 cctcatcatc cttattgtca ttgtcatcct tgtcaacctg actttccttg ctaatctcgt
126361 tgtccccatt atcctcgcca gcctgattat tttcggaaca ttctttttca ttcttggatg
126421 cttcttctgc aatctccgca aggagcacca acatggctgt gtcatcaccc caggatccct
126481 cagacgggga tgatgatcct atggagatgg gagatgtagg cggttggcgt ggcggagtat
126541 cgccatcgct ggatgatccc acgtagatcg gggactctgt ggcccatggg gggtacacac
126601 tacggttggc gaagtcacat ctagggggag agactggggg cgactgacat attgggttta
126661 gtgtagaggg accttggggg gacgatagcc ttctttttct caggctacgc agggtagacg
126721 gagctaaaga gtctggtgac gacttggagg gaggctcggg tggaggagtc gtgggtgagt
126781 gtggaggtgt agtctgctgc gagggtggcg gacgcatagg tgttgaagag tctggccttc
126841 ctgtaggact tgaaagcggt ggcctttgag aagactctgg agactgcgtg ggtggcaatg
126901 caggagatgg agaatgagta tccgtggtcc ccggagacac aggatgggat ggagggattg
126961 gggaggaaga cgtggttacg gggggtaaga gtgccggtgg aggtaaaggt gttgcgggag
127021 cgggtgaagg aatgggagcc accggtaaag taggactaga cacaaatgct ggcagcccgg
127081 atgtgaacac tgtgggactt ccaggtatag gcaaggtgtg gggtccacat tcccggccgt
127141 cgatggagtc ggcgacatgc ttccttcgcg gttgtagatg taggtcatcg ccaaggtcac
127201 atctttccgg agacctgttt cgtttcctac aacttcctct cgttaagggc gcgccggtgc
127261 tccgtcccga cctcaggcgc attcccgggg gcgccatcct cgggaaatct ggtctgacaa
127321 ccaaagtaaa attatggagg cggtggcagt atattcacat tatgcaatac ccgtagtgac
127381 cacaaggggg agctctcaga caattaagcg gttacacaca gtagcaggct gcagtaccgc
127441 ccatggccac aggatgtaga tcgcagacac tgaaacgctg aaacacagca ttaagctgca
127501 ataccgccga tggccaccag atggcacgcg ccgccagcaa atttaagtcc tggtggctca
127561 cctgccaggt aaacaaggtt aaagtgggtt tgctggcctt gcgttgccat ggatgctacc
127621 taggcaagtc cagatatata atccgggcgt gagaaacaga aacggccaat aacccatgtt
127681 tttcgaaaac caccacacac cttaacacaa atcatgtaca cctggtatta ctatttccca
127741 cacatcttat agcatttcaa agataagggt gccttacggg ccgcccgaaa caagtgggcg
127801 ggcgctactc actgtttata agtcagccgg accaagctgc tgctcttggg gacgtgactg
127861 cttcgtggcg cagctgcctc caaatgatac acacattttt tgattgtccc gggcgccgcg
127921 tagtggaggg cggagttata tcaagctact ttctgattgg tgccccaggc aggactgcca
127981 taaaaactga agaaggcgtg tctgctttgc agaatttacc ccccactgtg ctcccggttg
128041 ctggcaccgg ttcagtggtc cgacctgtcg tctgtgctcc cccgtggacg acgccgagtg
128101 cctctcgggg gtccatgtct agcctcttca tttcattacc ttgggtggcg ttcatctggc
128161 tagccctcct tggcgcggtt gggggtgccc gcgttcaggg gcccatgcgg ggctctgctg
128221 ccctcacctg cgccatcacg ccccgtgctg acatagttag cgttacctgg caaaaaaggc
128281 agctccccgg tcccgtaaac gtcgccacgt acagccattc atatggggtg gtggttcaga
128341 cccagtaccg ccacaaggca aatataacct gtcctgggct ttggaactct acccttgtta
128401 tccataacct tgcagtggat gatgagggct gttacctgtg tatctttaac tcatttggtg
128461 gccggcaggt gtcatgcaca gcctgcctgg aagtgacatc tccccctact ggacacgtgc

Fig. 3 (cont.)

128521 aggtaaatag cacagaagac gcagacaccg tcacctgttt ggcaactggt cgcccacccc
128581 ccaatgtcac ctgggccgca ccctggaaca acgcctcttc tacccaggag cagttcactg
128641 acagtgatgg tcttacagtt gcgtggagga ccgtgaggct gccgcgtggg gataatacca
128701 ccccaagtga gggaatatgt ctcatcacct ggggaaatga gagcatatca atcccggctt
128761 ctattcaagg ccccttggcc catgaccttc ccgcggccca gggaactctt gccggggttg
128821 ccattactct ggtgggccta ttgggatat tcgcattaca tcattgccgc cgcaagcagg
128881 gcggtgcatc acctacttca gatgacatgg acccccctatc cacccagtga ctagatggac
128941 accccgtgaa ccgtcgtgct tacccacccc cttctgattc tgacagacaa cactactatg
129001 tcccaaagac tgttttttac agcccgatgg cccttcaggc ctccttgagt gtctagctgg
129061 tcccgtggtc attgtgtggt ttggcagtca cttccccatt ttggtgtcgc gttttgggtt
129121 ttgccctgcc cccagccaac gtggatcata ttctttcccg tcaggggagt gacaagctat
129181 aggacagaaa ggtcacctgg cccaaacgga ggatcctagg tgggtgtgca tttattagac
129241 gttggtgtgt tgaaggacgg atcaggcggg gaggaggggg tgggggagac ttactgcagc
129301 actaggttag gttgaaagcc ggggtaaaag gcgtggctaa acaacaccta tactacttgt
129361 tattgtaggc catggcggcc gaggatttcc taaccatctt cttagatgat gatgaatcct
129421 ggaatgaaac tctaaatatg agcggatatg actactctgg aaacttcagc ctagaagtga
129481 gcgtgtgtga gatgaccacc gtggtgcctt acacgtggaa cgttggaata ctctctctga
129541 ttttcctcat aaatgttctt ggaaatggat tggtcaccta catttttgc aagcaccgat
129601 cgcgggcagg agcgatagat atactgctcc tgggtatctg cctaaactcg ctgtgtctta
129661 gcatatctct attggcagaa gtgttgatgt tttgtttcc caatatcatc tccacaggct
129721 tgtgcagact tgaaattttt ttttactatt tatatgtcta cttggatatc ttcagtgttg
129781 tgtgcgtcag tctagtgagg tacctcctgg tggcatattc tacgcgttcc tggcccaaga
129841 agcagtccct cggatgggta ctgacatccg ctgcactgtt aattgcattg gtgctgtcgg
129901 gggatgcctg tcgacacagg agcagggtgg tcgacccggt cagcaagcag gccatgtgtt
129961 atgagaacgc gggaaacatg actgcagact ggcgactgca tgtcagaacc gtgtcagtta
130021 ctgcaggttt cctgttaccc ctggccctcc ttattctgtt ttatgctctc acctggtgtg
130081 tggtgaggag gacaaagctg caagccaggc ggaaggtaag gggggtgatt gttgctgtgg
130141 tgctgctgtt ttttgtgttt tgcttccctt accacgtact aaatctactg gacactctgc
130201 taaggcgacg ctggatccgg gacagctgct atacgcgggg gttgataaac gtgggtctgg
130261 cagtaacctc gttactgcag gcactgtaca gcgccgtggt tcccctgata tactcctgcc
130321 tgggatccct ctttaggcag aggatgtacg gtctcttcca aagcctcagg cagtctttca
130381 tgtccggcgc caccacgtag cccgcggatg tctacgtgcc cttccccctt aatttaatct
130441 agcctcccgt tcccatgatg cagagaggcg aatttggttt gtacacagat gtgactatgt
130501 atttgtttta ttatgcgatt aaatgagggg tctgatccca aaagcaatgt ttagtggtgg
130561 tcgttgatct tcttgacgct ccataggtag attgactgga acgccatggc ccacggggac
130621 atggacaggg gtgttaggtc tggtggaaca tgctgccact gccacggatg gaacatcaga
130681 gatgggtcta tgatcagggc agcgtgtcgc ccgtcactgg atgtaagtcc ggccaccgtg
130741 gagttgcctg tggggtttct gggatagtgt ctggctggca gggtctcatc cgcggcattt
130801 ccatggtagg tgagggttat ctcgcctcgc tgtctcagta tgtactcgag ggcgtcctgc

Fig. 3 (cont.)

130861 tcgtaccgga cccccaggta ctctccctgg gcccagctgg gcagcaccgt cccccgcaac
130921 actcggagga aaacgctctt agtgttctga gggatctgta tgtttagcca gtggctgtca
130981 tacagcttgg acacgttggt ctccaggttt accgcccagc gctggggtgg tgtgggtccg
131041 tacgtgtatg gtgaggattc cgaccggccc actacaccca gggccaccag cagctggaag
131101 cccacctcgc cacagcagat ggagaatgtg tcgggtctgt ttagaaactc tgtcagggtg
131161 gaggcacagg tagggtcgtt acacagcgcc aggacccatc ccctggcgct ggcgtagctg
131221 gcctggcagc ctgttctgag acatgtaatc agaccagaga accccgacaa ggactgtcct
131281 cgtttaagct cttccacagt caccgtggcc acctcaaagc ccgtgttctg caacgcggcc
131341 atgagcgcgt acggggcact gctcccaggc agcaccaacg cggccacacg gcgcggggag
131401 gtggggcacg aaaacaggcg cagctgactc ccaaggcaca tggcccttag gctgcccagg
131461 tgatgctcca gacgacccag gtccttcctg tgcatgtcct ccagtgggtg caggggaggc
131521 gtcaccaggt tccacatttc gtcagaaaag gaggtccatg agacttgcaa ggaagtcagg
131581 gtctcttgaa acacaactgt ctcgttctgc aaaaccgtga cgttgttgcc ttgtccctcg
131641 gggccaacgg tgcccagtgg gtgtgccacg cagcggtagt ccctggccgc ccgcagcacc
131701 tctgacaagt gtacctgggg cacctcaacc agtgccccag gggtctctga aaccataagt
131761 tcgagcgggt tagggtgggc gggtagtgag agctgcagtc ccctgcagcc ggccagggcc
131821 atctcgattg cagatgggag aagccctccg tcccctatgt cgtgcccaga tacaatgagc
131881 ctcttggaca tcaggtactt aacaagcatg aacaggctgg cgaccgtgga cgggttcaga
131941 gggggtattg ggtgcctgga tgccaggaag ttgtgctcga aggtggaccc ggctatgaga
132001 cagctctgat tcacggccag gtataccagg gcgttgcctt cgacctttac gtccggggtg
132061 accctgtatc tggatccctt gacctcggcc cagctggtaa acaccaccga gttgaaggga
132121 aggacctcca ccgtttcttg ctgttgtgtg atgcgcacat ggcgctccga aagcgtcgga
132181 gagctggcag ccgaggagat ggacagtgcc actcccagct cccggcagaa ttccttgcag
132241 gcgaagaggc actcctgtag gaggccggct tggtggtcct ctggactcca cgccacggcg
132301 ccagttagca ctacgtcctg gagcttggac acgggactga acatgaggtt ggtgagagcc
132361 tcggtgatgg cataggtggc cccggtggat acattagtag ccatcttgta ggcctgctcc
132421 cccatggcca ttgcctgacc cctccacgct ggcactggaa gcagctcctg gggcagggcc
132481 ttcacccagg tctcgaagtc cttgtgtagg aggttggcca tggacggagt gatggcctcc
132541 accgtgtcgg gcactctggg cgccaccctc tcggccagca tggacgagtg cagcaccagg
132601 tggtagtctg aaaccggtat gtccaggggt cccacgccag cctgttgggc gatgaggccg
132661 ttggagcatc ggtccatgtg tcgcgtaaag aactccttgc tgccaaccgt cgagtggcga
132721 agtaactggt ggattgtgga gccggtggca aaaaggcccc agtcaacatc ctcggggtgc
132781 cccgagacgc ggacaccatc ggacagcgcc agccaggggg acgggggggt ggacgacggc
132841 tggtctacag agaagaccct cgtggtctcc ccggtcaggt cgtctactat tctgatgcct
132901 gggtgctccg aggtcctccc gaggaccgtt acctggcacg cgcacaggcg cgcggcgcgc
132961 tgcagtacct ccaacggggt ctcgcccaga tccccaggca ccgcgcccga ctctgccacc
133021 accgcaaaca ccagggagca atacacgttg agaaagtgct ctgccaccgc cgccttcacg
133081 gcatccggac cggccgcggg atccgcaggc aggtgggtgc gcacctcgtc gggtagcttg
133141 gagacaaaca gctccaggcc ggtccgcggc gccagcgcct gcaggtgcct caccaccggg

Fig. 3 (cont.)

133201 gccgggtcat gcgatctgtt tagtccggag aagatagggc ccttggcaag ccgctggacc
133261 agcttcaggg tctccaagat gcgcaccgca ttgtcggagc tgtcgcgata gaggttaggg
133321 taggtgtccg gtccatccgt gggctcaaac ctgcccagac acaccactgt ctgctggggg
133381 atcatccttc tcagggagat gcattctttg gaagtagtgg tagagatgga gcagactgcc
133441 agggcgttgc caggagtggt ggcgatggtg cgcaccgttt ttaagaaacc ccccagggtg
133501 gggactcccg ctccctgcag catctcggcc tgctgtacgc ccttggcgaa tatgcgacgg
133561 aatcggctgt gcgcacgggg tcccagggcc ggttcggtgg catacaggcc ggtgagggcc
133621 ccctgtgtct gtccgcctgg aaacagggtg ctgtgaaaca gcaggttgcc aaggccgcga
133681 atacccctct gcacgctgct gtggacgtgg gtgtacgctc cgtggatccc gaacgcctgt
133741 ctggcacagt tccagggcca ccgttccatg gtgcatcttc ccggtatcac aaagtacctg
133801 gccacgttat aattgtcccc ggttgaagcc tgcaccgcca gcggtagcag gtctgccccc
133861 agggatatca taacagcctg cataatgaca tcatcttcaa tgtgtggcct agccacgggc
133921 tggggaccct cgggcacttc caacccctcg tacggtacca ggtcggtatt ttgtgtaaat
133981 gccctgataa actgaggtgg gtgtggttct agcagggtct gtgtgatttt ggacaccagg
134041 tgcctgccca cttccactct agcccactcc tgcaatccta gctcttgcag cagaactgca
134101 agctctgttg acaatgttgt gggccggtgg tgcatgtttg gcccgtagcc aaaggataca
134161 acacgctcgc tcccccgtgg cacagaccgc ctgatgacat ggggatatcc aaggagcggt
134221 gacagcacag cgagcaccgt ctgtatttcc acatcccgtc tctctcgctc ctccctcgaa
134281 gtgggaggtc ttcggaaagt tatccatagc agatagtagc ctccggtgcc accgggtacg
134341 agagtgagtg tgcccgtacg gcttgtataa aagttcacaa aagcttcctc atccgcggtg
134401 agatcactct ccaaccacag cccagtgacg tcgtaggcca tgcctagagg gcgcaccgcc
134461 cccggggaca ccctctgtag tcaggctgcc gagaaacccg cgagatctct ggggagtagg
134521 aagaaactta gaatccccaa atatgtcgca gtcacaggtt gtcgggcaga gtctgtttcc
134581 gctttcatgg gatccacagt tacttgtagc catgtcacta acctcaaata ctcaaaaaaa
134641 gctatcgatg gaaaaatgct gtggtcctag gttagtccgt gggaaacaaa acttcctcat
134701 acacttcatc tgcaggctga aatggtggcg gatccagact ccttacacca cagttgctca
134761 cattagagat acctgattgg ttaatacaag cggacgcacg cgttggtgga ggcgtgttgt
134821 cgcccaagat actagcatag gtgactgtgc gttcgctatg tagttgctgc atttcaagtt
134881 gggtcgttac ttctgtgttg caaaccctta ctggagataa tgccatgtct gttgtggaac
134941 ttaaaatacg cgagtgtata acatttctag atggtagagg tggtaaacgg cgagctaaat
135001 gattaacatc gggacatatc ctgcctgcat gagcatgtgg tgtgtcgtgt ggtgtatata
135061 ttggtaatct tgttgttaca ttgttgaacg acacaagtct gctctctcgg tagagataac
135121 ccaccagtac ggcttggcca gtacctaata agaaaaaata aaatcgttaa tctctgtttt
135181 tatgtggcgc tggtgttcca attataaata aaaacacaac tcacttaata tcacaattac
135241 acaaatcagt cctgaagtaa cacctgtagt ccaaccgtca gtgtagagca ggactaactt
135301 aacacagcat ccagcacatg tccatgctaa ggaaataaac caaagttatg tttcggtttg
135361 ctttatgacc agggagctgc tacccaggta caaaaaatcc ttacccaaaa atagaaacag
135421 gaagccacca gagagtgaag ctttgtgaaa gctttgccag cagaagaaac aatataataa
135481 aaagccacag cctgctagta atgttatact ccctgtaaat aaaaaatatg gacagtaata

Fig. 3 (cont.)

135541 atttatgaca cccaataagt atgtggaaaa aatgtaatgt aaaccactat actggtaaaa
135601 acataccttc gttattggtg tcttgttcgc gctttataaa cagtatccct attgttgtgg
135661 ttagtgtaac caacactcct ccttgtaaaa gtaaaaatga cataagcccc ttagttgatc
135721 caatccaatg tcgtttcatt gttataaaca agccggtcat acctgtaata aagttattca
135781 ttacaaaatg ttataatagt attggtaatg tttagttaag ataatgtaaa cttcacagta
135841 gtcatatacc aatatgtatg cagcttatgc atcctgcgat gattacagaa aggcatgaat
135901 gggaaacgca aaaaaaggcc ggtgttgcct tgagtatacc tgtagtaaaa aataaataat
135961 attgttggtt gcaatgctta ggtgcaagca gacataattg catagcagta aaaaccagac
136021 ttaccaccac atattgcaaa cacacatgca gcgagcttga gacaaggccc attatctgtt
136081 gcaaagatat gtataaaaaa aacaagcaac aatgtccata atggcaaaaa aaactggcaa
136141 tgtgtccagt tgttgtaaat ctgcaatccc attgagaata taagtaccaa caccataaca
136201 atgcacagta atccgctatc aatagtgcat ttaacgactc ttaatgttcc accaagtgat
136261 agaatggctg aaaaacacat acaggggaat tacgtttttt taaaaaattg gaaatattag
136321 atacataatt tttatttaat aaaaaacctt tagtaaaact taccagtaat tatagacaat
136381 aaacttataa tacaaacaca aacagtactc aaagtacttt gagtagagaa actccaactg
136441 gcaaaggcaa tacatcctaa aacaaaagac aaatacacga gacatttaaa caatgtatac
136501 ttagaaagaa ataagttaaa catttaaaaa atgtaactta ccaacaatta tagatggtcc
136561 aatgggaggg gaagcttgaa aacgttgttt ttttgactgc acatatatgt tgttattgta
136621 caaaaaagtt ggtagtaaac acttatgtta ctgagcaaaa atatggtgtt ttgtaaattt
136681 atagttaaaa gacaaaacat aatagacaaa cacccacaac atgttataag tgctgcaaac
136741 caagtacccc acaggtattt tttgtaattc attgtagaca aaaagcccaa ggcccaaaaa
136801 tgaagtggac aaaagaaata tgtaattaag tgtagttgga caaggaatta tatagctgga
136861 tgagttagtt ttgcacagaa ccagacatcc tatttttgtt tggaaaccta aaatccggat
136921 gaagggctta taaaatggca cagctgcaaa aagctgataa tgtaacactg catcctggtg
136981 tttttgattg tagcggaaaa atgtaataaa ttttacagac agttttgcct actgagaaca
137041 tgttgaaaaa aaggcactaa gggctttttt gccaaaggaa aaatgccccc gtggggttag
137101 gggaaagggg ggatggggtg atgggggaat ggtgggaaag gggggatggg gtgatggggg
137161 aatggtggga aaggggtgat ggggtgatgg gggaatgggg ggaaaggggg aatgggggga
137221 aagggggaat gggggggaaag ggggaatggg gggaaagggg ggatgggggg aaagggggaa
137281 tggggggaaa gggggaatgg ggggaaaggg gggatggggg gaaaggggga atggggggaa
137341 agggggggatg gggggaaacg ggggatgggg ggaaaggggg gatggggggg aaagggggga
137401 tggggggggaa agggggggatg ggggggaaag gggggatggg ggggaaaggg gggatgggga
137461 aggggggggg gagggggaag ggggtgaagg gggaaggggg gaggcgaa

Fig. 3 (cont.)

Human gene for granulocyte-macrophage colony stimulating factor (GM-CSF).

ACCESSION X03021

VERSION X03021.1 GI:31858

TITLE Structure of the chromosomal gene for granulocyte-macrophage colony stimulating factor: comparison of the mouse and human genes

JOURNAL EMBO J. 4 (10), 2561-2568 (1985)

1 ttctcagagt ggctgcagtc tcgctgctgg atgtgcacat ggtggtcatt ccctctgctc
61 acaggggcag gggtcccccc ttactggact gaggttgccc cctgctccag gtcctgggtg
121 ggagcccatg tgaactgtca gtggggcagg tctgtgagag ctcccctcac actcaagtct
181 ctctcacagt ggccagagaa gaggaaggct ggagtcagaa tgaggcacca gggcgggcat
241 agcctgccca aaggcccctg ggattacagg caggatgggg agccctatct aagtgtctcc
301 cacgccccac cccagccatt ccaggccagg aagtccaaac tgtgcccctc agagggaggg
361 ggcagcctca ggcccattca gactgcccag ggagggctgg agagccctca ggaaggcggg
421 tgggtgggct gtcggttctt ggaaaggttc attaatgaaa acccccaagc ctgaccacct
481 agggaaaagg ctcaccgttc ccatgtgtgg ctgataaggg ccaggagatt ccacagttca
541 ggtagttccc ccgcctccct ggcattttgt ggtcaccatt aatcatttcc tctgtgtatt
601 taagagctct tttgccagtg agcccagcta cacagagaga aaggctaaag ttctctggag
661 gatgtggctg cagagcctgc tgctcttggg cactgtggcc tgcagcatct ctgcacccgc
721 ccgctcgccc agccccagca cgcagccctg ggagcatgtg aatgccatcc aggaggcccg
781 gcgtctcctg aacctgagta gagacactgc tgctgagatg gtaagtgaga gaatgtgggc
841 ctgtgctagg caccagtggc cctgactggc cacgcctgtc agcttgataa catgacattt
901 tcctttttcta cagaatgaaa cagtagaagt catctcagaa atgtttgacc tccaggtaag
961 atgcttctct ctgacatagc tttccagaag cccctgccct ggggtggagg tggggactcc
1021 atttagatg gcaccacaca gggttgtcca ctttctctcc agtcagctgg ctgcaggagg
1081 agggggtagc aactgggtgc tcaagaggct gctggccgtg cccctatggc agtcacatga
1141 gctcctttat cagctgagcg gccatgggca gacctagcat tcaatggcca ggagtcacca
1201 ggggacaggt ggtaaagtgg gggtcacttc atgagacagg agctgtgggt ttggggcgct
1261 cactgtgccc cgagaccaag tcctgttgag acagtgctga ctacagagag gcacagaggg
1321 gtttcaggaa caacccttgc ccacccagca ggtccaggtg aggccccacc cccctctccc
1381 tgaatgatgg ggtgagagtc acctccttcc ctaaggctgg gctcctctcc aggtgccgct
1441 gagggtggcc tgggcggggc agtgagaagg gcaggttcgt gcctgccatg gacagggcag
1501 ggtctatgac tggacccagc ctgtgcccct cccaagccct actcctgggg gctgggggca
1561 gcagcaaaaa ggagtggtgg agagttcttg taccactgtg ggcacttggc cactgctcac
1621 cgacgaacga cattttccac aggagccgac ctgcctacag acccgcctgg agctgtacaa
1681 gcagggcctg cggggcagcc tcaccaagct caagggcccc ttgaccatga tggccagcca
1741 ctacaagcag cactgccctc caaccccggt gagtgcctac ggcagggcct ccagcaggaa
1801 tgtcttaatc tagggggtgg ggtcgacatg gggagagatc tatggctgtg gctgttcagg

Fig. 3 (cont.)

1861 accccagggg gtttctgtgc caacagttat gtaatgatta gccctccaga gaggaggcag
1921 acagcccatt tcatcccaag gagtcagagc cacagagcgc tgaagcccac agtgctcccc
1981 agcaggagct gctcctatcc tggtcattat tgtcattacg gttaatgagg tcagaggtga
2041 gggcaaaccc aaggaaactt ggggcctgcc caaggcccag aggaagtgcc caggcccaag
2101 tgccaccttc tggcaggact ttcctctggc cccacatggg gtgcttgaat tgcagaggat
2161 caaggaaggg aggctacttg gaatggacaa ggacctcagg cactccttcc tgcgggaagg
2221 gagcaaagtt tgtggccttg actccactcc ttctgggtgc ccagagacga cctcagccca
2281 gctgccctgc tctgccctgg gaccaaaaag gcaggcgttt gactgcccag aaggccaacc
2341 tcaggctggc acttaagtca ggcccttgac tctggctgcc actggcagag ctatgcactc
2401 cttggggaac acgtgggtgg cagcagcgtc acctgaccca ggtcagtggg tgtgtcctgg
2461 agtgggcctc ctggcctctg agttctaaga ggcagtagag aaacatgctg gtgcttcctt
2521 cccccacgtt acccacttgc ctggactcaa gtgtttttta tttttctttt tttaaaggaa
2581 acttcctgtg caacccagat tatcaccttt gaaagtttca aagagaacct gaaggacttt
2641 ctgcttgtca tcccctttga ctgctgggag ccagtccagg agtgagaccg gccagatgag
2701 gctggccaag ccggggagct gctctctcat gaaacaagag ctagaaactc aggatggtca
2761 tcttggaggg accaaggggt gggccacagc catggtggga gtggcctgga cctgccctgg
2821 gcacactgac cctgatacag gcatggcaga agaatgggaa tattttatac tgacagaaat
2881 cagtaatatt tatatattta tatttttaaa atatttattt atttatttat ttaagttcat
2941 attccatatt tattcaagat gttttaccgt aataattatt attaaaaata tgcttctact
3001 tgtccagtgt tctagtttgt ttttaaccat gagcaaatgc cat

Fig. 3 (cont.)

CANCER IMMUNOTHERAPY WITH A VIRAL ANTIGEN-DEFINED, IMMUNOMODULATOR-SECRETING CELL VACCINE

This application is a national phase of international patent application no. PCT/US2003/029684, filed Sep. 19, 2003, which claims the benefit of U.S. patent application No. 60/411,990, filed Sep. 19, 2002, the entire content of which is incorporated herein by reference.

STATEMENT REGARDING FEDERALLY SPONSORED RESEARCH AND DEVELOPMENT

A sequence listing is submitted herewith on compact disc (file name: "P2142US_Seq.ST25.TXT", created Mar. 24, 2006, File size: 506 KB). The material contained on the compact disc is explicitly incorporated herein by reference in its entirety.

This invention was made, in part, as a result of funding from the National Cancer Institute (NCI) Supplement through the University of Alabama for work sponsored by the AIDS Malignancy Consortium, grant no. 3U01CA70019-07S1, from the NCI through Project 4, EBV Malignancies, Bone Marrow Transplantation in Human Disease, grant no. PO1 CA15396-28, and from the NCI through grant no. P50 CA 96888. Therefore, the U.S. government may have certain rights in the invention.

FIELD OF THE INVENTION

The present invention relates to cancer immunotherapy and cancer vaccine development.

BACKGROUND OF THE INVENTION

Despite ongoing efforts to define immunologically relevant tumor antigens, very little is known about most tumor rejection antigens for the majority of human cancers. Consequently, most cancer vaccine approaches currently use tumor cells as a source of antigen. Early generations of cell-based cancer vaccines have consisted of killed tumor cells or tumor cell lysates mixed with adjuvants, such as *Bacillus Calmette Guerin* (BCG) and *Corynebacterium parvum*, in an attempt to amplify tumor-specific immune responses (Berd et al., J. Clin. Oncol. 8: 1858-1867 (1990)). Subsequently, genetically modified tumor vaccines replaced the most complex and inconsistent mixtures of tumor cells and bacteria. Currently, the most popular genetically modified cell-based vaccines take advantage of the large set of cloned genes encoding cytokines and co-stimulatory molecules (Pardoll, Ann. Rev. Immunol. 13: 399-415 (1995)).

Among the different cytokines used to modify tumor immunogenicity, granulocyte-macrophage colony stimulating factor (GM-CSF) appears to be the most potent (Dranoff et al., PNAS USA 90: 3539-3543 (1993)). GM-CSF induces the differentiation of primitive hematopoietic precursors into dendritic cells (DC), a type of antigen-presenting cell (APC) that initiates the most potent T-cell responses (Banchereau et al., Nature 392 (6673): 245-252 (1998)) and promotes DC recruitment and differentiation at the site of vaccination. Thus, DC play a central role in priming immunological response.

GM-CSF-secreting cellular vaccines have been shown to eradicate small, pre-established tumors in mice (Dranoff et al., supra; and Levitsky et al., J. Immunol. 156: 3858-3865 (1996)). Furthermore, promising results have been obtained in human patients afflicted with melanoma (Soiffer et al., PNAS USA 95: 13141-13146 (1998)), prostate and renal cell carcinoma (Simons et al., Cancer Res. 59: 5160-5168 (1999); and Simons et al., Cancer Res. 57: 1537-1546 (1997)), and pancreatic cancer (Jaffee et al., J. Clin. Oncol. 19: 145-156 (2001)). These trials consistently demonstrated systemic anti-tumor immunity in patients and suggest an improvement in overall survival in those patients in whom evidence of vaccine efficacy was demonstrated by the development of tumor-specific delayed type hypersensitivity (DTH) responses (Jaffee et al., supra).

Unfortunately, modification of autologous tumor cells to express a cytokine, such as GM-CSF, is highly individualized, expensive, and labor-intensive. Therefore, simpler approaches that maintain the immunological activity of paracrine cytokine production have been developed. One such approach utilizes a universal bystander cell line altered to produce a large and stable amount of GM-CSF (see, e.g., Levitsky et al., U.S. Pat. No. 6,464,973 and Int'l Pat. App. No. PCT/US99/02253) in combination with an antigen of the cancer to be treated, such as, for example, tumor cells isolated from the patient (Borrello et al., Hum. Gene Ther. 10: 1983-1991 (1999); Borrello et al., Blood 95: 3011-3019 (2000)). This approach obviates the need for in vitro passaging or modification, such as by transduction, of each patient's tumor cells, thereby guaranteeing a constant amount of cytokine production without any intra- or inter-patient variability, while utilizing the patient-specific antigenic repertoire. An allogeneic, GM-CSF-secreting human erythroleukemia cell line, namely K562, is currently being used in two phase I trials at Johns Hopkins University for vaccination of multiple myeloma and acute myelogenous leukemia (AML), in combination with irradiated autologous tumor cells.

Vaccination of mice afflicted with lymphoma with a mixture of autologous tumor cells and GM-CSF-producing MHC class I- and MHC class II-negative cells, namely B78H1/GM-CSF cells, primed an anti-tumor immune response. The anti-tumor immune response was equivalent to or better than those achieved using autologous tumor cells directly transduced to secrete GM-CSF.

GM-CSF-secreting cellular vaccines, which are currently in use, are not specific for a defined tumor antigen. Hence, it is not possible to target such vaccines and evaluate fully their anti-tumor immune responses. It is an object of the present invention, therefore, to provide a GM-CSF-secreting cellular vaccine that is specific for a defined tumor antigen. Such a vaccine will enable one to evaluate more fully anti-tumor immune responses. This and other objects and advantages of the present invention, as well as additional inventive features, will become apparent from the detailed description provided herein.

BRIEF SUMMARY OF THE INVENTION

The present invention provides a human cell line, which lacks major histocompatibility class I (MHC-I) antigens and major histocompatibility class II (MHC-II) antigens and which has been modified to comprise and express (i) a nucleotide sequence encoding an immunomodulator and (ii) a nucleotide sequence encoding an antigen of Epstein-Barr virus (EBV). Further provided is a composition comprising a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV. Still further provided is a composition comprising an immunomodulator and a human cell line, which lacks MHC-I and MHC-II antigens and which has been modified to comprise and express a nucleotide sequence encoding an antigen of EBV.

Also provided by the present invention is a method of inducing or stimulating an immune response in a human to an EBV-associated cancer. The method comprises administering to the human the aforementioned human cell line or one of the aforementioned compositions in an amount sufficient to induce or stimulate an immune response to the antigen of EBV expressed by the human cell line, whereupon an immune response to the EBV-associated cancer is induced. Alternatively, a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer. Also, alternatively, an immunomodulator and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer.

BRIEF DESCRIPTION OF THE DRAWINGS

FIG. 3 is a compilation of various nucleotide (genomic, mRNA, cDNA; etc.) sequences (SEQ ID NOS: 1-60) that can be used in the context of the present invention.

DETAILED DESCRIPTION OF THE INVENTION

Figure 1:
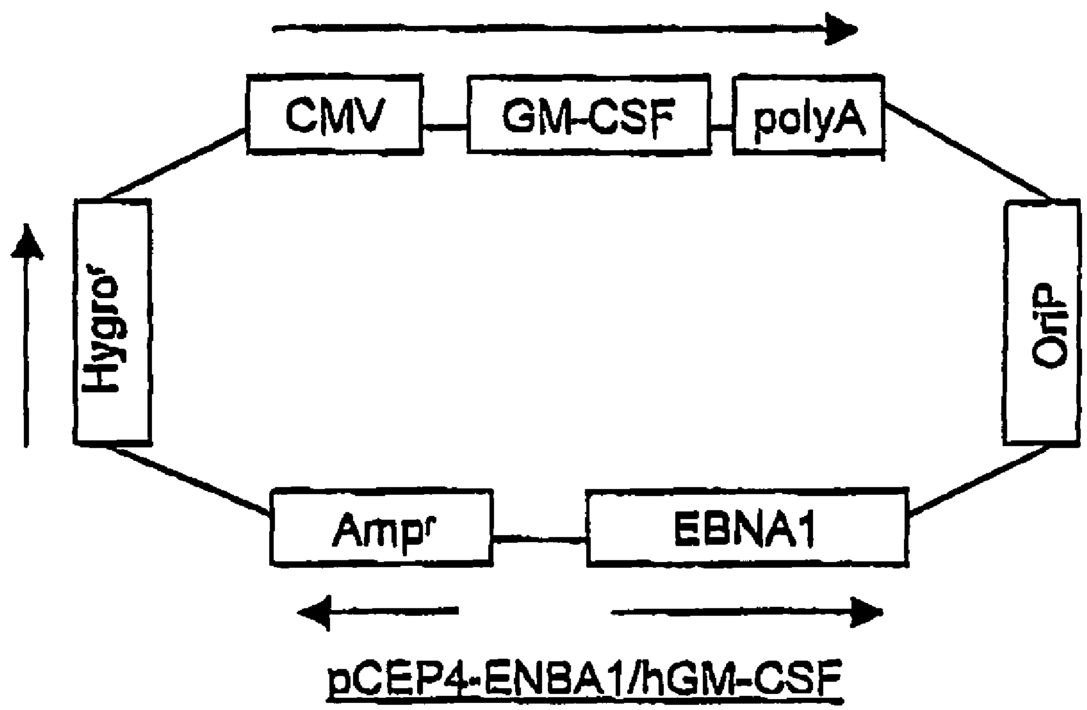
FIG. 1 is a diagram of a bi-cistronic plasmid (arrows indicate direction of transcription) containing the human GM-CSF gene (GM-CSF) operably linked to the CMV promoter (CMV) and a polyA tail (polyA), a hygromycin resistance gene (Hygro$^r$), an EBV EBNA1 gene (EBNA1), an EBV origin of replication (OriP), and an ampicillin resistance gene (Amp$^r$). The plasmid is designated pCEP4-EBNA1/hGM-CSF.

The present invention provides a human cell line, which lacks MHC-I antigens and MHC-II antigens and which has been modified to comprise and express (i) a nucleotide sequence encoding an immunomodulator and (ii) a nucleotide sequence encoding a viral antigen, in particular an antigen of a virus associated with a disease, such as cancer, e.g., EBV, human papilloma virus (HPV), or Kaposi sarcoma herpes virus (KSHV; also known as human herpes virus 8 (HHV8)). The human cell line can be any suitable cell line. Theoretically, any human cell line that is capable of paracrine production of an immunomodulator can be used. The capacity for paracrine production of an immunomodulator is not required when the cell line will not be used to express an immunomodulator in accordance with certain embodiments of the present invention as set forth herein.

The cell line can naturally lack MHC-I and MHC-II antigens or it can be manipulated or modified so that it does not express MHC-I and MHC-II antigens. In this regard, it will be understood by one of ordinary skill in the art that a cell line is deemed to lack MHC-I and MHC-II antigens if it does not constitutively express such antigens under normal biological conditions. However, a cell line that does not constitutively express MHC-I and MHC-II antigens can, under certain artificially created conditions, such as conditions that can be created in vitro, be induced to express MHC-I and/or MHC-II antigens. Such cell lines are considered to lack MHC-I and MHC-II antigens for purposes of the present invention. Likewise, cells having inactivated MHC antigens are also considered to lack such antigens for purposes of the present invention.

The cell line preferably grows in defined medium. One of ordinary skill in the art appreciates that defined medium is medium, the composition of which is known. In other words, the identity and amount of each and every component of the medium is known. Defined medium does not contain serum inasmuch as the composition of serum is undefined. Preferably, the cell line grows as a suspension.

A preferred human cell line for modification in accordance with the present invention is K562, which is deposited with the American Type Culture Collection (ATCC) as CCL-243. The K562 cell line is described by Lozzio et al., Blood 45(3): 321-334 (1975), and Klein et al., Int. J. Cancer 18: 421-431 (1976). Other suitable human cell lines include, but are not limited to, SK-MEL-33 (Wang et al., J. Clin. Invest. 91: 684-692 (1993)) and various melanoma cell lines (Ferrone et al., Immunol. Today 16(10): 487-494 (1995); K. ageshita et al., Cancer Res. 53(14): 3349-3354 (1993); and Wang et al., Tissue Antigens 47(5): 382-390 (1996)).

A human cell line that expresses MHC-I antigens can be modified so that it does not express such antigens in any of a number of different ways. For example, one can interfere with the expression and/or transport of the α chain. A human cell line that expresses MHC-II antigens also can be modified in various ways so that it does not express such antigens. For example, one can interfere with the expression and/or transport of the α chains and the β chains. MHC-I and -II antigens also can be inactivated for purposes of the present invention. This can be accomplished in a variety of ways (see, for example, U.S. Pat. No. 5,574,205). For example, a "dominant negative" can be created. A single modified $\beta_2$ microglobulin gene, whose protein product effectively complexes with MHC-I molecules and acts as a decoy, thereby preventing the insertion of MHC-I antigens into the membrane, can be overexpressed. A similar approach can be used with respect to MHC-II antigens by overexpressing modified genes encoding defective α or β subunits that complex with the host cells' subunits, thereby rendering them nonfunctional. Transfection, retroviral infection or homologous recombination can be used to achieve expression of modified MHC or $\beta_2$ microglobulin genes or inactivation of genes.

Levels of MHC-I antigen on the cell surface can be reduced by introducing into cells a sequence encoding adenoviral E19 protein by transfection or retroviral infection. The protein forms complexes specifically with MHC-I antigens in the rough endoplasmic reticulum preventing normal transport of MHC-I molecules to the plasma membrane (Andersson et al., Cell 43: 215-222 (1985); and Pabo et al., Advances in Cancer Research 42: 151-163 (1989)).

In addition to lacking MHC-I and MHC-II antigens, the human cell line is modified to comprise and express a nucleotide sequence encoding an immunomodulator and a nucleotide sequence encoding a viral antigen. By "modified" is meant the introduction into the cell line of a nucleic acid molecule, e.g., a vector, comprising a nucleotide sequence encoding a gene product, which, in the context of the present inventive cell line, is an immunomodulator or an antigen, such as an antigen of EBV, HPV, or KSHV, in operable linkage with a promoter and, as required for expression, various other regulatory sequences. Either the immunomodulator is not expressed in the cell line or, as a result of the introduction of the nucleic acid molecule is now expressed at a greater level.

A "vector" encompasses a nucleic acid molecule, such as a plasmid, virus or other vehicle, which contains one or more heterologous or recombinant nucleotide sequences, e.g., a nucleotide sequence encoding an immunomodulator and/or a nucleotide sequence encoding an antigen of EBV, HPV or KSHV, wherein the nucleotide sequences can be under the control of the same or different functional promoters, alone or in further combination with enhancer(s), and that is capable of functioning as a vector as that term is understood by those of ordinary skill in the art.

Any suitable vector can be employed that is appropriate for introduction of nucleic acids into eukaryotic cells, or more particularly animal cells, such as mammalian, e.g., human, cells. Preferably, the vector is compatible with the cell, e.g., can impart expression of the immunomodulator and/or viral antigen, and is stably maintained or relatively stably maintained in the cell. Desirably, the vector comprises an origin of replication. When an immunomodulator coding sequence or viral antigen coding sequence is transferred (i.e., as opposed to an immunomodulator gene having its own promoter or a viral antigen gene having its own promoter), optimally the vector also contains a promoter that can drive expression of the coding sequence and that is operably linked to the coding sequence. A coding sequence is "operably linked" to a promoter (e.g., when both the coding sequence and the promoter together constitute a native or recombinant immunomodulator gene or viral antigen gene) when the promoter can direct transcription of the coding sequence.

Appropriate viral vectors include, but are not limited to simian virus 40, bovine papilloma virus, Epstein-Barr virus, adenovirus, herpes virus, vaccinia virus, Moloney murine leukemia virus, Harvey murine sarcoma virus, murine mammary tumor virus, and Rous sarcoma virus. Any plasmid suitable for use in a eukaryote, in particular a mammal, e.g., a human, can be used in the context of the present invention. Desirably, the plasmid comprises a promoter, such as the cytomegalovirus promoter, an origin of replication, such as the SV40 origin of replication, a selectable marker, such as antibiotic resistance, and provides for mRNA with poly A tails. A preferred example of a plasmid is pCEP4 (See Examples 1 and 3).

Reference to a vector or other DNA sequences as "recombinant" merely acknowledges the linkage of DNA sequences, which are not typically conjoined as isolated from nature. A "gene" is any nucleic acid sequence coding for a protein or a nascent mRNA molecule. Whereas a gene comprises coding sequences and non-coding (e.g., regulatory) sequences, a "coding sequence" does not include any non-coding DNA. As used herein, "gene" or "coding sequence" includes genomic or cDNA sequences, greater and lesser sequences and mutations thereof, whether isolated from nature or synthesized in whole or in part, as long as the gene or coding sequence can express a protein having the characteristic function of the immunomodulator, i.e., the ability to stimulate the host immune response, or the characteristic antigenicity of an antigen of a virus. The means of modifying genes or coding sequences are well-known in the art, and also can be accomplished by means of commercially available kits (e.g., New England Biolabs, Inc., Beverly, Mass.; Clontech, Palo Alto, Calif.).

A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

The "immunomodulator" can be any suitable immunomodulator, such as a cytokine, a chemokine or an adjuvant, for example, obtained from any suitable source, such as a mammal, e.g., a human. Desirably, the immunomodulator induces or stimulates an immune response to the viral antigen expressed by the cell line. Cell-targeting means also can be considered immunomodulators. Likewise, antibodies (or antigenically reactive fragments thereof), antisense molecules, dsRNAi, and the like also can be considered immunomodulators to the extent that they inhibit or block the ability of a viral gene product to block the action of an interferon, if so desired. For example, the EBNA-2 protein of EBV blocks signal transduction of interferons, the EBER RNA of EBV blocks activation of Pkr, and BCRF1 of EBV is an IL-10 homolog that inhibits IFN-γ, IL-1, IL-2, and TNF synthesis.

Examples of suitable immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10, IL-12 and IL-20), tumor necrosis factors (e.g., TNFα and TNFβ), erythropoietin (EPO), FLT-3 ligand, gIp10, TCA-3, MCP-1, MIF, MIP-1α, MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing. The most preferred immunomodulatory cytokine is GM-CSF, such as human GM-CSF, including a functional fragment thereof. An alternatively preferred immunomodulatory cytokine is IL-2 or a functional fragment thereof Any immunomodulatory chemokine that binds to a chemokine receptor, i.e., a CXC, CC, C, or CX3C chemokine receptor, can be used in the context of the present invention. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing. Examples of adjuvants include, but are not limited to, heat shock protein, CpG, *Listeria monocytogenes*, aluminum hydroxide (for use with soluble antigen), aluminum phosphate (alum; for use with soluble antigen), muramyl dipeptide, muramyl tripeptide, *Mycobacterium tuberculosis*, QuilA (a purified saponin from the plant *Quillaja saponaria*), alone or in further combination with glycosides, cholesterol, and/or phospholids, empty adenoviral capsids; etc. One of ordinary skill in the art will appreciate that some of these adjuvants cannot be expressed from a vector, in which case the adjuvant, when used, in combination with one or more cell lines as described herein, is administered simultaneously or sequentially, in any order, with the one or more cell lines. Preferably, the adjuvant is administered with the viral-antigen-expressing cell line or the defined viral antigen, itself. Preferably, however, the immunomodulator nucleotide sequence encodes a GM-CSF sequence, particularly a human GM-CSF gene or coding sequence, including a human GM-CSF cDNA (e.g., as described by Cantrell et al., PNAS USA 82: 6250-6254 (1985)) or genomic sequence (e.g., as described by Miyatake et al., EMBO J. 4(10): 2561-2568 (1985)).

The viral antigen can be any defined antigen of a virus that is associated with a disease, such as cancer, in a human. For example, the viral antigen can be any defined antigen of an oncogenic virus. Oncogenic viruses include, but are not limited to, RNA viruses, such as Flaviviridae and Retroviridae, and DNA viruses, such as Hepadnaviridae, Papovaviridae, specifically papillomaviruses, Adenoviridae, Herpesviridae, and Poxviridae. Desirably, the viral antigen is one to which an immune response can be induced or stimulated in a human and is universally recognized. Preferably, the antigen is from EBV, HPV, or KSHV. Examples of suitable EBV antigens for expression in a human cell line in accordance with the present invention are described, for example, in Herbst et al., PNAS USA 88: 4766-4770 (1991). Preferred antigens of EBV include, but are not limited to, Epstein-Barr nuclear antigen-1 (EBNA1), latent membrane protein 1 (LMP1), or latent membrane protein 2 (LMP2). LMP2 is an especially preferred antigen of EBV. A cell line that expresses an antigen of EBV, in particular EBNA1, LMP1 or LMP2, can be used to induce or stimulate an immune response in a human to an EBV-associated disease or cancer. In the event that immune responses are to be measured in accordance with methods set forth herein, preferably the EBV antigen is one that results in a CD8+ T-cell response that can be readily/easily measured. Examples of suitable HPV antigens for expression in a human cell line in accordance with the present invention are described, for example, in Van Ranst et al.; Virology 190(2): 587-596 (1992); and Rho et al.; Virology 203(1): 158-161 (1994). Preferred antigens of HPV include, but are not limited, E5, E6, and E7. Examples of suitable KSHV antigens for expression in a human cell line in accordance with the present invention are described, for example, in Russo et al., PNAS USA 93(25): 14862-14867 (1996). Preferred antigens of KSHV include, but are not limited to, latency nuclear antigen (LANA) and v-cyclin.

Preferably, all proper transcription, translation and processing signals (e.g., splicing and polyadenylation signals) are correctly arranged on the vector, such that the immunomodulator (viral antigen) nucleotide sequence will be appropriately transcribed and translated in the cell into which it is introduced. The manipulation of such signals to ensure appropriate expression in host cells is well within the knowledge and expertise of the ordinary skilled artisan. Whereas an immunomodulator gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, can be employed to command expression of the immunomodulator coding sequence. The CMV promoter is a preferred promoter. The same can also be said for the viral antigen gene.

Alternately, a tissue-specific promoter (i.e., a promoter that is preferentially activated in a given tissue and results in expression of a gene product in the tissue where activated) can be used in the vector. Such promoters include, but are not limited to, the elastase I gene control region, which is active in pancreatic acinar cells as described by Swift et al., Cell 38: 639-646 (1984) and MacDonald, Hepatology 7: 425-515 (1987); the insulin gene control region, which is active in pancreatic beta cells as described by Hanahan, Nature 315: 115-122 (1985); the hepatocyte-specific promoter for albumin or $\alpha_1$-antitrypsin described by Frain et al., Mol. Cell. Biol. 10: 991-999 (1990), and Ciliberto et al., Cell 41: 531-540 (1985); and the albumin and alpha$_1$-antitrypsin gene control regions, which are both active in liver as described by Pinkert et al., Genes and Devel. 1: 268-276 (1987), and Kelsey et al., Genes and Devel. 1: 161-171 (1987).

Similarly, a tumor-specific promoter, such as the carcinoembryonic antigen for colon carcinoma described by Schrewe et al., Mol. Cell Biol. 10: 2738-2748 (1990), can be used in the vector. Along the same lines, promoters that are selectively activated at different developmental stages (e.g., globin genes are differentially transcribed in embryos and adults) can be employed for gene therapy of certain types of cancer.

Another option is to use an inducible promoter, such as the IL-8 promoter, which is responsive to TNF, or the 6-16 promoter, which is responsive to interferons, or to use other similar promoters responsive to other cytokines or other factors present in a host or that can be administered exogenously. Use of a cytokine-inducible promoter has the added advantage of allowing for auto-inducible expression of a cytokine gene. According to the invention, any promoter can be altered by mutagenesis, so long as it has the desired binding capability and promoter strength.

Various methods can be employed for delivering a nucleic acid molecule, e.g., a vector, to a cell in vitro. For instance, such methods include electroporation, membrane fusion with liposomes, high velocity bombardment with DNA-coated microprojectiles, incubation with calcium phosphate-DNA precipitate, DEAE-dextran mediated transfection, infection with modified viral nucleic acids, direct microinjection into single cells, and the like. Other methods are available and are known to those skilled in the art. The immunomodulator and the EBV antigen can be encoded on the same or different nucleic acid molecules.

If the cell line is to be used in the context of cancer immunotherapy, the immunomodulator desirably is one that induces or stimulates an immune response against a cancer cell or a cancer antigen, i.e., any protein, carbohydrate or other component that can elicit an immune response, in particular, a defined viral antigen as expressed by a cell line in accordance with the present invention. An inhibitory cytokine or a cytokine that prevents priming cannot be used in the context of cancer immunotherapy. While the nucleic acid molecule preferably encodes a single immunomodulator, the nucleic acid molecule can encode two or more immunomodulators, which can be of the same type, e.g., both cytokines, such as cytokines that act synergistically, or of different types, e.g., a cytokine and an adjuvant.

For purposes of identification and selection, preferably the nucleic acid molecule comprising a nucleotide sequence encoding an immunomodulator operably linked to a promoter and/or a nucleotide sequence encoding a viral antigen operably linked to a promoter further comprises a nucleotide sequence encoding a selectable marker operably linked to a promoter. In other words, the nucleotide sequence encoding the immunomodulator, the nucleotide sequence encoding the viral antigen, and the nucleotide sequence encoding the selectable marker can be on the same nucleic acid molecule or on different nucleic acid molecules in various combinations. Likewise, the nucleotide sequences can be under the control of the same or different promoters.

Preferably, the selectable marker is an antibiotic resistance gene, such as hygromycin resistance. When the selectable marker is hygromycin resistance, preferably the cell line is selected by growth in a culture medium comprising at least about 400 μg/ml hygromycin, more preferably at least about 1,000 μg/ml hygromycin.

A composition or implant, either one of which comprises an above-described cell line and which is appropriate for administration in vivo, can comprise appropriate carriers or diluents, which further can be pharmaceutically acceptable. The means of making such a composition or an implant have been described in the art, see, for instance, *Remington's Pharmaceutical Sciences,* 16th Ed., Mack, ed. (1980). Use of a balanced salt solution, such as Hanks' balanced salt solution, is preferred in the composition.

Alternatively, the composition can comprise a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of a virus that causes disease or cancer, such as an antigen of EBV, HPV or KSHV. Also, alternatively, the composition can comprise an immunomodulator and a human cell line, which lacks MHC-I and MHC-II antigens and which has been modified to comprise and express a nucleotide sequence encoding an antigen of a virus that causes disease or cancer, such as an antigen of EBV, HPV or KSHV.

In pharmaceutical dosage form, a composition can be used alone or in appropriate association, as well as in combination, with other pharmaceutically active compounds as are known in the art.

A composition of the present invention can be provided in unit dosage form, wherein each dosage unit contains a predetermined amount of the composition, alone or in appropriate combination with other active agents. The term "unit dosage form" as used herein refers to physically discrete units suitable as unitary dosages for human and other mammalian subjects, each unit containing a predetermined quantity of the composition of the present invention, alone or in combination with another active agent, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular host.

In view of the foregoing, the present invention also provides a method of inducing or stimulating an immune response in a human to a virus associated with a disease, such as cancer. The induction or stimulation of an immune response can be prophylactic or therapeutic and use of the phrase "inducing or stimulating" is intended to cover prophylactic and therapeutic embodiments. For example, evidence is emerging that humans who have had infectious mononucleosis are at risk for developing Hodgkin's disease. Thus, the method of the present invention can be used to inhibit the onset of a virus-associated disease or virus-associated cancer/malignancy. In this regard, one of ordinary skill in the art will appreciate that, while prevention is desirable, "prophylactic" means any degree in the inhibition of the onset of virus-associated disease or virus-associated cancer inasmuch as any inhibition is beneficial. Likewise, one of ordinary skill in the art will appreciate that, while cure is desirable, "therapeutic" means any degree of inhibition/treatment of virus-associated disease or virus-associated cancer, ranging from no change in the disease or cancer, which can be beneficial inasmuch as the disease or cancer does not get worse, to a lessening or an improvement of the disease or a reduction in cancer (size of a tumor and/or number of tumor) or an inhibition of metastasis of the cancer.

In particular, the present invention provides a method of inducing or stimulating an immune response to an EBV-associated disease or cancer, in particular an EBV-associated cancer. Likewise, the present invention provides a method of inducing or stimulating an immune response to a KSHV-associated disease or cancer, such as a KSHV-associated cancer, and a method of inducing or stimulating an immune response to an HPV-associated disease or cancer, in particular an HPV-associated cancer. The method comprises administering to the human an above-described human cell line in an amount sufficient to induce or stimulate an immune response to the virus-associated disease or cancer, e.g., malignancy. Upon administration of the cell line, an immune response to the virus-associated disease or cancer, e.g., malignancy, is induced or stimulated.

Alternatively, a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer. Also, alternatively, an immunomodulator and a human cell line, which lacks MHC-I and MHC-II antigens and which has been modified to comprise and express a nucleotide sequence encoding an antigen of EBV, can be administered, simultaneously or sequentially in either order, by the same or different routes, to the human in amounts sufficient to induce or stimulate an immune response to an EBV-associated cancer.

Examples of EBV-associated cancers/malignancies include Burkitt's lymphoma, T-cell lymphoma, nasopharyngeal carcinoma, Hodgkin's lymphoma, B-cell lymphoma, gastric carcinoma, parotid carcinoma, breast carcinoma, and leiomyosarcoma. An example of an HPV-associated cancer/malignancy is cervical cancer. KSHV is associated with Kaposi's sarcoma, for example.

"Administering" means the actual physical introduction of the composition into or onto (as appropriate) the host. Any and all methods of introducing the composition into the host are contemplated according to the invention; the method is not dependent on any particular means of introduction and is not to be so construed. Means of introduction are well-known to those skilled in the art, and also are exemplified herein.

Any suitable route of administration can be used. Preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

The amount of cells to be administered to induce or stimulate an immune response to the defined viral antigen can be determined empirically (see, also, Examples 2 and 4 herein). For example, an initial low dosage of cells can be administered and the immune response to the defined viral antigen can be measured. If no immune response is induced or stimulated or it is deemed to be too low, the dosage of cells can be increased. This process can be repeated every week or two weeks or so until an effective dosage is administered.

One skilled in the art also is aware of means to monitor a therapeutic (i.e., systemic immune) response upon administering a composition of the present invention. In particular, the therapeutic response can be assessed by monitoring attenuation of tumor growth and/or tumor regression. The attenuation of tumor growth or tumor regression in response to treatment can be monitored using several end-points known to those skilled in the art including, for instance, number of tumors, tumor mass or size, or reduction/prevention of metastasis. Methods of assessing cervical cancer are described, for example, in U.S. Pat. No. 6,388,064. These described methods are by no means all-inclusive, and further methods to suit the specific application will be apparent to the ordinary skilled arts.

Any type of viral-associated cancer can be treated in accordance with the present inventive method as long as an antigen of the virus associated with the cancer has been defined and, desirably, is present on the surfaces of the cancerous cells. "Cancer" as used herein includes cancers, in particular those of epithelial origin, characterized by abnormal cellular proliferation and the absence of contact inhibition, which can be evidenced by tumor formation. The term encompasses cancer localized in tumors, as well as cancer not localized in tumors, such as, for instance, cancer cells that expand from a tumor locally by invasion. Thus, the method has applicability as a local adjuvant therapy for resected cancers as well as a local control of tumor growth.

The method of the present invention can be combined with other methods of cancer treatment. Examples of such methods include radiation, surgery and chemotherapy. In addition, the method of the present invention can be adapted for non-human mammals, for example, by employing a nonhuman mammalian cell line and a non-human mammalian source of an immunomodulator and viral antigen, as appropriate.

The present inventive cell line has other uses, other than as described above. For example, the present inventive cell line can be used to characterize a human's immune response to the antigen, e.g., viral antigen, such as an EBV, HPV or KSHV antigen, expressed by the cell line. For example, if the antigen expressed by the cell line is an EBV antigen, the human's immune response to the EBV antigen can be measured before and after administration of the cell line. By comparing the immune responses before and after administration, it is possible to determine whether or not a given human responds immunologically to the antigen of EBV and, if desired, characterize the nature and extent of the response. Tetramer assay and cytokine secretion assay can be used. If the human is to be treated for an EBV-expressing cancer, this information can be used to determine if the human can be treated using the EBV antigen-expressing cell line. This information also can be used to determine how best to administer the EBV antigen-expressing cell line, e.g., what dosage at what frequency. In much the same way, an immunocompromised human can be evaluated to determine suitability for cancer immunotherapy and, if found suitable, the manner of treatment, i.e., dosage and frequency of administration.

The present inventive cell line also can be used to assess an immune response to a cancer cell vaccine for which the antigen is undefined. For example, the present inventive cell line can be administered to a human in combination with the cancer cell vaccine, and the present inventive cell line can be used as a marker. The immune response to the defined antigen expressed by the present inventive cell line can be used to determine the human's immune responsiveness, thereby enabling grading of immune responses to the cancer cell vaccine under similar vaccine conditions, for example.

In view of the teachings set forth herein, Applicants reserve the right to pursue claims to the following embodiments. This reservation is not to be construed as a waiver of the right to pursue claims directed to other embodiments and modifications thereof as described herein.

A. A human cell line, which lacks MHC-I antigens and MHC-II antigens and which has been modified to comprise and express (i) a nucleotide sequence encoding an immunomodulator and (ii) a nucleotide sequence encoding an antigen of HPV or KSHV.

B. The human cell line of A, wherein the antigen of HPV is E5, E6 or E7 and the antigen of KSHV is LANA or v-cyclin.

C. The human cell line of A or B, wherein the immunomodulator is a cytokine, a chemokine or an adjuvant.

D. The human cell line of C, wherein the cytokine is an interferon, an interleukin, a tumor necrosis factor, erythropoietin, FLT-3 ligand, macrophage colony stimulating factor (M-CSF), granulocyte colony stimulating factor (G-CSF), or granulocyte-macrophage colony stimulating factor (GM-CSF).

E. The human cell line of D, wherein the interferon (IFN) is IFNα, IFNβ or IFNγ.

F. The human cell line of D, wherein the interleukin (IL) is IL-1, IL-2, IL-3, IL-4, IL-5, IL-6, IL-7, IL-8, IL-8, IL-10 or IL-12.

G. The human cell line of D, wherein the tumor necrosis factor (TNF) is TNFα or TNFβ.

H. The human cell line of C, wherein the chemokine is Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-α, Gro-β, Gro-γ, Nap-2, Ena-78, Gcp-2, Ip-10, Mig, I-Tac, Sdf-1, or Bca-1 (Blc).

I. The human cell line of C, wherein the adjuvant is a heat shock protein or CpG.

J. The human cell line of A, wherein the immunomodulator is GM-CSF, and the antigen of HPV is E6 or E7.

K. The human cell line of A or B, wherein the human cell line that is modified is K562.

L. The human cell line of C, wherein the human cell line that is modified is K562.

M. The human cell line of J, wherein the human cell line that is modified is K562.

N. A method of inducing or stimulating an immune response in a human for an HPV-associated cancer, which method comprises administering to the human the human cell line of A or B in an amount sufficient to induce or stimulate an immune response to the HPV-associated cancer, whereupon an immune response to the HPV-associated cancer is induced or stimulated.

O. The method of N, wherein the human is female and has cervical cancer.

P. A method of inducing or stimulating an immune response in a human for an HPV-associated cancer, which method comprises administering to the human the human cell line of C in an amount sufficient to induce or stimulate an immune response to the HPV-associated cancer, whereupon an immune response to the HPV-associated cancer is induced or stimulated.

Q. The method of P, wherein the human is female and has cervical cancer.

R. A method of inducing or stimulating an immune response in a human for an HPV-associated cancer, which method comprises administering to the human the human cell line of J in an amount sufficient to induce or stimulate an immune response to the HPV-associated cancer, whereupon an immune response to the HPV-associated cancer is induced or stimulated.

S. The method of R, wherein the human is female and has cervical cancer.

T. A method of inducing or stimulating an immune response in a human for an HPV-associated cancer, which method comprises administering to the human the human cell line of K in an amount sufficient to induce or stimulate an immune response to the HPV-associated cancer, whereupon an immune response to the HPV-associated cancer is induced or stimulated.

U. The method of T, wherein the human is female and has cervical cancer.

V. A method of inducing or stimulating an immune response in a human for an HPV-associated cancer, which method comprises administering to the human the human cell line of L in an amount sufficient to induce or stimulate an immune response to the HPV-associated cancer, whereupon an immune response to the HPV-associated cancer is induced or stimulated.

W. The method of V, wherein the human is female and has cervical cancer.

X. A method of inducing or stimulating an immune response in a human for an HPV-associated cancer, which method comprises administering to the human the human cell line of M in an amount sufficient to induce or stimulate an immune response to the HPV-associated cancer, whereupon an immune response to the HPV-associated cancer is induced or stimulated.

Y. The method of X, wherein the human is female and has cervical cancer.

Z. A composition comprising a human cell line, which lacks MHC-I and MHC-II antigens and which has been modified to comprise and express a nucleotide sequence encoding an immunomodulator, and a human cell line, which lacks MHC-I and MHC-II antigens and which has been modified to comprise and express a nucleotide sequence encoding an antigen of HPV or KSHV.

AA. A composition comprising an immunomodulator and a human cell line, which lacks MHC-I and MHC-II antigens and which has been modified to comprise and express a nucleotide sequence encoding an antigen of HPV or KSHV.

AB. A method of inducing or stimulating an immune response in a human to an HPV-associated or KSHV-associated cancer, which method comprises administering to the human the composition of Z (expressing an antigen of HPV or KSHV, respectively) in an amount sufficient to induce or stimulate an immune response to the HPV-associated or KSHV-associated cancer, whereupon an immune response to the HPV-associated or KSHV-associated cancer is induced or stimulated.

AC. The method of AB, wherein the human is female and has cervical cancer associated with HPV or the human has Kaposi's sarcoma.

AD. A method of inducing or stimulating an immune response in a human to an HPV-associated or KSHV-associated cancer, which method comprises administering to the human the composition of AA (expressing an antigen of HPV or KSHV, respectively) in an amount sufficient to induce or stimulate an immune response to the HPV-associated or KSHV-associated cancer, whereupon an immune response to the HPV-associated or KSHV-associated cancer is induced or stimulated.

AE. The method of AD, wherein the human is female and has cervical cancer associated with HPV or the human has Kaposi's sarcoma.

AF. A method of inducing or stimulating an immune response in a human to an HPV-associated or KSHV-associated cancer, which method comprises administering to the human a composition comprising a human cell line, which lacks MHC-I and MHC-II antigens and which has been modified to comprise and express a nucleotide sequence encoding an immunomodulator, in an amount sufficient to induce or stimulate an immune response, and simultaneously or sequentially, in either order, by the same route or a different route, a human cell line, which lacks MHC-I and MHC-II antigens and which has been modified to comprise and express a nucleotide sequence encoding an antigen of HPV or KSHV, respectively, in an amount sufficient to induce to stimulate an immune response, whereupon an immune response to the HPV-associated or KSHV-associated cancer is induced or stimulated.

AG. The method of AF, wherein the human is female and has cervical cancer associated with HPV or the human has Kaposi's sarcoma.

AH. A method of inducing or stimulating an immune response in a human to an HPV-associated or KSHV-associated cancer, which method comprises administering to the human an immunomodulator in an amount sufficient to induce to stimulate an immune response, and simultaneously or sequentially, in either order, by the same route or a different route, a human cell line, which lacks MHC-I and MHC-II antigens and which has been modified to comprise and express a nucleotide sequence encoding an antigen of HPV or KSHV, respectively, in an amount sufficient to induce to stimulate an immune response, whereupon an immune response to the HPV-associated or KSHV-associated cancer is induced or stimulated.

AI. The method of AH, wherein the human is female and has cervical cancer associated with HPV or the human has Kaposi's sarcoma.

EXAMPLES

Antibody generation and purification, diagnostic platforms, cloning procedures; etc., to the extent that they are not described herein, can be found in references such as the following:

Sambrook et al., *Molecular Cloning, A Laboratory Manual*, Vols. I-III, 1989, Cold Spring Harbor Laboratory Press, USA;

Harlowe and Lane, *Antibodies: A Laboratory Manual*, 1988 and 1998, Cold Spring Harbor Laboratory Press, USA; and Ausubel et al., *Current Protocols*, 2001, John Wiley and Sons, Inc.

The following examples serve to illustrate the present invention and are not intended to limit its scope in any way.

Example 1

This example describes the generation of an EBV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/$10^6$ cells/24 hrs was selected. The high degree of expression of this clone minimizes the number of cells needed for vaccination, while leaving the margin for efficacy well above the threshold of 36 ng/$10^6$ cells/24 hrs. The K562-EBNA1/GM-CSF clone also was determined to express EBNA1 by Western blot using a monoclonal antibody to EBNA1.

Figure 2:
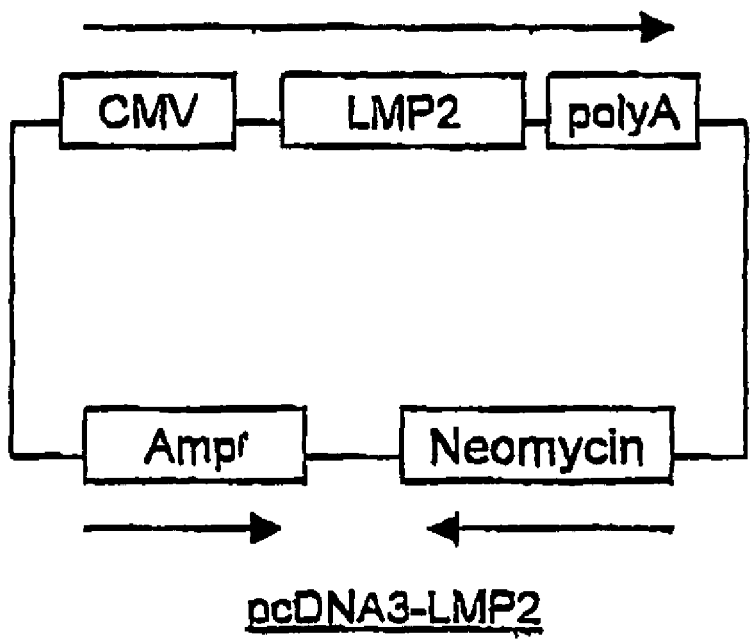
FIG. 2 is a diagram of a bi-cistronic plasmid (arrows indicate direction of transcription) containing the LMP2 coding sequence (LMP2) operably linked to the CMV promoter (CMV) and a polyA tail (polyA), a neomycin resistance gene (Neomycin), and an ampicillin resistance gene (Amp$^r$). The plasmid is designated pcDNA3-LMP2.

The K562-EBNA1/GM-CSF clone was transfected with a plasmid expressing latent membrane protein 2 (LMP2) under the control of a CMV promoter. The plasmid, which is designated pcDNA3-LMP2, also contains a neomycin resistance gene and is shown in FIG. 2. G418-resistant clones were analyzed for the expression of LMP2 by immunofluorescent staining with a monoclonal antibody to LMP2. A clone expressing high levels of LMP2 was selected and designated K562-EBNA1/LMP2/GM-CSF. The clone has been determined to express high levels of LMP2 (of expected size) and GM-CSF, as well as EBNA1 RNA and LMP2 RNA. A master cell bank can be generated and a clinical grade vaccine can be generated from the master cell bank. The cells can be irradiated, frozen under controlled conditions, and stored in liquid nitrogen in vials containing $3.3\times10^7$ cells.

Example 2

This example describes an EBV antigen-specific, GM-CSF-secreting cellular vaccine for treating EBV+ tumors.

Patients with EBV+ Hodgkin's lymphoma (HL) or nasopharyngeal carcinoma (NPC) at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/LMP2/GM-CSF) is removed from the liquid nitrogen storage and rapidly thawed in a 37° C. water bath. Viability of the cellular vaccine is assessed by trypan blue exclusion, and the number of viable cells is used for calculation of dosages. The patients are intradermally injected with a total dose of $3.3\times10^7$ cells per vaccination divided into 9 injections of $3.6\times10^8$ cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of LMP2/EBNA1-specific CD4 and CD8 T cell responses to LMP2 and EBNA1 are assessed using a modified IFN-γ ELISPOT assay, which utilizes dendritic cells infected with recombinant vaccinia virus expressing LMP2 or EBNA1 as a stimulator. This abolishes the need to HLA-type each patient. Briefly, peripheral blood mononuclear cells (PBMCs) from patients are fractioned into CD4 and CD8 cells by a magnetic cell separation (MACS) system. Purified CD4 or CD8 cells are stimulated with dendritic cells transduced with recombinant vaccinia vector encoding LMP2 or EBNA1 in multiscreen hemagglutinin (HA) plates coated with a monoclonal antibody to IFN-γ (capture antibody) for 16-18 hrs. The plates are then washed and stained for IFN-γ with an immunoperoxidase technique. The IFN-γ-positive spots are counted using a stereomicroscope. A tetramer assay also is used for HLA-A2, A11 and A24 patients in order to correlate with results from the IFN-Y ELISPOT assay.

Patients are compared at baseline and at six months or earlier after completion of vaccination. The baseline cellular response to LMP2 is expected to be less than about 50/million PBMCs. A vaccination is considered to be successful if the cellular response exceeds about 200/million PBMCs.

Example 3

This example describes the generation of an HPV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/$10^6$ cells/24 hrs was selected. The high degree of expression of this clone minimizes the number of cells needed for vaccination, while leaving the margin for efficacy well above the threshold of 36 ng/$10^6$ cells/24 hrs. The K562-EBNA1/GM-CSF clone also was determined to express EBNA1 by Western blot using a monoclonal antibody to EBNA1.

The K562-EBNA1/GM-CSF clone is transfected with a plasmid expressing E6 under the control of a CMV promoter. The plasmid, which is designated pcDNA3-E6, also contains a neomycin resistance gene. G418-resistant clones were analyzed for the expression of E6 by immunofluorescent staining with a monoclonal antibody to E6. A clone expressing high levels of E6 was selected and designated K562-EBNA1/E6/GM-CSF. A master cell bank can be generated and a clinical grade vaccine can be generated from the master cell bank. The cells can be irradiated, frozen under controlled conditions, and stored in liquid nitrogen in vials containing $3.3\times10^7$ cells.

Example 4

This example describes an HPV antigen-specific, GM-CSF-secreting cellular vaccine for treating HPV+ tumors.

Patients with HPV+ cervical cancer at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/E6/GM-CSF) is removed from the liquid nitrogen storage and rapidly thawed in a 37° C. water bath. Viability of the cellular vaccine is assessed by trypan blue exclusion, and the number of viable cells is used for calculation of dosages. The patients are intradermally injected with a total dose of $3.3\times10^7$ cells per vaccination divided into 9 injections of $3.6\times10^8$ cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of E6-specific CD4 and CD8 T cell responses to E6 is assessed using a modified IFN-Y ELISPOT assay, which utilizes dendritic cells infected with recombinant vaccinia virus expressing E6 as a stimulator. This abolishes the need to HLA-type each patient. Briefly, PBMCs from patients are fractioned into CD4 and CD8 cells by MACS separation system. Purified CD4 or CD8 cells are stimulated with dendritic cells transduced with recombinant vaccinia vector encoding E6 or EBNA1 in multiscreen HA plates coated with a monoclonal antibody to IFN-γ (capture antibody) for 16-18 hrs. The plates are then washed and stained for IFN-γ with an immunoperoxidase technique. The IFN-γ-positive spots are counted using a stereomicroscope. A tetramer assay also is used for HLA-A2, A11 and A24 patients in order to correlate with results from the IFN-γ ELISPOT assay.

Patients are compared at baseline and at six months or earlier after completion of vaccination. The baseline cellular response to E6 is expected to be less than about 50/million PBMCs. A vaccination is considered to be successful if the cellular response exceeds about 200/million PBMCs.

Example 5

This example describes the generation of a KSHV antigen-specific, GM-CSF-secreting cellular vaccine.

The allogeneic human erythroleukemia cell line K562 was transfected with a plasmid containing human GM-CSF operably linked to the cytomegaloviral (CMV) promoter, a hygromycin resistance gene, and the Epstein-Barr virus (EBV) nuclear antigen-1 (EBNA1) gene, which is required for the function of the plasmid origin of replication. The plasmid, designated pCEP4-EBNA1/hGM-CSF, is shown in FIG. 1. Hygromycin-resistant clones were screened for the secretion of GM-CSF. A K562-EBNA1/GM-CSF clone producing over 2,000 ng of GM-CSF/$10^6$ cells/24 hrs was selected. The high degree of expression of this clone minimizes the number of cells needed for vaccination, while leaving the margin for efficacy well above the threshold of 36 ng/$10^6$ cells/24 hrs. The K562-EBNA1/GM-CSF clone also was determined to express EBNA1 by Western blot using a monoclonal antibody to EBNA1.

The K562-EBNA1/GM-CSF clone is transfected with a plasmid expressing LANA under the control of a CMV promoter. The plasmid, which is designated pcDNA3-LANA, also contains a neomycin resistance gene. G418-resistant clones were analyzed for the expression of LANA by immunofluorescent staining with a monoclonal antibody to LANA. A clone expressing high levels of LANA was selected and designated K562-EBNA1/LANA/GM-CSF. A master cell bank can be generated and a clinical grade vaccine can be generated from the master cell bank. The cells can be irradiated, frozen under controlled conditions, and stored in liquid nitrogen in vials containing $3.3\times10^7$ cells.

Example 6

This example describes an KSHV antigen-specific, GM-CSF-secreting cellular vaccine for treating KSHV+ tumors.

Patients with Kaposi sarcoma at high risk for relapse after primary therapy or those with relapsed or metastatic disease are treated. The patients are given a first vaccination six weeks after the completion of primary therapies, such as chemotherapy, radiation, or a combination thereof. Follow-up vaccinations are given monthly thereafter for a total of four vaccinations, spanning weeks 6 to 18 during immune reconstitution. On the day of vaccination, the cellular vaccine (K562-EBNA1/LANA/GM-CSF) is removed from the liquid nitrogen storage and rapidly thawed in a 37° C. water bath. Viability of the cellular vaccine is assessed by trypan blue exclusion, and the number of viable cells is used for calculation of dosages. The patients are intradermally injected with a total dose of $3.3\times10^7$ cells per vaccination divided into 9 injections of $3.6\times10^8$ cells in a volume of 0.5 ml. Three injections spaced 5 cm apart will be placed on each anterior thigh and the non-dominant arm. Patients are monitored for possible toxicities at the site of vaccination. Systemic toxicities are assessed from paracrine secretion of GM-CSF.

If desired, the generation and enhancement of LANA-specific CD4 and CD8 T cell responses to LANA is assessed using a modified IFN-γ ELISPOT assay, which utilizes dendritic cells infected with recombinant vaccinia virus expressing LANA as a stimulator. This abolishes the need to HLA-type each patient. Briefly, PBMCs from patients are fractioned into CD4 and CD8 cells by MACS separation system. Purified CD4 or CD8 cells are stimulated with dendritic cells transduced with recombinant vaccinia vector encoding LANA or EBNA1 in multiscreen HA plates coated with a monoclonal antibody to IFN-γ (capture antibody) for 16-18 hrs. The plates are then washed and stained for IFN-IFN-γ with an immunoperoxidase technique. The IFN-γ-positive spots are counted using a stereomicroscope. A tetramer assay also is used for HLA-A2, A11 and A24 patients in order to correlate with results from the IFN-γ ELISPOT assay.

Patients are compared at baseline and at six months or earlier after completion of vaccination. The baseline cellular response to LANA is expected to be less than about 50/million PBMCs. A vaccination is considered to be successful if the cellular response exceeds about 200/million PBMCs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated human cell line K562, which lacks major histocompatibility class I (MHC-I) antigens and major histocompatibility class II (MHC-II) antigens and which has been modified to comprise and express (i) a gene encoding an immunomodulator selected from the group consisting of macrophage colony factor (M-CSF), granulocyte colony stimulating factor (G-CSF), granulacyte-macrophage colony stimulating factor (GM-CSF) and (ii) a gene encoding an antigen of Epstein-Barr virus (EBV).

2. The human cell line of claim 1, wherein the antigen of EBV is Epstein-Barr nuclear antigen-1 (EBNA1), latent membrane protein 1 (LMP1), or latent membrane protein 2 (LMP2).

3. The human cell line of claim 1, wherein the immunomodulator is GM-CSF and the antigen of EBV is LMP2.

4. A composition comprising the isolated human cell line K562 of claim 1 and a pharmaceutical accepted carrier or diluent.

5. A method of inducing or stimulating an immune response in a human to an EBV-associated cancer, which method comprises administering to the human the human cell line of claim 1 in an amount sufficient to induce or stimulate an immune response to the EBV-associated cancer, whereupon an immune response to the EBV-associated cancer is induced or stimulated.

6. The method of claim 5, wherein the human has or is at risk for Hodgkin's lymphoma.

7. The method of claim 5, wherein the human has or is at risk for nasopharyngeal carcinoma.

8. The method of claim 5, wherein the human has or is at risk for gastric carcinoma, Burkitt's lymphoma, T-cell lymphoma, B-cell lymphoma, parotid carcinoma, breast carcinoma, and leiomyosarcoma.

9. The method of claim 5, which further comprises quantifying the human's immune response to the antigen of EBV encoded by the human cell line before and after administration of the human cell line to the human and comparing the immune responses before and after administration, whereupon the immune response of the human to the antigen of EBV is characterized.

10. The method of claim 9, which further comprises adjusting the amount of the human cell line administered to the human and/or the frequency of administration of the human cell line as necessary in view of the human's immune response to the antigen of EBV, whereupon the treatment of the human is adjusted.

11. A method of inducing or stimulating an immune response in a human to an EBV-associated cancer, which method comprises administering to the human the human cell line of claim 3 in an amount sufficient to induce or stimulate an immune response to the EBV-associated cancer, whereupon an immune response to the EBV-associated cancer is induced or stimulated.

12. The method of claim 11, wherein the human has or is at risk for Hodgkin's lymphoma.

13. The method of claim 11, wherein the human has or is at risk for nasopharyngeal carcinoma.

14. The method of claim 11, wherein the human has or is at risk for gastric carcinoma, Burkitt's lymphoma, T-cell lymphoma, B-cell lymphoma, parotid carcinoma, breast carcinoma, and leiomyosarcoma.

15. A method of inducing or stimulating an immune response in a human to an EBV-associated cancer, which method comprises administering to the human the composition of claim 14 in an amount sufficient to induce or stimulate an immune response to the EBV-associated cancer, whereupon an immune response to the EBV-associated cancer is induced or stimulated.

16. The method of claim 15, wherein the human has or is at risk for Hodgkin's lymphoma.

17. The method of claim 15, wherein the human has or is at risk for nasopharyngeal carcinoma.

18. The method of claim 15, wherein the human has or is at risk for gastric carcinoma, Burkitt's lymphoma, T-cell lymphoma, B-cell lymphoma, parotid carcinoma, breast carcinoma, and leiomyosarcoma.

* * * * *

SEQUENCE LISTING

<160> NUMBER OF SEQ ID NOS: 60

<210> SEQ ID NO 1
<211> LENGTH: 876
<212> TYPE: DNA
<213> ORGANISM: homo sapien

<400> SEQUENCE: 1

```
agaacctaga gcccaaggtt cagagtcacc catctcagca agcccagaag tatctgcaat     60
atctacgatg gcctcgccct ttgctttact gatggtcctg gtggtgctca gctgcaagtc    120
aagctgctct ctgggctgtg atctccctga gacccacagc ctggataaca ggaggacctt    180
gatgctcctg gcacaaatga gcagaatctc tccttcctcc tgtctgatgg acagacatga    240
ctttggattt ccccaggagg agtttgatgg caaccagttc cagaaggctc cagccatctc    300
tgtcctccat gagctgatcc agcagatctt caacctcttt accacaaaag attcatctgc    360
tgcttgggat gaggacctcc tagacaaatt ctgcaccgaa ctctaccagc agctgaatga    420
cttggaagcc tgtgtgatgc aggaggagag ggtgggagaa actcccctga tgaatgcgga    480
ctccatcttg gctgtgaaga aatacttccg aagaatcact ctctatctga cagagaagaa    540
atacagccct tgtgcctggg aggttgtcag agcagaaatc atgagatccc tctctttatc    600
aacaaacttg caagaaagat taaggaggaa ggaataacat ctggtccaac atgaaaacaa    660
ttcttattga ctcatacacc aggtcacgct ttcatgaatt ctgtcatttc aaagactctc    720
acccctgcta taactatgac catgctgata aactgattta tctatttaaa tatttattta    780
actattcata agatttaaat tatttttgtt catataacgt catgtgcacc tttacactgt    840
ggttagtgta ataaaacatg ttccttatat ttactc                              876
```

<210> SEQ ID NO 2
<211> LENGTH: 1142
<212> TYPE: DNA
<213> ORGANISM: homo sapien

<400> SEQUENCE: 2

```
gagaacctgg agcctaaggt ttaggctcac ccatttcaac cagtctagca gcatctgcaa     60
catctacaat ggccttgacc tttgctttac tggtggccct cctggtgctc agctgcaagt    120
caagctgctc tgtgggctgt gatctgcctc aaacccacag cctgggtagc aggaggacct    180
tgatgctcct ggcacagatg aggagaatct ctcttttctc ctgcttgaag gacagacatg    240
actttggatt tccccaggag gagtttggca accagttcca aaaggctgaa accatccctg    300
tcctccatga gatgatccag cagatcttca atctcttcag cacaaaggac tcatctgctg    360
cttgggatga gaccctccta gacaaattct acactgaact ctaccagcag ctgaatgacc    420
tggaagcctg tgtgatacag ggggtggggg tgacagagac tcccctgatg aaggaggact    480
ccattctggc tgtgaggaaa tacttccaaa gaatcactct ctatctgaaa gagaagaaat    540
acagcccttg tgcctgggag gttgtcagag cagaaatcat gagatctttt tctttgtcaa    600
caaacttgca agaaagttta agaagtaagg aatgaaaact ggttcaacat ggaaatgatt    660
ttcattgatt cgtatgccag ctcacctttt tatgatctgc catttcaaag actcatgttt    720
ctgctatgac catgacacga tttaaatctt ttcaaatgtt tttaggagta ttaatcaaca    780
ttgtattcag ctcttaaggc actagtccct tacagaggac catgctgact gatccattat    840
ctatttaaat atttttaaaa tattatttat ttaactattt ataaaacaac ttatttttgt    900
```

-continued

```
tcatattatg tcatgtgcac ctttgcacag tggttaatgt aataaaatgt gttctttgta    960

tttggtaaat ttattttgtg ttgttcattg aacttttgct atggaacttt tgtacttgtt   1020

tattctttaa aatgaaattc caagcctaat tgtgcaacct gattacagaa taactggtac   1080

acttcatttg tccatcaata ttatattcaa gatataagta aaaataaact ttctgtaaac   1140

ca                                                                  1142
```

<210> SEQ ID NO 3
<211> LENGTH: 1193
<212> TYPE: DNA
<213> ORGANISM: Homo Sapien

<400> SEQUENCE: 3

```
tgaagatcag ctattagaag agaaagatca gttaagtcct ttggacctga tcagcttgat     60

acaagaacta ctgatttcaa cttctttggc ttaattctct cggaaacgat gaaatataca    120

agttatatct tggcttttca gctctgcatc gttttgggtt ctcttggctg ttactgccag    180

gacccatatg taaaagaagc agaaaacctt aagaaatatt ttaatgcagg tcattcagat    240

gtagcggata atggaactct tttcttaggc attttgaaga attggaaaga ggagagtgac    300

agaaaaataa tgcagagcca aattgtctcc ttttacttca aactttttaa aaactttaaa    360

gatgaccaga gcatccaaaa gagtgtggag accatcaagg aagacatgaa tgtcaagttt    420

ttcaatagca acaaaaagaa acgagatgac ttcgaaaagc tgactaatta ttcggtaact    480

gacttgaatg tccaacgcaa agcaatacat gaactcatcc aagtgatggc tgaactgtcg    540

ccagcagcta aaacagggaa gcgaaaaagg agtcagatgc tgtttcaagg tcgaagagca    600

tcccagtaat ggttgtcctg cctgcaatat ttgaatttta aatctaaatc tatttattaa    660

tatttaacat tatttatatg gggaatatat ttttagactc atcaatcaaa taagtattta    720

taatagcaac ttttgtgtaa tgaaaatgaa tatctattaa tatatgtatt atttataatt    780

cctatatcct gtgactgtct cacttaatcc tttgttttct gactaattag gcaaggctat    840

gtgattacaa ggctttatct caggggccaa ctaggcagcc aacctaagca agatcccatg    900

ggttgtgtgt ttatttcact tgatgataca atgaacactt ataagtgaag tgatactatc    960

cagttactgc cggtttgaaa atatgcctgc aatctgagcc agtgctttaa tggcatgtca   1020

gacagaactt gaatgtgtca ggtgaccctg atgaaaacat agcatctcag gagatttcat   1080

gcctggtgct tccaaatatt gttgacaact gtgactgtac ccaaatggaa agtaactcat   1140

ttgttaaaat tatcaatatc taatatatat gaataaagtg taagttcaca act          1193
```

<210> SEQ ID NO 4
<211> LENGTH: 7896
<212> TYPE: DNA
<213> ORGANISM: Human papillomavirus type 59

<400> SEQUENCE: 4

```
gttaagaccg aaaacggtgc atataaaggt agttgaaaag aaaagggcaa cggcatggca     60

cgctttgagg atcctacaca acgaccatac aaactgcctg atttgagcac aacattgaat    120

attcctctgc atgatattcg catcaattgt gtgttttgca aaggggaact gcaagaaaga    180

gaggtatttg aatttgcttt taatgactta tttatagtgt atagagactg tacaccgtat    240

gcagcgtgtc tgaaatgcat ttcattttat gcaagagtaa gagaattaag atattataga    300

gattccgtgt atggagaaac attagaggct gaaaccaaga caccgttaca tgagctgctg    360
```

-continued

```
atacgctgtt atagatgcct aaaacctcta tgtccaacag ataaattaaa gcatataact    420
gaaaaaagaa gattccataa tatagctgga atatatacag gacagtgtcg tgggtgtcgg    480
acccgagcaa gacacctaag acagcaacga caagcgcgta gtgaaacact ggtgtaaaac    540
aatgcatgga ccaaaagcaa cactttgtga cattgtttta gatttggaac cacaaaatta    600
tgaggaagtt gaccttgtgt gctacgagca attacctgac tccgactccg agaatgaaaa    660
agatgaacca gatggagtta atcatccttt gctactagct agacgagctg aaccacagcg    720
tcacaacatt gtgtgtgtgt gttgtaagtg taataatcaa cttcagctag tagtagaaac    780
ctcgcaagac ggattgcgag ccttacagca gctgtttatg gacacactat cctttgtgtg    840
tcctttgtgt gcagcaaacc agtaacctgc aatggccgat tcggaaggta cagatgggga    900
agggacgggg tgcaatggat ggtttttgt gcaggcaata gtagataaaa aaacaggtga    960
caaaatttca gatgacgagg atgaaaatgc aacagataca ggttcagact tggtagattt   1020
tattgatgat accacaacaa tttgtgtaca ggcagagcgc gagacagcac aggccttgtt   1080
taatgtgcag gaagcccaaa gggatgcacg ggaaatgcat gttttaaaac gaaagtttgg   1140
gtgcagtata gaaaacagta gtgagaaagc ggcggcagga aaaaaagcta agtcaccatt   1200
acaagaaata tcagtaaatg ttaaccaccc aaaagtaaaa agaaggttaa taacagtgcc   1260
agacagcggc tatggctatt ctgaagtgga aatgctcgag actcaggtaa ccgtggagaa   1320
tactggaaat ggggatagca atggcagtgt ttgtagcgac agtcaaatag actgtagcga   1380
cagcagtaac atggatgttg aaaacatagt tccaacatcc cccactaatc aattgttaca   1440
gttattacat agcaaaaata agaaagcagc tatgtatgca aaatttaaag aattgtatgg   1500
gttatcattt caagatttgg ttaggacatt taaaagtgac agaactacct gtagcgattg   1560
ggtaaccgcc atttttggtg ttaatccaac tgtagcagaa ggatttaaaa cattaataca   1620
accctatgtg ctatatgcac atatacaatg cttagattgt gcatggggag tagtaatatt   1680
agcattatta agatataaat gtggaaaaaa tagaataaca gttgcaaaag gacttagcac   1740
attactacat gtaccagata cgtgcatgtt aattgaacca cccaaattgc gtagtggtgt   1800
tgcagcacta tattggtaca gaacaggaat gtccaatatt agtgaagtta taggggaaac   1860
gcccgaatgg atacaaagac taacaattat acaacatgga gttgatgata gcgtgtttga   1920
cctgtcagaa atgatacaat gggcgtttga taatgaccta acagatgaaa gtgatattgc   1980
atatgaatat gcattaatag cagatagtaa tagtaacgcc gctgcatttt taaaaagcaa   2040
ctgccaggca aaatacctaa aagattgtgc agttatgtgt aggcattata aaagagcaca   2100
aaaaagacaa atgagtatgt cacagtggat aaaatggaga tgtgataaaa tagaagaggg   2160
gggagattgg aaacccatag tacaattttt aagatatcaa ggagtagaat ttataacgtt   2220
tttatgtgca ttaaaagatt ttttaaaagg taccccaaaa agaaattgca ttgtgctgtg   2280
tgggccagca aatacaggca agtcatactt tggaatgagc ctgctacatt ttttacaagg   2340
aactgtaatt tcacatgtaa attcaaatag tcacttttgg ctagaacctt taacagatcg   2400
taaattagct atgctagacg atgcaacaga tagttgttgg acatattttg atacatatat   2460
gcgaaatgct ttggatggca atcctataag tgtagataga aagcataggc acctagtaca   2520
aattaaatgt ccaccaatgc ttattacatc aaatacaaat ccagttacag ataacaggtg   2580
gccatattta aatagcagat taatggtatt taaatttcca aacaaattgc catttgacaa   2640
aaatagaaat ccagtatata caattaatga cagaaactgg aaatgttttt ttgaaaggac   2700
gtggtgcaga ttagatttga acgaggaaga ggaagatgca gacagtgatg gacacccttt   2760
```

-continued

```
cgcagcgttt aagtgtgtta caggatcaaa tattagaaca ttatgaaaac gatagtaaag   2820
acattaatga acacataaac tattggaaac tggtgcgtat ggaaaatgta attttatttg   2880
cagcaagaga gaacaatata catacattaa accaccaggt ggtgccaacg tttttggtgt   2940
ctaaaaacaa ggcatgtgaa gctattgaac tgcagtcaaa ccgtacttcc actgtaatgc   3000
cctgtttttt aaaacatttt ttaggtgctg tttgccatag ttcttggcat gtttcttgca   3060
ttgtccattg ctcattttta aactcagttt gtgccaaact ctctaacgcc atctgcagca   3120
aggaaaacac aatgcattac acaagctgga catttatata ttatgtaaat gatgtaggac   3180
agtggtgtaa aaccacagga aatgtggact tttggggact atattataaa gtggaagagg   3240
aacaggtgta ctatgtaaaa tttatacatg atgccaaaaa atatgggact acagacaagt   3300
gggaagtgca ttataatggc aaggttattg attgttatga ctctatgtgc agtaccagtg   3360
acgagcaagt atccactgct ggatcttctg agcaactatc ataccccctcc gcaacgcccc   3420
ccgaagccac gtacttgggc ccccaaacgt ggaaccgtca gacgaagact ggaaagcgac   3480
caagacagtg tggatacaca cagcaccctc agtctaccag cgtgtcagtg gactactgtg   3540
acaacccagt cgtccgtttg catccaggca acaacccgcg acggcacatc ccttgcagta   3600
acactacgcc tataatacac ttaaaaggtg acaaaaatgg ccttaagtgt ttaaggtata   3660
gattaagaaa agtacactgg ttatttgaaa atatttcctc tacctggcat tggacaggaa   3720
acagaggatc agccaaaaca ggcattttaa cattaacata tacaagcgaa acacaacgca   3780
atgaattttt agatactgta aaaattccta atagtgtaca aatacatgtt gggtatatga   3840
gtgtgtaatg gttgttatgc aaatgtaaca caagccaata ctgctgctat attgtatagc   3900
tgaggaaatg ataacccttg tatttgtgtg ttgtgtttgt gtttgcttgt gtgtgtgttg   3960
caatgtcccg cttctgcaat ctgtctatat gtgtgcatat acatggttac tagtatttgt   4020
gtatattgtg gttatcacct cctcatatga gtgtttttta ctatatatat tgttttttat   4080
aattccactg ttactactat atgcccatgc aatactgtcc atacaataat tgctgtatat   4140
tgtaaattac attgcactgt attgtacagt atattttaaa cacattatta tttttgttag   4200
gtgttggttt tgttacattt ataataaaac atggtttccc atcgtgctgc tcgtcgtaaa   4260
cgtgcctcag caacagactt atataaaact tgcaagcagg caggtacatg cccttctgat   4320
gttattaata aagttgaagg tacaacttta gctgataaaa tattgcagtg gaccagccta   4380
ggaatatttt taggtggact aggtattggt actggatctg gtaccggtgg cagaacaggg   4440
tacatacctt tagggggcg tacaaacact atagtagatg tatcgcctgc taaaccacca   4500
gtagttattg aacctgttgg acctacagat ccatctatag ttacattagt tgaggattct   4560
agtgttataa catctggagc ccctgcccca acatttacag gtacttcagg atttgaaata   4620
tctacctcta gtacaacaac accagctgtt ttggatataa ccccaacctc ttctgttcaa   4680
attagtagct ctagttttat aaatcctgca tttacagacc cttctgtcat tgaggttccc   4740
caaacaggtg aaatttctgg taatatatta attagtaccc ctacctctgg tgcacatggc   4800
tatgaagaaa ttccaatgca aacgtttgct acggaaggta ctggtttgga acccattagc   4860
agtacccccca atccaacagt acgtcgtgtg gctggaccta gattgtacag tagggctaat   4920
caacaagttc gggtgtctaa cgctgacttt ttaacacgtc catccacatt tgttacatat   4980
gataaccctg cttatgatcc aattgatact acattaactt ttgacccctc atcagaggtt   5040
ccagacccgg actttatgga tatagttcgt ttgcataggc ctgcattaac atccagacgc   5100
```

-continued

```
agcactgtaa ggtttagtag gctaggacaa cgggcaacca tgtttacccg tagtggtaaa   5160
caaattgggg cccgtgtaca tttttatcat gatataagcc ctataccaca tgctgaagat   5220
attgaattgc aacctcttgt ttcttcccag gctgctactg atgatatata tgatatatat   5280
gcagatatta cagatgaagc acctactagt actgccaaca ctgcatttac aattcctaaa   5340
tcttcttttc aaagtttgtc attaacacgg tcggcatcta gcaccttttc aaatgtaact   5400
gttcctttgg ctactgcctg ggatgttcct gtaaatacag gacccgatat agttttacct   5460
aatactaata ttgttgaacc cacttattct actacaccct ttaccaccat acagtctatt   5520
aatatagaag gcacaaatta tttttatgg cctatatatt atttttacc tcgtaaacgt   5580
aaacgtgttc cctattttt tacagatggc tctatggcgt tctagtgaca acaaggtgta   5640
tctacctcca ccttcggtag ctaaggttgt cagcactgat gagtatgtca cccgtaccag   5700
tattttctac cacgcaggca gttccagact tcttacagtt ggacatccat attttaaagt   5760
acctaaaggt ggtaatggta gacaggatgt tcctaaggtg tctgcatatc aatacagagt   5820
atttagggtt aagttacctg atcccaataa atttggcctt ccagataaca cagtatatga   5880
tcctaactct caacgcttgg tctgggcctg tgtaggtgtt gaaatcggtc ggggccaacc   5940
tttaggggta ggactcagtg gtcatccatt atataataaa ttggatgaca ctgaaaactc   6000
tcatgtagca tctgctgttg ataccaaaga tacacgtgat aatgtatctg tggattataa   6060
acaaactcag ctgtgtatta ttggctgtgt acctgccatt ggagaacact ggacaaaggg   6120
cactgcttgt aagcctacta ctgtggttca gggcgattgt cctccactag aattaataaa   6180
tacaccaatt gaagatggtg atatggtaga cacaggatat ggggctatgg actttaaatt   6240
gttgcaggat aacaaaagtg aagtaccatt ggatatttgt cagtctattt gtaaatatcc   6300
tgattattta caaatgtcag cagatgctta tggagacagt atgtttttt gtttaaggcg   6360
agaacaggtt tttgccagac atttttggaa tagatctggt actatgggtg atcaacttcc   6420
tgaatcacta tatattaaag gtactgacat acgtgccaac ccaggcagtt atttatattc   6480
cccttcccca agtgggtctg tggttacttc tgattcacaa ttatttaata aaccatattg   6540
gctgcacaag gctcagggtt taaacaatgg tatatgttgg cacaatcaat tgtttttaac   6600
agttgtagat actactcgca gcaccaatct ttctgtgtgt gcttctacta cttcttctat   6660
tcctaatgta tacacaccta ccagttttaa agaatatgcc agacatgtgg aggaatttga   6720
tttgcagttt atatttcaac tgtgtaaaat aacattaact acagaggtaa tgtcatacat   6780
tcataatatg aataccacta ttttggagga ttggaatttt ggtgttacac cacctcctac   6840
tgctagttta gttgacacat accgttttgt tcaatctgct gctgtaactt gtcaaaagga   6900
caccgcaccg ccagttaaac aggaccctta tgacaaacta aagttttggc ctgtagatct   6960
taaggaaagg ttttctgcag atcttgatca gtttcctttg ggacgtaaat tttattgca   7020
attaggagct agacctaagc ccactatagg cccacgcaaa cgtgcagcgc ctgcccctac   7080
ctctacccca tcaccaaaac gtgttaagcg tcgcaagtct tccagaaaat agtgttgttt   7140
gttatgtgtt tgtatgtgtg catgttgtat gttttgtatt gtttgcctgt ttgtatgttg   7200
tgtatatgta catgtttgtt tgtctgctgt atgtgtgtat ttgtttttgt acataataaa   7260
gtatgcatga cagtttcatg tgtggttgca cccaatgagt aaggtactgt ccctttattg   7320
tttctttgtc cttattacac attattacac attgccctac ttacataggt gtgtttgttc   7380
cttcattttg tcctgaatgt ccagttttgc atttgcacat tatatggcgt ccattttatc   7440
ctttaaatcc tccattttgc tgtgcaaccg ttttcggtta ccttggttta accttacctt   7500
```

```
tttgaacaat taatctgttt aaacatcagc aaaacagtta atccccatct tgtttcctcc   7560

tacacgccta gactactaac acaacttaca aacgccaaat agttagtcat catcctgtcc   7620

aggtgcactc taacaatact tgcataactt tggtggcgcc cttgttaata aaacagcttt   7680

taggcacata ttttcactgt ttttactact ttaattgcat aattggcttg caaaactact   7740

gtgcaatcca agaatgtgtc tataatttat tgtaaaaaac atgactaagg tttttgtcat   7800

tgttaagcaa ccgaaaaagg tcgggcaagt acatgcacac tttctactta ttacttttta   7860

caatcatagt aataaaaaag ggtgtaaccg aaaacg                             7896

<210> SEQ ID NO 5
<211> LENGTH: 222
<212> TYPE: DNA
<213> ORGANISM: Human papillomavirus type 59

<400> SEQUENCE: 5

atgataaccc ttgtatttgt gtgttgtgtt tgtgtttgct tgtgtgtgtg ttgcaatgtc     60

ccgcttctgc aatctgtcta tatgtgtgca tatacatggt tactagtatt tgtgtatatt    120

gtggttatca cctcctcata tgagtgtttt ttactatata tattgttttt tataattcca    180

ctgttactac tatatgccca tgcaatactg tccatacaat aa                       222

<210> SEQ ID NO 6
<211> LENGTH: 483
<212> TYPE: DNA
<213> ORGANISM: Human papillomavirus type 59

<400> SEQUENCE: 6

atggcacgct ttgaggatcc tacacaacga ccatacaaac tgcctgattt gagcacaaca     60

ttgaatattc ctctgcatga tattcgcatc aattgtgtgt tttgcaaagg ggaactgcaa    120

gaaagagagg tatttgaatt tgcttttaat gacttattta tagtgtatag agactgtaca    180

ccgtatgcag cgtgtctgaa atgcatttca ttttatgcaa gagtaagaga attaagatat    240

tatagagatt ccgtgtatgg agaaacatta gaggctgaaa ccaagacacc gttacatgag    300

ctgctgatac gctgttatag atgcctaaaa cctctatgtc caacagataa attaaagcat    360

ataactgaaa aaagaagatt ccataatata gctggaatat atacaggaca gtgtcgtggg    420

tgtcggaccc gagcaagaca cctaagacag caacgacaag cgcgtagtga aacactggtg    480

taa                                                                  483

<210> SEQ ID NO 7
<211> LENGTH: 324
<212> TYPE: DNA
<213> ORGANISM: Human papillomavirus type 59

<400> SEQUENCE: 7

atgcatggac caaaagcaac actttgtgac attgttttag atttggaacc acaaaattat     60

gaggaagttg accttgtgtg ctacgagcaa ttacctgact ccgactccga gaatgaaaaa    120

gatgaaccag atggagttaa tcatcctttg ctactagcta gacgagctga accacagcgt    180

cacaacattg tgtgtgtgtg ttgtaagtgt aataatcaac ttcagctagt agtagaaacc    240

tcgcaagacg gattgcgagc cttacagcag ctgtttatgg acacactatc ctttgtgtgt    300

cctttgtgtg cagcaaacca gtaa                                           324

<210> SEQ ID NO 8
```

-continued

<211> LENGTH: 7880
<212> TYPE: DNA
<213> ORGANISM: Human papilloma virus type 13

<400> SEQUENCE: 8

```
gtttctaaca atcttaagtt taaaaaatag gtgggaccga aaacggtttt aaccgaaaac     60
ggtgatatat aaaccagccc aaaaattgag caagcggggc ataatggaaa gtgcaaatgc    120
ctccacgcct gcaaaaacta tagaccagtt gtgcaaggag tgcaaccttt ctatgcacag    180
cttgcaaatt ctatgcgtgt tctgcaggaa aaccctgtcc acggcagagg tttatgcatt    240
tcagtataag agtttatata tagtgtggcg aggacagttt ccatttgcgg cttgtgcatg    300
ctgcttagaa atacaaggaa agattaacca gtttaggcat tttgacttcg cgggatttgc    360
tgtaacagtt gaagaagaca caaagcagtc aattttggat gtgctaattc gctgctattt    420
atgccacaaa ccattgtgtg aagtggagaa actaagacat attttgcaga aggcacgatt    480
tattaaatta aacagcagtt ggaaaggccg ctgttttcat tgctggtcat catgcatgga    540
aaatatccta ccttaaaaga cattgtttta gagctgactc ctgaccctgt aggtctacat    600
tgcaatgagc aattagacag ctcagaagac gaggtggacg aacaagccac gcaagccacg    660
caagccacgc aacatagcac actattacaa tgctaccaaa tactaacgtc ctgtagtaaa    720
tgttgtagca acgtccggct ggtggtggag tgtacaggac ctgacattca cgacctacac    780
gacctactgc tgggcacgct gaatatagtg tgccctttgt gtgcaccaaa aagctaacca    840
cgatggcaga ggatacaggt actaataatg aggggacggg atgctcagga tggtttttag    900
tagaggctgt agtagaacga acaactgggc aacaaatatc agatgatgag gatgaaacag    960
tggaagatag tgggttggat atggtggatt tcatagatga cagacctatt acacacaatt   1020
ccgtggaagc acaggcattg ttaaacgagc aggaggcgga tgctcattat gcggctgtgc   1080
aggacctaaa acgaaagtat ttaggcagtc catatgttag tcccctagga catgttgaac   1140
agtcagtgga ctgtgatata agtcctcgat tggacgctat aaaattaagt agaaattcta   1200
aaaaagtaaa gcgacggctg tttcaatcaa gggaaataac ggacagtgga tatggctatt   1260
ctgaagtgga agctgaaacg caggtagaga gaaatggcga accggaaaat gattgtgggg   1320
gtggtggaca cggaagggac aaagaggggg agggacaggt gcacacggaa gtgcacacag   1380
gcagccagat agaagagcac acagggacca cgcgggtgtt agaactcctt aaatgtaagg   1440
atgtaagggc tacattgtat ggtaagttta aagactgtta tgggttatca tttacagatt   1500
taattagacc atttaaaagt gataaaacaa catgtgggga ctgggtggtt gcagcatttg   1560
gtatacatca tagtgtatca gaggcatttg aaaagttaat gcagccatta acaacatata   1620
tgcatataca atggcttaca aatgcatggg ggatggtatt gttagtatta ataagattta   1680
aagtaaataa aagtagatgc acagtggcgc gaacactggc aacctttctt aatattcctg   1740
aggaccacat gttaattgaa cctcccaaaa tacaaagcag tgtggcagca ttatactggt   1800
ttagaacagg tatttctaat gctagtatag taactggtga aacaccagaa tggataaaaa   1860
ggcaaacaat tgtagagcat ggacttgcag ataatcaatt taaattaact gaaatggtgc   1920
agtgggcata tgataatgat ttttgtgatg aaagcgaaat agcatttgaa tatgcacaac   1980
gaggagattt tgattcaaat gccagggcat ttttaaatag taattgtcag gcaaaatatg   2040
taaaagattg tgcaacaatg tgcaagcatt ataaaaatgc agaaatgaaa aaaatgtcta   2100
tgaaacaatg gataacatat agaagtaaaa aaatagagga agcaggaaat tggaaaccaa   2160
tagtacaatt tttaaggcat caaaatatag aatttattcc atttttaagt aaattaaaat   2220
```

-continued

```
tgtggcttca tggcacgcca aagaaaaact gtattgcaat agtggggcca ccagatacag   2280
gcaaatcatg tttttgcatg agcttaatta agtttttagg gggcacagta attagttatg   2340
taaattcaag tagccatttt tggctgcagc cattatgtaa tgcaaaggta gctttgctag   2400
atgatgcaac gcagtcatgc tggtatata tggacacata catgagaaat ttattagatg   2460
gcaatccaat gagcattgat agaaaacata agtctttagc attaataaaa tgtccgccat   2520
tattagtaac atctaatgta gacattacca aagatgacaa atataaatat ttgtatagta   2580
gagtaacaac acttacattt ccaaatccat tccctttga cagaaatggg aatgcagtat   2640
atgagttgtc tgatgcaaac tggaaatgtt tttttacaag attgtcagca agcctagata   2700
tacaggactc tgaggacgag gacgatggag acaatagcca agcatttaga tgcgtgccag   2760
gaacagttgt tagaactgta tgaagaaaat agtaatgaac ttaaaaaaca tatacaacat   2820
tggaaatgct taaggtacga aagtgtactc ttacacaaag cacgccaaat gggcctaagc   2880
cacattggat tacaagtggt gccaccattg acagtatcac aagctaaggg acatgaggca   2940
attgaaatgc aaatgacttt agagacatta ctagagtctg agtttggtat ggaaccatgg   3000
actttacaag atacaagtcg tgaaatgtgg ctaacacccc caaaacgctg ttttaagaaa   3060
cagggacaaa ctgtggaagt aaaatatgac tgtaatacag acaatagaat ggattatgtg   3120
tcgtggacat acatatatgt gtttgacaca gataaatgga caaaggtgaa aggaatggta   3180
gattataaag ggttgtacta catacatgga aatttgaaaa catattattt agagtttgaa   3240
aaggaggcta aaaaatatgg ggaaacgtta caatgggaag tatgtattgg cagcacagtc   3300
atatgttctc ctgcatctgt atctagtact gtacaagaag tatccattgc tgggcctgct   3360
tcatactcca ccaccacctc cacacaggcc tccaccgcag tgtcctgcag cgcctcggaa   3420
gaatgtgtgc aagcgccgcc ttgtaaacga caacgaggac cttcacgtcc cattggaaac   3480
ccccagaaca cacaaagcat tgtgtgtgtc acagactacg acaccctgga cagtgcaaac   3540
aacaacatca acgttaacca ttacaacaat aacaaaggac gggacaacag ttactgtgca   3600
gctacaccta tagttcaatt acaaggtgac tctaattgtc taaagtgttt tcgatataga   3660
ttacatgaaa aatataaaga tttatttttg ttagcatcat ctacatggca ttggaccgcc   3720
cctaataatt cacaaaaaca tgcactggta accttaacct atgtaaatga acaacaaaga   3780
caagactttt taaaaactgt aaaaatacct ccaaccataa cacataaact aggttttatg   3840
tcattgcaat tgttataaca gcatatattg tatgtaaata tttgttgtgt gtgtgtatat   3900
attgtaaatg gaatttatac ctgtggatgt tagtacacag gcaaccagca agtcattact   3960
gccacttgta attgcactta cagtgtgtgt agttagcatt ataacaatat tgtgcatatc   4020
agagttcttg gtgtacacaa acgttttagt actaacatta attttatatg tacttttgtg   4080
gcttttacta acaactccct tgcaattcta tttactaacc ctgtctcttt gctttcttcc   4140
tgcgttgtgt gtacaccaat atattttaca aacacaagaa taactataca caatgttaac   4200
ctgtactttt gatgatggtg acacatggtt gctattatgg ttaattttat catttattgt   4260
agccattcta gggttactgt tgctgtatat aagaactgga catatgcatt gccagtgctg   4320
gagtaaataa gtggttttat attttgtgtg tattcattta attatggcac atagtagggc   4380
tcgcagacgc aaacgcgctt cagctacaca actatatcaa acttgtaagg cttctggaac   4440
atgtcctcct gatgttatac caaaggttga acaaaacact cttgcagata aaatattaaa   4500
gtggggcagt ttaggagtat tttttggggg gcttggcatt ggcacaggct ctggtactgg   4560
```

-continued

```
cggtaggact ggctatgtac cagtaggatc caccccacgc cctgccatat caactgggcc   4620
tactgcacgt cctcctattg ttgttgatac tgttgggcct acagaccctt ctattgtatc   4680
tttggtagag gaatcagcta ttattaattc tggagtacct gaccctttgc ctcccgttca   4740
tgggggtttt gaaatcacca catctcaatc agccactcca gcaatattgg atgtgtctgt   4800
tacaacacaa aacactacgt ccacaagtat atttagaaat cctgtttttt cagaaccttc   4860
tattacacaa tctcaacctt ctattgaaag tggtgcacac gtgtttatat cgccatctac   4920
tatttcccct cattctacag aagacattcc tttagataca tttattgtat cttcctcaga   4980
tagtaatcct gcatcaagca cccctgttcc agcaactgtt gcacgtccac gtctaggcct   5040
ttacagtagg gccttacatc aagtacaggt tactgatcct gcctttttat cgtcgcccca   5100
acgccttata acctttgata accctacata tgaaggtgaa gatataagtt tgcagtttgc   5160
acacaatacc attcatgaac cccctgatga ggcatttatg gatattataa gactacatag   5220
gccagccata acatcacggc gtggtcttgt taggtttagt agaattggtc agagggggtc   5280
tatgtatact cgaagcggca agcatatagg tggaagggtc catttcttta aggatatttc   5340
tcctatatct gcagctgcag aagaaataga attacacccc cttgtggctg ctgcacagga   5400
tcacagtggt ttgtttgata tttatgcaga acctgaccct gaccctgtgg ctgtaaacac   5460
ctctgggtca ttgtcttctg cctccacacc atttgcacaa tcttctttgt cttccgcccc   5520
atggggtaat actactgttc ctctttcact accaggtgat atatttatac agcctggtcc   5580
tgacataaca ttcccaactg cacctacagt aacgccttat aatcctgtta cgcctgcttt   5640
acctacaggt cctgttttta ttactgcttc tggattttat ttatatccta catggtattt   5700
tacacgcaaa cgccgtaaac gtgtttcctt gtttttttaca gatgtggcgg cctagtgaca   5760
acaaactata tgtgcctcct cccgcccctg tatcaaaagt aattactacg gatgcctatg   5820
ttacacgtac caacatattt tatcatgcta gcagttctag actacttgca gtgggaaatc   5880
cttattttcc tattaagaaa caaaacaaaa ctgttgtccc taaggtatct ggttatcagt   5940
ttagggtatt taaagttgta ttacctgacc ctaataaatt tgccctgcct gacacatcta   6000
tatttgactc aactagtcaa cgcttagtgt gggcctgtac aggtttagag gttggtaggg   6060
gtcaaccctt aggtgttggt attagtggtc atccattatt aaataaatat gatgatgtgg   6120
aaaattctgc aagttatgct gccaatcctg gtcaggataa tagggttaat gtggccatgg   6180
actataaaca aacacagtta tgtttagtgg gctgtgcacc tcctttaggt gaacattggg   6240
gacagggcaa gcaatgtact ggtgtaaatg tacaacctgg agattgccct cctttagaat   6300
taattagtag tgtaattcag gatggtgaca tggtggatac aggatttgga gccatgaatt   6360
ttgcggaatt gcaatctaat aaatctgatg tgccactaga catatgcacg tccacatgca   6420
aatatcctga ctatttacaa atggctgcgg atccttatgg agacagatta ttttttttatc   6480
tgcgaaagga acaaatgttt gcaaggcatt tctttaacag ggcaggctct gttggtgaac   6540
aaatcccagc agaattatat gttaagggta gtaatacact ttctaatagt atttactata   6600
atactcccag tggctctctt gtgtcttctg aggcccagtt gtttaataaa ccttattggt   6660
tacaaaaggc ccagggacac aataatggta tatgttgggg caatcacttg tttgttactg   6720
tagttgatac tacacgcagt actaacatga ctgtgtgtgc agccactaca tcatctcttt   6780
cagacacata taaggccaca gaatataaac agtacatgcg acatgtagaa gaatttgatt   6840
tacaatttat ttttcaattg tgcactatta aattaactgc agaggttatg tcatatattc   6900
atactatgaa tcctacaatt ctagaagact ggaactttgg gctatctccc cctcctaatg   6960
```

-continued

```
gaacattaga agacacatat agatatgtac aatctcaggc cataacgtgt caaaagccta   7020
cacctgataa agaaaaacag gatccgtatg cgggtcttag tttttgggag gttaatctta   7080
aggaaaagtt ttctagtgaa ctagatcagt atccccttgg cagaaagttt ttattacaaa   7140
caggcgttca gtctaggtcc cctattcgtg taggtaggaa acgtgctgca tctacatcta   7200
ctgccacacc tactacacgt aaaaaagcta aaaggaaata atagtttgtt tatgattgtg   7260
tatgtatgtc acgtttgttt gtactgtatg tatgttgtgt actgtatgtg taatgttgta   7320
tgtatgtgca tgttacttat taaagaatgt gtgtgtgtgt ttgtatgcaa taaatctaat   7380
ctgtggtgtc ctgttccacc ctatgagtaa gtggtatgtt gtgtctcgtg tggtgttttg   7440
tatactatac tataacatta gtgcaaccat tttgtaactt ttcttacatt ttacgtctcc   7500
atattaagtg caaccgattt cggttgctat tgtttctgcg accgatttgt tgcagcacgc   7560
tgtttatata atcttaccta ccgcctgcca aaattatcca ccgcttgcca aaatcaccca   7620
cacacctggc gttgctaggg cgcggttata tatatttact aaatcttact aatctttcta   7680
tcactcattt tacctttata acaatacttt tgcttttcaa gtacattttt gtacttacta   7740
gccaatgcct gaaaggtttt ttggctacca gcactacatt tttgtacagt taatgttaca   7800
tgtataaaat gagtaaccta aggtcacaca cctgcaaacc ggtatcggtt aaaacacacc   7860
ctctatagtt ccttataatt                                               7880
```

<210> SEQ ID NO 9
<211> LENGTH: 276
<212> TYPE: DNA
<213> ORGANISM: Human papilloma virus type 13

<400> SEQUENCE: 9

```
atggaattta tacctgtgga tgttagtaca caggcaacca gcaagtcatt actgccactt     60
gtaattgcac ttacagtgtg tgtagttagc attataacaa tattgtgcat atcagagttc    120
ttggtgtaca caaacgtttt agtactaaca ttaattttat atgtactttt gtggctttta    180
ctaacaactc ccttgcaatt ctatttacta accctgtctc tttgctttct tcctgcgttg    240
tgtgtacacc aatatatttt acaaacacaa gaataa                              276
```

<210> SEQ ID NO 10
<211> LENGTH: 453
<212> TYPE: DNA
<213> ORGANISM: Human papillomavirus type 13

<400> SEQUENCE: 10

```
atggaaagtg caaatgcctc cacgcctgca aaaactatag accagttgtg caaggagtgc     60
aacctttcta tgcacagctt gcaaattcta tgcgtgttct gcaggaaaac cctgtccacg    120
gcagaggttt atgcatttca gtataagagt ttatatatag tgtggcgagg acagtttcca    180
tttgcggctt gtgcatgctg cttagaaata caaggaaaga ttaaccagtt taggcatttt    240
gacttcgcgg gatttgctgt aacagttgaa gaagacacaa agcagtcaat tttggatgtg    300
ctaattcgct gctatttatg ccacaaacca ttgtgtgaag tggagaaact aagacatatt    360
ttgcagaagg cacgatttat taaattaaac agcagttgga aaggccgctg ttttcattgc    420
tggtcatcat gcatggaaaa tatcctacct taa                                 453
```

<210> SEQ ID NO 11
<211> LENGTH: 306
<212> TYPE: DNA

<213> ORGANISM: Human papillomavirus type 13

<400> SEQUENCE: 11

```
atgcatggaa aatatcctac cttaaaagac attgttttag agctgactcc tgaccctgta     60
ggtctacatt gcaatgagca attagacagc tcagaagacg aggtggacga acaagccacg    120
caagccacgc aagccacgca acatagcaca ctattacaat gctaccaaat actaacgtcc    180
tgtagtaaat gttgtagcaa cgtccggctg gtggtggagt gtacaggacc tgacattcac    240
gacctacacg acctactgct gggcacgctg aatatagtgt gccctttgtg tgcaccaaaa    300
agctaa                                                               306
```

<210> SEQ ID NO 12
<211> LENGTH: 1342
<212> TYPE: DNA
<213> ORGANISM: Homo sapiens erythropoietin

<400> SEQUENCE: 12

```
cccggagccg gaccggggcc accgcgcccg ctctgctccg acaccgcgcc ccctggacag     60
ccgccctctc ctccaggccc gtggggctgg ccctgcaccg ccgagcttcc cgggatgagg    120
gcccccggtg tggtcacccg gcgcgcccca ggtcgctgag ggaccccggc caggcgcgga    180
gatgggggtg cacgaatgtc ctgcctggct gtggcttctc ctgtccctgc tgtcgctccc    240
tctgggcctc ccagtcctgg gcgccccacc acgcctcatc tgtgacagcc gagtcctgga    300
gaggtacctc ttggaggcca aggaggccga gaatatcacg acgggctgtg ctgaacactg    360
cagcttgaat gagaatatca ctgtcccaga caccaaagtt aatttctatg cctggaagag    420
gatggaggtc gggcagcagg ccgtagaagt ctggcagggc ctggccctgc tgtcggaagc    480
tgtcctgcgg ggccaggccc tgttggtcaa ctcttcccag ccgtgggagc ccctgcagct    540
gcatgtggat aaagccgtca gtggccttcg cagcctcacc actctgcttc gggctctgcg    600
agcccagaag gaagccatct cccctccaga tgcggcctca gctgctccac tccgaacaat    660
cactgctgac actttccgca aactcttccg agtctactcc aatttcctcc ggggaaagct    720
gaagctgtac acaggggagg cctgcaggac aggggacaga tgaccaggtg tgtccacctg    780
ggcatatcca ccacctccct caccaacatt gcttgtgcca caccctcccc cgcccactcct   840
gaaccccgtc gaggggctct cagctcagcg ccagcctgtc ccatggacac tccagtgcca    900
gcaatgacat ctcaggggcc agaggaactg tccagagagc aactctgaga tctaaggatg    960
tcacagggcc aacttgaggg cccagagcag gaagcattca gagagcagct ttaaactcag   1020
ggacagagcc atgctgggaa gacgcctgag ctcactcggc accctgcaaa atttgatgcc   1080
aggacacgct ttggaggcga tttacctgtt ttcgcaccta ccatcaggga caggatgacc   1140
tggagaactt aggtggcaag ctgtgacttc tccaggtctc acgggcatgg gcactccctt   1200
ggtggcaaga gcccccttga caccggggtg gtgggaacca tgaagacagg atgggggctg   1260
gcctctggct ctcatggggt ccaagttttg tgtattcttc aacctcattg acaagaactg   1320
aaaccaccaa aaaaaaaaaa aa                                            1342
```

<210> SEQ ID NO 13
<211> LENGTH: 1152
<212> TYPE: DNA
<213> ORGANISM: Mus musculus

<400> SEQUENCE: 13

```
gaattcgcgg ccgcgtcgac attctgggga cgtcggtcgg ggttcttaga agaggagatg     60
```

-continued

```
acttttcaca gtcactgagg ctcgtgcagg aagcctgggg gagcaggagg cggaaaccga    120

cccacatcaa gggcggcagg gccgggcggc ggggtacagg ggttgggggg gaaggggctg    180

cagggtatga gcccgagacc tgccctcctg tcacttccaa gaacctgtca caggcatgag    240

gggtccccgg cagagatgac agtgctggcg ccagcctgga gcccaaattc ctccctgttg    300

ctgctgttgc tgctgctgag tccttgcctg cgggggacac ctgactgtta cttcagccac    360

agtcccatct cctccaactt caaagtgaag tttagagagt tgactgacca cctgcttaaa    420

gattacccag tcactgtggc cgtcaatctt caggacgaga agcactgcaa ggccttgtgg    480

agcctcttcc tagcccagcg ctggatagag caactgaaga ctgtggcagg gtctaagatg    540

caaacgcttc tggaggacgt caacaccgag atacattttg tcacctcatg taccttccag    600

cccctaccag aatgtctgcg attcgtccag accaacatct cccacctcct gaaggacacc    660

tgcacacagc tgcttggtct gaagccctgt atcgggaagg cctgccagaa tttctctcgg    720

tgcctggagg tgcagtgcca gccggactcc tccaccctgc tgcccccaag gagtcccata    780

gccctagaag ccacggagct cccagagcct cggcccaggc agctgttgct cctgctgctg    840

ctgctgctgc ctctcacact ggtgctgctg gcagccgcct ggggccttcg ctggcaaagg    900

gcaagaagga ggggggagct ccaccctggg gtgcccctcc cctcccatcc ctaggatgcg    960

agccttgtgc atcgttgact cagccagggt cttatctcga tgaggtctca atatgttgcc   1020

caaactgact ttgaaaacct cgatgcacct tcctgcccca caaacttcca aacagctggg   1080

cttacgggca tgctatatac aacaaggctt tcttttcttc tttcttggtg ctagagttgg   1140

gaaccaaaac aa                                                       1152
```

<210> SEQ ID NO 14
<211> LENGTH: 2475
<212> TYPE: DNA
<213> ORGANISM: Homo sapiens

<400> SEQUENCE: 14

```
agccgctctc cgcatcccag gacagcggtg cggccctcgg ccggggcgcc cactccgcag     60

cacccagcga gcgagcgagc gagcgagggc ggccgacgcg cccggccggg acccagctgc    120

ccgtatgacc gcgccggcgcg ccgccgggcg ctgccctccc acgacatggc tgggctccct    180

gctgttgttg gtctgtctcc tggcgagcag gagtatcacc gaggaggtgt cggagtactg    240

tagccacatg attgggagtg gacacctgca gtctctgcag cggctgattg acagtcagat    300

ggagacctcg tgccaaatta catttgagtt tgtagaccag gaacagttga aagatccagt    360

gtgctacctt aagaaggcat ttctcctggt acaagacata atggaggaca ccatgcgctt    420

cagagataac acccccaatg ccatcgccat tgtgcagctg caggaactct ctttgaggct    480

gaagagctgc ttcaccaagg attatgaaga gcatgacaag gcctgcgtcc gaactttcta    540

tgagacacct ctccagttgc tggagaaggt caagaatgtc tttaatgaaa caaagaatct    600

ccttgacaag gactggaata ttttcagcaa gaactgcaac aacagctttg ctgaatgctc    660

cagccaagat gtggtgacca agcctgattg caactgcctg taccccaaag ccatccctag    720

cagtgacccg gcctctgtct cccctcatca gcccctcgcc ccctccatgg cccctgtggc    780

tggcttgacc tgggaggact ctgagggaac tgagggcagc tccctcttgc ctggtgagca    840

gcccctgcac acagtggatc caggcagtgc caagcagcgg ccacccagga gcacctgcca    900

gagctttgag ccgccagaga ccccagttgt caaggacagc accatcggtg gctcaccaca    960
```

```
gcctcgcccc tctgtcgggg ccttcaaccc cgggatggag gatattcttg actctgcaat   1020

gggcactaat tgggtcccag aagaagcctc tggagaggcc agtgagattc ccgtacccca   1080

agggacagag ctttcccccct ccaggccagg agggggcagc atgcagacag agcccgccag  1140

acccagcaac ttcctctcag catcttctcc actccctgca tcagcaaagg gccaacagcc   1200

ggcagatgta actggtaccg ccttgcccag ggtgggcccc gtgaggccca ctggccagga   1260

ctggaatcac accccccaga agacagacca tccatctgcc ctgctcagag accccccgga   1320

gccaggctct cccaggatct catcaccgcg cccccagggc ctcagcaacc cctccaccct   1380

ctctgctcag ccacagcttt ccagaagcca ctcctcgggc agcgtgctgc cccttgggga   1440

gctggagggc aggaggagca ccagggatcg gaggagcccc gcagagccag aaggaggacc   1500

agcaagtgaa ggggcagcca ggcccctgcc ccgttttaac tccgttcctt tgactgacac   1560

acatgagagg cagtccgagg gatcctccag cccgcagctc caggagtctg tcttccacct   1620

gctggtgccc agtgtcatcc tggtcttgct ggccgtcgga ggcctcttgt tctacaggtg   1680

gaggcggcgg agccatcaag agcctcagag agcggattct cccttggagc aaccagaggg   1740

cagcccccctc actcaggatg acagacaggt ggaactgcca gtgtagaggg aattctaaga  1800

cccctcacca tcctggacac tctcgtttgt caatgtccct ctgaaaatgt gacgcccagc   1860

cccggacaca gtactccaga tgttgtctga ccagctcaga gagagtacag tgggactgtt   1920

accttccttg atatggacag tattcttcta tttgtgcaga ttaagattgc attagttttt   1980

ttcttaacaa ctgcatcata ctgttgtcat atgttgagcc tgtggtctat aaaaccccta   2040

gttccatttc ccataaactt ctgtcaagcc agaccatctc taccctgtac ttggacaact   2100

taactttttt aaccaaagtg cagtttatgt tcacctttgt taaagccacc ttgtggtttc   2160

tgcccatcac ctgaacctac tgaagttgtg tgaaatccta attctgtcat ctccgtagcc   2220

ctcccagttg tgcctcctgc acattgatga gtgcctgctg ttgtctttgc ccatgttgtt   2280

gatgtagctg tgaccctatt gttcctcacc cctgcccccc gccaacccca gctggcccac   2340

ctcttccccc tcccacccaa gcccacagcc agcccatcag gaagccttcc tggcttctcc   2400

acaaccttct gactgtcttt tcagtcatgc cccctgctct tttgtatttg gctaatagta   2460

tatcaatttg cactt                                                    2475
```

<210> SEQ ID NO 15
<211> LENGTH: 1531
<212> TYPE: DNA
<213> ORGANISM: Homo Sapiens

<400> SEQUENCE: 15

```
cggagcctgc agcccagccc cacccagacc catggctgga cctgccaccc agagccccat     60

gaagctgatg gccctgcagc tgctgctgtg gcacagtgca ctctggacag tgcaggaagc    120

cacccccctg ggccctgcca gctccctgcc ccagagcttc ctgctcaagt gcttagagca    180

agtgaggaag atccagggcg atggcgcagc gctccaggag aagctggtga gtgagtgtgc    240

cacctacaag ctgtgccacc ccgaggagct ggtgctgctc ggacactctc tgggcatccc    300

ctgggctccc ctgagcagct gccccagcca ggccctgcag ctggcaggct gcttgagcca    360

actccatagc ggccttttcc tctaccaggg gctcctgcag gccctggaag ggatctcccc    420

cgagttgggt cccaccttgg acacactgca gctggacgtc gccgactttg ccaccaccat    480

ctggcagcag atggaagaac tgggaatggc ccctgccctg cagcccaccc agggtgccat    540

gccggccttc gcctctgctt tccagcgccg ggcaggaggg gtcctggttg cctcccatct    600
```

```
gcagagcttc ctggaggtgt cgtaccgcgt tctacgccac cttgcccagc cctgagccaa     660
gccctcccca tcccatgtat ttatctctat ttaatattta tgtctattta agcctcatat     720
ttaaagacag ggaagagcag aacggagccc caggcctctg tgtccttccc tgcatttctg     780
agtttcattc tcctgcctgt agcagtgaga aaaagctcct gtcctcccat cccctggact     840
gggaggtaga taggtaaata ccaagtattt attactatga ctgctcccca gccctggctc     900
tgcaatgggc actgggatga gccgctgtga gcccctggtc ctgagggtcc ccacctggga     960
cccttgagag tatcaggtct cccacgtggg agacaagaaa tccctgttta atatttaaac    1020
agcagtgttc cccatctggg tccttgcacc cctcactctg gcctcagccg actgcacagc    1080
ggcccctgca tccccttggc tgtgaggccc ctggacaagc agaggtggcc agagctggga    1140
ggcatggccc tggggtccca cgaatttgct ggggaatctc gtttttcttc ttaagacttt    1200
tgggacatgg tttgactccc gaacatcacc gacgcgtctc ctgtttttct gggtggcctc    1260
gggacacctg ccctgccccc acgagggtca ggactgtgac tctttttagg gccaggcagg    1320
tgcctggaca tttgccttgc tggacgggga ctggggatgt gggagggagc agacaggagg    1380
aatcatgtca ggcctgtgtg tgaaaggaag ctccactgtc accctccacc tcttcacccc    1440
ccactcacca gtgtcccctc cactgtcaca ttgtaactga acttcaggat aataaagtgt    1500
ttgcctccaa aaaaaaaaaa aaaaaaaaaa a                                   1531
```

<210> SEQ ID NO 16
<211> LENGTH: 2960
<212> TYPE: DNA
<213> ORGANISM: Homo sapiens

<400> SEQUENCE: 16

```
ctgccgcttc caggcgtcta tcagcggctc agcctttgtt cagctgttct gttcaaacac      60
tctggggcca ttcaggcctg ggtggggcag cgggaggaag ggagtttgag gggggcaagg     120
cgacgtcaaa ggaggatcag agattccaca atttcacaaa actttcgcaa acagcttttt     180
gttccaaccc ccctgcattg tcttggacac caaatttgca taaatcctgg gaagttatta     240
ctaagcctta gtcgtggccc caggtaattt cctcccaggc ctccatgggg ttatgtataa     300
agggccccct agagctgggc cccaaaacag cccggagcct gcagcccagc cccacccaga     360
cccatggctg gacctgccac ccagagcccc atgaagctga tgggtgagtg tcttggccca     420
ggatgggaga gccgcctgcc ctggcatggg agggaggctg gtgtgacaga ggggctgggg     480
atccccgttc tgggaatggg gattaaaggc acccagtgtc cccgagaggg cctcaggtgg     540
tagggaacag catgtctcct gagcccgctc tgtccccagc cctgcagctg ctgctgtggc     600
acagtgcact ctggacagtg caggaagcca ccccccctggg ccctgccagc tccctgcccc     660
agagcttcct gctcaagtgc ttagagcaag tgaggaagat ccagggcgat ggcgcagcgc     720
tccaggagaa gctggtgagt gaggtgggtg agagggctgt ggagggaagc ccggtgggga     780
gagctaaggg ggatggaact gcagggccaa catcctctgg aagggacatg ggagaatatt     840
aggagcagtg gagctgggga aggctgggaa gggacttggg gaggaggacc ttggtgggga     900
cagtgctcgg gagggctggc tgggatggga gtggaggcat cacattcagg agaaagggca     960
agggcccctg tgagatcaga gagtgggggt gcagggcaga gaggaactga acagcctggc    1020
aggacatgga gggagggggaa agaccagaga gtcggggagg acccgggaag gagcggcgac    1080
ccggccacgg cgagtctcac tcagcatcct tccatcccca gtgtgccacc tacaagctgt    1140
```

-continued

```
gccaccccga ggagctggtg ctgctcggac actctctggg catcccctgg gctcccctga   1200

gcagctgccc cagccaggcc ctgcagctgg tgagtgtcag gaaaggataa ggctaatgag   1260

gagggggaag gagaggagga acacccatgg gctcccccat gtctccaggt tccaagctgg   1320

gggcctgacg tatctcaggc agcaccccct aactcttccg ctctgtctca caggcaggct   1380

gcttgagcca actccatagc ggccttttcc tctaccaggg gctcctgcag gccctggaag   1440

ggatctcccc cgagttgggt cccaccttgg acacactgca gctggacgtc gccgactttg   1500

ccaccaccat ctggcagcag gtgagccttg ttgggcaggg tggccaaggt cgtgctggca   1560

ttctgggcac cacagccggg cctgtgtatg ggccctgtcc atgctgtcag cccccagcat   1620

ttcctcattt gtaataacgc ccactcagaa gggcccaacc actgatcaca gctttccccc   1680

acagatggaa gaactgggaa tggcccctgc cctgcagccc acccagggtg ccatgccggc   1740

cttcgcctct gctttccagc gccgggcagg aggggtcctg gttgcctccc atctgcagag   1800

cttcctggag gtgtcgtacc gcgttctacg ccaccttgcc cagccctgag ccaagccctc   1860

cccatcccat gtatttatct ctatttaata tttatgtcta tttaagcctc atatttaaag   1920

acagggaaga gcagaacgga gccccaggcc tctgtgtcct tccctgcatt tctgagtttc   1980

attctcctgc ctgtagcagt gagaaaaagc tcctgtcctc ccatcccctg gactgggagg   2040

tagataggta aataccaagt atttattact atgactgctc cccagccctg gctctgcaat   2100

gggcactggg atgagccgct gtgagcccct ggtcctgagg gtccccacct gggacccttg   2160

agagtatcag gtctcccacg tgggagacaa gaaatccctg tttaatattt aaacagcagt   2220

gttccccatc tgggtccttg caccccctcac tctggcctca gccgactgca cagcggcccc   2280

tgcatcccct tggctgtgag gcccctggac aagcagaggt ggccagagct gggaggcatg   2340

gccctggggt cccacgaatt tgctggggaa tctcgttttt cttcttaaga cttttgggac   2400

atggtttgac tcccgaacat caccgacgtg tctcctgttt ttctgggtgg cctcgggaca   2460

cctgccctgc ccccacgagg gtcaggactg tgactctttt tagggccagg caggtgcctg   2520

gacatttgcc ttgctggatg gggactgggg atgtgggagg gagcagacag gaggaatcat   2580

gtcaggcctg tgtgtgaaag gaagctccac tgtcaccctc cacctcttca ccccccactc   2640

accagtgtcc cctccactgt cacattgtaa ctgaacttca ggataataaa gtgtttgcct   2700

ccagtcacgt ccttcctcct tcttgagtcc agctggtgcc tggccagggg ctggggaggt   2760

ggctgaaggg tgggagaggc cagagggagg tcggggagga ggtctgggga ggaggtccag   2820

ggaggaggag gaaagttctc aagttcgtct gacattcatt ccgttagcac atatttatct   2880

gagcacctac tctgtgcaga cgctgggcta agtgctgggg acacagcagg gaacaaggca   2940

gacatggaat ctgcactcga                                               2960


<210> SEQ ID NO 17
<211> LENGTH: 3221
<212> TYPE: DNA
<213> ORGANISM: Homo Sapiens

<400> SEQUENCE: 17

ccgagatgtt cccagcacag ccccatgtga gagctccctg gctccgggcc cagtatctgg     60

aatgcaggct ccagccaaat gcattctctt ctacgggatc tgggaacttc caaagctgcc    120

tcctcagagt gggaatttcc actcacttct ctcacgccag cactgacctc ccagcggggg    180

agggcatctt ttcttgacag agcagaagtg ggaggcagac agctgtcact ttccagaaga    240

ctttcttttc tgattcatac ccttcacctt ccctgtgttt actgtctgat atatgcaaag    300
```

-continued

```
gccaagtcac tttccagaga tgacaactcc ttcctgaagt agagacatgc ttccaacact    360
cagaagccta tgtgaacact cagccagcaa agctgggaag tttttctctg tgaccatggg    420
ctaattggtc tccttctctg gattgtggct ttatcagata aaaacaagtg gtcatgccac    480
aggatgtcta taagcccatt gattctggga ttctatgagt gatgctgata tgactaagcc    540
aggagagact tatttaaaga tctcagcatc tttcagcttg ttaacctaga gaaaacccga    600
agcatgactg gattataaag ggaaattgaa tgcggtccac caagttcatg gtaaaggatg    660
cactaacaga ttagagagag gtttcccctg atatgaggaa aacttcttgg aagatgaggt    720
gagatggcct aggaagaaat tcctacacaa aattgcacag tctctagtcc tggaaacatt    780
ttattcattg gataagaatg gattgaggca tgagcagagg actgagacaa acacagagaa    840
gtttcaacac tggttgggga gaaaaggagt aactagtgag attcaggcag aacaagaata    900
aggctcctca agaggcacaa gcaaagcagg gctcgagttg atttgttctc tcttcatcct    960
gctttttgta attccaccag agtctgaaat gaccactcca tagagtctct gctctgggat   1020
tctccaggaa accaatatcc atcatgagac atcaagtcta gtcccaggaa gaagagattc   1080
tggaatggaa acatcctggg tgggagtctc agcacatcta ctattctgtc tgagttactg   1140
gacaaataac ttcagtttta acctaacgaa agctgggttg gttggaggac tgggcaggca   1200
gcgctggaaa gtatgtcagc accatacctg actccctgaa tgcactcaac aatgccatta   1260
ctgaccactt actagaaata aaacagtcat ttgttgaata caacccgttt ctttttacaa   1320
gtgtagtgaa aagtgttttc tttcaagaaa ccccatgcat ttatagacat tgcctcagtg   1380
accctttatg aaagaagtca ctagtctttg tatgcccatt gggcaagggc accgcaaggc   1440
tcagaaggag gaggcagtgg gctaggagaa tggagagatc agaattttaa actcagccca   1500
gccattaaca tgcctcaagt actcctatca tatttgtaag agacaacagt tcactgaaat   1560
gaattctaag gtctttgggt ttttatcagt gtgcttctgt agtttctgag gaaatctaag   1620
gcacaactga ggaatgaagt caggctttcc aattcccgaa atactcctcc actgcttact   1680
catgtccctt ggaaattaag aaggaagcca ggagaatagc tgccataacc agggatgaac   1740
ttcttgtcca ctgctgcctg ctatgctagc aacagcctcc taactcataa tgacttagcc   1800
atgaggaatg tttctagatt ctcctttagc tgtctgccca tttggaagat gctgaggaca   1860
gagagaggac ccaagcaggc aactagttgg aggacttgta cacgtttcct tccagcagta   1920
tgtcagagag gtgagcagcc cactggggac agggctgcct gggttctgtg ctcgagggga   1980
ccttgagcag gctatttaac ccttctgtgc ctcagttgcc tgatctataa catgaaaatt   2040
agcaatccct actagataaa gttggggaat ttacagagtt aatatttgta aaggtctgag   2100
aatattcctg gcagagtaag cactctgtga gtatgacact ggcatttctt ctgcagcact   2160
acatgctgtc tatgcctttg tccaagtctg aaaccctaga actcttagaa ttcagttcaa   2220
tgtttacaca atcctacagt tctgctaggc ttctatgatg ctactattct gcatttgaat   2280
gagcaaatgg atttaatgca ttgtcaggga gccggccaaa gcttgagagc tccttcctgg   2340
ctgggaggcc ccttggaatg tggcctgaag gtaagctggc agcgagcctg acatgctttc   2400
atctagtttc ctcgcttcct tccttttctg cagttttcgc ttcacagaaa gcagaatcct   2460
taaaaataac cctcttagtt cacatctgtg gtcagtctgg gcttaatggc accccatcct   2520
ccccatttgc tcatttggtc tcagcagtga atggaaaaag tgtctcgtcc tgaccccctg   2580
cttccctttc ctacttcctg gaaatccaca ggatgctgca tttgctcagc agatttaaca   2640
```

-continued

```
gcccacttat cactcatgga agatccctcc tcctgcttga ctccgccctc tctccctctg   2700

cccgctttca ataagaggca gagacagcag ccagaggaac cgagaggctg agactaaccc   2760

agaaacatcc aattctcaaa ctgaagctcg cactctcgcc tccagcatga aagtctctgc   2820

cgcccttctg tgcctgctgc tcatagcagc caccttcatt ccccaagggc tcgctcagcc   2880

aggtaaggcc ccctcttctt ctccttgaac cacattgtct tctctctgag ttatcatgga   2940

ccatccaagc agacgtggta cccacagtct tgctttaacg ctacttttcc aagataaggt   3000

gactcagaaa aggacaaggg gtgagcccaa ccacacagct gctgctcggc agagcctgaa   3060

ctagaattcc agctgtgaac cccaaatcca gctccttcca ggattccagc tctgggaaca   3120

cactcagcgc agttactccc ccagctgctt ccagcagagt ttggggatca gggtaatcaa   3180

agagagggtg ggtgtgtagg ctgtttccag acacgctgga g                       3221
```

<210> SEQ ID NO 18
<211> LENGTH: 561
<212> TYPE: DNA
<213> ORGANISM: Homo Sapiens

<400> SEQUENCE: 18

```
accacagtgg tgtccgagaa gtcaggcacg tagctcagcg gcggccgcgg cgcgtgcgtc     60

tgtgcctctg cgcgggtctc ctggtccttc tgccatcatg ccgatgttca tcgtaaacac    120

caacgtgccc cgcgcctccg tgccggacgg gttcctctcc gagctcaccc agcagctggc    180

gcaggccacc ggcaagcccc cccagtacat cgcggtgcac gtggtcccgg accagctcat    240

ggccttcggc ggctccagcg agccgtgcgc gctctgcagc ctgcacagca tcggcaagat    300

cggcggcgcg cagaaccgct cctacagcaa gctgctgtgc ggcctgctgg ccgagcgcct    360

gcgcatcagc ccggacaggg tctacatcaa ctattacgac atgaacgcgg ccaatgtggg    420

ctggaacaac tccaccttcg cctaagagcc gcagggaccc acgctgtctg cgctggctcc    480

acccgggaac ccgccgcacg ctgtgttcta ggcccgccca ccccaacctt ctggtgggga    540

gaaataaacg gtttagagac t                                              561
```

<210> SEQ ID NO 19
<211> LENGTH: 2156
<212> TYPE: DNA
<213> ORGANISM: Homo Sapiens

<400> SEQUENCE: 19

```
ggcacgagcc cagaaacaaa gacttcacgg acaaagtccc ttggaaccag agagaagccg     60

ggatggaaac tccaaacacc acagaggact atgacacgac cacagagttt gactatgggg    120

atgcaactcc gtgccagaag gtgaacgaga gggcctttgg ggcccaactg ctgccccctc    180

tgtactcctt ggtatttgtc attggcctgg ttggaaacat cctggtggtc ctggtccttg    240

tgcaatacaa gaggctaaaa aacatgacca gcatctacct cctgaacctg gccatttctg    300

acctgctctt cctgttcacg cttcccttct ggatcgacta caagttgaag gatgactggg    360

tttttggtga tgccatgtgt aagatcctct ctgggtttta ttacacaggc ttgtacagcg    420

agatcttttt catcatcctg ctgacgattg acaggtacct ggccatcgtc cacgccgtgt    480

ttgccttgcg ggcacggacc gtcacttttg gtgtcatcac cagcatcatc atttgggccc    540

tggccatctt ggcttccatg ccaggcttat acttttccaa gacccaatgg gaattcactc    600

accacacctg cagccttcac tttcctcacg aaagcctacg agagtggaag ctgtttcagg    660

ctctgaaact gaacctcttt gggctggtat tgcctttgtt ggtcatgatc atctgctaca    720
```

```
cagggattat aaagattctg ctaagacgac caaatgagaa gaaatccaaa gctgtccgtt    780
tgatttttgt catcatgatc atcttttttc tcttttggac cccctacaat ttgactatac    840
ttatttctgt tttccaagac ttcctgttca cccatgagtg tgagcagagc agacatttgg    900
acctggctgt gcaagtgacg gaggtgatcg cctacacgca ctgctgtgtc aacccagtga    960
tctacgcctt cgttggtgag aggttccgga agtacctgcg gcagttgttc cacaggcgtg   1020
tggctgtgca cctggttaaa tggctcccct tcctctccgt ggacaggctg gagagggtca   1080
gctccacatc tccctccaca ggggagcatg aactctctgc tgggttctga ctcagaccat   1140
aggaggccaa cccaaaataa gcaggcgtga cctgccaggc acactgagcc agcagcctgg   1200
ctctcccagc caggttctga ctcttggcac agcatggagt cacagccact tgggatagag   1260
agggaatgta atggtggcct ggggcttctg aggcttctgg ggcttcagtc ttttccatga   1320
acttctcccc tggtagaaag aagatgaatg agcaaaacca aatattccag agactgggac   1380
taagtgtacc agagaagggc ttggactcaa gcaagatttc agatttgtga ccattagcat   1440
ttgtcaacaa agtcacccac ttcccactat tgcttgcaca aaccaattaa acccagtagt   1500
ggtgactgtg ggctccattc aaagtgagct cctaagccat gggagacact gatgtatgag   1560
gaatttctgt tcttccatca cctccccccc cccgccaccc tcccactgcc aagaacttgg   1620
aaatagtgat ttccacagtg actccactct gagtcccaga gccaatcagt agccagcatc   1680
tgcctcccct tcactcccac cgcaggattt gggctcttgg aatcctgggg aacatagaac   1740
tcatgacgga agagttgaga cctaacgaga aatagaaatg ggggaactac tgctggcagt   1800
ggaactaaga aagcccttag gaagaatttt tatatccact aaaatcaaac aattcaggga   1860
gtgggctaag cacgggccat atgaataaca tggtgtgctt cttaaaatag ccataaaggg   1920
gagggactca tcatttccat ttacccttct tttctgacta tttttcagaa tctctcttct   1980
tttcaagttg ggtgatatgt tggtagattc taatggcttt attgcagcga ttaataacag   2040
gcaaaaggaa gcagggttgg tttcccttct ttttgttctt catctaagcc ttctggtttt   2100
atgggtcaga gttccgactg ccatcttgga cttgtcagca aaaaaaaaaa aaaaaa       2156
```

<210> SEQ ID NO 20
<211> LENGTH: 638
<212> TYPE: DNA
<213> ORGANISM: Mus musculus

<400> SEQUENCE: 20

```
gcttctgaag cttctgggcc ctgcagtccc agctctgtgc aaacctaacc ccgagcaaca     60
ccatgaagct ctgcgtgtct gccctctctc tcctcttgct cgtggctgcc ttctgtgctc    120
cagggttctc agcaccaatg ggctctgacc ctcccacttc ctgctgtttc tcttacacct    180
cccggcagct tcacagaagc tttgtgatgg attactatga gaccagcagt ctttgctcca    240
agccagctgt ggtattcctg accaaaagag gcagacagat ctgtgctaac cccagtgagc    300
cctgggtcac tgagtacatg agtgacttgg agttgaactg agcagctcca gcggcagggc    360
aggaggagcc acttcaggag aggcctcctc agccctgatg cttctcactg agaagcgtcc    420
ttgctcctca cgttcagatt tcctgcccct cttcttaatt taaatctctg tgtagacttt    480
gttttgtttt tttgggggag tattatttct attatttatg ttttagttat aggacgcgtg    540
tctcccatgg agatggtcca ccattgctgt ttctctgcta ttgtggatat gactgtgaaa    600
ttgatttcat gcattttcat aataaatctt tctttaag                            638
```

<210> SEQ ID NO 21
<211> LENGTH: 764
<212> TYPE: DNA
<213> ORGANISM: Homo sapiens

<400> SEQUENCE: 21
atgtgctgta ccaagagttt gctcctggct gctttgatgt cagtgctgct actccacctc 60
tgcggcgaat cagaagcagc aagcaacttt gactgctgtc ttggatacac agaccgtatt 120
cttcatccta aatttattgt gggcttcaca cggcagctgg ccaatgaagg ctgtgacatc 180
aatgctatca tctttcacac aaagaaaaag ttgtctgtgt gcgcaaatcc aaaacagact 240
tgggtgaaat atattgtgcg tctcctcagt aaaaaagtca agaacatgta aaaactgtgg 300
cttttctgga atggaattgg acatagccca agaacagaaa gaaccttgct ggggttggag 360
gtttcacttg cacatcatgg agggtttagt gcttatctaa tttgtgcctc actggacttg 420
tccaattaat gaagttgatt catattgcat catagtttgc tttgtttaag catcacatta 480
aagttaaact gtattttatg ttatttatag ctgtaggttt tctgtgttta gctatttaat 540
actaattttc cataagctat tttggtttag tgcaaagtat aaaattatat ttgggggga 600 ataagattat atggactttt ttgcaagcaa caagctattt tttaaaamma actatttaac 660
attcttttgt ttatattgtt ttgtctccta aattgttgta attgcattat aaaataagaa 720
aaatattaat aagacaaata ttgaaaataa agaaacaaaa agtt 764

<210> SEQ ID NO 22
<211> LENGTH: 545
<212> TYPE: DNA
<213> ORGANISM: Homo sapiens

<400> SEQUENCE: 22
atggccctgc tactggccct cagcctgctg gttctctgga cttccccagc cccaactctg 60
agtggcacca atgatgctga agactgctgc ctgtctgtga cccagaaacc catccctggg 120
tacatcgtga ggaacttcca ctaccttctc atcaaggatg gctgcagggt gcctgctgta 180
gtgttcacca cactgagggg ccgccagctc tgtgcacccc cagaccagcc ctgggtagaa 240
cgcatcatcc agagactgca gaggacctca gccaagatga agcgccgcag cagttaacct 300
atgaccgtgc agagggagcc cggagtccga gtcaagcatt gtgaattatt acctaacctg 360
gggaaccgag gaccagaagg aaggaccagg cttccagctc ctctgcacca gacctgacca 420
gccaggacag ggcctggggt gtgtgtgagt gtgagtgtga gcgagagggt gagtgtggtc 480
tagagtaaag ctgctccacc cccagattgc aatgctacca ataaagccgc ctggtgttta 540
caact 545

<210> SEQ ID NO 23
<211> LENGTH: 4037
<212> TYPE: DNA
<213> ORGANISM: Homo sapiens

<400> SEQUENCE: 23
gagctccgtt gggagtccca tgtttcttta tggcataatg ggtgagaaca cagacttgga 60
agccaaacca cctgaatttg aaccccagtt ccatttacca actgtcaaaa gcttaggctt 120
tgattctaag cctgtttcct caactgctgt tctaaagatt aaataggcta atattcataa 180
ggcaactggg acagtggctt gtgtgtatag caaccattat ataagtgaat tatctactga 240
gcaccacagc acttcttcac tccatggtgt ggtgaccaga atggagatga gacagagaac 300

-continued

```
tgcaggttct gcttcgagtt taagttagga tttcccttga ccaatgagac ctgacttgga    360
ggagtcctgg cctcattcca ttaccccaaa caccctctag tctctagatg aacagatcct    420
gaatgtccag gccccacgtg gcctgttcta aggcctgaga tggaattgga tacaggacac    480
atccagcctt gagatctttt gctaagtgtg acacagtgcc cccagccctg tgctcatgtt    540
catgcctagg gaaaggcttc tatcaaaaga gttgaacttc ttcccactgg ggatggaaga    600
ccatttcctc ccttaaacct tggctctccc tgcttccttc aggccaccaa caacacatgt    660
gcaggatatg aaattgctga ggcatcactg ctttcctact tcccttccaa gtctcagctc    720
ccttatttta aaaaatattt ggcctcaatg atcatttctc aacaattcct caccgcagga    780
gcctctgaag ctcccaccag gccagctctc ctcccacaac agcttcccac agcatgaaga    840
tctccgtggc tgccattccc ttcttcctcc tcatcaccat cgccctaggg accaagactg    900
aatcctcctc acgtgagtgc aatgccttgt cttccttcca acctagagcc tgcagggaaa    960
taagcaggag tgaggttggg gctcagggga agaccaggag cagggactca gaaaggaggg   1020
ctggtatctt cttgaaattg tgtgtatagc aacattatat aaatgaatta tctactgagc   1080
accacagcac ttcaccccat ggtgtggtga gcaggatgga gatgagactt aggactgtag   1140
gttctgctta agagtttaag ttgggatctt ccagccttga ccaatgagac ttgacttggg   1200
agactccagg cttcattcca ctaccccaaa tgccctctag tctccaaata aacagatcct   1260
gaatctccag gcctcacatg gccttgatct cttatcattg ccccccagga ccagtccccc   1320
cttgccctca aggacatgga gtgagaccag cctgcctctc tactccctca atttctctct   1380
ctttgccgct aagcaaaaga gtggcccacc ccatttgggg tatatttcct cagggagatt   1440
aggagcagtg tcttgagccc ctcaagggca tttttctatt ggcctcctga ggtttgggcc   1500
cagcctgctt ccagcgtcac ctgtgcccag tgagtgcagc attgcttggg tatgggctgg   1560
ggggaaacac gacagtgtgg ggtccatcct aggccccctt ttctcagctg atttcttaga   1620
ataagctgcc tttagagata accaaaacta tttatcactc ttccatttta cctactctcc   1680
ttttcagaaa ctggggggaa accgaaggtt gttaaaatac agctaaagtt ggtgggtatg   1740
tgcacagttt gacttgccct ctccgatgtc atttgtcagc tcagaggaac aaggtgggag   1800
agtataggag ctctgactgg gtctcaggaa acaggggccc cttatgccgt tctttggatc   1860
gtgaggatgc tgcctggaat ggagctggaa aacaggatga gacccttcca cccagacatc   1920
tggccaccct cagtgacctc tgaggccatt gtgatgcaca tccatgattc tatgaagcag   1980
ggtcacataa catgcacaca cctgatttct ccactccata accacaacat gtgcctgttt   2040
gtacagggct cttggcctac aatgtccttc ctgctacctc tataattcaa gcttggggtg   2100
gctgctgtca ccttgcttct cctataaaag ccatgaaact tctcaatcag aaaatagatg   2160
aaaaaatcac ccaatccagt gatttttaaa actttttaga ccacaaaacc ttttcttcaa   2220
gcaatatctt ccacagaggc ccaatatgta aaacagaaaa aatgggttga gtagggtaca   2280
agacaccact ctcaaatgca gcaaggcctc cacaatagtc cctgaggccc ccagagctca   2340
gtgtaaaaac cactgatgca gtccaagggc ctcatttaca gaggagggaa caggggggaaa  2400
gtaaaatggc cacagtacac aggaagcaca ggcaaggtta ggttaggatt tgggtgccct   2460
gactctgtgg cctttgtcct tggggcttgc tgtgggcatc ctgctctctc tgcaggttgt   2520
cggttcaatg gggacatggg cagggtggag cactaggagg ggctgggttt gcattcccaa   2580
atggcatgtc tccaaatccc tattgggatt tcttccaaat attcctccta tttggagcac   2640
```

-continued

```
ctttcccgaa taaggcatga aggctgcatg atattggcca agtccctagc cttctctgcc   2700

agtcggcccc cagagatggt gtaagaagat ctgagtgtgc tgctcttcaa tcctggagtt   2760

gaaagtcatc caccagtctt tccaagaggg gttgaagaaa aggaggaagg gtgattgatg   2820

atgagggagg agaaaaagaa gagcccagga gtaccatgga gaaggagaag agaagatgag   2880

gaaagcctac tctcccctcc aagttctgag ggctgtctc ctccttcctt ccctcctcca   2940

tgccctcagc ttgcaggagc agccaatggt atggccttta acaaggggcc cctcctcagc   3000

atctgatgct ctctcctcag gggacctta ccacccctca gagtgctgct tcacctacac   3060

tacctacaag atcccgcgtc agcggattat ggattactat gagaccaaca gccagtgctc   3120

caagcccgga attgtgtagg tggtacacac acatcacact ggggggagag ggagccagca   3180

gggcctcctg gagggaagca gggagtggtg gtggaatggg gacccccagc gtacctccca   3240

ggtgtgacta catggggaga ggcagctgag gggcaatctg agcgctttct ggctggagcc   3300

tgcaggagcc atggggaaac tgaccccatg gatggggaga tgacagagaa gggagaagaa   3360

ggcaagaggg cacttcctca gggggacaca gagactagat gggtctaggg gtcctaggaa   3420

ccgaagagta tgtctcagag aggagactgg ctctaagctg cctctgtgga agaaaggaaa   3480

agcagtatag gtcaggtggg gaatttagga gggagggaag atgggctgtc tcttccggcc   3540

actgggcccc tcggtttgtg atccttctcc ctcttgctcc acagcttcat caccaaaagg   3600

ggccattccg tctgtaccaa ccccagtgac aagtgggtcc aggactatat caaggacatg   3660

aaggagaact gagtgaccca gaaggggtgg cgaaggcaca gctcagagac ataaagagaa   3720

gatgccaagg ccccctcctc cacccaccgc taactctcag ccccagtcac cctcttggag   3780

cttccctgct ttgaattaaa gaccactcat gctcttccct ggcctcattc ctttctacgg   3840

gatttactca ttggccatgc actgaggaca ccagggtgtg gcaccctcgg catcaagcct   3900

cgctctgcag aagttttggt ggagcctggt acaaaaaata ggtcaggcct gcaatgcagg   3960

tagtgagaag cagaaagtga gaaagaaaag cagtgtaaag accgtctcct cctcagcagc   4020

aacagtagca gaccccg                                                  4037
```

<210> SEQ ID NO 24
<211> LENGTH: 481
<212> TYPE: DNA
<213> ORGANISM: Homo sapiens

<400> SEQUENCE: 24

```
agcctctgaa gctcccacca ggccagctct cctcccacaa cagcttccca cagcatgaag     60

atctccgtgg ctgccattcc cttcttcctc ctcatcacca tcgccctagg gaccaagact    120

gaatcctcct cacggggacc ttaccacccc tcagagtgct gcttcaccta cactacctac    180

aagatcccgc gtcagcggat tatggattac tatgagacca acagccagtg ctccaagccc    240

ggaattgtct tcatcaccaa aaggggccat tccgtctgta ccaaccccag tgacaagtgg    300

gtccaggact atatcaagga catgaaggag aactgagtga cccagaaggg gtggcgaagg    360

cacagctcag agacataaag agaagatgcc aaggcccccct cctccaccca cccctaactc    420

tcagccccag tcaccctctt ggagcttccc tgctttgaat taaagaccac tcatgctctt    480

c                                                                    481
```

<210> SEQ ID NO 25
<211> LENGTH: 360
<212> TYPE: DNA
<213> ORGANISM: Homo sapiens

<400> SEQUENCE: 25
atggcaggcc tgatgaccat agtaaccagc cttctgttcc ttggtgtctg tgcccaccac 60
atcatcccta cgggctctgt ggtcataccc tctccctgct gcatgttctt tgtttccaag 120
agaattcctg agaaccgagt ggtcagctac cagctgtcca gcaggagcac atgcctcaag 180
ggaggagtga tcttcaccac caagaagggc cagcagttct gtggcgaccc caagcaggag 240
tgggtccaga ggtacatgaa gaacctggac gccaagcaga agaaggcttc ccctagggcc 300
agggcagtgg ctgtcaaggg ccctgtccag agatatcctg gcaaccaaac cacctgctaa 360

<210> SEQ ID NO 26
<211> LENGTH: 492
<212> TYPE: DNA
<213> ORGANISM: Mus musculus

<400> SEQUENCE: 26
gaagaccttc acctcagctt ttggtaccat gaggtcactt cagatgctgc tcctggctgc 60
tctgcttctg ggacttttc tgcagcatgc cagagctgct cgagccacca atgtaggccg 120
agagtgctgc ctggattact tcaaaggggc cattcctatc aggaagttgg tgagctggta 180
taagacctca gtggagtgtt ccagggatgc catcgtgttt ctgactgtcc agggcaagct 240
catctgtgca gaccccaaag acaaacatgt gaagaaggcc atcagattgg tgaaaaaccc 300
aaggccgtga ccttcccgct gaggcatttg gagacgccag ggctgctgtc catggtttca 360
acataaagcg gcctgtgacc agcagagccc aagagcagcc acagagcaga agtccctgtt 420 cccttttta tggactctta tgcactacag gcgaacacaa aaaaaagcaa cggaataaag 480
ccttcctccc tc 492

<210> SEQ ID NO 27
<211> LENGTH: 3460
<212> TYPE: DNA
<213> ORGANISM: Homo sapiens

<400> SEQUENCE: 27
aagaaagtca ttggtagctt gatggggatg gtattgaatc tataagttac cttgggcagt 60
atggccatat tcacgatatt gatttttcct acccatgagc atggaatatt cttccatttg 120
tttgtatcct cttttatttc attgagcagt ggtttgtagt tctccttgaa gaggtccttc 180
atgtcccttg taagttggat tcctaggtat tttattctct ttgaagcaat tgtgaatggg 240
agttcactca tgatttggct ctctgtttgt ttgttattgg tgtataagaa tgcttgtgat 300
ttttgtgcat tgattttgta tcctgagact ttgctgaagt tgcttatcag cttaaggaga 360
ttttgggctg agaccatggg gttttctaga tatacaatta tgtaatttgc aaatagggac 420
aatttgactt cctcttttcc taattgaata ccctttattt ccttctcctg cctaattgtc 480
ctggccattg gagaggagga gcatctccca gacagctgcg tgcctcagag aagccagcct 540
cgctaacccc tcaagcccag gggatgagac cctcctgaat cgctgctcta ttttggctgg 600
agccacagct ccctccaccg cggggcgggg ctaaaatgtc ctcccccta agggagcagg 660 cagctcctcc cagccaccca ccccaccaat tcccatcctc ccgcccccct ccaccaaccc 720
cttctttcca cactgccccc tgagttcagg gaatttcccc agcatcccaa agcttgagtt 780
tcctgccagt cgggagggat gaatgcagat aaagggagtg cagaaggcac gaggaaacca 840
aagtgctctg tatcctccag tctccgcgcc tccacccagc tcaggaaccc gcgaaccctc 900

-continued

```
tcttgaccac tatgagcctc ccgtccagcc gcgcggcccg tgtcccgggt ccttcgggct    960
ccttgtgcgc gctgctcgcg ctgctgctcc tgctgacgcc gccggggccc ctcgccagcg   1020
gtgagagctc ctggcactgg ggtgcatccc agcctctgcg gggccgctgc gttccaggga   1080
actctcccag caacctgccc tataaaaatg tctttcttcc ccagctggtc ctgtctctgc   1140
tgtgctgaca gagctgcgtt gcacttgttt acgcgttacg ctgagagtaa accccaaaac   1200
gattggtaaa ctgcaggtgt tccccgcagg cccgcagtgc tccaaggtgg aagtggtgta   1260
agttctcctg tgttgctgtg tccactgtga cttaggcaag tcctccagcc tgggtcgtca   1320
acctttgtgg ctcatgggtg catcctcttt ttctttactt cagagcctcc ctgaagaacg   1380
ggaagcaagt ttgtctggac ccggaagccc cttttctaaa gaaagtcatc cagaaaattt   1440
tggacaggta tttgtccctt tgatctttgt ggtgttttaa tatcttctat ggaaagcata   1500
tacttcacaa tgtccttatt ctctctgtag gatttagact atgcttagaa ttataaggtt   1560
gttaagaaga ataaggaaac tttttttctg gaatgttctg ggtaaacctt tatcaccaat   1620
cttacatgcc tgaacaatta cacagagctc attactgaca tctatttttt gtctgctctt   1680
tgcttttatt gatttttttc ccccaccaaa cgcttttgaa aaccaaatgt agcatacaag   1740
agtgtgggaa ttggttatac taatataact cttttctcaa cagtggaaac aagaaaaact   1800
gagtaacaaa aaagaccatg catcataaaa ttgcccagtc ttcagcggag cagttttctg   1860
gagatccctg gacccagtaa gaataagaag gaagggttgg tttttttcca ttttctacat   1920
ggattcccta ctttgaagag tgtgggggaa agcctacgct tctccctgaa gtttacagct   1980
cagctaatga agtactaata tagtatttcc actatttact gttattttac ctgataagtt   2040
attgaaccct ttggcaattg accatattgt gagcaaagaa tcactggtta ttagtctttc   2100
aatgaatatt gaattgaaga taactattgt atttctatca tacattcctt aaagtcttac   2160
cgaaaaggct gtggatttcg tatggaaata atgttttatt agtgtgctgt tgagggaggt   2220
atcctgttgt tcttactcac tcttctcata aaataggaaa tattttagtt ctgtttcttg   2280
gggaatatgt tactctttac cctaggatgc tatttaagtt gtactgtatt agaacactgg   2340
gtgtgtcata ccgttatctg tgcagaatat atttccttat tcagaatttc taaaaattta   2400
agttctgtaa gggctaatat attctcttcc tatggtttta gacgtttgat gtcttcttag   2460
tatggcataa tgtcatgatt tactcattaa actttgattt tgtatgctat tttttcacta   2520
taggatgact ataattctgg tcactaaata tacactttag atagatgaag aagcccaaaa   2580
acagataaat tcctgattgc taatttacat agaaatgtat tctcttggtt ttttaaataa   2640
aagcaaaatt aacaatgatc tgtgctctga aagttttgaa aatatatttg aacaatttga   2700
atataaattc atcatttagt cctcaaaata tatacagcat tgctaagatt ttcagatatc   2760
tattgtggat cttttaaagg ttttgaccat tttgttatga ggaattatac atgtatcaca   2820
ttcactatat taaaattgca cttttatttt ttcctgtgtg tcatgttggt ttttggtact   2880
tgtattgtca tttggagaaa caataaaaga tttctaaacc actgatgttg tttctccttc   2940
ttatacagtt actatttatc tttaattcta cattattcaa aatattacct ctgctcttct   3000
ctggctggca gagaggccct cattacccaa taccattgca ttggttcaac ttttctccat   3060
gttcagcccc cttccagtta ctccttcaca gcaccaatag cctctggggt ctttagaaaa   3120
cacaaatagg ataagatttt cctatctaaa ttcttaaatg gctccctgtt tcctagacat   3180
gaaataaaag ttgctaaaca tgatgaatga ggttctgtct catctcactc ctgatcatcg   3240
gtacttcaac ttcccttgtg cctcacattc actatagtca ggcgttcagt tccctaacta   3300
```

```
ggcatgttct ttccccaggc tcatgacttt gtatttgcta gggtctctac ctggaaagca   3360

tttacgtttt cctgcgtata agaggaggct tattcatcct tcagaactca gttcaagcaa   3420

tatctccttc gtgaattttc cttggcacac tcagcaaagc                         3460


<210> SEQ ID NO 28
<211> LENGTH: 254
<212> TYPE: DNA
<213> ORGANISM: Homo Sapiens

<400> SEQUENCE: 28

ggtcctgtct ctgctgtgct cacggagctg cgttgcactt gtttacgcgt tacgctgaga     60

gtaaacccca aaacgattgg taaactgcag gtgttccccg caggcccgca gtgctccaag    120

gtggaagtgg tagcctccct gaagaacggg aagcaagttt gtctggaccc ggaagcccct    180

tttctaaaga aagtcatcca gaaaattttg gacagtggaa acaagaaaaa ctgagtaaca    240

gtcgacgcgg ccgc                                                      254


<210> SEQ ID NO 29
<211> LENGTH: 393
<212> TYPE: DNA
<213> ORGANISM: Homo sapiens

<400> SEQUENCE: 29

tcccacctct caggtggtat cttcagcgca ggctgccact cagccccccct ccagggatct     60

ggggcagaag gcgaatatcc cagagtctca gagtccacag gagttactct gaagggcgag    120

ccgcgggctg catcagtgga cccccacacc ccacccgcac cccaagcgct ccaccctggg    180

ggcggggccg tcgccttcct tccggactcg ggatcgatct ggaactccgg gaatttccct    240

ggcccggggg ctccgccctt tccagcccca accatgcata aaaggggttc gcggatctcg    300

gagagccaca gagcccgggc cgcaggcacc tcctcgccag ctcttccgct cctctcacag    360

ccgccagacc cgcctgctga gccccatggc ccg                                 393


<210> SEQ ID NO 30
<211> LENGTH: 374
<212> TYPE: DNA
<213> ORGANISM: Homo sapiens

<400> SEQUENCE: 30

cgcctcctcg caggcggtta tctcggtatc tctgagagcg gcgggctctc gctcccgctc     60

cagggattcg gggcagaaag agaacatccc acagttggcg ggagttacgc aagacagtca    120

gacccggacg tcactcgtga gtgccccgac ccccctccac cccagaggcg gggccatcgc    180

cttccttccg aactcgggat cgatctggag ctccgggaat ttccctggcc cgggactccg    240

gctttccagc cccaaccatg cataaaaggg gttcgccgtt ctcggagagc cacagagccc    300

gggccacagg cagctccttg ccagctctcc tcctcgcaca gccgctcgaa ccgcctgctg    360

agccccatgg cccg                                                      374


<210> SEQ ID NO 31
<211> LENGTH: 1064
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
```

<221> NAME/KEY: misc_feature
<222> LOCATION: (766)..(766)
<223> OTHER INFORMATION: n is a, c, g, t or u

<400> SEQUENCE: 31

```
cacagccggg tcgcaggcac ctccccngcc agctctcccg cattctgcac agcttcccga      60
cgcgtctgct gagccccatg gcccacgcca cgctctccgc cgcccccagc aatccccggc     120
tcctgcgggt ggcgctgctg ctcctgctcc tggtgggcag ccggcgcgca gcaggagcgt     180
ccgtggtcac tgaactgcgc tgccagtgct tgcagacact gcagggaatt cacctcaaga     240
acatccaaag tgtgaatgta aggtcccccg gaccccactg cgcccaaacc gaagtcatag     300
ccacactcaa gaatgggaag aaagcttgtc tcaaccccgc atcccccatg gttcagaaaa     360
tcatcgaaaa gatactgaac aaggggagca ccaactgaca ggagagaagt aagaagctta     420
tcagcgtatc attgacactt cctgcagggt ggtccctgcc cttaccagag ctgaaaatga     480
aaaagagaac agcagctttc tagggacagc tggaaaggga cttaatgtgt ttgactattt     540
cttacgaggg ttctacttat ttatgtattt atttttgaaa gcttgtattt taatatttta     600
catgctgtta tttaaagatg tgagtgtgtt tcatcaaaca tagctcagtc ctgattattt     660
aattggaata tgatgggttt taaatgtgtc attaaactaa tatttagtgg gagaccataa     720
tgtgtcagcc accttgataa atgacagggt ggggaactgg agggtngggg gattgaaatg     780
caagcaatta gtggatcact gttagggtaa gggaatgtat gtacacatct atttttttata     840
cttttttttt taaaaaagaa tgtcagttgt tatttattca aattatctca cattatgtgt     900
tcaacatttt tatgctgaag tttcccttag acattttatg tcttgcttgt agggcataat     960
gccttgttta atgtccattc tgcagcgttt ctctttccct tggaaaagag aatttatcat    1020
tactgttaca tttgtacaaa tgacatgata ataaaagttt tatg                     1064
```

<210> SEQ ID NO 32
<211> LENGTH: 2177
<212> TYPE: DNA
<213> ORGANISM: Homo Sapiens

<400> SEQUENCE: 32

```
gaattctcag taagcggact taccaaagta ggtgatctgt aggggagtta acaaaattca      60
gtggtccttt caggccactg acttcaagtg gcaagagaca agggtctctt gttatcatgt     120
tatcttggct tccaaagctg gttgaagtcc agagattcat aaagtcattc aagaaaccta     180
gaatgacctg cctgcaagaa gacaggaagg actttcagtt tatagcaatt caaacatgaa     240
taacatttcc tgattaatag taataataat tagaaaggat tgactttcag aaatttttct     300
caaatcaagg ctcctgttac tttggttcca cctttctct ctagaaggag aggaggagca     360
tctcccagat gctgcgtgct ccagaaaagc cggcatccct agcccgctct ggcacaggcc     420
atgaggcgct gctgaatcct gctgaatagc tactcccttc tagctggagc cacagctccc     480
tccaccgcgg aacagggtta caacgtccct ctcggtagag gtgcacgcag ctcctcctgg     540
ccaccctccc caccagttcc cattgtctgg ccccccctccc ccaacctctt ctttccacac     600
tgccccatga gttcagggaa tttccccagc atcccaaagc ttgagtttcc tgtcagtggg     660
gagagatgag tgtagataaa aggagtgcag aaggaacgag gaagccacag tgctccggat     720
cctccaatct tcgctcctcc aatctccgct cctccaccca gttcaggaac ccgcgaccgc     780
tcgcagcgct ctcttgacca ctatgagcct cctgtccagc cgcgcggccc gtgtccccgg     840
tccttcgagc tccttgtgcg cgctgttggt gctgctgctg ctgctgacgc agccagggcc     900
```

```
catcgccagc ggtgagagcg catggcgcgc gggacgcact cgcactcggg cacagaggtg    960

catcccagcc tctgcggggt cgctgcgttc cagggaactc tcccagcaac ctgccctata   1020

aagggtgtct ctctttcttc cccagctggt cctgccgctg ctgtgttgag agagctgcgt   1080

tgcgtttgtt tacagaccac gcaaggagtt catcccaaaa tgatcagtaa tctgcaagtg   1140

ttcgccatag gcccacagtg ctccaaggtg gaagtggtgt aagttctgtg ctgctgtgtc   1200

cgctgtgacc ttggcaagag agaaatcccg cagcctgggt cttcaacctt ggtatctcat   1260

gagtgtatct tctttttctt tccttcagag cctccctgaa gaacgggaag gaaatttgtc   1320

ttgatccaga agcccctttt ctaaagaaag tcatccagaa aattttggac gggtacttgt   1380

cactttgatc tttgtggttt ctaaatctga tctagggaga ccatagactt cacaaggtct   1440

ttattctctg tacgatttaa gtaacacttt tcatgtttag aattaaaagg ttgttgaatt   1500

gggaaagttt ttctggattg tcctgggaaa atataccaat cttacatgta attacttgag   1560

caattacaca cagcttgtca ctaagttatg ttttttgttt acccattgct tttattgatt   1620

tttgtattct cctttttttac caaacatcat aaacgctgag ttttgacaag ggtggagtag   1680

aaaggagtgt gaaaaatggt taaactaata taacattttt ctcaacagtg gaaacaagga   1740

aaactgatta agagaaatga gcacgcatgg aaaagtttcc cagtcttcag cagagaagtt   1800

ttctggaggt ctctgaaccc agggaagaca agaaggaaag attttgttgt tgtttgttta   1860

tttgtttttc cagtagttag ctttcttcct ggattcctca ctttgaagag tgtgaggaaa   1920

acctatgttt gccgcttaag ctttcagctc agctaatgaa gtgtttagca tagtacctct   1980

gctatttgct gttattttat ctgctatgct attgaagttt tggcaattga ctatagtgtg   2040

agccaggaat cactggctgt taatctttca aagtgtcttg aattgtaggt gactattata   2100

tttccaagaa atattcctta agatattaac tgagaaggct gtggatttaa tgtggaaatg   2160

atgtttcata agaattc                                                  2177


<210> SEQ ID NO 33
<211> LENGTH: 554
<212> TYPE: DNA
<213> ORGANISM: Rattus norvegicus

<400> SEQUENCE: 33

tttcctaaat aaatatgacc accaagaaca tgttctctga agacattctc agccttgact     60

ccagcacggt gacttaatag agctcggctc tgccatgaag tccgttgctc tattcctcat    120

gggcatcatc ttcctggatc actgtggagt tcgaggaacc ctagtgataa ggaatcagcg    180

atgctcctgc atcagcacca gccaaggcac attccactac aaatccctca aagacctcaa    240

acagtttgcc ccaagcccta actgcaacaa aactgaaatc atcgctacac tgaagaacgg    300

agatcaaacc tgcctagacc cagattcagc aagggtgaag aagctgatga aagaatggga    360

gaaaaagatc agccaaaaga aaaagcaaaa gagggggaaa aaccatcaaa ggagcaagaa    420

aacccgaaaa gctaaaacac cccaccatcc ggagtcaaag aagactgcat aagagaccac    480

tttaccaaca agcgctctgc atctaaacgg cttttagatc atactaaaac gccttccctt    540

taatacacaa ctcg                                                      554


<210> SEQ ID NO 34
<211> LENGTH: 514
<212> TYPE: DNA
<213> ORGANISM: Rattus norvegicus
```

<400> SEQUENCE: 34
atcaccagag ccacagcaga gagctgcagc tgccgctgag atgaacagga cgggcatggc 60
cgtagccctg gctatgatca tctgggccac aacggttcca ggcttcgtta tgttcaaagg 120
ggggcgctgt ctttgcatcg accgcggagt gaaagtggtc aaaatggcag caatcaagga 180
agtttctgta atttacccga gtaacggctg tgacaaagtt gaagtgattg ttaccctgaa 240
ggctcataaa ggacaaaggt gcctggaccc cacatccaag caagctcgcc tcataatgca 300
gacaatacaa aaaaagaatt ttttaaggcg ccagaacatg tgatgggccc tcaaattcga 360
gctctgtgcc aagaagctga ccctctcctg tcttggaata tgcatccgtt ttgccagatt 420
gcagaactcg ctaggaggtc ggatacctct aaactattct gcttggctat gaaaatattt 480
atctcgaaga gtcatgtgtc tctgtgtgtg caca 514

<210> SEQ ID NO 35
<211> LENGTH: 3524
<212> TYPE: DNA
<213> ORGANISM: Homo Sapiens

<400> SEQUENCE: 35
tctccgtcag ccgcattgcc cgctcggcgt ccggcccccg acccgtgctc gtccgcccgc 60
ccgcccgccc gcccgcgcca tgaacgccaa ggtcgtggtc gtgctggtcc tcgtgctgac 120
cgcgctctgc ctcagcgacg ggaagcccgt cagcctgagc tacagatgcc catgccgatt 180
cttcgaaagc catgttgcca gagccaacgt caagcatctc aaaattctca acactccaaa 240
ctgtgccctt cagattgtag cccggctgaa gaacaacaac agacaagtgt gcattgaccc 300
gaagctaaag tggattcagg agtacctgga gaaagcttta aacaagaggt tcaagatgtg 360
agagggtcag acgcctgagg aacccttaca gtaggagccc agctctgaaa ccagtgttag 420
ggaagggcct gccacagcct cccctgccag ggcagggccc caggcattgc caagggcttt 480
gttttgcaca ctttgccata ttttcaccat ttgattatgt agcaaaatac atgacattta 540
tttttcattt agtttgatta ttcagtgtca ctggcgacac gtagcagctt agactaaggc 600
cattattgta cttgccttat tagagtgtct ttccacggag ccactcctct gactcagggc 660
tcctgggttt tgtattctct gagctgtgca ggtggggaga ctgggctgag ggagcctggc 720
cccatggtca gccctagggt ggagagccac caagagggac gcctgggggt gccaggacca 780
gtcaacctgg gcaaagccta gtgaaggctt ctctctgtgg gatgggatgg tggagggcca 840
catgggaggc tcaccccctt ctccatccac atgggagccg ggtctgcctc ttctgggagg 900
gcagcagggc taccctgagc tgaggcagca gtgtgaggcc agggcagagt gagacccagc 960
cctcatcccg agcacctcca catcctccac gttctgctca tcattctctg tctcatccat 1020
catcatgtgt gtccacgact gtctccatgg ccccgcaaaa ggactctcag gaccaaagct 1080
ttcatgtaaa ctgtgcacca agcaggaaat gaaaatgtct tgtgttacct gaaaacactg 1140
tgcacatctg tgtcttgtgt ggaatattgt ccattgtcca atcctatgtt tttgttcaaa 1200
gccagcgtcc tcctctgtga ccaatgtctt gatgcatgca ctgttccccc tgtgcagccg 1260
ctgagcgagg agatgctcct tgggcccttt gagtgcagtc ctgatcagag ccgtggtcct 1320
ttggggtgaa ctaccttggt tcccccactg atcacaaaaa catggtgggt ccatgggcag 1380
agcccaaggg aattcggtgt gcaccagggt tgaccccaga ggattgctgc cccatcagtg 1440
ctccctcaca tgtcagtacc ttcaaactag ggccaagccc agcactgctt gaggaaaaca 1500
agcattcaca acttgttttt ggtttttaaa acccagtcca caaaataacc aatcctggac 1560

-continued

```
atgaagattc tttcccaatt cacatctaac ctcatcttct tcaccatttg gcaatgccat   1620

catctcctgc cttcctcctg ggccctctct gctctgcgtg tcacctgtgc ttcgggccct   1680

tcccacagga catttctcta agagaacaat gtgctatgtg aagagtaagt caacctgcct   1740

gacatttgga gtgttcccct cccactgagg gcagtcgata gagctgtatt aagccactta   1800

aaatgttcac ttttgacaaa ggcaagcact tgtgggtttt tgttttgttt ttcattcagt   1860

cttacgaata cttttgccct ttgattaaag actccagtta aaaaaaattt taatgaagaa   1920

agtggaaaac aaggaagtca aagcaaggaa actatgtaac atgtaggaag taggaagtaa   1980

attatagtga tgtaatcttg aattgtaact gttcgtgaat ttaataatct gtagggtaat   2040

tagtaacatg tgttaagtat tttcataagt atttcaaatt ggagcttcat ggcagaaggc   2100

aaacccatca acaaaaattg tcccttaaac aaaaattaaa atcctcaatc cagctatgtt   2160

atattgaaaa aatagagcct gagggatctt tactagttat aaagatacag aactctttca   2220

aaaccttttg aaattaacct ctcactatac cagtataatt gagttttcag tggggcagtc   2280

attatccagg taatccaaga tattttaaaa tctgtcacgt agaacttgga tgtacctgcc   2340

cccaatccat gaaccaagac cattgaattc ttggttgagg aaacaaacat gaccctaaat   2400

cttgactaca gtcaggaaag gaatcatttc tatttctcct ccatgggaga aaatagataa   2460

gagtagaaac tgcagggaaa attatttgca taacaattcc tctactaaca atcagctcct   2520

tcctggagac tgcccagcta aagcaatatg catttaaata cagtcttcca tttgcaaggg   2580

aaaagtctct tgtaatccga atctcttttt gctttcgaac tgctagtcaa gtgcgtccac   2640

gagctgttta ctagggatcc ctcatctgtc cctccgggac ctggtgctgc ctctacctga   2700

cactcccttg ggctccctgt aacctcttca gaggccctcg ctgccagctc tgtatcagga   2760

cccagaggaa ggggccagag gctcgttgac tggctgtgtg ttgggattga gtctgtgcca   2820

cgtgtatgtg ctgtggtgtg tccccctctg tccaggcact gagataccag cgaggaggct   2880

ccagagggca ctctgcttgt tattagagat tacctcctga gaaaaaagct tccgcttgga   2940

gcagaggggc tgaatagcag aaggttgcac ctcccccaac cttagatgtt ctaagtcttt   3000

ccattggatc tcattggacc cttccatggt gtgatcgtct gactggtgtt atcaccgtgg   3060

gctccctgac tgggagttga tcgcctttcc caggtgctac accctttttcc agctggatga   3120

gaatttgagt gctctgatcc ctctacagag cttccctgac tcattctgaa ggagccccat   3180

tcctgggaaa tattccctag aaacttccaa atcccctaag cagaccactg ataaaaccat   3240

gtagaaaatt tgttattttg caacctcgct ggactctcag tctctgagca gtgaatgatt   3300

cagtgttaaa tgtgatgaat actgtatttt gtattgtttc aagtgcatct cccagataat   3360

gtgaaaatgg tccaggagaa ggccaattcc tatacgcagc gtgctttaaa aaataaataa   3420

gaaacaactc tttgagaaac aacaatttct actttgaagt cataccaatg aaaaaatgta   3480

tatgcactta taattttcct aataaagttc tgtactcaaa tgta                    3524
```

<210> SEQ ID NO 36
<211> LENGTH: 2140
<212> TYPE: DNA
<213> ORGANISM: Homo sapiens

<400> SEQUENCE: 36

```
ccgacctaga acccgcccgc tgcctgccac gctgccactg ccgcttcctc tataaaggga     60

cctgagcgtc cgggcccagg ggctccgcac agcaggtgag gctctcctgc cccatctcct    120
```

-continued

```
tgggctgccc gtgcttcgtg ctttggacta ccgccccgca gtgtcctgcc ctctgcctgg    180

gcctcggtcc ctcctgcacc tgctgcctgg atccccggcc tgcctgggcc tgggccttgg    240

tgggtttggt tttggtttcc ttctctgtct ctgactctcc atctgtcagt ctcattgtct    300

ctgtcacaca ttctctgttt ctgccatgat tcctctctgt tcccttcctg tctctctctg    360

tctccctctg ctcaccttgg ggtttctctg actgcatctt gtccccttct ctgtcgatct    420

ctctctcggg ggtcgggggg tgctgtctcc cagggcggga ggtctgtctt ccgccgcgtg    480

ccccgccccg ctcactgtct ctctctctct ctctctttct ctgcaggttc tccccatgac    540

accacctgaa cgtctcttcc tcccaagggt gtgtggcacc accctacacc tcctccttct    600

ggggctgctg ctggttctgc tgcctggggc ccaggtgagg cagcaggaga atgggggctg    660

ctggggtggc tcagccaaac cttgagccct agagcccccc tcaactctgt tctccccctag   720

gggctccctg gtgttggcct cacaccttca gctgcccaga ctgcccgtca gcaccccaag    780

atgcatcttg cccacagcac cctcaaacct gctgctcacc tcattggtaa acatccacct    840

gacctcccag acatgtcccc accagctctc ctcctacccc tgcctcagga acccaagcat    900

ccacccctct cccccaactt cccccacgct aaaaaaaaca gagggagccc actcctatgc    960

ctccccctgc catcccccag gaactcagtt gttcagtgcc cacttcctca gggattgaga   1020

cctctgatcc agacccctga tctcccaccc ccatccccta tggctcttcc taggagaccc   1080

cagcaagcag aactcactgc tctggagagc aaacacggac cgtgccttcc tccaggatgg   1140

tttctccttg agcaacaatt ctctcctggt ccccaccagt ggcatctact tcgtctactc   1200

ccaggtggtc ttctctggga aagcctactc tcccaaggcc ccctcctccc cactctacct   1260

ggcccatgag gtccagctct tctcctccca gtaccccttc catgtgcctc tcctcagctc   1320

ccagaagatg gtgtatccag ggctgcagga accctggctg cactcgatgt accacggggc   1380

tgcgttccag ctcacccagg gagaccagct atccacccac acagatggca tcccccacct   1440

agtcctcagc cctagtactg tcttctttgg agccttcgct ctgtagaact tggaaaaatc   1500

cagaaagaaa aaataattga tttcaagacc ttctccccat tctgcctcca ttctgaccat   1560

ttcaggggtc gtcaccacct ctcctttggc cattccaaca gctcaagtct tccctgatca   1620

agtcaccgga gctttcaaag aaggaattct aggcatccca ggggaccaca cctccctgaa   1680

ccatccctga tgtctgtctg gctgaggatt tcaagcctgc ctaggaattc ccagcccaaa   1740

gctgttggtc ttgtccacca gctaggtggg gcctagatcc acacacagag gaagagcagg   1800

cacatggagg agcttggggg atgactagag gcagggaggg gactatttat gaaggcaaaa   1860

aaattaaatt atttatttat ggaggatgga gagaggggaa taatagaaga acatccaagg   1920

agaaacagag acaggcccaa gagatgaaga gtgagagggc atgcgcacaa ggctgaccaa   1980

gagagaaaga agtaggcatg agggatcaca gggccccaga aggcagggaa aggctctgaa   2040

agccagctgc cgaccagagc cccacacgga ggcatctgca ccctcgatga agcccaataa   2100

acctcttttc tctgaaatgc tgtctgcttg tgtgtgtgtg                         2140
```

<210> SEQ ID NO 37
<211> LENGTH: 1498
<212> TYPE: DNA
<213> ORGANISM: Homo Sapiens

<400> SEQUENCE: 37

```
accaaacctc ttcgaggcac aaggcacaac aggctgctct gggattctct tcagccaatc     60

ttcattgctc aagtgtctga agcagccatg gcagaagtac ctgagctcgc cagtgaaatg    120
```

-continued

```
atggcttatt acagtggcaa tgaggatgac ttgttctttg aagctgatgg ccctaaacag    180
atgaagtgct ccttccagga cctggacctc tgccctctgg atggcggcat ccagctacga    240
atctccgacc accactacag caagggcttc aggcaggccg cgtcagttgt tgtggccatg    300
gacaagctga ggaagatgct ggttccctgc ccacagacct tccaggagaa tgacctgagc    360
accttctttc ccttcatctt tgaagaagaa cctatcttct tcgacacatg ggataacgag    420
gcttatgtgc acgatgcacc tgtacgatca ctgaactgca cgctccggga ctcacagcaa    480
aaaagcttgg tgatgtctgg tccatatgaa ctgaaagctc tccacctcca gggacaggat    540
atggagcaac aagtggtgtt ctccatgtcc tttgtacaag gagaagaaag taatgacaaa    600
atacctgtgg ccttgggcct caaggaaaag aatctgtacc tgtcctgcgt gttgaaagat    660
gataagccca ctctacagct ggagagtgta gatcccaaaa attacccaaa gaagaagatg    720
gaaaagcgat ttgtcttcaa caagatagaa atcaataaca agctggaatt tgagtctgcc    780
cagttcccca actggtacat cagcacctct caagcagaaa acatgcccgt cttcctggga    840
gggaccaaag gcggccagga tataactgac ttcaccatgc aatttgtgtc ttcctaaaga    900
gagctgtacc cagagagtcc tgtgctgaat gtggactcaa tccctagggc tggcagaaag    960
ggaacagaaa ggtttttgag tacggctata gcctggactt tcctgttgtc tacaccaatg   1020
cccaactgcc tgccttaggg tagtgctaag aggatctcct gtccatcagc caggacagtc   1080
agctctctcc tttcagggcc aatccccagc ccttttgttg agccaggcct ctctcacctc   1140
tcctactcac ttaaagcccg cctgacagaa accacggcca catttggttc taagaaaccc   1200
tctgtcattc gctcccacat tctgatgagc aaccgcttcc ctatttattt atttatttgt   1260
ttgtttgttt tattcattgg tctaatttat tcaaaggggg caagaagtag cagtgtctgt   1320
aaaagagcct agtttttaat agctatggaa tcaattcaat ttggactggt gtgctctctt   1380
taaatcaagt cctttaatta agactgaaaa tatataagct cagattattt aaatgggaat   1440
atttataaat gagcaaatat catactgttc aatggttctg aaataaactt cactgaag     1498
```

<210> SEQ ID NO 38
<211> LENGTH: 2943
<212> TYPE: DNA
<213> ORGANISM: Homo Sapiens

<400> SEQUENCE: 38

```
accaggcaac accattgaag gctcatatgt aaaaatccat gccttccttt ctcccaatct     60
ccattcccaa acttagccac tggcttctgg ctgaggcctt acgcatacct cccggggctt    120
gcacacacct tcttctacag aagacacacc ttgggcatat cctacagaag accaggcttc    180
tctctggtcc ttggtagagg gctactttac tgtaacaggg ccagggtgga gagttctctc    240
ctgaagctcc atcccctcta taggaaatgt gttgacaata ttcagaagag taagaggatc    300
aagacttctt tgtgctcaaa taccactgtt ctcttctcta ccctgcccta accaggagct    360
tgtcacccca aactctgagg tgatttatgc cttaatcaag caaacttccc tcttcagaaa    420
agatggctca ttttccctca aaagttgcca ggagctgcca agtattctgc caattcaccc    480
tggagcacaa tcaacaaatt cagccagaac acaactacag ctactattag aactattatt    540
attaataaat tcctctccaa atctagcccc ttgacttcgg atttcacgat ttctcccttc    600
ctcctagaaa cttgataagt ttcccgcgct tcccttttc taagactaca tgtttgtcat    660
cttataaagc aaaggggtga ataaatgaac caaatcaata acttctggaa tatctgcaaa    720
```

-continued

```
caacaataat atcagctatg ccatctttca ctattttagc cagtatcgag ttgaatgaac    780

atagaaaaat acaaaactga attcttccct gtaaattccc cgttttgacg acgcacttgt    840

agccacgtag ccacgcctac ttaagacaat tacaaaaggc gaagaagact gactcaggct    900

taagctgcca gccagagagg gagtcatttc attggcgttt gagtcagcaa agaagtcaag    960

atggccaaag ttccagacat gtttgaagac ctgaagaact gttacagtga aaatgaagaa   1020

gacagttcct ccattgatca tctgtctctg aatcagaaat ccttctatca tgtaagctat   1080

ggcccactcc atgaaggctg catggatcaa tctgtgtctc tgagtatctc tgaaacctct   1140

aaaacatcca agcttacctt caaggagagc atggtggtag tagcaaccaa cgggaaggtt   1200

ctgaagaaga gacggttgag tttaagccaa tccatcactg atgatgacct ggaggccatc   1260

gccaatgact cagaggaaga aatcatcaag cctaggtcag caccttttag cttcctgagc   1320

aatgtgaaat acaactttat gaggatcatc aaatacgaat tcatcctgaa tgacgccctc   1380

aatcaaagta taattcgagc caatgatcag tacctcacgg ctgctgcatt acataatctg   1440

gatgaagcag tgaaatttga catgggtgct tataagtcat caaaggatga tgctaaaatt   1500

accgtgattc taagaatctc aaaaactcaa ttgtatgtga ctgcccaaga tgaagaccaa   1560

ccagtgctgc tgaaggagat gcctgagata cccaaaacca tcacaggtag tgagaccaac   1620

ctcctcttct tctgggaaac tcacggcact aagaactatt tcacatcagt tgcccatcca   1680

aacttgttta ttgccacaaa gcaagactac tgggtgtgct tggcaggggg gccaccctct   1740

atcactgact ttcagatact ggaaaaccag gcgtaggtct ggagtctcac ttgtctcact   1800

tgtgcagtgt tgacagttca tatgtaccat gtacatgaag aagctaaatc ctttactgtt   1860

agtcatttgc tgagcatgta ctgagccttg taattctaaa tgaatgttta cactctttgt   1920

aagagtggaa ccaacactaa catataatgt tgttatttaa agaacaccct atattttgca   1980

tagtaccaat cattttaatt attattcttc ataacaattt taggaggacc agagctactg   2040

actatggcta ccaaaaagac tctacccata ttacagatgg gcaaattaag gcataagaaa   2100

actaagaaat atgcacaata gcagttgaaa caagaagcca cagacctagg atttcatgat   2160

ttcatttcaa ctgtttgcct tctactttta agttgctgat gaactcttaa tcaaatagca   2220

taagtttctg ggacctcagt tttatcattt tcaaaatgga gggaataata cctaagcctt   2280

cctgccgcaa cagtttttta tgctaatcag ggaggtcatt ttggtaaaat acttcttgaa   2340

gccgagcctc aagatgaagg caaagcacga aatgttattt tttaattatt atttatatat   2400

gtatttataa atatatttaa gataattata atatactata tttatgggaa ccccttcatc   2460

ctctgagtgt gaccaggcat cctccacaat agcagacagt gttttctggg ataagtaagt   2520

ttgatttcat taatacaggg cattttggtc caagttgtgc ttatcccata gccaggaaac   2580

tctgcattct agtacttggg agacctgtaa tcatataata aatgtacatt aattaccttg   2640

agccagtaat tggtccgatc tttgactctt ttgccattaa acttacctgg gcattcttgt   2700

ttcaattcca cctgcaatca agtcctacaa gctaaaatta gatgaactca actttgacaa   2760

ccatgagacc actgttatca aaactttctt ttctggaatg taatcaatgt ttcttctagg   2820

ttctaaaaat tgtgatcaga ccataatgtt acattattat caacaatagt gattgataga   2880

gtgttatcag tcataactaa ataaagcttg caacaaaatt ctctgacaaa aaaaaaaaaa   2940

aaa                                                                 2943
```

<210> SEQ ID NO 39
<211> LENGTH: 1047

<212> TYPE: DNA
<213> ORGANISM: Homo sapiens

<400> SEQUENCE: 39

```
cgaattcccc tatcacctaa gtgtgggcta atgtaacaaa gagggatttc acctacatcc     60
attcagtcag tctttggggg tttaaagaaa ttccaaagag tcatcagaag aggaaaaatg    120
aaggtaatgt tttttcagac aggtaaagtc tttgaaaata tgtgtaatat gtaaaacatt    180
ttgacacccc cataatattt ttccagaatt aacagtataa attgcatctc ttgttcaaga    240
gttccctatc actctcttta atcactactc acagtaacct caactcctgc cacaatgtac    300
aggatgcaac tcctgtcttg cattgcacta agtcttgcac ttgtcacaaa cagtgcacct    360
acttcaagtt ctacaaagaa aacacagcta caactggagc atttactgct ggatttacag    420
atgattttga atggaattaa taattacaag aatcccaaac tcaccaggat gctcacattt    480
aagttttaca tgcccaagaa ggccacagaa ctgaaacatc ttcagtgtct agaagaagaa    540
ctcaaacctc tggaggaagt gctaaattta gctcaaagca aaaactttca cttaagaccc    600
agggacttaa tcagcaatat caacgtaata gttctggaac taaagggatc tgaaacaaca    660
ttcatgtgtg aatatgctga tgagacagca accattgtag aatttctgaa cagatggatt    720
accttttgtc aaagcatcat ctcaacactg acttgataat taagtgcttc ccacttaaaa    780
catatcaggc cttctattta tttaaatatt taaattttat atttattgtt gaatgtatgg    840
tttgctacct attgtaacta ttattcttaa tcttaaaact ataaatatgg atcttttatg    900
attcttttg taagccctag gggctctaaa atggtttcac ttatttatcc caaaatattt    960
attattatgt tgaatgttaa atatagtatc tatgtagatt ggttagtaaa actatttaat   1020
aaatttgata aatataaaaa aaaaaaa                                       1047
```

<210> SEQ ID NO 40
<211> LENGTH: 924
<212> TYPE: DNA
<213> ORGANISM: Homo sapiens

<400> SEQUENCE: 40

```
cagagcccca cgaaggacca gaacaagaca gagtgcctcc tgccgatcca aacatgagcc     60
gcctgcccgt cctgctcctg ctccaactcc tggtccgccc cggactccaa gctcccatga    120
cccagacaac gcccttgaag acaagctggg ttaactgctc taacatgatc gatgaaatta    180
taacacactt aaagcagcca cctttgcctt tgctggactt caacaacctc aatggggaag    240
accaagacat tctgatggaa aataaccttc gaaggccaaa cctggaggca ttcaacaggg    300
ctgtcaagag tttacagaac gcatcagcaa ttgagagcat tcttaaaaat ctcctgccat    360
gtctgcccct ggccacggcc gcacccacgc gacatccaat ccatatcaag gacggtgact    420
ggaatgaatt ccggaggaaa ctgacgttct atctgaaaac ccttgagaat gcgcaggctc    480
aacagacgac tttgagcctc gcgatctttt gagtccaacg tccagctcgt tctctgggcc    540
ttctcaccac agagcctcgg gacatcaaaa acagcagaac ttctgaaacc tctgggtcat    600
ctctcacaca ttccaggacc agaagcattt cacctttcc tgcggcatca gatgaattgt     660
taattatcta atttctgaaa tgtgcagctc ccatttggcc ttgtgcggtt gtgttctcat    720
ttttatccca ttgagactat ttatttatgt atgtatgtat ttatttattt attgcctgga    780
gtgtgaactg tatttatttt agcagaggag ccatgtcctg ctgcttctgc aaaaaactca    840
gagtggggtg gggagcatgt tcatttgtac ctcgagtttt aaactggttc ctagggatgt    900
```

-continued

```
gtgagaataa actagactct gaac                                        924


<210> SEQ ID NO 41
<211> LENGTH: 873
<212> TYPE: DNA
<213> ORGANISM: Homo sapiens

<400> SEQUENCE: 41

ttctatgcaa agcaaaaagc cagcagcagc cccaagctga taagattaat ctaaagagca    60

aattatggtg taatttccta tgctgaaact ttgtagttaa ttttttaaaa aggtttcatt   120

ttcctattgg tctgatttca caggaacatt ttacctgttt gtgaggcatt ttttctcctg   180

gaagagaggt gctgattggc cccaagtgac tgacaatctg gtgtaacgaa aatttccaat   240

gtaaactcat tttccctcgg tttcagcaat tttaaatcta tatatagaga tatctttgtc   300

agcattgcat cgttagcttc tcctgataaa ctaattgcct cacattgtca ctgcaaatcg   360

acacctatta atgggtctca cctcccaact gcttccccct ctgttcttcc tgctagcatg   420

tgccggcaac tttgtccacg gacacaagtg cgatatcacc ttacaggaga tcatcaaaac   480

tttgaacagc ctcacagagc agaagaacac aactgagaag gaaaccttct gcagggctgc   540

gactgtgctc cggcagttct acagccacca tgagaaggac actcgctgcc tgggtgcgac   600

tgcacagcag ttccacaggc acaagcagct gatccgattc ctgaaacggc tcgacaggaa   660

cctctggggc ctggcgggct tgaattcctg tcctgtgaag gaagccaacc agagtacgtt   720

ggaaaacttc ttggaaaggc taaagacgat catgagagag aaatattcaa agtgttcgag   780

ctgaatattt taatttatga gtttttgata gctttatttt ttaagtattt atatatttat   840

aactcatcat aaaataaagt atatatagaa tct                                873


<210> SEQ ID NO 42
<211> LENGTH: 921
<212> TYPE: DNA
<213> ORGANISM: Homo sapiens

<400> SEQUENCE: 42

ttctatgcaa agcaaaaagc cagcagcagc cccaagctga taagattaat ctaaagagca    60

aattatggtg taatttccta tgctgaaact ttgtagttaa ttttttaaaa aggtttcatt   120

ttcctattgg tctgatttca caggaacatt ttacctgttt gtgaggcatt ttttctcctg   180

gaagagaggt gctgattggc cccaagtgac tgacaatctg gtgtaacgaa aatttccaat   240

gtaaactcat tttccctcgg tttcagcaat tttaaatcta tatatagaga tatctttgtc   300

agcattgcat cgttagcttc tcctgataaa ctaattgcct cacattgtca ctgcaaatcg   360

acacctatta atgggtctca cctcccaact gcttccccct ctgttcttcc tgctagcatg   420

tgccggcaac tttgtccacg gacacaagtg cgatatcacc ttacaggaga tcatcaaaac   480

tttgaacagc ctcacagagc agaagactct gtgcaccgag ttgaccgtaa cagacatctt   540

tgctgcctcc aagaacacaa ctgagaagga aaccttctgc agggctgcga ctgtgctccg   600

gcagttctac agccaccatg agaaggacac tcgctgcctg ggtgcgactg cacagcagtt   660

ccacaggcac aagcagctga tccgattcct gaaacggctc gacaggaacc tctggggcct   720

ggcgggcttg aattcctgtc ctgtgaagga agccaaccag agtacgttgg aaaacttctt   780

ggaaaggcta aagacgatca tgagagagaa atattcaaag tgttcgagct gaatatttta   840

atttatgagt tttgatagc tttatttttt aagtatttat atatttataa ctcatcataa    900

aataaagtat atatagaatc t                                             921
```

<210> SEQ ID NO 43
<211> LENGTH: 3230
<212> TYPE: DNA
<213> ORGANISM: Homo sapiens

<400> SEQUENCE: 43

```
atcctaatca agaccccagt gaacagaact cgaccctgcc aaggcttggc atttccattt     60
caatcactgt cttcccacca gtattttcaa tttcttttaa gacagattaa tctagccaca    120
gtcatagtag aacatagccg atcttgaaaa aaaacattcc caatatttat gtattttagc    180
ataaaattct gtttagtggt ctaccttata ctttgttttg cacacatctt ttaagaggaa    240
gttaattttc tgattttaag aaatgcaaat gtggggcaat gatgtattaa cccaaagatt    300
ccttccgtaa tagaaaatgt ttttaaaggg gggaaacagg gatttttatt attaaaagat    360
aaaagtaaat ttatttttta agatataagg cattggaaac atttagtttc acgatatgcc    420
attattaggc attctctatc tgattgttag aaattattca tttcctcaaa gacagacaat    480
aaattgactg gggacgcagt cttgtactat gcactttctt tgccaaaggc aaacgcagaa    540
cgtttcagag ccatgaggat gcttctgcat ttgagtttgc tagctcttgg agctgcctac    600
gtgtatgcca tccccacaga aattcccaca agtgcattgg tgaaagagac cttggcactg    660
ctttctactc atcgaactct gctgatagcc aatgaggtaa ttttctttat gattcctaca    720
gtctgtaaag tgcataggta atcatttgtg atggttcctt tactatatat agagatctgt    780
tataaataat aagattctga gcacattagt acatgggtga taactacatc accagcaaac    840
attctgttaa aagttatgaa tgctggtgtg ctgtaaaaat gattgtattt cctttcctct    900
ccagactctg aggattcctg ttcctgtaca taaaaatgta agttaaatta tgattcagta    960
aaatgatggc atgaataagt aaatttcctg ttttaagctg taaatcatta gttatcattg   1020
gaactattta attttctata ttttgttttc atatgggtgg ctgtgaatgt ctgtacttat   1080
aaatatgagg aatgactttt tatcaagtag aatcctttaa acaagtggat taggctcttt   1140
ggtgatgttg ttagtttgcc ttcccaaaga gcatcgtgtc aggattcttt ccagaaggat   1200
tccacactga gtgagaggtg cgtgctagtc tccgtgcagt tctgactctt tctcactcta   1260
acgtgtttct gaaagtatta gcaactcaga attatatttt tagaaccatg atcagtagac   1320
attaaaatat ataacaaatg ccctatatta ataattctgc atacttaaat aattatgact   1380
atatgatggt gtgtatgcat tgaatatgcc tggtcatatt aaaatgtaaa atatatagtt   1440
tattagtcta aatagaataa aactaccagc tagaactgta gaaacacatt gatatgagtt   1500
taatgtataa tgcattacac ttccaaaaca ttttttttcca gttacataat taagttatat   1560
cctttataaa actcctcagt aatcatataa gcttcatcta ctttttgaaa attttatctt   1620
aatatgtggt ggtttgttgc ctagaaaaca aacaaaaaac tctttggaga agggaactca   1680
tgtaaatacc acaaaacaaa gcctaacttt gtggaccaaa attgttttaa taattatttt   1740
ttaattgatg aattaaaaag tatatatatt tattgtgtac aatatgatgt tttgaagtat   1800
gtatacattg cagaatggac aatggaccaa atttttatac cttgtcttga ttatttgcat   1860
tttaaaaatt ttcctcattt agcaccaact gtgcactgaa gaaatctttc agggaatagg   1920
cacactggag agtcaaactg tgcaaggggg tactgtggaa agactattca aaaacttgtc   1980
cttaataaag aaatacattg acggccaaaa agtaagttac acacattcaa tggaagctat   2040
atttgtcctg gctgtgccta tttctatgga attgacagtt tcctgtaata cctattgtca   2100
```

-continued

```
tttttctttt ttcacagaaa aagtgtggag aagaaagacg gagagtaaac caattcctag   2160

actacctgca agagtttctt ggtgtaatga acaccgagtg gataatagaa agttgagact   2220

aaactggttt gttgcagcca aagattttgg aggagaagga cattttactg cagtgagaat   2280

gagggccaag aaagagtcag gccttaattt tcaatataat ttaacttcag agggaaagta   2340

aatatttcag gcatactgac actttgccag aaagcataaa attcttaaaa tatatttcag   2400

atatcagaat cattgaagta ttttcctcca ggcaaaattg atatactttt ttcttattta   2460

acttaacatt ctgtaaaatg tctgttaact taatagtatt tatgaaatgg ttaagaattt   2520

ggtaaattag tatttattta atgttatgtt gtgttctaat aaaacaaaaa tagacaactg   2580

ttcaatttgc tgctggcctc tgtccttagc aatttgaagt tagcacagtc cattgagtac   2640

atgcccagtt tggaggaagg gtctgagcac atgtggctga gcatccccat ttctctggag   2700

aagtctcaag gttgcaaggc acaccagagg tggaagtgat ctagcaggac ttagtgggga   2760

tgtggggagc agggacacag gcaggaggtg aacctggttt tctctctaca gtatatccag   2820

aacctgggat ggtcgaaggg taaatggtag ggaataaatg aatgaatgtc gtttccaaga   2880

tgattgtaga actaaaatga gttgtaagct cccctggaag aagggatgtg gaacctgtaa   2940

ctaggttcct gcccagcctg tgagaagaat ttggcagatc atctcattgc cagtatagag   3000

aggaagccag aaaccctctc tgccaaggcc tgcaggggtt cttaccacct gaccctgcac   3060

cataacaaaa ggacagagag acatggtagg gcagtcccat tagaaagact gagttccgta   3120

ttcccggggc agggcagcac caggccgcac aacatccatt ctgcctgctt atggctatca   3180

gtagcatcac tagagattct tctgtttgag aaaacttctc tcaaggatcc              3230
```

```
<210> SEQ ID NO 44
<211> LENGTH: 1125
<212> TYPE: DNA
<213> ORGANISM: Homo sapiens

<400> SEQUENCE: 44

ttctgccctc gagcccaccg ggaacgaaag agaagctcta tctcgcctcc aggagcccag     60

ctatgaactc cttctccaca agcgccttcg gtccagttgc cttctccctg ggctgctcc    120

tggtgttgcc tgctgccttc cctgccccag tacccccagg agaagattcc aaagatgtag    180

ccgccccaca cagacagcca ctcacctctt cagaacgaat tgacaaacaa attcggtaca    240

tcctcgacgg catctcagcc ctgagaaagg agacatgtaa caagagtaac atgtgtgaaa    300

gcagcaaaga ggcactggca gaaaacaacc tgaaccttcc aaagatggct gaaaaagatg    360

gatgcttcca atctggattc aatgaggaga cttgcctggt gaaaatcatc actggtcttt    420

tggagtttga ggtataccta gagtacctcc agaacagatt tgagagtagt gaggaacaag    480

ccagagctgt gcagatgagt acaaaagtcc tgatccagtt cctgcagaaa aaggcaaaga    540

atctagatgc aataaccacc cctgacccaa ccacaaatgc cagcctgctg acgaagctgc    600

aggcacagaa ccagtggctg caggacatga caactcatct cattctgcgc agctttaagg    660

agttcctgca gtccagcctg agggctcttc ggcaaatgta gcatgggcac ctcagattgt    720

tgttgttaat gggcattcct tcttctggtc agaaacctgt ccactgggca cagaacttat    780

gttgttctct atggagaact aaaagtatga gcgttaggac actattttaa ttatttttaa    840

tttattaata tttaaatatg tgaagctgag ttaatttatg taagtcatat ttatattttt    900

aagaagtacc acttgaaaca ttttatgtat tagttttgaa ataataatgg aaagtggcta    960

tgcagtttga atatcctttg tttcagagcc agatcatttc ttggaaagtg taggcttacc   1020
```

tcaaataaat ggctaactta tacatatttt taaagaaata tttatattgt atttatataa 1080
tgtataaatg gtttttatac caataaatgg cattttaaaa aattc 1125

<210> SEQ ID NO 45
<211> LENGTH: 2116
<212> TYPE: DNA
<213> ORGANISM: Homo sapiens

<400> SEQUENCE: 45
acatccgcgg caacgcctcc ttggtgtcgt ccgcttccaa taacccagct tgcgtcctgc 60
acacttgtgg cttccgtgca cacattaaca actcatggtt ctagctccca gtcgccaagc 120
gttgccaagg cgttgagaga tcatctggga agtcttttac ccagaattgc tttgattcag 180
gccagctggt tttcctgcg gtgattcgga aattcgcgaa ttcctctggt cctcatccag 240
gtgcgcggga agcaggtgcc caggagagag gggataatga agattccatg ctgatgatcc 300
caaagattga acctgcagac caagcgcaaa gtagaaactg aaagtacact gctggcggat 360
cctacggaag ttatggaaaa ggcaaagcgc agagccacgc cgtagtgtgt gccgcccccc 420
ttgggatgga tgaaactgca gtcgcggcgt gggtaagagg aaccagctgc agagatcacc 480
ctgcccaaca cagactcggc aactccgcgg aagaccaggg tcctgggagt gactatgggc 540
ggtgagagct tgctcctgct ccagttgcgg tcatcatgac tacgcccgcc tcccgcagac 600
catgttccat gtttctttta ggtatatctt tggacttcct cccctgatcc ttgttctgtt 660
gccagtagca tcatctgatt gtgatattga aggtaaagat ggcaaacaat atgagagtgt 720
tctaatggtc agcatcgatc aattattgga cagcatgaaa gaaattggta gcaattgcct 780
gaataatgaa tttaactttt ttaaaagaca tatctgtgat gctaataagg aaggtatgtt 840
tttattccgt gctgctcgca agttgaggca atttcttaaa atgaatagca ctggtgattt 900
tgatctccac ttattaaaag tttcagaagg cacaacaata ctgttgaact gcactggcca 960
ggttaaagga agaaaaccag ctgccctggg tgaagcccaa ccaacaaaga gtttggaaga 1020
aaataaatct ttaaaggaac agaaaaaact gaatgacttg tgtttcctaa agagactatt 1080
acaagagata aaaacttgtt ggaataaaat tttgatgggc actaaagaac actgaaaaat 1140
atggagtggc aatatagaaa cacgaacttt agctgcatcc tccaagaatc tatctgctta 1200
tgcagttttt cagagtggaa tgcttcctag aagttactga atgcaccatg gtcaaaacgg 1260
attagggcat ttgagaaatg catattgtat tactagaaga tgaatacaaa caatggaaac 1320
tgaatgctcc agtcaacaaa ctatttctta tatatgtgaa catttatcaa tcagtataat 1380
tctgtactga tttttgtaag acaatccatg taaggtatca gttgcaataa tacttctcaa 1440
acctgtttaa atatttcaag acattaaatc tatgaagtat ataatggttt caaagattca 1500
aaattgacat tgctttactg tcaaaataat tttatggctc actatgaatc tattatactg 1560
tattaagagt gaaaattgtc ttcttctgtg ctggagatgt tttagagtta acaatgatat 1620
atggataatg ccggtgagaa taagagagtc ataaacctta agtaagcaac agcataacaa 1680
ggtccaagat acctaaaaga gatttcaaga gatttaatta atcatgaatg tgtaacacag 1740
tgccttcaat aaatggtata gcaaatgttt tgacatgaaa aaaggacaat ttcaaaaaaa 1800
taaaataaaa taaaaataaa ttcacctagt ctaaggatgc taaaccttag tactgagtta 1860
cattgtcatt tatatagatt ataacttgtc taaataagtt tgcaatttgg gagatatatt 1920
tttaagataa taatatatgt ttacctttta attaatgaaa tatctgtatt taattttgac 1980

-continued

```
actatatctg tatataaaat attttcatac agcattacaa attgcttact ttggaataca   2040

tttctccttt gataaaataa atgagctatg tattaacaaa aaaaaaaaaa aaaaaaaaaa   2100

aaaaaaaaaa aaaaaa                                                   2116


<210> SEQ ID NO 46
<211> LENGTH: 1666
<212> TYPE: DNA
<213> ORGANISM: Homo sapiens

<400> SEQUENCE: 46

ctccataagg cacaaacttt cagagacagc agagcacaca agcttctagg acaagagcca     60

ggaagaaacc accggaagga accatctcac tgtgtgtaaa catgacttcc aagctggccg    120

tggctctctt ggcagccttc ctgatttctg cagctctgtg tgaaggtgca gttttgccaa    180

ggagtgctaa agaacttaga tgtcagtgca taaagacata ctccaaacct ttccacccca    240

aatttatcaa agaactgaga gtgattgaga gtggaccaca ctgcgccaac acagaaatta    300

ttgtaaagct ttctgatgga agagagctct gtctggaccc caaggaaaac tgggtgcaga    360

gggttgtgga gaagtttttg aagagggctg agaattcata aaaaaattca ttctctgtgg    420

tatccaagaa tcagtgaaga tgccagtgaa acttcaagca aatctacttc aacacttcat    480

gtattgtgtg ggtctgttgt agggttgcca gatgcaatac aagattcctg gttaaatttg    540

aatttcagta aacaatgaat agtttttcat tgtaccatga aatatccaga acatacttat    600

atgtaaagta ttatttattt gaatctacaa aaaacaacaa ataattttta aatataagga    660

ttttcctaga tattgcacgg gagaatatac aaatagcaaa attgaggcca agggccaaga    720

gaatatccga actttaattt caggaattga atgggtttgc tagaatgtga tatttgaagc    780

atcacataaa aatgatggga caataaattt tgccataaag tcaaatttag ctggaaatcc    840

tggatttttt tctgttaaat ctggcaaccc tagtctgcta gccaggatcc acaagtcctt    900

gttccactgt gccttggttt ctcctttatt tctaagtgga aaaagtatta gccaccatct    960

tacctcacag tgatgttgtg aggacatgtg gaagcacttt aagttttttc atcataacat   1020

aaattatttt caagtgtaac ttattaacct atttattatt tatgtattta tttaagcatc   1080

aaatatttgt gcaagaattt ggaaaaatag aagatgaatc attgattgaa tagttataaa   1140

gatgttatag taaatttatt ttattttaga tattaaatga tgttttatta gataaatttc   1200

aatcagggtt tttagattaa acaaacaaac aattgggtac ccagttaaat tttcatttca   1260

gataaacaac aaataatttt ttagtataag tacattattg tttatctgaa attttaattg   1320

aactaacaat cctagtttga tactcccagt cttgtcattg ccagctgtgt tggtagtgct   1380

gtgttgaatt acggaataat gagttagaac tattaaaaca gccaaaactc cacagtcaat   1440

attagtaatt tcttgctggt tgaaacttgt ttattatgta caaatagatt cttataatat   1500

tatttaaatg actgcatttt taaatacaag gctttatatt tttaacttta agatgttttt   1560

atgtgctctc caaatttttt ttactgtttc tgattgtatg gaaatataaa agtaaatatg   1620

aaacatttaa aatataattt gttgtcaaag taaaaaaaaa aaaaaa                  1666


<210> SEQ ID NO 47
<211> LENGTH: 591
<212> TYPE: DNA
<213> ORGANISM: Homo sapiens

<400> SEQUENCE: 47

ccgctgtcaa gatgcttctg gccatggtcc ttacctctgc cctgctcctg tgctccgtgg     60
```

```
caggccaggg gtgtccaacc ttggcgggga tcctggacat caacttcctc atcaacaaga    120

tgcaggaaga tccagcttcc aagtgccact gcagtgctaa tgtgaccagt tgtctctgtt    180

tgggcattcc ctctgacaac tgcaccagac catgcttcag tgagagactg tctcagatga    240

ccaataccac catgcaaaca agatacccac tgattttcag tcgggtgaaa aaatcagttg    300

aagtactaaa gaacaacaag tgtccatatt tttcctgtga acagccatgc aaccaaacca    360

cggcaggcaa cgcgctgaca tttctgaaga gtcttctgga aattttccag aaagaaaaga    420

tgagagggat gagaggcaag atatgaagat gaaatattat ttatcctatt tattaaattt    480

aaaaagcttt ctctttaagt tgctacaatt taaaaatcaa gtaagctact ctaaatcagt    540

atcagttgtg attatttgtt taacattgta tgtctttatt ttgaaataaa t             591
```

<210> SEQ ID NO 48
<211> LENGTH: 1629
<212> TYPE: DNA
<213> ORGANISM: Homo sapiens

<400> SEQUENCE: 48

```
acacatcagg ggcttgctct tgcaaaacca aaccacaaga cagacttgca aaagaaggca     60

tgcacagctc agcactgctc tgttgcctgg tcctcctgac tggggtgagg gccagcccag    120

gccagggcac ccagtctgag aacagctgca cccacttccc aggcaacctg cctaacatgc    180

ttcgagatct ccgagatgcc ttcagcagag tgaagacttt ctttcaaatg aaggatcagc    240

tggacaactt gttgttaaag gagtccttgc tggaggactt taagggttac ctgggttgcc    300

aagccttgtc tgagatgatc cagttttacc tggaggaggt gatgccccaa gctgagaacc    360

aagacccaga catcaaggcg catgtgaact ccctggggga gaacctgaag accctcaggc    420

tgaggctacg gcgctgtcat cgatttcttc cctgtgaaaa caagagcaag gccgtggagc    480

aggtgaagaa tgcctttaat aagctccaag agaaaggcat ctacaaagcc atgagtgagt    540

ttgacatctt catcaactac atagaagcct acatgacaat gaagatacga aactgagaca    600

tcagggtggc gactctatag actctaggac ataaattaga ggtctccaaa atcggatctg    660

gggctctggg atagctgacc cagccccttg agaaacctta ttgtacctct cttatagaat    720

atttattacc tctgatacct caacccccat ttctatttat ttactgagct tctctgtgaa    780

cgatttagaa agaagcccaa tattataatt tttttcaata tttattattt tcacctgttt    840

ttaagctgtt tccatagggt gacacactat ggtatttgag tgttttaaga taaattataa    900

gttacataag ggaggaaaaa aaatgttctt tggggagcca acagaagctt ccattccaag    960

cctgaccacg ctttctagct gttgagctgt tttccctgac ctccctctaa tttatcttgt   1020

ctctgggctt ggggcttcct aactgctaca aatactctta ggaagagaaa ccagggagcc   1080

cctttgatga ttaattcacc ttccagtgtc tcggagggat tcccctaacc tcattcccca   1140

accacttcat tcttgaaagc tgtggccagc ttgttattta taacaaccta aatttggttc   1200

taggccgggc gcggtggctc acgcctgtaa tcccagcact ttgggaggct gaggcgggtg   1260

gatcacttga ggtcaggagt tcctaaccag cctggtcaac atggtgaaac cccgtctcta   1320

ctaaaaatac aaaaattagc cgggcatggt ggcgcgcacc tgtaatccca gctacttggg   1380

aggctgaggc aagagaattg cttgaaccca ggagatggaa gttgcagtga gctgatatca   1440

tgcccctgta ctccagcctg ggtgacagag caagactctg tctcaaaaaa taaaaataaa   1500

aataaatttg gttctaatag aactcagttt taactagaat ttattcaatt cctctgggaa   1560
```

-continued

```
tgttacattg tttgtctgtc ttcatagcag attttaattt tgaataaata aatgtatctt   1620

attcacatc                                                           1629
```

<210> SEQ ID NO 49
<211> LENGTH: 1444
<212> TYPE: DNA
<213> ORGANISM: Homo sapiens

<400> SEQUENCE: 49

```
tttcattttg ggccgagctg gaggcggcgg ggccgtcccg gaacggctgc ggccgggcac     60

cccgggagtt aatccgaaag cgccgcaagc cccgcgggcc ggccgcaccg cacgtgtcac    120

cgagaagctg atgtagagag agacacagaa ggagacagaa agcaagagac cagagtcccg    180

ggaaagtcct gccgcgcctc gggacaatta taaaaatgtg gccccctggg tcagcctccc    240

agccaccgcc ctcacctgcc gcggccacag gtctgcatcc agcggctcgc cctgtgtccc    300

tgcagtgccg gctcagcatg tgtccagcgc gcagcctcct ccttgtggct accctggtcc    360

tcctggacca cctcagtttg gccagaaacc tccccgtggc cactccagac ccaggaatgt    420

tcccatgcct tcaccactcc caaaacctgc tgagggccgt cagcaacatg ctccagaagg    480

ccagacaaac tctagaattt taccctttgca cttctgaaga gattgatcat gaagatatca   540

caaaagataa aaccagcaca gtggaggcct gtttaccatt ggaattaacc aagaatgaga    600

gttgcctaaa ttccagagag acctctttca taactaatgg gagttgcctg gcctccagaa    660

agacctcttt tatgatggcc ctgtgcctta gtagtattta tgaagacttg aagatgtacc    720

aggtggagtt caagaccatg aatgcaaagc ttctgatgga tcctaagagg cagatctttc    780

tagatcaaaa catgctggca gttattgatg agctgatgca ggccctgaat ttcaacagtg    840

agactgtgcc acaaaaatcc tcccttgaag aaccggattt ttataaaact aaaatcaagc    900

tctgcatact tcttcatgct ttcagaattc gggcagtgac tattgataga gtgatgagct    960

atctgaatgc ttcctaaaaa gcgaggtccc tccaaaccgt tgtcattttt ataaaacttt   1020

gaaatgagga aactttgata ggatgtggat taagaactag ggagggggaa agaaggatgg   1080

gactattaca tccacatgat acctctgatc aagtattttt gacatttact gtggataaat   1140

tgtttttaag ttttcatgaa tgaattgcta agaagggaaa atatccatcc tgaaggtgtt   1200

tttcattcac tttaatagaa gggcaaatat ttataagcta tttctgtacc aaagtgtttg   1260

tggaaacaaa catgtaagca taacttattt taaaatattt atttatataa cttggtaatc   1320

atgaaagcat ctgagctaac ttatatttat ttatgttata tttattaaat tatttatcaa   1380

gtgtatttga aaaatatttt taagtgttct aaaaataaaa gtattgaatt aaagtgaaaa   1440

aaaa                                                                1444
```

<210> SEQ ID NO 50
<211> LENGTH: 925
<212> TYPE: DNA
<213> ORGANISM: Homo sapiens

<400> SEQUENCE: 50

```
ctttgaattc ctagctcctg tggtctccag atttcaggcc taagatgaaa gcctctagtc     60

ttgccttcag ccttctctct gctgcgtttt atctcctatg gactccttcc actggactga    120

agacactcaa tttgggaagc tgtgtgatcg ccacaaacct tcaggaaata cgaaatggat    180

tttctgagat acggggcagt gtgcaagcca aagatggaaa cattgacatc agaatcttaa    240

ggaggactga gtctttgcaa gacacaaagc ctgcgaatcg atgctgcctc ctgcgccatt    300
```

```
tgctaagact ctatctggac agggtattta aaaactacca gacccctgac cattatactc    360

tccggaagat cagcagcctc gccaattcct ttcttaccat caagaaggac ctccggctct    420

gtcatgccca catgacatgc cattgtgggg aggaagcaat gaagaaatac agccagattc    480

tgagtcactt tgaaaagctg gaacctcagg cagcagttgt gaaggctttg gggaactag     540

acattcttct gcaatggatg gaggagacag aataggagga aagtgatgct gctgctaaga    600

atattcgagg tcaagagctc cagtcttcaa tacctgcaga ggaggcatga ccccaaacca    660

ccatctcttt actgtactag tcttgtgctg gtcacagtgt atcttattta tgcattactt    720

gcttccttgc atgattgtct ttatgcatcc ccaatcttaa ttgagaccat acttgtataa    780

gatttttgta atatctttct gctattggat atatttatta gttaatatat ttatttattt    840

tttgctattt aatgtattta tttttttact tggacatgaa actttaaaaa aattcacaga    900

ttatatttat aacctgacta gagca                                          925
```

```
<210> SEQ ID NO 51
<211> LENGTH: 3127
<212> TYPE: DNA
<213> ORGANISM: human herpesvirus 8

<400> SEQUENCE: 51

agaccagatt tcccgaggat ggcgcccccg ggaatgcgcc tgaggtcggg acggagcacc     60

ggcgcgccct taacgagagg aagttgtagg aaacgaaaca ggtctccgga aagatgtgac    120

cttggcgatg acctacatct acaaccgcga aggaagcatg tcgccgactc cgtcgacggc    180

cgggaatgtg gaccccacac cttgcctata ccaggaagtc ccacagtgtt cacatccggg    240

ctgccagcat ttgtgtctag tcctacttta ccggtggctt ccattccttc acccgctccc    300

gcaacacctt tacctccacc ggcactctta ccccccgtaa ccacgtcttc ctccccaatc    360

cctccatccc atcctgtgtc tccggggacc acggatactc attctccatc tcctgcattg    420

ccacccacgc agtctccaga gtcttctcaa aggccaccgc tttcaagtcc tacaggaagg    480

ccagactctt caacacctat gcgtccgcca ccctcgcagc agactacacc tccacactca    540

cccacgactc ctccacccga gcctccctcc aagtcgtcac cagactcttt agctccgtct    600

accctgcgta gcctgagaaa aagaaggcta tcgtcccccc aaggtccctc tacactaaac    660

ccaatatgtc agtcgccccc agtctctccc cctagatgtg acttcgccaa ccgtagtgtg    720

taccccccat gggccacaga gtccccgatc tacgtgggat catccagcga tggcgatact    780

ccgccacgcc aaccgcctac atctcccatc tccataggat catcatcccc gtctgaggga    840

tcctcgggtg atgacacagc catgttggtg ctccttgcgg agattgcaga agaagcatcc    900

aagaatgaaa aagaatgttc cgaaaataat caggctggcg aggataatgg ggacaacgag    960

attagcaagg aaagtcaggt tgacaaggat gacaatgaca ataaggatga tgaggaggag   1020

caggagacag atgaggagga cgaggaggat gacgaggagg atgacgagga ggatgacgag   1080

gaggatgacg aggaggatga cgaggaggat gacgaggagg atgacgagga ggatgacgag   1140

gaggatgacg aggaggatga cgaggaggat gacgaggagg atgacgagga ggaggacgag   1200

gaggaggacg aggaggagga cgaggaggag gaggacgagg aggaggagga ggacgaggag   1260

gatgacgatg atgaggacaa tgaggacgag gaggatgacg aggaggagga caagaaggag   1320

gacgaggagg acgggggcga tggaaacaaa acgttgagca tccaaagttc acaacagcag   1380

caggagccac aacagcagga gccacagcag caggagccac aacagcagga gccacagcag   1440
```

-continued

```
caggagccac agcagcagga gcccctgcag gagccacaac agcaggagcc acagcagcag   1500
gagccacaac agcaggagcc acagcagcag gagcccctgc aggagccaca gcagcaggag   1560
ccacagcagc aggagccaca gcagcaggag ccacaacagc aggagccaca gcagcaggat   1620
gagcagcagc aggatgagca gcagcaggat gagcagcagc aggatgagca gcagcagcag   1680
gatgagcagc agcaggatga gcagcagcag gatgagcagc agcaggatga gcaggagcag   1740
caggatgagc agcagcagga tgagcagcag cagcaggatg aacaggagca gcaggaggag   1800
caggagcagc aggaggagca ggagcaggag ttagaggagc aggagcagga gttagaggag   1860
caggagcagg agttagagga gcaggagcag gagttagagg agcaggagca ggagttagag   1920
gagcaggagc aggagttaga ggagcaggag caggagttag aggagcagga gcaggagtta   1980
gaggagcagg agcaggagtt agatgagcag gagcaggagt tagaggagca ggagcaggag   2040
ttagaggagc aggagcagga gttagaggag caggagcagg agttagagga gcaggagcag   2100
gagttagagg agcaggagca ggagttagag gagcaggagc aggagttaga ggagcaggag   2160
caggagttag aggagcagga gcaggagtta gaggagcagg agcaggagca ggagttagag   2220
gaggtggaag agcaagagca ggagcaggaa gagcaggaat tagaggaggt ggaggagcaa   2280
gagcaggagc aggaggagca ggaggagcag gagttagagg aggtggaaga gcaggaagag   2340
caggagttag aggaggtgga agagcaggaa gagcaggagt tagaggaggt ggaagagcag   2400
gagcagcagg gggtggaaca gcaggagcag gagacggtgg aagagcccat aatcttgcac   2460
gggtcgtcat ccgaggacga aatggaagtg gattaccctg ttgttagcac acatgaacaa   2520
attgccagta gcccaccagg agataataca ccagacgatg acccacaacc tggcccatct   2580
cgcgaatacc gctatgtact cagaacatca ccacccccaca gacctggagt tcgtatgagg   2640
cgcgttccag ttacccaccc aaaaaagcca catccaagat accaacaacc accggtccct   2700
tacagacaga tagatgattg tcctgcgaaa gctaggccac aacacatctt ttatagacgc   2760
tttttgggaa aggatggaag acgagatcca aagtgtcaat ggaagtttgc agtgattttt   2820
tggggcaatg acccatacgg acttaaaaaa ttatctcagg ccttccagtt tggaggagta   2880
aaggcaggcc ccgtgtcctg cttgccccac cctggaccag accagtcgcc cataacttat   2940
tgtgtatatg tgtattgtca gaacaaagac acaagtaaga aagtacaaat ggcccgccta   3000
gcctgggaag ctagtcaccc cctggcagga aacctacaat cttccatagt taagtttaaa   3060
aagcccctgc cattaaccca gccaggggaa aaccaaggtc ctggggactc tccacaggaa   3120
atgacat                                                             3127
```

<210> SEQ ID NO 52
<211> LENGTH: 3012
<212> TYPE: DNA
<213> ORGANISM: Human herpesvirus 8

<400> SEQUENCE: 52

```
atggcgcccc cgggaatgcg cctgaggtcg ggacggagca ccggcgcgcc cttaacgaga     60
ggaagttgta ggaaacgaaa caggtctccg gaaagatgtc accttggcga tgacctacat    120
ctacaaccgc gaaggaagca tgtcgccgac tccgtcgacg gccgggaatg tggaccccac    180
accttgccta taccaggaag tcccacagtg ttcacatccg ggctgccagc atttgtgtct    240
agtcctactt taccggtggc tcccattcct tcacccgctc ccgcaacacc tttacctcca    300
ccggcactct taccccccgt aaccacgtct tcctccccaa tccctccatc ccatcctgtg    360
tctccgggga ccacggatac tcattctcca tctcctgcat tgccacccac gcagtctcca    420
```

-continued

```
gagtcttctc aaaggccacc gctttcaagt cctacaggaa ggccagactc ttcaacacct    480
atgcgtccgc caccctcgca gcagactaca cctccacact cacccacgac tcctccaccc    540
gagcctccct ccaagtcgtc accagactct ttagctccgt ctaccctgcg tagcctgaga    600
aaaagaaggc tatcgtcccc ccaaggtccc tctacactaa acccaatatg tcagtcgccc    660
ccagtctctc cccctagatg tgacttcgcc aaccgtagtg tgtacccccc atgggccaca    720
gagtccccga tctacgtggg atcatccagc gatggcgata ctccgccacg ccaaccgcct    780
acatctccca tctccatagg atcatcatcc ccgtctgagg gatcctgggg tgatgacaca    840
gccatgttgg tgctccttgc ggagattgca gaagaagcat ccaagaatga aaaagaatgt    900
tccgaaaata atcaggctgg cgaggataat ggggacaacg agattagcaa ggaaagtcag    960
gttgacaagg atgacaatga caataaggat gatgaggagg agcaggagac agatgaggag   1020
gacgaggagg atgacgagga ggatgacgag gaggatgacg aggaggatga cgaggaggat   1080
gacgaggagg atgacgagga ggatgacgag gaggatgacg aggaggagga cgaggaggag   1140
gacgaggagg aggaggacga ggaggaggag gaggaggacg aggaggatga cgatgatgag   1200
gacaatgagg acgaggagga ggacaagaag gaggacgagg aggacggggg cgatggaaac   1260
aaaacgttga gcatccaaag ttcacaacag cagcaggagc cacagcagca ggagccacaa   1320
cagcaggagc cacagcagca ggagccacag cagcaggagc ccctgcagga gccacagcag   1380
caggagccac aacagcagga gccacaacag caggagccac aacagcagga gccacaacag   1440
caggagccac aacagcagga gccacagcag caggatgagc agcagcagga tgagcagcag   1500
caggatgagc agcagcagga tgagcagcag caggatgagc aggagcagca ggatgagcag   1560
cagcaggatg agcagcagca ggatgagcag cagcagcagg atgaacagga gcagcaggag   1620
gagcaggagc agcaggagga gcaggagcag caggaggagc aggagcagga gttagaggag   1680
caggagcagg agttagagga gcaggagcag gagttagagg agcaggagca ggagttagag   1740
gagcaggagc aggagttaga ggagcaggag caggagttag aggagcagga gcaggagtta   1800
gaggagcagg agcaggagtt agaggagcag gagcaggagt tagaggagca ggagcaggag   1860
ttagaggagc aggagcagga gttagaggag caggagcagg agttagagga gcaggagcag   1920
gagttagagg agcaggagca ggagttagag gagcaggagc aggagttaga ggagcaggag   1980
caggagttag aggagcagga gcaggagtta gaggagcagg agcaggagtt agaggagcag   2040
gagcaggagt tagaggagca ggagcaggag ttagaggagc aggagcagga gcaggagtta   2100
gaggaggtgg aagagcaaga gcaggagcag gaagagcagg aattagagga ggtggaggag   2160
caagagcagg agcaggagga gcaggaggag caggagttag aggaggtgga agagcaggaa   2220
gagcaggagt tagaggaggt ggaagagcag gaagagcagg agttagagga ggtggaagag   2280
caggagcagc agggggtgga acagcaggag caggagacgg tggaagagcc cataatcttg   2340
cacgggtcgt catccgagga cgaaatggaa gtggattacc ctgttgttag cacacatgaa   2400
caaattgcca gtagcccacc aggagataat acaccagacg atgacccaca acctggccca   2460
tctcgcgaat accgctatgt actcagaaca tcaccacccc acagacctgg agttcgtatg   2520
aggcgcgttc cagttaccca cccaaaaaag ccacatccaa gataccaaca accaccggtc   2580
ccttacagac agatagatga ttgtcctgcg aaagctaggc cacaacacat cttttataga   2640
cgctttttgg gaaaggatgg aagacgagat ccaaagtgtc aatggaagtt tgcagtgatt   2700
ttttggggca atgacccata cggacttaaa aaattatctc aggccttcca gtttggagga   2760
```

-continued gtaaaggcag gccccgtgtc ctgcttgccc caccctggac cagaccagtc gcccataact 2820
tattgtgtat atgtgtattg tcagaacaaa gacacaagta agaaagtaca aatggcccgc 2880
ctagcctggg aagctagtca cccccctggca ggaaacctac aatcttccat agttaagttt 2940
aaaaagcccc tgccattaac ccagccaggg gaaaaccaag gtcctgggga ctctccacag 3000
gaaatgacat aa 3012

<210> SEQ ID NO 53
<211> LENGTH: 774
<212> TYPE: DNA
<213> ORGANISM: Human herpesvirus 8

<400> SEQUENCE: 53
atggcaactg ccaataaccc gccctcggga cttctggatc ccacgctatg tgaggatcgg 60
atcttttaca atattcttga aattgagccg cgctttttaa cttctgactc tgtatttggg 120
tcctttcaac aatctcttac ttcgcatatg cgtaagttac tgggcacatg gatgttttca 180
gtttgccagg aatacaacct agaacctaac gtggtcgcgt tggcccttaa tcttttggac 240
agactcctac ttataaagca ggtgtccaaa gaacactttc aaaagacagg gagcgcctgc 300
ctgttagtgg ccagtaagct cagaagcctc acgcctattt ctaccagttc actttgctat 360
gccgcggcag actccttttc ccgccaagaa cttatagacc aggagaaaga actccttgag 420
aagttggcgt ggcgaacaga ggcagtctta gcgacggacg taacttcctt cttgttactt 480
aaattgctgg ggggctccca acacctggac ttttggcacc acgaggtcga caccctgatt 540
acaaaagcct tagttgaccc aaagactggc tcattgcccg cctctattat cagcgctgca 600
ggctgtgcgc tgttggttcc tgccaacgtc attccgcagg atacccactc gggtggggta 660
gttcctcagc tggcaagcat attgggatgc gatgtttccg ttctacaggc ggcagtggaa 720
cagatcctaa catctgtttc ggactttgat ctgcgcattc tggacagcta ttaa 774

<210> SEQ ID NO 54
<211> LENGTH: 557
<212> TYPE: DNA
<213> ORGANISM: Human herpesvirus 4

<400> SEQUENCE: 54
ttagagagtg gctgctacgc attagagacc actttgagcc acccacagta accacccagc 60
gccaatctgt ctacatagaa gaagaagagg atgaagacta agtcacaggc ttagccagta 120
acccagcact ggcgtgtgac gtggtgtaaa gttttgcctg aacctgtggt tgggcaggta 180
acttaggaag cgtttcttga gcttccctgg gatgagcgtt tgggagagct gattctgcag 240
cccagagagt agtctcaggg catcctctgg agcctgacct gtgatcgtcg catcatagac 300
cgccagtaga cctgggagca gattcaccgc cgcggccgtc tcctttaagt gtgaatcatg 360
tctgacgagg ggccaggtac aggacctgga aatggcctag gagagaaggg agacacatct 420
ggaccagaag gctccggcgg cagtggacct caaagaagag ggggtgataa ccatggacga 480
ggacggggaa gaggacgagg acgaggaggc ggaagaccag gagccccggg cggctcagga 540
tcagggccaa gacatag 557

<210> SEQ ID NO 55
<211> LENGTH: 2031
<212> TYPE: DNA
<213> ORGANISM: Human herpesvirus 4

<400> SEQUENCE: 55

-continued

```
aatccgccac ctcattctga aattcccata tcccccgtct gctgcttcgt cacccgccga      60
cccttagccc tctatccgcc tcacccgcct cccctacggt taccccacag ccttgcctca     120
cctgaacccc cctaaagcac agcctcccgc ctgccgacaa cgacctccca acgttgcgcg     180
ccctacgcct ctttgtgtgg attacactgc cgcttcccac aacactgctc actccccctt     240
gtgattgccg cactgccttt ccatttccct gtacgcttta ccaccgcatt cccacagctt     300
gcccctcggg gactcgcttt tctaacacaa acacacgctt tctacttcct cttttaacgc     360
ttacatgcac acacactacg cgctttcggg aaagcggcgc ccgtaccctg tccggcagac     420
cccgcaaatc cccccgggcc tccatcccca gaaacacgcg ttactctctc gtaggcggcc     480
tacataagcc tctgtcactg ctctgtcagc ttctttcctc agttgccttg ctcctgccac     540
actaccctga ccatggaacg cgaccttgag aggggcccac cgggcccgcc acggccccct     600
ctaggacccc ccctctcctc ttccataggc cttgctctcc ttctcctgct cttggcgcta     660
ctgttctggc tgtatatcgt tatgagtaac tggactggag gagcgctcct tgtcctctat     720
tcctttgctc tcatgcttat tattatcatt ctcatcatct ttatcaacag aagagacctt     780
ctctgtccac ttggaggcct tggtctactc ctactgatga gtaagtatta caccctttgc     840
cccccacccc ctttccctta cgcttccttc tctaacgcac tttctcctct ttccccagtc     900
accctcctac tcatcgctct ctggaatttg cacggacagg cattgtacct tggaattgtg     960
ctgttcatct ttggctgctt acttggtaag atctaacatt ccctaggact tatttaccac    1020
accctcacct ttccagccct aacactcttt tttcaacgca gtcttaggtc tctggatcta    1080
cttggagatt ctctggcggc ttggtgccac catctggcag cttttggcct tcatcctagc    1140
cttcttccta gccatcatcc tgcttattat tgctctctat ctacaacaaa actggtggac    1200
tctattggtt gatctccttt ggctcctcct gtttatggcc attttaatct ggatgtatta    1260
tcatggacca cgacacactg atgaacacca ccacgatgac tccctcccgc accctcaaca    1320
agctaccgtc gattctagcc atgaatctga ctctaactcc aacgagggca gacaccacct    1380
gctcgtgagt ggggccggcg acggaccccc actctgctct caaaacctag gcgcacctgg    1440
aggtggtcct gacaatggcc cacaggaccc tgacaacact gatgacaatg gcccacagga    1500
ccctgacaac actgatgaca atggcccaca ggaccctgac aacactgatg acaatggccc    1560
acaggaccct gacaacactg atgacaatgg cccacaggac cctgacaaca ctgatgacaa    1620
tggcccacat gacccgctgc ctcataaccc tagcgactct gctggaaatg atggaggccc    1680
tccaaaattg acggaagagg ttgaaaacaa aggaggtgac cggggcccgc cttcgatgac    1740
agacggtggc ggcggtcatc cacaccttcc tacactgctt ttgggtactt ctggttccgg    1800
tggagatgat gacgaccccc acggcccagt tcagctaagc tactatgact aacctttctt    1860
tacttctagg cattaccatg tcataggctt gcctgactga ctctccctcc atttactggg    1920
aatgccttag ctaatcacct taactggcac acactccctt agccacactg tctgtctagg    1980
ctgaaaagcc acattcatat tctatttcaa aacaagggga aggaggacat a             2031
```

<210> SEQ ID NO 56
<211> LENGTH: 351
<212> TYPE: DNA
<213> ORGANISM: Human herpesvirus 4

<400> SEQUENCE: 56

```
ccaatgggcg cgggtccccc tagccccggc ggggatccgg atggggacga tggcggaaac      60
```

```
aactcccaat atccatctgc ttctggctct tctgggaaca cccccacccc accgaacgat    120

gaggaacgtg aatctaatga agagccccca ccgccttatg aggacctaga ttggggcaat    180

ggcgaccgtc actcggacta tcaaccacta ggaaaccaag atccaagttt gtacttggga    240

ttgcaacacg acgggaatga cgggctccct cccccctccct actctccacg ggatgactca    300

tctcaacaca tatacgaaga agcgggcaga ggaagtatga atccagtatg c              351
```

<210> SEQ ID NO 57
<211> LENGTH: 553
<212> TYPE: DNA
<213> ORGANISM: Human herpesvirus 4

<400> SEQUENCE: 57

```
actatggggt ccctagaagt gatgccaatg ggcgcgggtc cccctagccc cggcggggat     60

ccggatgggg acgatggcgg aaacaactcc caatatccat ctgcttctgg ctcttctggg    120

aacaccccca ccccaccgaa cgatgaggaa cgtgaatcta atgaagagcc cccaccgcct    180

tatgaggact cagattgggg caatggcgac cgtcactcgg actatcaacc actaggaaac    240

caagatccaa gtttgtactt gggattgcaa cacgacggga atgacgggct ccctcccccct    300

ccctactctc cacgggatga ctcatctcaa cacatatacg aagaagcggg cagaggaagt    360

atgaatccag tatgcctgct tgtaattgtt gcgccctacc tgttttggct ggcggctatt    420

gccgcctcgt gtttcacggc ctcagttagt accgttgtga ccgccaccgg cttggccctc    480

tcacttttac tcttggcagc agtggccagc tcatatgccg ctgcacaaag gaaactgctg    540

acaccggtga cag                                                        553
```

<210> SEQ ID NO 58
<211> LENGTH: 172281
<212> TYPE: DNA
<213> ORGANISM: Human herpesvirus 4

<400> SEQUENCE: 58

```
agaattcgtc ttgctctatt caccccttact tttcttcttg cccgttctct ttcttagtat     60

gaatccagta tgcctgcctg taattgttgc gccctacctc ttttggctgg cggctattgc    120

cgcctcgtgt ttcacggcct cagttagtac cgttgtgacc gccaccggct tggccctctc    180

acttctactc ttggcagcag tggccagctc atatgccgct gcacaaagga aactgctgac    240

accggtgaca gtgcttactg cggttgtcac ttgtgagtac acacgcacca tttacaatgc    300

atgatgttcg tgagattgat ctgtctctaa cagttcactt cctctgcttt tctcctcagt    360

ctttgcaatt tgcctaacat ggaggattga ggacccacct tttaattctc ttctgtttgc    420

attgctggcc gcagctggcg gactacaagg catttacggt tagtgtgcct ctgttatgaa    480

atgcaggttt gacttcatat gtatgccttg gcatgacgtc aactttactt ttatttcagt    540

tctggtgatg cttgtgctcc tgatactagc gtacagaagg agatggcgcc gtttgactgt    600

ttgtggcggc atcatgtttt tggcatgtgt acttgtcctc atcgtcgacg ctgttttgca    660

gctgagtccc ctccttggag ctgtaactgt ggtttccatg acgctgctgc tactggcttt    720

cgtcctctgg ctctcttcgc caggggggcct aggtactctt ggtgcagccc ttttaacatt    780

ggcagcaggt aagccacacg tgtgacattg cttgcctttt tgccacatgt tttctggaca    840

caggactaac catgccatct ctgattatag ctctggcact gctagcgtca ctgattttgg    900

gcacacttaa cttgactaca atgttccttc tcatgctcct atggacactt ggtaagtttt    960

cccttccttt aactcattac ttgttctttt gtaatcgcag ctctaacttg gcatctcttt   1020
```

-continued

```
tacagtggtt ctcctgattt gctcttcgtg ctcttcatgt ccactgagca agatccttct   1080
ggcacgactg ttcctatatg ctctcgcact cttgttgcta gcctccgcgc taatcgctgg   1140
tggcagtatt ttgcaaacaa acttcaagag tttaagcagc actgaattta tacccagtga   1200
gtatctattt gttactcctg tttagttgaa gaaaacaagc tattggattg taacacacat   1260
tttacgcttt gttccttaga tttgttctgc atgttattac tgattgtcgc tggcatactc   1320
ttcattcttg ctatcctgac cgaatggggc agtggaaata gaacatacgg tccagttttt   1380
atgtgcctcg gtggcctgct caccatggta gccggcgctg tgtggctgac ggtgatgtct   1440
aacacgcttt tgtctgcctg gattcttaca gcaggattcc tgattttcct cattggtaag   1500
tgtgacacca acaggtgttg ccttgttatg tcaccgttct gacacatgac ttacatgggt   1560
ttggcttttg taggctttgc cctctttggg gtcattagat gctgccgcta ctgctgctac   1620
tactgcctta cactggaaag tgaggagcgc ccaccgaccc catatcgcaa cactgtataa   1680
aggtaagtat tattaaattt tagagacact atcacgtgta acttgacgtg caaggatgga   1740
agagaggggc agggaaacgc aaatgccggt tgcccggtat gggggcccgt ttattatggt   1800
aaggctcttc gggcaagatg gagaggcaaa catacaggag gaaaggctat atgagctact   1860
ctctgaccca cgctccgcgc tcggcctaga cccggggccc ctgattgctg agaacctgct   1920
gctagtggcg ctgcgtggca ccaacaacga tcccaggcct cagcgtcagg agagggccag   1980
agaactggcc ctcgttggca ttctactagg aaacggcgag cagggtgaac acttgggcac   2040
ggagagtgcc ctggaggcct caggcaacaa ctatgtgtat gcctacggac cagactggat   2100
ggcaaggcct tccacatggt ccgcggaaat ccagcaattc ctgcgactcc tgggcgccac   2160
gtacgtgctt cgcgtggaga tgggcaggca gtttggcttc gaggtgcata gaagccggcc   2220
ctccttccgt cagttccagg ccatcaatca ccttgtcctg tttgacaacg cccttcgcaa   2280
gtacgattcc ggccaggtgg cggcgggctt ccagagggcc cttctggtgg ccgggccaga   2340
gaccgctgac acgaggccgg acctccgcaa gctgaatgag tgggtgtttg gtggcagggc   2400
tgctggtggc agacagctgg ccgacgagct aaagatcgtg tccgcgctgc gagacactta   2460
ctcgggccac ttggtccttc agcccacgga gacccttgac acatggaagg tgttgagcag   2520
ggacacacga accgctcata gtttggagca cggattcatt catgccgcgg ggaccatcca   2580
ggccaactgc ccacagctgt ttatgagacg ccagcacccc ggcctctttc ccttcgttaa   2640
tgcaatagca tcatcgctgg gctggtacta ccagaccgcc accggccccg gagcagatgc   2700
cagggcggcg gcccggcgcc aacaggcctt tcagaccagg gcggcggctg aatgccatgc   2760
caaaagcggg gtgccggtcg tggccggctt ctacaggacc atcaacgcca cgctcaaggg   2820
aggagagggc ctacagccca ctatgtttaa cggggagctg ggggccatca agcaccaggc   2880
acttgacact gtgaggtatg actacggcca ctatctcata atgttggggc cattccagcc   2940
atggagcgga ctgacggccc ctccgtgccc ctacgccgaa agttcatggg cacaggcggc   3000
cgtgcagacg gccctcgagc tgttctcggc cctgtacccg gccccgtgca tctcgggcta   3060
cgcgcgcccc ccgggcccca gtgctgtgat cgagcatctg ggtccctag ttccaaaggg    3120
gggtctgctg ttgtttctgt ctcacctacc ggatgatgtt aaggacgggc tcggagaaat   3180
ggggccggcc agggccacgg gacctggaat gcagcagttt gtcagcagct acttcctcaa   3240
ccccgcctgt tccaacgtct tcattacagt gaggcagcga ggggagaaga tcaacggccg   3300
taccgtcctc caagcgctcg gacgcgcatg cgatatggca ggctgccagc actatgtgct   3360
```

-continued gggctccacg gttcccctcg gtggactcaa ctttgtcaac gacctggcgt ccccggtttc 3420
caccgccgag atgatggatg atttctctcc cttcttcacc gtggagtttc ccccgattca 3480
agaggagggc gcaagttctc cggtaccctt agatgtggac gagagcatgg acatctctcc 3540
gtcttacgag ttgccctggc tctcgctgga gtcatgcctc acaagcatcc tgtcacaccc 3600
caccgtggga agcaaggagc acttggtcag gcacacggac agggtcagcg gaggacgcgt 3660
ggcacagcag cccggggtag gtcccctgga cctgccgctg gcggactacg ccttcgttgc 3720
ccacagtcag gtctggacca ggcccggtgg ggctcctccc ttgccctatc gtacctggga 3780
tcgaatgaca gagaagctgc ttgtctccgc aaaacccggc ggagagaacg ttaaggtttc 3840
aggtaccgtg attacattgg gagaacaggg gtacaaagtg tcgttggatc tgagggaggg 3900
aaccaggctg gcaatggctg aggcgctgct gaacgcagca tgtgccccaa tcttggatcc 3960
ggaagacgtc ttgctcaccc tgcatctaca cctggatccg cgccgggcag acaactcggc 4020
cgtgatggag gctatgacgg cggcgagtga ctacgcgcgt ggcctgggcg tgaagctgac 4080
ctttggctcg gcctcctgcc ccgagaccgg ctcgtccgcc tccaacttca tgaccgtggt 4140
ggcctctgtc tccgccccag gggaattctc gggtcctctg atcacgccag tgcttcagaa 4200
gacgggcagt ctcctgattg cggtgcgttg cggggatggc aagatccagg gagggtcgct 4260
gtttgagcag ctctttagcg acgtggccac gaccccacgg gcacccgagg cgttgtctct 4320
gaagaatctc ttccgggcag tccagcagct ggtcaagagc ggcatcgtgc tgtcagggca 4380
tgacatcagc gacgggggcc tggtgacctg cctggtggag atggccctgg ccgggcagcg 4440
gggagtgacc atcactatgc cggtggcctc cgactacctc ccggagatgt ttgcagagca 4500
ccccggcctg gtgtttgagg tggaggagcg cagcgtgggt gaggtgctgc agaccctgcg 4560
ctccatgaac atgtacccgg cagtcctcgg tcgagtgggc gagcaaggtc cagatcaaat 4620
gtttgaggtg cagcacggcc cagagacggt gttgcgccag tcgctgcgcc tgctgctggg 4680
aacctggtca tcctttgcca gcgagcagta cgagtgcctg cgaccagatc ggattaaccg 4740
gtccatgcac gtgtccgact acggctataa cgaagcactg gcagtctccc cgttgacagg 4800
aaagaatctc agcccacgcc ggttggtgac agagcctgac ccacgatgtc aggtggccgt 4860
gctatgcgcc ccgggcacca ggggccatga aagcctcctg gcggccttca cgaatgccgg 4920
atgcctgtgc cgacgggtgt tctttcgcga ggttagggac aacacgttcc tcgacaagta 4980
cgtgggtctg gccatcggag gagttcatgg ggccagggac tctgccctgg caggccgtgc 5040
caccgtggcg ctgattaatc gtttccccgc cctgcgtgac gctattctaa agttcctcaa 5100
caggccagat acgttctcgg tggccttggg ggagctgggg gtgcaagttt tggctggcct 5160
gggggccgtg gggtcaacag ataatccacc cgcccctggc gtggaagtta atgtccagag 5220
atcacctctg attctggccc ccaacgcctc tggcatgttt gagtcccgct ggctgaacat 5280
tagcatcccg gcgaccacca gctctgtcat gctgcgtggc ctccggggct gcgtcctgcc 5340
ttgttgggtg caaggctcgt gcctgggcct gcaatttact aacctcggga tgccatatgt 5400
tttgcagaat gcccaccaga tcgcctgcca cttccacagc aatggcacgg atgcctggcg 5460
ctttgctatg aattatccaa gaaaccccac ggagcagggc aacattgcag ggctctgttc 5520
acgcgatggt cgtcatctgg ctctcctgtg tgacccctca ctttgtacag acttttggca 5580
atgggagcac attccccccg cctttgggca ccccacgggg tgctccccct ggacacttat 5640
gtttcaagca gctcacctat ggtcactcag gcacggtcgc ccctccgagt gaccagtcac 5700
cttccagact atgcatacac tgaatttagc ctgatattgt ccccctagcc ccgggcccag 5760

```
ccctcctcag aaaactctgc atggagaagc tggacgtgaa cctccccccc agacctgtgt   5820
gctgtattta caaacactac aataaaccca atgtgcaaat gtggtttgta tggctacttt   5880
gtgttcctaa aaaatgcaac aatagaagtg gaaaccctca gtcacgggac attaacctca   5940
accacaaaat gggggttgga gaaagtaacc acatatactg gagatgattc atgggctggg   6000
ggttcccgga caatacaccc atctggagtt caacctaatt acatggtaga taaattaaga   6060
gtccctcctc accactcgaa actatggcag acattctata agataacgag gagagatgag   6120
gtgagggcag aggacattgg gcaggtgtgg gccacggggc agctggccat atcccccgca   6180
ctacagaagt gtaagcaaag tgaagggctc ggaaggcagg cggggcctag caatgtcaca   6240
gctaaatgcc caccagggca cacactcaag cggggtctcg gagctcctag gtcagaccac   6300
gaaaggtcag cctgcaaggt ggatggcgtg ttttctgagg ttatccccgc tacgtgcagt   6360
gctgggtgat agagacccta gaatgtgtcg aaatgaccaa gcgtccccgc agcggggctc   6420
ccaacacggg ttcccagaga gggtaaaaga gggggccata aagcccaggg tgtaaaacac   6480
cgaccgcgcc accagatggc acacgtgggg gaaatgaggg ttagcatagg caaccccogc   6540
ctacacacca actatagcaa accccgcccc gtcacggtga cgtagtctgt cttgaggaga   6600
tgtagacttg tagacactgc aaaacctcag gacctacgct gccctagagg ttttgctagg   6660
gaggagacgt gtgtggctgt agccacccgt cccgggtaca agtcccgggt ggtgaggacg   6720
gtgtctgtgg ttgtcttccc agactctgct ttctgccgtc ttcggtcaag taccagctgg   6780
tggtccgcat gttttgatcc aaacttttgt tttaggattt atgcatccat tatcccgcag   6840
ttccacctaa acggggctta acgttgcatc ccagaagatg cacgcttaac cccgcctaca   6900
accgtgacgt agctgtttac cagcatgtat agagttacgg ttcgctacat caaacaggac   6960
agccgttgcc ctagtggttt cggacacacc gccaacgctc agtgcggtgc taccgacccg   7020
aggtcaagtc ccgggggagg agaagagagg cttcccgcct agagcatttg caagtcagga   7080
ttctctaatc cctctgggag aagggtattc ggcttgtccg ctattttttt gtggctagtt   7140
ttgcacccac aacatgtaag ggcccgctac ccctacaaca caaaacaaac tatctcccct   7200
aaccatcctt ttgccaatca attctgtgac agggtttcct ggacacccag tcttagttca   7260
ggtagacacc cagttatgca gtgccaccaa ttccaaccat ttttaaacct cctggaattc   7320
tatcattaaa cggcatgcag gaaaaggaca agcagcgaaa attcacgccc ccttgggagg   7380
tggcggcata tgcaaaggat agcactccca ctctactact gggtatcata tgctgactgt   7440
atatgcatga ggatagcata tgctacccgg atacagatta ggatagcata tactacccag   7500
atatagatta ggatagcata tgctacccag atatagatta ggatagccta tgctacccag   7560
atataaatta ggatagcata tactacccag atatagatta ggatagcata tgctacccag   7620
atatagatta ggatagccta tgctacccag atatagatta ggatagcata tgctacccag   7680
atatagatta ggatagcata tgctatccag atatttgggt agtatatgct acccagatat   7740
aaattaggat agcatatact accctaatct ctattaggat agcatatgct acccggatac   7800
agattaggat agcatatact acccagatat agattaggat agcatatgct acccagatat   7860
agattaggat agcctatgct acccagatat aaattaggat agcatatact acccagatat   7920
agattaggat agcatatgct acccagatat agattaggat agcctatgct acccagatat   7980
agattaggat agcatatgct atccagatat ttgggtagta tatgctaccc atggcaacat   8040
tagcccaccg tgctctcagc gacctcgtga atatgaggac caacaaccct gtgcttggcg   8100
```

-continued

```
ctcaggcgca agtgtgtgta atttgtcctc cagatcgcag caatcgcgcc cctatcttgg   8160
cccgcccacc tacttatgca ggtattcccc ggggtgccat tagtggtttt gtgggcaagt   8220
ggtttgaccg cagtggttag cggggttaca atcagccaag ttattacacc cttattttac   8280
agtccaaaac cgcagggcgg cgtgtggggg ctgacgcgtg cccccactcc acaatttcaa   8340
aaaaaagagt ggccacttgt ctttgtttat gggccccatt ggcgtggagc cccgtttaat   8400
tttcgggggt gttagagaca accagtggag tccgctgctg tcggcgtcca ctctctttcc   8460
ccttgttaca aatagagtgt aacaacatgg ttcacctgtc ttggtccctg cctgggacac   8520
atcttaataa ccccagtatc atattgcact aggattatgt gttgcccata gccataaatt   8580
cgtgtgagat ggacatccag tctttacggc ttgtccccac cccatggatt tctattgtta   8640
aagatattca gaatgtttca ttcctacact agtatttatt gcccaagggg tttgtgaggg   8700
ttatattggt gtcatagcac aatgccacca ctgaaccccc cgtccaaatt ttattctggg   8760
ggcgtcacct gaaaccttgt tttcgagcac ctcacataca ccttactgtt cacaactcag   8820
cagttattct attagctaaa cgaaggagaa tgaagaagca ggcgaagatt caggagagtt   8880
cactgcccgc tccttgatct tcagccactg cccttgtgac taaaatggtt cactaccctc   8940
gtggaatcct gaccccatgt aaataaaacc gtgacagctc atggggtggg agatatcgct   9000
gttccttagg accctttac taaccctaat tcgatagcat atgcttcccg ttgggtaaca   9060
tatgctattg aattagggtt agtctggata gtatatacta ctacccggga agcatatgct   9120
acccgtttag ggttaacaag gggccttat aaacactatt gctaatgccc tcttgagggt   9180
ccgcttatcg gtagctacac aggcccctct gattgacgtt ggtgtagcct cccgtagtct   9240
tcctgggccc ctgggaggta catgtccccc agcattggtg taagagcttc agccaagagt   9300
tacacataaa ggcaatgttg tgttgcagtc cacagactgc aaagtctgct ccaggatgaa   9360
agccactcag tgttggcaaa tgtgcacatc catttataag gatgtcaact acagtcagag   9420
aaccccttg tgtttggtcc ccccccgtgt cacatgtgga acagggccca gttggcaagt   9480
tgtaccaacc aactgaaggg attacatgca ctgccccgcg ggaaatacgt cctacccagg   9540
aacccgaaac agtgtttccc agaagctgta aaaatagaac gccctggaac tgccccactg   9600
tgcaatgcag cttttagcca tgccatgctc tataaatcac ttccctatct caggtaggcc   9660
tgcacacctt aggtatggag cgaaggttag tggtcactct gcagtgcctg gtgctgcttt   9720
acctggcacc tgagtgtgga ggtacagacc aatgtgacaa ttttccccaa atgttgaggg   9780
acctaagaga tgccttcagt cgtgttaaaa ccttttcca gacaaaggac gaggtagata   9840
accttttgct caaggagtct ctgctagagg actttaaggg ctaccttgga tgccaggccc   9900
tgtcagaaat gatccaattc tacctggagg aagtcatgcc acaggctgaa aaccaggacc   9960
ctgaagccaa agaccatgtc aattctttgg gtgaaaatct aaagacccta cggctccgcc  10020
tgcgcaggtg ccacaggttc ctgccgtgtg agaacaagag taaagctgtg gaacagataa  10080
aaaatgcctt taacaagctg caggaaaaag gaatttacaa agccatgagt gaatttgaca  10140
tttttattaa ctacatagaa gcatacatga caattaaagc caggtgataa ttccataccc  10200
tggaagcagg agatgggtgc atttcacccc aacccccct ttcgactgtc atttacaata  10260
aaatgaaacc ttttattctt gattgcctct tgtgttcttg ccgcccaggt accttcctgt  10320
gttctcccca cgggaaaaag aatagcttct gcagaaggcc attgacgcaa gttttgcccg  10380
tggggattac ccgacccagc cacttacagc acattttgtt ctaggtccat cttaggagcc  10440
cgggccagca ttctatcagc ttaacgggaa gagaagtggg gagggcactc gcccactaac  10500
```

```
cttaacacct gcagcctaca aaagtacact agctgtttgc tctattcgcc actagagacc  10560
gccaagatgc gaaactacag gcccgggccc aggccttgca gggcagacgg ttaggctgac  10620
aaggggacaa gtgtggcagg tgggcgggaa ggggcacaag aatgccggcg aaactggacc  10680
acggtccacc ccgccctcaa gcgtccggga gccgggcggc tcggctaagg agggcggcct  10740
tgcgaacaat tattagtagc taccaacaag ggcccccaga tgccccccac cagtcacccg  10800
gccgtgtcca ctcacatatt ccactcttat ttttaaatta atgtgtccca attagaaacc  10860
caagcgcaga aattagttga gaggctagtg ttttaaacat gcaccctagg ccagccagag  10920
ataatgtcac aagattatca agttggtgta aacacgccgt gggaaaaaat ttatggttca  10980
gtgcgtcgag tgctatcttt ggaacagtag aaaattgaac cttgttggcg ggagaaggaa  11040
taacgcctta tctgggagga gcgacggatt atagccaata agagagctca agacgcaggg  11100
ctcgcaaagt atagtggccc cgtgggacct tagaggtgga gcaacgtcta aagtggtaat  11160
aacaccaggc ggggctgggc aaaggggtcc tacgggcggg attaattacg ccttgcttac  11220
gcaagctcag ttaattcgcc cacgacttga aaaatgtagc ccttaaccaa ttggcggccc  11280
ctaagggggg gactaaggtc ccactacaaa aactctgtgt tctgctgcaa attttagatc  11340
agatggcata gagacaagga caccgaagac ccccagagcc ctcatcgcag ggttcttacc  11400
atgcggccat gtaggcccac ttaacactac aagacctacg cctctccatt catcatgtaa  11460
cccacaaatc atctaaaccg taagtctaag ggcctcctga ggttttctca ggaggcccta  11520
atgtataatt aatcatgcat ttgattttaa aaaagtaggt tacactcatt ttaggccaga  11580
ctttatttgc agattaataa tttatgtgat tctccttccc tctaggactg aagaaacagc  11640
ctcctgcacg tgagcatgta tctgaaataa ttattatgtc ataagtgtaa tgattagaaa  11700
gtcataaacc cacttccctt tacatgaatc tgggcactga attttggggt acttctaaag  11760
actaacgtgt tcgatttcgg ggtcacttcc ccttttataa gtgtgtgaac agtgatttca  11820
gtaaaaccta agagatattt ggtgtcactt ccgcatttta agtttcagaa aattttaaaa  11880
ttaaaattga aatttctctc aaaataattc caatgaaaac ttcaaagaat cttatgtatg  11940
taattctttt gccccaaact gggcttcaga tgccttctat tgcactctca caaaaacatt  12000
ctggacacat gtgccagacg cctgggcctc taaggccctc gggtccccct ggaccccggc  12060
ctcagcaacc ctgctgctcc cctcctgcca ccccagcctc ccccctcccc cgtccccctt  12120
cgctcctgtt cctcccccgg tccccagtag ggccgcctgc cccccctgcac ccagtacctg  12180
cccctcttgg ccacgcaccc cgggccaggc caccttagac ccggccaagc cccatccctg  12240
aagacccagc ggccattctc tctggtaacg agcagagaag aagtagaggc ccgcggccat  12300
tgggcccaga ttgagagacc agtccagggg cccgaggttg gagccagcgg gcacccgagg  12360
tcccagcacc cggtccctcc ggggggcaga gacaggcagg gccccccggc agctggcccc  12420
gaggaggcgc ccggagtggg gccggtcggc tgggctggcc gagcccgggt ctgggaggtc  12480
tggggtggcg agcctgctgt ctcaggaggg gcctggctcc gccgggtggc cctggggtaa  12540
gtctgggagg cagagggtcg gcctaggccc ggggaagtgg agggggatcg cccgggtctc  12600
tgttggcaga gtccgggcga tcctctgaga ccctccgggc ccggacggtc gccctcagcc  12660
ccccagacag accccagggt ctccaggcag ggtccggcat cttcaggggc agcaggctca  12720
ccaccacagg ccccccagac ccgggtctcg gccagccgag ccgaccggcc ccgcgcctgg  12780
cgcctcctcg gggccagccg ccggggttgg ttctgcccct ctctctgtcc ttcagaggaa  12840
```

```
ccagggacct cgggcacccc agagcccctc gggcccgcct ccaggcgccc tcctggtctc  12900
cgctcccctc tgagccccgt taaacccaaa gaatgtctga ggggagccac cctcggggcc  12960
caggccccag agtccagagg tcaggggcac ctcagggtgc ctccccgggt cccaggccag  13020
ccggagggac cccggcagcc cgggcggccc cagaggccgg ttcctcgccc cttccccggg  13080
cttcagagcc caggatgtcc cccagaaggg accctaggcg tcccctctcc tcccctccag  13140
gcccgagcct ctccctcgcg gagaggggcc tctttgggcc ctcaagtcca gccccaccga  13200
gacccgagtg gcccggatcc ccccaccggc ccttctctct gtccccctgc tcctctccaa  13260
ccttcgctcc accctagacc ccagcttctg gcctccccgg gtccaccagg ccagccggag  13320
ggaccccggc agcccgggcg agtcgccttc cctctcccct ggcctctcct tcccgcctcc  13380
cacccgagcc ccctcagctt gcctccccac cgggtccatc aggccggccg gagggacccc  13440
ggcggcccgg tgtcagtccc ccctgcagcc gcccagtctc tgcctccagg caagggcgcc  13500
agcttttctc cccccagcct gaggcccagt ctcctgtgca ctgtctgtaa agtccagcct  13560
cccacgcccg tccacggctc ccgggcccag cctcgtccac ccctccccac ggtggacagg  13620
ccctctgtcc acccgggcca tccccgcccc cctgtgtcca ccccagtccc gtccaggggg  13680
gactttatgt gacccttggg cctggctccc catagactcc catgtaagcc tgcctcgagt  13740
aggtgcctcc agagcccctt ttgccccccct ggcggcccag cccgaccccc gggcgccccc  13800
aaactttgtc cagatgtcca ggggtccccg agggtgaggc ccagcccccct cccgcccctg  13860
tccactgccc cggtcccccc agaagccccc aaaagtagag gctcaggcca tgcgcgccct  13920
gtcaccaggc ctgccaaaga gccagatcta aggccgggag aggcagcccc aaagcgggtg  13980
cagtaacagg taatctctgg tagtgatttg gacccgaaat ctgacacttt agagctctgg  14040
aggactttaa aactctaaaa atcaaaactt tagaggcgaa tgggcgccat tttgtcccca  14100
cgcgcgcata atggcggacc taggcctaaa acccccagga agcgggtcta tggttggctg  14160
cgctgctgct atctttagag gggaaaagag gaataagccc ccagacaggg gagtgggctt  14220
gtttgtgact tcaccaaagg tcagggccca agggggttcg cgttgctagg ccaccttctc  14280
agtccagcgc gtttacgtaa gccagacagc agccaattgt cagttctagg gagggggacc  14340
actgcccctg gtataaagtg gtcctgcagc tatttctggt cgcatcagag cgccaggagt  14400
ccacacaaat gtaagagggg gtcttctacc tctccctagc cctccgcccc ctccaaggac  14460
tcgggcccag tttctaactt ttccccttcc ctccctcgtc ttgccctgcg cccggggcca  14520
ccttcatcac cgtcgctgac tccgccatcc aagcctaggg gagaccgaag tgaaggccct  14580
ggaccaaccc ggcccgggcc ccccggtatc gggccagagg taagtggact ttaatttttt  14640
ctgctaagcc caacactcca ccacacccag gcacacacta cacacaccca cccgtctcag  14700
ggtcccctcg gacagctcct aagaaggcac cggtcgccca gtcctaccag agggggccaa  14760
gaacccagac gagtccgtag aagggtcctc gtccagcaag aagaggaggt ggtaagcggt  14820
tcaccttcag gggtaagtaa cctgacctct ccagggctca cataaaggga ggcttagtat  14880
acatgcttct tgcttttcac aggaacctgg gggctagtct gggtgggatt aggctgcctc  14940
aagttgcatc agccagggct tcatgccctc ctcagttccc tagtccccgg gcttcaggcc  15000
ccctccgtcc ccgtcctcca gagacccggg cttcaggccc tgcctctcct gttacccttt  15060
tagaaccaca gcctggacac atgtgccaga cgccttggcc tctaaggccc tcgggtcccc  15120
ctggaccccg gcctcagcaa ccctgctgct cccctcctgc caccccagcc tcccccccctc  15180
cccgtccccc ttcgctcctg atcctccccc ggtccccagt agggccgcct gcccccctgc  15240
```

-continued acccagtacc tgcccctctt ggccacgcac cccgggccag gccaccttag acccggccaa 15300
gccccatccc tgaagaccca gcggccattc tctctggtaa cgagcagaga agaagtagag 15360
gcccgcggcc attgggccca gattgagaga ccagtccagg ggcccgaggt tggagccagc 15420
gggcacccga ggtcccagca cccggtccct ccggggggca gagacaggca gggcccccccg 15480 gcagctggcc ccgaggaggc gcccggagtg gggccggtcg gctgggctgg ccgagcccgg 15540
gtctgggagg tctggggtgg cgagcctgct gtctcaggag gggcctggct ccgccgggtg 15600
gccctggggt aagtctggga ggcagagggt cggcctaggc ccggggaagt ggagggggat 15660
cgcccgggtc tctgttggca gagtccgggc gatcctctga gaccctccgg gcccggacgg 15720
tcgccctcag ccccccagac agaccccagg gtctccaggc agggtccggc atcttcaggg 15780
gcagcaggct caccaccaca ggcccccccag acccgggtct cggccagccg agccgaccgg 15840
ccccgcgcct ggcgcctcct cggggccagc cgccggggtt ggttctgccc ctctctctgt 15900
ccttcagagg aaccagggac ctcgggcacc ccagagcccc tcgggcccgc ctccaggcgc 15960
cctcctggtc tccgctcccc tctgagcccc gttaaaccca aagaatgtct gaggggagcc 16020
accctcgggg cccaggcccc agagtccaga ggtcaggggc acctcagggt gcctccccgg 16080
gtcccaggcc agccggaggg accccggcag cccgggcggc cccagaggcc ggttcctcgc 16140
cccttccccg ggcttcagag cccaggatgt cccccagaag ggaccctagg cgtcccctct 16200
cctcccctcc aggcccgagc ctctccctcg cggagagggg cctctttggg ccctcaagtc 16260
cagccccacc gagacccgag tggcccggat ccccccaccg gcccttctct ctgtccccct 16320
gctcctctcc aaccttcgct ccaccctaga ccccagcttc tggcctcccc gggtccacca 16380
ggccagccgg agggaccccg gcagcccggg cgagtcgcct tccctctccc ctggcctctc 16440
cttcccgcct cccacccgag ccccctcagc ttgcctcccc accgggtcca tcaggccggc 16500
cggagggacc ccggcggccc ggtgtcagtc ccccctgcag ccgcccagtc tctgcctcca 16560
ggcaagggcg ccagcttttc tccccccagc ctgaggccca gtctcctgtg cactgtctgt 16620
aaagtccagc ctcccacgcc cgtccacggc tcccgggccc agcctcgtcc accccctccc 16680
acggtggaca ggccctctgt ccacccgggc catccccgcc cccctgtgtc caccccagtc 16740
ccgtccaggg gggactttat gtgacccttg ggcctggctc cccatagact cccatgtaag 16800
cctgcctcga gtaggtgcct ccagagcccc ttttgccccc ctggcggccc agcccgaccc 16860
ccgggcgccc ccaaactttg tccagatgtc caggggtccc cgagggtgag gcccagcccc 16920
ctcccgcccc tgtccactgc cccggtcccc ccagaagccc ccaaaagtag aggctcaggc 16980
catgcgcgcc ctgtcaccag gcctgccaaa gagccagatc taaggccggg agaggcagcc 17040
ccaaagcggg tgcagtaaca ggtaatctct ggtagtgatt tggacccgaa atctgacact 17100
ttagagctct ggaggacttt aaaactctaa aaatcaaaac tttagaggcg aatgggcgcc 17160
attttgtccc cacgcgcgca taatggcgga cctaggccta aaacccccag gaagcgggtc 17220
tatggttggc tgcgctgctg ctatctttag aggggaaaag aggaataagc ccccagacag 17280
gggagtgggc ttgtttgtga cttcaccaaa ggtcagggcc caagggggtt cgcgttgcta 17340
ggccaccttc tcagtccagc gcgtttacgt aagccagaca gcagccaatt gtcagttcta 17400
gggaggggga ccactgcccc tggtataaag tggtcctgca gctatttctg gtcgcatcag 17460
agcgccagga gtccacacaa atgtaagagg gggtcttcta cctctcccta gccctccgcc 17520
ccctccaagg actcgggccc agtttctaac ttttcccctt ccctccctcg tcttgccctg 17580

-continued

```
cgcccggggc caccttcatc accgtcgctg actccgccat ccaagcctag gggagaccga  17640
agtgaaggcc ctggaccaac ccggcccggg ccccccggta tcgggccaga ggtaagtgga  17700
ctttaatttt ttctgctaag cccaacactc caccacaccc aggcacacac tacacacacc  17760
cacccgtctc agggtcccct cggacagctc ctaagaaggc accggtcgcc cagtcctacc  17820
agagggggcc aagaacccag acgagtccgt agaagggtcc tcgtccagca agaagaggag  17880
gtggtaagcg gttcaccttc aggggtaagt aacctgacct ctccagggct cacataaagg  17940
gaggcttagt atacatgctt cttgcttttc acaggaacct gggggctagt ctgggtggga  18000
ttaggctgcc tcaagttgca tcagccaggg cttcatgccc tcctcagttc cctagtcccc  18060
gggcttcagg cccccctccgt ccccgtcctc cagagacccg ggcttcaggc cctgcctctc  18120
ctgttaccct tttagaacca cagcctggac acatgtgcca gacgccttgg cctctaaggc  18180
cctcgggtcc ccctggaccc cggcctcagc aaccctgctg ctcccctcct gccaccccag  18240
cctccccccc tccccgtccc ccttcgctcc tgatcctccc ccggtcccca gtagggccgc  18300
ctgccccccct gcacccagta cctgcccctc ttggccacgc accccgggcc aggccacctt  18360
agacccggcc aagccccatc cctgaagacc cagcggccat tctctctggt aacgagcaga  18420
gaagaagtag aggcccgcgg ccattgggcc cagattgaga gaccagtcca ggggcccgag  18480
gttggagcca gcgggcaccc gaggtcccag cacccggtcc ctccgggggg cagagacagg  18540
cagggccccc cggcagctgg ccccgaggag gcgcccggag tggggccggt cggctgggct  18600
ggccgagccc gggtctggga ggtctggggt ggcgagcctg ctgtctcagg aggggcctgg  18660
ctccgccggg tggccctggg gtaagtctgg gaggcagagg gtcggcctag gcccggggaa  18720
gtggaggggg atcgcccggg tctctgttgg cagagtccgg gcgatcctct gagaccctcc  18780
gggcccggac ggtcgccctc agccccccag acagacccca gggtctccag gcagggtccg  18840
gcatcttcag gggcagcagg ctcaccacca caggcccccc agacccgggt ctcggccagc  18900
cgagccgacc ggccccgcgc ctggcgcctc ctcggggcca gccgccgggg ttggttctgc  18960
ccctctctct gtccttcaga ggaaccaggg acctcgggca ccccagagcc cctcgggccc  19020
gcctccaggc gccctcctgg tctccgctcc cctctgagcc ccgttaaacc caaagaatgt  19080
ctgaggggag ccaccctcgg ggcccaggcc ccagagtcca gaggtcaggg gcacctcagg  19140
gtgcctcccc gggtcccagg ccagccggag ggaccccggc agcccgggcg gccccagagg  19200
ccggttcctc gccccttccc cggcttcag agcccaggat gtcccccaga agggacccta  19260
ggcgtcccct ctcctcccct ccaggcccga gcctctccct cgcggagagg ggcctctttg  19320
ggccctcaag tccagcccca ccgagacccg agtggcccgg atccccccac cggcccttct  19380
ctctgtcccc ctgctcctct ccaaccttcg ctccacccta gaccccagct tctggcctcc  19440
ccgggtccac caggccagcc ggagggaccc cggcagcccg ggcgagtcgc cttccctctc  19500
ccctggcctc tccttcccgc ctcccacccg agccccctca gcttgcctcc ccaccgggtc  19560
catcaggccg gccggaggga ccccggcggc ccggtgtcag tccccccctgc agccgcccag  19620
tctctgcctc caggcaaggg cgccagcttt tctcccccca gcctgaggcc cagtctcctg  19680
tgcactgtct gtaaagtcca gcctcccacg cccgtccacg gctcccgggc ccagcctcgt  19740
ccacccctcc ccacggtgga caggccctct gtccacccgg gccatccccg ccccccctgtg  19800
tccaccccag tcccgtccag gggggacttt atgtgaccct tgggcctggc tccccataga  19860
ctcccatgta agcctgcctc gagtaggtgc ctccagagcc ccttttgccc ccctggcggc  19920
ccagcccgac ccccgggcgc ccccaaactt tgtccagatg tccaggggtc cccgagggtg  19980
```

aggcccagcc ccctcccgcc cctgtccact gccccggtcc ccccagaagc ccccaaaagt 20040
agaggctcag gccatgcgcg ccctgtcacc aggcctgcca aagagccaga tctaaggccg 20100
ggagaggcag ccccaaagcg ggtgcagtaa caggtaatct ctggtagtga tttggacccg 20160
aaatctgaca ctttagagct ctggaggact ttaaaactct aaaaatcaaa actttagagg 20220
cgaatgggcg ccattttgtc cccacgcgcg cataatggcg gacctaggcc taaaaccccc 20280
aggaagcggg tctatggttg gctgcgctgc tgctatcttt agaggggaaa agaggaataa 20340
gcccccagac aggggagtgg gcttgtttgt gacttcacca aaggtcaggg cccaaggggg 20400
ttcgcgttgc taggccacct tctcagtcca gcgcgtttac gtaagccaga cagcagccaa 20460
ttgtcagttc tagggagggg gaccactgcc cctggtataa agtggtcctg cagctatttc 20520
tggtcgcatc agagcgccag gagtccacac aaatgtaaga gggggtcttc tacctctccc 20580
tagccctccg cccccctccaa ggactcgggc ccagtttcta acttttcccc ttccctccct 20640
cgtcttgccc tgcgcccggg gccaccttca tcaccgtcgc tgactccgcc atccaagcct 20700
aggggagacc gaagtgaagg ccctggacca acccggcccg ggccccccgg tatcgggcca 20760
gaggtaagtg gactttaatt ttttctgcta agcccaacac tccaccacac ccaggcacac 20820
actacacaca cccacccgtc tcagggtccc ctcggacagc tcctaagaag gcaccggtcg 20880
cccagtccta ccagaggggg ccaagaaccc agacgagtcc gtagaagggt cctcgtccag 20940
caagaagagg aggtggtaag cggttcacct tcaggggtaa gtaacctgac ctctccaggg 21000
ctcacataaa gggaggctta gtatacatgc ttcttgcttt tcacaggaac ctgggggcta 21060
gtctgggtgg gattaggctg cctcaagttg catcagccag ggcttcatgc cctcctcagt 21120
tccctagtcc ccgggcttca ggccccctcc gtccccgtcc tccagagacc cgggcttcag 21180
gccctgcctc tcctgttacc cttttagaac cacagcctgg acacatgtgc cagacgcctt 21240
ggcctctaag gccctcgggt ccccctggac cccggcctca gcaaccctgc tgctcccctc 21300
ctgccacccc agcctccccc cctccccgtc ccccttcgct cctgatcctc ccccggtccc 21360
cagtagggcc gcctgccccc ctgcacccag tacctgcccc tcttggccac gcaccccggg 21420
ccaggccacc ttagacccgg ccaagcccca tccctgaaga cccagcggcc attctctctg 21480
gtaacgagca gagaagaagt agaggcccgc ggccattggg cccagattga gagaccagtc 21540
caggggcccg aggttggagc cagcgggcac ccgaggtccc agcacccggt ccctccgggg 21600
ggcagagaca ggcagggccc cccggcagct ggccccgagg aggcgcccgg agtggggccg 21660
gtcggctggg ctggccgagc ccgggtctgg gaggtctggg gtggcgagcc tgctgtctca 21720
ggaggggcct ggctccgccg ggtggccctg gggtaagtct gggaggcaga gggtcggcct 21780
aggcccgggg aagtggaggg ggatcgcccg ggtctctgtt ggcagagtcc gggcgatcct 21840
ctgagaccct ccgggcccgg acggtcgccc tcagcccccc agacagaccc cagggtctcc 21900
aggcagggtc cggcatcttc aggggcagca ggctcaccac cacaggcccc ccagacccgg 21960
gtctcggcca gccgagccga ccggccccgc gcctggcgcc tcctcggggc cagccgccgg 22020
ggttggttct gcccctctct ctgtccttca gaggaaccag ggacctcggg caccccagag 22080
cccctcgggc ccgcctccag gcgccctcct ggtctccgct cccctctgag ccccgttaaa 22140
cccaaagaat gtctgagggg agccaccctc ggggcccagg ccccagagtc cagaggtcag 22200
gggcacctca gggtgcctcc ccgggtccca ggccagccgg agggaccccg gcagcccggg 22260
cggccccaga ggccggttcc tcgccccttc cccgggcttc agagcccagg atgtccccca 22320

-continued

```
gaagggaccc taggcgtccc ctctcctccc ctccaggccc gagcctctcc ctcgcggaga  22380
ggggcctctt tgggccctca agtccagccc caccgagacc cgagtggccc ggatccccc   22440
accggccctt ctctctgtcc ccctgctcct ctccaacctt cgctccaccc tagaccccag  22500
cttctggcct ccccgggtcc accaggccag ccggagggac cccggcagcc cgggcgagtc  22560
gccttccctc tcccctggcc tctccttccc gcctcccacc cgagcccccct cagcttgcct  22620
ccccaccggg tccatcaggc cggccggagg gaccccggcg gcccggtgtc agtcccccct  22680
gcagccgccc agtctctgcc tccaggcaag ggcgccagct tttctccccc cagcctgagg  22740
cccagtctcc tgtgcactgt ctgtaaagtc cagcctccca cgcccgtcca cggctcccgg  22800
gcccagcctc gtccacccct ccccacggtg gacaggccct ctgtccaccc gggccatccc  22860
cgcccccctg tgtccacccc agtcccgtcc agggggggact ttatgtgacc cttgggcctg  22920
gctccccata gactcccatg taagcctgcc tcgagtaggt gcctccagag cccctttttgc  22980
cccctggcg gcccagcccg acccccggc gcccccaaac tttgtccaga tgtccagggg   23040
tccccgaggg tgaggcccag ccccctcccg cccctgtcca ctgccccggt cccccccagaa  23100
gcccccaaaa gtagaggctc aggccatgcg cgccctgtca ccaggcctgc caaagagcca  23160
gatctaaggc cgggagaggc agccccaaag cgggtgcagt aacaggtaat ctctggtagt  23220
gatttggacc cgaaatctga cactttagag ctctggagga ctttaaaact ctaaaaatca  23280
aaactttaga ggcgaatggg cgccattttg tccccacgcg cgcataatgg cggacctagg  23340
cctaaaaccc ccaggaagcg ggtctatggt tggctgcgct gctgctatct ttagagggga  23400
aaagaggaat aagcccccag acaggggagt gggcttgttt gtgacttcac caaaggtcag  23460
ggcccaaggg ggttcgcgtt gctaggccac cttctcagtc cagcgcgttt acgtaagcca  23520
gacagcagcc aattgtcagt tctagggagg gggaccactg cccctggtat aaagtggtcc  23580
tgcagctatt tctggtcgca tcagagcgcc aggagtccac acaaatgtaa gagggggtct  23640
tctacctctc cctagccctc cgccccctcc aaggactcgg gcccagtttc taacttttcc  23700
ccttccctcc ctcgtcttgc cctgcgcccg gggccacctt catcaccgtc gctgactccg  23760
ccatccaagc ctaggggaga ccgaagtgaa ggccctggac caacccggcc cgggcccccc  23820
ggtatcgggc cagaggtaag tggactttaa ttttttctgc taagcccaac actccaccac  23880
acccaggcac acactacaca cacccacccg tctcagggtc ccctcggaca gctcctaaga  23940
aggcaccggt cgcccagtcc taccagaggg ggccaagaac ccagacgagt ccgtagaagg  24000
gtcctcgtcc agcaagaaga ggaggtggta agcggttcac cttcaggggt aagtaacctg  24060
acctctccag ggctcacata aagggaggct tagtatacat gcttcttgct tttcacagga  24120
acctgggggc tagtctgggt gggattaggc tgcctcaagt tgcatcagcc agggcttcat  24180
gccctcctca gttccctagt ccccgggctt caggcccccct ccgtccccgt cctccagaga  24240
cccgggcttc aggccctgcc tctcctgtta ccctttttaga accacagcct ggacacatgt  24300
gccagacgcc ttggcctcta aggccctcgg gtccccctgg accccggcct cagcaaccct  24360
gctgctcccc tcctgccacc ccagcctccc cccctccccg tccccccttcg ctcctgatcc  24420
tcccccggtc cccagtaggg ccgcctgccc ccctgcaccc agtacctgcc cctcttggcc  24480
acgcaccccg ggccaggcca ccttagaccc ggccaagccc catccctgaa gacccagcgg  24540
ccattctctc tggtaacgag cagagaagaa gtagaggccc gcggccattg ggcccagatt  24600
gagagaccag tccaggggcc cgaggttgga gccagcgggc acccgaggtc ccagcacccg  24660
gtccctccgg ggggcagaga caggcagggc cccccggcag ctggccccga ggaggcgccc  24720
```

-continued ggagtggggc cggtcggctg ggctggccga gcccgggtct gggaggtctg gggtggcgag 24780
cctgctgtct caggaggggc ctggctccgc cgggtggccc tggggtaagt ctgggaggca 24840
gagggtcggc ctaggcccgg ggaagtggag ggggatcgcc cgggtctctg ttggcagagt 24900
ccgggcgatc ctctgagacc ctccgggccc ggacggtcgc cctcagcccc ccagacagac 24960
cccagggtct ccaggcaggg tccggcatct tcaggggcag caggctcacc accacaggcc 25020
ccccagaccc gggtctcggc cagccgagcc gaccggcccc gcgcctggcg cctcctcggg 25080
gccagccgcc ggggttggtt ctgcccctct ctctgtcctt cagaggaacc agggacctcg 25140
ggcaccccag agcccctcgg gcccgcctcc aggcgccctc ctggtctccg ctcccctctg 25200
agccccgtta aacccaaaga atgtctgagg ggagccaccc tcggggccca ggccccagag 25260
tccagaggtc aggggcacct cagggtgcct ccccgggtcc caggccagcc ggagggaccc 25320
cggcagcccg ggcggcccca gaggccggtt cctcgcccct tccccgggct tcagagccca 25380
ggatgtcccc cagaagggac cctaggcgtc ccctctcctc ccctccaggc ccgagcctct 25440
ccctcgcgga gaggggcctc tttgggccct caagtccagc cccaccgaga cccgagtggc 25500
ccggatcccc ccaccggccc ttctctctgt ccccctgctc ctctccaacc ttcgctccac 25560
cctagacccc agcttctggc ctccccgggt ccaccaggcc agccggaggg accccggcag 25620
cccgggcgag tcgccttccc tctcccctgg cctctccttc ccgcctccca cccgagcccc 25680
ctcagcttgc ctccccaccg ggtccatcag gccggccgga gggaccccgg cggcccggtg 25740
tcagtccccc ctgcagccgc ccagtctctg cctccaggca agggcgccag cttttctccc 25800
cccagcctga ggcccagtct cctgtgcact gtctgtaaag tccagcctcc cacgcccgtc 25860
cacggctccc gggcccagcc tcgtccaccc ctccccacgg tggacaggcc ctctgtccac 25920
ccgggccatc cccgcccccc tgtgtccacc ccagtcccgt ccagggggga ctttatgtga 25980
cccttgggcc tggctcccca tagactccca tgtaagcctg cctcgagtag gtgcctccag 26040 agccccttt gccccccctgg cggcccagcc cgaccccccgg gcgcccccaa actttgtcca 26100
gatgtccagg ggtccccgag ggtgaggccc agccccctcc cgcccctgtc cactgccccg 26160
gtccccccag aagcccccaa aagtagaggc tcaggccatg cgcgccctgt caccaggcct 26220
gccaaagagc cagatctaag gccgggagag gcagccccaa agcgggtgca gtaacaggta 26280
atctctggta gtgatttgga cccgaaatct gacactttag agctctggag gactttaaaa 26340
ctctaaaaat caaaacttta gaggcgaatg ggcgccattt tgtccccacg cgcgcataat 26400
ggcggaccta ggcctaaaac ccccaggaag cgggtctatg gttggctgcg ctgctgctat 26460
ctttagaggg gaaaagagga ataagccccc agacagggga gtgggcttgt ttgtgacttc 26520
accaaaggtc agggcccaag ggggttcgcg ttgctaggcc accttctcag tccagcgcgt 26580
ttacgtaagc cagacagcag ccaattgtca gttctaggga gggggaccac tgcccctggt 26640
ataaagtggt cctgcagcta tttctggtcg catcagagcg ccaggagtcc acacaaatgt 26700 aagaggggt cttctacctc tccctagccc tccgccccct ccaaggactc gggcccagtt 26760
tctaactttt ccccttccct ccctcgtctt gccctgcgcc cggggccacc ttcatcaccg 26820
tcgctgactc cgccatccaa gcctagggga gaccgaagtg aaggccctgg accaacccgg 26880
cccgggcccc ccggtatcgg gccagaggta agtggacttt aattttttct gctaagccca 26940
acactccacc acacccaggc acacactaca cacacccacc cgtctcaggg tcccctcgga 27000
cagctcctaa gaaggcaccg gtcgcccagt cctaccagag gggccaaga acccagacga 27060

-continued

```
gtccgtagaa gggtcctcgt ccagcaagaa gaggaggtgg taagcggttc accttcaggg  27120
gtaagtaacc tgacctctcc agggctcaca taaagggagg cttagtatac atgcttcttg  27180
cttttcacag gaacctgggg gctagtctgg gtgggattag gctgcctcaa gttgcatcag  27240
ccagggcttc atgccctcct cagttcccta gtccccgggc ttcaggcccc ctccgtcccc  27300
gtcctccaga gacccgggct tcaggccctg cctctcctgt taccctttta gaaccacagc  27360
ctggacacat gtgccagacg ccttggcctc taaggccctc gggtcccccct ggaccccggc  27420
ctcagcaacc ctgctgctcc cctcctgcca ccccagcctc ccccccctccc cgtccccctt  27480
cgctcctgat cctcccccgg tccccagtag ggccgcctgc ccccctgcac ccagtacctg  27540
cccctcttgg ccacgcaccc cgggccaggc caccttagac ccggccaagc cccatccctg  27600
aagacccagc ggccattctc tctggtaacg agcagagaag aagtagaggc ccgcggccat  27660
tgggcccaga ttgagagacc agtccagggg cccgaggttg gagccagcgg gcacccgagg  27720
tcccagcacc cggtccctcc ggggggcaga gacaggcagg gcccccccggc agctggcccc  27780
gaggaggcgc ccggagtggg gccggtcggc tgggctggcc gagcccgggt ctgggaggtc  27840
tggggtggcg agcctgctgt ctcaggaggg gcctggctcc gccgggtggc cctggggtaa  27900
gtctgggagg cagagggtcg gcctaggccc ggggaagtgg agggggatcg cccgggtctc  27960
tgttggcaga gtccgggcga tcctctgaga ccctccgggc ccggacggtc gccctcagcc  28020
ccccagacag accccagggt ctccaggcag ggtccggcat cttcaggggc agcaggctca  28080
ccaccacagg ccccccagac ccgggtctcg gccagccgag ccgaccggcc ccgcgcctgg  28140
cgcctcctcg gggccagccg ccggggttgg ttctgcccct ctctctgtcc ttcagaggaa  28200
ccagggacct cgggcacccc agagcccctc gggcccgcct ccaggcgccc tcctggtctc  28260
cgctcccctc tgagccccgt taaacccaaa gaatgtctga ggggagccac cctcggggcc  28320
caggccccag agtccagagg tcaggggcac ctcagggtgc ctccccgggt cccaggccag  28380
ccggagggac cccggcagcc cgggcggccc cagaggccgg ttcctcgccc cttccccggg  28440
cttcagagcc caggatgtcc cccagaaggg accctaggcg tcccctctcc tcccctccag  28500
gcccgagcct ctccctcgcg gagaggggcc tctttgggcc ctcaagtcca gccccaccga  28560
gacccgagtg gcccggatcc ccccaccggc ccttctctct gtccccctgc tcctctccaa  28620
ccttcgctcc accctagacc ccagcttctg gcctccccgg gtccaccagg ccagccggag  28680
ggaccccggc agcccgggcg agtcgccttc cctctcccct ggcctctcct tcccgcctcc  28740
cacccgagcc ccctcagctt gcctccccac cgggtccatc aggccggccg gagggacccc  28800
ggcggcccgg tgtcagtccc ccctgcagcc gcccagtctc tgcctccagg caagggcgcc  28860
agcttttctc cccccagcct gaggcccagt ctcctgtgca ctgtctgtaa agtccagcct  28920
cccacgcccg tccacggctc ccgggcccag cctcgtccac ccctccccac ggtggacagg  28980
ccctctgtcc acccgggcca tccccgcccc cctgtgtcca ccccagtccc gtccaggggg  29040
gactttatgt gacccttggg cctggctccc catagactcc catgtaagcc tgcctcgagt  29100
aggtgcctcc agagcccctt ttgccccccct ggcggcccag cccgaccccc gggcgccccc  29160
aaactttgtc cagatgtcca ggggtccccg agggtgaggc ccagccccct cccgcccctg  29220
tccactgccc cggtcccccc agaagccccc aaaagtagag gctcaggcca tgcgcgccct  29280
gtcaccaggc ctgccaaaga gccagatcta aggccgggag aggcagcccc aaagcgggtg  29340
cagtaacagg taatctctgg tagtgatttg gacccgaaat ctgacacttt agagctctgg  29400
aggactttaa aactctaaaa atcaaaactt tagaggcgaa tgggcgccat tttgtcccca  29460
```

-continued

```
cgcgcgcata atggcggacc taggcctaaa acccccagga agcgggtcta tggttggctg  29520
cgctgctgct atctttagag gggaaaagag gaataagccc ccagacaggg gagtgggctt  29580
gtttgtgact tcaccaaagg tcagggccca agggggttcg cgttgctagg ccaccttctc  29640
agtccagcgc gtttacgtaa gccagacagc agccaattgt cagttctagg gagggggacc  29700
actgcccctg gtataaagtg gtcctgcagc tatttctggt cgcatcagag cgccaggagt  29760
ccacacaaat gtaagagggg gtcttctacc tctccctagc cctccgcccc ctccaaggac  29820
tcgggcccag tttctaactt ttccccttcc ctccctcgtc ttgccctgcg cccggggcca  29880
ccttcatcac cgtcgctgac tccgccatcc aagcctaggg gagaccgaag tgaaggccct  29940
ggaccaaccc ggcccgggcc ccccggtatc gggccagagg taagtggact ttaatttttt  30000
ctgctaagcc caacactcca ccacacccag gcacacacta cacacaccca cccgtctcag  30060
ggtcccctcg gacagctcct aagaaggcac cggtcgccca gtcctaccag agggggccaa  30120
gaacccagac gagtccgtag aagggtcctc gtccagcaag aagaggaggt ggtaagcggt  30180
tcaccttcag gggtaagtaa cctgacctct ccagggctca cataaaggga ggcttagtat  30240
acatgcttct tgcttttcac aggaacctgg gggctagtct gggtgggatt aggctgcctc  30300
aagttgcatc agccagggct tcatgccctc ctcagttccc tagtccccgg gcttcaggcc  30360
ccctccgtcc ccgtcctcca gagacccggg cttcaggccc tgcctctcct gttacccttt  30420
tagaaccaca gcctggacac atgtgccaga cgccttggcc tctaaggccc tcgggtcccc  30480
ctggaccccg gcctcagcaa ccctgctgct cccctcctgc caccccagcc tccccccctc  30540
cccgtccccc ttcgctcctg atcctccccc ggtccccagt agggccgcct gccccccctgc  30600
acccagtacc tgcccctctt ggccacgcac cccgggccag gccaccttag acccggccaa  30660
gccccatccc tgaagaccca gcggccattc tctctggtaa cgagcagaga agaagtagag  30720
gcccgcggcc attgggccca gattgagaga ccagtccagg ggcccgaggt tggagccagc  30780
gggcacccga ggtcccagca cccggtccct ccggggggca gagacaggca gggccccccg  30840
gcagctggcc ccgaggaggc gcccggagtg gggccggtcg gctgggctgg ccgagcccgg  30900
gtctgggagg tctggggtgg cgagcctgct gtctcaggag gggcctggct ccgccgggtg  30960
gccctggggt aagtctggga ggcagagggt cggcctaggc ccggggaagt ggagggggat  31020
cgcccgggtc tctgttggca gagtccgggc gatcctctga gaccctccgg gcccggacgg  31080
tcgccctcag ccccccagac agaccccagg gtctccaggc agggtccggc atcttcaggg  31140
gcagcaggct caccaccaca ggccccccag acccgggtct cggccagccg agccgaccgg  31200
ccccgcgcct ggcgcctcct cggggccagc cgccggggtt ggttctgccc ctctctctgt  31260
ccttcagagg aaccagggac ctcgggcacc ccagagcccc tcgggcccgc ctccaggcgc  31320
cctcctggtc tccgctcccc tctgagcccc gttaaaccca aagaatgtct gaggggagcc  31380
accctcgggg cccaggcccc agagtccaga ggtcaggggc acctcagggt gcctccccgg  31440
gtcccaggcc agccggaggg accccggcag cccgggcggc cccagaggcc ggttcctcgc  31500
cccttccccg ggcttcagag cccaggatgt cccccagaag ggaccctagg cgtcccctct  31560
cctcccctcc aggcccgagc ctctccctcg cggagagggg cctctttggg ccctcaagtc  31620
cagccccacc gagacccgag tggcccggat ccccccaccg gcccttctct ctgtccccct  31680
gctcctctcc aaccttcgct ccaccctaga ccccagcttc tggcctcccc gggtccacca  31740
ggccagccgg agggaccccg gcagcccggg cgagtcgcct tccctctccc ctggcctctc  31800
```

-continued

```
cttcccgcct cccacccgag ccccctcagc ttgcctcccc accgggtcca tcaggccggc  31860
cggagggacc ccggcggccc ggtgtcagtc ccccctgcag ccgcccagtc tctgcctcca  31920
ggcaagggcg ccagcttttc tccccccagc ctgaggccca gtctcctgtg cactgtctgt  31980
aaagtccagc ctcccacgcc cgtccacggc tcccgggccc agcctcgtcc acccctcccc  32040
acggtggaca ggccctctgt ccacccgggc catccccgcc cccctgtgtc caccccagtc  32100
ccgtccaggg gggactttat gtgacccttg ggcctggctc cccatagact cccatgtaag  32160
cctgcctcga gtaggtgcct ccagagcccc ttttgccccc ctggcggccc agcccgaccc  32220
ccgggcgccc ccaaactttg tccagatgtc caggggtccc cgagggtgag gcccagcccc  32280
ctcccgcccc tgtccactgc cccggtcccc ccagaagccc ccaaaagtag aggctcaggc  32340
catgcgcgcc ctgtcaccag gcctgccaaa gagccagatc taaggccggg agaggcagcc  32400
ccaaagcggg tgcagtaaca ggtaatctct ggtagtgatt tggacccgaa atctgacact  32460
ttagagctct ggaggacttt aaaactctaa aaatcaaaac tttagaggcg aatgggcgcc  32520
attttgtccc cacgcgcgca taatggcgga cctaggccta aaacccccag gaagcgggtc  32580
tatggttggc tgcgctgctg ctatctttag aggggaaaag aggaataagc ccccagacag  32640
gggagtgggc ttgtttgtga cttcaccaaa ggtcagggcc caagggggtt cgcgttgcta  32700
ggccaccttc tcagtccagc gcgtttacgt aagccagaca gcagccaatt gtcagttcta  32760
gggagggggga ccactgcccc tggtataaag tggtcctgca gctatttctg gtcgcatcag  32820
agcgccagga gtccacacaa atgtaagagg gggtcttcta cctctcccta gccctccgcc  32880
ccctccaagg actcgggccc agtttctaac ttttcccctt ccctccctcg tcttgccctg  32940
cgcccggggc caccttcatc accgtcgctg actccgccat ccaagcctag gggagaccga  33000
agtgaaggcc ctggaccaac ccggcccggg ccccccggta tcgggccaga ggtaagtgga  33060
ctttaatttt ttctgctaag cccaacactc caccacaccc aggcacacac tacacacacc  33120
cacccgtctc agggtcccct cggacagctc ctaagaaggc accggtcgcc cagtcctacc  33180
agagggggcc aagaacccag acgagtccgt agaagggtcc tcgtccagca agaagaggag  33240
gtggtaagcg gttcaccttc aggggtaagt aacctgacct ctccagggct cacataaagg  33300
gaggcttagt atacatgctt cttgcttttc acaggaacct gggggctagt ctgggtggga  33360
ttaggctgcc tcaagttgca tcagccaggg cttcatgccc tcctcagttc cctagtcccc  33420
gggcttcagg ccccctccgt ccccgtcctc cagagacccg ggcttcaggc cctgcctctc  33480
ctgttaccct tttagaacca cagcctggac acatgtgcca gacgccttgg cctctaaggc  33540
cctcgggtcc ccctggaccc cggcctcagc aaccctgctg ctcccctcct gccaccccag  33600
cctccccccc tccccgtccc ccttcgctcc tgatcctccc ccggtcccca gtagggccgc  33660
ctgccccccct gcacccagta cctgcccctc ttggccacgc accccgggcc aggccacctt  33720
agacccggcc aagccccatc cctgaagacc cagcggccat tctctctggt aacgagcaga  33780
gaagaagtag aggcccgcgg ccattgggcc cagattgaga gaccagtcca ggggcccgag  33840
gttggagcca gcgggcaccc gaggtcccag cacccggtcc ctccgggggg cagagacagg  33900
cagggccccc cggcagctgg ccccgaggag gcgcccggag tggggccggt cggctgggct  33960
ggccgagccc gggtctggga ggtctggggt ggcgagcctg ctgtctcagg aggggcctgg  34020
ctccgccggg tggccctggg gtaagtctgg gaggcagagg gtcggcctag gcccggggaa  34080
gtggaggggg atcgcccggg tctctgttgg cagagtccgg gcgatcctct gagaccctcc  34140
gggcccggac ggtcgccctc agccccccag acagacccca gggtctccag gcagggtccg  34200
```

```
gcatcttcag gggcagcagg ctcaccacca caggcccccc agacccgggt ctcggccagc  34260
cgagccgacc ggccccgcgc ctggcgcctc ctcggggcca gccgccgggg ttggttctgc  34320
ccctctctct gtccttcaga ggaaccaggg acctcgggca ccccagagcc cctcgggccc  34380
gcctccaggc gccctcctgg tctccgctcc cctctgagcc ccgttaaacc caaagaatgt  34440
ctgaggggag ccaccctcgg ggcccaggcc ccagagtcca gaggtcaggg gcacctcagg  34500
gtgcctcccc gggtcccagg ccagccggag ggaccccggc agcccgggcg gccccagagg  34560
ccggttcctc gccccttccc cgggcttcag agcccaggat gtcccccaga agggacccta  34620
ggcgtcccct ctcctcccct ccaggcccga gcctctccct cgcggagagg ggcctctttg  34680
ggccctcaag tccagcccca ccgagacccg agtggcccgg atccccccac cggcccttct  34740
ctctgtcccc ctgctcctct ccaaccttcg ctccacccta gaccccagct tctggcctcc  34800
ccgggtccac caggccagcc ggagggaccc cggcagcccg ggcgagtcgc cttccctctc  34860
ccctggcctc tccttcccgc ctcccacccg agccccctca gcttgcctcc ccaccgggtc  34920
catcaggccg gccggaggga ccccggcggc ccggtgtcag tccccccctgc agccgcccag  34980
tctctgcctc caggcaaggg cgccagcttt tctcccccca gcctgaggcc cagtctcctg  35040
tgcactgtct gtaaagtcca gcctcccacg cccgtccacg gctcccgggc ccagcctcgt  35100
ccacccctcc ccacggtgga caggccctct gtccacccgg gccatccccg ccccccctgtg  35160
tccaccccag tcccgtccag gggggacttt atgtgaccct tgggcctggc tccccataga  35220
ctcccatgta agcctgcctc gagtaggtgc ctccagagcc ccttttgccc ccctggcggc  35280
ccagcccgac ccccgggcgc ccccaaactt tgtccagatg tccaggggtc cccgagggtg  35340
aggcccagcc ccctcccgcc cctgtccact gccccggtcc ccccagaagc ccccaaaagt  35400
agaggctcag gccatgcgcg ccctgtcacc aggcctgcca aagagccaga tctaaggccg  35460
ggagaggcag ccccaaagcg ggtgcagtaa caggtaatct ctggtagtga tttggacccg  35520
aaatctgaca ctttagagct ctggaggact ttaaaactct aaaaatcaaa actttagagg  35580
cgaatgggcg ccattttgtc cccacgcgcg cataatggcg gacctaggcc taaaaccccc  35640
aggaagcggg tctatggttg gctgcgctgc tgctatcttt agaggggaaa agaggaataa  35700
gcccccagac aggggagtgg gcttgtttgt gacttcacca aaggtcaggg cccaaggggg  35760
ttcgcgttgc taggccacct tctcagtcca gcgcgtttac gtaagccaga cagcagccaa  35820
ttgtcagttc tagggagggg gaccactgcc cctggtataa agtggtcctg cagctatttc  35880
tggtcgcatc agagcgccag gagtccacac aaatgtaaga gggggtcttc tacctctccc  35940
tagccctccg ccccctccaa ggactcgggc ccagtttcta acttttcccc ttccctccct  36000
cgtcttgccc tgcgcccggg gccaccttca tcaccgtcgc tgactccgcc atccaagcct  36060
aggggagacc gaagtgaagg ccctggacca acccggcccg ggccccccgg tatcgggcca  36120
gaggtaagtg gactttaatt ttttctgcta agcccaacac tccaccacac ccaggcacac  36180
actacacaca cccacccgtc tcagggtccc ctcggacagc tcctaagaag gcaccggtcg  36240
cccagtccta ccagaggggg ccaagaaccc agacgagtcc gtagaagggt cctcgtccag  36300
caagaagagg aggtggtaag cggttcacct tcaggggtaa gtaacctgac ctctccaggg  36360
ctcacataaa gggaggctta gtatacatgc ttcttgcttt tcacaggaac ctgggggcta  36420
gtctgggtgg gattaggctg cctcaagttg catcagccag ggcttcatgc cctcctcagt  36480
tccctagtcc ccgggcttca ggccccctcc gtccccgtcc tccagagacc cgggcttcag  36540
```

-continued

```
gccctgcctc tcctgttacc cttttagaac cacagcctgg acacatgtgc cagacgcctt  36600
ggcctctaag gccctcgggt cccctggac cccggcctca gcaaccctgc tgctcccctc  36660
ctgccacccc agcctccccc cctccccgtc cccttcgct cctgatcctc ccccggtccc  36720
cagtagggcc gcctgccccc ctgcacccag tacctgcccc tcttggccac gcaccccggg  36780
ccaggccacc ttagacccgg ccaagcccca tccctgaaga cccagcggcc attctctctg  36840
gtaacgagca gagaagaagt agaggcccgc ggccattggg cccagattga gagaccagtc  36900
caggggcccg aggttggagc cagcgggcac ccgaggtccc agcacccggt ccctccgggg  36960
ggcagagaca ggcagggccc cccggcagct ggccccgagg aggcgcccgg agtggggccg  37020
gtcggctggg ctggccgagc ccgggtctgg gaggtctggg gtggcgagcc tgctgtctca  37080
ggaggggcct ggctccgccg ggtggccctg gggtaagtct gggaggcaga gggtcggcct  37140
aggcccgggg aagtggaggg ggatcgcccg ggtctctgtt ggcagagtcc gggcgatcct  37200
ctgagaccct ccgggcccgg acggtcgccc tcagcccccc agacagaccc cagggtctcc  37260
aggcagggtc cggcatcttc aggggcagca ggctcaccac cacaggcccc ccagacccgg  37320
gtctcggcca gccgagccga ccggccccgc gcctggcgcc tcctcggggc cagccgccgg  37380
ggttggttct gcccctctct ctgtccttca gaggaaccag ggacctcggg caccccagag  37440
cccctcgggc ccgcctccag gcgccctcct ggtctccgct cccctctgag ccccgttaaa  37500
cccaaagaat gtctgagggg agccaccctc ggggcccagg ccccagagtc cagaggtcag  37560
gggcacctca gggtgcctcc ccgggtccca ggccagccgg agggaccccg gcagcccggg  37620
cggccccaga ggccggttcc tcgccccttc cccgggcttc agagcccagg atgtccccca  37680
gaagggaccc taggcgtccc ctctcctccc ctccaggccc gagcctctcc ctcgcggaga  37740
ggggcctctt tgggccctca agtccagccc caccgagacc cgagtggccc ggatcccccc  37800
accggccctt ctctctgtcc ccctgctcct ctccaacctt cgctccaccc tagaccccag  37860
cttctggcct ccccgggtcc accaggccag ccggagggac cccggcagcc cgggcgagtc  37920
gccttccctc tcccctggcc tctccttccc gcctcccacc cgagccccct cagcttgcct  37980
ccccaccggg tccatcaggc cggccggagg gaccccggcg gcccggtgtc agtccccccct  38040
gcagccgccc agtctctgcc tccaggcaag ggcgccagct tttctccccc cagcctgagg  38100
cccagtctcc tgtgcactgt ctgtaaagtc cagcctccca cgcccgtcca cggctcccgg  38160
gcccagcctc gtccacccct ccccacggtg gacaggccct ctgtccaccc gggccatccc  38220
cgccccccctg tgtccacccc agtcccgtcc agggggggact ttatgtgacc cttgggcctg  38280
gctccccata gactcccatg taagcctgcc tcgagtaggt gcctccagag cccctttttgc  38340
cccccctggcg gcccagcccg acccccgggc gcccccaaac tttgtccaga tgtccagggg  38400
tccccgaggg tgaggcccag cccccctcccg cccctgtcca ctgccccggt cccccccagaa  38460
gcccccaaaa gtagaggctc aggccatgcg cgccctgtca ccaggcctgc caaagagcca  38520
gatctaaggc cgggagaggc agccccaaag cgggtgcagt aacaggtaat ctctggtagt  38580
gatttggacc cgaaatctga cactttagag ctctggagga ctttaaaact ctaaaaatca  38640
aaactttaga ggcgaatggg cgccattttg tccccacgcg cgcataatgg cggacctagg  38700
cctaaaaccc ccaggaagcg ggtctatggt tggctgcgct gctgctatct ttagagggga  38760
aaagaggaat aagcccccag acaggggagt gggcttgttt gtgacttcac caaaggtcag  38820
ggcccaaggg ggttcgcgtt gctaggccac cttctcagtc cagcgcgttt acgtaagcca  38880
gacagcagcc aattgtcagt tctagggagg gggaccactg cccctggtat aaagtggtcc  38940
```

```
tgcagctatt tctggtcgca tcagagcgcc aggagtccac acaaatgtaa gagggggtct  39000
tctacctctc cctagccctc cgccccctcc aaggactcgg gcccagtttc taacttttcc  39060
ccttccctcc ctcgtcttgc cctgcgcccg gggccacctt catcaccgtc gctgactccg  39120
ccatccaagc ctaggggaga ccgaagtgaa ggccctggac caacccggcc cgggcccccc  39180
ggtatcgggc cagaggtaag tggactttaa ttttttctgc taagcccaac actccaccac  39240
acccaggcac acactacaca cacccacccg tctcagggtc ccctcggaca gctcctaaga  39300
aggcaccggt cgcccagtcc taccagaggg ggccaagaac ccagacgagt ccgtagaagg  39360
gtcctcgtcc agcaagaaga ggaggtggta agcggttcac cttcaggggt aagtaacctg  39420
acctctccag ggctcacata aagggaggct tagtatacat gcttcttgct tttcacagga  39480
acctgggggc tagtctgggt gggattaggc tgcctcaagt tgcatcagcc agggcttcat  39540
gccctcctca gttccctagt ccccgggctt caggcccccct ccgtccccgt cctccagaga  39600
cccgggcttc aggccctgcc tctcctgtta cccttttaga accacagcct ggacacatgt  39660
gccagacgcc ttggcctcta aggccctcgg gtccccctgg accccggcct cagcaaccct  39720
gctgctcccc tcctgccacc ccagcctccc cccctccccg tccccccttcg ctcctgatcc  39780
tcccccggtc cccagtaggg ccgcctgccc ccctgcaccc agtacctgcc cctcttggcc  39840
acgcaccccg ggccaggcca ccttagaccc ggccaagccc catccctgaa gacccagcgg  39900
ccattctctc tggtaacgag cagagaagaa gtagaggccc gcggccattg ggcccagatt  39960
gagagaccag tccaggggcc cgaggttgga gccagcgggc acccgaggtc ccagcacccg  40020
gtccctccgg ggggcagaga caggcagggc cccccggcag ctggccccga ggaggcgccc  40080
ggagtggggc cggtcggctg ggctggccga gcccgggtct gggaggtctg gggtggcgag  40140
cctgctgtct caggaggggc ctggctccgc cgggtggccc tggggtaagt ctgggaggca  40200
gagggtcggc ctaggcccgg ggaagtggag ggggatcgcc cgggtctctg ttggcagagt  40260
ccgggcgatc ctctgagacc ctccgggccc ggacggtcgc cctcagcccc ccagacagac  40320
cccagggtct ccaggcaggg tccggcatct tcaggggcag caggctcacc accacaggcc  40380
ccccagaccc gggtctcggc cagccgagcc gaccggcccc gcgcctggcg cctcctcggg  40440
gccagccgcc ggggttggtt ctgcccctct ctctgtcctt cagaggaacc agggacctcg  40500
ggcaccccag agcccctcgg gcccgcctcc aggcgccctc ctggtctccg ctcccctctg  40560
agccccgtta aacccaaaga atgtctgagg ggagccaccc tcggggccca ggccccagag  40620
tccagaggtc aggggcacct cagggtgcct ccccgggtcc caggccagcc ggagggaccc  40680
cggcagcccg ggcggcccca gaggccggtt cctcgcccct tccccgggct tcagagccca  40740
ggatgtcccc cagaagggac cctaggcgtc ccctctcctc ccctccaggc ccgagcctct  40800
ccctcgcgga gaggggcctc tttgggccct caagtccagc cccaccgaga cccgagtggc  40860
ccggatcccc ccaccggccc ttctctctgt cccccctgctc ctctccaacc ttcgctccac  40920
cctagacccc agcttctggc ctccccgggt ccaccaggcc agccggaggg accccggcag  40980
cccgggcgag tcgccttccc tctcccctgg cctctccttc ccgcctccca cccgagcccc  41040
ctcagcttgc ctccccaccg ggtccatcag gccggccgga gggaccccgg cggcccggtg  41100
tcagtccccc ctgcagccgc ccagtctctg cctccaggca agggcgccag cttttctccc  41160
cccagcctga ggcccagtct cctgtgcact gtctgtaaag tccagcctcc cacgcccgtc  41220
cacggctccc gggcccagcc tcgtccaccc ctccccacgg tggacaggcc ctctgtccac  41280
```

-continued

```
ccgggccatc cccgcccccc tgtgtccacc ccagtcccgt ccagggggga ctttatgtga  41340
cccttgggcc tggctcccca tagactccca tgtaagcctg cctcgagtag gtgcctccag  41400
agcccctttt gcccccctgg cggcccagcc cgacccccgg gcgcccccaa actttgtcca  41460
gatgtccagg ggtccccgag ggtgaggccc agccccctcc cgcccctgtc cactgccccg  41520
gtccccccag aagcccccaa aagtagaggc tcaggccatg cgcgccctgt caccaggcct  41580
gccaaagagc cagatctaag gccgggagag gcagccccaa agcgggtgca gtaacaggta  41640
atctctggta gtgatttgga cccgaaatct gacactttag agctctggag gactttaaaa  41700
ctctaaaaat caaaacttta gaggcgaatg ggcgccattt tgtccccacg cgcgcataat  41760
ggcggaccta ggcctaaaac ccccaggaag cgggtctatg gttggctgcg ctgctgctat  41820
ctttagaggg gaaaagagga ataagccccc agacagggga gtgggcttgt ttgtgacttc  41880
accaaaggtc agggcccaag gggggttcgcg ttgctaggcc accttctcag tccagcgcgt  41940
ttacgtaagc cagacagcag ccaattgtca gttctaggga gggggaccac tgcccctggt  42000
ataaagtggt cctgcagcta tttctggtcg catcagagcg ccaggagtcc acacaaatgt  42060
aagagggggt cttctacctc tccctagccc tccgccccct ccaaggactc gggcccagtt  42120
tctaactttt ccccttccct ccctcgtctt gccctgcgcc cggggccacc ttcatcaccg  42180
tcgctgactc cgccatccaa gcctagggga gaccgaagtg aaggccctgg accaacccgg  42240
cccgggcccc ccggtatcgg gccagaggta agtggacttt aattttttct gctaagccca  42300
acactccacc acacccaggc acacactaca cacacccacc cgtctcaggg tcccctcgga  42360
cagctcctaa gaaggcaccg gtcgcccagt cctaccagag gggggccaaga acccagacga  42420
gtccgtagaa gggtcctcgt ccagcaagaa gaggaggtgg taagcggttc accttcaggg  42480
gtaagtaacc tgacctctcc agggctcaca taaagggagg cttagtatac atgcttcttg  42540
cttttcacag gaacctgggg gctagtctgg gtgggattag gctgcctcaa gttgcatcag  42600
ccagggcttc atgccctcct cagttcccta gtccccgggc ttcaggcccc ctccgtcccc  42660
gtcctccaga gacccgggct tcaggccctg cctctcctgt taccctttta gaaccacagc  42720
ctggacacat gtgccagacg ccttggcctc taaggccctc gggtccccct ggaccccggc  42780
ctcagcaacc ctgctgctcc cctcctgcca ccccagcctc ccccccctccc cgtccccctt  42840
cgctcctgat cctcccccgg tccccagtag ggccgcctgc ccccctgcac ccagtacctg  42900
cccctcttgg ccacgcaccc cgggccaggc caccttagac ccggccaagc cccatccctg  42960
aagacccagc ggccattctc tctggtaacg agcagagaag aagtagaggc ccgcggccat  43020
tgggcccaga ttgagagacc agtccagggg cccgaggttg gagccagcgg gcacccgagg  43080
tcccagcacc cggtccctcc ggggggcaga gacaggcagg gccccccggc agctggcccc  43140
gaggaggcgc ccggagtggg gccggtcggc tgggctggcc gagcccgggt ctgggaggtc  43200
tggggtggcg agcctgctgt ctcaggaggg gcctggctcc gccgggtggc cctggggtaa  43260
gtctgggagg cagagggtcg gcctaggccc ggggaagtgg agggggatcg cccgggtctc  43320
tgttggcaga gtccgggcga tcctctgaga ccctccgggc ccggacggtc gccctcagcc  43380
ccccagacag accccagggt ctccaggcag ggtccggcat cttcaggggc agcaggctca  43440
ccaccacagg ccccccagac ccgggtctcg gccagccgag ccgaccggcc ccgcgcctgg  43500
cgcctcctcg gggccagccg ccggggttgg ttctgcccct ctctctgtcc ttcagaggaa  43560
ccagggacct cgggcacccc agagcccctc gggcccgcct ccaggcgccc tcctggtctc  43620
cgctcccctc tgagccccgt taaacccaaa gaatgtctga ggggagccac cctcggggcc  43680
```

-continued

```
caggccccag agtccagagg tcaggggcac ctcagggtgc ctccccgggt cccaggccag  43740
ccggagggac cccggcagcc cgggcggccc cagaggccgg ttcctcgccc cttccccggg  43800
cttcagagcc caggatgtcc cccagaaggg accctaggcg tcccctctcc tcccctccag  43860
gcccgagcct ctccctcgcg gagaggggcc tctttgggcc ctcaagtcca gccccaccga  43920
gacccgagtg gcccggatcc ccccaccggc ccttctctct gtccccctgc tcctctccaa  43980
ccttcgctcc accctagacc ccagcttctg gcctccccgg gtccaccagg ccagccggag  44040
ggaccccggc agcccgggcg agtcgccttc cctctcccct ggcctctcct tcccgcctcc  44100
cacccgagcc ccctcagctt gcctccccac cgggtccatc aggccggccg gagggacccc  44160
ggcggcccgg tgtcagtccc ccctgcagcc gcccagtctc tgcctccagg caagggcgcc  44220
agcttttctc cccccagcct gaggcccagt ctcctgtgca ctgtctgtaa agtccagcct  44280
cccacgcccg tccacggctc ccgggcccag cctcgtccac ccctccccac ggtggacagg  44340
ccctctgtcc acccgggcca tccccgcccc cctgtgtcca ccccagtccc gtccaggggg  44400
gactttatgt gacccttggg cctggctccc catagactcc catgtaagcc tgcctcgagt  44460
aggtgcctcc agagcccctt ttgcccccct ggcggcccag cccgaccccc gggcgccccc  44520
aaactttgtc cagatgtcca ggggtccccg agggtgaggc ccagccccct cccgcccctg  44580
tccactgccc cggtcccccc agaagccccc aaaagtagag gctcaggcca tgcgcgccct  44640
gtcaccaggc ctgccaaaga gccagatcta aggccgggag aggcagcccc aaagcgggtg  44700
cagtaacagg taatctctgg tagtgatttg gacccgaaat ctgacacttt agagctctgg  44760
aggactttaa aactctaaaa atcaaaactt tagaggcgaa tgggcgccat tttgtcccca  44820
cgcgcgcata atggcggacc taggcctaaa acccccagga agcgggtcta tggttggctg  44880
cgctgctgct atctttagag gggaaaagag gaataagccc ccagacaggg gagtgggctt  44940
gtttgtgact tcaccaaagg tcagggccca agggggttcg cgttgctagg ccaccttctc  45000
agtccagcgc gtttacgtaa gccagacagc agccaattgt cagttctagg gagggggacc  45060
actgcccctg gtataaagtg gtcctgcagc tatttctggt cgcatcagag cgccaggagt  45120
ccacacaaat gtaagagggg gtcttctacc tctccctagc cctccgcccc ctccaaggac  45180
tcgggcccag tttctaactt ttccccttcc ctccctcgtc ttgccctgcg cccggggcca  45240
ccttcatcac cgtcgctgac tccgccatcc aagcctaggg gagaccgaag tgaaggccct  45300
ggaccaaccc ggcccgggcc ccccggtatc gggccagagg taagtggact ttaatttttt  45360
ctgctaagcc caacactcca ccacacccag gcacacacta cacacaccca cccgtctcag  45420
ggtcccctcg gacagctcct aagaaggcac cggtcgccca gtcctaccag agggggccaa  45480
gaacccagac gagtccgtag aagggtcctc gtccagcaag aagaggaggt ggtaagcggt  45540
tcaccttcag ggtaagtaa cctgacctct ccagggctca cataaaggga ggcttagtat  45600
acatgcttct tgcttttcac aggaacctgg gggctagtct gggtgggatt aggctgcctc  45660
aagttgcatc agccagggct tcatgccctc ctcagttccc tagtccccgg gcttcaggcc  45720
ccctccgtcc ccgtcctcca gagacccggg cttcaggccc tgcctctcct gttacccttt  45780
tagaaccaca gcctggacac atgtgccaga cgccttggcc tctaaggccc tcgggtcccc  45840
ctggaccccg gcctcagcaa ccctgctgct cccctcctgc caccccagcc tccccccctc  45900
cccgtccccc ttcgctcctg atcctccccc ggtccccagt agggccgcct gcccccctgc  45960
acccagtacc tgcccctctt ggccacgcac cccgggccag gccaccttag acccggccaa  46020
```

-continued

```
gccccatccc tgaagaccca gcggccattc tctctggtaa cgagcagaga agaagtagag  46080
gcccgcggcc attgggccca gattgagaga ccagtccagg ggcccgaggt tggagccagc  46140
gggcacccga ggtcccagca cccggtccct ccggggggca gagacaggca gggccccccg  46200
gcagctggcc ccgaggaggc gcccggagtg gggccggtcg gctgggctgg ccgagcccgg  46260
gtctgggagg tctggggtgg cgagcctgct gtctcaggag gggcctggct ccgccgggtg  46320
gccctggggt aagtctggga ggcagagggt cggcctaggc ccggggaagt ggagggggat  46380
cgcccgggtc tctgttggca gagtccgggc gatcctctga gaccctccgg gcccggacgg  46440
tcgccctcag ccccccagac agaccccagg gtctccaggc agggtccggc atcttcaggg  46500
gcagcaggct caccaccaca ggccccccag acccgggtct cggccagccg agccgaccgg  46560
ccccgcgcct ggcgcctcct cggggccagc cgccggggtt ggttctgccc ctctctctgt  46620
ccttcagagg aaccagggac ctcgggcacc ccagagcccc tcgggcccgc ctccaggcgc  46680
cctcctggtc tccgctcccc tctgagcccc gttaaaccca aagaatgtct gaggggagcc  46740
accctcgggg cccaggcccc agagtccaga ggtcaggggc acctcagggt gcctccccgg  46800
gtcccaggcc agccggaggg accccggcag cccgggcggc cccagaggcc ggttcctcgc  46860
cccttccccg ggcttcagag cccaggatgt cccccagaag ggaccctagg cgtcccctct  46920
cctcccctcc aggcccgagc ctctccctcg cggagagggg cctctttggg ccctcaagtc  46980
cagccccacc gagacccgag tggcccggat ccccccaccg gcccttctct ctgtccccct  47040
gctcctctcc aaccttcgct ccaccctaga ccccagcttc tggcctcccc gggtccacca  47100
ggccagccgg agggaccccg gcagcccggg cgagtcgcct tccctctccc ctggcctctc  47160
cttcccgcct cccacccgag ccccctcagc ttgcctcccc accgggtcca tcaggccggc  47220
cggagggacc ccggcggccc ggtgtcagtc ccccctgcag ccgcccagtc tctgcctcca  47280
ggcaagggcg ccagcttttc tccccccagc ctgaggccca gtctcctgtg cactgtctgt  47340
aaagtccagc ctcccacgcc cgtccacggc tcccgggccc agcctcgtcc acccctcccc  47400
acggtggaca ggccctctgt ccacccgggc catccccgcc cccctgtgtc caccccagtc  47460
ccgtccaggg gggactttat gtgacccttg ggcctggctc cccatagact cccatgtaag  47520
cctgcctcga gtaggtgcct ccagagcccc ttttgccccc ctggcggccc agcccgaccc  47580
ccgggcgccc ccaaactttg tccagatgtc caggggtccc cgagggtgag gcccagcccc  47640
ctctcgccca agctgctttg attcctggga tatttttggg aatggtgtta actttctccc  47700
cttgtatttg ctattcaatc aacctgattc cccctgctca tacctccact tacaaccaag  47760
ccactacggc cacgtccccg gcctcccgct cgggtaagtg ctttttcatt tttagcccca  47820
gcccctcctc tataagttct aggcaaacct ccaatcacca gccaccttcc aatgtagtct  47880
cttagagagt ggctgctacg cattagagac cactttgagc cacccacagt aaccacccag  47940
cgccaatctg tctacataga agaagaagag gatgaagact aagtcacagg cttagccagg  48000
tgatttgtga atttcagttt atttactttc ttccaatcaa gctttcccag cctccgcttg  48060
ttaggtccta gttatgggtt ttccatgggg gacttagtat ccgttctatt agattaacgt  48120
gcaagacgct aaacttaacc aaggtcagcc aagggacgcg tgttatccca ggctgcccac  48180
cctgaggatt tccccccaaa atcctcctac cctctcttta tgccatgtgt gttgttggct  48240
tgtgttagtg ctatgtaatg cgttgccgcc aggtggcagc ctgtttatag atgtgcagta  48300
ccccttaatg ttaggtctgc tttagggctg ccaggtggcg caatctagga ttaattcacc  48360
tgtatccctt tccctccacc cgcagtaacc cagcactggc gtgtgacgtg gtgtaaagtt  48420
```

-continued

```
ttgcctgaac ctgtggttgg gcaggtacat gccaacaacc ttctaagcac ccgcgcttgt  48480
gttttgcttt atctgccgcc atcatgccta cattctatct tgcgttacat gggggacaaa  48540
catatcatct aattgttgac acggatagtc ttggaaaccc gtcactctca gtaattccct  48600
cgaatcccta ccaggaacaa ctgtcagaca ctccattaat tccactaaca atctttgttg  48660
gggaaaacac gggggtgccc ccaccactcc caccaccccc cccaccacca cccccaccac  48720
ccccaccacc cccaccaccc ccaccacccc caccacctcc accaccttca ccaccacccc  48780
cgcccccacc acccccacca cctcagcgca gggatgcctg gacacaagag ccatcacctc  48840
ttgataggga tccgctagga tatgacgtcg ggcatggacc tctagcatct gctatgcgaa  48900
tgctttggat ggctaattat attgtaagac aatcacgggg tgaccggggc cttattttgc  48960
cacaaggccc acaaacagcc cctcaggcca ggttggtcca gccacatgtc ccccctctac  49020
gcccgacagc acccaccatt ttgtcacctc tgtcacaacc gaggcttacc cctccacaac  49080
cactcatgat gccaccaagg cctacccctc ctacccctct gccacctgca acactaacgg  49140
tgccaccaag gcctacccgt cctaccactc tgccacccac accactactc acggtactac  49200
aaaggcctac cgaacttcaa cccacaccat caccaccacg catgcatctc cctgtcttgc  49260
atgtgccaga ccaatcaatg caccctctta ctcatcaaag caccccaaat gatccagata  49320
gtccagaacc acggtccccg actgtatttt ataacattcc acctatgcca ttacccccct  49380
cacaattgcc accaccagca gcaccagcac agccacctcc aggggtcatc aacgaccaac  49440
aattacatca tctaccctcg gggccaccat ggtggccacc catctgcgac cccccgcaac  49500
cctctaagac tcaaggccag agccggggac agagcagggg gaggggcagg ggcaggggca  49560
ggggcagggg caagggcaag tccagggaca agcaacgcaa gcccggtgga ccttggagac  49620
cagagccaaa cacctccagt cctagcatgc ctgaactaag tccagtcctc ggtcttcatc  49680
agggacaagg ggctggggac tcaccaactc ctggcccatc caatgccgcc cccgtttgta  49740
gaaattcaca cacggcaacc cctaacgttt caccaataca tgaaccggag tcccataata  49800
gcccagaggc tcccattctc ttccccgatg attggtatcc tccatctata gaccccgcag  49860
acttagacga aagttgggat tacatttttg agacaacaga atctcctagc tcagatgaag  49920
attatgtgga gggacccagt aaaagacctc gcccctccat ccagtaaaaa cccttgccct  49980
ctccagcaac caatgtatcc caaataaatg ttacttcttt tgctcttaac cattgacacg  50040
cctgtcattc tatcaattaa acaagggaaa aaggtttagc tattccacca acacgacccc  50100
aaggaaggct tgccaaaatt ggtgccttgc tctcagcact ttgccagcaa cttatagcat  50160
ggtaggcagc tcaactcggc ccgtcttact gcccagccta ctctccactc ccagtccatg  50220
ttcgcactcc tatgcatttc ctgccctccc acttttaccc cagtcccaac ccaaaaccac  50280
acacaacaca tagaattgtt agtttaaaca gtttattgat aggtggctgc ttttagccta  50340
attgtgtatt gctctcgttg ccaaaacctg ttgtaagggc cggcacccgc aacatgggga  50400
aaacataacc gccgccatcc catggggagg gtagaggcgg ttgacatgta ggtgagtagt  50460
gtaagaagca tggcgaagta gacaggttac ttttagagtg tagtgtacag ggccgggcgc  50520
aacagtgcca ccaacccggg gtctgagcat tccatgggca gcagggacac tgcactaccg  50580
ccaggtcctg ggcagccgg ggttcctggc gctccggggg cagccgggcg gccgccggtg  50640
ggtccgctgg gccgctgccc cgctccgggt ggggggtggc cccgctgggc accgctgcgc  50700
cgccgccagg tcctggggca gccggggttc ctggcgctcc gggggcagcc gggcggccgc  50760
```

-continued

```
cggtgggtcc gctgggccgc tgccccgctc cgggtggggg gtggccccgc tgggcaccgc  50820
tgcgccgccg ccaggtcctg gggcagccgg ggttcctggc gctccggggg cagccgggcg  50880
gccgccggtg ggtccgctgg gccgctgccc cgctccgggt ggggggtggc cccgctgggc  50940
accgctgcgc cgccgccagg tcctggggca gccggggttc ctggcgctcc gggggcagcc  51000
gggcggccgc cggtgggtcc gctgggccgc tgccccgctc cgggtggggg gtggccccgc  51060
tgggcaccgc tgcgccgccg ccaggtcctg gggcagccgg ggttcctggc gctccggggg  51120
cagccgggcg gccgccggtg ggtccgctgg gccgctgccc cgctccgggt ggggggtggc  51180
cccgctgggc accgctgcgc cgccgccagg tcctggggca gccggggttc ctggcgctcc  51240
gggggcagcc gggcggccgc cggtgggtcc gctgggccgc tgccccgctc cgggtggggg  51300
gtggccccgc tgggcaccgc tgcgccgccg ccaggtcctg gggcagccgg ggttcctggc  51360
gctccggggg cagccgggcg gccgccggtg ggtccgctgg gccgctgccc cgctccgggt  51420
ggggggtggc cccgctgggc accgctgcgc cgccgccagg tcctggggca gccggggttc  51480
ctggcgctcc gggggcagcc gggcggccgc cggtgggtcc gctgggccgc tgccccgctc  51540
cgggtggggg gtggccccgc tgggcaccgc tgcgccgccg ccaggtcctg gggcagccgg  51600
ggttcctggc gctccggggg cagccgggcg gccgccggtg ggtccgctgg gccgctgccc  51660
cgctccgggt ggggggtggc cccgctgggc accgctgcgc cgccgccagg tcctggggca  51720
gccggggttc ctggcgctcc gggggcagcc gggcggccgc cggtgggtcc gctgggccgc  51780
tgccccgctc cgggtggggg gtggccccgc tgggcaccgc tgcgccgccg ccaggtcctg  51840
gggcagccgg ggttcctggc gctccggggg cagccgggcg gccgccggtg ggtccgctgg  51900
gccgctgccc cgctccgggt ggggggtggc cccgctgggc accgctgcgc cgccgccagg  51960
tcctggggca gccggggttc ctggcgctcc gggggcagcc gggcggccgc cggtgggtcc  52020
gctgggccgc tgccccgctc cgggtggggg gtggccccgc tgggcaccgc tgcgccgccg  52080
ccaggtcctg gggcagccgg ggttcctggc gctccactgc acctggaatg cagggtgggg  52140
gcgtggtccc ctggacccca gccccgccga tccctccccc agggcgtacc cggcttgcct  52200
ggttctgggg ctcctctggg ggtcgctgca tccgccggta gggttcgaat gggcgtggtc  52260
cgcttgctct gctggcccgg tacgcctgga ttgccggctg gggctgggg tcccgggacg  52320
cccctccct gctcccaccc ggttccctcc cccagggcgt gccccgcttg cctggtcctg  52380
gagctcatcc ggggatgctg catccgctag tccgacctgg gtgggtgcgg tccgctggcc  52440
ccaccctggg ggtagccgcc gggtctgctg gtccggtgca cctggaaggc aggggggggg  52500
gcagtgaggg aggggcgtgg tcctgggacc ccgcgccgac tggcaggggg tccccatggc  52560
acaggcctag gggtccaggg ggcagccgcg gcccagcgcg ccccgttcac gggggaggac  52620
cgcggccgag ccaccagggg cccggcgggg gtggggggtg cgctcccagg ccggaccctg  52680
gtgccaggca gggaccccgc gccacccgct tcatgggggg ggaggccgcc gcaaggacgc  52740
cgggccggct gggaggtgtg cacccccga gcgtctggac gacgctggcg agccgggccg  52800
gctcgccttc ttttatcctc tttttggggt ctctgtgtaa tactttaagg tttgctcagg  52860
agtgggggct tcttattggt taattcaggt gtgtcatttt agcccgttgg gtttcattaa  52920
ggtgtgtcac caggtgggtg gtacctggag gttattctat tgggataacg agaggaggag  52980
gggctagagg tccgcgagat ttggggtagg cggagcctca ggagggtccc ctccataggg  53040
ttgaaccagg agggggagga ttgggctccg ccccgatata cctagtgggt ggagcctaga  53100
ggtaggtatc catagggttc cattatcctg gaggtatcct aagctccgcc cctatatacc  53160
```

-continued

```
aggtgggtgg agctaggtag gattcagcta ggttcctact ggggtacccc cctaccctac  53220
cttaaggtgc gccacccttc ctccttccgt tttaatggta gaataaccta taggttatta  53280
acctagtggt ggaatagggt attgcagctg ggtatatacc tataggtata tagaacctag  53340
aggaagggaa ccctatagtg taatccctcc ccccctacc cccccctccc ttacggttgc  53400
ctgagcccat cccccacccc agcaccccgg ggtgacgtgg caccccgcgt gccttactga  53460
cttgtcacct ttgcacattt ggtcagctga ccgatgctcg ccacttcctg ggtcatgacc  53520
tggcctgtgc cttgtcccgt ggacaatgtc cctccagcgt ggtggctgcc tttgggatgc  53580
atcactttga gccactaagc ccccgttgct cgccttgcct gcctcaccat gacacactaa  53640
gcccctgcta atccatgagc cccgccttta ggaagcacca cgtcccgggg acggaagggg  53700
acttggggtg attttctatg tgggggtgga aatatgagca agaataagga cggctcctta  53760
ttaacctgat cagccccgga gttgcctgtt tcatcactaa ccccgggcct gaagaggttg  53820
acaagaaggg tcaaggtttc gtctgtgtgt tgaagggcag gggctgttgg gtgcatctgg  53880
aacggcttac ctcgggtaac tgtttgccat taaaaggttg gggattaggt ttagcccctt  53940
tagctgccat ttcgaaccgg ggtgtgcaga tgcaggtctc cgggtgggca ggcagtacga  54000
gatgtcacgt tgtgttgtct ttcctcccac ccctgtcctg gctgtggcaa atgcgaccct  54060
catagagttg tgtttcaggt ctgtgtcctg ttttgcggtg ggttatttct tccctcagtg  54120
tttgccagct tatttcccca gttttcacgt actggggcct gtggacacct gagggagcgg  54180
ccgttggtgg gtatgtgttg gaattgctcc caccctcaat tttcgcttgc cttcttccct  54240
tgttaacctg atagcatagc ctctaggttt ccttgtaggt ctgtttgggt ttgttggttc  54300
acgtggtgct aacttgaatt ttttggtttt ctagttccct cttaattaca tttgtgccag  54360
atcttgtaga gcaagatggc ctattcaaca agggagatac tgttagccct gtgtatacgg  54420
gacagtcgtg tgcatggaaa tggtaccctg catcctgtgt tggagctagc agcaagagaa  54480
acacctctcc gcctttcgcc agaggacact gtagttctgc gttatcatgt gttgcttgag  54540
gagataattg aacgaaattc agagacattt acagaaactt ggaacagatt tataacacac  54600
accgaacatg tggatctgga ttttaactca gtatttttag agatatttca ccgtggagac  54660
ccaagccttg ggcgcgcgtt ggcctggatg gcctggtgca tgcatgcctg caggacattg  54720
tgttgtaacc agtctactcc ttactatgtt gtggacctgt cagttcgtgg gatgttagaa  54780
gccagcgaag gcctggatgg ttggattcat caacagggcg gctggtctac attaattgaa  54840
gacaacattc ctggatccag aaggtttagc tggactttgt ttcttgctgg actgactttg  54900
agtctgttag ttatatgtag ttatttattt atctccagag gaagacacta atctatacat  54960
tttctcagca ctttatatga atcagggtca ttgggcctgc ggggaactga gccagtagga  55020
tattaggcaa gggtgacaca gtgcccatgc attataattt aaccaaacag tggtcgtgag  55080
ttttaggccg gccatggggg cttacaagaa taacatgcca atgacccggc ccccactttt  55140
aaattctgtt gcagcagata gctgataccc aatgttatct tttgcggcag aaattgaaag  55200
tgctggccat atctacaatt gggtgtccta ggtgggatat acgcctgtgg tgttctaacg  55260
ggaagtgtgt aagcacacac gtaatttgca agcggtgctt cacgctcttc gttaaaataa  55320
cacaaggaca agatactaaa gaaataactg aggtgagtgt gggaagatgg gaatactatg  55380
tgttatgtta acgggtgaga gcctatactg cagcccagac tcgggggag gaggaaatgg  55440
taagagttat actctactta tcttttttga cactacattt aactgttatg taacaatgtt  55500
```

-continued

```
tgcttatttt catgttcaat aaacgctatg ttaatgatga agaacctgtg ttctttggaa 55560
gtgggcccaa tggggtagta ggttttggga gggtgccgtg ctagatattt caactgccac 55620
agaccccatt ttgtcccacc tgttaccaca ttctaggtcc tgcatccagt gggccaggtg 55680
tctcaccatg gctctttcta ggtggatacc acagtccagg cccccaaggc taccgtgcta 55740
attacctcct catgtccacc cccaccctgt gttactgtcg cctgattatc ctggcttagc 55800
agcctccaag ttttacaaga cgtcccattg ccctgccctt ggtccaagtc tcgccggttt 55860
tcagcagcct gttgtagcct gcccccaagt ttcgcaggtt tcccccatgc ttccacccgt 55920
taacccaata gcatgacagc caatccaaca cgaggcaagt tttaagagtt aaaagcaact 55980
actgtttatt ttccaaaatg agctgggtat agttgatgat ctgtaggcgc agctcatccc 56040
cacattccag gtccttgatg gcctcgtaga tggcatcttc gtcgacattg acagccttct 56100
catataccgt gtctctgggg ctgaccttta tacagaaggc gtcccctact aggtccacgg 56160
ccagctcgta ggtggggcct atgttttcac ataacagttt caagcaggtc tctgggatgt 56220
gaagggaggt gccctggagc aggagatgca tgattaggcg cccttttcca tttgtgctga 56280
agatggggca gatggtgcca caaaagtgtc cggtgaccag gtaagcgtag agaaggctgg 56340
gttgggaaag tccagccttt actgcactgg gagagctgct gagcagagac acatagaagg 56400
tcttgttggg tattatcttg tggacattgt tgaagaagga gagctgggtg gagctaaact 56460
cctgaggcac atgaacctgg gacctattga tgcagatctc gcagtgagac cccagagtca 56520
ggctgtggcc gaagggagac aggcgaaggc agcgcccggg ggagagagtg cacagtgaca 56580
gtgggagaaa cacggcctct gagacatgta tgggggtgtt catctcacgc agaaaatctt 56640
tgcccagctc aaagttggca gagattcccc tgaagaagtc ccgtagtgaa aaatgggatc 56700
tgtctacacc atgtctggtg tgccgggaac atattgatcg ggccacactg ccaacccttt 56760
ccattcttcc cagctctgag cgagattttc cacacctgga caccgacttc acgctatgcg 56820
ccgaggcctt tgaggccgtg tagtttctgt ggtgcggatg cattaggcgg cgcaatgcgg 56880
gatctgccgg tcgctgttgg cgtgcattca cggcatctgg ggtgaccggg gccatcgggt 56940
ttacttttca cacgtagacc tgggaagttt gataggactg taccaggtca aggccgtgga 57000
tgcgcaggac cacgtccagt tccttagtga catccacgag gattgttttg cccactctgg 57060
ccacttgtgt ggatttaaat atgtacacaa gcgtaattaa cgagtcacag accccctgtt 57120
ccagattctg accggctgca agcgctgcct taaaggcctg gaagctgggt gggtaaatct 57180
gaccaaacag cacgctcgga ttcgtgatgc tgtggttgat ggcacacagg gggtcgcaga 57240
acaggtgctt gtggaagtct tgcggggtgc acatctgcag ccaggccctt agcctggggc 57300
atggcacatc cagcagcgtg ttttgggtct tgatgaggaa cacgatcctg tctaggattt 57360
tgatgttgtt gccgaacgag tcaagaatca ggctcttgaa gcggtcaagg gtgtccttgg 57420
cgtccgggtg ggccccgagg ctctcgcaga gtgggcagat ggtccgtgag gcattcttgt 57480
gccttagtcc aaacatgggg gccaggaggc aggggccctg cgaatggtcg ccagcctccg 57540
gtctggtgat ggccagggcc aactccgcca gctcatcgcc gctgtattcc gcgtttaaac 57600
cgatagcatg gtggcctggc cccccgagca ggtccgtccc ctgccacgta cctaatagta 57660
gtccacagta gtcggccttg gttgtaattt caggagagag tcctcccttt tcggccctga 57720
gaaatggatg ctgaactcgg tttctggtag gcaggtggca gcacagggcg gtgtacaggc 57780
ccctgccgac gtcccctggg acatcctggg aatctttgca ggttctgggt ccagggaggg 57840
taagaaaagt gggggtggtt ctgggccaca tggacttgaa gcagaagttg gccggggact 57900
```

-continued

```
ggccggtgag gatggatttc agaaactcca atttgtagta gccgaggttg gcatttctaa 57960
tcatgtcaga agaggacaca gggaggaagc accggcaaat gtaaaagtga agctggatgt 58020
caatggcaag aatcctggag ggcatgaaga gggaatccaa ccccccggcc atggggaagt 58080
attttatcag gatgtgtaaa aagtccatgc ctgtgatgag gctagagatc caggctcgtg 58140
gggcatttag acagtagtag cagagcaggg catagtcctc aaagaaggcc acgggggcat 58200
ctgagtgatt gaccagggtg tcgagcagat cacaaactcg gcaggtgctg gctggagaga 58260
gggactcgta ggtgtggacg agtggtgggt aggctatgcc ttcttccgcg ttggctggaa 58320
gataggagtg ggccatcaaa aggccgactg cctcgaactg gcttttcaga ttgtccacgg 58380
tccagggcac aaagtcctcc atctttggag ttctgcccgc gatctgtgcc acctctgtta 58440
cgccactcct cgtgaggggg cagctggaca gtctttttcc ggtcaggggg tttggctcgt 58500
ttgcgctcgt gactttgtga gccatgacac atctgggtgg caaggtgagg tcttctgggt 58560
ttttaatacc ggggtcggca ccagtttctg ggacaccgcc acaaggacaa ggtgggctag 58620
caagttctcg agtctacgaa gactccgggg gcagtctttt gagtttctcg cctatgatcc 58680
accccaatct cgccccccta attgcgccat ctgcctacgc gaggctgaac ctcctgaatc 58740
actgcatctt tcttgaggcg tttaaagaag agaatagtgg ccagggcctc ggtggggtcc 58800
agcgtgaggt cttatttttg aaaagggata ttataaaaca ggtcattgct cggattgtgg 58860
cagccgatag caccctagat ctagtgaatc atggcgagcc cggaagagag gctcctagac 58920
gagctcaata acgtaattgt gtcatttctg tgtgactctg ggtctctgga agtggagaga 58980
tgctccgggg cgcatgtgtt ctccaggggc agctcccaac ccctctgcac cgtgaagctg 59040
cgccacggac agatttacca cctggagttt gtctacaagt tcctggcctt taagctgaag 59100
aactgcaact acccctcctc gcccgtgttt gtgatatcca acaacggcct ggccaccacc 59160
ctgaggtgct ttttgcacga gccgtcgggt ctcagatcgg gccagagcgg cccttgcctg 59220
ggtctctcaa cggatgttga cctaccaaag aactccatca ttatgctggg ccaggatgac 59280
ttcattaagt tcaaaagccc cctggtcttc cctgctgagc ttgatctcct gaaatctatg 59340
gtggtctgcc gggcctacat cacggaacac cggacgacga tgcagtttct ggtgtttcag 59400
gccgccaacg cccagaaggc ctcgcgggtc atggatatga ttagtgatat gtctcagcaa 59460
ctgtctcggt ctggtcaagt cgaggatacg ggcgccagag tcacaggtgg aggaggtccc 59520
aggcctggcg tcacgcactc ggggtgtctt ggggactcac acgttagggg gcgcggtggt 59580
tgggacttgg ataacttttc agaagctgag accgaagacg aggcgagtta cgctccttgg 59640
agggacaaag actcgtggtc ggaatccgag gcggcgccgt ggaagaagga actcgtgagg 59700
caccccatcc gcaggcaccg gacacgcgag actcgccgta tgcgcgggag ccattcacgg 59760
gtggaacacg tgcccccega gacccgggag acggtggtgg ggggagcatg gcgttattct 59820
tggcgcgcca caccttatct ggcacgggtg ctggctgtca cggccgtggc cctgctcctg 59880
atgtttctga ggtggacctg acgttgcagg cccttgggga gcgggggttc tccaggctcc 59940
tggatctggg gctggcctgc ctggatctga gctatgtgga aatgagggaa tttgtggttt 60000
ggggcaggcc cccagcttct gaggcggctg tggcctctac gccaggctcg cttttccgaa 60060
gccactcgtc cgcctactgg ttgtcggagg tggagaggcc cgggggcctt gtccgctggg 60120
ccaggtcaca gaccagcccc tcatccctga ccctcgcgcc ccatcttggc ccgtccctct 60180
tgtccctttc agtggtcacc ggtggtgggt gtggagccgt ggccttttgc aacgcctttt 60240
```

-continued

```
tcctagctta ttttttggtt gtgcggtctg ttttccccgc gttttccgat agaatagctg  60300
cctggatctg cgaccggtcc cctttctgcg aaaacacccg ggccgtggcc aggggttacc  60360
gaggcctcgt gaagaggttc ttggcattcg tgtttgagcg tagtagctat gacccccccct  60420
tgttgaggca aaactctagg cctgtggagc gctgctttgc catcaagaat tatgtcccgg  60480
gcctggactc acaaagctgt gtgacggtcc cgagcttctc ccgctgggcc cagtctcacg  60540
ccagcgagct cgatccccgg gagattcgcg acagagttac accagcgact gcaccttcgt  60600
tcgtggctga tcatgcctcg gctctattgg cctccctcca gaagaaggcc tccgacaccc  60660
cctgtgggaa tcccattcag tggatgtggt accgcctgtt ggtaaactcg tgcctgagga  60720
gtgcccactg tcttctgcct atacctgccg tctctgaggg ggggagaaag acgggcgggg  60780
gcgtagggga ggagctcgtg ggggccgggg ggccctgcct gagccgggat gttttcgtgg  60840
cgatcgtaag ccgcaatgtt ctctcgtgtc tgctgaacgt gcctgccgcg ggtccccggg  60900
cctacaagtg tttcagatcc cacgcctcca gaccggtgtc tggcccggat taccctccct  60960
tggccgtgtt ttgcatggac tgcggttact gcttgaactt tggaaagcag acaggtgtag  61020
gaggcaggct caattccttt agacccactc tccagtttta tccccgtgac cagaaggaga  61080
agcatgtgct gacctgccat gccagcggcc gtgtgtactg ctccaactgc ggctctgcgg  61140
cggtgggctg ccagaggctg gctgagccac cgagcgcccg ctcgggctgg cggccccgaa  61200
tccgggcagt gctgccgcac aacgcggcct acgagctcga ccgtggctcc cgcctcttgg  61260
atgccatcat cccctgcttg ggacccgacc gcacttgcat gcggccggtg gtcctgcggg  61320
gggtgacggt caggcagctc ctgtatttaa ctttgcggac agaggccaga gccgtttgct  61380
ccatctgtca gcaacgccaa gctccagagg acgcccgcga cgagcctcac ctgttctcct  61440
cctgtttaga ggtagaattg ccacctggtg agcggtgtgc gggctgccgt ctctatcaga  61500
cgcgttatgg cacgccggct gcccaagccc accctccagg ggaggctgga ggcggatttt  61560
ccagacagtc ccctgcttcc taaatttcaa gagctgaacc agaataatct ccccaatgat  61620
gtttttcggg aggctcaaag aagttacctg gtatttctga catcccagtt ctgctacgaa  61680
gagtacgtgc agaggacttt tggggtgcct cggcgccaac gcgccataga caagaggcag  61740
agagccagtg tggctggggc tggtgctcat gcacaccttg gcgggtcatc cgccaccccc  61800
gtccagcagg ctcaggccgc cgcatccgct gggaccgggg ccttggcatc atcagcgccg  61860
tccacggccg tagcccagtc cgcgaccccc tctgtttctt catctattag cagcctccgg  61920
gccgcgactt cgggggcgac tgccgccgcc tccgccgccg cagccgtcga taccgggtca  61980
ggtggcgggg gacaacccca cgacaccgcc ccacgcgggg cacgtaagaa acagtagagg  62040
gcacgaaaca tggtgtatgc actttattaa taaacaatta cagatacaaa aacttgagtc  62100
tctcgaggtc tgcgatgagg cggtgggtgg aacgctccag cttgcggcga agctggctca  62160
cgaagcgaga cagtactcgg ctagcctgac taagggtgag gctataacgc aggtcctgtt  62220
ccggggcggc ggtggataga gaggaggggg atccggaggg gaccactagg tcgccggagg  62280
tcgaccctcc tgtcaccacc tccctgataa tgtcttcaat agacagaaat tgggtgacca  62340
ctgagggagt gttccacagt aatgttgtct ggtcgctaga tggcgcgggt gaggccacgc  62400
tttgcgaaaa cgaaagtgct tgaaaaggcg cgggatagcg tgcgctaccg gatggcgggt  62460
aatacatgct atccttacat tttggcattt tgggcagctg ggaggcggcg gatgggggtg  62520
cttcttttcg cacggtgtat gtttggggac ccgcatgccg gtactgggat aggcgcacct  62580
cgggccgcgc gccaggctcc gagccggaat gcattggggg caatgggatt gcgggggatt  62640
```

-continued

```
gttgctgtct gctcctgaca gggagagaca cgcgcggcgg agatgcagcc gacggcgggg  62700
ccgcggtggg ctgcccccga ggacgggcgc cggccgccag cgcccccgtg gcctttggca  62760
cgggcctggc acccaccgct ttaattgtgg gggtgggcag ggcagctgca tcttggggcc  62820
tttgtgcttg cgtttttttgg gggcgcggtg ccaatgcacc aactggggtg tgcgccgggg  62880
cggccaagcc ggaccccagg gcgggtgcct gggggatggg aaagccggac ggcgcttctc  62940
ccgggtcgaa cgctggagta gcggaggctg ctgcgccggc ggccaccacg ggcgcacggg  63000
gtcgcagccc gacggccgtg gggaggcggg tggcggaggg ccgaatctcc gcggcttctt  63060
cccggccccc ctgctgtttc ttctcccgtt gcatgataga atggccatag ggtgggtcct  63120
gagaggaggc ttgtgtgtcc tggggctgga gcccaaaagt cgttaaagat gccgctgatg  63180
gtgtgggagc tatgcctccc gtcgactggc cgggcttgta gggggctgag ggtggataac  63240
tgggcttctg tgaaggcacc aaccctggaa tctggatggt atgtttcttc tgtgaccccg  63300
aggcagtcga tggtgtagag tgtggagaca atgtgtagac gatgggccct tgttcagaag  63360
cccagggact tgagggggc tgttgtggtg ctggttgggg aaggagctcc agggaatctt  63420
tgggccatgg ccttggggag cttcccggag accggtctgg gctctcggaa gccctcgttt  63480
cggccccgaa atagggcctt gccatcaatc gggggcctgg gagagtgatg ggggcggcca  63540
atcccggggt aactgtcacg tcccgggggg aggaggtagg agacagccag tccctgggcc  63600
tgccaggggc caccttctct aagagggggc tctgtgggct gggagggcca gaggcctcag  63660
attcagcagt agtgctcccc ttttccccct ggtccgtctc ccctcctccc aactgctgga  63720
gccggtcgga ggaggccggg gtgttatctg ctgactgaaa cccgtccccg ctgaccagtc  63780
cgtgccccac ccttgggggg aaaccggaga acagctcctg gacgttgcgt ggattcgggg  63840
gaagctggta tccaaccggc agtggaggat cttcgtgctc gtagaaggag gggttgagta  63900
catcggtcgg ccatcgtgag gccccggccg cgttaaagta gaactgcacg tccggcagat  63960
tgtgccgata ggtgaaacac ttccagatga tgttttttct gttggccagg atggccacgg  64020
tggggggcct ggcctcctta ggtttggcgg ccctggcctc ggtgagaagc tcgcgtagcc  64080
acacggcctg gcgtgcaaag atggacatct ctggctcgaa agactcggag tagccgtcca  64140
ggtcctgcag aaaattcagc gagatggtct ccaccaggga ccggaagggc tcagagtgcc  64200
cgtcgcagta gaggagggga gcaacgaccc tgacctgtcc cagggtcttc aggttaaaca  64260
gatattgaga ggagacaaag agagttaggg gccgaccgag gaaggccgcc gccacggccg  64320
cctcaaaaac ggagacgggg atggtgtcac cggagcccct cttaggaccg gtaatgggag  64380
tgccataagg cataagattt ctcagggccc ggccggtaac ggtgccgtag gaagacgggg  64440
tttcgcgggg gacctcgagt ccctccgccc tggggagctc ttctccgcgt gtataggcct  64500
gcttcacaaa gtcgcgcagg tagtcctgaa atgcgaccgg gccctccagc gggcgcaatg  64560
agtgccagag ctgctgaagg gcctcggggg cgaagcaccg gcgtgcgagg agcagcatgc  64620
aggctcgggc gcgggccgta ctttggttgt ggaccaggcc caagaactcg gggtgcggcc  64680
agagggcggc tcgggtatcc atctcctccc aggcgtcctg gaagaagatg aagccggtgg  64740
gtggaccggc gatgcggtgg cgggtgaggc ggcgcgcgtc ttccccgtcg ttgctgccgc  64800
gggtggttga gggcatgccc cccctcccgg aggctggact cctgaccagc ctgtaggtga  64860
ggaccgagtc cgacaggagg tctcccaaac ccccatctct cgctagagcc gagaccaggc  64920
cgagtcctgc gtagaacgat ggggcgccca ggaaggcggc agcgtaggcc ggatgtgtgc  64980
```

-continued

```
cgaccagcag cgccatcatc tcccgttgtt ccaatagaat aacttcccgg tctgtggccg  65040
gggctggata aggggggtga ttcctagagg cgatgagact ggcgtgcgct aaaagtgtca  65100
tggccacaat ggggttgtct gccaggtctt ccatcagggc tttgggcgca gagacgtatt  65160
cccgaagcag ctccccggcg ttggactcca cgtcgggcca ggtgtcccag taggagtcgg  65220
cggcggcggc gctgaggcgg gcggaagcta cactggccag ggttcttctc ctcctctctt  65280
ggtcatcctg cgggggacca atagcttggg ggcgtccggc tggggtcagg gaaaaggcct  65340
ctgggttctc cagcacggtg ggcatgacat attccagaaa gttgtggtag acggggatgt  65400
agttgagcgg ctcctgggtg tctgcggaga cgtaggccgg gttaaggggg tcgcagggag  65460
actctgtttc cagccagagg gtgccggcgt atttcgccgg ccctgccgcc gccagaaatt  65520
gtgcccgccg ggtcggggct ccattgcccc atccagttgg tggtgccgaa atcgtgatga  65580
ggaggggcag gttgttggtc aagggatgct taacgaaaac ggtaggctgg gcggtctcgt  65640
aaaaagccag gaaactctgc ttggccgagg catagcgcag cagcttgtcc ttgaggaggg  65700
catactggga gccagccgag gccccaagcg ccaggcccct ggcagcctcc accacgatct  65760
tgagctggcg cgggtcggtg tggcccctgg cctgggtgac cagatcctgc agcgttccct  65820
gcagctggga ctcttcctgg gcctcctgga tgatggcctc cagtcgggag aggcgccttt  65880
tccagtctgc gacggtctcc ttgccccccg cgacccgctt ggggtccaac gtggccagag  65940
ccaacctcag ctcctccatg ccatccatgg agttctgggc catgccctcg acttccagga  66000
gccgtgttag ctcatgaatt tcaccgtcag ccgcagcggc taggttcagc caggcacccg  66060
cgcccccagc taaggccagg gctccttcgg aaagaccccg cacggcctcg cagatgcccc  66120
ggatccactt ggcggctgcc agggatttcc ggtagggcca tgagccgttc ccggccgctg  66180
cccgggccag ggcggcctcg aggggagcct ggacaggggc tttgggcggg gagggaagca  66240
ggctccggag ttcatcgtcg ggggcttcgt cgcgtgacct ggagaggacg gcctccagag  66300
ccgtgtgaaa gccccgccga gtgcttgccg ccatctcgtg ggccttcgcc atcagggtct  66360
ggctctcccg gacctgctct tccagcgccc ggacctcggc cgcctcggcc tcggtcagca  66420
gctccgagaa gaagtccccc gtggcctgga ggagatcgtc ccgctctcgc cttgtcagca  66480
gctggggctt cttaggccag agcgccgagt ccgaggccag cctgggcggg gcggttgcct  66540
gggggatagt tggaggagga ggcaggttag cctggcctgg gtcattagtg gcttcgggta  66600
gcgtccgatc cacgtactcg ctcacgatgg ccgtcagggc agcctcggct gctcgtcttt  66660
tttccagaag cccggccagc ccccgctcgt actccgcgta gggggcctcc agatccgtgt  66720
tgaccaccgc tgatttcatg tccggggact gcagggcctg gcgcgtctgc gcgagggccg  66780
aacggatggc atcggccgcc gtcctggcgc gaaagagggc cccggccgct tcctccgctc  66840
ctcgccctcc tcctccttct ttggcggtag ccgcgggggt ggcgggccaa gcgtccagtc  66900
tggccagagg gccggtctcg atatccgtga accagccggg ttccgcggcc tccattctct  66960
ccgccgcacc accatcgtcc acgagcaggg atcgcagtct ctccctcctc accctcgtta  67020
ttcccaatag catagcggca aggatctgtg tgagggagtc caagatgtcc gtgtttctgg  67080
ctactgccgc cgctgctgcc gcggctgagt ccgtattgtc tggcagcagg gaggccagca  67140
gggtgttcca gtcatcgggc gaagtgggag cgggctctgg gcgtgccccc agcgccttcc  67200
taattctggc ccaggcctca ttcgcctctc gcgctcgccg ctcctgcctc tccttgtctt  67260
cctgttctcg gagcttctcc ttttccttgc gcccggtctc cataagctgc cgcagcttct  67320
tctcatactg tcgcttgagc tctttgttgg gggcagtgtc cagaaaggcc tcgagctgtt  67380
```

```
cctcggtggc gggcttaaag ccttcggcct ccaggcgcca ggcctgcacc tccttctgtc  67440
tgagctgatc gttgttgtta ttcttcaatt tctgcaggta acttaggaag cgtttcttga  67500
gcttccctgg gatgagcgtt tgggagagct gattctgcag cccagagagt agtctcaggg  67560
catcctctgg agcctgacct gtgatcgtcg catcatagac cgccagtaga cctgggagca  67620
gattcaccgc cgcggccgtc tcctttaagg tgctgtgagt agcaaaattc tgcaaggcca  67680
ctaggcgcgc tggctccagc gtcagccggt tgcccatctc gaatgtgtgc agggcctctg  67740
agaccatggg gtccaggatg cggtcaatgc catcctgcac ctcagggtca aggaccggca  67800
agtcacgata gaggtggtct atgctctcct cgaaggaggc aatgtagtta tcgatggtgt  67860
agaaggtgat ggatttcagg atgttcatca ggtacttttt ggagcgaaca atctgctgta  67920
tagtgtcacg taggcggatg tacgtggggt tctttgcggc cccgactatc gaccctgcat  67980
ttgcgatgta cttttctatg acggggatgg tgagggccgc ggtgtcggcc agcggtggcg  68040
tggcttcggg gttgtcgtgg ttggcgggtg tcgcagaggg agaggcggga gagatggggg  68100
cgcctggggc cgaggccaca ccggccaggc ccaacattgc ctcgatgtcg tccaggatgg  68160
tgcggaggcg cttttcgttt tctctggtgg tctcgagctc cttctgtttt ttcgcgactg  68220
tctcaaactc tggaaggggg gcaatgctgg ggtcgtcctc ctcaactcgc tccaggggcc  68280
aggggatacc gctcatatca ctaagggcgg tgcccaggta gaggagctcg cgatagtccc  68340
attcaatgga cgtgtaccgg atgtttagga gaggcaggga ggcgatgatc tggcatgtgt  68400
gccgcaggtg tgtcaggagg tcgtcaaaat ccatcactgt tgggaggctt gggtcctcaa  68460
ggtaggagag ataatcggag gccgccgagg ccaccttgtc cctgatgtcc gccgtacacc  68520
tgcgcacgtg cagggccgca ttcttggacc ggacggccac gttgtggaca aagggggca  68580
ctgaggcggc gggaggggcc ccatactcta tcgctgtcaa cagcgccaaa aagcggacgt  68640
cctcctcatc taccccagcc tgttgtctgg ccacggccgt tcgggcggcc tccgccaggg  68700
ataggaggcg cttccagctt tcgtcgtcca ggaccaaggg gacgtccacg tgcgggcccc  68760
tgtagatgga attatcctcg ggttctcctc ctccttcccc cgcctcctga tctccgcccg  68820
agagcaggtc ggtcaggcgt ctgcgggccg cctccaggtc aaattttcca tcgtcgctct  68880
cggccagctg gggaatttca gccagcatct tagcaccggc atctacacgg accgcgtcct  68940
tcgtggccag ggacggcagg caggcctcca gctttgcggc caggtgctta tggaactctc  69000
ccgctcttcc cttgttttct gatagcatgt ttgcgaggtt ttggatgtta agttcggaag  69060
tgagcagttg ctccaggtcc agcgtgggga cctgcagatg tcccgaccag tcctttaaga  69120
attccagcag atttagcaca gacgatcggt ccctactcct tattagcccc tgctcgagga  69180
ccactgtcac aagaagatag tctatcatgc tcaaggcatc tgcctctggc acttcccggt  69240
tagaggccgg gtcgtagacg atggcctgtt cctggtaggt atgtccggct attctcgcaa  69300
tgttgctctc gaggggcaca aagtccatct caggagtctc tatgtcaaag gtggtctgat  69360
agtattggct cctggcggtg tccagtgtga tgggggacgt gggggcactg gatcccgatt  69420
ccaggctgtt ggagaacact tcatcttcga acatgtcttc atcctctgtg gtggggatat  69480
cggaggctaa gtcgctctcc gcttcttcag agtcggacat ggataggaaa ggctcctcta  69540
ggtcagacag gtagcggacg aggccagaac ccccagatgc atcatcccca aaggagggct  69600
gctgcccgaa gggaggtgat ggggatatct ccgttccagc cctgtcagcg gccgggggat  69660
ggttttttc tggttcgagt gtcgtggctg atggtgggag ctgctgagca ggaggaggag  69720
```

-continued

```
ccggggtagc tgatggcagg ggctgctgct gaggaggaag aggagaagga gcccgggcgg 69780
ctgatggcgg gggctgctgc tgaggaagaa gtggagaagg agccggggcg gctgatggcg 69840
tgggctgctg ctgaggaaga agtggagaag gagccggggc ggctgattgc gggggctgct 69900
gctgagttgg aggaggagaa agagtcgtgg tggtgggggc tgctgctgca gtcggggaag 69960
gggatggggt ggtcagaggg atttttgggt tcgagggagc tgcctgtggc agagggatgg 70020
gtatttgcaa agggaggcga ggagatggag tgactgaagg agcgatagtt gagactggcg 70080
cggggtgggg tgtcggggag gcgggtggtg attggtgagg gatggggatt actggagggg 70140
gaaggcgagc tgctgaaggg gggcgatggg gcggaacgtg ggtgcgtggc agctgatcat 70200
cctctgtgtc agtggtggag gacagaggga ggcggcggcc ggaggtgggc ttcttgtggg 70260
ggctatcttt gcccaatccc tttttcctct tgggagtctg aggcgctgcg ccgctcgacg 70320
cccttggtgg cgtggaggga gcggggaccc cgggggtgtg acctaggccg gggatgggga 70380
tgaagagggg agggctggag gccggggccg cggaggccgg ggccgcggag gccggggccg 70440
cggaggccgg ggccgcggag gccggggccg cggaggccgg ggccgcagag gccggggccg 70500
cagaggccgg ggccgcagag gccggagacg acggcgggga gttggtcttt gcaggactat 70560
acctggcggc agggaatgag tcggatgtga aagatcgaga gggcagtggc ctgaggttat 70620
acggtattat tcgccgttca aacggtagca tgacgggagg gctgctatca gcaccgggcg 70680
tccccgccgc ctccccatca ctggacacaa gctcgggccc caccaggtca aagccgctgc 70740
cgttggcctc ataaaagtca tacacgccat agtgttccag cataaagatg cgggggtcct 70800
ctgtctcaaa ggcctcgggt agaaaataga gatgcacgca agtgtactgg gcccctggtg 70860
cccccacgta ctgcaggatg tcgtgcgcat aggtgctgac tctgacatgg gcgggggtgc 70920
ccggggccgc atccttctgg cagtgggggt caaacaagta gaaggagcca tctgtctcga 70980
tgatgatggc ccccgcgtag atgtcgcaga tgtagaggat gaactgggcc accccgttgt 71040
aactgccgtg caggacctcg gccagggact gaacaactgc cgagtttgcg atctgggcag 71100
ggaataggac gaggccaaag atctccgccg agcggtatat gtgcacgcgc ccaccgcccc 71160
tcaggaccac ggagctgggc acgtccgtca actgggccat ctcgtgcccc ttgaggatgc 71220
cgctctggcg catgagggca tccagccgcg ccccctcgtc caggacctcg tccagctcag 71280
ggcgggaggt caggggcgg ccggccagga agctcttgac caggtagagg acgcagttgc 71340
tgacgcactg gatgccggca aagcggccaa acttgcagtg ggcctggttg cacgaggccg 71400
tgcctaggat gcggagggcc gagcctccac tcccgccccc gggggcattc acatccatgg 71460
tcctgattcc gcgcacgggg ccggttcccc gggtgcgctg gctttgcccc cagtcgccgt 71520
tactcatctt cggcggtggg gcggggagga cgccttgtcg cccccttct ggtccggggt 71580
cttacgcggc tggcggcggc agccgccgag agataagggg ggtacgtgtg tgcctccgcc 71640
tctcctctgt ctgggccgcc gccgccgctt gcccgccttg aaggagaggg ggtagtccgc 71700
ggactgcgtc tgcgggggca ggaggtctca accttctggg ctcgggccgc ggtgtcgata 71760
tccgatggcc tttccctgtc ttcctcgtat gctccttctc ctcctcctcc cggcacgccc 71820
ctgagatctg cctcccctcc ctctccctcg tcctggtcgg aaaagtctga ggaggagaag 71880
gagaatgggg aggagtccaa aacggcacgc cacctgccgt ggggcggtgg tgacaggtcc 71940
cggctggccc ggcgcttgct cgcgttcctg ccgttaccca ggagaatggc cgcgagtttt 72000
ttggcgggga ggatgcggaa tggcgggggc gtttgtccca cgggtgaggg ggaatcgtcg 72060
gttagggccg gcacgaggtg gtgggtctgg acccgggccg tgcgagcaaa ggcggcgaga 72120
```

```
accgaggggc ttctgggggt gactgtgatc tgttccggat ttaggtccat ggcgggtgtg  72180
tatgttttaa taggggtggt ctctggcgcg gcaggatgat ggtcgaggac gtccaccagg  72240
gccttgcaga tgctcttgcc tagatacagg atgtcgtcca tgctgagggg aggtggggtg  72300
tctgctcccc cctgcggaag ccgcctgggt gcggggatga agacaggtgg tgggcgggcg  72360
tctcgccgga ctatggcctc ggcacgctcg gcgtcgatgg cgggtggctg gaacaggcgg  72420
gcgaatgtgt aatcccggaa ccggtaggcg acgctgcgcc tgagggcgcc cgtcaggctg  72480
tatcccagct ccagggcgtg ctccacccgc tcgttgagct cctcgagatc cggacgcagg  72540
ggctcgctgg tgtgggccca gagggggtga tccgcgatgc cccggctctc cctgagggcc  72600
ggcaccagga ggcgccttct gagggtggcc gtgtcggccg tggccagggc ccacctggcg  72660
gcggcgtccc ggcacacatc ctggatgccc tccacgacgc tctttagcgt ctggaggtcc  72720
gtggagtagt ggcgggggga ggatgaaacg ctcttttcct tcaccgctac caccgcctcc  72780
tcctcctctt ccgtcgccag agggatctgc accctcccgg tctctgcgtc gtacaggagc  72840
gggcgggagc acagcctcca agctgccccc gtcaagcgcg agatgtcctc cgagagggtc  72900
tcacccgaga ccagaaagcg gcgggtggcc aggcccaacg actccgccgt cgtgctgtat  72960
ctcagggtga agaggagtga aaagagggag gtgggccagg caagcggtgg tgcttccgcc  73020
gcccgctctg aagctgagat agtctcggag atgatgcctg agacctctcg gacggcgtcc  73080
atgatcctaa ggactgcgtc gtgggacgac agcccccagg ggcccccgcc ctcttcgtct  73140
tctgcaccct cggctcctgc gtccccggcc ttgccttccc cctctaagtt gagggggcgc  73200
agtccgaccg cctgggggga ctccccaggc atcggagggg ccccgtcata gatctcccag  73260
acggtggcgt atatgagctc gagaggacgg cgggcccggg tcagctcggg ggaagggagg  73320
gccaggtcgc tgccgaagga gaccagccag cgcagggcgg ccagagagcg ggttttgggc  73380
agctcgttgg agaggacccg gcgaagggcg ggccagattt ggaactcgat gaaggcggcc  73440
gggaagaagg ggctgtggac ataggccgga tccgcgcgcg ccgtttggcc ggccctcagg  73500
gaccggcagt atgcctcgac gtctgtccgc ggggccgccg ccaccgctgc cgtccactgc  73560
cttcttccct gctcgccggg gagtaggggg ggcttacagg ggagggccgg agccggggcc  73620
ggggcctgcc acaggcggct gtagcggacc catagcagag acctgaggag ttcggatgaa  73680
aggtcccccg ccacctgctc atactcggcc gcgggagggg ggacgatgaa gatgcgcaga  73740
ggggttacgg cgtcccaagg gtccgccgcc gcccccacac ccacagccgt cgcggcgggg  73800
gcggcggcgg gcgtagaggg gccgctggtg cgccgggctc gtctgtccac ggcctcggcc  73860
tccgcccgca ggtaggccgc ccgggccaca cgggcgaagc ggctcgtggg gctcgcggtg  73920
ggcagcagtc ggaaaaagtg cagggcaaag cccgatagac tctctaggag ggcggcggtg  73980
gcctcgagcc acctccaccg cgagcgggac acccggggca cagaggccag catcatggcg  74040
tagtcccccg ccacggtctc gttgagcccg gccgagagca gaaccgtggc cacctgctcg  74100
atggcggctg gagagaagga tgcccggctc cccgccgcct cctgcacacg agcggccagg  74160
gcctccatct ctgccgccat cccggccagg aaggcctcga tgaccgagtc tgggacgccg  74220
taagtctggt cccagagcag ggcctcgtac acatagtcgt aaaagagggc ccctgagggc  74280
tccaaaagcc ggagccgggc ggcgtcaaag gccaggacgg gcacagccgc gacgggggc  74340
gtttgtcccc cgctggcctc cgcgtacacg cccaggatct ctaccgcccg ccgccgggcc  74400
aggggcagcg aggccaccac gctggaaagt gactcggggc ggtgaaagag accaccaccg  74460
```

-continued

```
ctttcttcac cctctccccc gccggccccg cccccactgt gctccaccag ctccacggcc  74520
atggccttga tgtccgcggc cgtgggctga ccctgccctg cagccgccca ggggtagcgg  74580
ttggtctccg cgtatacggt gaccagccat ctccccagcg tcgttttcgc cgcgttaaaa  74640
gcgtagaatg acagcccctc ccgcgggaag gcgtcccacc gggccagata agtgtcggcc  74700
accagctctt ccacgaaggc aaaggtggcc gttgggccag agaccgcgag cacctccccg  74760
ctgccctctt cgatgatgcg ccggtacgcg gccgccaggg cccgggtctc tgcgatgagc  74820
cgagagccgt ccagcggatc gtcggtggcc ggagaggctg tcgtgggggg cagtgaggat  74880
gccagcacgt ccagggccgc ctccagatgg ccgaggccga agctgcgcct ggaaaaggag  74940
gccgcccgga gtaggtagta ggcgtggtgg cggaggaccg ccgccgggta agcgtggccg  75000
ctcatgaggg tgagagtatt taaaaaatcg cgcaccagca ccggctgggc caaatccccc  75060
agtccaaaga tccccagctc cagaggcatc agcgcgcgca ggcgggcagc ggggtcgtcc  75120
ccagacagca gcaactgacg cgtcacgcgg gcgagccccc cgtccacctc tgccaggggt  75180
ggctgggcgt ctgcccctcc gctaccgccg ctgctgtcac tctccatagc ggacgccatg  75240
aaggtccagg ggtccgtcga tcgccgccgt ctgcaacgcc gaatcgcggg gctgctgccc  75300
cctccggccc ggcgtctaaa tatttcccgg gggtccgaat tcacgcggga cgttcgtggg  75360
ctggttgagg aacacgcgca ggcctcctcg ctgagtgcgg cggccgtctg gcgcgcaggg  75420
ctgctggccc cgggggaggt ggcggtcgcc gggggtggca gtggaggggg gagcttcagc  75480
tggtctgggt ggcggccgcc agtctttggg gactttctga tacacgccag ctccttcaac  75540
aacgccgagg ccactggaac gccccttttc caattcaagc agagtgaccc gttctcgggc  75600
gtcgacgcgg tattcactcc tctctccctg tttatcctaa tgaatcacgg ccggggtgta  75660
gccgcccggg tcgaggcagg tgggggcctg acgcggatgg ccaacctgct gtacgacagc  75720
cccgcaaccc tggctgacct ggtcccggac tttgggcggc tggtggccga ccgccgcttc  75780
cacaacttca tcacccctgt gggcccccctg gtggagaata taaagagcac ctatctgaat  75840
aaaatcacca cggtggtcca cgggcctgtg gtcagcaagg ccatccctcg cagcaccgtc  75900
aaggtgacgg tgccccagga ggcctttgtg gatctggacg cgtggctctc cggcggcgcc  75960
gggggtggcg gtggagtatg cttcgtcggg gggctgggcc tgcagccgtg ccccgccgat  76020
gcgcgcctct atgtcgctct gacctatgag gaagccgggc cgcggtttac gtttttccag  76080
tcgtcccgcg gccactgtca gatcatgaat atcttaagaa tttattactc accatccatc  76140
atgcaccgct atgctgtggt ccagccccta catatagagg agctaacctt cggggcggtt  76200
gcctgtctgg ggacatttag tgctactgac ggttggagga ggtctgcctt caattaccgt  76260
ggctctagcc tccccgtggt ggagattgac agcttttatt ccaacgtctc tgactgggag  76320
gtgattctct agacttaacg ggaggaaaca ggaggaggag ggggacaaga gcacaaaagt  76380
ggttcagtgg acacccacca cacagcatgg caacgaccag tcatgtcgag catgagctcc  76440
tctccaaatt gattgatgag ttaaaggtca aggccaactc agaccccgag gctgatgtcc  76500
tggccgggcg cctgctccac cgccttaagg ccgagtcagt tacacacaca gtagccgaat  76560
atctggaggt cttctctgac aaattctacg atgaggaatt cttccagatg caccgggatg  76620
agctggagac ccgagtctct gctttcgcgc agagcccggc ctacgagcgc atcgtctcca  76680
gcggctacct gtcggccctg cgctactatg acacctatct gtatgtgggg cgcagcggga  76740
agcaggagag tgtgcagcac ttttacatgc ggttagccgg cttctgtgcc tcaaccacct  76800
gcctctacgc gggtctcagg gcagccctgc agcgggccag gccggagatt gagagtgaca  76860
```

-continued

```
tggaggtgtt tgattactac tttgagcacc taacctccca gacggtgtgc tgctccacgc  76920
cctttatgcg ctttgccggg gtggaaaact ccactctggc cagctgcatc ctcaccaccc  76980
ccgacctcag ctccgagtgg gacgtgaccc aggccctcta taggcacctg gggcgctacc  77040
tctttcagcg agccggggtg ggtgtagggg tgacgggggc tggccaggat gggaaacaca  77100
tcagcctcct gatgaggatg atcaacagcc acgtggagta ccacaactat ggctgcaaga  77160
ggccggtcag tgtggcggcc tacatggagc cctggcacag ccagattttc aagtttttgg  77220
aaacgaagct gccggagaac cacgagaggt gcccgggcat ctttacgggg ctctttgtcc  77280
ccgagctctt cttcaagctt tttagggaca cgccctggtc ggactggtac ctgtttgacc  77340
ccaaggacgc cggggacctg gagaggctct acggggagga gtttgagcgc gagtactatc  77400
ggctggtgac agcgggcaag ttttgtgggc gggtctccat caagtccctg atgttctcta  77460
tcgtcaactg cgccgtcaag gccggcagcc ccttcatcct tttgaaggag gcctgcaacg  77520
cccacttttg gcgcgacctg cagggcgagg ccatgaacgc cgccaacctg tgcgccgagg  77580
tgctgcagcc ctcgaggaag tctgtggcca cctgcaatct ggccaacatc tgcctcccgc  77640
gctgcctggt gaatgcgcct ctggcggtgc gggcacagcg ggccgacacg caggggggatg  77700
aactcctgct ggccctccct cgactctcag tcaccctacc tggagagggg gcagtcggtg  77760
atggattctc gctagcccgc ctcagagatg ccacccagtg tgccaccttt gtggtggcct  77820
gctccattct tcagggatcc cccacttatg attccaggga tatggcctcc atgggcctcg  77880
gggtgcaggg cctggccgat gtctttgcgg acctgggctg gcagtacact gaccctccct  77940
ctcgctcgtt aaacaaggaa atattcgaac atatgtactt tacggccctc tgcaccagta  78000
gtctgattgg acttcacacc aggaagattt ttccgggttt caaacagagc aagtatgccg  78060
gggggtggtt tcactggcac gattgggcag gaacagacct ttctattccc agggaaattt  78120
ggtctcgcct ctctgaacgc attgtgaggg atgggctttt caattcacag tttatcgccc  78180
tgatgcccac ctcaggctgt gcccaggtga cgggctgttc ggacgccttc taccccttct  78240
atgccaatgc gtccaccaag gtcaccaaca aggaggaggc ccttaggcca aaccggtctt  78300
tttggcgtca tgtgcgtctg gatgacaggg aagctttgaa tcttgtcggg ggccgtgtct  78360
cctgcctccc ggaggctctg cggcagcgct acctgcgttt ccaaacggcc tttgattaca  78420
accaggagga cctgattcag atgtcccggg acagggcccc ctttgtggac cagagccaat  78480
ctcacagcct gtttttgcgt gaggaagatg ccgcgcgggc cagcacgcta gccaacctac  78540
tggtgcgcag ctacgagctg ggcctgaaga ctatcatgta ctattgtcgc attgagaagg  78600
ccgccgatct gggggtgatg gagtgtaagg ccagcgcggc tctgtcggtg ccgcgggagg  78660
aacagaatga gcggagtccc gctgagcaga tgccgcctcg tcccatggaa ccggcgcagg  78720
ttgcggggcc ggttgacatc atgagcaagg gcccagggga gggaccaggt gggtggtgtg  78780
tgcccggggg attggaagtg tgctataagt accgtcagct cttctcagag gatgatctgt  78840
tggagactga cggttttact gaacgagcct gtgaatcttg ccaataaacg tttattgcca  78900
tgtccaagtt gttgtacgtg cgtgatcatg agggctttgc ctgcctaacg gtcgaaaccc  78960
accgcaaccg ctggttcgcg gctcacattg tcctcaccaa ggactgcggg tgtctcaagc  79020
tactcaatga gagggacttg gagttttaca agttcctctt tacgttcctg gccatggccg  79080
agaagcttgt gaactttaac attgatgaac tggtcaccag cttcgagagc cacgacattg  79140
atcactacta caccgagcag aaggccatgg agaacgtcca cggggagact tatgctaaca  79200
```

-continued ttttaaacat gctctttgat ggggacaggg cggcgatgaa cgcctacgca gaggccatca 79260
tggccgacga ggccctgcaa gccaagattt cctggctccg tgacaaggtg gcggccgccg 79320
tcaccctgcc ggagaagatt cttgtgttcc tgctgattga aggcatcttc ttcattagct 79380
ccttctacag catagccctg ctgcgggtcc ggggcctaat gcctggcatc tgcctggcca 79440
ataactacat aagtagggat gagctgctcc acacccgcgc tgcctccctg ttatacaata 79500
gcatgacagc caaggctgac cgaccaaggg ccacctggat ccaggagctg tttcgcactg 79560
cggtggaggt agagactgcc ttcatcgagg ctcgtggaga gggggttacc ttggtggatg 79620
tgcgagccat aaagcagttt ctggaggcca cggccgatcg catcctgggt gacattggtc 79680
aggctccctt gtatggcaca ccaccccca aggactgccc gctcacctac atgactagca 79740
tcaagcaaac taatttcttt gagcaagaga gttccgatta caccatgctg gtggtagatg 79800
acctttgagt cagggtggct acttgctcag gtttctgggc ataaattctc ctgcctgcct 79860
ctgctctggt acgttggctt ctgctgctgc ttgtgatcat ggaaaccact cagactctcc 79920
gctttaagac caaggcccta gccgtcctgt ccaagtgcta tgaccatgcc cagactcatc 79980
tcaagggagg agtgctgcag gtaaaccttc tgtctgtaaa ctatggaggc ccccggctgg 80040
ccgccgtggc caacgcaggc acggccgggc taatcagctt cgaggtctcc cctgacgctg 80100
tggccgagtg gcagaatcac cagagcccag aggaggcccc ggccgccgtg tcatttagaa 80160
accttgccta cgggcgcacc tgtgtcctgg gcaaggagct gtttggctcg gctgtggagc 80220
aggcttccct gcaattttac aagcggccac aagggggttc ccggcctgaa tttgttaagc 80280
tcactatgga atatgatgat aaggtgtcca agagccacca cacctgcgcc ctgatgccct 80340
atatgccccc ggccagcgac aggctgagga acgagcagat gattgggcag gtgctgttga 80400
tgcccaagac ggcttcctcg ttgcagaagt gggcacgcca gcaaggctca ggcggcgtta 80460
aggtgacact caatccggat ctctacgtca ccacgtatac ttctggggag gcctgcctca 80520
ccctagacta caagcctctg agtgtggggc catacgaggc cttcactggc cctgtggcca 80580
aggctcagga cgtgggggcc gttgaggccc acgttgtctg ctcggtagca gcggactcgc 80640
tggcggcggc gcttagcctc tgccgcattc cggccgttag cgtgccaatc ttgaggtttt 80700
acaggtctgg catcatagct gtggtggccg gcctgctgac gtcagcgggg gacctgccgt 80760
tggatcttag tgttatttta tttaaccacg cctccgaaga ggcggccgcc agtacggcct 80820
ctgagccaga agataaaagt ccccgggtgc aaccactggg cacaggactc caacaacgcc 80880
ccagacatac ggtcagtcca tctccttcac ctccgccacc tcctaggacc cctacttggg 80940
agagtccggc aaggccagag acaccctcgc ctgccattcc cagccactcc agcaacaccg 81000
cactggagag gcctctggct gttcagctcg cgaggaaaag gacatcgtcg gaggccaggc 81060
agaagcagaa gcaccccaag aaagtgaagc aggcctttaa ccccctcatt taacaccatg 81120
ttctcgtgca agcagcacct gtccctgggg gcctgtgtct tctgtctcgg cctcctggcc 81180 agcacccccct tcatttggtg ctttgtcttt gccaacctgc tctctctgga gatcttctca 81240
ccgtggcaga cacacgtgta caggcttgga ttcccgacgg catgcctaat ggccgtcctc 81300
tggacgctgg tacccgccaa gcacgcggtg agggccgtca ctccagccat catgctgaat 81360
attgccagcg ccttgatctt cttctccctc agagtctact cgaccagcac gtgggtttct 81420
gccccctgtc tctttctggc caacctgcct ctcttatgcc tgtggccccg gctggccatc 81480
gagattgttt acatctgccc ggctatacac caaaggttct ttgaacttgg gttgctcttg 81540
gcctgcacca tctttgccct gtccgtggtc tccagggccc tggaggtgtc ggctgtcttc 81600

```
atgtctccat ttttcatctt tctggctttg ggctctggaa gcctggccgg tgctcggcgt  81660
aaccagattt acacctcggg tctcgagcgg agacgcagca ttttctgcgc ccggggagat  81720
cattcggtgg catccctgaa ggagaccctc cataaatgcc cgtgggatct gctggccatc  81780
tctgccttga ccgttcttgt cgtctgtgtg atgattgtgt tgcatgtgca cgcagaggtg  81840
ttctttggac tctctagata cctgcccctc tttctctgtg gggcgatggc ctccgggggg  81900
ctgtacctgg gccattccag catcattgca tgtgtcatgg ccaccctctg caccctgaca  81960
tctgttgtgg tatatttcct ccatgaaacc cttggacccc tgggcaagac cgtgctgttt  82020
atctcaatct ttgtctatta ctttagcggg gtagcggccc tgagcgcagc tatgcgctac  82080
aagcttaaga agtttgtgaa cggacccctg gtccatctcc gtgtggtata catgtgctgt  82140
tttgtcttta ctttttgtga atatctgttg gtgacattca ttaaatccta acgaccggag  82200
tcctgtctct ttgtgttctt gggggacttg agttagctgt ctttcctctt attacattgg  82260
gctaacggga ggaaatgaac ccaggggtgg cagtggatgg ggtcatttat gggcaaaact  82320
cacaggacat gtttggggag ttagcattgg cgtcgggaaa cacagctctg gcagttataa  82380
ccgcaccagc taacaggaca tgtttggggg agttggcatt ggcgtcagga gacacggctc  82440
tgtcagttat caccgtacca tgagtgccat gtgtgtccag tgcctaatca ccgttcctca  82500
ttttgtgtgc ctcctcaaat gttccagaag tcggccacag gggaggtggc tgaattaggg  82560
ccttttccct cattccccca tgagacccac gtggcaggcc taggggctac attcgcctcc  82620
cacgtttccc ttcgcgtgag gcatccgata tgactgaatt ttcgcagtct cttttccctc  82680
ttcccttgtt attcccatag aattacagtg aggttacaca ggtggagatt cagtttaacc  82740
atttattgat ttaatccagg aacaaaaaac agtcctagtg acccagtgcc cggagagaga  82800
atggccctga caagtcggct gcatgatgca cttcggcagt cacgtgtgtg agtctccacg  82860
gcctctgtca aaagggagct tagcgtgcca gggttgtaat tcttgatgta gtggcccagg  82920
aattcaactt catcgtgtct ccgtctgcag ttggcgttaa tgtaggctgg ggctactgcc  82980
gcatatgctg ccaagagaca gaggggctgc ttcacatatg agctgctcag ggtctccacc  83040
accttgtttt gacgggccgt ggcacaggtg atgtagaaga gttgcttcac aaagttgtag  83100
tctcgcgtgt taggaaggaa gcagggtgcc agctctttga gcttggtcag gatcaccttg  83160
ctaagactca tggcgcaggc caggaggatg tcttccgcgg gagctagggg caggtcgccg  83220
tggtaggtga tctcctggag ccaaaagatg gtctcttcta gcatggccac cagggtgcag  83280
agccccgcgt tctggatcgc ctgcatgcgt gcatccagcc atgtgtcctt gttggttgac  83340
ttggtgaaaa actcacgtag tgtcttgtag ctcctgcgca gctcgtgtct gggttgcact  83400
ttctgccagg ctccaatctc tggatgggcg gccaccgcca gcatcgactg taggaacggg  83460
tcttggatgg gctctagggt cagagaggcc agggggctgg gcaaggtgac aaatgtaatc  83520
ttggagacag gcttaaccag actcatgtca aaccacggtt tgttcggcag gggcctctgg  83580
ctgcgttctt gcctcgcctg cttccttgtg ctcctgccgg cccctcgaga ttctgaccgg  83640
ggacctctgg ttgctctgtt gcttcgggga gctcttggag acctcggtgc tctaggcacc  83700
ctgggggccc ttggggctct gggcgctctt gctcccgggg gcaggtgtcg gcgcttgcca  83760
taactttcat cggtgcagcc atggacctct ccgcgtcgcc ttttgtggcc tctggtgtaa  83820
gaggagttgc cagtctcctc cttctcgtcc tcgtccctgc acaggggtga gcgatgcaat  83880
gtgactgtct tgtcctgtag gtcccacttc tttctgggaa tcacaaacga tgccgaggta  83940
```

-continued

```
ggggttatga ccacgctgga gggccgtgca ggtatggcgt gggccggagt tggatcttca  84000
tcctcctcct ctgaggatga aatctctcca tctgtggagt gttcttcgct gccctccata  84060
gggtccagat cgcagtctgt gttggtgtct gagaccgctt cgagttccag aatgtggctc  84120
tctgcagagg ggagacaaaa ggtggagact gccttgagca cctctgtctc aggcaccgga  84180
tgcccccggc tccacggccc cggccactgg ccggtgtagc ttcttacctg cgggatcctc  84240
gttggaggaa atgctgctag ttcgggagag tctctgagaa ggaaccatct tgtctgtctc  84300
tacgacgggc tagctgggat gtagtgctgt cttgactggc ctcagcccta tttatgattc  84360
tggaggcggg cacgctgatg gagaaatggg cggtcggttg attggcccca cagcgaccgg  84420
cgaagcactg actcatgaag gtgaccgtga tggcctgtga tgtgtagtag agtaccagaa  84480
acaccctcac attcttggag ctggccctgt gggtatgcct caggcacgca aagttcctgc  84540
cccgggcatg gcacacctga actaagtttg gcccggtttg ctcaaacgtg acatggagaa  84600
actgggggaa tttgtcttct ggcacagctg ttgccagggt gctcatgagc gagggccaga  84660
tgcaggagct gacccaggcg acgagatcca ggcccagatg tccctctatc atggcgcaga  84720
cattctccac ggtggggggc agggtctcgc gggtcctctg gattagatag tcacgcccat  84780
catccgcgat gtggtagcag aaggttttgg gggccggcca gcccacgtgc agtgagtgat  84840
gtaagaggtt ttgaatgttg agggcattct taacatagct gtgcttgtct tcctcttccg  84900
gatgacagac aaagaggcgc agctgccggc taagaccacc gcccctgtcc accttgtagg  84960
tatgcggcag ccggatgcac cgcccggcgt gatacacgcc gctgtcaaaa agcggggccc  85020
caatctcttt gatcttgtga cgcatgcggc gcaggcaggc cgttaggccc atgagcttct  85080
gcagcacaga cacaaaccct tgtactgcgc ttgttcccac aatagcatgg cctctaggta  85140
ggggggtgat gacgcgaaag cccagttttc ccgtgcatat gcaaaagggg agcacatctt  85200
ccatattatc cgggtcggcg ggtggacaag ctgatttgaa aaaatagact gggtgggccc  85260
tggacactgg acccaggcgg cgcatgaggc gcagtacctc acgccgcacg gtccggcaca  85320
ggtcatagat ttcctccagc gaccaggggg ccccccttgat ctttagatcc aggtccaaga  85380
ccaggttgca gaccggaagc cggggattaa agtattcatg ccgggagaca aagagctgct  85440
cgctcaggct gttctgtgaa tagtacactg ggtgtagga gagggccctg gtgagacacg  85500
tgtctgggag gcggcagttg gtcggggtgg agacgacctc cgccaggtgg gatgagaagg  85560
ggtcagcggc tgtcattaca aagtagtgcc tgtctgcaaa atggcagagg aagaccggta  85620
gccgctgcac ccttcgaagg acggtgggtg ggaggaattg ttccttggga ttccactggc  85680
cccggcaggt ggcctggccg gccaagcata gaaacccttg aagcgtgggg gggtatgtgg  85740
gaccctcatc cgcgtgccag cgcgcgagct ccaccagctc ccgggccacg tccacactga  85800
gcccggccca ggcccgcatg agtccgtcat cggggtcggg gtcccacgtg tatggggccg  85860
ggggctccat gcggattttc agctgctgga cacgcacatg ctcagccagg taagtctccc  85920
gggtgaagta ggtgcgcatg tgctccgcaa agcccctgtc caggagcgag gggagcacga  85980
cgccccccga aggcagacac ccaatttctc ccatgctcgt taactgagag tatcgcttaa  86040
aggttccctc gttgaagcac tgtgcgtggg ccaaatagac gtagcgcacg agatcggccg  86100
aggccagggg aaggcgcccc ctgtaggcgt ctatcgtcct tgccacagcg cggatctctc  86160
gcgagtcccg ccgcagtttc tcgtgtgcaa agtgggcaaa agcctcggtc tgctccgccc  86220
atgccgagga gccaaagacc tcccccagct cggccaggga cgtgacggcg gccaggctct  86280
gaccagactc ggaagtaaat agctccgtga ggtgcgccag ggtctcaatc gtacaaggaa  86340
```

-continued

```
tgccccaaaa atagtaagca gccgtgacta gcacgaactg ggcctcgtgg gagccaaagg  86400
tgctaatgaa ccacctggcc gagatgttaa cgcggtagat gcggcgcaga cagcccacga  86460
tcttgggacg cagccacgcc acgcggcctc tggcatcccc ctgtggctgt ttcttagcgc  86520
tcagtgtgag cagttccacg aggggcgtga gcgagcgcag ggcccccgcg cgatctaggt  86580
aggtggatag acggtccgcg gtgagcggcg tgaggccgcg caggaagggg aaggcctcct  86640
ccgccggcag gtgcagcgtc agaaccaggc cgcagcggct ctgtgaggtc agccgcttct  86700
tgggcaggtg aagctgcagt tccacgagag aacccgccac gtggtggagg ggcgaggcgt  86760
tgtggcacaa acaaaacagg cggaagccct cgtcaggccg cgagaggatg gcatcgagga  86820
tggcctccgc aatgtcagtg tttgaggcca caagggcctt gatgacgacg ggggcggaca  86880
ttatttaaga ccgggaggcc ccaacggcgg gctaaacaga acgatggcct tctatctccc  86940
agactggtcg tgctgcgggc tctggctctt tggccggccc aggaatagat acagccagct  87000
ccctgaggag ccggagacct ttgagtgccc ggaccgctgg cgagccgaga tagatctggg  87060
cctgccccct ggtgtgcagg tgggagattt gctaagaaat gagcagacga tgggctcact  87120
gagacaggtt tatttgctcg ctgttcaagc caatagcatc acggatcacc tgaagcgctt  87180
tgacgccgtc cgcgtccctg agagctgtcg tggggtggtg gaggcccagg tggccaagct  87240
tgaggccgtg cgctcagtca tctggaatac catgatctct ctggctgtaa gcggcatcga  87300
gatggacgag aatgggctca aggccctgct ggacaaacag gctggcgaca gcctggccct  87360
gatggagatg gagaaggtgg ccacggcgct caagatggac gagaccggtg cctgggcgca  87420
agagatctcg gccgttgtct catcggtgac cgccccctca gcctcggccc ctttcatcaa  87480
ctccgccttt gagcccgagg tgcccacccc cgtccttgca ccgcctcccg tggtgcggca  87540
gccggagcac tctgggccca cggagctcgc gttaacgtag caaccagact ccacaccaaa  87600
taaacatttt attggtaaaa caagggatat gaaggtgtca ttgacccgag gatccaaacc  87660
ccctccccctg tctcccctcg agcgcctcgc tcagcccact atcacccatg gccaggctcg  87720
gcacctcctc gaaggtgcag ctggcccacc taaagagaga tctggggcca aggacccccg  87780
cgtcactgtg gggctgtag aaggaggtga ggtggtgctt gtgaaggtaa acaagctgac  87840
agaagcgccg gtacttgtta aggaacacgg tctggtcact aaagttggtc aggctgacgt  87900
ccaccccacc ccggcgccac ctgcagggct tcactagaat accctgcatg gccaggcccg  87960
acctgccaaa gattgtcggc ctgtggtgag ggatagaagg ggggggcacg gtgagtgtca  88020
ctgagacggt ctgatggggg aagagggcca ggtcctttgg caaagagacg tccaggccca  88080
cgtccccggg gtactggggg tggttgatgg gacccttgtc ctcctccatc tggggggtgg  88140
catatctgaa ggcagccagg tggattttga gctccgatgg acgcagcgtg gagttgtagc  88200
gccgctgatt ctggaggatt agccggagtt cccccgtgta gccgggatcg atgatgccaa  88260
catgagacgt gaccggacgg gaggtgctgc cccacagcat gagcccatga ccctcgggtg  88320
ggcgggcata gaggcctagg tccacagttg tggtcttcat cgggcgcagc aggatggtgg  88380
tcttgttgac caaggtgagc cgccctacac tagcctgctg gagcaacagc ttgtcattct  88440
ggaaggcgta gcgtatgtgt ggacaggcct ccatggtgat gatctaacag acagggacgg  88500
cggcgctata tataagagcc caagacccgg ctctctttac tgcgaaatgg ggaaggtcct  88560
aagaaagccg tttgcaaagg ctgtgccact gctcttcctc gccgccacct ggcttctgac  88620
cggggtgctg ccggccggcg cttccagtcc cacaaacgcg gcggcggctt ccctgactga  88680
```

-continued

```
agcccaggac cagttctact cctacacatg taatgcggac acattctcgc cttctttgac  88740
cagctttgcc tccatctggg cacttctgac gcttgtctta gtcattatag cctcagccat  88800
ctacctgatg tacgtctgct ttaacaagtt tgtgaacacg ctgctgacgg attagatggg  88860
gatatttaaa aggggcagca atctcggctg tttgtacttc ttctctgctc gttaaaccaa  88920
tagcatgtca gctccacgca aagtcagatt gccttctgtt aaggctgttg acatgagcat  88980
ggaagacatg gccgcccgcc tggctcgcct ggagtctgag aataaggctc tgaagcaaca  89040
ggtcctcaga gggggtgcct gtgcctcgtc tacctctgtt ccttctgctc cagtgcctcc  89100
gcctgagccg cttacagctc gacagcgaga ggtaatgatt acgcaggcca cgggccgttt  89160
ggcgtctcag gctatgaaga agattgaaga caaggttcgg aaatctgttg acggtgtaac  89220
tacccgcaat gaaatggaaa atatattgca aaatctgacc ctccgcattc aagtatctat  89280
gttgggtgca aaaggccaac ccagccctgg tgagggaaca cgaccacgag aatcaaacga  89340
ccccaacgcc acccgacgtg cccgctcccg ctcccgggga cgtgaagcaa agaaagtgca  89400
aatttctgat taataaattt ttattgactt tatacatagg tctcggcgtc atcatatggt  89460
ggggtggtgt aggtatggga tgtagacaag ttacgcctaa aggcgcagtc cgccatgacc  89520
agcagcagca gaagggtcag cacagccaga gaggcccact gcagtactag catggagagg  89580
tttgagaatc tgggctggga cgttggcggg actggcacgg tggcttgggc tgtggtaacc  89640
ggtgggctcg taaaagtcca gcggggccgc agtttgctag aagtgctggg aggtagatag  89700
gtggtcgcat tgtatctcgg tcttggcgta gttgaatcac cgccgtaatc tgtggtgggc  89760
tctgtacttg tccgggctcc atgtcctgtg gtgtgctttc caccggtggt agaattggcc  89820
tttccacctg ttgaggtgac cgtgggaacc gccgtctttt ggccactggg ggcctggggc  89880
gacgttgcat tttggggggg cgtgcctttg gtgacattaa cctcccccgg ttttgtggat  89940
gtggaactgt ttccagggcc tgacgcttgg ctggtggtgc ctgggcgggg tgctggcgaa  90000
ctggtggaca catgatgtgt gctgatagag gctggtgtca cctgtgttat attttcacca  90060
cctgttgggt gagcggaggt tagtaaaggc atatgtgacg ttgaattgtc actggtggag  90120
gggctgagtg tctctgggtt tgaactgggt ctcagtgaca tggaagaggt tgaacttgaa  90180
gttatgttat gttggcctgt ggtaacagca ctggttgcat tttttggttg gctggtaact  90240
actggggtgg gacttgttcc tcctaaggtg tggttggtgg catttgcctg tggacttgtt  90300
tctcccacag tagggccggt ggcatttggg gttggggtag tcactgctga ggtggggctt  90360
gtttttccca aggtggggct ggtggcattt ggggttgggg tagtcactgc tgaggtgggg  90420
cttgtttttc ccaaggtggg gctggtggca tttggggttg gggtagtcac tgctgaggta  90480
ggacttgttt ttcccaaggt ggggctggtg gcatttgggg ttggggtagt cactgctggg  90540
gtggggctgg tggcatttgg ggttggggta gtcactgctg gggtggggct ggtggcattt  90600
ggggttgggg tagtcactgg tgaggtggag ctggtcatgt cgggggcctt actttctgtg  90660
ccgttgtccc atggagatgg acttggtgtc accggtgatg cgcctgacgt tgtgccggct  90720
ggtgttgggc tggtgacatc cgcggtggat acagtggggc ctgtgcttgc aggtgcggtg  90780
aggttggtag gcacgtgagt agagctgggt agacctgtcg ttgtattggg atcagcaaat  90840
ccagttgtat tcaaggtagg ggaggtggtg gtgctctcgg gtgccttgga gaatataacc  90900
ttgtgggttg ttgtggtggc attggtagcc gttcgtgtga taatgagtgt cttgggggcc  90960
gtgccaagac ccgagacagt aatgtcaaat gtccgattgc tcgcaaatgc accagaaata  91020
ttttcacaac ccgaaggtgt ccccgaggtg agagtccatt tgcacttaaa gtcagtttca  91080
```

-continued gtgttgtttg gccaggccca aaaggcagtc actgtaacat ttggcgagtt tgcgtcctca 91140
gaagtgacca ttggcactga ataggtagca ttgtcaccca catatgtgat gtctgtggtg 91200
tttgtcggca tgtcctgtga agctggaatc tcatcagaga acacaatgtt ggactgaatg 91260
cagtaatctc ccccgctcgc cttcggtcca ttcccagagt aaaacacgta caggatactg 91320
ttattgccaa gaaatcgtga cactggacgt ggtgtcagac gcaggctgta tgcataccct 91380
gtaccaggta ttggggtggc cacgggactc gttgatgtga gaattccgcc gctgggaaca 91440
tggctctcgt atccactgca ggtgatgtta aatttgttgt ctccgggcag aacttgtgaa 91500
atttcgccat cctccataat acactcaata tctatctcat taccgagcat ttctgttttt 91560
acgctgaaat tcgagtcttg agctgacgtt ggcaaactta agggtagcgt gacatccagc 91620
ccctgtgccc tcactactgc cgttatattg gtagaattac agttatccca ctttatgtat 91680
ggcactgttt ctggtatcag gtacacgggg ttttgcattt ctgcatggtg gcaccacatg 91740
gttccaaaca catcttgaaa gtagacatct acagattcca ggcttacttg ttgctcctct 91800
ccggtggtga cgttaattgg aagcttctta gaccgcatag ttagagccaa ttctcctgca 91860
ccaaggagct ccagtagaaa gagattggtg gcattttctg agccaccaaa tgcacctcga 91920
ggttggtaga cagccttcgt atggggtgtc agctggccaa agtcaagatc aagttgatgc 91980
tttttgcccc cgacatcgaa attgatagtt acattgacat ctgccgtgca aacattgcat 92040
gtggggtaaa atgggaattc cggaatctca acattgaaaa aaccaggatc ttcacccgtg 92100
agatggatca ggctctggat ggtgtactga cacacaagca aggctgcctc cattgtctcg 92160
gcaccgattt ctaggcagca tcctctttaa taggtacaag gggggtgcgg tgttggtgag 92220
tcacactttt gttgcagaca aaatggacaa ggacaggccg ggtcccccgg ccctggatga 92280
caacatggaa gaagaagtcc catctacctc ggttgtgcag gaacaggtat cggcgggaga 92340
ttgggaaaat gtcctcatag agttatcaga tagcagctca gaaaaggaag cagaagatgc 92400
ccacctggag ccggcccaga agggtacgaa gagaaagcgg gtcgatcatg atgccggtgg 92460
gtcagctcca gcacgaccca tgctcccacc ccagccggat ctccctgggc gagaagccat 92520
tctccgcagg tttccactag atctaagaac acttcttcaa gcgattggag ccgcggctac 92580
ggtgagcatc cctatggcct aagtgtgtga tgtgtgtttt tacccatcac acaacaacaa 92640
ggtaagtaat ttgttgccgt tggtttcagc gcatcgacac acgagccata gaccagtttt 92700
tcggatccca gatttcaaat accgagatgt acataatgta tgccatggcc attcgacagg 92760
ccattagaga tcgtcggaga aatccagctt ctcgtagaga tcaggccaaa tggagactgc 92820
aaaccctggc cgccggatgg cctatgggtt accaggcata cagcagctgg atgtacagct 92880
acaccgatca ccagacgact cccacattcg tacatctcca ggcgacactt gggtgcacag 92940
gtggccgtag gtgtcacgtg accttttccg ccggcacctt taagctgccg cgatgtaccc 93000
ccggggatcg ccagtggttg tatgttcaga gctccgtggg taacattgta cagagctgta 93060
atccccgcta cagtattttc tttgactata tggctataca caggagcctc acgaaaatct 93120
gggaggaagt tttaacacct gaccagcgtg tttcatttat ggaattccta ggatttttgc 93180
agagaacgga tttgtcctat atcaagagct ttgtcagcga tgccctgggc accactagta 93240
tccaaacacc gtggatcgat gacaatccta gcacggagac ggcacaggct tggaatgccg 93300
gctttctccg ggtcgtgcg tatgggatag acttgcttag aactgaaggg gaacatgtcg 93360
aaggtgctac cggtgaaacg cgagaagaaa gtgaggacac ggagagcgat ggagatgatg 93420

-continued

```
aagatcttcc ttgtatagtg tccagaggtg gacctaaggt caaacgaccc cctatattta  93480
taagacgtct gcacaggttg ctgctgatga gagcgggcaa acgaacagaa cagggcaagg  93540
aggtactgga aaaggcccgt gggagcactt atggcacacc taggccgcct gttccgaaac  93600
caagaccaga ggtcccacaa agcgacgaga cagctaccag tcacgggtcg gcgcaagtcc  93660
cagaaccccc aaccattcac ctagcagctc agggaatggc atacccatta catgaacaac  93720
acggcatggc cccgtgtccg gtagcacagg ccccacctac gcccttgccc cctgtatctc  93780
caggggatca actcccaggt gtttttagcg acgggcgagt ggcgtgtgca ccagtacccg  93840
ccccggctgg gcctattgtc cggccctggg agccatccct gacacaggct gcggggcagg  93900
cctttgcacc cgttagacca caacacatgc cagtagaacc cgtccctgtc ccgacagtgg  93960
cacttgagcg accagtttac cccaagccag ttcgtccggc acctcctaag attgctatgc  94020
agggccccgg ggaaacttct ggcattagac gcgcgcggga gcgttggagg cccgcacctt  94080
ggacgccaaa tccaccccgt tctcccagtc agatgtccgt gcgtgaccgt ctggctcgtt  94140
tgcgtgctga ggcacaggtc aaacaggcta gtgttgaggt gcagcccccc cagttgaccc  94200
aagtatcccc tcagcaacca atggaggggc cgttggtacc agagcagcag atgttccctg  94260
gtgccccctt tagccaggtt gctgatgtgg tccgggcacc tggggtaccg gcgatgcagc  94320
cacagtactt tgacctcccc ttaattcaac ccattagcca gggggcaccc gtggccccgt  94380
tgagggctag tatgggcccg gtacctccgg taccggcaac acagccacag tattttgaca  94440
tccccttaac tgaacccatt aaccaggggg catccgcggc ccattttctc cctcagcaac  94500
cgatggaggg gccgttggta cctgagcagt ggatgttccc aggtgccgcc ctgagccaga  94560
gtgttaggcc aggggtagcg cagtcacaat attttgacct ccccttaact caacccatta  94620
accatggggc acccgcagcc catttcctcc atcagccacc aatggagggg ccgtgggtac  94680
ccgagcagtg gatgttccaa ggtgcccccc ctagccaagg cactgacgtg gtccaacatc  94740
agctggatgc tttggggtat acactccatg gtcttaacca tcccggggtt cccgtgtctc  94800
ctgccgttaa ccaatatcat ctcagccagg ctgcctttgg gttacctatt gatgaggatg  94860
agagtggcga ggggtccgat acctccgagc cgtgtgaagc tcttgatttg tcaatccatg  94920
gcaggccctg ccctcaggcc cccgagtggc ctgttcaaga ggagggtggc caggatgcca  94980
ccgaggttct tgatttgtca atccatggca ggccccgccc tcggaccccc gagtggcctg  95040
ttcaagggga aggtggccaa aatgtcacag gccctgaaac tagaagggtg gtggtgtcag  95100
ctgttgttca catgtgtcag gatgacgagt ttccggatct acaagatcct ccagatgagg  95160
cctaagcaaa ggtgtagaag tgtgtccccc tccattccac ccactgataa tacgcccgac  95220
aataaagttg atgatattga attccacacc tgcttgtgtt tgtgatttta tttcatattc  95280
catgagagag acctcgcata tttgcagaag ggtcactgaa acatcttatc ttaaaacagt  95340
tacacctgaa taatgaagaa agcgtggctc agcagagcac agcaagccga tgccgggggg  95400
gcatctggct ccgaggaccc accagattat ggagatcaag gtaatgtgac acaggtggga  95460
tctgagccta tttcacctga gattggcccc tttgaactct ctgcggccag tgaggatgat  95520
cctcaatctg ggccagtgga agagaattta gatgccgctg caagagagga agaggaacct  95580
catgagcagg agcacaatgg tggtgacgat cccttggatg tccatactcg ccagcctaga  95640
tttgtggatg tgaacccaac gcaggctcca gtgatccaac tagtccacgc tgtctatgat  95700
tccatgttgg taagaggcac ctagaacatt tccagatgtt tcgcttggat tttttggcca  95760
gtcttaattg attgtcattg gtttcagcaa tcggacctcc ggcccctagg cagtttattc  95820
```

```
cttgagcaaa acctgaacat cgaagaattt atatggatgt gcatgaccgt gcgtcacaga  95880
tgtcaggcca tcagaaaaaa accattacca attgttaagc agaggcgttg gaagctcctg  95940
tcatcttgca gatcctggcg tatgggttac cgcacgcata acctcaaagt aaacagtttt  96000
gagtcagggg gggacaatgt ccacccggtc cttgtgactg ctacgctagg atgtgatgag  96060
ggcacgcggc atgcaacaac gtacagtgct ggcattgtac agataccacg aatatcagac  96120
caaaaccaaa agatcgaaac agccttcctg atggcacgtc gtgctaggtc actttcggca  96180
gaaagatata ctttgttctt tgatttagta tcctccggaa acaccctgta tgctatatgg  96240
attgggctgg gcacgaaaaa ccgagtttca tttattgagt ttgtaggatg gttatgcaag  96300
aaggaccaca ctcatatacg cgaatggttc cgccagtgca ccgggagacc caaagcagcc  96360
aagccatggt taagagcgca tcctgtcgcc attccttatg atgatccgtt aacaaacgag  96420
gagattgatc tggcctatgc ccgcgggcag gccatgaata ttgaggctcc tagactgcca  96480
gatgatccta taattgttga ggatgacgac gaaagtgagg aaattgaagc tgaaagcgac  96540
gaggaggaag acaagagtgg aatggaatct cttaaaaata taccgcaaac actgccgtac  96600
aatccaacag tatacggcag gcccgcggtg tttgaccgaa agtcagatgc aaaatcaacc  96660
aaaaaatgca gggccatagt aactgacttt agtgtaatca aggccattga agaggaacac  96720
agaaagaaga aggcagccag aacagagcag ccaagagcca cgcctgaatc ccaggccccc  96780
acagtggtcc tccagcgacc acccacgcag caagagcctg gccccgtcgg cccactgagt  96840
gtccaggctc ggctggagcc atggcaacct ttgcctgggc cccaagtgac agcagttcta  96900
cttcacgaag aatccatgca gggtgtccaa gtacatggtt cgatgctaga ccttcttgaa  96960
aaagacgatg aagtcatgga gcagagggtt atggcaaccc tactgccacc agtaccacaa  97020
cagccccggg ctggcagaag aggccccttgt gtcttcaccg gtgacctagg catagagagt  97080
gatgagcccg cttcgacaga gccggttcat gatcagctac tgcctgcccc aggacctgac  97140
cctcttgaaa tccaaccact aacgtccccc accacgtctc aacttagcag ttcggcacca  97200
agctgcgcac aaactccatg gccggtggtt cagccaagtc agactccaga tgacccaacg  97260
aaacagtccc ggccaccgga aacagctgcc ccacgccagt ggccaatgcc cctgcgacct  97320
atccctatgc gcccccttgcg gatgcagcca atcccattta atcatccagt gggacccact  97380
ccccatcaga cacctcaagt ggaaataaca ccatataagc ccacttgggc tcagataggg  97440
cacattccat atcagcctac accaacgggt cctgctacca tgctgttgcg ccagtgggca  97500
cccgccacca tgcagacacc accgagagcg cccactccca tgtcaccacc tgaggtgcca  97560
cccgttcccc ggcagaggcc tcggggggcg cccactccca cgccacctcc tcaggtgccg  97620
cccgttcccc ggcagaggcc tcggggggcg cccactccca cgccacctcc tcaggtgctg  97680
cccactccca tgcagctggc actaagggct cctgctggtc agcaggggcc gacaaagcaa  97740
attttgcgcc aattgttaac ggggggcgtc aagaaaggga gaccatcact taagttacag  97800
gccgcccttg agcgtcaagc cgctgcgggc tggcagcctt caccagggtc cggcaccagt  97860
gacaagattg tgcaggcgcc tattttctac ccacccgttt tgcagcccat acaggttatg  97920
gggcaagggg gttccccaac ggccatggcc gcctcagcgg tgacacaggc acccacggaa  97980
tataccaggg aaaggagggg agtggggcct atgcctccca ccgatattcc gccgtctaaa  98040
cgagcgaaga tcgaggccta tacagagccc gagatgccgc acggggggggc ctcgcactct  98100
cccgtcgtta tcttggagaa tgtcggccag gggcaacagc agactctgga gtgcggagga  98160
```

-continued

```
actgctaaac aggaaaggga catgttgggg ctgggggaca ttgcagtttc ttccccttcc  98220
tcttctgaaa catcgaacga tgagtgattt cgcccatgta acaagaactg ggatgaaccc  98280
tggggcaaca gactgcgggg aggagggggg cagtgataag tcatgacaat tttagatgag  98340
gtagaaattt tgcatatttt cagacccacc atggaatcat ttgaaggaca gggggactct  98400
agacagtcac ccgacaatga gcggggagat aatgtacaga ctaccggcga gcatgatcag  98460
gaccctgggc cggggcctcc atccagtggg gcttctgaga gattggtacc agaagagtca  98520
tactcaagag atcagcaacc ttgggggcaa agcaggggtg atgaaaacag aggctggatg  98580
cagcgcatca ggcgaaggcg gagaagacgg gctgccttgt ccggccatct tttagacacg  98640
gaagacaatg tgccgccatg gttgcctcca cacgacatca caccatatac cgcaaggaat  98700
atcagggatg ctgcctgccg ggctgtcaag gtgagtatgc ctctaactgg gttcatgggg  98760
gccatctaag gcccacgtgt gacccatgtt tccattaatt ttagcaatcg cacctgcaag  98820
cgctatcaaa cctgatactc gatagtgggt tagacacaca acacatcttg tgcttcgtga  98880
tggcagccag gcagcgtctt caggacattc gacgtggacc cttggttgcg gagggcggtg  98940
tgggttggcg acattggctt ctaacatctc ccagccaatc ctggcccatg ggatatcgta  99000
cagcaacact acgcacatta actcccgtgc ctaacagggt tggggctgac agcatcatgt  99060
taactgccac atttggatgc caaaatgcgg cacgaactct aaacaccttc tctgccaccg  99120
tgtggacacc accccatgct ggaccaagag agcaagaaag atacgctcgg gaagccgagg  99180
tacgcttcct tcgtggtaaa tggcagaggc ggtaccgaag aatctatgat ttgatagaac  99240
tgtgtggctc tctgcaccac atctggcaaa acttgctcca gaccgaggag aacctttag   99300
atttcgtgcg tttcatgggt gtcatgtcca gctgcaataa tccagctgtg aattactggt  99360
ttcacaagac aatcggaaac tttaagccat attacccgtg gaatgcacca cctaatgaaa  99420
atccatatca cgcgcggaga ggcataaaag aacacgtaat ccagaacgca tttcgaaagg  99480
cacaaataca gggtttatca atgttagcaa cgggaggtga acccagaggt gatgctacta  99540
gtgaaacgag cagtgatgag gacaccggta gacagggttc ggacgtggag ctagagtcct  99600
cggacgatga gctgccatat atcgatccca atatggagcc ggttcagcag aggcccgtca  99660
tgtttgtgag ccgtgtgcct gcaaagaaac cgaggaaact gccttggccc acgcccaaga  99720
cgcacccagt gaagcgcaca aatgttaaga cctctgatag atctgataag gcagaagcac  99780
aaagcacccc tgaaaggccg ggcccttccg aacaatcatc agtgaccgtg gagcccgccc  99840
acccgacccc ggtggagatg ccaatggtga ttctccatca accacctcca gtgcccaaac  99900
cggttccagt caagcctacg ccaccgcctt cccgtaggag aaggggagcg tgtgttgtgt  99960
acgacgatga tgtcatagag gtgattgatg ttgaaaccac cgaagattca tcgtcagtgt 100020
cacagccaaa taagccacat cggaaacatc aagacggctt tcaacgttca ggccgacgtc 100080
aaaaacgagc cgcgcctccc accgtgagtc cttcggatac tgggcctcct gccgtggggc 100140
ctcctgccgc ggggcctcct gccgcggggc ctcctgccgc ggggcctcct gccgcggggc 100200
ctcctgccgc ggggcctcct gccgcggggc ctcgcatact ggcgcctctt tccgctgggc 100260
ctcctgccgc ggggcctcac atagtgacgc ctccttccgc ccggcctcgt ataatggcgc 100320
ctcccgtcgt acgtatgttt atgagggagc gacagctccc ccagtccacc ggccgtaaac 100380
ctcagtgctt ctgggaaatg cgggctggtc gtgaaattac acaaatgcaa caagaaccaa 100440
gttcacacct gcagtccgcc actcagccta caacgcctcg cccatcatgg gccccatcag 100500
tctgcgccct ctcggtgatg gatgctggta aggcccagcc catagaaagt tcacacttga 100560
```

-continued gttccatgtc gcccacacag ccgatatcgc acgaagaaca accccggtat gaggatcctg 100620
acgctcctct ggatttaagt ttacatccag acgttgctgc tcaaccagct ccccaggctc 100680
cataccaggg ataccaggag ccgccggccc cccaggctcc ataccaggga taccaggagc 100740
cgccgccccc ccaggctcca taccagggat accaggagcc gccggcccac gggctccaat 100800
catcttcata tccaggatat gcgggtccct ggaccccaag gtctcaacat ccatgttata 100860
ggcacccctg ggcaccatgg tctcaagatc ctgtgcatgg gcacacccag ggtccatggg 100920
atcccagggc accacatctc ccacctcagt gggatggatc tgcaggacat ggccaggatc 100980
aggtctccca gttcccacat ctgcaatcgg agacaggccc accacgtctt caactttcat 101040
tggtgccact ggtctcatcc tctgcaccat catggtcatc tccccagccc cgagccccca 101100
tacgccccat tccaacaaga ttccccccctc cccctatgcc gttacaagat agcatggccg 101160
tggggtgtga ctcatcaggt acagcatgcc caagcatgcc ctttgccagt gattacagtc 101220
aaggtgcatt taccccactg gacattaatg ccaccacgcc aaaaaggcct cgagtagaag 101280
aaagttctca cggacctgcc cggtgttccc aagctactgc tgaagcacag gagattctca 101340
gtgacaattc tgagatctcc gtgttcccaa aggacgcgaa gcagactgac tacgatgcat 101400
ccactgaaag tgagctagat taaggggatc caaggtgacc cctgttagct atttgatctt 101460
tgactgacac ataaacatgg tttaaggaat gaacactcat ggtgtgagac tggaactgta 101520
ctaaatttgc tgacatatgt acaatgagag ccaaaaattt gataaacctt aaaagtcccc 101580
ccatctaatg atgtccagtt cccttctccc accctgtaca ccccgaccca aagggactca 101640
atggcattca gatttctagt taccacaggt agaatatcgg gcgttggccc ataaaaataa 101700
gtgcatggat atagctctgc acaggcttgg aaacacccat tccaggtgtg cttcttttg 101760 gtgaaataaa aacagcatcc tttatatgaa aatgtgtatt ctctggtgtt gcagtatgta 101820
cagttagctt tggtatagtt ttggggtacc tgaaatgtgt gcagggtggg tgtccaatgt 101880
ggcagtttta cctctttgtc cccatactcc tgctcggccg tcttgttaaa gttaaccggc 101940
ggtggaggat ccaccggcca gacctctaca tttggtttgg gtacccaggt gatggccgcg 102000
gctgccaccc gccctcctcc tcttaccctg ggtggcaaaa agtatgccag gagtagaaca 102060
ataacaagtg cgatggcggt aaacaatggc accctcacct gcttaaatga aaccatggca 102120
accacttcaa agagagccga caggaagata tttattaata ttccattagt aaacgaggcg 102180
tgaagcaggc gtggtttcaa taacgggagt tagaaattta agagatcctc gtgtaaaaca 102240
tctggtgtcc gggggataat ggagtcaaca tccaggcttg ggcacatctg cttcaacagg 102300
aggcgcagcc tgtcattttc agatgatttg gcagcagcca cctgcggaca aaaatcaggc 102360
gtttagatgg ggcatttatg tttgggacgc tagccgcctg ggcattcgtg ttagtatata 102420
ctgacctcac ggtagtgctg cagcagttgc ttaaacttgg cccggcattt tctggaagcc 102480
acccgattct tgtatcgctt tatttctagt tcagaatcgc attcctccag ctgcgagcaa 102540
gggaatgcgt tactacaagt ggtgcctagt cagttgaaac aagccccacc atccgctgcc 102600
gcccctccat gagccccacc gtccgctgcc gcccctcctt gagcccctcc ttaccgattc 102660
tggctgttgt ggtttccgtg tgcgtcgtgc cggggcagcc actggtgcag gctgtggaac 102720
accaatgtct gctagctgtt gtccttggtt agccccgggg caagcaaaca ccactgctgc 102780
tgctgtttga acagtagaat tgtctccagg ttgaggtgct tctcccccgg cttggttagt 102840
ctgttgattc tgggttatgt cggagactgg gaacagctga ggtgctgcat aagcttgata 102900

-continued agcattctca ggagcaggct gaggggcaga aaaccacgac ccagtcggag cggttgaaac 102960
atgataggca gttagctggc cttgtggcag aggctctggc agcaccggcc acagcacaca 103020
aggcaaagga gcttgcgatg gccctcccag gtcctgatag actctggtag cttggtcaaa 103080
agcttgtaca aaaggcacct ggtatgggtc aggtgtaaat tttacatctt cagaagtcga 103140
gtttgggtcc atcatcttca gcaaagatag caaaggtggc cggcaaggtg caatgtttag 103200
tgagttacct gtctaacatc tccccctttaa agccaaggca ccagcctcct ctgtgatgtc 103260
atggtttggg acgtgctaaa tttaggtgtg tctatgaggt acattagcaa tgcctgtggc 103320
tcatgcatag tttctaaaag aggaggaggc agttttcaga agtgtctaaa ataagctggt 103380
gtcaaaaata gacagcccag ttgaaatatg catggcatgc agcagacatt catcatttag 103440
aaatgtatcc aagatttcat taagttcggg ggtcaggggg gagtccagat tcaaatcctc 103500
tgtcatggac tctagtgttg tggtcagttc gtccaaatgg ccacgagggg gcgggtggct 103560
caggtccatc tgtccacata tggctgcttc ctccttctgg ggaataacag tgtcagccat 103620
ctcccttagg gccttcacgg cctgactggt ttcttcatca gggtcctcca acagatgact 103680
tgcctcgggg gttactgcgg gggccgggtc aagtggctgg ggcaccgggg ctggcgttag 103740
ggatccgacc ggttcatgga caggtcctgt gggggtggga gccaaagagg caggcagggg 103800
ccggttggcc cacggggatc cgggtggatg gaagggcctg atcctctttg gctgacacac 103860
ctctcgcccc tcgaacacgt cagatatggc actgcccgct tccggctttg gcaggaacat 103920
accttcccgg ctatccctga ggcccttctt ccttttaacg ggaggaagaa aggtgggctt 103980
tgaggggtgg gggaatatgg gtctctcatc gctctcttgg tggaccgctg ctatccaagg 104040
ctgttcaggt tccgccgcgt tggaaggaca tggagtttga ccacggttgg gcctggatgt 104100
ccggcgcgac tttggggccc gcaggcgcgg ggcctcggcc ctggcctctt cccgctcgct 104160
ctgctcggtg tcactgttgc ccgagtcact gctgctggaa ctgctgtcac cgcagtcggc 104220
gctttgggca ccgggcttca ggggcatggt cgggctcggg agactttcga gttcatctgt 104280
aaaagcatga aactgtccgg actccgagta gcgggcctcg gtgtgagagg cacccccatc 104340
attccccatg agctcctcgt ccatcctgtc ggctccggac acgaggatag gagtttccac 104400
tgccttggac ttggttgaca gcaggcacgc gggaagcacg ccgctcacgt agctcctctg 104460
tccggcgtgg ctggagtagg aggcccgggg cagtgtctta atcagagccc tgacatcctt 104520
aacatcgtcc gtcagatggc ctgtcttgga cgagaccata gtctggaaca tctcctcgag 104580
gacgggatag gtgaacaccc acttgcaaaa ggccttgaac ttggagctta ggaggccttc 104640
cttctccatc ctgttcaggt gttccactac ctgcttgccg gaggccatga tggccgcgcg 104700
gtccacgccc agcaccttgc tgtaggtgta ggcccgcacc cgactgtgtt ttaggagctt 104760
gtacatagcg gtgcctatgg tggcaggaat catcacccgg ttgctggggg cctggatgaa 104820
gaatctgtca gtgaccacta tcaggtggtc taacacgtag cgcatcacta tagggcacgc 104880
gatggaacat gcgtcgttgc cggcattctc agcccgtctt cttaccctgt tgtttcggag 104940
aatggcccaa aaattgcaga tgttgagcgt ggccattagc ccgccccatt ctcgcccgtg 105000
ggccttggcc tcatttataa atgccttgca tattttgtag gatctcagag taatctccac 105060
actcccggct gtaaattcct tgttgaggac gttgcagtag tcagagacca gagagcccag 105120
ctgctttttg atttcaggag ttagcctcag aaagtcttcc aagccatcct ttttaggcct 105180
catggctagt agtaacagag gaaatgcccg accattaaaa tctttcctcc atgagcttta 105240
cctgaaacac tatcccgaag tgggggatgt ggtgcatcta ctgaacacca tcggggtcga 105300

-continued

```
ctgcgacctc ccacctagcc acccactcct gacagcccag agggggctgt tcctggcaag 105360
agtcttgcag gctgtacagc agcacaagct gctggaagac accatcgtcc ccaagatctt 105420
aaagaagctg gcttatttct tagagctgct aagctactac tcccccaagg atgaacagcg 105480
tgacatcgcc gaggttcttg accacctcaa gacgaatcgg gacctggggc tggacgacag 105540
actctgggcc ctgattagga aactgcgcca agacagacac catgcctctg taaatgtcct 105600
catgccagga agcgactaca cagccgtgtc gctgcagtac tacgacggca tctccatagg 105660
tatgaggaag gtaatcgcgg atgtctgccg cagtggctat gcctccatgc cctccatgac 105720
ggccacgcac aacctctccc accagctctt gatggcgtcc gggcccagtg aggaaccgtg 105780
cgcctggcgc gggttcttta accaggtcct cctctggact gtggccctct gcaagtttcg 105840
cagatgcatt tactataact acattcaggg atctatagcc accatctccc agcttctgca 105900
cctcgagatc aaggccctct gcagctggat aatatcccag gatggcatgc gcctctttca 105960
acacagcagg cctctcctca ccctctggga gagcgtggcc gcaaatcagg aggtcacgga 106020
tgccattacc ctgcctgact gcgctgaata catagaccta ctaaagcaca caaaacatgt 106080
cttagaaaac tgttctgcca tgcaatacaa ataaatttct cttacctgcg tctgtttgtg 106140
tagtgaggtg ttgtgtcctg tatggtattc tactttaaaa aggccggctg acatggatta 106200
ctggtctttt atgagccatt ggcatgggcg ggacaatcgc aatataaaac cctgaccatc 106260
acatggggca ttaggcgact ctgcatcagc atcgcttaag tatgagtggg cagcagagag 106320
gctcggttat tttggttcct gaacatctgg ctggggcatt aactaagctt atgagcgatt 106380
ttatcacagg acaagatgtc actctttctg gaggaaatat tgcagtcaaa attcgcgatg 106440
ctataaacca gacccccggg ggtggtgatg tagctatact ttcttccctg tttgctttat 106500
ggaatgccct cccaacatct ggtagacaat cctccaggga cgatttaatc ccagccgccg 106560
tgcaggcctt aaccacggcc cacaacttat gtctgggtgt tattccaggt gagacctcac 106620
acaaggacac acccgagtca ttgctccggg ctatcgtgac gggtctccaa aaattgtggg 106680
tggattcgtg cggatgtcca gagtgcctac aatgtcttaa gggattgaag gcaattaagc 106740
ccggccttta tgaaatccct aggataatac cacacactaa gcagtgtagt cctgtcaatc 106800
tcctgaacat gttggtccac aagcttgtgg ctttacgtgg tcatgtgcag cttgcatacg 106860
acgcccgtgt cctgacgcct gactttcacg aaatccctga cctcgatgac tccgatgctg 106920
ttttcgcacg caccttattg gcagccttat ttcacctcaa tatgttcttt attctcaaag 106980
attacataac acaagactcc atgagcttga agcaggccct cagtggtcat tggatgtctg 107040
ccacgggcaa ccccctgcct gcagcaccgg aaaccctgcg agactacttg gaagctttcc 107100
gaaattcgga taatcacttt tatctcccga cgacagggcc tttaaacacc ttccaatttc 107160
ccgaagagct tctggggcgc gttgttgtta ttgattcctc tttgtgtgcc gccagtcacg 107220
ttcaggacgt tatcacccat ggtgttgggg cgggtgttcc tcgtcctcgg ttttcggccc 107280
tgcctccggc cccatcccgc gagccccagc agacatgctc tcagttaacg agcagaggga 107340
atgaaagctc acggcgaaac ttgggccagc ccggggggac ctcccctgct gttcccccag 107400
tttgccccat cgtttccctg acggcctcag gggccaagca aaaccgcggg ggcatgggat 107460
ccttgcactt agccaagcct gaggaaacct cccccgccgt ctccccagta tgccccatcg 107520
cttccccagc ggcctccagg tccaagcagc actgcggggt cactggatcc tcacaggccg 107580
cacccagctt ttcttccgtt gccccagtag catctctgtc tggtgacctt gaagaggaag 107640
```

-continued aggaggggtc ccgagaatcc ccatccctac cgtccagcaa aaagggggac gaggaatttg 107700
aggcctggct tgaggctcag gacgcaaatc ttgaggatgt tcagcgggag ttttccgggc 107760
tgcgagtaat tggtgatgag gacgaggatg gttcggagga tggggaattt tcagacctgg 107820
atctgtctga cagcgaccat gaaggggatg agggtggggg ggctgttgga gggggcagga 107880
gtctgcactc cctgtattca ctgagcgtcg tctaataaag atgtctattg atctctttta 107940
gtgtgaatca tgtctgacga ggggccaggt acaggacctg gaaatggcct aggagagaag 108000
ggagacacat ctggaccaga aggctccggc ggcagtggac ctcaaagaag agggggtgat 108060
aaccatggac gaggacgggg aagaggacga ggacgaggag gcggaagacc aggagccccg 108120
ggcggctcag gatcagggcc aagacataga gatggtgtcc ggagacccca aaaacgtcca 108180
agttgcattg gctgcaaagg gacccacggt ggaacaggag caggagcagg agcgggaggg 108240
gcaggagcag gaggggcagg agcaggagga ggggcaggag caggaggagg ggcaggaggg 108300
gcaggagggg caggaggggc aggagcagga ggaggggcag gagcaggagg aggggcagga 108360
ggggcaggag gggcaggagc aggaggaggg gcaggagcag gaggaggggc aggaggggca 108420
ggagcaggag gaggggcagg aggggcagga ggggcaggag caggaggagg ggcaggagca 108480
ggaggagggg caggaggggc aggagcagga ggaggggcag gaggggcagg aggggcagga 108540
gcaggaggag gggcaggagc aggaggggca ggaggggcag gaggggcagg agcaggaggg 108600
gcaggagcag gaggaggggc aggaggggca ggaggggcag gagcaggagg ggcaggagca 108660
ggaggggcag gagcaggagg ggcaggagca ggaggggcag gaggggcagg agcaggaggg 108720
gcaggagggg caggagcagg aggggcagga ggggcaggag caggaggagg ggcaggaggg 108780
gcaggagcag gaggaggggc aggaggggca ggagcaggag gggcaggagg ggcaggagca 108840
ggaggggcag gaggggcagg agcaggaggg gcaggagggg caggagcagg aggaggggca 108900
ggagcaggag gggcaggagc aggaggtgga ggccggggtc gaggaggcag tggaggccgg 108960
ggtcgaggag gtagtggagg ccggggtcga ggaggtagtg gaggccgccg gggtagagga 109020
cgtgaaagag ccaggggggg aagtcgtgaa agagccaggg ggagaggtcg tggacgtgga 109080
gaaaagaggc ccaggagtcc cagtagtcag tcatcatcat ccgggtctcc accgcgcagg 109140
ccccctccag gtagaaggcc atttttccac cctgtagggg aagccgatta ttttgaatac 109200
caccaagaag gtggcccaga tggtgagcct gacgtgcccc cgggagcgat agagcagggc 109260
cccgcagatg acccaggaga aggcccaagc actggacccc ggggtcaggg tgatggaggc 109320
aggcgcaaaa aaggagggtg gtttggaaag catcgtggtc aaggaggttc caacccgaaa 109380
tttgagaaca ttgcagaagg tttaagagct ctcctggcta ggagtcacgt agaaaggact 109440
accgacgaag gaacttgggt cgccggtgtg ttcgtatatg gaggtagtaa gacctccctt 109500
tacaacctaa ggcgaggaac tgcccttgct attccacaat gtcgtcttac accattgagt 109560
cgtctcccct ttggaatggc ccctggaccc ggcccacaac ctggcccgct aagggagtcc 109620
attgtctgtt atttcatggt ctttttacaa actcatatat ttgctgaggt tttgaaggat 109680
gcgattaagg accttgttat gacaaagccc gctcctacct gcaatatcag ggtgactgtg 109740
tgcagctttg acgatggagt agatttgcct ccctggtttc cacctatggt ggaagggget 109800 gccgcggagg gtgatgacgg agatgacgga gatgaaggag gtgatggaga tgagggtgag 109860
gaagggcagg agtgatgtaa cttgttagga gacgccctca atcgtattaa aagccgtgta 109920
ttcccccgca ctaaagaata aatccccagt agacatcatg cgtgctgttg gtgtatttct 109980
ggccatctgt cttgtcacca ttttcgtcct cccaacatgg ggcaattggg catacccatg 110040

-continued ttgtcacgtc actcagctcc gcgctcaaca ccttctcgcg ttggaaaaca ttagcgacat 110100
ttacctggtg agcaatcaga catgcgacgg ctttagcctg gcctccttaa attcacctaa 110160
gaatgggagc aaccagctgg tcatcagccg ctgcgcaaac ggactcaacg tggtctcctt 110220
ctttatctcc atcctgaagc gaagcagctc cgccctcacg ggccatctcc gtgagttgtt 110280
aaccaccctg gagactcttt acggttcatt ctcagtggaa gacctgtttg gtgccaactt 110340
aaacagatac gcatggcatc gcgggggcta gacctctggc tggatgagca cgtgtggaag 110400
aggaaacagg agattggtgt gaaaggagaa aatctgcttc tccccgactt atggctagat 110460
ttcctacaac tcagccccat cttccagcgc aagcttgctg ccgttattgc ctgtgtccga 110520
cgcctgcgga ctcaggccac cgtctaccca gaggaggaca tgtgcatggc ctgggcccgc 110580
ttttgcgacc cctctgatat taaggtggtt attttgggcc aggaccccta tcacgggggt 110640
caagcaaacg gcctggcatt cagcgtcgca tacggctttc cagttccccc cagcctgagg 110700
aacatctacg cggagctgca ccggagcctg ccggagtttt ctcccccaga tcacggctgt 110760
ctagacgcgt gggcctccca gggggtgttg ctactcaaca ccatcctgac cgtgcaaaag 110820
ggcaagcccg gctcgcacgc agacattggc tgggcgtggt ttactgacca cgtaatttca 110880
ttgctctctg agcggttaaa agcgtgcgtg tttatgctgt ggggtgcgaa ggcgggagac 110940
aaagcttcac taatcaactc caagaagcat ctggttctga cctctcagca tccctctccc 111000
ctggcccaga acagcacccg aaagagtgcc cagcagaagt tcctgggcaa caaccacttt 111060
gtcctcgcta acaacttttt gcgtgagaag ggctcggtg agatagattg gaggctgtag 111120
aggggtcatc actatggcca tgtttctgaa gtcgcgtggg gtccggtctt gcagggaccg 111180
gcgcctcttg tcggacgagg aggaagagac ttcacagagc agcagctaca ctctggggtc 111240
tcaggcctcc cagtctatcc aggaggagga cgtgagtgac actgatgagt ctgactactc 111300
agatgaagac gaggagattg atttggagga agagtacccc agtgacgaag acccatctga 111360
gggcagtgat agcgacccct cgtggcatcc ttcagattca gacgagtctg actacagcga 111420
gagcgacgag gatgaagcaa cccccggctc tcaggcctca cgatcttcaa gagtctcgcc 111480
atctacccaa cagtcttcag gtctgacacc cacgccttcg ttctcccgac cacgcacccg 111540
ggcacctccg aggccgccgg ctcccgcgcc ggtcagggga cgggcctcag cacctcccag 111600
gccaccagcc ccagttcagc aatccaccaa agacaagggt ccccatagac ctacgcgacc 111660
tgtacttaga ggcccagctc cacgccgccc ccctccacct tcaagtccca atacatacaa 111720
taaacacatg atggaaacca cccccccat taagggcaat aacaactaca attggccatg 111780
gctgtaaata aaatgtcata acctggagtc tgcatgtctg ttgttttatt cagtaaacca 111840
gtagtgcgcg tgagttcttt agggcatcca cgatgtagcc gctcgcgggg ttcccctccc 111900
cagtgatcat ctcggatagg ggattcctgt ccatgaccac gcaattagag tgccgggccc 111960
gggacagcgc cacatacaca tggccgggtt tgatgtttct gtggctgccg aagcagatgg 112020
cgactttgtt tagggacaga ccctgggcct tggctatggt catggccagc tttgagctaa 112080
tgccatagtc acggatgctg cagaggttca gggacttgtc ctctatcgtc tcatacagtt 112140
tgttagtatt gtgttccagg cagcacacga agcctgcctc atccttgacc attagcctgg 112200
gcatgcgtga actgccagcg tcctgaggct gctgctttcc tcggatgcca aagaagacgt 112260
tgagatgcgt gtagcccaga agcgtgtagt tctcggtggt ggaggcgtag tccaggaggc 112320
cgtgaaggag aggctcgtct gaggtgaact ctatgttgtc gcgaatcagc atgttgttgg 112380

-continued taaatgtgca gaaggggagg tccctgaact cccttccgcc atagcggacg gccacatcca 112440
ggcattgcct gaaataggcc ctgaggtcat tatatatgtt taacagggag cagagggggg 112500
cagaatttgc ggccggggga gccagtactc gggcatagaa gacagcggcg gggctccgct 112560
ccccatccca ggcaacctcc agcggcagtt cgcccagctc catcccagca gtcacctccg 112620
gatcccacgt acgcccgggc aggggcacag caccaagctc cgccacgtat tccccgtttt 112680
cacagagaga atgtcctccg tggctaaaag cgtagatgcc tccgtagatg agtcgggcca 112740
ggaagctgta gacatactcg ggctgctcat gcccgtgggc ctccacgaag ctgtccgcct 112800
cgagcgtgtc cataaagtcc ccgaaggtgc cggtatagcc acagatggac tttttggtct 112860
tgcagttgac cgacaccgag ctgtgcttga cgtaggtgac attgtaggtg accttgaccc 112920
gttcttcgtc ctgctcggtg cccaccggga ccatgtcttg gtcggcgaac tgcgagtagt 112980
taccgaggcg tgcataattc ttttggagcc aggtgtgggc cgtgaggccc ggaagcccga 113040
ccagggtctt gtactgggcc aggggatcga ggaagacctc gcactccacc gggcaggtaa 113100
acatggtcac cccgccccca tctcccccgg ttccccgcgc ggcacgcccc tgcccggcag 113160
tcttgagcgt ggcatggagg gtggtgagga aggtcttgac ctcggcgtgg gagaggaaga 113220
gccgggtcca gcccacgtac tgcgcggggt ccattatggc cgccctgggg acgacgaagc 113280
ggtcgacgta ggccaggatg tccggcgaga gctcgaggcc gtactcgagg gtcttcatga 113340
ggtgtccaaa ctggacgtcg gtgcagcgct tgttgttgat gaagagggcc cagttgcggg 113400
ccacgtccac gtaggtcgcg gccctggggt tgcccaccag gaaggtgagg atgttgtcgc 113460
actcgcgaat cttgtttacc tgggtctcgt ggctaaagga ggactgaaag gcgtctgtct 113520
gggtgggaga gcccacgcag acgatgcagg gaatgcggcc ccggcggtag agtggggtac 113580
gcagccaggc gttgaagaac cagtagcaaa agaccacggc tgttagaatg tgcacggaaa 113640
gcgttccagc ttcgtccacc acgatcacat tggtggtcca tagctgcccc tggtgcatgt 113700
ctctcaggac ctcaaaggcg gggccagaga ctcccgagta gagccccctg ggcttggttc 113760
gcctgaactc ggcggcaatg tcggagagta ccggccagta tttggccagg tcccgccgct 113820
ggagttcctc tagggcggcg tccgtagagc gaccatgact gctgacccgc tgcgtcatat 113880
ttatgtggcg gctcttgaac ccaaaggcgc tatagacggt tgggcagtag gctcggagtg 113940
tctgggagag gttctgtgcg gccacggttg tggctcccgt gaccaggcag tccatcgtgt 114000
ggtggaggca gctaacgctg gtgctcttgc cagcccccgc cgttcccgta attacatagg 114060
ctgaaaaggg caggaagggg ggctccgaga gctccgggtc aaactcgggg gagaacgtct 114120
ccatatccgg gagttgttgg acgcggcgcc tagccagggt ccctatcctc ctgactatac 114180
gcctcacgga ggcgtctgag gtcatgttca acatgaacgt ggacgagagc gcctctggcg 114240
ccctcggctc ctcggccatt cctgttcacc ccacgccggc ctcggtccga ctttttgaga 114300
tcctgcaggg aaagtacgcc tacgtccagg gacagaccat ctacgccaac ctccgcaacc 114360
ccggagtctt ctcgaggcag gtgtttaccc atttgtttaa acgagccatc tctcattgca 114420
cgtacgatga cgtgctacat gactggaaca agttcgaggc ctgcatccag aagcgatggc 114480
cgagcgatga ctcgtgtgcg agccggtttc gtgagtccac cttcgagtcg tggtccacga 114540
ccatgaagct gaccgtgcgt gacctgctga ccaccaacat ctaccgagtg ctacacagcc 114600
gctccgtgct ctcctatgag cgttatgtgg actggatctg cgccaccggc atggtgcccg 114660
ccgttaagaa gcccataacc caagagctcc actccaagat aaagagcctg agggacaggt 114720
gcgtctgtcg ggaattgggg cacgagagga ccatcaggag tatcgggacg gaattatatg 114780

-continued aggcaacgaa ggaaataata gagtcgctca actccacgtt catcccccag tttacggagg 114840
tgaccatcga gtaccttccg aggagcgacg agtatgtggc ctactactgt ggccgccgca 114900
tcaggctgca tgtgctcttc cccccggcca tctttgccgg aacggtgacc ttcgacagcc 114960
cggtgcagcg cctctaccag aacattttca tgtgctaccg cacgctggag catgccaaga 115020
tctgccagct cctgaacacg gcccctctca aggccatcgt gggccacggg gggcgagaca 115080
tgtacaagga catcctggcc catctggagc agaactcaca gcgcaaggac cccaagaagg 115140
agctgctgaa cctgctggtc aagctctcgg agaacaagac catcagcggg gtcacggacg 115200
tggtggagga gttcataacg gatgcctcca acaacctggt ggaccgcaac cgtctatttg 115260
gccagcccgg ggagacagct gcacagggcc taaagaaaaa ggtctccaac acggtggtca 115320
agtgtctgac tgatcagata aacgagcaat ttgaccagat taatggccta gagaaggaga 115380
gggagctcta tctaaagaag atccgctcca tggagtctca gctgcaggcc tccctgggtc 115440
ccggcggcaa caacccagcg gcgtcagccc ccgccgcagt tgcggcagaa gccgcgtctg 115500
tagatatact gacgggcagc accgcctccg caatcgaaaa gctgttcaac tccccgtccg 115560
ccagcctggg tgccagggtg tctggtcaca atgaaagcat cctaaacagt ttcgtttctc 115620
aatacatccc cccttcgcgg gaaatgacta aggatctgac tgaactttgg gaaagcgagc 115680
tgtttaacac cttcaagtta acacccgtgg ttgataatca ggggcagcgt ctctacgtca 115740
gatactcgtc agacacgatc tctatattat tgggcccctt cacctatctg gtggcagagc 115800
tttcaccggt ggaactcgtg acagatgtct acgccaccct aggcatcgtg gagatcatcg 115860
acgagctcta ccggagcagt cgcctggcca tctacatcga ggacctcggt cgaaaatact 115920
gccccgcgag cgcgaccggg ggagatcatg gcatccggca agcaccatca gcccgggggg 115980
acacggagcc tgaccatgca aaaagtaagc ctgcgcgtga ccccccgcct ggtgctggaa 116040
gttaaccgcc ataacgccat ctgcgtggcc accaacgtcc ctgagttcta caatgccagg 116100
ggggacctta acatccgaga cctccgggcc cacgtcaagg cccggatgat ctcgtcccag 116160
ttttgcggct acgtcctcgt gagtctgctg gactccgagg accaggtcga ccacctcaac 116220
atattccccc acgtgttctc cgagaggatg atcctgtaca aacccaacaa tgtgaacctt 116280
atggagatgt gcgccctgct ctcgatgatt gagaatgcca agagcccctc cataggcctc 116340
tgccgggagg tgctgggtcg cctgaccctc ttgcactcca agtgcaacaa tctggactct 116400
ctgtttctgt acaatggggc caggacgctg ctgtccaccc tggtcaagta ccacgacctg 116460
gaggaggggg ctgccacccc cgggccgtgg aatgagggcc tgagtctctt taagctgcac 116520
aaggagctga agcgcgcccc atccgaagcc cgggacctca tgcagagcct ctttctgacc 116580
tcggggaaga tggggtgcct ggccaggtca cccaaggatt actgcgcgga tctaaacaag 116640
gaggaagatg ccaactcggg cttcacattt aacctgtttt atcaagattc tttattgacc 116700
aagcatttcc agtgccagac cgtcctccag accttgagac gcaagtgcct cgggagtgac 116760
acggtctcaa aaataattcc ctagaataaa ctgagaacag tcatcagtaa atctgtctct 116820
cgcgtgattt ccataggaat ggtgtagccg gggtggaggg ccgatatcac atcaagcaga 116880
aaggccataa tctctcgaaa gtaggcggtg gggctgagac catgctcagt ggccgtctgg 116940
cagggggccg ggcgcgctcc gtccttgtcc aggagacaca cgtggcttcc agagaggcgc 117000
agcccagccc tccgcagccg ctgaagccag gctcgcggaa gagcccaaaa cctgtttcgg 117060
cgccgcccgg gggccagtct ccgggtcagg tcgcggacca gggtcaacag gtggtcgtgg 117120

-continued

```
gatggcgggg ccttgtctgc ctcgggtctc gccgctagtt ggtccagggt ccaggagaag 117180
gcttcgtgcc aaaccaaaaa gggccccgag tgctccctac atccacccac gtaaagatcc 117240
ccctgaaaga tggccatcag taggcacccg ggcccgcgtc gagccttcac ccgaatgtgt 117300
ctgcgggcca cggtggcctc tccacccatc acatcccggt cgagccggct ggcatcctcc 117360
gagtctttca cgccttgcag gaaagcctag gagatacagc aacagaaagc tattagccgg 117420
tggttccccc accatcattc ttcctgttaa cgggaagaat aagagttggg caaaccccgg 117480
gggccgcgct ctcccaccca gccccgcttc tcacctgtgc tagtggctcc tctgaaggat 117540
gggcggaggt tggtgccaca aagcccagga tgaactcgtc tgcataagcc caggtcagtc 117600
ctaggtcagc ggccgcgtgt aggagaaccc gggtgacggc ggtgtagagg cccccgagtg 117660
cccgtcgcgt gtctgaggtg ccatagcggt gaagggcccg cagccaggtt tgcgcgtccc 117720
gcgcctgccc tccgccatca ggcgttccca cgggggcgcc cctggcagag aggtggcagc 117780
gggccaattc gtagagccac caagtggcat cagcctcaag gatggctgtg gcctccgcgc 117840
gcccgaccac cgtcgtctcg tcctcccccc ctccctcgcc gccttcccgc gtgcaaacgt 117900
ggcgagggtt aatctccttt cgggtcgggg gccagatttg ttgtaggagc agcgagccgc 117960
gtcgttgccc tgaccgcgcg tcgaggccca ggagggcgtc tgccaggggc gtcccagaga 118020
ctcccaggtt caggtccagt agcaggagac cctcgctgtg tggcgcccgg tgccagaagg 118080
ccggcctcgc ccgtcccaca taatggatgg gcaggaaggg aaagcccggg acatagggct 118140
ggaaatctga gccccctggg cagagttcgg ggtccaggag gtagaagatg ggcttggtgc 118200
ctctgtggtt ggcgtagcag gaggcataga tactgcggag gaaggcgtag agcccgcccc 118260
cggccatact ccaagagttg acaagccagg actcgaatcc cccagccggc tcaagaattt 118320
tcaggctgac gcggtgccgt cgggcgtccc caccacggcc ggtggccccg tcggacgaca 118380
ccagatctac ttcataagtg accggtcgca ggatgtccct aaaggggacg ggagaggggt 118440
cgtcgggagt ctcggtggaa taggtgaaaa catccccacg cggtgtcctg atgtatacgt 118500
ccaactgtcc gggagactca gagtgcctct gagcatgggg gcatgtctgt tccccctcca 118560
tctcggaccc gaagccatca acaggtgggg gttgttggtc ccgcccatca tcccccgagc 118620
agctttggca gaccacctgt gctggaaaga gaggctggaa gatgaggccc tgctcatcct 118680
ccaccctggc ggcggacaag agtctgcggt ctcgggttct aaatgaaagg tcaaataggt 118740
ccttctcggc ggcatcggcg agcatagcaa tgagcccccc gctgcgcctg agctcccgct 118800
cccatcgcaa aaagttgagt tcggtagtcg agggcgcgtt gaccacgggg ggctccaggg 118860
agcctccaag cggcggctgg caggcctgca ccacgatcag agtctcaacg tcctcccttt 118920
tgatgggcac gatgcccacg acccaaatcg cccaccaccg ccctgcggtc tgggtaacat 118980
tataaaaggt aaccgagctg acgcgggccc tgacgctctc cgcgggtgtt tccatcattg 119040
tttgagatct gaggaggact ggacccttta aaacatccgg tcacgccctt tgcaaattat 119100
ttaaaaggtg aatgctcaac tgagaccatc gcaatcatga agtcctccaa gaatgacacg 119160
ttcgtctata gaacgtgggt caaaacgctt gttgtgtact ttgtgatgtt tgtcatgtcg 119220
gcggtggtcc ccatcaccgc catgttcccc aacctggggt acccctgcta ctttaacgca 119280
ctggttgatt acggggcact taacctgacc aattacaacc tggcccacca cctgaccccc 119340
acgctctatc tggagccgcc ggagatgttt gtctacatca cactggtctt tatcgcggac 119400
tgcgtggctt tcatctacta cgcctgcggc gaggtggcgc taatcaaggc ccgaaaaaag 119460
gtctcgggtc ttacagacct ctcggcctgg gtctcggcag tgggctcccc aaccgtgctg 119520
```

-continued

```
tttttggcca tcctcaagct ctggtccata caggtcttca tccaggtcct ttcctacaag 119580
cacgtctttc tctcggcctt tgtgtacttt ttgcactttc tggcctcagt tctacacgcc 119640
tgcgcatgtg tgacccgctt ctccccggtc tgggtggtca aggcccagga caactctatt 119700
ccccaggaca ccttcttgtg gtgggtggtc ttctacctga agcccgtagt tacaaacctg 119760
tacctggggt gccttgccct ggagacgctg gtcttctcgc tcagcgtgtt cctggccctg 119820
ggcaacagct tttactttat ggtgggggac atggtgctgg gagccgtgaa cctcttcctc 119880
atcctgccca tcttctggta cattctgacg gaggtgtggc tggcctcctt cctgcggcac 119940
aactttggct tctactgcgg catgttcatc gcctccatca tcctgatcct gcccttggtc 120000
aggtacgagg ccgtctttgt ctccgccaag ctgcacacca ctgtggccat caatgtggcc 120060
atcataccta tcctgtgctc ggtggccatg ctcatcagga tatgccggat tttcaaaagc 120120
atgcgccagg gcactgacta tgtccctgtc tcggagacgg tggaactgga gctagagtca 120180
gagccgaggc ctaggccctc gcgcacgcca tcacccgggc gcaaccgccg ccgctcttct 120240
acgtcctcat cttcctccag gtcaaccagg agacagaggc ccgtctctac ccaagccctc 120300
gtctcctccg ttttaccgat gacgacggac agcgaggagg agatcttccc ctaatgcaat 120360
aaaaacttaa aacactgagg ttactttccc gtcattcttt cgggggaacg aggggaggcg 120420
ggaattgggt taagataggg gcgaagggtg ggggtgggtg caagaattgg ggctgggaat 120480
ggagagggga gtgggctagg tgccgacacc ggggtgccaa gataatggat tgagtaagca 120540
tggggctctg atcgggtccg ccgggttctc aggggtgtag tgggtgggca ttgcatattt 120600
ttgccgcggt gctgttgggc cttggactcg gggtgatcat ccgtaccatc acccgcaccc 120660
gcaccccagt ccacagccac cggccaaggt cctgggcctc ccaccaccgt tatgcctccc 120720
cctttaccca ttaattacaa gagatgttag tttggttttt tatttggcaa aaacagcaat 120780
tcatcatttt cagagtcctc atcatattcg agcccctcgt tggtttcccc gcaggccctc 120840
ccttcttcgg ccgctattag cttagtagtc tccaggttaa actcctcata gtcattatac 120900
aggttgatta ttcccccgtc cacgtcgcct atggagttga ctcgtcgtcg gcaaagagac 120960
cagagggcac ccatggcgcg gtgtcaaaag tattgtctgc gtacgctttc caggagccag 121020
ccgcggtgct caaggtctta cggatgacag agtccggcag gaccacgggt gtcaccagca 121080
ccgccacggg aatctccacc gaggcgtcca gaagcaggtc tgagccgagc gtgcaggtcg 121140
ccgggtctag aggcgaccgt tttcgaaaga aggccgtcac aatgttcacc cggggtgagc 121200
agtctctccc gggcttgcca cccccactgt ggcggacgta gtctccaaca attttgtatt 121260
ggaggagcac ctggtagaag tagttgtgcc gtggattgat gaagatgttg actgggaccc 121320
ggtctttaat accaatgcgc cccgcatttt cgcttgggtc cgtcattacg tagagcatag 121380
actccacccc cctgttggca gctaggctgt ctgccaccag gtcatgaccg gggcccagtt 121440
tgcgcttacg gacatcttta agattccagg cctcatcctg cgtcaacaga tagtcaccct 121500
ccgagggcaa ccgcccatcc gggacgtact ccacggtagg acgagctata gaattgataa 121560
atctgataaa tgacctcttg catggcctct tgtaaagcgc agtgtaggat gggtagatgg 121620
ggtcaaattc tgacttggaa aagaggtact tgaagcggca cttaatctca taaatgcagc 121680
tccggtcggt gaacagtata aagtctccct gtgactccac attgacgcaa agatccagag 121740
acaccccaaa aatgccatcc gtgggactaa tcataaagcc aaattgacgg ttggcggatg 121800
cgtccccgca gatgagctta cagacaatgt ccttgaccgt gtcctcacac cgcaggccaa 121860
```

-continued aggccacagg tcccccaaag tagtgatttg tggagatggg agctggctca aacaccttgg 121920
tgggtccatt cttaatggtg gagagcagct tggaagagga aattatgcca tttcgcaata 121980
tgtcccacat caggttctca gactgccccc tggtcatgga ctccacgtac gagcagagaa 122040
cagtcctctg ctcgtcggtg gcctcctgta gcccccagta aatggatttc agggagggac 122100
cgtccttgct gtcattctct tggactaacg aggagacaaa gtcacagaag ccagtttcac 122160
cagagaactc ttgtatttgt ttacagaggc aatagagata gacaaagcgc atggccggca 122220
tctgaggtgg acggtcaagg ttacggacaa aggcctcagt ctccggactg cggaggaagc 122280
gggcaaacgt gtaggaggtc atctcctcca tgggatcctc gagctcatcc acgtcggcca 122340
tctggaccaa agaagtcgtc tgccaagagt tcagctacca gacctggaag atgagggtgc 122400
tcaaaccgtg ggcgacagtt gaagaagtag ctctccttga acctcttttt aaggctccgg 122460
caccactgca agaattgact catatgctcc gccgtgacat ccacgcacgg actctcgcca 122520
cacgaggtca ggcccatgtc taagttcagg ttccacatct gcgacagcac ctccaacagc 122580
accacctttg gggctgcaaa ttgcaaaaag tagagcgggt cggatcggtc aaatcccatg 122640
tcagggttgg ggtaggggat tttgtgggtg gagtcagcga ggtgcatgat accatagagc 122700
agcgagtagc cgagcgactg cagatccagg cgaagggccg tctgcgcccc cacggggcca 122760
cacgccgagg ggtcagggat gtgcccagcc cccctcaaga tgtagcactt gctcaaaagg 122820
cagaggggct tataggtgtc cttggctata gaaaatggtt ccctctggca atagaggcga 122880
tagagctgcc ggcccttaga agactttagc cgcacatcca gcatcttgtt gcggtcgtgg 122940
agggaagcag tcccataatc agtcaggacc agcctaccca tgccccacat ggtgtctgtg 123000
aaatccacca ggatgttgct ggggctaatg tccgaatgga agaggccgca gtgccgattc 123060
agaaagtaaa cggcatcttt gaggccctga aagccccgca ccaggggctc aatactacca 123120
tcatgccagt ggccataatc ctggagactg catctgaact ggggcataaa cagggcgtgg 123180
caggacgtgc aggccgacag gtagtccacc agggccttgt cctgcccatc ctcggccgtg 123240
gccttcccaa tctgaatcat gtcacacacc atgagctcgt gatacagctc cgtcacagag 123300
tcatagagtt tgaccgtggc attatctgca tgtgcataca cggccccgta gctcccccgc 123360
cccagcagat actcgcaggt aatggggagg tgatcacagc gcgtcatgtt ctccggcagc 123420
tttacataga gggtctccgt catgtcatca atgttggtca ccttcaggtg tttgtgctga 123480
aaggtgaagt aatcaatgac agtcaccttc cccaaaaagg cctgggtctc tcgagggggt 123540
tctggggaga cactcaactc gccactgctg gaggagttcg tcgggctcaa ctccgcagcc 123600
atattcacat ccatgttcct caaatggctc gagggcctgt cgcagctcgt ctctggcctc 123660
aagctcctgc tcacggagct cctccacccg ctctagctgc ttgtagttga tttttggaaa 123720
ttgagtcttg gtcgcggtga ccaccctctg ataggtagaa attagctgtt tggactcaaa 123780
cgtctccctt gcgtggcgca gggactctaa ggcaccccga gcagatgtaa actgtgtttc 123840
aaacagagcg tggtccctcc caaatctgtc acgtgcgctc acagccgctc tcttttctac 123900
cgaggctctt agttgctggg ccaccagatc tcgcttagaa ctactcatct tcataagtca 123960
ccatgtccgc aactatggag cccagatcat acgtggggta gagtacggta gttccagtgg 124020
aggcttcccg gtaatttccc acagcgtcca ccatatatct ttctgcctct cccgttagaa 124080
ttaggcaagg atcatacgtg tccaccggcc ttttatactg agcgtttagg ttttgtttat 124140
gtagcaagca caaaaggcac acacgagtga tgcaaaaggg ttcctgaggc agcaggcaga 124200
gctgttttgc cattttattc aggcggctaa cgtcaaaggg aggagctata tcctcaccct 124260
tccagtcacg cacgtccaag tacagggcat acacacacct ggtgaggtgt gccaggaatg 124320
cctctatgtt ggcacatggt gtataaaccg cagtgggtag cagaataggg ccccttttgc 124380
cccgtgccgc agcgtaaacg cagtgacgct cttcgcagtg ggacctgggg ccgtagaaga 124440
gggcccacat ccaagggagt gggtcttcag gcaccaggga ggtccaggtt tgggagtggg 124500
ccaatatttg caaggcctga cctataacct catctttgtt ccaggccagc gcaattcgca 124560
taaggtcccc atcaaacacc tcaaaacaca gacccatgcc catttcaggc tgagagggct 124620
ccatccggct cgaccaacct tgtccaccaa actgccattc ttctggtaaa cgggggttga 124680
ggggcaagag ctccaaagcc aggctcgaga agtcatagtc atcctcggcc acacggccgg 124740
agctccgggc ctcgtgccag ggcctgttgt cctgggggag gatattggac acgagcagga 124800
agctcttgag tggcgtctcc accagcttaa attgctcggg cgtgtcctgg caggcctcca 124860
gtgccagttc cagacactgc ccatacctgc gggcgagcat cgggtcatcg ggcatatcgg 124920
ccttgaccgc gttgaacatg ctgtatgcct cgcagcgcgg ccgtctgacc gagaacctaa 124980
gaaacgccct tcagcaggac agcaccacgc aaggctgcct gggtgccgag accccgagta 125040
ttatgtacac aggggccaag tcagacaggt gggctcaccc tctggtgggc acaattcacg 125100
ccagtaattt atattgccca atgcttcgag catactgccg ccactatggc cccaggcccg 125160
tgtttgtagc ttctgatgaa tcattaccca tgttcggtgc gagccctgcc cttcacaccc 125220
cagtccaggt ccagatgtgc ctactaccag agctacgcga cacgttacag cgcctgctgc 125280
caccacccaa tcttgaagac tccgaggcct tgacggaatt caagaccagc gtgtcctctg 125340
cccgtgccat ccttgaggac cccaactttt tggagatgag agagtttgtc accagcctgg 125400
ccagcttcct gagtggtcag tacaagcaca agcccgcccg cctagaagca ttccagaaac 125460
aagtagtgtt acattctttt tattttctga tctcaatcaa atctttagag attacagaca 125520
ccatgtttga catctttcaa agtgctttcg gattggaaga aatgacgctg gagaagctgc 125580
acatttttaa gcaaaaagcc agcgtgtttc ttatccccag gcgccacggc aagacctgga 125640
tagtcgtggc catcatcagc ctcatcctct cgaatctctc caacgtgcaa ataggctacg 125700
tggctcacca gaaacatgtc gcgtccgccg ttttcactga aattattgac accttgacca 125760
agagcttcga ctccaagcgt gtagaggtca acaaggagac cagcaccatc acgtttaggc 125820
acagtgggaa aatctccagc accgtaatgt gtgccacctg cttcaataag aatgtaagac 125880
ctgacgtttc agtacttggc aattgtagag catagcccgg ctgtaaaggt cagaaaatcg 125940
cagcagggtc caaggttgtg ctgtacatgg gacctctttc ccattagcaa gaacccccctg 126000 caggacacgt gacatgtccg ggtgcatttt gggtgggtta aatctcagtc ccaccacaaa 126060
gggggcatcc tccggtttga acatcagacc caacaaagcc cgatgcccag ttatgggtac 126120
gtagtcgttg ttcagggccg tgcatggcag cagacaagga caggtgccag atgtgcctgg 126180
gctatcgtcc tccgtccagc cacgcaggat gttcacgtgg gccccggcac catagcatgt 126240
cacacattcc ccgttatcac atctggttag caggttgata aaatgggtca gtgatggaaa 126300
ggttggcata ttggggcagc acatcagcat gtccatgtta acgaaaaaca tgtacagggc 126360
cccttctgca taccaggcac caccccgtcc cagtgggatg atctccgagg gtgtgatatc 126420
ttgcagttct tctactgttt taacggcggt tgaggtggta aagacgtggg ccgtggtcag 126480
atctgtgcag gtgactacag ggttacccct aatctccaca ggcaccgcct cacccactgc 126540
atctgagaat accccaaagt acatgagagt caggctgtgt ggcccctgga ctgccttagt 126600

-continued

```
gaagagaacc tcgggcctgg ccacggtggc tagggttcca ttgatgtaga cggtcacata 126660
ggtgggcttc ttcttgggct tcagcacaat gagggtaaca ttcatgtagg ttttaggagg 126720
tccggctatc tgaggcacgt acacagctga cacggcggtt gtggccgtat agactttcat 126780
ctggggcgta gaggcatcgc tcagcaccca gaggcactcc ttgttgagga acttgcgaag 126840
ctgttcccgg ctactgttcg cggcggatgc catgacgtgc cagaatatat cccctctcct 126900
cgggggtgag tgccaattgg cctttaataa caaagccccc aggcagcacc aaaaatgcct 126960
gcccgtccga tgtggtggcc aggtggacgc agtgcccgtc agttccaagg gctactagct 127020
gggaagcagc cccaaccagc ccacccgggg gcctggagtc gatcacctta ccccaggccg 127080
aggccccttc ctcatacagc gggtggctat ctatccatag gcaggcatcc ggcgtctttg 127140
gtgcattgga gatagtagct ttcacccaac aactttccca actaacccgt gtctggacag 127200
tgaagaacgc ttccctgatc aggtctgaat ttttatagat acgggagtag gaggtgggaa 127260
taacaactgg gatttcttgt tgtgctgtcc aggcctgcat ggccagtttt tccctgaagc 127320
tagcagaaat tctgagggcc actgaaatga ggaagcgaaa ctccctctct ggagctccca 127380
aaattgaaac ctcagcaaga tctgttgctg gggaggcatg ggtgacagct gtcatcctgt 127440
gcagtctgcc ctgggcactc agctctggat atgtgacaac atagagagcg tgggggctaa 127500
aaatatgagc aattcccctg accagggccc tggactcacg aatggcccga cgggtcttag 127560
agaaagaaac aggcaccctc gagagtgccc ccgacccgac ccccacagtg ccgccagtcc 127620
ctgctcggcc tccgccgcct tccccaccgg cgctgccccg gatgttgctg gggttctcga 127680
gggctgggtg gtgcttggac acagaggtct cagcagccgc cttggtctcg gccccggccc 127740
taagtctgag ccccaggcaa agggccggac tcccagcgtg gcccaacctc tgctcccctc 127800
tattctcctc ttgcgttatc tccaatagaa tttgcttgag gtcatacgtt ttagggtgct 127860
cgacctgggc cgcggccacc ggcatatgct ctatacccgc ccctccgggg ggcccaggat 127920
ctataggtat gggctgcata gccgcagcag actcctggac cccagaggcc tctctgataa 127980
gatgcccgtc ggtcagagcc cttttggccc cctcaaagag agacaggtaa taaatctgta 128040
gctccccaac cagccctcct tcatcgtaaa atcgaagggc ggccacgtgg aaggggttgt 128100
agagctctgg aaggccctca tcgcagtaca ctggcacact ggtaaacgtg ccccgatggc 128160
taggccgtcc gggcagcatg ccccgagcag caaacacgcg gcagaccctc gtgagacccg 128220
tccggtcact gaagagagtc tggcaccagg ccccctcgca gtttggcacg cgattggggc 128280
aaagctctgc cataaccgtg tcgggaacaa ataggtgcac gaggaggggg gtcccgaggc 128340
cactcaacac ttggttgtca atgtggacat ccatagctct ctcatgcgtt tggctacagc 128400
atcatagcgc ttgtttctgg tggatttaaa taacagggcc ccgtagacag tcttttgtga 128460
gtaaatagag atgatgacat ggatgtagag actgaggacc acatccacca ccttctcgga 128520
ggaggccccc ctaaacagca tcaggcagca agggaacaca aaggaaacca gggccgggat 128580
gtgaggcctc agcgccccct cctgatcaaa gagggcctcg ctgaccccgg agatgacatt 128640
ctcattcaga aagtagtgat agaggtgatt gaccacagtc ttaaccaggc cctggacttg 128700
ttcaggctcc cacttgtccc gctggtcctg tgtgtcttgt cggatctcgg tccagggcct 128760
cagcgccggc tggaaatgcg gccccatgta gttgcctgta agggcgcaca ccactccctc 128820
atgggtctca atcagggtgc actcgctgga tccatcacat acgtggtact cgccacagcc 128880
ccagcaggca aacacggagg ccatgctctc aggtaacggg agatggaact ccagcttact 128940
atacgagcac aggtggcgag gattgggctc atccgtgccc ccctcccccc gcgggaggct 129000
```

caatcggcct tggtctgaca ttccaccccg gccaggtcca ggagggtgca aatattctcc 129060
aggcgctgca cctcagagac ctcctgctca aagagacctc ccaccgccac gtagacgcgg 129120
gccaccgtcc ggggaaggtc agtggggtcc cagctcagca attctccaaa ttctctctcc 129180
ccaatagtgc ctcgcttctt atcctgtctt tcagagcatc cgggggcaga catttcacct 129240
cttgtttgtg gacgaggcta actttatcaa gaaggaggcc ctgccggcga tcctgggctt 129300
tatgcttcag aaggatgcca agattatctt catctcgtct gtgaactcgg ctgaccaggc 129360
caccagcttt ctttataagc tgaaggatgc tcaggagcgg ctgctgaacg tggtaagtta 129420
tgtgtgtcag gagcatcggc aagattttga catgcaggac agcatggtct catgcccctg 129480
ctttcgcctg cacatcccgt cctacatcac catggacagc aacatccgag caaccaccaa 129540
cctctttctg gacggggcct ttagcaccga gctgatgggt gacacctcct cgctgagcca 129600
gggtagcctg agccgcactg tgcgtgacga tgccatcaac cagctggagc tctgccgggt 129660
tgacaccctc aacccccgag tagccggacg cctagcctcc tccctctacg tgtacgttga 129720
tccggcctat accaacaaca catccgcatc aggcaccgga atcgccgccg tgactcacga 129780
cagggcggac cctaacaggg tcatcgtcct gggcctggaa cacttcttcc tcaaggacct 129840
aacaggggac gctgccctcc agatcgccac ctgcgtcgtg gccctcgtct cctcgatcgt 129900
caccctgcac ccccacttgg aggaggtgaa ggtagccgtg gagggcaaca gcagtcagga 129960
ctctgcggtg gccattgcct caatcattgg ggaatcctgc cccctcccct gcgccttcgt 130020
gcacaccaag gacaagacgt ccagcctgca gtggcccatg tacctcctga ctaatgagaa 130080
gtccaaggcc tttgagaggc tcatctacgc agtgaacacg gccagccttt ctgccagtca 130140
ggtcaccgtc tccaacacca tccagctctc cttcgatccg gtcctctatc tcatctccca 130200
gatcagggcc atcaagccca tccctctccg cgacggtacc tacacctaca ccggcaagca 130260
gcgcaacctc tctgacgacg tgctggttgc gctagtcatg gctcattttc tcgcaacaac 130320
acagaagcac acgttcaaga aagttcatta aactttattg actacaccag tcccttgtaa 130380
agcgacgggt ctcgcgtgac ggcattcgtg agcagggctt cgtccagggg cttgttcttg 130440
gcggacatca ttagcccagc cgcaaatatc agaattagca tcagaaaagt gagccccaca 130500
aacaccagtg tccagagagg aagaccgtaa gataaagatg gctgcctctc atctggaacg 130560
gtgggaagct cagcagttgt ttttgtggca ttggacgtcc ctttggagga cagcgtgggg 130620
gccaaggtgg tagcgttggt aatacgggta gtagcactgg tggtggagga ggacctggtg 130680
gtgacattgc tagtcacacc cgtggaggtt cctgttccgg cctcggtggc agtgatgttc 130740
tgtgcagtaa ccttagtggt gacattgatg gtggatgcgt tggaagttgt tgggactggt 130800
gtgacagttg tcccagtgaa tgtcaccgtg gttgtgttgg tgctcagaat agcagttgtg 130860
gttatagggg cgctagtcgt ggtcaaggtc gtagactggt ttgtgctagg acccgatgcc 130920
gacggtgatg gtgtagtcac agccgttgtg cctgtcacgt tccccgccga ggccgtcgaa 130980
ctgccactag atgtccaaat aaggcttgtc tcacagatga gtatcatggc cataacagcg 131040
cctgccttgt ctctggcgtg tgccatcgcg tctggacgca gaaggcctcc cggcctcttt 131100
tatagctagt ctccacaccc aatactctac tgaaccatca catacatgac ctcctcgagg 131160
tatgcaggga atgagcggtc cgtgagccgg tcaacacgac attgcttccg tttcatgcct 131220
ccagctgccc ctgaccagtt aggacccttg acggatgtct ttaacggcgc ggtgcagttg 131280
gtcaccaatg acggcctaaa ggccaacaca tccttgaagc agggcgtagg aatggtacca 131340

-continued aactcggggc ccaccccatc aaagacataa tatgtctcat agtggcagtg atgatgcatc 131400
accaccacag cactcgccag gaccctctgc atatcttgta caaggcgcct ttcaactcgg 131460
ccactggctc tggtgacgtt aaatgtcctg ttcctattag tcacagcctg tagatttggg 131520
cacccagact caaaaagtgc agctacatga agggcagccg cctcaaatcc accatgaccc 131580
ccatggctgt ccgtgttgtt ggggtaataa gtcacattgt taatgaccac ggccgggata 131640
agggtgtaaa ccttgcagaa tggattggtc ggacacccat aagacagggg caccccaaaa 131700
tcacgcccct taccccgaag caccttggcc cccaccggca taaagctggg caaaaagagt 131760
gggttaaaac caaaggcgag tagggccagg aacgccaaat agcagcagta atagatgaaa 131820
acaaagctca gcatgaaaca gcgtggaggc tcagctaggg tctctgcctc tccatcatag 131880
acatcttcct tgaatctcat tctctcaccg catacctcgc tcttcatcca ggagggggcc 131940
atggctgcca ttctaccagt taacgaggag agagagagta ggtccgcgga aattggtgcc 132000
cctctctgcc ctcctgacga ggccatggtg tcatccatct ccgcagtccg ttcttcagct 132060
ttggcattgg tccgggtccg ggtggtctga ttttgattct gatcctgggt attggtcttg 132120
gtctctcctc ccccattggc atggattggc ataggtgggt gtggctcagg ctcaggttcc 132180
ggccctggga cggcagcagc cgccgggacg gtgaagtcgt ggaaggtaga ggcccgtccc 132240
tcccgaggtc gtggggccgg agccttataa aagacttcca ccctctcccc gctggccaag 132300
acacgccgct cgtggaccac gccatcttcc tcccggctga ttgtgtggct gacggtgccg 132360
tgttccaccg ccacttgttc atcgaccatg gtaccccctt tatcttaacc agcaagtggc 132420
cgtcagggtc tcttgagagt atgccgctgt ggccaagcga ggccccaaat taaatagtga 132480
tgccaaagac tgtaggtagg tcatcatcac acgcatgcgt gataaatcat ccgccactga 132540
caggtcatcc aggtctatcc gggctatctc atccggcacc atttcctgga agagattcaa 132600
gaggtcgtga tgctcatgcc ggataaggcc tcggaccagg cgcatactgg ccctgggcag 132660
cagggtcacc atgatgcaaa agtagagact cagattgtcc agcagggcca agccaagggg 132720
ccctggcacc tccgggaggg ccaactcgta gtggtgcccc aggtatgaaa cagagccaag 132780
atgcatgtgt acatcgagca tgtctgcgtt cccgggagcc tgcatgacaa cccgggagta 132840
cacgttaaac aggagaatct tctgcagcac ctcctctgct atgggcgtag gcagcaccat 132900
ggggaaaaca atgtccacat cattggactc taacttcacg gtggcatgct ctcgtccaaa 132960 taccggggc ataacactga ggctcccggt cccatgccac tggaaaaagg gctggtactt 133020
gttcttaatg gcgtaggtct gacctggaac aatcttggtg agtatcaaac tgtccacgct 133080
aacctcatcc agcacggcca gggtgcaatc agacaggtag ttgtacatgg acacgtagtc 133140
cgggaccgtc tctagagagt acacctgacc caagcccaat ccctgcacat tctgcgtccc 133200
gtgagtggaa gccaggggta agatgcagcc aatcctctgt tgcatcttgg caatctcatc 133260
ggtatacaga cgagaggaga gagacactac cactttcaaa tccatcttta ttgacaatta 133320
tcaaaaaacc accttatttc caaactttaa tattcttcgt accggcgcca cctcttcaat 133380
tatatagtgt ccgtaatgga tgggggcgtg ggtctgtttg acagacataa actcatcgat 133440
gagtgcccgg gaggaggctg agagtgcggg gaatgcctcc tgcagaaagc tgcagggctg 133500
ctccagaaac acgtcagtgc cagcaatcac tacaaactgc acctctgtgt tgctggtggc 133560
tgggtgccct ccaagtcgct ggctgtactc gttgaccatg ttgtagagtc ccctgttgtt 133620
gcgcagaagc tcctccttgt tgaaaaatgc ccggcagggg ctgtagaggc ccgggacggc 133680
cgtctggcga taggaggagt tgtacatgat gtcacccaga gaacccagct gagatgccca 133740

-continued gggattcaca gtgctccggt attcataggc ggcatccggg cgagaatggt catagatgag 133800
cccctcggca acctcctgat tgtagttttc acaggagacc acacaggcgg cccgtcccct 133860
tggagagttg gacttttgaa aataagccac gtctgccgtg accggtgtta cgataatctc 133920
acaggtggcc tgctggccgt ggcagagtcc tggagctcca ttaacattag tcatacctgc 133980
caggtatgtc ctggggtccc gaagcagcgt cccattgcgc tgagcgccca ccttggcctt 134040
gatgtagtca ttgacttgct ggttgccaaa ggcctcggcc ggaaagacgc taaagaagtc 134100
ttgggtgtgg atacccatgt cagtagtgat ggccgccacc ctggccggag tcatggtcga 134160
gctataacta agcccggtgt cgatggaggc catctcgtga tgcacctcaa aggttaccgc 134220
gtccaccctg gcctcccggc ggctaacatt tggggtccca atgaacatgg atgttgaggc 134280
cctggagcta aacaatatgt tttcagagag gatctcatcg gtcctgacca cggtcatggc 134340
cacccctggg tggatcttga gcttggcctg ggcaatatag gccatggggg acatcttgat 134400
gtgcatggcg gtcattccac tgattgaaac gagggaagga agacattcgg ccgcgtattt 134460
gcccatgggc gagcggtgcc actcccggta ctctgcaaag agctgctctg gccggttgaa 134520
ggcttccacg gcccgctgct gaggattgcg cataacaaag gtggcaacat cctggtgcat 134580
ggtggcagcc actcgcgggt ccccgtaaaa catatggaaa ggaatggcgt gaaagagaca 134640
ctgggtgacg gcccgggtcc tctcggagaa ggcaaaggcc accagcccgt tcaccaaaac 134700
agtctgctct gtccgcttgt cggcgggatt cggggccagc tgctgcgtaa cgtcattgtc 134760
caccgacaca cgcacggcac gggtgaaagt ggggcaggtc atgaatgagg cgctgaggtc 134820
cctgatcatg cccacggtgg ggcggaggtc ggagatctcc agcagatccc tgagcgtccc 134880
attctccaaa ttgtcgagga tgtcctcgtc cctggtaaaa tggtggctga aggctggccc 134940
gttgtaggcc agggtctggg ccacgtgctg aaagtccacc ccgaggccgc acatgtgggc 135000
attggtgcag gttgggagga aaacgtagta aaagatcttt tccagcacat ccgcatgccc 135060
ctcatctaca taagggccta ggtgcagacg gaaatcgtgg tcgtggtctc cgttaacccg 135120
gtagccgtac aaggccacaa attgggcagc catctcatcc atgtttccaa ccctctcaat 135180
aaactggggc gcggccaggg tgtcagcgta aacctcattt ccgataataa tctgggggc 135240
ccggtcacta acggtgagaa gatgggtgaa aatgtctgtg taggccaccg gggggagcag 135300
gttagggtcc aggagagcgc agacatactg acccacgctc tcatccccca caacatctga 135360
cccggccagg cgcatcaggg cctgctctag ggctataagt tccccataga tttttctata 135420
catggaatag gcctccttgg agatggcgtt atttcccagg tggcggcaga tgaacttgat 135480
catggaaaag ctgttcacaa aggcaagcct ccctgaccgt tcccagtagg tgttgatgca 135540
cagggacacc aaaggcacgt tcatgacaaa cttttcctca aacccgtgga tcatagcctc 135600
gactacgtag aagaaggctg gataggcagt gtcataggca gtatcctgca cagtctcaat 135660
aacggcctga tccaccacgt gggccagaga tgtggcggtc tcaaactgct gcccccgggc 135720
ctcttggaat gcagctgggg ccaggggagt cggcaggtta cccaccatta gccggtgcac 135780
agccctgtgc ctggccctct ccccggcatc cctgccaatg taaatatcat aaagggggtg 135840
cagctccagc cgcagcaggt cataattgga cgggtggagg aagtcttcgg tgggcagccc 135900
gcacttgaga gctatatctg tcacgggggc tgcatacttg ttatcataga actcgtccac 135960
aataacaagc acattcatgt gattgggcct cctgtgttgc agggagtagg tctcgcgcct 136020
gtctcgcggg gccggggccg cgttgaggct gtttagggta tgggcgggtg tgtggagtcg 136080

-continued ggggtgacag agaaccttga gagcattctg taggttaaac gcgaggagaa ggttattctt 136140
gtttacgatc catgcctcca ccggtagctg ctgtgtgggg ttgtccagca ttttgatggc 136200
ggcggaggtc gtgtacttgg gattgggcat aaacaggccc actgggaaat agtagctgta 136260
ctgcattctt ctgttgaggg ggtatgggga ctgagtgtca ttgtacatct tttgcaggct 136320
ttccacggcc accgcgtggt tgcccagctt gatgacggcg gctgagatcg gcacccgggg 136380
ctgatcctcg acccctgcgg ccacagccgg caggtcagac ttggtgcttc cggctttttc 136440
cggtgagtcc acgatcctag ccatgaaatg ctcaaacgta cgcatcacgc gcccgtagct 136500
cacggcagtg accaggttct ccccccgtac cacaaaagaa gcatagctcg agggccccat 136560
aatctggttg tcggcctcct cacccaggaa ggtcaagagc tggcgcagaa cgttgtcggt 136620
gacaataaac accccccca ctggctctcc cccttggcg gtcgtgtagg tactgacccc 136680
cttgagcacg ctctccccgg acacggccgc taccatctca gagagacggc ttcgcacgta 136740
ctgagaaaac ccggagccca tgttctcggc ccggtccagg aagaaggagt gctccagcag 136800
atgcctcttg aacatggcaa tgaggtcaga cttgacagtc ttggagaacc ccctctcagt 136860
gaaggtggga tccgccaggg tctgcaggat aaacatggga ggggcatggc gaagcttcac 136920
actcaggacg gtgttaatga ggcccctctc cagggcatcg accccaaact gtagggccga 136980
ggccacggtc ttgacagccc ccacgtactc tgcgtactcg accggggtct cggggatact 137040
atgcaggatc tccagatcca gcatggacag ttccatttcc gtactaatgt ggtgtttgtg 137100
gcaattttg accacaatga atgtccgctg cttgctgggt ctccttccgt ccccgtgagc 137160
aatggtgggg acggagattc gaaattgaat cttgccatcc gtcatacgac tcaggtcttt 137220
gaattccgtg ttcacacagg acacggccag tgccgtctcc aggaagcgaa catattggat 137280
ggcgttcgtg tagaccccga gtagcacctc aaacttgatg cccgcctctc tggcatcctt 137340
gcccaccagc aggtcaaagc tatgaaacaa cccctcagcc gctgactgcc gcaggttcga 137400
gagcaggtcg gcatccaccg tcagataggg gaagggtctg ttttccacac cctcatttga 137460
ggccatgaca caaggtaaga gggagatggg gggaggtctc gagggcttct cttcacagct 137520
gggtctcttt tacgccctgg cctgcaaccg cagcccaccc acacttcccg aggatgctac 137580
ccttctaatc aaatggttgg acacggccct gggcagggag gccacctttt acgcgtgtcg 137640
ggctatgcgt cggcttctac tcggcgttat ccgaatgaat gactgccagg agctgccacc 137700
cggtttaata attctgagtc cggcaccgt ccctggcccc cttggagtcc agagtctgga 137760
gcatacagac tgcgaaatat ggtcctctgc ccaccctgac cacgctgccc acctcccggt 137820
gcccagggtc atcacataca ccgactgccc gggttccata aacacgagct caatgtttcg 137880
ccttatcatc cgctacttgt ctcatcacca atttgagcgc tgcttcgagc agttctgccg 137940
cgtggtcccg cgtcggcttc ctagggacct gtaagcgaaa ctctgcaaag atgctggctc 138000
atctgaatca ggttaccagg atcccccccct gtccgccctt cagcgggcgg gaggccagac 138060
tcaagttcca cttcttctcc tggagcacat tcatgctgtc atggccaaac aatgccacac 138120
tccgggagat caggacgagg gccgccacca acctcaccca ccacccacat ctagtggata 138180
ctctgtacca cgcctctccg cagaccccat ttctgacacg cagcggtgct ctataccgct 138240
tcgtcacctg ttgcaactgc accctgccca atatctccat ccagcagtgc aaggccgggg 138300
acagaccggg ggacctggag atcattctac agagtaacgg cggagggagg cccgcgagct 138360
tccagttccc ctcctcccca actggctccc tattgcgatg catagttgct gcgtccctgc 138420
tgccggaggt gtccgtgggg caccaggagc tgtctccgct gcggtccaga agccagggag 138480

-continued ggcagacgga tgtcaggtcg ggcccggacc cggcccggag actggtggcc ctcctgcgaa 138540
gggaagatgg ggcacctaaa gacccccctc tgggaccgtt tggacacccc cgggggcccg 138600
gcccggccaa gagcgaagac gaggagtctg agcgtcgaga cgcccctcca cccccgctcg 138660
attccagctt ccaagcttcc cggttggtgc ccgtggggcc tgggtttcgc ctgctcgtgt 138720
tcaacaccaa tcgggtgatc aacactaaat tggtgtgctc agagcccctg gtgaagatgc 138780
gagtttgcaa tgtcccccgc ctcatcaaca actttgtagc ccgcaagtac gtggtgaaag 138840
agacggcgtt caccgtcagt ctattcttta cggacggggt gggggccaac ctagccatca 138900
atgtcaatat cagtggcacc tatctgagct tcctattggc catgacgtca ctgcggtgct 138960
tcctgcctgt ggaggctatt tatcccgcgg ccgtgtcaaa ctggaactcg actctagatc 139020
tccatgggct ggaaaatcag agcctagtca gagagaaccg aagcggggtc ttttggacta 139080
ccaactttcc ctcggtggtg tcctgccggg acggtctcaa cgtgtcctgg tttaaggccg 139140
caactgccac catatctcga gtgcacgggc agacattgga gcagcacctg atccgtgaaa 139200
tcacccccat cgtgacgcat cgagaggcaa aaatctcccg gattaaaaac cggctcttta 139260
ccctgctaga gctacgcaat cggagtcaga ttcaagtgct gcacaagcgt ttcctggaag 139320
gcctgctaga ctgcgcctcc ctcctgcgcc tggatcccag ctgtatcaac cgaatcgcct 139380
ccgagggcct gtttgatttc tccaagagaa gcatcgccca ctccaaaaac cgacacgagt 139440
gcgcgcttct gggtcacaga cattcggcga acgtgacaaa gctggtggta aacgagcgca 139500
agacccgcct ggacatactg ggccgtaacg ctaacttttt aacgaggtgt aagcatcagg 139560
ttaatctaag acagtcacct attttcctga ccctcctgag gcacatccgc cgacgtctgg 139620
gcctgggccg tgcttccgta aaacgagaga ttacccttct cctggcccac ctgcgcaaaa 139680
agacagcccc catccactgc cgtgatgctc aagtgtaagc agcccggggc ccgcttcatt 139740
cacggggccg tgcacctgcc atcgggacag attgtcttcc acaccatcca cagccccact 139800
cttgcctcgg cgctgggact gcctggggaa aatgtaccca tcccggccct cttccgtgcc 139860
tcgggcctca acgtccgtga gagcctaccc atgaccaaca tgagggcacc gatcatctcg 139920
ctggctcgcc tcatcctggc ccccaacccc tatatcctag agggacagct gacggtgggc 139980
atgacacagg acaacggcat tcccgtgctt tttgccaggc ctgtcattga ggtaaaaagc 140040
gggcctgagt ccaacattaa agcctcctcg caacttatga tagcagaaga ctcctgcctg 140100
aatcagatcg ccccctttc cgcatcagag cacccgcct tctccatggt tgagtccgta 140160
aaacgagtcc gggtcgatga gggagcaaac acccggcgca ccatccggga tattctggag 140220
atccccgtga ctgtgctctc atccctgcaa ctgtctccca ccaagtccat cctgaaaaag 140280
gcaccggagc ccccacctcc ggagccccaa gccaccttcg atgccacccc ctatgcccgc 140340
atcttttacg acatcgggcg acaggtgccc aagctgggca atgcccccgc cgcgcaggtc 140400
agcaacgtgc tcatcgccaa ccgctcccac aactctctaa ggctggtgcc caatccggac 140460
ttgctgcctc tccagcattt gtacctcaag cacgtagtgc taaagagtct gaatctggag 140520
aatatagtgc aggactttga ggccatcttc acctccccgt ctgataccat cagtgaggct 140580
gaaaccaagg cctttgagaa gctggtggag caagccaaaa acaccgtaga gaacatagtc 140640
ttttgcctca acagcatctg ttccacctct acactcccag atgtcgtccc cgatgtcaat 140700
aacccaaaca ttagcctggc tctagagaag tattttctca tgttccctcc ctcaggcacc 140760
attatgagaa atgtcagatt cgccaccccc atcgtccggc tcttgtgcca aggggctgag 140820

-continued

```
cttggcacca tggcacagtt tctaggaaag tacatcaagg tcaagaagga aactggaatg 140880
tacacactgg tcaagcttta ttacctgctg cgcatctaaa ggaaaaacat aacaatcttg 140940
tgaaccagaa agatacccag agcaaaagca ataaagtaca ggattattgc caaaacaacg 141000
tgtgctcttt cttcatacag gcccgcaatt tccatgacag tcccgttggt ggtcagcagc 141060
agatagtgaa cgtggaggtt gtcaaaatca aagtagttgg agctcaagat ggagttttgg 141120
acttcctggg aggtgatgta ggttgtagtt tccaggcctt ccttttcatc ataactgagc 141180
agggcaaagc cacaaaaaat gcaggatttc tgcgtcctgg taaaattctg gatctttgga 141240
atctggcggg gctccccagc cacagcaccc tgcgaacatt tattcattat aacgggggag 141300
agaaagagag agctgctgag ataggtggtg ctggcctcgt atagcgccga gcctcggacc 141360
tcacggtcac tagagattat gaatgtcaca ttgatgagcg ggataatcat cagaactttg 141420
tcgagcctgt ccacgcattt gtaggcgggg agatgccacg catccctgtc ttctcgctcc 141480
aaagagagcc gcccaagaaa cccatccaca gcatttgaaa cggccgcctg gtccagcgtt 141540
gcctcctggg gggccatgct cagcagcttg tctcgtgtga ggtcaaatcg taggctgagg 141600
tagcacggtg agaagagccc gctctctgtc cccagggcta gcccccgcaa aacctcccca 141660
atctctaggg ccgagcacag ggcggtggac agcagttggt atagggcaag gttgggcccc 141720
tgggtagtca cgttcagccg caactcgcgt agcaccacgt ggctgccgat aaacagggtc 141780
tctctcatca cggtatgcag gggctggaaa agggggtggc ggttgtaggc cgagagaagc 141840
acagatgtgg cgcctccaat gaggccactg taaaccccgg ccttggggta gccgacggtg 141900
gctaacctca gcgcgtactc ctgtttctca gtagtcaggt gacccagctc ctccatcttg 141960
accgtggcca tcagcatggc ggccaagcgc tccagcccgt aggattgcat gcccttgaca 142020
gtggccccat aacatatgcc gatgatgtct ttcaggacag tcagctcaaa gaagctcttg 142080
gccaaccagc ggaggtccac gcagccattg ccagtctcac ccacagcatg acccacctta 142140
aagaaggcca cagaaacctc aaacatggta gtcagcgttt ccgtgtccag ttccggctcc 142200
cggcagcctc ccttcatctc cagcaggacc agtttctgga gaacgtagcg agcgtagctg 142260
gcggctgtca tggtgacggc tcgggaaaac atatccttca ggttgggtac aaagtagttg 142320
tgaaagttgg cataatgcac aaaggttgta acaatcacca gggaatagtc cccgctttgg 142380
gcactggtta aggatgggta actaaaaggc cccctcagat ccggcaggtc cttcgtcttg 142440
ccaaagacca ggctcaacac atgctcatct cccttctcgg tcactcgctt gtaggtgccc 142500
atcagaaatt tagaagtcat ggcccccgtg tactgaaact tgtccccgtt gatggacagg 142560
gccacataag acaagtgaca gcgcagctga taaaagacat agctgtgtgg ccgcgtgttg 142620
ggcagcatgg tgccaatata gtagaagagc tgcttctcaa ggggggcact aagcatgcag 142680
gcaggggaat tcaggccgct aatgactccg ggatggacct tagatgcatc cacttgcatg 142740
gatccttcag agacagcagg gatatcgaca ggctcggcca gcgcaatacc aagggtacca 142800
gacgtcttgt aaattaactt gtagcggtta agcatagacg ccaaatcttc ggtgacattt 142860
gcctctctcc acagcgcctc tgggctaagg cctgggacct ttgccatcag ttcggtccat 142920
gggatggtgt aatgcgaagc atgcccctct atgtccaggt gcagcttaac ctcgctgagg 142980
ctggcagccc ccacctccca tagcaacacc aggcaaaaaa cacagagcaa ctgcatccta 143040
gtcccgattt cccctctcaa aatcagagat caccttgctc agaccagccc aatcgaaaaa 143100
ctgagatcgt attgccggat tcttcaatgc ctgcatgtaa atctccgtcc agcatccagg 143160
taaatcgtcc tgaaactctg agaggtccac aagcacaaac tgaaggtagg ctagcgttcg 143220
```

ggtgaacgca agacaaactt ccaacaacac cgcgtcggct cggaaaggct gtatgacttc 143280
cttaagtaca ctaaagatgc tgttcttata cagcttctcg gccacaccac ttcgaattat 143340
gggggtgtgg ctttgatgac atactgtcgt gattgttgtt agaccggcac ataccttcac 143400
aatgtcctcg gggcaaaat actgtgttag gagccaggca cagtaaacgg cgtgatatgc 143460
atcgttgaca ctcttcaggt agccagcatc cagtcctgac tcatgtttcc tccctcgctt 143520
cttcaggcgg cgcatgttct cctccacgtt taacttcatc cagactatgg tgtcccccgg 143580
gtctgcggta aacgtggcca aaacttgaat aaagtcacta taggagagaa gctggctccg 143640
gagcagcatt agagggaaaa ccacggaggc cgacagcaaa tggcgatcat gcaaaatcca 143700
acaatccagg ggcgcgactg acctggcacc agactcggta accagcaagc tccgcttcct 143760
agaggccaag actctgaaag gggtggtaaa tttcatctgg catgctaaaa cctcagccga 143820
cgtgtcttcc cttccatgcc tcgcccgagt cacattcttg tgcatggcct taatggcatt 143880
ttcatacaca tgagtccagt accgcatcgg ttcagggact acaatggtca ggtccccaaa 143940
gacagccttc aaatgattca gcatagtagt ctttcccaca ccaggggcac cttccaaaaa 144000
tagggaacag gcaggtttga ttactggtac atgatttgtt aggtgggtca caattggaac 144060
ccgcatgctc tccttcctct gagccttggc ctggcgggtg tcttgggcat catccagatt 144120
cagaacattc atcacactcc cacttagccg cttcagctgg gcagcatgct tggataactt 144180
actaaactcg cgcccatggg cggccaggtg ttcgaagaga ccagaaggct taccccttgcc 144240 accattcttt tgttttaacg cggaatgaga agagggcctg cggaaattag actcatcctc 144300
agactcacag tcagatttgt catcgagccc aaggccggcc aggccctcct caaagccttt 144360
ctggtacatg aagctccggc tcgtggagtc cgcacctcct tctgtgcacg aagttttgcg 144420
gaaccaggag aaggggtctg gcgtcttgct ggggccacac tcccggctac ggggcttcgg 144480
ggtaggggca gtaggctttt ggtgtgcggg tgctggtggc tgggctcccc tgggcagggt 144540
aaaggggcac gatgtgtgcc ggctacccgg agagtttcca gtattagatg tcacggcagc 144600
ctgggtccgg cacggcaccc tctccccaga cagtccggtc ggagccatca aggggggcca 144660
gtgggtgggc acctggtaga ggccgtcgtc atcttcctca cctgcccctg agtcactacc 144720
ggttggggta agaactgagg gggcaaagtc atcaatctca gcgtaaaagt tttcgtgtct 144780
ttcgttttca ggggactcat cctcctgaca ttttcgccag ccgccgggcg ggccggcctc 144840
ctttcctgga aatccagcca tggatcccac ccggggtctg tgtgccctct ccacacacga 144900
cctggcaaaa tttcacagtc ttcccccggc tagaaaggcg gcaggtaagc gagcgcacct 144960
tcggtgttac tccaagctgc tctctcttaa gagctgggag caactggcct cttttttgtc 145020
tctgcccccg ggacccacgt ttacagactt tagactattt ttcgaagtca ccctgggtcg 145080
gagaatcgca gattgcgttg tggtagctct gcagccttat ccccggtgtt atattgtaga 145140
atttaagacg gccatgagca acacggccaa cccgcaaagc gttactcgca aggcacagag 145200
gctagagggc accgcccagt tgtgtgactg tgccaatttt cttcgcacgt cctgcccccc 145260
cgtgctgggc agtcagggcc tggaagtctt ggcggcgttg gtatttaaaa accagcgatc 145320
cctgagaacg ctccaggtag agtttccagc cctgggccaa aagaccctcc ccacctccac 145380
caccggcctg ctaaacctcc tctcccgctg gcaggatggc gctctccggg cacgtcttga 145440
tagaccccgc ccgactgccc agggacacag gccccgaact catgtgggcc ccaagccttc 145500
gcaactcact gcgcgtgtcc cccgaagcgc tcgagctggc agagcgggag gccgaaaggg 145560

-continued ccaggtcgga gcggtgggac aggtgtgccc aggtgctcaa aaataggctg ctccgcgtgg 145620
agctggacgg catcatgcgt gaccacctgg ccagggcgga ggagatccgc caggacctgg 145680
atgctgtagt ggccttctct gatggcctgg agagcatgca ggtcaggtcc ccctccacgg 145740
gagggcgctc tgcgccagcc ccgccctccc catccccagc ccagccgttc actcggctca 145800
ccgggaacgc ccagtatgca gtctcaatct ctcccacgga cccccctctg atggtggccg 145860
gcagcctggc tcaaacgctg cttggtaatc tgtacgggaa catcaaccag tgggtaccgt 145920
ccttcggacc ctggtacagg accatgtcgg ctaatgccat gcagcggcgc gtgttcccta 145980
agcagctgag gggcaacctg aactttacca actccgtctc cctaaagctg atgacagaag 146040
tggtggcggt gcttgagggc accacccagg actttttctc agacgtcagg cacctgccag 146100
acctccaggc tgccctgatc ctctcggtgg cctacctgct actccagggg ggctcctcac 146160
accagcagcg ccccctccct gcctcacggg aagagctgct ggagctgggc ccggagagcc 146220
tagagaaaat catcgccgac ctcaaggcca agtcacccgg cggaaatttt atgattttaa 146280
caagcggaaa caaggaagcg cgccagtcaa tagcccctct caaccgacag gcggcatatc 146340
cacccggcac attcgcggac aataagattt acaacctgtt tgtgggagcg ggactactgc 146400
ccacgacggc cgcgctgaac gtgcccgggg cggcgggtcg ggaccgggac ctggtgtacc 146460
ggatcgccaa ccagatcttt ggggaggatg tgccccccttt ctcatctcac cagtggaacc 146520
tgcgcgtagg tttagccgca ctcgaggccc tgatgctcgt ctacacgctc tgcgagaccg 146580
ccaacctggc cgaggcggcc acccggcgtc tacacctatc gtccctgctc ccccaggcaa 146640
tgcagcggcg caagcctgcc atggcgtcag ctggtatgcc gggcgcctat ccagtccaga 146700
cgcttttccg ccacggggag ctcttccgct tcatctgggc ccactacgtg aggcccacgg 146760
tggcggcaga cccccaggcc tccatcagct ctcttttccc cgggctggtt ttgctggccc 146820
tggagctgaa gttgatggat gggcaggctc cctcccatta tgccataaac ctgaccggac 146880
aaaagtttga caccctcttt gagattatca accagaagct tttatttcac gacccggctg 146940
ccatgctggc ggcgcgcaca cagctgcgtc tagccttcga ggacggcgtc ggtgttgccc 147000
tggggcgccc ctcgcccatg cttgcggcgc gggagatcct ggagcgtcag ttctcagcct 147060
cggatgacta cgaccggctg tacttcctga cgctgggcta cctggcctcc ccggtggccc 147120
caagctgagc cagttcctcg cactggagtg ggtcattggc aaaaaggtaa ataaactcat 147180
cgcacggggg ttttgcctcc ttctcgtctc ttgtttcggg taggggagta aggccgctgc 147240
caggccgcca tgctcagggc cacggcgtgc cagaggccct cgtagtcgtg cgcatccgag 147300
aggatggcac ggtccagaag cagatagccg gccaggcaga ggaaggccac aaagaggggg 147360
cgaaggcgtg cccgaacccg ggtttcatgc tcgtctgcac cccagtggac aaggcagtag 147420
aggacaccca ccaccaggcg gttagggagg acactgccaa ggttgaagag cagatttccg 147480
tcagccaggg tgacctggct caggtccggc gccctgcgag tccaagctgc gcccacacac 147540
atgcacagac ggcccctgtg acatcaggcc ggtcatgcaa aaacagacaa agagaccgtg 147600
agcggttacc ggggcgcagg gcctctgccg ggaagcccac ccgggccagg gcccggtaaa 147660
gcaggtacca gtattcatcc ggcaccttgc gtgccaacac acgattcgtg cggtttccag 147720
tatttatcac ggcttcccgc cacaggtaaa agttaacact tagggtcagc agcttggtca 147780
gggataggtg caaaaacctg agctcgtcct cgcgcagagc gcaaagcggc cagttcttta 147840
gcatcttcag gaggagcccg tgaatcccag gtgtcattcg cgcgtcatcc ccgcgcaccc 147900
ccagtcccat taacatagcg ggcacaatgg tgcaggcacc gtctgtatac gtctgcggct 147960

-continued tcgtggagcg cccggacgcc ccacccaagg acgcctgcct tcacctggat cccctcaccg 148020
tcaagagcca gctccctctg aagaagccct tgccactcac ggtggaacac ctgccggatg 148080
ctccggtcgg ctcagtcttt ggcctttacc agagccgagc gggtctcttt agcgcagcct 148140
cgattacctc tggggacttc ctgtccctgc tggactcaat ttaccacgat tgcgatattg 148200
cacagagtca gcgcctgccc ctccctcgag aacccaaggt ggaggctctg cacgcctggc 148260
tcccctcact gtcactggcc tccctccacc cagacatacc ccaaaccacc gcagatggag 148320
gcaagctgtc cttctttgac cacgtgtcta tctgtgccct gggtcgtcgg cgcggcacca 148380
cggcagtcta cggtacagac cttgcgtggg tcctgaagca ctttagtgac ctggaaccgt 148440
ctatcgccgc ccagattgag aatgacgcca atgccgcaaa gcgtgaatcc ggatgcccgg 148500
aagaccaccc tctgcccctc acgaagctca tagctaaggc aatcgatgct ggatttctga 148560
gaaaccgcgt ggagactctg aggcaggaca ggggtgtggc caatatccca gccgagtcgt 148620
atttaaaggc cagcgacgcc ccggacctac aaaagccgga caaggcactt cagagcccac 148680
caccggcctc cacagaccca gccaccatgc tatcaggtaa cgcaggagaa ggagcaacag 148740
cctgcggagg ttcggccgcc gcgggccagg acctcatcag cgtcccccgc aacaccttta 148800
tgacactgct tcagaccaac ctggacaaca aaccgccgag gcagaccccg ctaccctacg 148860
cggccccgct gcccccccttt tcccaccagg caatagccac cgcgccttcc tacggtcctg 148920
gggccggagc ggtcgccccg gccggcggct actttacctc cccaggaggt tactacgccg 148980
ggcccgcggg cggggacccg ggtgccttct tggcgatgga cgctcacacc taccaccccc 149040
acccacaccc ccctccggcc tactttggct tgccgggcct ctttggcccc cctccacccg 149100
tgcctcctta ctacggatcc cacttgcggg cagactacgt ccccgctccc tcgcgatcca 149160
acaagcggaa aagagacccc gaggaggatg aagaaggcgg ggggctattc ccgggggagg 149220
acgccaccct ctaccgcaag gacatagcgg gcctctccaa gagtgtgaat gagttacagc 149280
acacgctaca ggccctgcgc cgggagacgc tgtcctacgg ccacaccgga gtcggatact 149340
gcccccagca gggcccctgc tacacccact cggggcctta cggatttcag cctcatcaaa 149400
gctacgaagt gcccagatac gtccctcatc cgcccccacc accaacttct caccaggcag 149460
ctcaggcgca gcctccaccc ccgggcacac aggcccccga agcccactgt gtggccgagt 149520
ccacgatccc tgaggcggga gcagccggga actctggacc ccgggaggac accaaccctc 149580
agcagcccac caccgagggc caccaccgcg gaaagaaact ggtgcaggcc tctgcgtccg 149640
gagtggctca gtctaaggag cccaccaccc ccaaggccaa gtctgtgtca gcccacctca 149700
agtccatctt ttgcgaggaa ttgctgaata aacgcgtggc ttgaaagtaa actttattgc 149760
gtgttagtac ctgtccattc acaggggtat ccagcccttg cgccgcctcc cccagcccgc 149820
cagccacccc agacaggaga tgataatgat gaggagcacc ggagccacca cagcacaagt 149880
gattaggagc agggcccagt gcacccaggt ggtcttaggg cgccagggat cgattggaaa 149940
agggcccagg gtcactggct tatgcgtggg acgtttagaa acaggccgcc tatggggcct 150000
gtgactggtg cttgtggtgt gggagactaa tgtggtgggg gctatggtag tggctgggat 150060
aacagtaaga tgcatacgct gagtgagggt ccggttggca tggtattggt cgtcttcttc 150120
ccctgcagag taattgcagt ggaccccgga ggccacactg caatttctca gtgtcacatt 150180
gcacgtgtag taacctgcat gcgcaagggt cacattgggg attatcagag agacggaggt 150240
gttggagtca tttacccatt ctagggtaag gctataattg taacccccgt tagttatatg 150300

-continued agttccgttg ttggaagtag ctacggccaa gggcagttgt ccatccccgg gagtgtatcc 150360
ccggcccaac tcgatccgag agaccgactc attgctagga acgctgcagg tgagattcac 150420
tctagcacct gcatgggcgg tgacattttc aaatttaacc agatctgaga aaaatgcaca 150480
aacagacccc acacagcagc acaatagaag cactaaatga gtcattccta aactgtcagt 150540
tttaaaactc cctgcttctc aggcctaaat atgtggtggg gtgtgcttag gatcactttc 150600
atattctgca acaacagcca tacccggaag aggagctgcc ggttgccatt tttcaagctg 150660
ctaaaccacg agtggcagca ggcctaagaa gctcctcagc aacatggaga cctcgaaggg 150720
aaactggcag gagcagggag tcacgtaggc actagcctct tcatgtgagg taagagatcg 150780
ctaaaaatgg gatcagggta tgtaaaccga gttttgcggg ggatggtgag ccagacacgg 150840
cgggtggggg aaggagctga cacgattgag tagaaagggc caaaaataca ccagctataa 150900
ggaattgctc aggccaaagt tgttcctcag gtggctttag gcctaatgta ggcaattgcg 150960
tgcctagaac attgctaatg tgccctgggt ttcctgcctt catgcaaata ttctacctcc 151020
cccggcctgg tgcaaaatgt ctgcctcaga atactaacag ctaatccaag ctaacattct 151080
atcagtaaac gggcagaaaa ctgataagga ccgcggagtt tggccctccg cggtgtccgg 151140
tggtcctcac acgtgccctc cccccgggcc gatggctgag gcccggaata tgcaagtgca 151200
tctttctaac cagtaggggc ctccacctag gtgctttgtt aatctttagt gggaactagt 151260
gggagtgctg tgcctcgggt acccctatcc tataggtcct accggagctc cttgtcttga 151320
taatccctgt aaacacacac cacctaagaa caaggcattg ttaacctttg gtggaaccta 151380
gtgttagtgt tgtgctgtaa ataagtgtcc agcgcaccac tagtcaccag gtgtcaccgg 151440
aggctacttg cctcagtgcc acttttacct tctcaaatct atacgggggg gggggggggct 151500 ctgtaacatt tggtgggacc tgatgctgct ggtgtgctgt aaataagtgc ctagcacatc 151560
acgtaggcac caggtgtcac cagggctact tgcctcggca tctcctcacc ggagaagggg 151620
ttaacaaacc cgtggggggt cttagtggaa gtgacgtgct gtgaatacag gtccatagca 151680
ccgctatcca ctatgtctcg cccgggctat atgtcgcctt acctccccta tatagtcacg 151740
accccaccga accaggcatg atgtagaata aaattttatg catcatcttc taatctgtgc 151800
cgcttggagg gaaacatgac cacctgaagt ctgttaacca ggtcagtggt tttgtttcct 151860
tgatagagac acaaggactg ccagccccat tggggagggg gggtgggtac gggagagttt 151920
gggctcgttt aaacaaagtc tcatctgatg ctctgtggca cctcaaggtg aatatagctg 151980
cccatcgacg tatcgctgga aaccggtggg ccagggcctc gtaggccgag acgggcagcc 152040
ggagcttgtg gtactgtccc tccggcaggt ggagtgggac acagttagag aacattagtc 152100
ctctggtccc tatctccacc cgccaggcct gtgtgtcagt ttgcagggcc atcctcgcac 152160
tcaggtggac tggctaggca cccttctgaa gtatctggcg gtgactgtca cctggttctt 152220
gagagagtcc ataaaatggc tgaagctcca ggcgtatagt ataatgagca acagggccaa 152280
acaggcggcg gggcctgggt agtagcgggc aacgagagac tctgtgcaat caaaccccag 152340
gctcccggcc tcacccagga agagcagcgg cagggacagc ataaaccagg agaaggcgca 152400
aatgagtccg gtgaaggtga cgttgcatat caggcgcggc ttccttccga attttgtgcg 152460
caaaagtttc cagatgatga taactgtgag gaggacgatc aggactgccg ccagtaggta 152520
gcagccggct ttcagtcctt ggacggccgt gtgcatgcct ttggtggggc cttccctgca 152580
catgttgggg cctctgttga gattggcgtc ggggcccatg gtaatgagga ggatgataat 152640
cagcaggagt accagacaaa acacgcccat caggtacagg cacacatttc tgtgggaggt 152700

-continued tctcttgggc gttcggctga acaatgctag ggtcttctcc aacgccatac ccaagtgagt 152760
ccatacggag cacatcaggc ccaagaacat catgttctgg gtcaaaaggc agagaccggt 152820
agacgagaac tcctgaatca tttttcccag cacccagagc agcagttcta tgagaagagc 152880
tatcagccag acatccattc ggtgaaccaa ttttcttaca aagatgataa acaagatgcc 152940
agccagtgtt agcagaatca gcaggacgag cagcaggctt gtcatgccgc tgaggaaggc 153000
gctgtaggat ttagtgcacg catcttccgt tgcattgacg gaagtcatgt tggccaccag 153060
ggtccccacg gtggacccgg gggccatggt ggagagcatc ttgctggtca gagccagact 153120
gggtggtgtc tgcagcaaaa gaggaacttg cccaggcagt cagttatttt gcatgccacc 153180
tccctgcctg gtggacttcc agactatttt ctgcattcgc ccttgcgtgt ccattgttgc 153240
aaggagcgat ttggagaaaa taaactgtga gtttcacaga tccacgggcc acgctcccct 153300
gggggcttca tgatcccacc gcctttcccg atgatgatga caaccgcggc tgtctgaagc 153360
ggctgacgaa atcggttgag attctgatga gaggcttggg ggggtctttg ccctcaaggc 153420
gaggctcctt ctcctaggaa tgccgagccc cctgcactag cttcgctcca ctggggatct 153480
ttgccagcct tcatactaga ttcagcgatc ccccggttgg gaatcttcgc cagccccccg 153540
tcctgctatc ccgctcgtcg ccgcgcctcc catgctaagg gccccccttcc tttcccttga 153600 ctttggggat attcggagtc tgctctcgcc gctctcttct ctcgtttaaa cgagagaata 153660
gtagtagggt ccagtctcag gccccctcac tttgggtctt agaatggtgg ccgggctgta 153720
aaattctgga ggacggagag ggcggccccg gagttgttat caaagaggca ctggaggatg 153780
ttggccgctc cttggagcag cttgtcgaaa taatgatcca cggccacggg aacgccgtgc 153840
cgctcggcgt aggccgggtc ctcggccatc tccgtctttc tcgccccctt cactcccccc 153900
ttgggctcca caaagacgta ctggatgcgg tcgtggatct ggggcagttc ctcgttgcgc 153960
tcgacgaact tctggtagac ggccaggtga ggcatctggg tgctcttgta ggctgagagc 154020
ttgcggctga gctccgttga aaagcagagc tcccccatgg ggaccctgcc ttcacggagg 154080
tctgtgtagg cctggtttag gatgtcaatg acgggcaaaa agcccacagg tagcccttgt 154140
gtaaatgact cttggaaggg ccggtgggag aggaggctgg ccgcctcctt tacccgggca 154200
tccgccagca ccaggtcgag cacgcgccgg cagcgtgtct gcacaaactt gcaggccgtc 154260
ttccggacga gctccacccc cttcatcagg gtcttgccgt ccgtcagcac ccccacatat 154320
ctcttctttg taatcagcat caggcaggag aaggtcttct cggcctccag ggagatgggg 154380
gccacaaaca ggctccgggt ggtgtgggcg gccagggcat cggcaaagcg cagggtctcg 154440
ctctctgaaa acccccggca ctcgataaac agcgagtccg tgtccccgta gatgactcga 154500
agctggccct cggggttgag gggcgcccag gcgtccgggg agggggccag ggcctgcagg 154560
ttggcggggc tcagggcctc cacgaaggcc ttggcccgct ccaacatcgt gcggccctgc 154620
agcgtcaccg tctcggcgat ggagaggcag ggaaagaggc cgttggccac cccggtgaag 154680
ccgtagacgg cgttgcacgt gcacttgatg gccagctgct gcttgtcgag gatggtcctt 154740
tggcgcggat cctcgcaggc cgccagcagc ttcttgatgg ccttgcgctt ggccagccag 154800
gaggtcaaca gactagccaa gaaggactcg tgcacgtgct tctttacaaa gtggtagacg 154860
ccccccgtga gcctgaagga ctcatagtct tctcccgggc gcaggccggc tagcctgtgc 154920
tcttctcccg gcgttatcat ggtagaataa cagagattat gagcctgaat gatgctcggg 154980
tagaggctgg caaagtccac caccagaacc ggggagttgt agaatccgga caggggctgg 155040
atgacggtgg ccccctggta gccgtcccgg tcagaggccg agggcatggg caggataaag 155100
ttttcctttt gggcggccgc caggaggcag gagaacacgc ggatctgctg cccatcgtcc 155160
agcacccgcc tgcaggggat gtgagcgatc ttggcaatct ctgccacctc cacgtggatc 155220
acgaaatggt ttagcagatc catgaccagg gccgagtcct gcacgcagta catgccgagc 155280
cgcctgcgcc cctcggggcc cgctgcaaag aggcgaggaa tctccttgta atgcacatcc 155340
tccttcttgg cccccagtag gtgcctggct actgtgtcca gcttgtagtc tgagaggctg 155400
agcttgtccc ggcacacggc gtacatgtcg atggggatga ggccggtgat gcggaccttg 155460
gtgttggccc gcaagaagcc cttgcccgca tcatggggtc gcctgacctc gcagacgccc 155520
ccagccctaa ttttgcccag agaggctggg ttgatgctgt agatgtgcct ggctctgtcc 155580
agaatgtagg gccagtcaaa gttggccacg ttgtagccgg tcacaatctc cacgctgagg 155640
tctctgatga gctggaagaa ggcgtagagc atgtccagct ccgatgggaa ctcgtagacc 155700 tcaacccct ctatgtcttc gcaggtgccc agcgtcagca ggatgcgcct atagcgcccg 155760
gcctcctccc ctgtcgacca gaggacgcag gatatctgca ggatcaggtc agcctcgttg 155820
gtggccgtgg ggaagccctc ctcccccaga cactcgatat cgaaggccag ggcctggtag 155880
gagggccagg agctgtcttc acgccggacc gagaggtcgc ccacctcaca gtcgtactcg 155940
agctcggcgt acgagtcccg gtgctggagg cgggggatgg cgcggcggca gctgtaccag 156000
ccaaaggtga caaagtcatt gtccaggaca aagcggcgcg tggcatccac gttggcctca 156060
aagatccgac acccgtgctt gtcttgcagc cacgtggcca cgtgacacac actgttggga 156120
tgggagaggg tgatcttgtg gtagtcgccg gcatggttgc cgtagcccat aatggaacgg 156180
cgcgtgacct tctccaccga gacccggcag gggtcctgc ggtcgaaggt gctggccttg 156240
agggcgctga ggactgcaaa ctccacgtcc agaccctgag gcgcgctggc gtagaagtag 156300
gcctgctgcc caaacacgtt cacacacacg ctggccccat cggccttgcg ccggcccagt 156360
agcttgatga cgatgccaca tggcaccaca taccccctgtt tatccgatgg aatgacggcg 156420
catttctcgt gcgtgtacac cgtctcgagt atgtcgtaga catggaagtc cagagggctt 156480
ccgtgggtgt ctgcctccgg ccttgccgtg ccctcttggg cacgctggcg ccaccacatg 156540
ccctttccat cctcgtcacc ccccaccacc gtcagggagt cttggtagaa gcacaggggg 156600
ggctgaggcc cccgcacatc caccacccct gcggcgcctg gtgtctggaa acacttggga 156660
atgagacgca ggtactcctt gtcaggcttt ttcagaaggc ctttattagg tcttaggaaa 156720
gggttataga agagtccccc agacatggtt aaaactcagt ctctgcctcc ccaagcagtg 156780
cggcggcggt ctctggatcg tgatagcgtc ttctgcgtag gcctggaaaa cggtccctgg 156840
ctgcctgcaa tgctctgctg gccactgagg gtccggccgc cctctgagct gctctctttt 156900
gctcctggtt ttgctcatgc agcgctaaca tgatggcttg taattctgtc ttactaatgg 156960
gattaatgcc tggaccctca ccagaggcat gttgctgagc gagctcgtcg atcccggggt 157020
agagcatctg caccggctgc tgcgacatct ggcgcgtgcg cctcgtgagg gaaataacca 157080
ggatcaccac ccccgccacc aggaccagaa tgagcatgcc gccgaagggg tttttgaaga 157140
aggagatgaa accagagacc aggctgctaa acaaaccccc caccgtgctg actaggttgg 157200
tgatggactg acccacgcta cccagactgt ccataagttc ccccaggccg tccacgaatt 157260
gatttcttcc gtttgacact gcattgtcca aatccttccg caggccggcg atgttttgcg 157320
cctggaagtt gtactcccgg aagatgccct ccaggtcaaa gacgttggag gcacgctgtt 157380
cgtcccgtga gtacagctcc agggaggcaa agtcaatgtt ctcgatgagg gaggtgttta 157440
gtgagatgaa ggtctgcagg gtggcaatgc cgtccagctc gatggtttta aagtggtggt 157500
agtcgttgta gacgtggatc tcgttgccgg actggaagta gtactggctg gtcgcctggc 157560
acacctccgt catctttttt gtgaggaaga tctcgttgtc ggtgcccagc tgtccctcgt 157620
aggtcttggt gtcgttgata aagctgaagg acaccagggg gcgcgagtag cacatggtct 157680
cggagccagg gaccctcatg ctcttgcgca gggtgacggt ggcctggtta acgggcacgc 157740
actgggagac tgagatgaca tcccccaggc gcttggccgc caccgcctta ccgtagatgc 157800
tggacatgac ggtggttgga ttaatcttgg ttagttctct cagcaccatg ttctgcctct 157860
tctgctccag gcaccaggcc cgcgcaaggt ctcccagcat gcggttgatc tggcggcgca 157920
gggagtcgta ggcaaattgg atctggacgg tggcgggatt gttgagggtg cccagggact 157980
tcccgggggc cgtgggggc accggtgtgg tggcgttccc cgcatcccgc ctccgacgcc 158040
tcagaacggc ggcgggggtg ctcccgcggg ccgcggatgg ggctgggggc gatggactgc 158100
tggggggtga ggaagtcgga gtggtaagct ccgtcaggtt cttgacggtg gccaacgagc 158160
gcggggtcag aggtagccaa gctaataaca atcctccgct cgttataaaa tatgtaatgg 158220
cttcctggcc cttcgtgtaa cgatcctgga cggcctcgta cttctcatgc atggtcttgt 158280
tcacctgctc ttcgatgcac ttgaaggcgt ccgggagctc tatgcccacg gttgtgttgg 158340
tcacgaagct agaggtgccc tcgtcagtca caaaatgtat tgacttccct gtttctgtgg 158400
cgatggtcga gtcaaaggtt tgccagtgtt gaagcgggca gtaggctgtc ctgttctcga 158460
gcttccaaga tagcgtgtaa gtgcccttgt ccaggaaggc tcggcgttcg ccttgcgggt 158520
tcgtccctcg gttgtcgtag tccactatct tgtagttagt tctcacgtgg aaggagtctg 158580
cccgctcatg gaaggtttcc ttatttttcc cgtcatagaa aggggacatt tccacagtct 158640
gcccggtggt ggtcacaaag aagtcgaagg ggctgttgga cttggccatc atgtcagtta 158700
tcaggcagtt gacggtagtt cttgttctgt aagtccatat caaccacccg gggggcgtcat 158760 agagctccgt ctggctggcg tagcggcgca ccccgttggc caggcccccg gtgggcttta 158820
ggttgacggt gatgttaact ccgtcgcggt ctacatacac gcgcgtcagc ccatcttttg 158880
tcatcttgac cgcgttgtag cactggtaga tggtatccat ctggtcagtt tcgtagctgt 158940
caacggagaa cttctcctcg tgccggttgg tcacggagtc cgcgtaccag ccattgtaga 159000
tgagaatgtt ggtcactatc ttggtgtagg agcggacctt aaacgagtag ggaataatgt 159060
tgtctttaaa caccatcaac aggccctccg tgtgattctc ccgcgtgcca aacgagggac 159120
actggatgtc cgaggagaag cggaacaggt cgccgtggct ggagagctcg cagactcgga 159180
aaggaaagct ggtttgctga cgcgtggcgg taggctgcac cgtggtggcg gggggtgcgg 159240
gctgctctgg ggtctgcgca ccgagacggc acgccagggc ggctagcagc acgaccacgc 159300
ttagcaccct acgccgagtc atctctcatt tggaggtgca ggtagagaag ggcatataga 159360
tccttaaata cccacccccct gcccttatac agaagaatta gggggcggtc agagtcgtac 159420
gtgaggtaaa gcccatccgg gggcagggcc tggccggggc tgaccgcgtc cgcccggcgc 159480
aggatcaagg accgccccca ggtcttgttg tagagggaca cggttaggac ggcctcgcgc 159540
agcgcccggc acagaatttg ctggctagat gccagtgagc cccgggtac gctgtagaag 159600 ctgttgaagg aggtctctat ccagtcgctc ggctcgatgc ctggccatat cagggaagtc 159660
aggaatgcct tctggtgggg cagcgtacct gcggcgtcac agcagcgagc cagggccacg 159720
ttgctgggtg ggggaaagag cccgctctcc tccgccaggg gccccgtgat gaaggtgtac 159780

-continued

```
aggctgtgcg tcagcgcgtg caggtgctcc gagctcaggg tctgggtaaa caggtgtgtt 159840
ttgatgtact tggaattctc aaaggcggca ccctcgccgg cgcgcctgtc ctcccaggga 159900
cccgagacga aggcccgtct gtagaggaag tggttgcgca tgcgggccag ctcccagtag 159960
accacgtccc cccagacgcg caggcacagg gtctcggtca gggtctcgct ctgttgcgcc 160020
aggcaggact gcagcttggc cagaccctcg gtggccacct ggcgcaggta ctgctccttg 160080
cgcttgagcg cgtccgagag ggcgccggac gggccgggct ctcgtgcccc agccggccgg 160140
ggcacctccg ggctctcccg ggacgcctcc tcctcgcctc ggcccaaccg ctgcatggct 160200
cggttgagcc gcgtgtacag ctcgttcctc ttttgcagga tggcccggta ctgggggtgc 160260
gccgtgaagg cggcggcgca gtccgccttc agcgcctcca ccgcgtcgcc cgaggagctg 160320
tagaccccgc cgcagaagag ccgctccgtg gccccgggag ccacggcgtc aaacaggtga 160380
gtcagccttg cccccgccag cgcctcctcg caggcccccc gcaccagggc caggcgacgc 160440
tcccgggcaa acagggcaga gaggcgggaa tggccgccac cctccccctg ccccgttgca 160500
ccgatagcat ggccgccaga gttccaatag aggagctccg agagctccgc cacctccggg 160560
ggcactgtcg agaagacgtt gtaggtgtcc agcgctctgg tcgccccctc tgcctccggc 160620
cgccccgggc ccgggaccgc gccctcctct gggccgcccg gcctcgcctt ctcctcagcc 160680
tccaacaggt gcccgagccc cgcctggcgg acttcattct caaacagtcc cgagaccggc 160740
tccggattca ccggcaccgc caggtggtta caggagacgt gggtcccctc tgccgtggaa 160800
gggttgccgt ggttgggcag aaccatcagc tcgcccacac agcgccagca gggcacagag 160860
gtgatgtaga ggcgcgggtc tgggatggga cttacgcccc gaaagcggcc cagcagatcc 160920
agggcccgtt ccaggctctc cagccccatg gtgtgagaca tgcaataaaa cacgctattg 160980
attctcttca ttaaaatctc tatgtcattt attaggcaca aacttacatc gactttatgc 161040
cccccgtaaa actccacaga gtacgcgact gagggggtac ggagaggcgg gacccgggta 161100
ccctttctac caggggcgag cagcgcggca gaggcctctc tcgagttctc tagcaggtgc 161160
accagctcca gggacagggc gctgcatgca cggtcattct gccgtctcaa acggggaagg 161220
aggatggcct ccagctcggc cagcaggccg gcgttgcgca ccaccgcagc cacgtccaga 161280
ctccgggggt ccagccgggt gcacacgctc agctcaaccg ccagggcgta cacctggctg 161340
tacgccgccg ccagcagccc cgacatcgcc gccccagggg tctctagacc tcgagtccgg 161400
ggagaacggt ggccagacgg cgcttgcgtc tgcccccgga gccctgccct cctccaccca 161460
gcagcagccc ggccgaggcc tgcgacgcgg tgctgaccgg ctcggccacg ctgataaagt 161520
tgtcctgggc tgccccgggc ccaccccaca ctccctccag aaagtcccga gcggcctccg 161580
ccgtccactc tatcccgctg gaggcaatgg tcgccagggt ttctaggacg ctgtccgcca 161640
ggacggagaa gcggcccaat aagtactccg cgtcgtccct agtcagcgag gcgcatgcct 161700
cgcccatggc atccacaagg ttgcacacca catcaaacac acagtcttcc tcctgttttt 161760
gtgatataat ggcctccagg ccagccctga tgttctcaat ctcatatgtg gtcgcggctt 161820
gggtccggcg cttcacggtc aaccctaggg tgggggtggc aaagacaaac ttcttccgca 161880
tggaagagcc cccggcctgc ttgcgcagcc cagccccggg ggcctgcagc aggttcctgt 161940
ccacgccccg gcccataaag tatcccaggt tcccggcctg gaatatctgg ttgttgccgt 162000
tgacccccgt gtacttgttg atggtcactg gcagcgtgac aaccggacgg gccttgcaga 162060
cctggctaag acagtctgtg gccgcgcaga ccaccgtggt cgcagtaagg gaggaggtgg 162120
cctccgcgta ggccgctgcc gactccaccg cccgcgtgcc cagtacgtgg gggtagtcac 162180
```

-continued gggcgggcac cgactgcgtc ctcggcacca gtccctgaat caggctgatg tagaactggg 162240
tctggccgca cgccttcagg atggcgttgt tgagcctctg cttggcgtaa gtgaccaggt 162300
tgccaggcac cacatctatg acgttgctct cttcgtgggc ccgggagccc ccgtccacaa 162360
agagggccag gtcagagtac tcctccgcgc tggccccgct ggggacaggg accgagcgcc 162420
gcctggaaaa gttgtgccac aggtacaggc ttgagagctt agtgtccggg aatagggtct 162480
tgtggtaggt gttgaggaat ttcatgtagg gcccgttgat gatgtagttc tccctcctgg 162540
tagtggactt gatgaagctg ttctggaggg cggcattctc cccgtgaag accaccctgt 162600 tcttgatctt gatgttcctg gggcacagca tcagcacctt ggacatgcgc acaggcagcc 162660
gccggccgta cacccggccc tgcagggccg cgtccaggtc tggcaggtcg caggtgggct 162720
ccccatgcac caccttggcc tccttggccg tgaggacccc cttgtcgatg gccaggctcc 162780
taaagttggt gcacagcgtc tggtagtgac cctttagcca ctctgggggg ctctggccaa 162840
gcccggggtt gtcattctca tagcacatac agatgggcag ggagatgtcc tgcaggatgg 162900
tcagcagtga gcggtaaaac agctgggtga agatggggca ggcgggctgc gcaaaggggt 162960
tgcacgagta ctgcatcacg tggtagcagc tcttgaccag gtccttgtag gtgatgttgt 163020
tcttggccat gctgttcata aactggacca cttcggcgtc caccgccgca tccacgtcct 163080
tgaacatctt gacaaagtca cgcgggccat ggggctcctt ctctagcttt ccttcagcgt 163140
ctatgcccag ccgagacagc cgctccagca ggttctggtt cagctgccag taggtgtagc 163200
ggggctcgtc gtccggccgc tgcccgtcgt cctccttatc gatgaagttg agaaagttgc 163260
ccaaaaagtc cgtctcgttg taggagcccg aggcccccga gatcacatag gggtccctcc 163320
gctgcgtgga catgacgggg gggaagcggt ccctcagcct aaagaagagc gtgttcaggc 163380
acacggccgg ggcccggccc tcgcagagcg agcacatggg actggcggcc gcccccgcca 163440
cgtagctgcc cgtctccggc accggggtca gagagctctt ctgtccctgg caaaactgca 163500
ggtagtaggc atagcgggca agaaggttgg gcgagaagga ggccgcatag accaggtgct 163560
ccacagcgta gtttcccgga ccgttggttc cggtcacgtc tggcccaccc cagcccgaga 163620
agcagggtcg gcggcagggg tcccaggtcc cctcctgcag ggtccccagg ccgtgggtca 163680
tgtagaaact gttaaagaga ctctccttgc cctgaccggt tgacttcgag acccccgaga 163740
cgtagaggac ggaattggtg gcaaagatct gcgtggacac gtggggggcc aggctggcat 163800
tatatcggtg taacgcagcc acacgggcct ctggaccctc acagtcggca aacaggggcc 163860
acgagtcgta gttgaggctg gccggggtct cgtgcgaggc ctccagcatg gcgggtgcgt 163920
agctcaccgc cagctcgcat gccgcgctgt ccacaatcat taaggctccc gagtccgggt 163980
gactgatggt tgaggctggg aactccttga ggggggccac cttggccacc ttggcctggt 164040
cctgcaggct ctgcttctcc agcagctcca ccagcttgcc cacccgtcgg acgcgcagcg 164100
cctgcgccag cccggtgtac agcgcctcgt gcatgcagcg gctgaggtcc gagttgtaaa 164160
actggcggag ctggggcacg ccctctggga acacctcctt gtcgtagagc gggaccctaa 164220
cgctcgcaga ctgccccacc gctacctcct gttttaacga tggaatggcc accaggtttc 164280
cgctgtagag tcgctccttg aaggcctcgg ttattgccac cgcccccagg taggcagagg 164340
gatctagccc ttcggggaag aagtcccccg gcttggagct ttccctcggt agggcgctgt 164400
aggcgtcgta cccaaacacc tccctggtct cgccacagag ggcctcgaga cccggcccct 164460
caaagatggg gggaaccata tggcattgt ggaacacgta gatgtccctg tgataggagg 164520

-continued

```
tagcgcgtag gagcccgcag ttggggtcgg gcctcctgtg cagagccttg acattgatgc 164580
tgaagcccgg ctccacggtg atgccgcaaa ggagcggcac cgtcaggcac ctgtggcccg 164640
cgtagccggt ccccagtgtg gccacctccc taagagggta ggtggccagg gggtaaaagt 164700
agatgtagcc gcacggaccc ggctggctct ggctgcccag attatcctcg ctagtctgtg 164760
caccctgcat gatgcccaag gtatcgcccc ggcctcccag tcccacatta aatgttacac 164820
tttactcatc acgcaacacc cactgtttat tcatttacaa agatttcagg aagtcagtca 164880
ggctggccag ggcccacgtc acggggaact gacgtctcag cgatcttggc atgccgccca 164940
gcctcgcaaa ccagagtctg cgatagaggg ccaggtagtg ggcgattgcc cccagcacga 165000
aggcggcgct cttgtggtca tccaggtagt ttcgcaccgc aaacaccact gtgtagcaca 165060
gcaccaccct gagccgcgac cagtagtcgt agtggtcgtt gtacactgcg cgcaggacgc 165120
tgatgatgag ccgtacgtgc gtgtctttgc ccccgatgtc ggctgtcctg caggccagct 165180
ccgcgtacag cttcctatcc ttcctcaggg aggccttgat gagccggcag aggaccaggg 165240
ctggcaaagg caggtctttc tcatcccggg tgaacaccgc gtacatggcc ctgaacatga 165300
ggtagctgga ctcagccacc ttgtcgtccg gcggcgaggg cgcgacccac gcctcgaccg 165360
gggtcctcac aaacacagaa tctgtagact tggctggcct catggtctcg tcaggccagc 165420
tcacgggctt caggcttata tgataaaatg ggcgtggcag aatagtataa gacgcgaggc 165480
ctgggtgagg agagtccaga gcaatggcca ggttcatcgc tcagctcctc ctgttggcct 165540
cctgtgtggc cgccggccag gctgtcaccg ctttcttggg tgagcgagtc accctgacct 165600
cctactggag gagggtgagc ctcggtccag agattgaggt cagctggttt aaactgggcc 165660
caggagagga gcaggtgctt attgggcgca tgcaccacga tgtcatcttt atagagtggc 165720
ctttcagggg cttctttgat atccacagaa gtgccaacac cttcttttta gtagtcaccg 165780
ctgccaacat ctcccatgac ggcaactacc tgtgccgcat gaaactgggc gagaccgagg 165840
tcaccaagca ggaacacctg agcgtggtga agcctctaac gctgtctgtc cactccgaaa 165900
ggtctcagtt cccagacttc tctgtcctta ctgtgacatg caccgtgaat gcatttcccc 165960
atccccacgt ccagtggctc atgcccgagg gcgtggagcc cgcaccaact gcggcaaatg 166020
gcggtgttat gaaggaaaag gatgggagcc tctctgttgc tgttgacctg tcacttccca 166080
agccctggca cctgccagtg acctgcgttg ggaaaaatga caaggaggaa gcccacgggg 166140
tttatgtttc tggatacttg tcgcaataaa cgcacttgcc tatttcacct tgttttagtg 166200
tggcattggg ggggtggcat tgcgggtgga tagcctcgcg actcgtggga aaatgggcgg 166260
aagggcaccg tgggaaaata gttccaggtg acagcagcag tgtgtgaaga ttgtcacagc 166320
tgctggtttg gagaaaacgg gggtgggcgg tgatcaggga gaacaattcc ccggggacac 166380
ctgcacgaga cccctgggct ctcaggaact ccgcccaggt cttgccaatt ggggtgatcc 166440
tgtagcgccg cggtttcagc atcacaggtt attttgcctg aagcttgctg gggcgtaaat 166500
ccctctcgcc ttgtttctca gagagcattt caggccggtt ttgcagtcgc tgctgcagct 166560
atggggtccc tagaaatggt gccaatgggc gcgggtcccc ctagccccgg cggggatccg 166620
gatgggtacg atggcggaaa caactcccaa tatccatctg cttctggctc ttctgggaac 166680
acccccaccc caccgaacga tgaggaacgt gaatctaatg aagagccccc accgccttat 166740
gaggacccat attggggcaa tggcgaccgt cactcggact atcaaccact aggaacccaa 166800
gatcaaagtc tgtacttggg attgcaacac gacgggaatg acgggctccc tccccctccc 166860
tactctccac gggatgactc atctcaacac atatacgaag aagcgggcag aggaaggtaa 166920
```

-continued

```
gagtgccatc tatctgtact tttatttatt gcatcacaag tcacatcaat aataagggcg 166980
ccatctagcg ggagatgtta tccacaccat cccaattcac atctcaggga caacaggtca 167040
aagttctttg ttgacacccc cagcgctggc tccagggggt ggaagcgttg gatgcagtcc 167100
tccgcatcgg ggcggacgcc tcctcccaac gcgtttctgc ggatcagtcg ctggctggtg 167160
ggcatcggag tcggtgggcg gtcctccacg gggacacgct ccttcttggc cttgttcttt 167220
gaccttttgg acattcttct gaaggaacgg cggagagtag cgtagaatcc agccagtggt 167280
ctacccggtc gcatggtggc ttcttagatg aggagcaggc ataaaagtcc aaacaggaca 167340
cagagtacca ccaggagtag tcttagtctg ctgacgtctg ggtcctcggg gcaggggtgg 167400
ctaggcctgg tctccgtaga agagccgggc aggccgcagg cagaggactg ctgctctagc 167460
aaagcacgct ccaggacgtg taccatctcg agagtgaggc acagctgttt tcgtggactt 167520
ttatacagta aggacaagga aagaaggcca gaggaatgtg gaaagatgag cgaggacagg 167580
tgtggaggtt ttgggctagc tcttagtttc tgggtgtgag agagggatta aagtgcttat 167640
gcgcaaagaa tgtgtcaaca acaggtgttc ctgcctctgc tggcatgagt taggtgtggc 167700
ttgggctgaa tccaaatgtg tattggcaca agatggaaag caaagttgct ggagttactg 167760
ggtgggagac agggatgtat gtggtccccc gctggtatgc cagtaccctg tggaagtaag 167820
gggcctcatc tgcctggtag ttgtgttgtg cagaggtctg atgtgtgtag gaggggtggg 167880
ttcaacgcag gggcgttggt ggcggagtct ggcaacgccc gggtccttgc tacctgtgtg 167940
gtgtgttaag ggctgggtaa aggtgtctgc caattctcgc atgtcctcct ttccccttgt 168000
tttgaaatag aatatgaatg tggcttttca gcctagacag acagtgtggc taagggagtg 168060
tgtgccagtt aaggtgatta gctaaggcat tcccagtaaa tggagggaga gtcagtcagg 168120
caagcctatg acatggtaat gcctagaagt aaagaaaggt tagtcatagt agcttagctg 168180
aactgggccg tgggggtcgt catcatctcc accggaacca gaagaaccca aaagcagcgt 168240
aggaaggtgt ggatcaccgc cgccatggcc ggaatcatga ctatgaccgc cgcctccgtc 168300
tgtcatcaaa ggcgggccct ggtcacctcc tttgttttca acctcttccg tcaattgtgg 168360
agggcctcca tcatttccag cagagtcgct agggctatga ggcagcgggt catgtgggcc 168420
attgtcatca gtgttgtcag ggtcctgtgg gccattgtca tcagtgttgt cagggtcctg 168480
aggcagcggg tcatgtgggc cattgtcatc agtgttgtca gggtcctgtg ggccattgtc 168540
atcagtgttg tcagggtcct gtgggccatt gtcaggacca cctccaggtg cgcctaggtt 168600
ttgagagcag agtgggggtc cgtcgccggc tccactcacg agcaggtggt gtctgccctc 168660
gttggagtta gagtcagatt catggccaga atcatcggta gcttgttgag ggtgcgggag 168720
ggagtcatcg tggtggtgtt catcactgtg tcgttgtcca tggtaataca tccagattaa 168780
aatcgccaga aacaggagga gccaaaggag atcaaccaat agagtccacc agttttgttg 168840
tagatagaga gcaataatga gcaggatgag gtctaggaag aaggctagga agaaggccaa 168900
aagctgccag atggtggcac caagtcgcca gagcatctcc aataagtaga tccagatacc 168960
taagactgcg ttgaaaaaag agtgttaggg ttggaaaagt gggggtgtgg taaataattc 169020
ctagggaatg ttagatctta ccaagtaagc acccgaagat gaacagcaca attccaagga 169080
acaatgcctg tccgtgcaaa ttccagagag cgatgagcag gagggtgact ggggaaagag 169140
gagaaagtgc gttagagaag gaagagtaag ggaaaggggg tgtggggcaa agggtgtaat 169200
acttactcat cagtaggagt atacaaaggg ctccaagtgg acagagaagg tctcttctga 169260
```

-continued agataaagat gatcaaaatt ataattataa gcatgagagc aaaggaatag aggacaagga 169320
gggctcctcc agtccagtca ctcataacga tgtacagcca aaacagtagc gccaagagga 169380
ggagaaggag agcaaggcct agggaagagg agaggggggg tcctcgaggg ggccgtcgcg 169440
ggcccggtgg gcccctctca aggtcgtgtt ccatcctcag ggcagtgtgt caggagcaag 169500
gcagttgagg aaagaagggg gcagagcagt gtgagaggct tatgtagggc ggctacgtca 169560
gagtaacgcg tgtttcttgg gatgtaggcc cggggggatt tgcggggtct gccggaggca 169620
gtacgggtac agatttcccg aaagcggcgg tgtgtgtgtg catgtaagcg tagaaagggg 169680
aagtagaaag cgtgtgtttg tgttagaaaa gcgggtcccc gggggggcaag ctgtgggaat 169740 gcggtggcca agtgcaacag gaaatggaaa ggcagtgcgg caatcagaag ggggagtgcg 169800
tagtgttgtg ggaagcggca gtgtaatctg cacaaagagg cgcggggcgc gcaacgttgg 169860
gaggtcgttg gcggcaggcg ggaggccgtg ctttaggggg gttcaggtga ggcaaggctg 169920
tggggtaacc gtaggggagg cgggtgaggc ggctaagagg gctaagggtc ggcgggtgac 169980
gaagcagcag acggcggata tgggaatttc agaatgaggt ggcggattca ggcgaaaagg 170040
gtgtgggctg tgcgagtgtc atgaggcagg cgcggaaagt cgctgcggct tgctggggca 170100
tggggggccg cgcattcctg gaaaaagtgg agggggcgtg gccttccccc gcggcccccc 170160
agcccccccg cacagagcgg cgctacggcg ggcgggcggc ggggggtcgg ggtccgcggg 170220
ctccgggggc tgcgggcggt ggatggcggc ggacgttccg gggatcgggg gggtcggggg 170280
gcgccgcgcg ggcgcagcca tgcgtgaccg tgatgagggg gcagggtcgc agggggtgtg 170340
tctggtgggg gcgggagcgg ggggcggcgc gggagcctgc acgccgttgg agggtagaat 170400
gacagggggc ggggacagag aggcggtcgc gcccccggcc gcgccagcca agcccccaag 170460
gggggcgggg agcgggcaat ggagcgtgac gaagggcccc agggctgacc ccggcaaacg 170520
tgacccgggg ctccggggtg acccagccaa gcgtgaccaa ggggcccgtg ggtgacacag 170580
gcaaccctga caaaggcccc ccaggaaaga cccccggggg gcatcggggg gtggggcatg 170640
gggggccgcg cattcctgga aaaagtggag ggggcgtggc cttcccccgc ggcccccccag 170700 cccccccgca cagagcggcg ctacggcggg cgggcggcgg ggggtcgggg tccgcgggct 170760
ccgggggctg cgggcggtgg atggcggcgg acgttccggg gatcgggggg gtcgggggc 170820 gccgcgcggg cgcagccatg cgtgaccgtg atgaggggc agggtcgcag ggggtgtgtc 170880
tggtgggggc gggagcgggg ggcggcgcgg gagcctgcac gccgttggag ggtagaatga 170940
cagggggcgg ggacagagag gcggtcgcgc ccccggccgc gccagccaag cccccaaggg 171000
gggcggggag cgggcaatgg agcgtgacga agggccccag ggctgacccc ggcaaacgtg 171060
acccggggct ccggggtgac ccagccaagc gtgaccaagg ggcccgtggg tgacacaggc 171120
aaccctgaca aaggcccccc aggaaagacc cccgtggggc atggggggcc gcgcattcct 171180
ggaaaaagtg gagggggcgt ggccttcccc cgcggccccc cagccccccc gcacagagcg 171240
gcgctacggc gggcgggcgg cggggggtcg gggtccgcgg gctccggggg ctgcgggcgg 171300
tggatggcgg cggacgttcc ggggatcggg ggggtcgggg ggcgccgcgc gggcgcagcc 171360
atgcgtgacc gtgatgaggg ggcagggtcg cagggggtgt gtctggtggg ggcgggagcg 171420
gggggcggcg cgggagcctg cacgccgttg gagggtagaa tgacaggggg cggggacaga 171480
gaggcggtcg cgcccccggc cgcgccagcc aagcccccaa ggggggcggg gagcgggcaa 171540
tggagcgtga cgaagggccc cagggctgac cccggcaaac gtgacccggg gctccggggt 171600
gacccagcca agcgtgacca aggggcccgt gggtgacaca ggcaaccctg acaaaggccc 171660
cccaggaaag acccccgggg ggcatcgggg ggtggggcat ggggggccgc gcattcctgg 171720
aaaaagtgga gggggcgtgg ccttcccccg cggcccccca gccccccccgc acagagcggc 171780 gctacggcgg gcgggcggcg gggggtcggg gtccgcgggc tccgggggct gcgggcggtg 171840
gatggcggcg gacgttccgg ggatcggggg ggtcgggggg cgccgcgcgg gcgcagccat 171900
gcgtgaccgt gatgaggggg cagggtcgca gggggtgtgt ctggtggggg cgggagcggg 171960
gggcggcgcg ggagcctgca cgccgttgga gggtagaatg acagggggcg gggacagaga 172020
ggcggtcgcg cccccggccg cgccagccaa gcccccaagg ggggcgggga gcgggcaatg 172080
gagcgtgacg aagggcccca gggctgaccc cggcaaacgt gacccggggc tccggggtga 172140
cccagccaag cgtgaccaag gggcccgtgg gtgacacagg caaccctgac aaaggccccc 172200
caggaaagac ccccgggggg catcgggggg ggtgttggcg ggggcatggg ggggtcggat 172260
ttcgccctta ttgccctgtt t 172281

<210> SEQ ID NO 59
<211> LENGTH: 137508
<212> TYPE: DNA
<213> ORGANISM: Human herpesvirus 8

<400> SEQUENCE: 59
tactaatttt caaaggcggg gttctgccag gcatagtctt tttttctggc ggcccttgtg 60
taaacctgtc tttcagacct tgttggacat cctgtacaat caagatgttc ctgtatgttg 120
tctgcagtct ggcggtttgc tttcgaggac tattaagcct ttctctgcta tcgtctccaa 180
atttgtgccc tggagtgatt tcaacgcctt acacgttgac ctgtctgtct aatgcatcct 240
tgccaatatc ctggtattgc aacaatactc ggcttttgcg actgacggag agaagagtca 300
ttcttgacac cattgcctgc aattttactt gtgtggaaca atctgggcat cgacagagca 360
tttggattac atggcgtgca caacctgtct tacaaacctt gtgtgcacag ccatcaaaca 420
cagtcacttg tggtcagcat gttactttgt attgttctac ctctggaaat aatgttaccg 480
tttggcatct accaaacgga cgaaatgaaa ccgtgtcaca aactaaatac tataatttta 540
cgctgatgag ccaaactgag ggtgttatac cttgttctaa cgggctgtcg tctcgcctgt 600
caaatcgtat atgtttttgg gcgcgttgtg ccaatataac tccagaaact catactgtat 660
ctgtcagcag tactacaggc tttagaacat tgagtactaa tagcttagtg aagataatcc 720
atgcaaccac acgtgatgta gttgtagtga aagaagcaaa atctacacat tttcatattg 780
aagtgcattt tcttgtattt atgacactcg tagctctgat aggaaccatg tgtggtatct 840
taggaactat tatctttgcc cattgtcaaa aacaacgtga ctcaaacaaa acagtgccac 900
aacaattgca ggattattat tccctacacg atttgtgcac ggaagactat acgcaaccag 960
tggattggta ctgacattca ggtaagataa tctaaatatt ctctataaca taattgtaat 1020
gtgttttatg tttatagcta caaatgtttt atgcaaaata cattttatga ggtcggatac 1080
ttattaaaag cattgtctta agtacattaa aaggacattg tataaccgtg ctacttacag 1140
catggccttt ttaagacaaa cactgtggat tttatggaca tttaccatgg ttattggcca 1200
ggacaatgaa aagtgttccc aaaaaacctt aattggatat agacttaaaa tgtctcgtga 1260
cggtgacatt gcagttggag aaacagtgga attacgttgt agatctggat acactactta 1320
tgcccgcaat ataacagcaa catgtttaca aggtgggacg tggtctgaac caacggcaac 1380
atgtaacaaa aagtcctgtc caaacccagg tgaaatacaa aatggaaagg ttatatttca 1440

-continued

```
tggtggacaa gatgccttaa aatatggggc aaacatttca tatgtttgta atgaaggata   1500
ttttttggtt ggtcgagaat acgtgcgata ttgtatgatt ggagcatctg gccaaatggc   1560
gtggtcatct tctcctcctt tttgtgaaaa agaaaagtgt cacagaccga aaatcaaaaa   1620
tggagatttt aagcctgata aagattatta tgagtataat gatgcagttc attttgaatg   1680
taatgaagga tatactctag ttggaccaca ttccattgca tgtgcagtta ataacacgtg   1740
gacatctaac atgccaacct gtgaactcgc aggctgtaaa tttccatcgg tgactcatgg   1800
ttatccaatc caaggttttt ctcttactta taaacataag caaagtgtta cttttgcatg   1860
caatgatgga tttgttctca gaggatcccc cacaattacg tgtaacgtta ctgaatggga   1920
cccaccactt cctaagtgtg ttttggaaga tatagatgat ccaaacaatt caaatcctgg   1980
acgtttgcat ccaacaccca atgaaaaacc aaatggtaat gtctttcaac gctcaaacta   2040
tacagaacct ccaacaaagc ctgaagacac ccatacagca gctacttgtg ataccaactg   2100
tgaacagcca cctaaaatcc tgccaacatc cgaaggtttt aatgagacta ccacatctaa   2160
tacaattaca aaacaattag aggatgagaa aactatatcc cagccaaata cacatattac   2220
atctgcctta acatccatga aagcgaaagg taactttacc aacaagacca ataactctac   2280
tgatctacat atagcgtcta cacccacttc ccaagatgat gctacgcctt caatacctag   2340
tgtacagaca cccaattata atactaacgc accgacacgt acactaacgt ctctccatat   2400
tgaagaaggc ccatccaatt ctactacttc agaaaaggcc acttcctcta ctctctcaca   2460
caactcacac aaaaatgaca ccggaggcat atacacaaca ttaaacaaaa caacacagtt   2520
gccatccact aataaaccta caaacagtca agccaagagt tccactaagc cacgcgttga   2580
gacacacaat aaaacaacca gtaatcctgc catttcttta acagattctg cagatgtgcc   2640
tcagagaccg cgagaaccaa cactccctcc cattttcagg ccaccggcgt ctaaaaatcg   2700
ctatctggaa aagcaactag ttattggact actaaccgct gtcgccctaa cgtgtggact   2760
gattacctta tttcactatc tgttctttcg ttagcctaga acttgctcca gtgttagaca   2820
gggctatgat tgcttctcca cgctgtccac cttaacactt cccaataaca aatccggtat   2880
gcagcagcgt gacactacta atgtaaccta aaaaatgtgc atgtggtatg tattgtacta   2940
aagataccga ccaatacaag acaactaata ttaaccatag tgtgcgtttc tttgtataaa   3000
atacgcgtgt gggaaagcga cagaaggggg cggcgtttcc atatgaggcc aagtgcattg   3060
gctattttag ggcggtgac cacgcactat agtgcgcggt gtggcagaaa attcacaccg   3120
tatataaaca aggaaagggg actctgcgcg cttaagcgcc aagccattat acacacgggt   3180
tttttgttgt cttggccaat cgtgtctcca tggcgctaaa gggaccacaa accctcgagg   3240
aaaatattgg gtctgcggcc cccactggtc cctgcgggta cctctatgcc tatctgacac   3300
acaacttccc catagggggaa gcctccctgc tgggcaatgg ctacccggag gcaaaagtat   3360
tttcactacc tcttttgcac gggctcacag tggaatccga tttcccctta aacgtaaagg   3420
cggtgcacaa gaaaatcgat gcaaccacag cttctgtgaa attaacttca taccacaggg   3480
aggccatcgt ctttcataat actcacttat ttcagccaat ctttcaagga aagggactgg   3540
aaaagttatg tcgagagagc cgagagctgt ttggattttc aacgtttgtt gagcaacaac   3600
acaaagggac gctctggagc ccagaggcat gccctcagct accctgcgcg aatgagattt   3660
ttatggcggt catagttaca gagggattca aggagagact gtacggcggc aaactggtgc   3720
ccgtgccctc tcagacaacg cccgtacaca ttggggaaca ccaggcgttc aagataccct   3780
tgtatgacga ggatctgttt ggtccaagtc gcgcccaaga actatgtagg ttttacaacc   3840
```

-continued

```
ccgatatcag tagataccta catgactcca tattcactgg aatagcacag gctctaaggg   3900
taaaggacgt tagcacggtc atccaagcct cagaaaggca atttgtgcac gaccaataca   3960
agataccaaa gctggtccaa gccaaggact tcccccagtg tgcttccagg ggaaccgacg   4020
ggtctaccct aatggtgata gacagtctgg tggctgaact tggtatgagt tatggtctgt   4080
cctttattga gggaccccag gatagctgcg aggttctaaa ttatgacacg tggcccatct   4140
ttgaaaactg cgagacgcca gatgcccgcc ttcgtgcact agaagtttgg cacgcagagc   4200
aggccttgca tattggcgcc cagctgtttg cggccaactc tgtgctctac ctgaccagag   4260
tggcaaagct gcctcagaag aatcagagag gagacgccaa catgtacaac tcattctacc   4320
tacagcatgg cctgggatac ctctcagagg caacagtaaa ggaaaatgga gcctctgcct   4380
tcaagggcgt gccagtgtct gcactggatg ggtcatctta caccctccag cacctggcct   4440
acgcgtcctc tttctcccca catctcctgg caaggatgtg ttactatctg cagttcttgc   4500
cccaccataa aaacaccaac agtcagtcat acaatgtggt ggactacgtg ggcaccgcgg   4560
cacctagtca aatgtgtgac ctgtgtcagg ggcaatgtcc agctgtatgc atcaacacgc   4620
tgttttacag gatgaaggac aggttcccac ctgttctgtc aaacgttaag agagacccat   4680
atgtgatcac gggcacagcg ggaacgtaca atgacctaga gattctcgga aactttgcca   4740
ccttcaggga gagagaggag gaggggaatc ctgtggaaga tgctccaaag tatacatatt   4800
ggcaactatg ccagaatata accgagaagc tagcgtccat gggcatctcg gagggcggcg   4860
atgccctaag aaccctcatt gtggacatcc ccagcttcgt caaagtgttc aaggggatag   4920
acagcacggt agaggcagag ctcctaaagt ttattaactg catgatcaaa aacaattaca   4980
acttcagaga gaacatcaaa tccgtccatc acatccttca gtttgcatgc aacgtatact   5040
ggcaggcgcc gtgcccggtt tttctgaccc tttactacaa gtcactgctg acggtcatac   5100
aggacatatg tctgacgtca tgtatgatgt acgagcagga caacccggcc gtgggaattg   5160
taccatccga gtggcttaaa atgcactttc agacaatgtg gaccaacttc aagggtgcct   5220
gcttcgacaa aggagcaatc acgggcgggg aactaaaaat agtccaccag tccatgttct   5280
gtgacctctt tgacaccgac gctgccatag gagggatgtt tgcacccgct cggatgcagg   5340
tcaggatagc cagagcaatg ctcatggttc caaaaaccat aaaaataaaa aacaggatca   5400
tcttttccaa ctccaccgga gcagagtcga tccaggcagg ttttatgaag ccggccagcc   5460
aaagggattc atacatcgtc ggaggaccct acatgaaatt cctaaacgcc ctgcacaaaa   5520
cactttttcc ttccacaaaa acttctgccc tgtacttgtg gcataagatt ggccagacca   5580
caaaaaatcc catactacca ggtgtctcgg gggaacacct aacggagtta tgtaattatg   5640
taaaggcaag tagccaggct ttcgaagaga taaatgtttt ggaccttgtg ccagacaccc   5700
tgacatcata tgcgaaaata aaactaaaca gttccattct ccgggcttgc ggacagacac   5760
agttttatgc aactactctc tcttgccttt cgccagtgac tcagctggtt ccggccgagg   5820
agtaccccca cgtactgggg ccagtggggt tgtcatctcc agatgaatac agggcaaaag   5880
tcgccggcag gtctgtaacc attgtacagt caacactgaa gcaagctgtt tccaccaacg   5940
gacgactccg gcctatcatt accgtgccac tggtggtcaa caaatataca gggagcaacg   6000
ggaacacaaa cgtctttcac tgtgcaaacc tgggatactt ctcggggaga ggggtggaca   6060
gaaatctcag gccagaaagc gtcccccttta aaaagaataa tgtcagctct atgctaagaa   6120
aacgccacgt gattatgacc cccctggtag acaggctggt aaagagaata gttggcatca   6180
```

-continued

```
actctgggga attcgaggca gaagcggtta agagaagtgt gcagaatgtc ctggaagaca   6240
gagataaccc aaacctgccg aagacagttg tattagagtt ggttaagcca cctcggtgga   6300
gctcctgtgc aagtctcaca gaggaggacg tgatttacta cctgggccct tatgccgtac   6360
ttggggacga ggtcctgtca ttactgagca cagtgggcca ggcgggggtg ccatggacgg   6420
ccgagggtgt ggcctcggtc atccaggaca taatagatga ttgcgagtta cagtttgtgg   6480
gcccagaaga gccttgcctt atccaaggac agtcggtagt ggaggagctt tttccgtccc   6540
cgggcgtccc aagcctgaca gtgggtaaaa aacgaaaaat cgcatccctg ctctctgacc   6600
tggatttgta gttgtgtacc cgtaacgatg gcaaaggaac tggcggcggt ctatgccgat   6660
gtgtcagccc tagccatgga cctctgtctt cttagttacg cagacccggc aacactggac   6720
actaaaagtc tggccctcac tacagggaag tttcagagcc ttcacggcac actactcccc   6780
ctcctcagac gacaaaacgc acacgaatgc tcaggtctgt cactagaatt ggagcacttt   6840
tggaaaacgt ggctgatgct ctggccacgt tgggagtgtg cactagcaga aaactgtctc   6900
cagaagagca tttttccctc ctgcatttgg acacaacatg caacaagcaa ccggagcgtt   6960
aggtttaatt tttacggaaa ttgggccttg gagttaaagc tgtcactaat aaacgacgtt   7020
gaaattttct ttaaacgtct tagtagcgtt ttttattgta taggatcggg cagtgctctg   7080
gagggtttag gggaggtatt gcgtttcgtt gggaagctga ggggtatctc acccgtacct   7140
gggccggacc tatatgtctc aaatctgccc tgcctagaat gccttcagga agtgtgtctg   7200
actcccaacc agggcaccag tctgcaggcc atgctcccag acacggcctg cagtcacata   7260
tgtacccccg catgcggtga gcctgtccgg ggcctctttg agaacgagct aaaacagctc   7320
gggcttcaaa cccctgagtc catacctact accccctgtc agtcccgggt aaggcaagat   7380
gatgaaatca gacagagctc tctaatggcg gtaggagatc accacatttt cggagaggtg   7440
accagatctg tcctggaaat ctcaaacctg atctattgga gctctggcca ctcggatgcc   7500
acctgcgacg gagacagaga ctgctctcac ctggcctcgc tgtttactca cgaggctgac   7560
atgcataaaa ggcgcgtcga cctggccgga tgcttgggcg aacgcggcac gcccaaacac   7620
tttttttgact gctttcgccc agactcccta gaaacccttt tctgtggtgg tctttttagc   7680
tccgtggagg acaccataga aagtctccaa aaggactgct cttctgcctt ctaccaacag   7740
gtaaactaca ctactgcact gcaaaaacag aacgagtttt acgtccgact cagcaaactg   7800
ctggcagctg gtcagctaaa tttgggcaaa tgttccactg aaagttgcca atccgaggcc   7860
cgtaggcagc tggtaggtgg gggcaaacca gaggaagtgc tgagggatgc aaaacaccgg   7920
caagaactat accttcagaa agtggcacgc gacggtttta aaaaactctc tgattgtata   7980
agacaccagg gccacatcct gtctcagacc ctgggtctaa gactgtgggg gtctgtcatc   8040
tacaacgagg catctgccct acaaaaccac tttttacaca gagcacagtt catatccctc   8100
ccctggcagg acctgacggt cgactgtcca acgcggtttg aaaattctaa atatatcaaa   8160
aattctctgt actgccagcg tctggggcgg gaacacgtag agatcctgac actggagttc   8220
tacaaactta tcacgggccc gctgtcaaag cgacatactt tatttcccag tcctccaaat   8280
gtgacgctgg ctcagtgctt cgaggctgcg ggcatgcttc cccatcaaaa gatgatggta   8340
tcagagatga tctggcccag catagagccg aaggactgga tagagcccaa cttcaaccag   8400
ttctatagct ttgagaatca agacataaac catctgcaaa agagagcttg ggaatatatc   8460
agagagctgg tattatcggt ttctctgtac aacagaactt gggagaggga gctaaaaata   8520
cttctcacgc ctcagggctc accggggttt gaggaaccga aacccgcagg actcacaacg   8580
```

-continued

```
gggctgtacc taacatttga gacatctgcg cccttggtgt tggtggataa aaaatatggc   8640
tggatattta aagacctgta cgcccttctg taccaccacc tgcaactgag caaccacaat   8700
gactcccagg tctagattgg ccaccctggg gactgtcatc ctgttggtct gcttttgcgc   8760
aggcgcggcg cactcgaggg gtgacacctt tcagacgtcc agttccccca cacccccagg   8820
atcttcctct aaggccccca ccaaacctgg tgaggaagca tctggtccta agagtgtgga   8880
cttttaccag ttcagagtgt gtagtgcatc gatcaccggg gagctttttc ggttcaacct   8940
ggagcagacg tgcccagaca ccaaagacaa gtaccaccaa gaaggaattt tactggtgta   9000
caaaaaaaac atagtgcctc atatctttaa ggtgcggcgc tataggaaaa ttgccacctc   9060
tgtcacggtc tacaggggct tgacagagtc cgccatcacc aacaagtatg aactcccgag   9120
acccgtgcca ctctatgaga taagccacat ggacagcacc tatcagtgct ttagttccat   9180
gaaggtaaat gtcaacgggg tagaaaacac atttactgac agagacgatg ttaacaccac   9240
agtattcctc caaccagtag aggggcttac ggataacatt caaaggtact ttagccagcc   9300
ggtcatctac gcggaacccg gctggtttcc cggcatatac agagttagga ccactgtcaa   9360
ttgcgagata gtggacatga tagccaggtc tgctgaacca tacaattact ttgtcacgtc   9420
actgggtgac acggtggaag tctccccttt ttgctataac gaatcctcat gcagcacaac   9480
ccccagcaac aaaaatggcc ttagcgtcca agtagttctc aaccacactg tggtcacgta   9540
ctctgacaga ggaaccagtc ccactcccca aaacaggatc tttgtggaaa cgggagcgta   9600
cacgctttcg tgggcctccg agagcaagac cacggccgtg tgtccgctgg cactgtggaa   9660
aaccttcccg cgctccatcc agactaccca cgaggacagc ttccactttg tggccaacga   9720
gatcacggcc accttcacgg ctcctctaac gccagtggcc aactttaccg acacgtactc   9780
ttgtctgacc tcggatatca acaccacgct aaacgccagc aaggccaaac tggcgagcac   9840
tcacgtccct aacgggacgg tccagtactt ccacacaaca ggcggactct atttggtctg   9900
gcagcccatg tccgcgatta acctgactca cgctcagggc gacagcggga accccacgtc   9960
atcgccgccc ccctccgcat cccccatgac cacctctgcc agccgcagaa agagacggtc  10020
agccagtacc gctgctgccg gcggcggggg gtccacggac aacctgtctt acacgcagct  10080
gcagtttgcc tacgacaaac tgcgggatgg cattaatcag gtgttagaag aactctccag  10140
ggcatggtgt cgcgagcagg tcagggacaa cctaatgtgg tacgagctca gtaaaatcaa  10200
ccccaccagc gttatgacag ccatctacgg tcgacctgta tccgccaagt tcgtaggaga  10260
cgccatttcc gtgaccgagt gcattaacgt ggaccagagc tccgtaaaca tccacaagag  10320
cctcagaacc aatagtaagg acgtgtgtta cgcgcgcccc ctggtgacgt ttaagttttt  10380
gaacagttcc aacctattca ccggccagct gggcgcgcgc aatgagataa tactgaccaa  10440
caaccaggtg gaaacctgca aagacacctg cgaacactac ttcatcaccc gcaacgagac  10500
tctggtgtat aaggactacg cgtacctgcg cactataaac accactgaca tatccaccct  10560
gaacactttt atcgccctga atctatcctt tattcaaaac atagacttca aggccatcga  10620
gctgtacagc agtgcagaga aacgactcgc gagtagcgtg tttgacctgg agacgatgtt  10680
cagggagtac aactactaca cacatcgtct cgcgggtttg cgcgaggatc tggacaacac  10740
catagatatg aacaaggagc gcttcgtaag ggacttgtcg gagatagtgg cggacctggg  10800
tggcatcgga aaaacggtgg tgaacgtggc cagcagcgtg gtcactctat gtggctcatt  10860
ggttaccgga ttcataaatt ttattaaaca cccccctaggt ggcatgctga tgatcattat  10920
```

-continued

```
cgttatagca atcatcctga tcatttttat gctcagtcgc cgcaccaata ccatagccca  10980
ggcgccggtg aagatgatct accccgacgt agatcgcagg gcacctccta gcggcggagc  11040
cccaacacgg gaggaaatca aaaacatcct gctgggaatg caccagctac aacaagagga  11100
gaggcagaag gcggatgatc tgaaaaaaag tacaccctcg gtgtttcagc gtaccgcaaa  11160
cggccttcgt cagcgtctga gaggatataa acctctgact caatcgctag acatcagtcc  11220
ggaaacgggg gagtgacagt ggattcgagg ttattgtttg atgtaaattt aggaaacacg  11280
gcccgcctct gaagcaccac atacagactg cagttatcaa ccctactcgt tgcacacaga  11340
cacaaattac cgtccgcaga tcatggattt tttcaatcca tttatcgacc caactcgcgg  11400
aggcccgaga aacactgtga ggcaacccac gccgtcacag tcgccaactg tcccctcgga  11460
gacaagagta tgcaggctta taccggcctg tttccaaacc ccggggcgac ccggcgtggt  11520
tgccgtggac accacatttc cacccaccta cttccagggc cccaagcggg gagaagtatt  11580
cgcgggagag actgggtcta tctggaaaac aaggcgcgga caggcacgca atgctcctat  11640
gtcgcacctc atattccacg tatacgacat cgtggagacc acctacacgg ccgaccgctg  11700
cgaggacgtg ccatttagct tccagactga tatcattccc agcggcaccg tcctcaagct  11760
gctcggcaga acactagatg gcgccagtgt ctgcgtgaac gttttcaggc agcgctgcta  11820
cttctacaca ctagcacccc aggggggtaaa cctgacccac gtcctccagc aggccctcca  11880
ggctggcttc ggtcgcgcat cctgcggctt ctccaccgag ccggtcagaa aaaaaatctt  11940
gcgcgcgtac gacacacaac aatatgctgt gcaaaaaaata accctgtcat ccagtccgat  12000
gatgcgaacg cttagcgacc gcctaacaac ctgtgggtgc gaggtgtttg agtccaatgt  12060
ggacgccatt aggcgcttcg tgctggacca cgggttctcg acattcgggt ggtacgagtg  12120
cagcaatccg gccccccgca cccaggccag agactcttgg acggaactgg agtttgactg  12180
cagctgggag gacctaaagt ttatcccgga gaggacggag tggcccccat actcaatcct  12240
atcctttgat atagaatgta tgggcgagaa gggttttccc aacgcgactc aagacgagga  12300
catgattata caaatctcgt gtgttttaca cacagtcggc aacgataaac cgtacacccg  12360
catgctactg ggcctgggga catgcgaccc ccttcctggg gtggaggtct ttgagtttcc  12420
ttcggagtac gacatgctgg ccgccttcct cagcatgctc cgcgattaca atgtggagtt  12480
tataacgggg tacaacatag caaactttga ccttccatac atcatagccc gggcaactca  12540
ggtgtacgac ttcaagctgc aggacttcac caaaataaaa actgggtccg tgtttgaggt  12600
ccaccaaccc agaggcggtt ccgatggggg caacttcatg aggtcccagt caaaggtcaa  12660
aatatcgggg atcgtcccca tagacatgta ccaggtttgc agggaaaagc tgagtctgtc  12720
agactacaag ctggacacag tggctaagca atgcctcggt cgacaaaaag atgacatctc  12780
atacaaggac ataccccgc tttttaaatc tgggcctgat ggtcgcgcaa aggtgggaaa  12840
ctactgtgtt attgactcgg tcctggttat ggatcttctg ctacggtttc agacccatgt  12900
tgagatctcg gaaatagcca agctggccaa gatccccacc cgtagggtac tgacggacgg  12960
ccaacagatc agggtatttt cctgcctctt ggaggctgct gccacggaag gttacattct  13020
ccccgtccca aaaggagacg cggttagcgg gtatcagggg gccactgtaa taagcccctc  13080
tccgggattc tatgacgacc ccgtactcgt ggtggatttt gccagcttgt accccagtat  13140
catccaagcg cacaacttgt gctactccac actgataccc ggcgattcgc tccacctgca  13200
cccacacctc tccccggacg actacgaaac ctttgtcctc agcggaggtc cggtccactt  13260
tgtaaaaaaa cacaaaaggg agtcccttct tgccaagctt ctgacggtat ggctcgcgaa  13320
```

-continued

```
gagaaaagaa ataagaaaga ccctggcatc atgcacggac cccgcactga aaactattct  13380
agacaaacaa caactggcca tcaaggttac ctgcaacgcc gtttacggct tcacgggcgt  13440
tgcctctggc atactgcctt gcctaaacat agcggagacc gtgacactac aagggcgaaa  13500
gatgctggag agatctcagg cctttgtaga ggccatctcg ccggaacgcc tagcgggtct  13560
cctgcggagg ccaatagacg tctcacccga cgcccgattc aaggtcatat acggcgacac  13620
tgactctctt ttcatatgct gcatgggttt caacatggac agcgtgtcag acttcgcgga  13680
ggagctagcg tcaatcacca ccaacacgct gtttcgtagc cccatcaagc tggaggctga  13740
aaagatcttc aagtgccttc tgctcctgac taaaaagaga tacgtggggg tactcagtga  13800
cgacaaggtt ctgatgaagg gcgtagacct cattaggaaa acagcctgtc gttttgtcca  13860
ggaaaagagc agtcaggtcc tggacctcat actgcgggag ccgagcgtca aggccgcggc  13920
caagcttatt tcggggcagg cgacagactg ggtgtacagg gaagggctcc cagaggggtt  13980
cgtcaagata attcaagtgc tcaacgcgag ccaccgggaa ctgtgcgaac gcagcgtacc  14040
agtagacaaa ctgacgttta ccaccgagct aagccgcccg ctggcggact acaagacgca  14100
aaacctcccg cacctgaccg tgtaccaaaa gctacaagct agacaggagg agcttccaca  14160
gatacacgac agaatcccct acgtgttcgt cgacgcccca ggtagcctgc gctccgagct  14220
ggcagagcac cccgagtacg ttaagcagca cggactgcgc gtggcggtgg acctgtactt  14280
cgacaagctg gtacacgcgg tagccaacat catccaatgc ctcttccaga acaacacgtc  14340
ggcaaccgta gctatgttgt ataacttttt agacattccc gtgacttttc ccacgcccta  14400
gtgactcaga cgcggaaaca gcgcctagaa agtttcctct tgcgctatgt gggacaacta  14460
gagtccaacc tggcaagcag tggagcaaga cgccagacag ccgatctcga aaaaaataat  14520
gcagacagag gcaacgttca tcctaggtga ctgggagata acggtgtcta actgccggtt  14580
tacttgcagc agcctaacat gtggccccct ttacagatct agcggcgact acacgcggct  14640
aagaatcccc ttctctctgg atcgactaat acgtgaccat gccatctttg ggctagtgcc  14700
aaatattgag gatctgttaa cccatgggtc atgcgtcgcc gtagtggccg acgcaaacgc  14760
cacaggcggc aacgcgcgac gcatcgtcgc gcctggcgtg ataaacaatt tttcagaacc  14820
catcggcatt tgggtacgcg gccctccgcc gcaaacgcgc aaggaagcta ttaagttctg  14880
catatttttt gtcagtcccc tgcccccgcg ggagatgacc acatatgtgt tcaagggcgg  14940
cgatttgcct cccggagcag aggaacccga aacactacac tccgccgagg caccccctacc  15000
gtcgcgcgag acgctggtaa ctggacagct gcgatccacc tcgccgcgaa cgtatacggg  15060
atactttcac agtcctgtcc cgctctcttt tttggacctc ctgacattcg agtccattgg  15120
gtgtgacaac gtggaaggtg accccgagca attgacaccc aagtacttga cgttcacgca  15180
gacgggagaa agactttgca aagtaaccgt ttacaacacc cattcgacag catgcaagaa  15240
ggcccgtgtt cgtttcgtct acagaccgac gccgtccgcc cgtcagcttg tcatgggtca  15300
ggcttcaccc ctcataacaa cccctctggg agccagggta ttcgcagtct atccagactg  15360
tgagaaaact atcccacctc aggaaaccac caccctgagg attcaattgc tgttcgagca  15420
gcatggtgcc aacgccggag actgcgcctt tgtcatcatg gggctcgccc gtgaaacaaa  15480
gtttgtctca tttcccgcag tactccttcc gggcaagcac gaacacctta ttgtattcaa  15540
cccacagaca catcctctga ccattcaacg ggacacaata gtgggcgtgg caatggcttg  15600
ctatatccac cccggtaagg cagccagcca ggcaccatac agcttctacg actgcaagga  15660
```

```
agagagctgg cacgtggggc tcttccagat caaacgcgga ccgggagggg tctgtacacc  15720
accttgccac gtagcgatta gggccgaccg ccacgaggaa cccatgcaat cgtgactgtc  15780
cgagcacata tggcgcagga gtcagagcag tgctcccgtg cgtttgcagt gtgcagtagt  15840
aaacgacagc tcgggcgcgg cgagcccgtg tgggattccg tcattcaccc gagccacatc  15900
gtcatctcta atcgagtacc cctcttacta agagaacagc acatatgtct cccttcgtgc  15960
cccagcgtcg gccagatcct ccacagagcc taccccaact ttacatttga caacacgcac  16020
cgcaagcagc aaacggagac ctacactgca ttctacgctt ttggggacca aaataacaag  16080
gttaggatct tgcccactgt tgtggaaagc tcctcgagcg tgctgatttt tagactgcgt  16140
gcatcggtct ctgcgaacat cgccgtggga gggctcaaaa taataatact tgctctcacc  16200
ctggtgcatg cccaaggagt gtacctgcgt tgcggtaagg acctttctac accacactgc  16260
gcaccggcta ttgttcagcg tgaggtgctg agcagcgggt ttgagccgca gtttaccgta  16320
actggcattc cagtgacatc ctcgaactta aaccaatgct actttctggt aagaaagcca  16380
aaaagccggc tggcaaagcc gtttgcacgc ctgtccgcgg agacgactga ggagtgtcgc  16440
gtcaggtcta tccgccttgg gaagacacac ctgcggatat cggtgactgc gcctgcgcag  16500
gaaacgcccg tctgggggct cgtgaccacg agcttcagcc ttacccccac cgcaccgctg  16560
gcctttgatc gtaacccgta caatcacgag acatttgcct gtaatgccaa gcactacatc  16620
ccagtcatct acagcggacc aaaaattacg ctggccccgc gcggccgcca ggtagtctgg  16680
cacaacaaca gctacacgtc ctccctgcca tgcaaagtca cagccatcgt gtcaaaccac  16740
tgctgtaact gtgacatatt tttagaggac tcggaatggc gcccaaacaa gccagcaccc  16800
ctgaaactgg tgaacacgag tgatcatccc gtcatattgg agccggacac acacattgga  16860
aacgccctct tcatcatcgc acccaaggcc cgaggtttac gcagactgac tcgcttaacc  16920
acaaaaacca ttgaacttcc tggcggggta aagatagaca gcaggaaatt acaaacattc  16980
agaaaaatgt atgttgccac cggacgcagt taggtgtccg gttcccaccc acacatttgt  17040
ctttattgct ttcaaataaa acggtgttct gtcaacctcc tccgggctca ctagtattgt  17100
gttcccatac gcgcctgtcg ccccaggatc aacacttcgt cccctatcca ccctaataca  17160
taacacacac aaagacatag tgactgtaga cagttaatct ttattgtcta gacacgcaaa  17220
gtatattagt gttataagaa attttatgtc acgtcgctct ttacttatcg tggacgtcag  17280
gagtcacgtc tgggatagag tccaaaacac gcaccgcttg acctgcaaac ttttccattg  17340
cactcagaac ataaaacgaa gcaaagtgtc tcacccaata cttaagtccc tgaagcctcc  17400
ctaatagacc gcggtcaaat ttgggtggac tgtagtgcgt cttagtcagc ttattgagct  17460
cttcctgtat gtcccatcct aaggtcttcg tcagaagctc catgacgtcc acgtttatca  17520
ctgattttcc aaactccgtc gttaaaaact taaacaacac ctcgaattca aaaaagccat  17580
cggcgagctt tttaaggcag ctagtctcat taaatcctat taacccgcag tgatcagtat  17640
cgttgatggc tggtagtttc agatgaaaaa tagcagcggg ctctagaata cccttgcaga  17700
tgccggtacg gtaacagagg tcgcggaagc attcatcgat cacccatagc atccaattga  17760
gtctctgaat gagaagatcc ttttcaaact cgggggcgtc cggcaacttg ccccgcgttc  17820
cagataccag cagtgaaccg accagcaaga gagaccacaa cttgaaccag cacatggctg  17880
ctaacgcggc atacactagc cggtggtgcc cgagcgggag ttacgaagtc tcactgaagg  17940
gcggggtcgc gggtcggggc cgctccaaat caggcaacgc cgtatccgaa ctctgagtca  18000
cttttatgta ggtctcaaac atgtaaaaga taccacgttc ttgaaaaacc ctctcttgct  18060
```

-continued

```
cgccaggctt ggggttcacg cgggcatacg cagccaagct atcatgcgag agaaacacgt  18120
cacacgcaaa gtcatgtaaa acccgggtta aaaatagcct aactggccag gggccagtga  18180
gcgcctcccg gtacaagtcc ccaccccega tgacccaaac cttgtcaatt tgctgtgcta  18240
gctctgggct tctcgccaac ccaagcgcgg catcgagcga actcgccaaa aagtgagcac  18300
cagggggcgg ggtttctaac gtgcgactta gaaccacatt gattctaccc gccaatggtc  18360
gacagcccgc gggaatcgaa agccatgtgc gccgccccat aacaaccatg ttttgttttc  18420
caggggcaca gtcggtagtc agctgtcgaa aacgcctcat gtctccccgc aatgcaggcc  18480
acgggagaca tctgtttttt ccgatcccga gtttggtatc aaccgcaact acacagtaaa  18540
gtgtaggatc catgccgcga gggtataggt aaacaccacc aaccacacag tgtgctctta  18600
tatactttta atgaaacata agggcagacg aaacagccga acgtttccta atcacgccca  18660
tggaaccata gccaccccca ggcaaaccct gtggaaggat atcaactaga gaggagggtc  18720
cagccttatt atggcaggag acactataag ccccatcgcc cgactgggca ccaacataac  18780
cgccacagta agtggcccta taccgctcag cgcccaagtt gttacagtca cacccaaccg  18840
cggttggctc tacattgtca tcacgtccat cattatgtgt tggttctccc gcttccttgt  18900
accctgcagc ttcatccacg gattcttctg agtcgcgatg cacaggagcg ccatccgcgg  18960
ggccatcttg gtcgcctgga gctgcccccg cggggccatt ttggtcgcct ggagctgccc  19020
ccgcgggccc ctcctcgtcc tggttatccc cacggggaag aatttcctga agctcgatct  19080
cctctactgc acactctggt gatgtcggcc gaggtctata tggaaacact tcaacccgcg  19140
tgtttacagc agcgtatgcc cgccccacgt ggcgcatcat gtggaaaaac gcacccaacc  19200
caaaaacgac aaacaattgg taaaacacga aaaaaacgta gtacgcggct gcagcgacgt  19260
gatctatctc tgggtcatga ccgcccacta tatatagcca aacccacgtc gcagcggcaa  19320
ggccagcggc ccccaatgtc ataatgaaaa taaaaacaat cagttccaga ccctcctggt  19380
aagtcagccg aggcaatagc gtcatttcgc gcaagggtcg ccagaccacg cgcgtgttgt  19440
atacgacgcc acatatctga caggccgtgt ttctagagat agtgagccag gtgcttaaac  19500
aacttctatg gacgttctcg agctctcctg tgcatccaca ggctctaaat ctctcatttc  19560
cgagctcctc gttgcaaatc cagcagacag gaacatcctc atcttccata tcctgagaga  19620
gaacccacaa taaaacatgg cattaacccc tgcaacaagt gaccgtacca gggcacgcgt  19680
ccaggcaacc ggggtccccc tcgttggtct atacaattcc atgactacct actggtaatg  19740
ctacagccac tcactgtaca agccggttaa ctgggaggcg acgctggcgt ggtatcggcc  19800
aactgaaaca caccactcca ctccaaacac ttatgtactt tgtggctcgg ctttattgta  19860
acagccaaga ggggcgtttg tggctcagct ttattgtaac agccaagagg gacgtatgtg  19920
gctatctcac aaaaagtcac cgattcatgt agacaacccg ctcccacgaa ttcggttttt  19980
aaaaagccct cacgtataca gacgggccac taaatacgca catgagcggg catcctgttt  20040
ccgccttgac gcccaccact ctgaccgcac gctaaacatc gccctacctg ctatactgcc  20100
atttccatac gaatggtagg atgcgggcag tagtccacca gtctaaaatc atcaggtgta  20160
aactcttcca tggaagaaac agaccggagt atctccaggc gcggaaaggg acgtggagtg  20220
cgcgtcagct gcagccgtag tggctctata tgcgttttgt agatgtgggc atctcccaac  20280
gtgtgaataa actccccggg tctaagacca gtaacatgag caagcatata agttaagagg  20340
gaatagctgg caatgttaaa aggaactccc aaacccatgt ctcccgacct ctgatacagc  20400
```

-continued

```
tgacaggaaa gctcaccgtc agctacataa aattgacata acaagtgaca gggcggaagc  20460
gccatcaacg acaagtccgc cggttccac gcacacataa tgattcttct atcgtgcgga  20520
ttatttttta ttaaatccac aatgtacgac aattggtcaa acccctggcc tgtatagtca  20580
gcatccgcgt ccacgtacgc cgccccaaag tgcctccact ggaaaccgta aacaggtccc  20640
aaatccccct cccttctgtg cgccaggccg cgcccggcca ggaactccct ggagccattt  20700
ttgtcccata tcttgactcc tgttcttgaa agctccctgg agtcagtact ccccttcaga  20760
aaccaaagca gctcttgcac tacgcctcgc caaaacaccc gctttgtggt tagtaaggga  20820
aagtggtccc gcagactata cctggcctgc atgccaaata gagagagggt gcctatgccg  20880
gtgcggtcga gtcgatcgct gccacggcac aaaatttccc tcaactgcct gagatactga  20940
agttcctcgt ggggcgtctc agccccagtt acctcatgct gaatcgaaca agggtcaacc  21000
tcgggggcca aagccaagac gccaggcttt tgacagaagc gaaacccccct ggcacggaat  21060
aactttttgg cgacatacaa gcttaaaggt acaaacggaa acatgataga tcctggaagt  21120
ttgtgaagcc ctgtgcccgg agagacaccc ctcaactcgc agtgctcgga gacctacatg  21180
tatactcagg ctcttctata aaccctcccc aaaagtttat aaaacaccgt acgtaataca  21240
cattactcac agttcccacg gtgacgccca aacccatgca cacgggcgtg atcgatacca  21300
gaaaacatca caagaacaaa aagtgtgtgt ctgacattca catttatttt tacaagacaa  21360
ttttgtgcag tagagttgtg ccttccgaca ccccgcgccg ttcgctgttc tcctgtaatt  21420
gggagatccc actccttggc aggcacgttt cacgaaacgc tcttgtctcg ctggccttag  21480
acttgtggac ccaacatggg tatcgttaga gatccgtcgc gtaaatgcgc agctggcaaa  21540
gcattcttca gcgagcagtg actggtaatt gctgcatcag cttcttcacc cagtctttcg  21600
atttgtcggc acacacctgg cgaccacgct ttgtcaaaaa tatcacaccc ggcttgctgc  21660
acagttggga ggtggggtac cagctggaca gaagcacctg tggtaatggt cttttctggt  21720
aaccgagaca gcacttgtcc ggtctatgcc aggacgctcc cagcgtgtcc ccagattgca  21780
aacaaagcaa ggcagtcagc acagcgacga gcaggatgcc cttggtgtcc ataactcccc  21840
tcgtgtgtcc tcgtgtaaat gcgaaacggc gatgttaggt caggcgcggt aaacagctca  21900
actcggttca aaacacgtac gtgatgtagt gctggttcta cgacgcctac ctgtaaactc  21960
caggatcctg ggcttttatt acgaaggcca acaccccaaa aaatccacgc ccccgtgacc  22020
gcaggggcgg ttactaacga cggttacagg tccctcccga gccacgcacc tgccatgtaa  22080
cctgcaaggt aaccagacaa acatctagga agcgtaaata tccccaggta ggagaagtat  22140
tgcatatgtc acagactcaa cacacacggg ccgttacgca acggctaggg gcataaccct  22200
ttaccggcgc gaagcgctac gcgcttcgcg agaggtatct ccgtgtgctt ctccatcaga  22260
agacgcgtgc gccgcttcgc aggcgacccg catactttcc gccccgagtg cgttacaaaa  22320
atgactgcct tctggcgaca atacacggtg gacgtccagt accacccgca tatcagctta  22380
tccggtggca atctggcact ggacagggaa ttctcgcaac aatccgaggc catgatggtg  22440
gcaggaccgc tggccgcaca tagctcaatc acggccaccc agaagagcag ccccaaatgt  22500
gcgcgcaaca cccagcacat gctccacata cagttctggc gccacaacga tgatgcgcaa  22560
aggggtgcat taccctaaat cccagcctag ttataaatta ttgaagccca ggcgaccagg  22620
ggtcgccgcg cttttcctcc ccaaacgcga cgataaagac cagcgttgcc aaatgtaact  22680
tatgtataac ccaaaatatt gcgcatcgat aaggtttgcc aaaacacccg aaagtacaca  22740
cacaaaaaaa cagcaacaag acgctcacta gacattcacc ccttccccca cccccgaaaa  22800
```

-continued

```
caaaacaact tgacacaggg gaaacaccag gggcggcgga ggttgtcaat agtgtccagt  22860
atttcgttag acgcgggttc ttggacccga tgtcccaggt cattaaagtc tcaaatggga  22920
ttaaaggatc atagttccca ggtttaatac tccaagctat cccagaacag gaccccggca  22980
gaaccccgct taacagcacc aaatccactt gcggtcccag aaaaggtcgc cgaggtggca  23040
aggtgactga aaaggtcata gagaggacac cggtcccatt tcccacggtc caaaaatcca  23100
gcgcgcccca ccggctttcc gagaacttcg gcaaagctaa tttgcatgcg ctaatccttt  23160
tatgtgcata aattatgtag atgaggagtc gcgcatgcgc agaaaaattc agagcgcccg  23220
ggtgcacggg gtcacctcca ggtcacgccg ctaggtggga ccgtgagcga ctcgaaaaat  23280
tataattttt ggccatttca tgggcgccgc catcttgaat ttgctaatcc cccataatcc  23340
tctgccccgc tcccattggt ccgccggccc gtcaatcaaa gttttccgag ccgccattgg  23400
cccatccggc cgaccaatcc cgttcgagct aggcgaccgc gccattccat tggacgcccc  23460
agccgtcaat caaattcgga ggcctcccat tggcccctat ccctagaact cccaagctga  23520
ttggcccaga gcgggaacca atcagcgatt agagttttgt tttgattttt cctatatata  23580
tatatataat cctttaatcc tagcgcagct gagtcatcgc agcccctatt ccagtaggta  23640
tacccagctg ggtaatccag taggtatacc caggtgggtg aacccagctg ggtataccca  23700
gctgcaattc tataattaaa caaggtagaa accaacgggg tcctcaggtg gtatttccgg  23760
aagcattacc aaataaggca acctcagctg ggaataccag cggactaccc ccaactgtat  23820
tcaaccctcc tttgttttcc ggaagtatat ccatttatgg aaatcagctg ggtcactcta  23880
ctgggttatt ctttataata gggcccgatg agtcatgggg ttgggatttt tctactaggt  23940
cgtttcggtg gatgggtgcc aggattatag gggccctgtc cacggggttg ttcggtggcg  24000
gggggggggc tagtgagtca cggggcctgga atctcgcctc tgggtggttt cggtagatgg  24060
gggccgggag gatggggccc cgcccaccgc tggcgcgccc cagaacatgg gtggctaacg  24120
cctacatggg cagcttgtcc tacggttacg cccatttgag acgggttaac caactgttac  24180
acccccttcgc cgggaacgct ataaaaacga gggacagcag cccccccctcg cgcactgcgc  24240
gcgcggcggc acgtgggacg gatctcttgg atttacccgt aacgaggagc cccggcagca  24300
ccccaggagc cccggcagca ccccaggagc cccggcagca ccccaggagc cccggcagca  24360
ccccaggagc cccggcagca ccccaggagc cccggcagca ccccaggagc cccggcagca  24420
ccccaggagc cccggcagca ccccaggagc cccggcagca ccccaggagc cccggcagca  24480
ccccaggagc cccggcagca ccccaggagc cccggcagca ccccaggagc cccggcagca  24540
ccccaggagc cccggcagca ccccaggagc cccggcagca ccccaggagc cccggcagca  24600
ccccaggagc cccggcgcgc caccctcccc ggagggggat cccggcgcgc caccctcccc  24660
ggagggggat cccggcgcgc caccctcccc ggagggggat cccggcgcgc caccctcccc  24720
ggagggggat cccggcgcgc caccctcccc ggagggggat cccggcgcgc caccctcccc  24780
ggagggggat cccggcgcgc caccctcccc ggagggggat cccggcgcgc caccctcccc  24840
ggagggggat cccggcgcgc caccctcccc ggagggggat cccggcgcgc caccctcccc  24900
ggcaacaacc tgttgccatg tatggcgatt tgtatcagtc acaagcacac aacccctgct  24960
agtattaatg gtgtttaaaa cgttctacac gtacggcgga ccgcatccgt cgcaagcacg  25020
cgcatataac ccccaaatgc accatgatga gaagcacagc cacgcgtcaa aaaactttaa  25080
aaacatcgtt atccaatatc attaaaaacc acaccgaaat ttacacaggt agcacgtcac  25140
```

-continued

```
cgtgttagtg tcacccactg tacacaaggc gtgtcgtata tgtagtatag gtatttgatg  25200
aggcggaagc atatcccgct tccagcgaac ggaaataaga atcatccgtt ccagcattta  25260
ttcaaagagg gcacagagga ttcacattgt ttagagagag tttttcttag tcaccattcc  25320
atacttgggc agtattggcc tacgatttgg gcgacgtttc aggctggtct attctccgtc  25380
cacttttccc cggctattct gtcccagcat aggctcttga aataaacaat gtttaccgag  25440
taaaaggttc cactcaccct catttgtcgt tgcacccatc ccccctttgc ttaatcaccc  25500
gaaaactaga ggacacggat ggaaaacata tcgcacgcgg gttgtttgaa agtcaacagc  25560
tacttgtttt taatgaggac agatttgggc acaggccaga gggtaaagcc ctacgtgtgc  25620
gcgggggggg gggtgtatac gctgcgaaaa cctgcacggt gcataacacc cagggcgtca  25680
cgtcacatat ctctgtgcac ccaagtggtt gttcaaccgt tgttttttgg atgatttttc  25740
cgcaccggct tttttgtggg cgcgcatagg tcggtacgcg ctgtccccct aagtcccgca  25800
cggtcgttcg ggcccccgtc cggctcgtct ccggatgaac cgtcacgttc tttgtctcca  25860
gaggcgacgt ctccttcaga tgactcgtcc gtgggctcct cgtccgtccc gcccgcgggt  25920
ccgacaagga ccgtcaattc gatgttatct tcgttcgcgg ttggccggcg cggccgtcgg  25980
tatggcagta cggtcacccg ggtgttattt gccgcgtata atgccctcac agtgccactt  26040
acgcggcata tgccgccaaa tgcaaacaca ataaatattt ggtaaaaccc aaagaagcag  26100
agaaaaccga gcacggcccc gggggagaat gttcccgcag gagcagttag gatgaccagg  26160
agcgtccagg tgcacaacgc cacgccgaca agcccagcca ccaccacaga catcagcaga  26220
aacagttcaa aaatttcttg gcgctccatc tccggccaca ggttaaggcg actacgccac  26280
tgcgtgcgcg tgcggtatat aacgcgacac atttgacagg ccgtgtttcg agacactgtt  26340
agccaagtgc ttaaacactg cgggtggacg acatccagct ctccggtaca ggcgcagggg  26400
tgtatgccct cgttccccac ctcttcccta catatccagc agatgggtcc ctctacaccc  26460
tcttctacgt ccttagacgc catctctgca gctggggtgg aagtctgaaa aagggaaagg  26520
ggaggtgagc agagtgccca gttagtctcc gacccgccgt ccgccctact gtcgctatcc  26580
cgccttgaca gatgtctaac gtattcacgg acgccacatg tgtgtctatt ttcctacatc  26640
caggctttcc ctggaaaact gtcacaaccc accctgcttt agctctacat ctgtattttt  26700
gtttacgcac aggatcaacg cttcgtgccc gtccaccccc gcgctctccg cctgtgtttg  26760
gaggttttat gagtggttag ttctaggcag ctccggacaa gttgtccaaa acacggcgcg  26820
ccccgccctt ccttccctcc ggatccgccc acaccggacc tatgaaataa gggacacgcg  26880
tcatcactag ttatgagaga aaaaccacaa cagctttatt ggaaaacacc tgagtggatc  26940
ccccaccccc cgcgtacgac aggcgtttct gtggtgcgct tctgggaaaa acgtttttcc  27000
cccatttctt cctcgacagg tcttctaagg tagataaatc cccccccttt gcgcgtctcc  27060
tagaatggcc taggcgcacg atggcgttgt cgcctcgagc agttgggccg cagtgatatc  27120
ttcaactttc gaccgtctaa gctatggcag gcagccgctg catcagctgc ctaacccagt  27180
ttttggaagg gtctgcgcag atctgacgcc ctcgcttggt cagcaaaata actccgggtt  27240
ttgggcacgc tggggacgtg ggataccact cttttagaat ttggacgggc ggtgggtgct  27300
gctggaaccc gtagcagcag ctattaggcg tgtacgacac gagtgacccc gcgctttctg  27360
tgggcgtcag gtaaaacgtg gcaagcagta cgctaacgca gcataaaacg tggacggggg  27420
ccatctggag gtgccaagtt cgcaacagtc taaagaaaac cgtaaaggct atttggggtt  27480
tctgttctgt cagatgtaac gccgagttcc ttatatgctt acctgattct ggtctcacct  27540
```

-continued

```
gtttatttat agtggcgtat gctaaccgcc agcttacatg cgggataagt tggcctaact  27600
caccaaaaac gggttgcaga caaaagtgat tgttggggcg cttacttaga aggtgtgagg  27660
gtttctaaga aaccccgcca acgcccggaa accgcatgcg ttccagtcgg tgcggcctgc  27720
gccggcgtcg ctgtggcgcc tttgtgggct ttgagttctg tcattaagcc aggtttccat  27780
tgccacccgg gcgaaaacaa gccgggtagt ttcaggggtc atctggcgat cagtgtacca  27840
tattcccacg acccatcaac accgctgctt gaggcgtgtc tctgtatgtg tcaccggaga  27900
ctgcatgtat cgtgcatatc tgtattgtgc gcttgcgcgg agacaacata ccgacgacca  27960
agtcaggggt cacctccagt gcacgccgct aggtgggacc gtgggcgagc cgaaataatt  28020
atatattttt ttggcacggt tgtgagcaac gccatcgtga gttggttaat accctctaaa  28080
cgcatagtct tttttatttt gtcaaccaac cagtcaatca cctgtcatcg ccgctcagaa  28140
gcacacgtct tcggccaatg ccgtgttggc gggtttgacc acggttactg ataggtagac  28200
gagtccgaca atcacacacg tccgccagcg atttgcagcg cagctaaaat cgcgtggccg  28260
ggttggtaga agcaaattat ccaatggtcg tgtttgggtt tgttttgggg ttatctacat  28320
attatattcc ttatcccgac tggttgcgga agtattcgca gcttggctac tctgctcgat  28380
taccccgtga ataactgggc ggggggtgac ccaacatagt gattcggtag atttggggga  28440
ctggatgaac attaatgaaa gtttattaat gttcatccgt attgtgtata tgtaatttgg  28500
tttccatatt tggtaggagt atggagtttt cttatggatt attaagggtc agcttgaagg  28560
atgatgttaa tgacataaag gggcgtggct tccaaaaatg ggtggctaac ctgtccaaaa  28620
tatgggaaca ctggagataa aaggggccag cttgagtcag tttagcactg ggactgccca  28680
gtcaccttgg ctgccgcttc acctatggat tttgtgctcg ctgcttgcct tcttgccgct  28740
tctggttttc attggtgccg ccgattgtgg gttgattgcg tcgcttttgg caatataccc  28800
atcctggctt tcggctaggt tttccgtcct acttttccca cattggcctg agagctgtag  28860
tacaaaaaac accgcgcggt ctggagctct ccataagccc gcagaacaaa agctgcgatt  28920
tgcccaaaaa ccttgccatg gcaactatac agtcacccct tgcgggttat tgcattggat  28980
tcaatctcca ggccagttgt agcccccttt tatgatatgc gaggatactt aacgtgtctg  29040
aatgtggaat ataatgtgaa aggaaagcag cgcccactgg tgtatcagaa cagtggtgca  29100
ctacctatct gctcattcgt tgtttcggtt ctgtgtttgt ctgattctta gatagtgttg  29160
aggtaattct agaaagcgga ttgagtgtaa atcgggccac tttgccctaa atgtgacaat  29220
ctggatgtgt atcttattgg tgcgttgtga agcattttaa aatgcgtttt agattgtatc  29280
aggctagtgc tgtaatggtg tgtttatttt tccagtgtaa gcaagtcgat ttgaatgaca  29340
taggcgacaa agtgaggtgg catttgtcag aagtttcaaa gtcgtgtaag aacattggac  29400
taaagtggtg tgcggcagct gggagcgctc tttcaatgtt aatgttttaa tgtgtatgtt  29460
gtgttggaag ttccaggcta atatttgatg ttttgctagg ttgactaacg atgttttctt  29520
gtaggtgaaa gcgttgtgta acaatgataa cggtgttttg gctgggtttt tccttgttcg  29580
caccggacac ctccagtgac cagacggcaa ggtttttatc ccagtgtata ttggaaaaac  29640
atgttatact tttgacaatt taacgtgcct agagctcaaa ttaaactaat accataacgt  29700
aatgcaactt acaacataaa taaaggtcaa tgtttaatcc atatttcctg acttgtgtct  29760
tgacttgcgt cgattgggat gggggtgtgg gatgggggtg tgggatgggg gtgtgggatg  29820
ggggtgtggg atgggggtgt gggatggggg tgtgggatgg gggtgtggga tgggggtgtg  29880
```

-continued ggatgggggt gtgggatggg ggtgtgggat gggggtgtgg gatgggggtg tgggatgggg 29940
gtaaatgaca atgggggtaa atgacaatgg ggcgcttggt gacacatttg ccccaccgtc 30000
gcctgcccgg aaccagcttg gtgatgtgct gtctggctct caggtgcact ttatgcaaag 30060
cagttgaggc gcattagata tataaaactt gggtacacac ccttggtgct gtgcgcgtgc 30120
tatgtgccct ggtgaccgtc cacaatggac gaggacgttt tgcctggaga ggtgttggcc 30180
attgaaggga tattcatggc ctgtggatta aacgaacctg agtacctgta ccatcctttg 30240
ctcagcccta ttaagctata catcacaggc ttaatgcgag acaaggagtc tttattcgag 30300
gccatgttgg ctaatgtgag atttcacagc accaccggta taaaccagct tgggttgagc 30360
atgctgcagg ttagcggcga tggaaacatg aactgggggc gagccctggc tatactgacc 30420
tttggcagtt ttgtggccca gaagttatcc aacgaacctc acctgcgaga ctttgctttg 30480
gccgttttac ctgtatatgc gtatgaagca atcggacccc agtggtttcg cgctcgcgga 30540
ggctggcgag gcctgaaggc gtattgtaca caggtgctta ccagaagaag ggacggaga 30600
atgacagcgc tattgggaag cattgcatta ttggccacta tattggcagc ggtcgcgatg 30660
agcaggagat aacgcgtaat tcgaggtccc cggaagagta gagggttgca tgttatacaa 30720
acaacataaa cattaaatga acattgttca aaacgtatgt ttattttttt tcaaacaggg 30780
gagtagggta ggaagggtac gtctaatacg taactgttcg ctactgcttg ttcaggagct 30840
cctcgcagaa catcttgcga attttagatt ttggactaga gcgactgctg gcttcaacgc 30900
ggttcgatgt agggttcggc gtaggagcgt ctttctccac cgccgcgcat ggtgtatgcg 30960
tggtctccgg tgcctgttgt tggatgctct gcgtgctgga ggcgggggtg ggttcagcgg 31020
gtggtgcgcc aactaccgcg agtcctgtag agactggcgg gtggctcaca tgtggctgag 31080
caaaaaggat gggcgccgct tgctggaact gaccgtgtgg cgcctgcacg taaatgggtg 31140
ggtgtacgta ggttcctccg tgctccttca ttgtcgggaa ttgacacggg accgctgaat 31200
tggcgtgggg cctgtagtgt ggatctactg cggctgctgc tgcagaggag gacggcggtg 31260
gccctgcgtg ccaaccgttc agtttcatct ctttgagttc agactgtatt tccgctatgt 31320
tctttgacat ggacaagata tccttgtgat acgccggctc ctctcctgga aagaggtgtc 31380
cttcgtcgtc ctctgcgccg cgcttgcgct tccccgtcct atatccaggc agctgtggcg 31440
agtaatacca tggatcgtat gggttcttgt aagcgtagcc gtatggtggc gctgggtttg 31500
aaacatacga aggtaggtga tggtcggtgg ggaacatctg gcccccacac cccattaggc 31560
ctggccctga aagtgtatgt gacatttttg ccgctgtggt cttcattcca tcgatgctgc 31620
tttgtagcat gctcaggaag gcggatttgg ggatggatat gatatcctct tgaccagagc 31680
tgttcatggc tggtctgggt ggtgtgacgg cttggatgcc gaccgggaat tggctggcct 31740
ttaaatacgc cgggctcaat atgctggcca cacctctgtc agttttcaat aggtcgaggc 31800
ggtcccgtat gaagctggca tctatagctt ttgccattaa ggtctccagg ggactgacga 31860
aatttggtgt ggaaaggtcc tccagcctgc agctacttac gtgctggagg atgtgggcgc 31920
gctccgactt agatactgat gagaatctgg aaaccaccca ctcggcgtcg tgtccgtaca 31980
cggccactgt gccgcgtcgg cgccccaggg cgcatagtga tacgtgttga aacacgggac 32040
cgctgggagt ctgggataac tcgcggggat gtatagacga taaagacagc cccgggagcc 32100
acgtgtggag tatctccaac agtggttcct tagggagatt tttcacgggg gctctggcca 32160
cgtgggaggt gtccgccagc ctggatgcca gctctaggaa ggctggcgac gtgatggctc 32220
cggtgcagaa aataccgtgg gacacttgaa atagacccag tgtccagccc acttctgtct 32280

-continued ctggtaggtg ttcgattgtt attggaaggg gttctgtgac tgggagataa tccgtcacct 32340
gatccggatc gagatagagc tcttgctcca gcttggggca ggacacaaca tctacaaacc 32400
ctccgacgta caggccctgt gccatgctcg gaaaatacgt gtgtgagacc gagccgctga 32460
gcccggggct taggaggctc atgtggcgct tttgcaaaa taagaattta aatacattcc 32520
acgcccaaga gctgcgtttt attcatttgg ttctctgcag gatgtacaat ttcggtctaa 32580
atgtgtacct gttaagggag gctactgcca atgccgggac ctacgacgag gtggtcctgg 32640
gacgcaaggt tcctgcggag gtgtggaagc tcgtgtacga tgggctcgag gagatgggcg 32700
tgtcaagtga gatgctgctg tgtgaggcat accgggacag cctctggatg cacttgaacg 32760
ataaggtggg gctcttgagg ggcctggcga attatctgtt tcaccggcta ggggtcaccc 32820
acgacgttcg catcgccccg gaaaacctgg tggacggaaa ctttttgttt aatctgggaa 32880
gtgtgctccc ctgcaggctg ctccttgcgg cgggctactg cctcgccttt tggggcagcg 32940
atgaacacga acgctgggtg cgcttcttcg cccagaagct tttcatttgc tacctgatag 33000
tctccgggcg tcttatgcca cagaggtctc tgctagtttg ggccagcgaa acgggctatc 33060
ccggtccggt ggaggcagtc tgtcgcgaca tccgctccat gtacggcata cgaacgtatg 33120
cggtctcggg ttatcttccg gctccgtccg aagcgcagct ggcctacctt ggtgcgttta 33180
acaacaacgc ggtttaaacg accgcgagga ccaccggcag gcagccaaga accataaagt 33240
acgctctatc gtagtcatcg ccgccgccaa actgggactt gataatctcc tggagaaggg 33300
tgggtgggga tgggtgtgaa agcaggacgt ccaggccctc ttctgttgcc aggcggaggg 33360
ctgttctcgc ctggagcagc gccagtggat ctcggaatgt aagctgctgg ttcaggattt 33420
cgaatatctc attaaaccta ctgcctgtca gatttacaaa tggtccgggt tgtttgtggg 33480
acacggtcga tcgcgcctcg agggcggcca gtattatgcc agggaagatg aaggacacgg 33540
gggcgtttgg attagcctgc agtgtgggga ttatgtagtg ctccgatatg aacgaaaata 33600
gctggcccct tttcagcatg gggcgtttg gatccggtag ggcaccgggc tgaaatttgg 33660
gtcccagcag ggataccagg ttcaagcggc ggtttgggtg ccctcgcgcg acttgcccaa 33720
actccagcaa tccatacgcg aggataaaca cctccagcgc aacaatcccc gctcgcaggt 33780
tccactggta tgcggaaaat ggtggtatat cggacccaaa catggcgctc gtaatggcga 33840
ataccaagtc catggcgggc gctgtccctg gcgcgcccgt acccttgttg tggggaaata 33900
atccagcctt agccatcatt gcgtgaagct tgtggcgctg gaagaaggct gtcggatagc 33960
ggctctcctt attgagaggc gccagcgagg cgcgctcctg gggggtttgag tatgtgaagc 34020 tgaagtcccc aggaccgctt tcctgtttta gctgagtgat tagcaggtct agcttttgag 34080
gcaggtctgc taacaggtca tcgggagtag cgggcagttg cctggatgtc ttttgacaaa 34140
agtacgcgtt gacgaggcaa agcgcggcct gggtgtccgt gagatgcctg gcgtcggcga 34200
aaaagtcagc ggtggtcgag gcgaccgtcg tcagggtgtg agagatgagt ttgagcgatg 34260
tggaattctg aaagttaaca gtccccttta gttctttagg gaagacgcgc cgctgcatgg 34320
cgttgtccgt gaggctgatg aaccacggcc caaaggatgg caaccactga ttctggttca 34380
tgtacagggt gggcatgagc tcgccgcgca ggtccctgtc aacggagaag tgagggtccc 34440
cggggacgat cgccacggtg aagttacggt ggctggcctg cgggggggat gtcactaagg 34500
gaggctcatg ggaacggctt tggggcatgt ctatgttgtc agaccatgtc atgttgccta 34560
tcatctgttt caccgcgtcg atatctgcgt taatgacgcg gacgcgtgag tcatggacct 34620

-continued

```
gaacaagccg gtccagctct agggaaagca ggtgtgcctt tgtctttcgt tctcgatttc  34680
gcacgagttg gctgcgcagt ccaagggcga cccttcttgt ttcttccatg gtgggcttgt  34740
gaataaacag cacgttttcc gggtgtgggg cccagaatct tcccgcctct gtccatcttc  34800
ggtttttgg gtaccttaga taggaccttt ctgatgtcag cattttctct agcagtgaga  34860
aaggcgcaca attttccttc ggtggtgtgc accggcgtgg gaaacgcccc gggtgattca  34920
gagtatactg tctttagtgt tttctgattc ttaaatatca gcaggggcgt gatagtccac  34980
gcctcggtac ccggaggggc cgagtgagcg atgtaatgga tcgagtcgga gagttggcac  35040
aggccttgag ctcgctgtga cgttctcacg gtgttggttg ggatcagctg gtgactcaga  35100
caagtcttga gctctacaac gtaacatacg ggctgatgcc cacccgatac cagaattacg  35160
cagtcggcaa ttctgtgccc tagagtcacc tcaaagaata atctgtggtg tccaagggga  35220
gggttctggg gccggctact tagaaaccgc catagatcgg gcagggtgga gtacttgagg  35280
agccggcggt aggtggccag gtgggcccgg ttacctgctc ttttgcgtgc tgctggaagc  35340
ctgctcaggg atttcttaac ctcggcctcg gttggacgta ccatggcaga aggcggtttt  35400
ggagcggact cggtggggcg cggcggagaa aaggcctctg tgactagggg aggcaggtgg  35460
gacttgggga gctcggacga cgaatcaagc acctccacaa ccagcacgga tatggacgac  35520
ctccctgagg agaggaaacc actaacggga aagtctgtaa aaacctcgta catatacgac  35580
gtgcccaccg tcccgactag caagccgtgg catttaatgc acgacaactc cctctacgca  35640
acgcctaggt ttccgcccag acctctcata cggcaccctt ccgaaaaagg cagcattttt  35700
gccagtcggt tgtcagcgac tgacgacgac tcgggagact acgcgccaat ggatcgcttc  35760
gccttccaga gccccagggt gtgtggtcgc cctccccttc cgcctccaaa tcacccacct  35820
ccggcaacta ggccggcaga cgcgtcaatg ggggacgtgg gctgggcgga tctgcaggga  35880
ctcaagagga ccccaaaggg atttttaaaa acatctacca agggggcag tctcaaagcc  35940
cgtggacgcg atgtaggtga ccgtctcagg gacggcggct ttgcctttag tcctaggggc  36000
gtgaaatctg ccatagggca aaacattaaa tcatggttgg ggatcggaga atcatcggcg  36060
actgctgtcc ccgtcaccac gcagcttatg gtaccggtgc acctcattag aacgcctgtg  36120
accgtggact acaggaatgt ttatttgctt tacttagagg gggtaatggg tgtgggcaaa  36180
tcaacgctgg tcaacgccgt gtgcgggatc ttgccccagg agagagtgac aagttttccc  36240
gagcccatgg tgtactggac gagggcattt acagattgtt acaaggaaat ttcccacctg  36300
atgaagtctg gtaaggcggg agacccgctg acgtctgcca aaatatactc atgccaaaac  36360
aagttttcgc tccccttccg gacgaacgcc accgctatcc tgcgaatgat gcagccctgg  36420
aacgttgggg gtgggtctgg gaggggcact cactggtgcg tctttgatag gcatctcctc  36480
tccccagcag tggtgttccc tctcatgcac ctgaagcacg gccgcctatc ttttgatcac  36540
ttctttcaat tactttccat ctttagagcc acagaaggcg acgtggtcgc cattctcacc  36600
ctctccagcg ccgagtcgtt gcggcgggtc agggcgaggg gaagaaagaa cgacgggacg  36660
gtggagcaaa actacatcag agaattggcg tgggcttatc acgccgtgta ctgttcatgg  36720
atcatgttgc agtacatcac tgtggagcag atggtacaac tatgcgtaca aaccacaaat  36780
attccggaaa tctgcttccg cagcgtgcgc ctggcacaca aggaggaaac tttgaaaaac  36840
cttcacgagc agagcatgct acctatgatc accggtgtac tggatcccgt gagacatcat  36900
cccgtcgtga tcgagctttg cttttgtttc ttcacagagc tgagaaaatt acaatttatc  36960
gtagccgacg cggataagtt ccacgacgac gtatgcggcc tgtggaccga aatctacagg  37020
```

-continued

```
cagatcctgt ccaatccggc tattaaaccc agggccatca actggccagc attagagagc  37080
cagtctaaag cagttaatca cctagaggag acatgcaggg tctagccttc ttggcggccc  37140
ttgcatgctg gcgatgcata tcgttgacat gtggagccac tggcgcgttg ccgacaacgg  37200
cgacgacaat aacccgctcc gccacgcagc tcatcaatgg gagaaccaac ctctccatag  37260
aactggaatt caacggcact agttttttttc taaattggca aaatctgttg aatgtgatca  37320
cggagccggc cctgacagag ttgtggacct ccgccgaagt cgccgaggac ctcagggtaa  37380
ctctgaaaaa gaggcaaagt cttttttttcc ccaacaagac agttgtgatc tctggagacg  37440
gccatcgcta tacgtgcgag gtgccgacgt cgtcgcaaac ttataacatc accaagggct  37500
ttaactatag cgctctgccc gggcaccttg gcggatttgg gatcaacgcg cgtctggtac  37560
tgggtgatat cttcgcatca aaatggtcgc tattcgcgag ggacaccccca gagtatcggg  37620
tgttttaccc aatgattgtc atggccgtca agttttccat atccattggc aacaacgagt  37680
ccggcgtagc gctctatgga gtggtgtcgg aagatttcgt ggtcgtcacg ctccacaaca  37740
ggtccaaaga ggctaacgag acggcgtccc atcttctgtt cggtctcccg gattcactgc  37800
catctctgaa gggccatgcc acctatgatg aactcacgtt cgcccgaaac gcaaaatatg  37860
cgctagtggc gatcctgcct aaagattctt accagacact ccttacagag aattacactc  37920
gcatatttct gaacatgacg gagtcgacgc ccctcgagtt cacgcggacg atccagacta  37980
ggatcgtatc aatcgaggcc aggcgcgcct gcgcagctca agaggcggcg ccggacatat  38040
tcttggtgtt gtttcagatg ttggtggcac actttcttgt tgcgcggggc attaccgagc  38100
accgatttgt ggaggtggac tgcgtgtgtc ggcagtatgc ggaactgtat tttctccgcc  38160
gcatctcgcg tctgtgcatg cccacgttca ccactgtcgg gtataaccac accacccttg  38220
gcgctgtggc cgccacacaa atagctcgcg tgtccgccac gaagttggcc agtttgcccc  38280
gctcttccca ggaaacagtg ctggccatgg tccagcttgg cgcccgtgat ggcgccgtcc  38340
cttcctccat tctggagggc attgctatgg tcgtcgaaca tatgtatacc gcctacactt  38400
atgtgtacac actcggcgat actgaaagaa aattaatgtt ggacatacac acggtcctca  38460
ccgacagctg cccgcccaaa gactccggag tatcagaaaa gctactgaga acatatttga  38520
tgttcacatc aatgtgtacc aacatagagc tgggcgaaat gatcgcccgc ttttccaaac  38580
cggacagcct taacatctat agggcattct cccccctgctt tctaggacta aggtacgatt  38640
tgcatccagc caagttgcgc gccgaggcgc cgcagtcgtc cgctctgacg cggactgccg  38700
ttgccagagg aacatcggga ttcgcagaat tgctccacgc gctgcacctc gatagcttaa  38760
atttaattcc ggcgattaac tgttcaaaga ttacagccga caagataata gctacggtac  38820
ccttgcctca cgtcacgtat atcatcagtt ccgaagcact ctcgaacgct gttgtctacg  38880
aggtgtcgga gatcttcctc aagagtgcca tgtttatatc tgctatcaaa cccgattgct  38940
ccggctttaa cttttctcag attgatagc acattcccat agtctacaac atcagcacac  39000
caagaagagg ttgccccctt tgtgactctg taatcatgag ctacgatgag agcgatggcc  39060
tgcagtctct catgtatgtc actaatgaaa gggtgcagac caacctcttt ttagataagt  39120
cacctttctt tgataataac aacctacaca ttcattattt gtggctgagg gacaacggga  39180
ccgtagtgga gataaggggc atgtatagaa gacgcgcagc cagtgctttg tttctaattc  39240
tctcttttat tgggttctcg gggttatct actttcttta cagactgttt tccatccttt  39300
attagacggt caataaagcg tagattttta aaaggtttcc tgtgcattct ttttgtatgg  39360
```

-continued

```
gcatatactt ggcaagaaat ccgagcacct cagaaagtgg attgccgtca catatcagtt  39420
cgaccacccc tgcacctagc catgcggcgc tttgacggtc tttggggcta cacatcataa  39480
agtacttttc catggcttct ataagcacct tggaacaatc tgggggttgg cgaatgggtt  39540
ccctaaacgg gaaatcctct atggtattca ggcagaagac cgcgtcctcc acccgacgtt  39600
tgagtctttc tagcagagcg ccgaagaact cccgctcgtg tgttttcgca ggggcaagtt  39660
ctgcgccgta cagcgatgag aaacacgaca cgatgttttc cagccccatg ctgcgcagca  39720
acacgtgctt caggaacagg tgttgtagcc ggttcagttt tagcttgggt agaaaagtta  39780
tcgagttgtt agcacgctcc atgatggtaa cggtgttgaa gtcacagacc gggctttctc  39840
cgagtctcgg ccgcctgagt ccaatcatgt agaacataga cgcggcctcg ttgtctgtgt  39900
taagtgacac gatatcccgt tcgcaaacct gtgcgatgtt gtgtttcagt atagatctgg  39960
tctgaccggc acggggtgtt atggggtgac gcggtaaagg cgactctggg tcaaacacct  40020
ttatgcggtt ggcggcctcg tcgatgacga cacgcttgtt cgcggcgtgt atggggacgc  40080
gacggcatcc cgctggcaga tctataatct taaagttggt ataagactgg tcgctcgtta  40140
tggccagccg gcactccggt agtatctgcg tgtcctcgaa ttcgtggccg cgtacgactg  40200
gcttggagtg caggtaaacg ccaagagatg cggtctcttc gcctacgcac aagtggcttc  40260
ttaacgcgta ggggtgcggt gagagcatga tccgtagcaa cgatagttcc gggtgcctag  40320
ccgcgtagag tggcagggta gacgagtccg gagtcccaaa cttttcgaac aacagtggca  40380
tcgggacttc aggattagag actcccacca tggccgccac cgccggagag gtcaagacgt  40440
gaaacacgcg ctcgcctgtc gacaggcgcg ccgcgccctc tactagacta gccttcacgt  40500
ccggaactcg taacatagct tagaccagcg gacggacgca acgtacgtgg ggatcggctg  40560
gcggtgtctg ctcgttggac gcggccgttc ggtggcgcca gtgcaggcct agtttgcgaa  40620
tggcgtgacg gacaatttgt ggctttagag cggcgaaccg atgacccgtg gtggcgacga  40680
acgaaatgaa gtttgcattg cggcccaact cgtctagcct ggtcttcttg tttcgggcat  40740
agattttcgg gattaggtta cactttttat atcccagtac tgcgcactcg tgtttgcttt  40800
tagtgtgact gattatcttc tttgagaagt caaacaggcc ccgggcggcg gctcgcctaa  40860
tgcaagccac gtcaagcctg agaaacgaac agcattccac cagacactcc aggaaccttt  40920
tgtgtagcgt ctgtatttgg gaacggtttc tgtgctcaag tagggagaat attctatttt  40980
tgtttccgtc gatgcgcgcg tgctggtccg tgagaatggg cgccagctcg tggcgaatct  41040
gttccacaag aggctgcccg tacactttag aaatcgtggc tgtcgcggcc ttaaaccagg  41100
acacgtttag cccatccttg ctggagacca cagatggaaa gtttgtggtc caaaatacgt  41160
tttttcgccc cattctcacc atgtactggt tttccagtcc gtgcaggtcc aacgtggagt  41220
tccaatttgc tatcgataca ggaaatatgt gcctgattgg cagaaagcat ttcagcgtac  41280
ccattgcgaa gagaaagtgc agcatgtccc cactgatgtt gatgtttatt gcggtgcctt  41340
gacacatgtt gtcggaaaaa aacacgctta tggtaaaaga aggttccttt acggagtact  41400
ttcgtataac aaaattgttg gtcaatctgg ggatgtttaa aatagtcttt tgcagggtgt  41460
taggaacgtg gcagcttatc ttagtgttaa tcaccatgtt ggtgttgaat atggtgatct  41520
tgaagttttc caaactgacg tgttttgtgg gttccagcat gtctgacact gtagagctgc  41580
ccagagtccg cgcgtccgtg gccgcgtatc gttggaagca cgcctgcaaa tttcctttca  41640
tggctgctcg ccggtctttc ggcgcgtacc ggattcttga aagcgtcgcc gccaggagac  41700
gcggtgtctc gtgggtgcct aaaaagtttg cgcaggggtg cagtccgctg cacgagtggc  41760
```

```
cgatgcagtc tgccactgcc atacacatga cgagtctgta gatggccggt gtgcccggat  41820
acactagata gtaggtacaa tctggggtac tgacgaccac cctgtatggc tttggtccgg  41880
ggtccttgcg ttggattttt acgtgcagac gggacacgag ctggtttaga gccagctgaa  41940
agcccaccag atcccgtccg ttaaccttga cgtcctggtg cttactctgt ttcgacaggt  42000
tcttcagcac ggtgggcagt cgctctacgt tgtgagcgat ggcacggcgc agcgagacca  42060
gctctccgtg ccaccccac gtggccatga agctgctgat gttaaacttt aaaaaatgta  42120
gctgtgcgtc tggggatgcg ggtggcatta ttgaaaacga gagatgcttc aggctctcca  42180
ggagtgcaaa ataattttga tagattgtgg gttgtagact atggggcaac accgccagaa  42240
acgcatgaaa acactgttcg aactcccaga actccaggta cctgcacact atcctgaaca  42300
tggctttgta acatatggtg cacgttagta gcgcgggaag atacagcgag cgtagctccc  42360
tgaattcgca gggtttatca caatcatcgg taagttccca tgatcccacc gcaggtaggt  42420
agttgtcggt gtctatctgt ccgcgcgtaa acactccacc accgtcaatt attaaacctt  42480
cgccgctgta ccgtcgaccc acttttccca aaagagtccc ttcttgatgt ataaaagggt  42540
ggaggcgttc ccccaggagt agtctgcgta tcgctctgca ggcgaaaaag gtgggctcgg  42600
gctgcatcat cttatcaaga ccttctaagg tcagctctgc ctgcaggtgc gagttggtgg  42660
ccagacagca gaatatttcc agctgtgatt cccaagtcgc ttgataacac gtggtctgcg  42720
gactcgtcgt cagggaggcg ctcggtggca gtagtagggg gccctcgagc gctgccatgg  42780
aggcgacctt ggagcaacga cctttcccgt acctcgccac ggaggccaac ctcctaacgc  42840
agattaagga gtcggctgcc gacggactct tcaagagctt tcagctattg ctcggcaagg  42900
acgccagaga aggcagtgtc cgtttcgaag cgctactggg cgtatatacc aatgtggtgg  42960
agtttgttaa gtttctggag accgccctcg ccgccgcttg cgtcaatacc gagttcaagg  43020
acctgcggag aatgatagat ggaaaaatac agtttaaaat ttcaatgccc actattgccc  43080
acggagacgg gaggaggccc aacaagcaga gacagtatat cgtcatgaag gcttgcaata  43140
agcaccacat cggtgcggag attgagcttg cggccgcaga catcgagctt ctcttcgccg  43200
agaaagagac gcccttggac ttcacagagt acgcgggtgc catcaagacg attacgtcgg  43260
ctttgcagtt tggtatggac gccctagaac gggggttagt ggacacggtt ctcgcagtta  43320
aacttcggca cgctccaccc gtctttattt taaagacgct gggcgatccc gtctactctg  43380
agaggggcct caaaaaggcc gtcaagtctg acatggtatc catgttcaag gcacacctca  43440
tagaacattc attttttcta gataaggccg agctcatgac aagggggaag cagtatgtcc  43500
taaccatgct ctccgacatg ctggccgcgg tgtgcgagga taccgtcttt aagggtgtca  43560
gcacgtacac cacggcctct gggcagcagg tggccggcgt cctggagacg acggacagcg  43620
tcatgagacg gctgatgaac ctgctggggc aagtggaaag tgccatgtcc gggcccgcgg  43680
cctacgccag ctacgttgtc aggggtgcca acctcgtcac cgccgttagc tacggaaggg  43740
cgatgagaaa ctttgaacag tttatggcac gcatagtgga ccatcccaac gctctgccgt  43800
ctgtggaagg tgacaaggcc gctctggcgg acggacacga cgagattcag agaacccgca  43860
tcgccgcctc tctcgtcaag atagggggata agtttgtggc cattgaaagt ttgcagcgca  43920
tgtacaacga gactcagttt ccctgcccac tgaaccggcg catccagtac acctatttct  43980
tccctgttgg ccttcacctt cccgtgcccc gctactcgac atccgtctca gtcaggggcg  44040
tagaatcccc ggccatccag tcgaccgaga cgtgggtggt taataaaaac aacgtgcctc  44100
```

-continued

```
tttgcttcgg ttaccaaaac gccctcaaaa gcatatgcca ccctcgaatg cacaacccca  44160
cccagtcagc ccaggcacta aaccaagctt ttcccgatcc cgacgggga catgggtacg  44220
gtctcaggta tgagcagacg ccaaacatga acctattcag aacgttccac cagtattaca  44280
tggggaaaaa cgtggcattt gttcccgatg tggcccaaaa agcgctcgta accacggagg  44340
atctactgca cccaacctct caccgtctcc tcagattgga ggtccacccc ttctttgatt  44400
tttttgtgca cccctgtcct ggagcgagag gatcgtaccg cgccacccac agaacaatgg  44460
ttggaaatat accacaaccg ctcgctccaa gggagtttca ggaaagtaga ggggcgcagt  44520
tcgacgctgt gacgaatatg acacacgtca tagaccagct aactattgac gtcatacagg  44580
agacggcatt tgaccccgcg tatcccctgt tctgctatgt aatcgaagca atgattcacg  44640
gacaggaaga aaaattcgtg atgaacatgc ccctcattgc cctggtcatt caaacctact  44700
gggtcaactc gggaaaactg gcgtttgtga acagttatca catggttaga ttcatctgta  44760
cgcatatggg gaatggaagc atccctaagg aggcgcacgg ccactaccgg aaaatcttag  44820
gcgagctcat cgcccttgag caggcgcttc tcaagctcgc gggacacgag acggtgggtc  44880
ggacgccgat cacacatctg gtttcggctc tcctcgaccc gcatctgctg cctccctttg  44940
cctaccacga tgtctttacg gatcttatgc agaagtcatc cagacaaccc ataatcaaga  45000
tcggggatca aaactacgac aaccctcaaa atagggcgac attcatcaac ctcaggggtc  45060
gcatggagga cctagtcaat aaccttgtta acatttacca gacaagggtc aatgaggacc  45120
atgacgagag acacgtcctg gacgtggcgc ccctggacga gaatgactac aacccggtcc  45180
tcgagaagct attctactat gttttaatgc cggtgtgcag taacggccac atgtgcggta  45240
tgggggtcga ctatcaaaac gtggccctga cgctgactta caacggcccc gtctttgcgg  45300
acgtcgtgaa cgcacaggat gatattctac tgcacctgga gaacggaacc ttgaaggaca  45360
ttctgcaggc aggcgacata cgcccgacgg tggacatgat cagggtgctg tgcacctcgt  45420
ttctgacgtg ccctttcgtc acccaggccg ctcgcgtgat cacaaagcgg gacccggccc  45480
agagttttgc cacgcacgaa tacgggaagg atgtggcgca gaccgtgctt gttaatggct  45540
ttggtgcgtt cgcggtggcg gaccgctctc gcgaggcggc ggagactatg ttttatccgg  45600
taccctttaa caagctctac gctgacccgt tggtggctgc cacactgcat ccgctcctgg  45660
caaactatgt caccaggctc cccaaccaga gaaacgcggt ggtctttaac gtgccatcca  45720
atctcatggc agaatatgag gaatggcaca agtcgcccgt cgcggcgtat gccgcgtctt  45780
gtcaggccac cccgggcgcc attagcgcca tggtgagcat gcaccaaaaa ctatctgccc  45840
ccagtttcat ttgccaggca aaacaccgca tgcaccctgg ttttgccatg acagtcgtca  45900
ggacggacga ggttctagca gagcacatcc tatactgctc cagggcgtcg acatccatgt  45960
ttgtgggctt gccttcggtg gtacggcgcg aggtacgttc ggacgcggtg acttttgaaa  46020
ttacccacga gatcgcttcc ctgcacaccg cacttggcta ctcatcagtc atcgccccgg  46080
cccacgtggc cgccataact acagacatgg gagtacattg tcaggacctc tttatgattt  46140
tcccagggga cgcgtatcag gaccgccagc tgcatgacta tatcaaaatg aaagcgggcg  46200
tgcaaaccgg ctcaccggga aacagaatgg atcacgtggg atacactgct ggggttcctc  46260
gctgcgagaa cctgcccggt ttgagtcatg gtcagctggc aacctgcgag ataattccca  46320
cgccggtcac atctgacgtt gcctatttcc agacccccag caacccccgg gggcgtgcgg  46380
cgtgcgtggt gtcgtgtgat gcttacagta acgaaagcgc agagcgtttg ctctacgacc  46440
attcaatacc agaccccgcg tacgaatgcc ggtccaccaa caacccgtgg gcttcgcagc  46500
```

-continued gtggctccct cggcgacgtg ctatacaata tcacctttcg ccagactgcg ctgccgggca 46560
tgtacagtcc ttgtcggcag ttcttccaca aggaagacat tatgcggtac aatagggggt 46620
tgtacacttt ggttaatgag tattctgcca ggcttgctgg ggcccccgcc accagcacta 46680
cagacctcca gtacgtcgtg gtcaacggta cagacgtgtt tttggaccag ccttgccata 46740
tgctgcagga ggcctatccc acgctcgccg ccagccacag agttatgctt gacgagtaca 46800
tgtcaaacaa gcagacacac gccccagtac acatgggcca gtatctcatt gaagaggtgg 46860
cgccgatgaa gagactatta aagctcggaa acaaggtggt gtattagcta acccttctag 46920
cgttggctag tcatggcact cgacaagagt atagtggtta acttcacctc cagactcttc 46980
gctgatgaac tggccgccct tcagtcaaaa atagggagcg tactgccgct cggagattgc 47040
caccgtttac aaaatataca ggcattgggc ctggggtgcg tatgctcacg tgagacatct 47100
ccggactaca tccaaattat gcagtatcta tccaagtgca cactcgctgt cctggaggag 47160
gttcgcccgg acagcctgcg cctaacgcgg atggatccct ctgacaacct tcagataaaa 47220
aacgtatatg cccccttttt tcagtgggac agcaacaccc agctagcagt gctaccccca 47280
ttttttagcc gaaaggattc caccattgtg ctcgaatcca acggatttga cctcgtgttc 47340
cccatggtcg tgccgcagca actggggcac gctattctgc agcagctgtt ggtgtaccac 47400
atctactcca aaatatcggc cggggccccg gatgatgtaa atatggcgga acttgatcta 47460
tataccacca atgtgtcatt tatggggcgc acatatcgtc tggacgtaga caacacggat 47520
ccacgtactg ccctgcgagt gcttgacgat ctgtccatgt acctttgtat cctatcagcc 47580
ttggttccca gggggtgtct ccgtctgctc acggcgctcg tgcggcacga caggcatcct 47640
ctgacagagg tgtttgaggg ggtggtgcca gatgaggtga ccaggataga tctcgaccag 47700
ttgagcgtcc cagatgacat caccaggatg cgcgtcatgt tctcctatct tcagagtctc 47760
agttctatat ttaatcttgg ccccagactg cacgtgtatg cctactcggc agagactttg 47820
gcggcctcct gttggtattc ccacgctaa cgatttgaag cggggggggg gtatggcgtc 47880
atctgatatt ctgtcggttg caaggacgga tgacggctcc gtctgtgaag tctccctgcg 47940
tggaggtagg aaaaaaacta ccgtctacct gccggacact gaaccctggg tggtagagac 48000
cgacgccatc aaagacgcct tcctcagcga cgggatcgtg gatatggctc gaaagcttca 48060
tcgtggtgcc ctgccctcaa attctcacaa cggcttgagg atggtgcttt tttgttattg 48120
ttacttgcaa aattgtgtgt acctagccct gtttctgtgc cccctaatc cttacttggt 48180 aactccctca agcattgagt ttgccgagcc cgttgtggca cctgaggtgc tcttcccaca 48240
cccggctgag atgtctcgcg gttgcgatga cgcgattttc tgtaaactgc cctataccgt 48300
gcctataatc aacaccacgt ttggacgcat ttacccgaac tctacacgcg agccggacgg 48360
caggcctacg gattactcca tggcccttag aagggctttt gcagttatgg ttaacacgtc 48420
atgtgcagga gtgacattgt gccgcggaga aactcagacc gcatcccgta accacactga 48480
gtgggaaaat ctgctggcta tgttttctgt gattatctat gccttagatc acaactgtca 48540
cccggaagca ctgtctatcg cgagcggcat ctttgacgag cgtgactatg gattattcat 48600
ctctcagccc cggagcgtgc cctcgcctac cccttgcgac gtgtcgtggg aagatatcta 48660
caacgggact tacctagctc ggcctggaaa ctgtgacccc tggcccaatc tatccacccc 48720
tcccttgatt ctaaatttta aataaaggtg tgtcactggt tacaccacga ttaaaaacca 48780
ctcactgaga tgtcttttta accgctaagg gattataccg ggatttaaaa ccgcccactg 48840

-continued

```
attttttac gctaagagtt gggtgcttgg ggggttttgc attgctctgt tgtaaactat  48900
atataagtta aaccaaaatt cgcagggaga caaggtgacg gtggtgagaa ctcagttgag  48960
agtcagagaa tacagtgcta atcagggtag atgagcatga cttccccgtc tccagtcacc  49020
ggaggaatgg tggacggctc cgtcctggtg cgaatggcca ccaagcctcc cgtgattggt  49080
cttataacag tgctcttcct cctagtcata ggcgcctgcg tctactgctg cattcgcgtg  49140
ttcctggcgg ctcgactgtg gcgcgccacc ccactaggca gggccaccgt ggcgtatcag  49200
gtccttcgca ccctgggacc gcaggccggg tcacatgcac cgccgacggt gggcatagct  49260
acccaggagc cctaccgtac aatatacatg ccagattaga acggggtgtg tgctataatg  49320
gatggctatg ggggggctgt agataattga gcgctgtgct tttattgtgg ggatatgggc  49380
ttgtacatgt gtctatcatc ggtagccata aaatgggcca tgacaactgc cacaagtaag  49440
tcgtccgaca tgtgcttttg cttggcgctg tatgactgcc ctccatccct aagcgggacg  49500
cacttgatcg cgcggacctg ttctaccagg taggtcaccg ggtcaaatga tattttgatg  49560
gtgttggaca ccaccgtctg gctggcgctc agggtgccgg agttcagagc gtagatgaat  49620
gtctcaaacg cggaggattt ctcgcctccc aacatgtaaa ttggccactg cagggcgctg  49680
ctcttgtcag tatagtgtag aaaatgtatg gggagcgggc atatttcgtt aaggacggtt  49740
gcaatggcca ccccagaatc ttggctgctg ttgccttcga ccgccgcgtt cacgcgctca  49800
attgtggggt ggagcacagc gatcgcctta atcatcgtgc atgcgcagga cgctatctcg  49860
taagcagctg cgccagtgag gtcgcgcagg aagaaatgct ccatgcccaa tatgaggctt  49920
ctggtgggag tctgagtact cgtgacaacg gcgcccacgc cagtaccgga cgcctccgtg  49980
ttgttcgtat acgcggggtc gatgtaaaca aacagctgtt ttccaaggca cttctgaacc  50040
tgctgggcgg tggtgtctac ccgacacatg tcaaactgtg tcagcgctgc gtcacccacc  50100
acgcggtaaa gcgtagcatt tgacgacgct gctccctcgc ccattagttc ggtgtcgaat  50160
gccccctcca taaagaggtt ggtggtggtt ttgatggatt cgtcgatggt gatgtacgtc  50220
ggaatgtgca gtctgtaaca aggacaggac actagtgcgt cttgcaggtg gaaatcttcg  50280
cggtggtccg cacacacgta actgaccaca ttcagcatct tttcctgggc gttcctgagg  50340
ttaagcagga aactcgtgga gcggtctgac gagttcacgg atgatataaa tataagcttg  50400
gcgtctttct gaagcatgaa acccagaata gccggcagtg catccttttt aataaaattc  50460
gcctcgtcta cgtagagcag gttaaaggtc tgtccccgaa tgctctgcag acacggaaag  50520
acacaaaaga ggggctcata agcggctaac agtaaaggag aggaggcgaa cagtgcgtgg  50580
ctcttgttct tgggaataaa agggggcgtg tgtgccgatc gtatgggtga gccagtggat  50640
cctggacatg tggtgaatga gaaagatttt gaggagtgtg aacaattttt cagtcaaccc  50700
cttagggagc aagtggtcgc gggggtcagg gcactcgacg gcctcggtct cgctgactct  50760
ctatgtcaca aaacagaaag actctgcctg ctgatggacc tggtgggcac ggagtgcttt  50820
gcgagggtgt gccgcctaga caccggtgcg aaatgaagag tgtggcgagt cccttatgtc  50880
agttccacgg cgtgttttgc ctgtaccagt gtcgccagtg cctggcatac cacgtgtgtg  50940
atgggggcgc cgaatgcgtt ctcctgcata cgccggagag cgtcatctgc gaactaacgg  51000
gtaactgcat gctcggcaac attcaagagg gccagttttt agggccggta ccgtatcgga  51060
ctttggataa ccaggttgac agggacgcat atcacgggat gctagcgtgt ctgaaacggg  51120
acattgtgcg gtatttgcag acatggccgg acaccaccgt aatcgtgcag gaaatagccc  51180
tgggggacgg cgtcaccgac accatctcgg ccattataga tgaaacattc ggtgagtgtc  51240
```

-continued

```
ttcccgtact gggggaggcc caaggcgggt acgccatggt ctgtagcatg tatctgcacg  51300
ttatcgtctc catctattcg acaaaaacgg tgtacaacag tatgctattt aaatgcacaa  51360
agaataaaaa gtacgactgc attgccaagc gggtgcggac aaaatggatg cgcatgctat  51420
caacgaaaga tacgtaggtc ctcgctgcca ccgtttggcc cacgtggtgc tgcctaggac  51480
ctttctgctg catcacgcca tacccctgga gcccgagatc atcttttcca cctacacccg  51540
gttcagccgg tcgccagggt catcccgccg gttggtggtg tgtgggaaac gtgtcctgcc  51600
aggggaggaa aaccaacttg cgtcttcacc ttctggcttg gcgcttagcc tgcctctgtt  51660
ttcccacgat gggaactttc atccatttga catctcggta ctgcgcattt cctgccctgg  51720
ttctaatctt agtcttactg tcagatttct ctatctatct ctggtggtgg ctatgggggc  51780
gggacggaat aatgcgcgga gtccgaccgt tgacggggta tcgccgccag agggcgccgt  51840
agcccaccct ttggaggaac tgcagaggct ggcgcgtgct acgccggacc cggcactcac  51900
ccgtggaccg ttgcaggtcc tgaccggcct tctccgcgca gggtcagacg gagaccgcgc  51960
cactcaccac atggcgctcg aggctccggg aaccgtgcgt ggagaaagcc tagacccgcc  52020
tgtttcacag aaggggccag cgcgcacacg ccacaggcca ccccccgtgc gactgagctt  52080
caaccccgtc aatgccgatg tacccgctac ctggcgagac gccactaacg tgtactcggg  52140
tgctccctac tatgtgtgtg tttacgaacg cggtggccgt caggaagacg actggctgcc  52200
gataccactg agcttcccag aagagcccgt gcccccgcca ccgggcttag tgttcatgga  52260
cgacttgttc attaacacga agcagtgcga ctttgtggac acgctagagg ccgcctgtcg  52320
cacgcaaggc tacacgttga gacagcgcgt gcctgtcgcc attcctcgcg acgcggaaat  52380
cgcagacgca gttaaatcgc actttttaga ggcgtgccta gtgttacggg ggctggcttc  52440
ggaggctagt gcctggataa gagctgccac gtccccgccc cttggccgcc acgcctgctg  52500
gatggacgtg ttaggattat gggaaagccg cccccacact ctaggtttgg agttacgcgg  52560
cgtaaactgt ggcggcacgg acggtgactg gttagagatt ttaaaacagc ccgatgtgca  52620
aaagacagtc agcgggagtc ttgtggcatg cgtgatcgtc acacccgcat tggaagcctg  52680
gcttgtgtta cctgggggtt ttgctattaa aggccgctat agggcgtcga aggaggatct  52740
ggtgttcatt cgaggccgct atggctagcc ggaggcgcaa acttcggaat ttcctaaaca  52800
aggaatgcat atggactgtt aacccaatgt caggggacca tatcaaggtc tttaacgcct  52860
gcacctctat ctcgccggtg tatgaccctg agctggtaac cagctacgca ctgagcgtgc  52920
ctgcttacaa tgtgtctgtg gctatcttgc tgcataaagt catgggaccg tgtgtggctg  52980
tgggaattaa cggagaaatg atcatgtacg tcgtaagcca gtgtgtttct gtgcggcccg  53040
tcccggggcg cgatggtatg gcgctcatct actttggaca gtttctggag gaagcatccg  53100
gactgagatt tccctacatt gctccgccgc cgtcgcgcga acacgtacct gacctgacca  53160
gacaagaatt agttcatacc tcccaggtgg tgcgccgcgg cgacctgacc aattgcacta  53220
tgggtctcga attcaggaat gtgaaccctt ttgtttggct cgggggcgga tcggtgtggc  53280
tgctgttctt gggcgtggac tacatggcgt tctgtccggg tgtcgacgga atgccgtcgt  53340
tggcaagagt ggccgccctg cttaccaggt gcgaccaccc agactgtgtc cactgccatg  53400
gactccgtgg acacgttaat gtatttcgtg ggtactgttc tgcgcagtcg ccgggtctat  53460
ctaacatctg tccctgtatc aaatcatgtg ggaccgggaa tggagtgact agggtcactg  53520
gaaacagaaa ttttctgggt cttctgttcg atcccattgt ccagagcagg gtaacagctc  53580
```

-continued

```
tgaagataac tagccaccca acccccacgc acgtcgagaa tgtgctaaca ggagtgctcg  53640
acgacggcac cttggtgccg tccgtccaag gcaccctggg tcctcttacg aatgtctgac  53700
tacttcagcc gcttgctgat atatgagtgt aaaaaactta aggccctggg cttacgttct  53760
tattgaagca tgttgcgcac atcagcgagc tggaccgtcc tccgggtcgc gtgtagatta  53820
tggttccgtt ctccttcttg atgtttaaat ttttgggggg gaaccaccga caaagcgtct  53880
ttatgatttc cgcgaacacg gagttggcta cgtgcttttg gtgggctacg tacccaatgt  53940
taatgttctc tacggatgcc agtagcatgc tgatgatcgc caccactatc catgtctttc  54000
cgtgtctcct tggtattagg aatacgcttg ccttttgctt aaacgtctgt aaaacactgt  54060
ttggagtttc aaataaaccg aagtactgct taaacaatcc aaacaactgg tgcgtctttt  54120
gtggggcctt gattgaaacc aaaaagaaaa aagtgtgcat tactagctgc tgttggaagg  54180
gctccagcca gtgcaccccg ggaacgtaac agccgttcag aaaggacgaa aggttaacca  54240
gaaaagcctg aagttcgcgg tagacagagc aggcgtgcag ggagtcgtgt gtttttctgg  54300
ccgcctggta ctcgaccagt tgatcggccg tggagacgtg cgcgtcctcg cgcacacacc  54360
gcatctgcaa gtatgttgat agggactcca ataggcgcgg ctttgcgggg acgttgtcct  54420
cggacggtct gggggttccc acgtcgggat ttgctgacgt gggcgtggcg ggatggtgcc  54480
gtgtgcagta tgtttccagg accgaactgt atgagtttat tctgtgcacc acgccaataa  54540
aagggtgcgc catccgtgcc gttttgggac agtgtcgcgt gaatgtcggg gcactcagtt  54600
cccacctctc tccggcgtct ttggcggtct cctgcaggtt ggcggcaagg cgctccctgt  54660
gacggctgag cagcatgttt gctttgagct cgctcgtgtc cgagggtgac ccggaggtga  54720
ccagtaggta cgtcaagggc gtacaacttg ccctggacct tagcgagaac acacctggac  54780
aatttaagtt gatagaaact cccctgaaca gcttcctctt ggtttccaac gtgatgcccg  54840
aggtccagcc aatctgcagt ggccggccgg ccttgcggcc agactttagt aatctccact  54900
tgcctagact ggagaagctc cagagagtcc tcgggcaggg tttcggggcg gcgggtgagg  54960
aaatcgcact ggacccgtct cacgtagaaa cacacgaaaa gggccaggtg ttctacaacc  55020
actatgctac cgaggagtgg acgtgggctt tgactctgaa taaggatgcg ctccttcggg  55080
aggctgtaga tggcctgtgt gaccccggaa cttggaaggg tcttcttcct gacgaccccc  55140
ttccgttgct atggctgctg ttcaacggac ccgcctcttt ttgtcgggcc gactgttgcc  55200
tgtacaagca gcactgcggt tacccgggcc cggtgctact tccaggtcac atgtacgctc  55260
ccaaacggga tcttttgtcg ttcgttaatc atgccctgaa gtacaccaag tttctatacg  55320
gagatttttc cgggacatgg gcggcggctt gccgcccgcc attcgctact tctcggatac  55380
aaagggtagt gagtcagatg aaaatcatag atgcttccga cacttacatt tcccacacct  55440
gcctcttgtg tcacatatat cagcaaaata gcataattgc gggtcagggg acccacgtgg  55500
gtggaatcct actgttgagt ggaaaaggga cccagtatat aacaggcaat gttcagaccc  55560
aaaggtgtcc aactacgggc gactatctaa tcatcccatc gtatgacata ccggcgatca  55620
tcaccatgat caaggagaat ggactcaacc aactctaaaa gagagtttat taagtcggct  55680
ctggaggcca acatcaacag gagggcagct gtatcgctat ttgatcgttt tgggggtagc  55740
agcgccgtgt ttgagaagca gtttcaggac gcacagcatg ccgtcagggc ccacggtgca  55800
ctgaagcgcg aagccgagct cgggactctg gtacgcaagg cgggccagag gtttgaggcg  55860
ctgaaaaggg aacggtcaat tttgcgccag ccgcgcgacc tcccacgggt cgccgacatt  55920
gacgccctgg tcgacgccgt cgcggacctc aaagaagagg tggccgtgcg cctagatgcg  55980
```

-continued

```
ctggaagaga atggagagga gacccccact cactcctctt cggagatcaa ggacacaatc  56040
gtcaggtgga ggcttgacga tttgcccccg gtgtgccctg aaactcccta aggctacccg  56100
gatttcagag agaccctggg cgtccacatg gcagctgaat cagcatatac aggtgtccaa  56160
gactaaaaag gccaccgcgt atcttaaagc gccccgtgaa tgggggcagt gcacgcacca  56220
ggatccagac tggtccaagc gtctgggtcg tggcgccttt ggcataatcg tccctatctc  56280
cgaggatctg tgtgtgaagc agtttgatag ccgccgggag tttttctacg aggcaattgc  56340
caacgacctg atgcaggcca cccgagagag gtaccccatg cattctggtg gatctagact  56400
gctaggattc gtgcagcctt gcataccctg tagatcgatt gtgtatccta gaatgaagtg  56460
caacctgctg cagctggact ggagtcaggt caacctgagt gtcatggcgg cggagttcac  56520
cggcctaatg gcggcggtgt cctttctaaa cagatactgt ggcatggtgc actgcgacgt  56580
tagtccagac aatattttgg ccacaggaga cctaacgccc atgaaccccg ggaggctggt  56640
ccttaccgat ttcggttccg ttgcgctaca ctctgggagc aagtggacta accttgtggt  56700
gacctctaac ctggggttta agcaacactg ctacgacttc agggtgccac ccaaactcat  56760
ttgtaagcat ctctataagc cgtcttgcgt cctcttccag tgttacctat ccagtctcgg  56820
taagatgcac gcgcaggtat tggaccaacc gtaccctatc agccctaaca tgggactgac  56880
catcgacatg tcctcgttgg gctacactct gctgacatgc ctggaactct atctcgatct  56940
gccgctaaac aaccctctga agttcttggg ttcagccacc agagacggac gccccgaacc  57000
catgtactac ttgggcttca tgattcccag ggtggtgatg actcagatcc tgtccgctgt  57060
gtggaccatg acgcttgacc tgggactaga ttgcaccggc aaagcccagg cgattcccat  57120
gcgacaggag caccagctgg cgtttcagaa gcagtgctat ttatataaag ccaaccaaaa  57180
ggcagagtcg ttagcgaact gctccgataa gctaaactgc cccatgttaa agtctctcgt  57240
tagaaagcta ctagagcgag actttttcaa ccatggaggc cacccccaca cccgcggact  57300
tgttttctga agactatctg gttgacaccc tggatgggtt aacagtggat gaccaacagg  57360
ctgtcctcgc aagcttgagc ttttcaaagt ttctaaagca cgccaaggtt cgagactggt  57420
gcgcacaggc caagatccaa cccagcatgc ctgcgctgcg catggcttac aactatttcc  57480
ttttttcaaa agtgggcgag tttattggta gtgaggatgt gtgtaacttt ttcgtggacc  57540
gtgtgtttgg tggtgtcagg ttactggacg tggccagcgt gtacgccgcc tgttcgcaaa  57600
tgaacgcaca tcagcggcac cacatctgct gtctagtgga gagggccact agtagtcaga  57660
gtctgaaccc cgtgtgggac gccctgcgag acggaattat atcttcatcc aagtttcact  57720
gggcagttaa acaacagaac acttcaaaaa agatattcag cccatggcct ataacgaaca  57780
accactttgt cgcgggcccg cttgcctttg ggctgcggtg cgaggaggtg gtgaaaacgt  57840
tgctggccac ccttttgcac ccggacgaga caaattgtct cgattatggg tttatgcaga  57900
gtccgcaaaa tggaatattt ggcgtgtcgc tggatttcgc ggcgaacgtc aaaactgaca  57960
ccgagggtcg tctacagttt gaccctaact gtaaagtgta tgaaataaaa tgcaggttca  58020
agtacacctt tgcgaaaatg gagtgtgacc ccatatacgc cgcgtatcag cggctgtacg  58080
aggcacccgg aaagctggca ctgaaggact tcttctatag catttccaag cctgcggttg  58140
agtacgtggg acttggaaaa ctgcccagtg aatctgatta cttggtggct tatgatcagg  58200
aatgggaggc gtgtcctcgc aaaaagagga aattaacgcc ccttcacaat cttattaggg  58260
agtgtatttt gcacaactcg accacggagt ctgacgtcta cgtacttact gatcctcaag  58320
```

-continued

```
atactcgggg tcaaatcagt attaaagccc gcttcaaagc caacctcttc gtgaacgtcc  58380
gtcacagcta cttttatcag gtattgctgc agagttcgat cgtcgaggag tacattggcc  58440
tagatagcgg cattcctcgc ctcggatcac cgaaatacta catcgccacc ggcttcttca  58500
gaaagcgggg ctatcaggat cctgtcaact gtaccatcgg tggcgatgct ttagacccgc  58560
acgtggagat tcctacgctg ctaatcgtaa cccccgtcta ctttccccga ggcgcaaagc  58620
atcgtctgct tcaccaagct gccaactttt ggtcaagaag tgcgaaggac acctttccat  58680
atatcaaatg ggatttctcc tatctatctg caaacgtccc tcacagcccg tagacgtgga  58740
cggggaaccg ctcgacgtag tcgtggacta tgaccccatt cgcgtttcag aaaagggcat  58800
gttgcttgag caatcgcaat ccccatatcc cgcattaaaa aagaagaaaa aaaataaaga  58860
agcaatttat taagcaaaca gtatggtttt ctgtacgtat tttattccgt ggtgggtgaa  58920
aaataacggg ggatggagga agagggatgg gtttataatg ccaatatatc agctaaatga  58980
atatcatttg cgtttcgtcg atttcactgt cactttcatg gtcggactgg tattgggtcc  59040
tcggggcggg cgtcgatatg tccttcactt tggcgcgggc tctggtcttt gctgggaggg  59100
gcggcggttt ctggtgaaca gtcggagttc tatcgaccgt cggcgccgac gtcgccagag  59160
gcatgtatgc cgcactcggc gtacagagtc cccagtcgct ccttataacg cgtataacga  59220
tggctaggat gcacagtata gggatacagg agatattgat agccactatg tagtggagat  59280
tagcctgcac gaacgcgttt tcatacctga tgacaggcag cagtagaatc agataaccca  59340
ccaatactcc cacgtaaaag cctacctgcc gtctcataaa ctttaccagg aaaaattccg  59400
tgtttatgta ccacacgacc gtcaaggcta ggaacatgtt caccgcacca aaaatggcgt  59460
ctgacacgag cacgtaaaag ctgttgccaa cggccatcat ggtgctcaat gaaaacagca  59520
gcatttccaa ggcggttgtt gataggtaca ggttgacgca gaccggtttc caccgagtca  59580
gcagtgactc catcatggta ttatcaggta cgtgctgttc caggagaggt atttcccact  59640
gggcggagtt acatgttatc agtgactgga tgtgggcaaa ggatatgcaa aaatgaatgc  59700
agtagacaaa ggctgccata agtacgtgtt tatatgacag aacatggata aacagttgca  59760
tgctccacat ccttaagatg gcgacataaa gcacgctatg tgatccaagt agcgctatcc  59820
aggattgcat gctcatcatg gtagtggcgt gaacatgctt ggcccgatat acggccaccg  59880
ccgcgagaca gtagtatact atggcaatgc cgtccacgat aaaagtccaa aatatgtaca  59940
ccagcatctc tggtttctct aaaaacaggg tcggggtgag gtgcttcgct gagttgcgca  60000
ccgtgaggtt tagcgcgctg tagtttacca gattgttgaa gtagcagggg aaaccaaggc  60060
cctcgtacgt ggcggccatg ggcacgactg cagagcaaat gtacataatt acagccacaa  60120
acaacagctt gacccaggag gacatgagaa aacggtcgct ctttgaagcg cgcatgtttc  60180
tcggtctttt taactttcgc caggcggcgc tgcggcggga gagccaatct gatgccactg  60240
cctatcgcgg ttgactttta aatacgcgcc ccgggcagaa gccagaggta gtcgactcat  60300
tgactcaatg gcaacgagcg aagaaacggc ggccggttat gtcatcggtg tctactttca  60360
cagcgttcac gtccactgcc gcattattgt ctggcaggtt aattttctac ccctggaccc  60420
aaacgacggg gagactgaat gctactttgt ggtggacacg ctgacgaaag aggcgatgga  60480
gcgcatgccc gaaatccagg aatgcgtccc gtctattact gaacacgccc gtgacctggc  60540
gatctgggag ttggcgctgc gactgcagaa tcagacgatc gtcaaggccg tccggacagc  60600
gtcgcttccg gtggttctaa ttatgactgt gggtcgcata gtgaatgatg tgattccctg  60660
ccccaacgtc agaacaccca gaccactagc ctgtgcttac ctacactgtg aggcgacggt  60720
```

gacctttgag gtcccactaa ccgggcccgc ggcgtccacc ggaacgtggc acagctctat 60780
ctatagggaa tgtgcgatct cggctatcga gatatgcttg aagaccagtc gaggcatata 60840
ctcctgccag tcgaacgagg cccctgaggc caagagggaa aagcgaggtt tagacatatc 60900
agatgtgttt gtctgtctca cgtatgatat ccctatcgca gggcgggtcc tttctctgct 60960
ggtgccccac gcgcccgctt ttcacgtctt atggatcaat gaggacagca agtggaacgg 61020
ggcagccgtc gaatttttca gagccctaca ccataagctg ttcagtgaac gcaatggtat 61080
accccctctg tggttgtacg tgttcccggg agctgtggaa gagggcacag cctttgcgcc 61140
attacttccc gcattccctt gcatacottt gcggtatggg tcgcctacct ctctggacag 61200
ggcgtccgtg cagtgggacc tatttgaacc gcacatcctg acccactttg acgggataaa 61260
gcgaacttct ttggcagata cagtgtttgg gtacgactcc ctggccattt caagggaatg 61320
tgaagatcag tatgtgtggc ccacgcctgt cactgacatt aatattaatt tgtgcacgga 61380
tagtgacact atggccatcg ttagagaacc atccggtctg gtggccgtga atctagaagc 61440
cctgttgcgc accgactccg tattatcgcg ggtctcgtcc attgtctcac tcgatacgct 61500
cttggacctt tccaccccgg agtgccgtag gagcgtggag cttagataca actcactttt 61560
gtcgactgta ttatcatggt ccacctctag ggtcacaaa tgggccgcaa tcgtgaagtg 61620
gaagttattt ttcctcgtcc aagctttgga gcctgaggtg agacctactg tccctgcttg 61680
aagcggagag gggtggtgc gagttggcag ttgacgggtt tgtgatagct ggagtgctga 61740
ccacggcaca ggacccatta actttcctat gtgtttattt ttagcaatgg tctccagaat 61800
tcaaggatct caaaagggcc tgccagatgg ccgggtttac tctgaagggg gggacttcgg 61860
gggatcttgt attctcatcg catgcgaact tgctcttttc aacctcgatg ggatatttcc 61920
tccatgcagg cagtccaagg tcgacagcgg ggacgggggg tgagcctaac ccacgtcaca 61980
tcaccggacc agacactgag ggaaatgggg aacacagaaa ctcccccaac ctctgcggct 62040
ttgttacctg gctgcaaagc ttaaccacat gcattgaacg agccctaaac atgcctcccg 62100
acacttcctg gctgcagctg atagaggaag tgatacccct gtattttcat aggcgaagac 62160
aaacatcatt ctggctcatc cccctatcgc actgtgaagg gatcccagta tgcccccctt 62220
taccatttga ctgcctagca ccaaggctgt ttatagtaac aaagtccgga cccatgtgtt 62280
accgggcagg cttttcgctt cctgtggatg ttaattacct gttctattta gagcagactc 62340
tgaaagctgt ccggcaagtt agcccacagg aacacaaccc ccaagacgca aaggaaatga 62400
ctctacagct agaggcctgg accaggcttt tatctttatt ttgaaaaaag ggaaacaatg 62460
gggggtttga aaagggtgca cattttcaga tattttaaaa cttcattgtt ctccaggtgc 62520
ttggtaaaga tggtatcaca ataaaaaatg tttactgggt ccgcgcaggt ttgtttgtca 62580
tcttcattct ctccactaga ctccagttta aaagactcta gataaatggg tttcattagt 62640
ccccccatgg gggttgaagc gtcgcctatc gccttatgaa gcttaaacat aacgagtggg 62700
gtggccctga aatgatcgtc cacggacagc tcgtaaacaa aggcggccgt ggcagtcaac 62760
gtctctatac cgtgcatgac gaaggccgcg tccatccccg gcgtcctctc atgtgtcttt 62820
ctggcgcgac aaataataga tctcaaaaac gttggtgaca tgtctcgaca gttctcgagc 62880
atcgataaca ggcagcagag ctcggttatg ccgggagatg taggtctaag gaggcacact 62940
cgctcttgga acacgtgagg gtgtaggtct atgtgggtca ccatgtcttc gtgctccacc 63000
aggcacacca ccgtaaatcc cacaaagttg ggcgaggaca ggcgagattt cacgtgctcc 63060

-continued

```
ctgagacacg ctatatctaa gtggcccatc acggacattt tgggggtatt gcttccaacc  63120
agtgcgttgt ttttcctatg cacttccagg acaaggcggg gcaccacagg gtgggggtat  63180
acgggacagg cctcttctga ctcgcgagtc ttcggggcat gagtactcat tggcactcca  63240
gtcagtctcg ccagggccct ttccagggac attctcgaag ggtggtgtaa ctagacagta  63300
tttctgtccc acgtcggtta tatacacaaa gagtctgcta gtctgatata aataggccgc  63360
gatgtcctgc aagctggagg atacgaagga gtgactaatg agctccatct gaagcaggtc  63420
cgcgatcaca tacgtgaatg gaccaagcag gatggatatg gtgtcctgag aataggtgac  63480
gctgagccgc tgcccttggt tgtcaacaac gggagccagc ttgtaggttt gaaacatctc  63540
gctttcccac aggttcgtga gatctttcat gctttctctc actgggggta tgtaagaaga  63600
gaaaaagcta tttagcacgg cactgcccga tgggatatgg gaagacgtta gctgcagaga  63660
ggggtcctgt aaacgtccca gagattgaaa tgtgttggcg gtcagcagat tcacactccc  63720
gggacccttt gcgtcaccgg gctgttggtg tgacagctgt gtctcaatac attttagcct  63780
cttcatgcag agctccctct ccttttcaag ttgagttatt gtgtcaaatt gttcgtttat  63840
ctggttggtg agacacttga aaacgctgtt ggacacctgg cgcctgagcc cctgagtggt  63900
cgtctcttgg cctgtgccga atagtttatt cttgtctact atgttttggg acacgtcggt  63960
gacaaagtcc tccacgacgt cggtgacacc gctcactgtc ttgttttctg ccagtttcat  64020
gagcaggttg aggagctctc gcttggggtc tgttctctga gaggcctgct ccaggtgggt  64080
catgatgtct ttgtacacat tgttacaggc gcttccaacg agggccttgg tgggggctgt  64140
gttcaggagc tggcaaagtt ttgcgtgctc tgccgtccgg tgacagctca taatgctggt  64200
atacatcctc tgaatggggc tgtcaaagat cacccgccca gccaagatgg cgggcatagt  64260
aatcacctcc acatgaaccc ttttctgctt atacaatccc acgaaagtgt ttttaacaca  64320
gtcatagtct atgctcacct ctgagtagcc cggaatatag agggcgctta aactagacac  64380
caggttgcta atctcctgag tcacgctggt gagtatccgg cctatggttt tttcaccaga  64440
ggccagacgc tggcaatctt tcatcagctg ttcctggata gagttaacca gcttgtggtc  64500
gggtgtgtgc ttgacgactg gtaccattcc taccgtgacc acccagtcta cgtatctctc  64560
atacgagagc tgtgtcttgg cgtagaggac ccggttgatg gcattgagaa gcaggtggtc  64620
taatgtcatg cgcatagtct gggcccagga gtcgaaggtt gaccttctgt aagaccccca  64680
ctgtgcttcc ttttctggcc acctggtttt tgctgaggac tcgtatgtcc tccagtcgga  64740
caagacgtgg tcgtagctac agttggccaa tgcattcttg tacaggtgga taaatagctg  64800
tctgaaaaaa acacccgggt ttcgcaggct gcagtgtaga gtctgacctc tgacataaga  64860
atacttgcct tgcaggatct caaagaggga gatggacagc tcggaagggt gcactgatat  64920
ggacgagccc agccccgggt tcatcctcaa catgacatcg gatgccaaag tcaggagcgt  64980
agtggaacag attgacaggt tgtcaaatat cactacctcg cccccggaga tgggctggta  65040
tgacctagag ttcgatccac tggaagacga aggccccttt ctgccgtttt cggcatacgt  65100
aataacgggg actgcaggag cggggaaaag caccagcgta tccgccctac atcagaatct  65160
caactgccta attacggggg ctacagtggt agcggcacag aatctttcca gggctttaaa  65220
gtcctactgt cccactatat accacgcctt cggattcaag agcagacaca ttaatatctg  65280
ccagaggaaa gtgcccaagg taactcagtc ctccatcgag caactccaga gatacgagct  65340
ggctaggtac tggccaactg tcaccgatat tattcgagaa tttatgcgca agaaacaaaa  65400
ggggcagtat agctccctct ctcaaagcgc tttcagactc ctttgccgta tgggtggagc  65460
```

-continued

```
caatttgtgg acgagtaaca ttatcgtgat agacgaagct ggaaccctct cgtcccatat  65520
tttgacggcc gtggtgttct tctattggtt ttacaacagt tggctggaca ccccgctata  65580
cagaaatggt gccgtgcctt gcatagtctg cgtggggtct cccacccaga cggacgcctt  65640
tcagtcggtc ttcaaccaca cgcagcagag aaacgagata tctgcctgtg ataatgtgct  65700
caccttccta ttgggaaaac gtgaggttgc agattatatt aggctggacg agaattgggc  65760
cctatttata aacaataagc gctgtacgga tccccagttt ggtcacttgc tgaagacctt  65820
agaatataat ctagacatat caccagagtt aatggactat atagataggt ttgtggttcc  65880
gaagagtaag attctggacc cgctcgagta tgcagggtgg acaagactct tcatctcaca  65940
ccaggaggtg aagtcttttc tggcaacgct gcacacctgc ctgtcgagta ataaggatgc  66000
tgtgtccaca aagcttttca cctgcccagt ggtctgtgag gtgtttacag agccatttga  66060
ggagtacaaa cgggcggtag gcctcacaca catgactccc atagaatggg taacaaaaaa  66120
tcttttcagg ctaagtaact actcgcagtt tgctgatcag gacatggctg tggttgggac  66180
ctatatcaca gacgcgtcca cacagatcac cttcgccact aaatttgtca aaaacagcta  66240
tgctaccctt actggaaaga ccaaaaaatg tatatgcggg tttcacgggt cataccaaag  66300
attcaagtcc atcctagacg gggagctatt tatcgaaagt cattcgcacg ataaccccgc  66360
ttatgtgtac agtttcctta gtaccctgct atataatgcc atgtactcat tttacgcgca  66420
cggggtgaag caggggcatg aagaattcct cagggacctc agggaactgc cggtgtctca  66480
agagctgatc tctgagatga gctccgagga cgttctgggg caggaggggg acacagatgc  66540
cttctacctc accgccagcc tcccaccatc ccccacccac gcggctcttc caacactggt  66600
ggcctattac tccggggcca aggaactatt ctgcaacagg ctggccctgg cacgccgaca  66660
ctttggtgac gagttcctcc actccgattt ttcaacgttt acggtgaaca tcgtggtgcg  66720
agatggcgtg gactttgtgt ccacttcccc cgggctccac ggtctagtgg catacgcatc  66780
cactatagac acctatataa tccagggata tacgttcctc ccagtgagat tcggccgtcc  66840
aggaggacag cgcctcagcg aggacctgcg cagaaagatg ccctccatag ttgtccagga  66900
ctcatcgggg ttcattgcct gcctggaaaa taacgtcacc aagatgacag agaccctcga  66960
aggtggcgac gtgtttaaca tatgttgtgc aggggactac ggtatcagtt ctaatctggc  67020
tatgaccata gtgaaggcac aggggggtttc actaagtagg gtggccatat cgttcggcaa  67080
ccaccgcaat atcagagcca gtctagtgta tgtgggtgta tccagggcca tcgacgctcg  67140
ttacctggta atggacagta atccccttaa gctaatggac cgcggtgacg cccagtcccc  67200
atcctcaaag tacatcatca aagccctatg caaccccaag actactctga tctactgacc  67260
cgtacccctc tcttaggaca ctgatgtgtt tgggaataaa gcatgagact tgacacctat  67320
aatggtctgt attgacacca ttcttttatt tatcagtcca gccacggcca gttatatgca  67380
ccgtttccac acaggggtgg cgtggaggcc aggatgcggg ttgggtcgct gcacctggac  67440
cccgcggtag ttgtgcttcc tgatgaaatc gagtgggcgg aagtactggg agattgggtt  67500
gggaggtgac cctttgtgct cgacggagac acgatcacgc tcacggcgga cgagggctcc  67560
tcgtctgtgt cactccccga ggatataatt atcacggacg ccactgcttt gcggcttaag  67620
tttggttgtc tctggcagcg caccacatcc tcgctaccag aggaggcggt agactgcctt  67680
ttgcgcttct ggcccacgtc catgagcccg attctctgac tcaatacttc cccttggtct  67740
tctccgtcct cctcggacga gggtggctgg tgggaaaaat ggcgcgcgtc ggtaaacgcg  67800
```

-continued gcctcattgt tcacgtccgg agagttggaa ctgtcatcgc tatcagagtc cgatgtcagg 67860
tcgacgatcg cggtgggtgc ggcgcgcagg gggcgccacg agggcccttc atcagggtcg 67920
ctgtatggtg aactttgtgt tccaggtaca ctatttctgg aagcaggtga aagtccgtat 67980
gccccggtcc cagtgtatgc cgccatcggt tccaggatag caaccccctc gtcgtctgaa 68040
ggtgagagcc cagcagggga aaatccgtca tcctgactaa cccatcccat ggacgcctcg 68100
gactccgccg tgtccgttga actgcgcacg cggcccgcta ccactgctac cggtttgggc 68160
gtatgggccc gtctggccag aggcctcggg cgcaagtgag ataaaggttg aaaaaagtct 68220
gcagggtacc cctctggctc gtcttcctcc tgaacatcgt cattttcttc ttcatcttca 68280
tcttcctcat cctcgtcata ttcagattcg ccgctcgact gatccgggga tatctgtaga 68340
tccagagggg ttgctggcgg cgatggcgtg tcctcggcga agacgtcgtc tggggcagac 68400
atatctatca ccgtgggtcc agcatagccg cgcggcctgc caaatcctgg aagtgatgaa 68460
agaggtggag gtgggaatat gaacttcacg gggggtcgtc tgcgaggcgc tccttcaatt 68520
ggaagcattc tctcttcatc gtgtgtgcta gacgaggtcc tcacaaacat cgccatggcc 68580
ttgtacgggg ttgaccgcta ggggcggaaa tttacaaagc acacgagtta ttgcctttac 68640
tgctccaaca ggccccagtc cacagtctca cgccggtggc gagtcaaata gtcgttggct 68700
aggttaaagt gattacagcc ctggaaccga ggccatcgcg agtgtcggcc accaagagag 68760
gccagcggag atggatgctg ggccgtaagc accaggtgtt tctgtgcgtt tatgagcgga 68820
gttctgtcaa tggccttgcg cccccacagg agaaaaacgc aatgttctaa ctttgaggat 68880
atgctactga tgatgaaact cgtgaaccaa tcccagccaa gtccctcgtg tgagccggcc 68940
ctccccttct ccaccgtcaa aactgtgttt agtagcaaca caccctggcg agcccagctg 69000
tcgaggcacc cgtgggaagg agtactgaaa ttggggacgg aagcctctag ctctctaaag 69060
atgcttctca aactgggtgg aacctgacat tgcggatcca cactaaacgc caggccagta 69120
gcttggccct tgtggtacgg gtcctggcct aagatcacca ctttaatatc ctctggatcg 69180
cagcagtggg accaccacat cagcttgtcc tgtgggggat acactgtggt ggttagccta 69240
agttcccgaa tctgtctgag cagcgagagc agtttctgtt tcagaaatga tgagaggctc 69300
agaaaggaaa tccacttagg tgccagtaac agatcccggt cgtccacccc ctgactgatg 69360
gatagggtgc ccctaaagac cgtctgttgc aaccatgcgt ccatgttgaa cttattttcc 69420
cttttgacct gcgtgcgctc tccggctgct gcttttagcc cgagtctgac ttccgctaac 69480
agaacctgtc cggttcatgg cctttcccac gcttattata attatgttta cgttgtgaat 69540
agagctatct gcagtggtcg cgttaaaacc tacagtatag gccgtcaaac ttcgttgtaa 69600
ataccacaac aacctcaggt tttcctgcga cgcccaggac cccaatcttc gaacgaccgc 69660
gactaaaaat gacctcagat taaacccatt cacgcatgtt tccacggtaa tgtcgcctgt 69720
tttgcttcgc agcttggcta tacagacccc gttgcagtga ttcggatcgg cgaagtggat 69780
agagtggacc gcaaagaaca acggcagggt agaggctgcc gatgcctgaa ttgcgcaaca 69840
tggtaaggcg acgtatgcgt gagatgtgac caatagggtg gtccacagga cggcaaatag 69900
cgcaaagatc cccatggggc aaatccgggt ttcacccttg tgttgcctgg ttcggtgctc 69960
cccagggagc ccccttccgt aatatctgtt ttatatagtg agggttcacg catgcgcgag 70020
tcccgactaa tgaggacaat tactgaaatt gaccttttcg cgacacgggg gtgaggtcta 70080
tttcccacga catacttccg cggaaaaata cccacgctcc ttaatttccg tgggaagacg 70140
atgggggaaa tgtggcatta cctgacacgg tttcaatcat actcatcgtc ggagctgtca 70200

-continued

```
cacgtctggc tgagattttc taaaaagtca tccaatgaat catcggaatc atcagcacac  70260
tctagaacta ctccatatgc cggggtgcgc gggggtcccg agtagtgcac gtcgccatcg  70320
ggagacacag atgatgggtt tgaaatgtcc atacgggccg tgtgcacaag ggtcacgtcc  70380
ccatccccaa cacaaggacc tttagatacc ctctcccggc atgtgcgcgt atccgggcaa  70440
gcaagctggt gttctggatt ccaaacgtgc ccagcggtac ccaaaatcgc cagggcgtgt  70500
tttattattt ccacaggaac cggtttctct aattgcatca ccagggtatc caaaagccgg  70560
gcttccacgt tgatccggct taccgacagt tctttccagg gtttcctggt ggggcgcggc  70620
agctgactca aaaaggtcac tgcctctgcc catgggcggg tgggtgacag tccgccatac  70680
tcttccagga cactggccat gcatgactcc aaccgtctca cgtccgaggt aatgtgctct  70740
atgaagatgt ggtagagcca gcagacgttc aaacacgatg aaatcaagct aagctcccgc  70800
cggaactcca catccacaaa ggggtattgc tccggtgtct gtattaggtc tggaatagaa  70860
aactcagaaa aagacactga cccaccaagg agaacctggc gtcttgcaaa gttgatgagc  70920
cccgcagaaa gaatgtgtct cccgtgggac aaagagcttg ggggggcaga gatggcgcta  70980
cagtgggtga tttcttctac cacggtcata cattggtggc acccacaggc ctgttccagt  71040
atcagcataa atctatcttt gcagtcatcc cagatcaaag tcatgtcaga tgctgttgcc  71100
tggcattttg cccgcatgta catttcctgt cccacatatt ttaacatctg taatactgga  71160
agtagattca gtctggtgtt gagccccccc ggggaagcca gcgtatgctt caggaccacc  71220
agggacgcta agaaccccgg gtgtccgcgc tccggaaaca gacctctgag aatacgctcg  71280
gtcttgacga aacccgatgt ggtaccgaat gccacaatct gtgccctcca gctctcacaa  71340
ttttcatctc caatacccgg aattgggata cacacctcca tgttcagtca catgtacgct  71400
agggtctccc cacccaaccc ccataggacc cagctacagc ttatcctcca ctaaatacca  71460
ggcagctacc ggcgactcat taagccccgc ccagaaacca gtagctgggt ggcaatgaca  71520
cgtccccttt aaaaagtcaa ccttactccg caaggggtag tctgttgtga gaatactgtc  71580
caggcagcca caaaaatggc gcaagatgac aaggtaaaga tcgacctttt tattgtatac  71640
tgaacaatgc gtgtttacaa tggtgtaggt gggagcagag ttcgccaagc tctacgtccg  71700
aacagtcggg tgtcagggct cttattaagt gttcggtgta cttgaccaaa gccgcggaac  71760
ctaggttggg tctgtacagg tcgtaccagg caaaaaagga tcgggcggtg cttttcagga  71820
gagttaggga cgtgctgatt atgtggacaa gcttctgctc gtaaatgcac cgctggtaca  71880
tctgaacgac agctgtccaa aaaaaacaaa ggttcagctg cacgttaaaa tctgtatcct  71940
gaaagtcctc gtaaatgaca gtttctacca agaaaaactt ttttaccacg ctggccatcc  72000
actgaaagga gggagcacac gtcccgttgt gcgttgttag gatatcccta acttcggagc  72060
ggagacggcc ggacgctccc acaaaatggg agaggcacca ctctgtgcag tccgcggtct  72120
ggggttctga ttccaggggc gccgtgtggg ggtattggag agtcaaaact ctgggcagtc  72180
ccttaatgag ctctctctca aaacctatgc agccagcgtc cactagtggc agcatgccgt  72240
taataacacc ccttatcttg tcgttgccaa gtttgtacaa ctgctgcagg gaataagcca  72300
aattcgccct agccgcggga accaggtacg gctcgctttg tcggtgctgg accaatatct  72360
gaatggtctt tgcaaggtat agggtcttct caacgtttag agcgggtacg tggcagtctg  72420
gattgagggt ggcgacggac agggtatcta actcctgaag tatctgatcc caggacgggt  72480
aatgatacct aaacagatgg ttgaacaggt gatctttaag ggccttctcc gatgtcattg  72540
```

-continued

```
taaaaactat gacacgccac tctctcctta gggtaagaag cttcggcggt cctgtgtgga  72600
aagcttcgtc ggcctctcgg acgaactgaa ggcccaactc taccagtgtg tgctccttat  72660
aaatgacgca tacgaaacaa tctacgatcc cagtgaccta aatagagtgg tggaagatgt  72720
gtgcattcgg attatgaaag aatgttccaa gcttggtgcg ctatgtggtc tgtttacaga  72780
cattaacatg tttaaccttt tctgcttttt tcgtgcctct cgaatgagga ccaaaggcgc  72840
ggccgggtac aacgtgccat gcgcagaggc atcccaaggc attattcgga tcctcacgga  72900
gaggatctta ttctgcacag aaaaggcatt tctgacagcc gcatgcagcg gggtgagcct  72960
gcctccagcc atatgtaagc tactacacga aatatacact gaaatgaagg ccaaatgcct  73020
gggggcctgg aggcgactcg tctgcaatcg gaggcccatt atgatattaa cctcttccct  73080
actgaagctc tacaacacgt acgataccgc cgggctgctc tctgagcagt ccagggccct  73140
ctgccttttg gttttccaac cggtctacct tccgaggatt atggcgccgc tggagatcat  73200
gaccaagggt cagctcgccc ctgaaaactt ttacagcatc accggttctg ctgagaaacg  73260
ccggccaatt accaccggca aggtcactgg actgtcctat ccaggaagcg gtctcatgcc  73320
agaatcttta attttgccaa tcctggagcc aggactgttg ccggcttcca tggtagacct  73380
cagcgatgtg ctggcaaaac ccgccgttat tctgagcgcc cctgccctga gccagtttgt  73440
cattagcaaa ccccatccca acatgccgca caccgtcagc atcatcccct ttaacccatc  73500
gggtacagac ccggcgttta ttagtacgtg gcaggccgcg tcacagaata tggtgtacaa  73560
cacatccacc gcgcccttaa aaccggccac cggtagttca cagacggtgt cagtcaaggc  73620
ggttgctcaa ggggccgtga ttactgcgac aacggtgccg caggcaatgc cagcgcgggg  73680
taccggaggg gagttgcctg taatgtcagc gtccactcct gcaagagatc aggtcgctgc  73740
atgttttgtc gcagagaaca ccggagattc tcccgacaac ccgagctctt tcctgacgtc  73800
atgtcaccct tgcgatccga acacggttat agtggcccag caatttcaac caccgcaatg  73860
cgttacgttg ttgcaggtta cctgtgcccc ctcttcgaca ccaccccccg attcaacagt  73920
ccgggccccg gtggtgcagt tgccaacagt agtccctctg ccggccagcg cgttcctccc  73980
ggcgctcgcc caaccagaag cctcgggcga agagcttccg ggcggtcatg acggagacca  74040
aggtgtgccg tgtagagatt caacggcggc ggctacggcg gcagaggcga caacacccaa  74100
acgaaagcag agaagcaaag agaggagctc aaagaagcgt aaggctttga ccgtgccaga  74160
agccgacacc acgccatcga ccacgacacc tggtacctct ttgggatcaa ttaccacccc  74220
ccaggatgtg cacgccacgg atgtcgccac gtctgaggga ccatcggagg cacaaccccc  74280
gctactgtcg ttaccccccgc cactggacgt agatcagagt ctattcgccc tgttagacga  74340
agcgggccct gaaacatggg atgtcgggtc gcctctctcc cccactgacg acgcgctgtt  74400
gtccagtatt ctgcaaggac tgtaccagct ggacacgcca ccgcctctgc ggtcaccctc  74460
cccgcttcc ttcggcccgg agtctccggc ggatataccg tcaccttctg gtggagagta  74520
tacgcaactg caaccggtca gggcgacctc ggcgacgccc gctaacgagg tacaggagtc  74580
cggcacactg taccagctgc accaatggcg taattacttc cgagactgaa gtgttcgcaa  74640
gggcgtctgt gcctgcgtta acttcccagg cagtttattt ttaacagttt ggtgcaaagt  74700
ggagttaacc tacagattct acttaaaata gctcattttc tcacgaatct ggttgattgt  74760
gactatttgt gaaacaataa tgattaaagg gggtggtatt tcctccgttg tcgactataa  74820
cctggcgtgt aaacgtgtaa ccctgccaaa tgcccagaat gaaggacata cctactaaga  74880
gttccccggg aacggacaat tctgagaaag atgaagctgt cattgaggaa gatctaagcc  74940
```

```
tcaacgggca accatttttt acggacaata ctgacggtgg ggaaaacgaa gtctcttgga  75000
caagctcgct gttgtcaacc tacgtaggtt gccagccccc ggccataccg gtctgtgaaa  75060
cggtcattga ccttacagcg ccttcccaaa gtggcgcgcc cggtgacgaa catctgccat  75120
gctcactgaa tgcagaaact aaattccaca tccccgatcc ttcctggacg ctctctcaca  75180
caccaccaag aggaccacac atttcgcaac agcttccaac tcgcagatcc aagaggcgac  75240
tacatagaaa gtttgaagag gaacgcttat gcactaaggc caaacagggc gcaggtcgcc  75300
ccgtgcctgc gtctgtagtt aaggtaggga acatcacccc ccattatggg gaagaactga  75360
caaggggtga cgccgtccca gccgccccta taacaccccc ctccccgcgc gttcaacgcc  75420
cagcacagcc cacacatgtc ctgttttctc ctgtttttgt ctctttaaag gccgaagtat  75480
gtgatcagtc acattctccc acgcgaaagc aaggcagata cggccgcgtg tcatcgaaag  75540
catacacaag acagctgcag caggtataga cgggaaacag gtgtctatct tggccggctg  75600
gttactcaaa tgggaacaat ggcgccacct tgctgtcttt gtaggcatta gaagaaaagg  75660
atgcacaact atgtttccta gcggcgagat tggaggcaca taaggaacag attattttcc  75720
ttcgcgacat gctgatgcga atgtgccagc agccagcgtc gccaacggac gcgccactcc  75780
caccatgttg aagcttggtt gtgccgtcgt ccgggagaac catgccagac tttgtgtggt  75840
aagaaggaat tgttatccgg cagcaatatt aaagggaccc aagttaatcc cttaatcctc  75900
tgggattaat aaccatgagt tccacacaga ttcgcacaga aatccctgtg gcgctcctaa  75960
tcctatgcct ttgtctggtg gcgtgccatg ccaattgtcc cacgtatcgt tcgcatttgg  76020
gattctggca agagggttgg agtggacagg tttatcagga ctggctaggc aggatgaact  76080
gttcctacga gaatatgacg gccctagagg ccgtctccct aaacgggacc agactagcag  76140
ctggatctcc gtcgagtgag tatccaaatg tctccgtatc tgttgaagat acgtctgcct  76200
ctgggtctgg agaagatgca atagatgaat cggggtcggg ggaggaagag cgtcccgtga  76260
cctcccacgt gacttttatg acacaaagcg tccaggccac cacagaactg accgatgcct  76320
taatatcagc cttttcaggt gtattacacg tttcaactgt aatccctcgc aattgggtaa  76380
accgtcggtg tgtagggata aagcgtaacc ttacgttctg tctcatctac aggatcatat  76440
tcatctgggg aaccatccag gaccacgcga attcgcgtat caccggtcgc agaaaacggc  76500
agaaatagtg gtgctagtaa ccgtgtgcca ttttctgcca ccactacaac gactagagga  76560
agagacgcgc actacaatgc agaaatacgg acccatcttt acatactatg ggctgtgggt  76620
ttattgctgg gacttgtcct tatactttac ctgtgcgttc cacgatgccg gcgtaagaaa  76680
ccctacatag tgtaacacaa aaccataaaa gtaaataaac gtgtttattg ttcacatgat  76740
aaagagtggt actctttact ggtttggggg ttgggttgtg gcgtggtggc tggtccgcgg  76800
ttcagtcatc aacccccgcc cgtgttgtcg aggctcctct tcgtcgcctg ttattggcac  76860
caggaggcgg tttagcggtg cccccgtctg acatgcagac gtcgattcta agcgaaagtc  76920
ccttcagggc atcgtccact tgcttttgtg ttacaacctt gctgaatatt gtcctgaccc  76980
tggcttcgat tttcttagcg gccgccgcac tcagtgcacc cacagtagcg gtaagctgcg  77040
cttccttctc ggtggccgtc agaggccgat ctctcggatc ggcagtggat cccagtgctt  77100
tccgaagctc ccgattctcc acagtcaatt ggcttatctt tgcggttagg tcttccatcg  77160
taaggtcctt tttgggtctg cccctgggcg cggccatgtc aggtacgcgt agatgtacgt  77220
gttggtgatg ctcacaacaa aagcccaaat ccctccttta tacccagctt taaatacttt  77280
```

-continued

```
attgaaaaac catagctttc gtcagcgctt gtgcgagtaa tcacatgcca gtctatgcat  77340
ggaccacctc gtccacaaac ttgaaaaaac aaagatatac cagatagaaa aatgtggcca  77400
cgacgactag taacgcgtta atcaaggccc agacgctaga aaagctagaa agggaggggc  77460
taaaactatc cgcggaacaa gcaacgtcat agaatcctgg ggtagtgact gatgtgggac  77520
cgggcgaagg cctggcgctg agcccagccg tactgggact agaacgctct gtagatgatg  77580
cgacacctgt cgagttggcc gtaacccagc agtgacctag tatcgaggcc acaaataaag  77640
ccagggccac cgtggacgct gtcattatga acaaccgccg aggctccaag ccgtctatcc  77700
aacgttccgc gttcgcctct tatatacact ctgcaatgca gtccgactct gcccctctac  77760
ccagggtgga atatgtgttc gaaacaagca aatttagaat gacgtcgaga gcaaatgaag  77820
ccagactcag actgacaaat gagtgtccga tactggtgag accccacgag ccgttcatca  77880
tgcccaccgg aatacacttc acgcgaaccc ctagctgcgc tttcatcctg accggagaga  77940
ccgacaagga tgtattttgc cacacgggcc taatcgacgg aggctaccgc ggggagatac  78000
aggttatttt actcaacaag aggaagtacc ctgtgacgct gtatcgcggg gagctcaaca  78060
tctgcctgtc tgctttcaat tacgtgctac ctccgttgag ggacgtatca ttcttaaccc  78120
cccctatgta tgcaaacgac gccggatttg acgtgatggt gatgcactct atggttatcc  78180
ctcctactac tgaccaaccg ttcatgatat atctaggagt ggagacccca ggcccccctg  78240
aaccccacgt ggctctagca ttggggcgat ccggtctagc atctaggggt atagttatag  78300
acgttagtga gtggggaccg cgaggattgc agctgaagtt ttataactac tcggggcagc  78360
cgtggctggc gcagcccggt agccgcatat gccagattgt gtttgtggaa cgcagacaca  78420
tcctcaaggg cttcaaaaag tgcttgcgcc ataggaagct agctcctggc gtccgtttcc  78480
gggaggctcg agtgcatttt cgcgaggata caaatagcgt ccgaaaacat acccacgaag  78540
acaaccccgt ccacgaaccc aacgtagcca ccgcttccgc tgacattcgt ggaaccaagg  78600
ggctggggtc gtctgggttt tagagccgcc gccaaatgcg gccagtttat tagggcgatt  78660
cgatcccgca acccacagca tcccccaaat aaaaaaacga gtgtacacag ccaatgtttt  78720
tattattgtt cgattcatta ctggtaccag agaataaagc caacctatgt cgaacctatc  78780
gcgctttctg tcgtctcttc cagggttgac gaaggccggg gagggattga cgaatgcatc  78840
gcggaaacgg acgggtcttc ggtgggtggc ttgggtaaag ttgcctccgg ctggcgcgta  78900
acggcaggcg tgagaggcaa tacagaagtg ggttccgaca aggagtggct gatctcagag  78960
gcccatatta ccgagtcgtc tgacgccata gcagtcgcca gtttttccat ctccatgagc  79020
gaaacgcatt ccccggccct tttgtttaag agggactgga gcgcactgtc gtccacggta  79080
atctcgccga ccgccaaggc cagcattgtg ttccacacga cgttctgaat agactgcagt  79140
tttttcacct gggttttcac ggtctcctgg cagcccgccg gaattttagc cacgtcaaaa  79200
cgcttcaggt agtctgtgat cttgtttgac tgtacagcca gaaggtaggt ctggtgcagc  79260
gccgtcgtgc caaggttcga ctggacaacg tcacccagac acactccggg ggggaggccc  79320
aaatctatct cttgccgcca gcgctctgga cagccttcca gagggtcacc gaggcgcttg  79380
taagcgtggt tgccgcgtcc aaaaaggttt ataccgcaac acgtccaggt gtaccatgga  79440
gacgacatac cgccgcgagg cgctgacagt aagggttatt ttttgtacga gtggcgacag  79500
cgccgagacg atcgccgacg tccttacggg ggccccaacg tcagcgtcct tcttttctgt  79560
actccacgac ctttttttatt cccagatact cgcccccagg gtaaccctaa aattgtgcct  79620
ccccgcacgg cgtcctggca acggcacaag gtgttcgccc gtgttggtcc tacgtactga  79680
```

-continued

```
cgcatcagtg gcctcggggt tccttggcgg ccggccactg gaggcgtccg acattaaata  79740
tatgctgctc agcgaccaga ccgcggggtt gttcaagccg ctgttggaga taatcggtgg  79800
cgcgcgcgca ccaccaaatc aggacgcgtg cactttccag agccaggtgg cctggctcag  79860
aacgaaattt gttaccgcat tgagaaaact ttacaagatg actccctcac cctactggat  79920
gctgtctgca tttggcgctc aggaagccca gttcgtcctg accagctcat tctatttttt  79980
tgaacacact gtggtctgta ccacagagac agtttctcac ctgtctagac tgttttcgcc  80040
tcaacaggga cagacgctgg tttccgttac cagccacgag gagctggggc agctatacgg  80100
cacttcccct ttcaggcggc gcgtccccgc gttcgtcgct tatgtaaaag agaaattagc  80160
gagagacagt ctggagacgg aggccatcga ccgcaccata gaccagatca ggggcaaact  80220
catgctgtct aaccaggacc tggtccattt catatatatc tccttttatc agtgcctcaa  80280
caaacgggcg ttcctgcgct actctagaca gacgtcctct tcaagtgctc taagggagct  80340
gggggaagac cctcaattgt gtggcgccct acacggggag tttcgtgacc acgtccagtc  80400
ctactaccac aaaaaaacct acctatccac ttacatagac attcggtacg tgggtggcgt  80460
attaccagac ggctattttg gcgggagtct tgtaggcgag cggtgcgttt attggtgcgg  80520
gcagtcaaag gacacggcca gcctgttggc caccattagc caacaggtgc cgcacctgag  80580
gttgcaaaac gagttcgctg gcatgctaga cgtggccgca ctgcgaggtt ccgatgacgg  80640
tcagtttaaa gagggccttt tctcccacag tcaagcccta cccctgtaca ggtgcgagtt  80700
tctgggcaag cagtttttca caatgcttca ggaagacggc ctagagcgat actgggagca  80760
aagtgtgata tttccaggcg accaggactg ggatatgtta tctgacaaag acctcaccta  80820
ccgaattttt taccatgacc tcagcctatc gctgccaaca ctgaaggaac agctccttgt  80880
ttcaagacac gaatacttca accctcgctt gccagtgtat agatgggtat tagactttga  80940
cctgcccgtc tgccgcgaca ttgacaggac attcgaggag gtgcactctc tctgttgttc  81000
cctgcgtgag gccatactcg acatcattca actccttgga ccagtggatc ctcgaacaca  81060
cccagtatat tttttcaaat cagcctgtcc accggacgag tggcgcggcg aagacgtcgc  81120
cagcaccagc ttctgtcggt gtcatgacaa actgggtatg cgtattatcg tcccgttccc  81180
agaaggagta tgcgtcgttg ggtcggagcc catggtggca ctcactggca ttctaaacag  81240
gacgataaag cttgatccgg agctggtcca cagattcccg tcaatacaaa aaaagggggg  81300
ccctttcgac tgtggcatat acggccgagg acgaagcgtc cggcttcccc actgttacaa  81360
ggtgggctta gtgggggaac tctgccgcct actgaagata ctagtctgtc accccgcccc  81420
caacggcaag gcgcagtacg tgcggcgcgc ctttacgctt cgcgaactgc tccatcactc  81480
cccgggccac agcgccggtc atgtcggccg aatcatctat agcatcatgg atcgcaatga  81540
gaatttttta gaaaacaaga ccattagcta tctgccggcc aaaatacctc acatctttca  81600
gcggatagag accctatccg gtcgttcaat agaggactgg ctacactcgg ccgtttggga  81660
taaagcatac gacactatat gtaaattttt cccagatgaa aaagcacaac agttttctca  81720
cgttgcattt acgcaacaag ggaaaaacat catccagtta agaccccgtc agggaagaca  81780
cttcctctgc atcaaccata atcataaaaa caagtcaaaa acagtccgtg tattccttac  81840
ccttcattcc attagggtga gcgaagtcac ggtaacactt atgagtcagt gttttgccag  81900
caagtgtaac aataatgttc ccacggccca tttttcgttt gtggtaccag tgggactggc  81960
cagttaatcc cactatataa cctggctgcc aggttcccaa aatagcccgc ggcatacggc  82020
```

-continued

```
tcacttcccc ccacattccc cccgtgcaca atataagaac caaaggacat ggtacaagca  82080
atgatagaca tggacattat gaagggcatc ctagagggta agtcctcgtc tacaacagac  82140
ttttcccatt tctaacgtat cgtgctatct tcgtcgcccg gcggaccatc cccccacccc  82200
tcatttatcg cgtttgatat tacagactct gtgtcctcct ctgagtttga cgaatcgagg  82260
gacgacgaga cggacgcacc gacactggaa gacgagcaat tgtccgaacc cgccgagcct  82320
ccggcagacg agcgcatccg tggtacccag tcggcccagg gaatcccacc ccccctgggc  82380
cgcatcccaa aaaaatctca aggtcgttct caactgcgca gtgagatcca gttttgctcc  82440
ccactgtctc gacccaggtc cccctcacca gtaaacaggt acggtaaaaa aatcaagttt  82500
ggaaccgccg gtcaaaacac acgtcctccc cctgaaaagc gtcctcggcg cagaccacgc  82560
gaccgcctac aatacggcag aacaacacgg ggcggacagt gtcgcgctgc accgaagcga  82620
gcgacccgcc gtccgcaggt caattgccag cggcaggatg acgacgtcag acagggtgtg  82680
tctgacgccg taaagaaact cagactccct gcgagcatga taattgacgg tgagagcccc  82740
cgcttcgacg actcgatcat cccccgccac catggcgcat gtttcaatgt cttcattccc  82800
gccccaccat cccacgtccc ggaggtgttt acggacaggg atatcaccgc tctcataaga  82860
gcagggggca aagacgacga actcataaac aaaaaaatca gcgcaaaaaa gattgaccac  82920
ctccacagac agatgctgtc ttttgtgacc agccgccata atcaagcgta ctgggtgagt  82980
tgccgtcgag aaaccgcagc cgccggaggc ctgcaaacgc ttggggcttt cgtggaggaa  83040
caaatgacgt gggcccagac ggttgtgcgc cacggggggt ggtttgatga gaaggacata  83100
gatataattt tggacaccgc aatatttgtc tgcaatgcgt ttgttaccag atttagatta  83160
cttcatcttt cctgcgtttt tgacaagcag agcgagctag cactgatcaa acaggtggca  83220
tatttggtag cgatgggaaa ccgcttagta gaggcatgta accttcttgg cgaggtcaag  83280
cttaacttca ggggagggct gctcttggcc tttgtcctaa ctatcccagg catgcagagt  83340
cgcagaagta tttctgcgcg cggacaggag ctgtttagaa cacttctgga atactacagg  83400
ccaggggatg tgatggggct actaaacgtg atagtaatgg aacatcacag cttgtgcaga  83460
aacagtgaat gtgcagcggc aacccgggcc gcaatggggt cggccaaatt taacaagggt  83520
ttattctttt atccactttc ttaaggattg ccaaacccca tggcagagtg tctcccgtat  83580
tccatgtaac tcacgtagcc tttctctaat aaacaagcta cctgcaaact atacacaaat  83640
gaaatgagtc aggcgtggtc tcttctctac cgtgaatcgc accttaaaca caacaccaga  83700
ccgccaccag gtggcaccca acatccatta tggaaaaacc ccgcgccacc ttccgccacg  83760
tggagccaac aaacaagaca cacccgccaa tgttttggtc tctttattga tatgatatac  83820
tccctcccat aacaatacgg tgtaggcatt ttgtattatt tattgcatgg catcccataa  83880
cggcttcggc attatttcga gtacgacgca ggcgtctgag aaattactgc acctcgccgc  83940
aaagtctcgc ggggacgggg cgtggggctc taacttgcca accgccaccg gtttccccag  84000
ccacagcttc accaaaggac acgtcacgtg agagggtgct ggtaacggtg aatttgccaa  84060
ccccaccaga aatgtattcg ggttaaatat cctcgtcggt tttccctggg gcagcaagag  84120
ggggccggag tcaggcggaa cggtatttcc aataaagtgc acgggcccgt tatgataaca  84180
tacgcaaaat atgccattac aagagctagt cagcagaatg ccttttgcac atgcgtccag  84240
cgtatcgcat agctcccgct tggctatctc gcaggccagg tttggcacat tgggtagcca  84300
tacctggccc ggagacccca ctgcacagta atgaactgcg gggtccctac gcaaggccga  84360
tgagattcga cagcccgact ggcttgtcgt cagtaactca tgaacctgtt cgccattata  84420
```

-continued atacatcctg ataaacaacc gaccccagtc aatgacggcc tcctgaccct ctgccgtcgt 84480
acaagatggc acgggcgtta caatctcgcc tggcaagcac tgccccgggg aaaaaaatcc 84540
ctcttgcaag agacgtgcca tattgttaaa atcgtggacg gctccggcca cgactccaca 84600
ttccacgcat tgttcttcct ccggtttacg tactctaaag accagaaaat ggtgtccatc 84660
ctgagaaatg cctttgccaa tctcttgtaa accccgcgtc ctgcgtagcg cggcaagcat 84720
tcgcctgcgc cccctggtgc ctttaaacga ggcgtccacg ggcatgttac ccctttcgcg 84780
gatatacaca acacccaatt ccccgtctct gcgccattca aaacaggggt ccgcgagggg 84840
cgtaactggt atacggaagc gggtgcgctc ttcgtcttcc cactctactc cgggaaattt 84900
tccactgttg acttgacata ctatccaatc cttgattgac gctttcccct cactggcacc 84960
ggtagatatt cttagttgtc gtgtccggct ccactccgtt atcgcagcca ccacagcctg 85020
ccgtgtaata tcgcctgcgg ctgcagaacc cccggtcccg gagggtcctt ctcccggtga 85080
ctccgacctg gatggttcat cgcaaggagc cccggagcca gatgttcccg gtgacccttg 85140
tgacaaacaa ggtttttttgg gtatcgcccc aggcgcccca aaagggttcg gtctttggcc 85200
tgggtccatt gtcccgcaac cagactagct cgcgccgcaa tgtccagtgg taagcacagc 85260
tatgccgggg agccaccggc catcagatat agagaggcga caggctctct atatatcacg 85320
gctaggtggc tgacatatta gtgggcctag ccgcagaatt gcctgggtag tcaaaaacca 85380
gcgtttctca aattaaccga aactacattt ttctatttta agtacgggat acaaagcagg 85440
gtctgaggca atctgccgcc ctccaccccc acccaccata cccaaaaaag atatgtcaga 85500
aagagcactc tacctattaa ctcgtggaga aacatcatac aaaatctgta cattattttt 85560
aatactttaa tttgtgcagg tttcttcacc ccacacctgc tttttgtctg gtacaaaaaa 85620
ccactgcagg gtcccgccta tagccaactc ctaagcgggt tttttgctaa agcacttttt 85680
tagactgtcc cagaaaccac atagcttcct tttcactcat ttgaaaaaca gccccgccca 85740
actgcctgga gaattttcca ccccctctac catttcgcgc ctttaccgct ggtgcgaaat 85800
ctagccatcc tatcaccgcg gatccgctgg accaatatac cacgcccact tttcgtaatc 85860
agcaaccctc tacgcctaca cccctatgac tgaatataac ccccaacaag gctatgaaat 85920
catgaatggt aactgtctgg acaccaatct tccgcggggt ggcggcagtg cgacgcaagt 85980
atccacaata aatggtgcaa taattggcga aatgtcgtgt ctggtttatt tggactacaa 86040
gattacatcc ggttttataa ttcacatata tgatcaatgt agactatccc aaatggagcc 86100
tataaaaatt ttaacagtca agggtacatt ttggaaattt tctgtagatg ccggggatgc 86160
gccgaaaaat accgtcccgc acgtcactgg gttgacgctc agcggtgtct gtgggattgc 86220
ggctgtggtt gccaggtatc gcgcggtgtt gaacagctgc tgcggaactc tggggctaaa 86280
gcttcggagg atgcgttcat agcgggaatt tggattacca aaccaccagc cttccacttg 86340
agtggcgttt ctggagtata ttccagacat cgagcaaaat attgggaatc cgtggccaag 86400
gccttcaaaa actcggttca aaatctccat ttgctcgggt gaggggactg taagacgcgg 86460
tatgcgaagc agttctggta cgaaactctg acataggtgc cccaacgtat ccccaacagg 86520
ccagctacat aacattgcct cgcccgcgtc accttcgcgt ctcagagttc cacgaaggtt 86580
cccatacaca aagatttcca caacaaaaga cacccgctga ctatcagggg gatcaaaaaa 86640
catctttgaa ggtggctttt cgggaccgga gtggctaacg ggcgtacgcc gcccgtgcgg 86700
ggacctggac ctcgggcgcc gcctatccgt ggcctgtctg gttgaggagc tcggttcctc 86760

-continued

```
ctgcagctca gacaaaatgt tacccaaccc ttcttcccac gtacatatat cctctccttg  86820
aaggttcgag agcgtaagag ggagacccaa aggcggcggc actaaagatt gttctggtcc  86880
ataacccccc actgcatatc tatctccagc atatgtacta acaagtggaa ctctgggcct  86940
ttcgccacta cccgggcaca cacactcccg ccgctccagc tctgtcggta aatgcgaaac  87000
ctcggggttc acagcgggct ccggtgcaga ataaagcacc gtaggttgga aaacgcgcgg  87060
cccactgaca ggtaggggcg tggatgctac agtggtagat ggggtatcgg aatccccagt  87120
gaggtcaata atctccactt cgagggcacc agaactagtt gtcacgcgtc tgtatccagt  87180
cgccatgttg tccccctggc agacgtacgg tattccagac gaggatggct cctgtcgctc  87240
tgccacctct ggggtgggtg gtgcgccggc ggagggcgtg gccgacgcgc caccctgcgt  87300
gtgggaaaga ccctggtttg gagcgcctcc actagaccac ggaatccaaa gcggtgtgcg  87360
aacttccggc accacggcgt gaccaactgg tgggtgccaa acaggcgcgc gtatgggtcg  87420
cgtagctggc ggttctgcca atggactcca attgtaacat gatggtttcg catacccggg  87480
cgcgggggcg ctgggcggtt gaggttcgaa gggatacacc cgctcactcg cagcaccctg  87540
aggagcccgg ccttctgtag atgccccgca agcgccttcg gcaccggttt cccggcgggg  87600
aagccacgcg cgagcacatt ggccgctttg ggggagcaat ccctgtggcg ccagaggtgc  87660
accctggctg aactcaccga caaatgttcc cgcttgggcg tgcggcggaa tccaactggg  87720
ggcagcagga ttcagctggc tgctaggaat ccccgtatat gtccaacggg gggaaagggg  87780
atcaaattgg cccgtggttg gcggatgcac tttctccggg agaccagacg cgccctgagg  87840
ccaccatccc gtgacaggaa gatctcccca tggaaaacac gcaggtatcc acggggacgt  87900
agatggcagc ctagacccat cgcgcatggg aggggctagt tgccccgtat cccccggcgt  87960
ctgtgcgacg ccggagaccc ctgacacagt accggcaagc cgtgtttcgt gctgcggctt  88020
gggcggcgcc gtgcccggta ggcctgcacc agatgagtga gggtctgaag ggccggtcag  88080
cgttgatgga gcaggcggat ctccgggaac ccgccacgta aaggacgagg cctgcgtaac  88140
ttgtcgcgtc ccagaggacc ccatacctga ggtagatgcg ccctcattca ctggtatcca  88200
cacggagcag gcagccttct gttcagtcgt tatatcgcca acattgtaat agcggttcga  88260
tttccgaggg cgacccctca gccccgatgg cgccttaggg ggagcaggtg ctgcagcccc  88320
tgcctcctcg tagctttgtt ctctaagtaa aaggcacgag agttaacgtg gttagggtac  88380
ctaaagtatt tcccgccgac accaacgcat caaacctcac accccccttcc ccgagttaca  88440
tacctagtgt cactgcgtcg cgtagccgtg gtttgcattg ggggggacaa cagacactga  88500
ataaatcgct gcagtttttc aggaccatac gcggccccat agcaatacgt acagttttta  88560
aacggcgttc gcaccaactg ccatactacg tagctaccac caaatgtgtc gctgtaccgt  88620
aaatcgttcc gcacgacggc cctcctggtt ccacgcaaca gtctcccaaa acgtccatac  88680
accgtctgtc ccacgacagg cgatggtccg tagactctat cacactcctc atcaaatgca  88740
tggtacaccg aataccagcc aggcgggata tcgctgccgg caggcagggg cgcgggggct  88800
gcaaaaagaa ggttgttcct atcaaaccag gaaaaatagg gaaacttatt gttttcaagg  88860
gcatcaataa tccataacgt ggcccattct gagccaccgg ctttaggcat ggtccgacac  88920
agaaaccgat cggcgttcgt ctttgaggca cagtcccgac tgagccttat agtgcccccc  88980
ttcttgctat gaaaaaaacc cacgaccgtt acgcaaattt gaggagctac tcacctaaaa  89040
gtagctcctt tgacaaatgt cctggtttta taccaattgt tcacaatgac atattgtgct  89100
ggcggaaaca ggtgtcccga tgtatcctcg gcaagtaagc accattacca tgtgccatca  89160
```

-continued

```
tattgtgtgg cacaaaaaaa gcaacttttc acgcacgcag cataagaccc gagccagtcg  89220
cgccctccat cgcgcctgcg aattttccca ccacccaata ttgtggcaga tctttcttat  89280
gtatatgtgg ttacaaacac cacgcccctt aagctgtcct ctctcccaag ggactagat  89340
tataacagtg acatacgaaa ccgagacgct ctcaaatgct ttctatttta tttatcgatt  89400
ccgggttaac ataatcacag gtagctataa aatccccatc ctcttgacct ggtaaccctg  89460
gcttgaggtt tcctctgtta tcaaacaaac ctgaccacaa ctgtacagag aaaagtgggt  89520
gaaatgtagt gtttatttta tcctcacact ttcacttaac cacagcccgt caaaccacag  89580
ggaccctgtt ggctgactat tagtcatcac atgtaactga acgcaatctg agcttgatga  89640
cgagggggac catatcgaac tgttctgccg acgttgggtc acctccgatg aacacagttg  89700
ttttttaat gtgctcatgt ccctgtatgc gatattgtgc cacattaaaa acatccagaa  89760
cagccctaga tgacagtccg cagatcacac caaacttctt tggaggatta tttccatgat  89820
ataatacggt agacttgcac aaattcttaa cataaatgcc agatcggaga gaaactatca  89880
caagacccga agcaaacgag cgcagcacgg ccgccagcag gttaacgtct cctggccctg  89940
tgttattgtc gtcaggtttg ggcaacaaaa ctcttaaccc tttgcgcgaa tgcaagcaag  90000
agtggctaat gtctgccagt gggttctggg aacatagaat aaacaccttt cgttccactt  90060
ccaaagacat tgcagggcgg ccaaaataaa acacttccac accaagccta tcggttatca  90120
ttactggcgg ccgtgccact ctataatatg cggatctaag cttcctgtgg cgaatgcgcc  90180
tcgtggtagg cctctcgtgt ctccgtggcc catcatccca taaaaattcg ccaacaactg  90240
gccggcgtct ggacgccggc ggcagtccag caccatcatc gacttcttcg tcacttatct  90300
ccaacacata ttcccctgct acattctggg cctcgagtgc cccagctaag tacacatcct  90360
ctacacccgc cccgacagcc gaggcggcga ttgagccctc tgttaccacg ccgcttgcat  90420
ccgtgtcgcc tccgggctgt gatgttgcga taacatcctc tgggatgcca agcagatcaa  90480
agaggtcttc atcgcacatc gccctcatta gcatgtccat ctcctgtccc acgtggtaca  90540
tcaatgcaca tgcagattct ttatcaagca gtgtgaggtc atcttcaacg ttgtctgtgt  90600
gcaccgttgt ttcatcggcc gggggggct gcgagtcgct atgacgcgtc gagggtcctt  90660
cgtctccaga gccaggagag tcggcattgg catcatcaac tggctgaacc ccagacgcac  90720
tatggcgcgt cgatggtccc tcgtctccag agtcctcaga ttccgcgccc gtctgcgtga  90780
ccggcacatc gcaaaaggct gggtgatcct cctcactgga atccgagttt tcacccacaa  90840
atggcctaca gaaaaaaaaa caaatatgtc aaccggacta gggtggccaa accatttgcc  90900
ccacccctcc ccactctttc cccaggggac acatcttacc ttggtcttct ccgatgcttc  90960
tcgagccgta cactgtgttg atacaaaatt tcccatagtg atgacccact gtgtaggtga  91020
gtcctggcat gaacgcacca ccagcattcc tttacctcgg cacacaggag gcgccacctt  91080
ctacaattaa ttccctgtac gacctcgtac tcttcacctg gcaagcgtct aaggcgccgc  91140
gacgtggtac atattttccc aaaagccgta atcggcgagc ccagtaaatc tctgggatgc  91200
aggcccttcg ataggcattc cctcttaaaa tcaatgaaaa actgtaggct atccagagga  91260
attacgtcat tacgggcagc cggagcaaga aatgttccag tagatctatc tagccacttg  91320
accaaaggat atttatcaga gtccaaagca cctacaataa actcagaaat ccaggtaagc  91380
ctgcgtcccg ccatgttgac ctgtcagaat ggtctgcctc cgagcattac cccacctcaa  91440
cagaagtaat ctactacgca aaccacaaca tgcttcctgc agctttaacc ttcagtcacg  91500
```

-continued

```
ggtcaaaaag cattgcctgt attagacaca tgtgtttctc actatgaatc gtgctctcca  91560
gcgctggcaa gaacatctgg ggtgatgctg ccccggacca gctttgaaac agggtattgc  91620
atgcataatg aagcccacat gtttgtctta ctttactaac ctcattacct tgcattgcag  91680
gggacacccc cttgccttgg cagctgagtg aatcccaacc gcctaggaaa aaaataacca  91740
ctcagacttt attttgcagc cacacggtgg cgctaacctt taatgatgtc ccactcagtg  91800
agtttggcca ctcccaagcc cacatgggcc tactataaca ggaaacatag aagttgcgga  91860
tagagcctgg tttctaacgg caatgatatt tatagtgcaa aacggagggc ggtaagacaa  91920
agggaggtac ccggacagag tgacaagaag acttgtcaaa attttagtct ctgtggtaaa  91980
atggggcaag gtaaatgtgc aaaatgactg gatagtgatc cgagtcatat tcaggcgacg  92040
gccggcggcc cagaaacagg gacgcgtacc gggacccttc aggttctcga ttatgtcgct  92100
ccacgtcaaa agcttgttgg atctcgtggc ggtgggacag gggcctacat ttgcctattc  92160
ttcttcgcga tgcatttcca acaaagtatg ctgggtattc caataatccc ttcagaaaaa  92220
tgcccatgtt tgtaccgatg gccacaactc ccatggaaaa cctgtccagc gtctgttcca  92280
aagttcggtt tgcgtccaca ctacagtggg ccgttctggg aagtaagcat ttatacgggg  92340
gtaccgtctg acatatgtgt tcaggggagg cctctgggac ttgggagcaa ataacgatgc  92400
cccccgttaa atcaaagtgg gtcttcacct tttctccgaa ataatacact tccaccacta  92460
ggggcacaag cttgtcaccc actttgtaaa tagcctgttt cttactcagg tatgctgcca  92520
cggattgggt ggcggttaag accttgggcc tcatgtcgct tccataccag taaaatgtct  92580
ggtcagcttt ctcttggtcc tcgacgtccc ggtcatcacg acacaacggt ggaatacaat  92640
caataaaatc atccacattg tcggaagctt ggaaagatga acccatgaca gaggccccag  92700
gtgccgaact ctcaagggga tgcgtggcgg gaagtactga gacactctcc gtggacccct  92760
cctcacctcc ctccgactgc atcgggccct gagggctcgc agtttcacac agaagttcac  92820
tcaggtcgcc taagtcagga agctcctggc ctgaacccat gacagaggcc ccaggtgccg  92880
aactctcaag gggatgcgtg gcgggaagta ctgagacact ctccgtggac ccctcctcac  92940
ctccctccga ctgcatcggg ccctgagggc tcgcagtttc acacagaagt tcacccaggt  93000
cgcctaagtc aggaagctcc tggccaacat ctgacaagag atctaacaaa cacccctcaa  93060
tgtgatccac catcggtagg caatcatcca gcccactgac atgactgggg acggggcctt  93120
ctggggaaaa tggggtttgc gactgtccag caggcggcgc taataagcct tgtgtctcat  93180
gtggaaaaat aacaggagaa ggtaaacccc ccgttggcaa acatagatcc gtcggggtgt  93240
gcacgtgtaa tgggccctgc acctggctcg tggagggacg cggggaatcc ggagctaata  93300
agctcgatga ctgaccagat gacccaaacc ccgacggttc tggctcttca aaaaacaaac  93360
tgtgcatatc cctccctaca aaaccctgag cccccaccca aagttcgttt tcgctgtcac  93420
tcgattccgt atcttcgctc tgtgaccgtg atgaaacttc agctgcggag gatgttgtgg  93480
gcgtggcgac tgccgccgcc tgtttcctgg cggcctccct aaacaaaagt taattacaca  93540
aaggtaagtc tgagtgacat ctccaatttc ccgtgatgcc cgctgcacgt acatcccgcc  93600
gcccacacaa cccaccgccc agtacatcaa ccatcctacc tctgggcttt ttttctaagg  93660
ctccttctaa gtgccttttc tctgtgtttg tcatcatggg gatagatccc aaacaatgct  93720
tttagcatgt ttttcatggc tggttcctgc gtcaagtaca caagacatcc ttcacatccc  93780
ttgtatggcc taggtgtcat aatccagcgg ttgagtttca tttttccctt atagatggta  93840
aagggcctct cctgtctggc tcgattggcg gtccttaata gccgtccaaa gcagcccagg  93900
```

-continued

```
ccagtctcag tctccgggat ttctggcagc ccgtgcctac gtcgctcctc caaaaatgcc  93960
tcatagaagt catcgaagcc ttctggcatt ctctcccgcc ggtttcgacc cggcacggtg  94020
aatattctct tttgttcatc caaccaccct accccccaga agcgtccact gtctaaagca  94080
tctataataa agtccgtgag ccattccgac tccgtgtagc gaggcatctt tttaggcaaa  94140
agccacgaca caaaacacct tttccgtggg cgactttctc gccacaacta gctggacccc  94200
aaccccactg gcacgtagac tctgtgccat ctaacaacaa aactcaatat atgcagctca  94260
acaccgcccc ccccagccgg ttgtcgggct gcggaaactt gtggttagaa ctcactacgg  94320
aaaagggaac caatgcagtt gaactactgg cacacaccca taacccggga cagcacccag  94380
gcactgtcca ccctctaata caagcggcct ttggacgcga gggaggggtg tcatggtcaa  94440
caaaccaaga aaaacacatg tattattcaa ttagccaaca actttattta ttaccgacag  94500
gagacatgag atacataaat ttccaaccgt gcatagggcc aataccatct gtggagcgtt  94560
aagtgccctg tggagttttc gcctaattag ctgaatctcg acccccattg cggccagcat  94620
gctcacgagg aataggcagc agaggcagga cctaactagg agcatatccg gacctgatcc  94680
aagtatgtgc accaaggtga gcaacactgc cgccaaaggc aggagaacaa atagcgctcg  94740
tcgggaggcg acggatacgc ccacgcatga cagtaaccca acataaaata gcgtcatata  94800
cttatccagg ccaatcagga ccggagtcag caggccgatc gaggccgtcg atatcagggt  94860
ggccagcagt aaggtcacaa acacgacaac ctcgcgccta cagtaggccc aggcctggaa  94920
cactgaatag gtgatgtact tcccgggcat gatgaatatg gccctcctcc tttgcattcc  94980
ggccctgatg tacacatgct gttccaggtg cctaaatgcc aaaagtcccc cgaccaagaa  95040
gacaatgaag ggcagccaga aaacgccgga cacaaagacc ttcttaaaca acagaaggta  95100
gtacaccata aatgctccgc agaagcccag ctcatagtac ctgtgtacta ttggcggcgc  95160
ctgatacacc gccgttgcgg tggctagcgg ataaggtaac agcagtaaac agttaagtac  95220
gcacagaccc ggtatgaagg gcacacgaga aaatgtaaac ccagaaaagg ccgcgcaaac  95280
tacagcagca aacactgctg acgcgcagat ccattccagc ctccggtcca gctgtttttg  95340
cgccgcaggg cacagacaca tgcatatcag ggccaagtgc gtgactggca gcgaccagaa  95400
aaacacggcc gtgatctctg tggtaaagag tgtgaacgag tacagggcct tgaagataaa  95460
acaccacaga aagggggtcg ccgccaacgt cccgctcaga taactgaaga gcgacagagc  95520
gcgctcactg tccaggcggc acatggtgtc aaatcagggg gttaaatgtg gttttgggca  95580
ccttcccacg atccctggac tggctcgagt ctgagcgcct cttgtgaggc ctctttgtgc  95640
tgtccttagt tggcgccgct ggggggcagc tggtgacaga ggcagcgtcc tcagaggcgt  95700
cctccagcgg cccaaaggga ccaactggtg tgagaggggg agaatccgga gactccaatt  95760
ccggctgcct cctggagtcc ggtatagaat cgggaacctt ttgcgaagac tcgcctccct  95820
cggcagacac agatcggttt acctctaaaa gtaggacact taactttacg tcacctgatt  95880
ggcagccagt gggcacacct tccacttcta atatttcgtt ggagtgccaa atcagcccgg  95940
gggtaaacca acccgggact ttacacagtc tcagggcggc gattaaggac tccaggctaa  96000
cccggctcag ggcgtcggtg tgcaccacgc ccacatccac cgacttcttc cccttcagac  96060
catcccagcc agaaacgggt ttggtttctg gcttgaaatc aatgatcttg ctcacgccac  96120
caagagaaaa tgtcacgatc gacagcgtct cgctgacaga cacagtcacc gtttggtcct  96180
cttttgtttt ttgctgcctt agccacttaa gtaggaatgc acccgttttg ccacagagga  96240
```

-continued

```
gaagcctggt ggtcctacca ccggcttcca tccgatcgtg gaaaggtagg ataccctttt  96300
ggtccaccac gcttttgtgc acggtggagg tgaggttgtc cccgtaggaa atggtggtcc  96360
tgacgaactg cggttgggcc cccgtatcgc atgcctcccc ctttcgataa aaggctatgc  96420
cagcgtcgag tacattcgca ccgaatagct cacgcgtgtg cgtgaagccg ctaccgacgg  96480
acgtattcct gaagctgaag ctaacgtctc cactgccttc cgtgtgtccc accaggggcg  96540
taagggcatt ctttattctt aaccccagaa cgccagctgt ccccacgctg gacagcacac  96600
tgagggttgg cgtgcaagcc gatccgtgca cttgcactac tccggtttta gtggcactct  96660
taatgtgttc attgaccctc ctgattttag acaggagggt cacgtccacc ctgaccccat  96720
agtgaaaatc cacaggcatg attgcggccg tagacgcaca gagaaatcac aggaaagctg  96780
cgcgcacact gggtgatctg gagacgatag actgccttaa atagaacttt taggggaggt  96840
ggaagtgtgc gacatggaca ggttaacctt cacaaatcgt cagtcacaca cgtggtgtaa  96900
tcagaattgt ctcgctcaaa aaaattcaca gccttgaaac tgccggtgta tgagaggggg  96960
cacgcttctg gcggaggcgt gccaaatatg ggaggaacga aaatatcacg cagaatcctg  97020
tcagcggtgg cttccaggaa cctccggatg tccaccacgt taacaagcgt caccccggcc  97080
gccttggcct ggataaaccg aatctcaata ttcactgcct ccctgaacag cgcctggacc  97140
tctgcgtgac tgggtttttc ctgtatctcc accatagtgt tgtacaacat actggcggcc  97200
ttggtgtgca gcagctcgtc cctggaaatg taatcgttgg caaggcacac cccgggcatg  97260
atgcctcgca ccctgcacaa actgatagag tagaaggagc taataaagta tatcccctcc  97320
acaatcaaaa acatcagaat cttctgagct ttggtggtcg ccttacgcac cctggagtga  97380
agccactcca gcttctcgca aagggcgggg tccaaaatga tcttggcagc atatgctaga  97440
agttcgcctc gactgttgtt gaaaaatatc ttcaagatat tggcatacac gacaccgtgg  97500
atattctcca tggcaacctg ttcggcataa tagtgggcca cgtcgtggct gttaaaattt  97560
gtgacaaggt cctcaatgtt aaagttaact aggcgttcgg ccattcccaa aaacgtaaac  97620
aaaaatctat aaaagtcctt gtcggcatcg ctgagctggt gcacgtggga aacatcaagg  97680
tgcaggggta tctggctagg aaaccatcgg ttctgccaag tctcgcgcgt tagcgccaaa  97740
aatccgtcgt gatcgcttgt atacagaaat cgatcaactg aatccattgg cctcacccgg  97800
cttgcagaga cctacctact gacagaccag gcactcgggg tctgccgcgc aggactcctc  97860
ctccgggttt ttaggtccgg gtaaccacgc cccatcttgt ttcatcccag agtgaggcgg  97920
tgaccctgga tctgccaggc actgaagagc cgtcagacta gattgcttct gaaccctaca  97980
gtagtacatg agggttttta gaccaagcct gtatccatgt agcagcaggt ccctaagata  98040
gctcgcattc ctgactctgt cctccttgag gaagaagctc atggactggc tctggtctac  98100
aaacggcgcc ctggcacgag ccctgtccag tagcttaaat ggacagtaat caaaggctgt  98160
taggaatacc ctatatcttt ccctgtgatg cttggggaac gtggaaacgt ccccaccata  98220
ctgtctaacc acccgaaggt cgtcggggag aaccttctta aaaaaagtca cattgggcct  98280
caacacctct tctttattgg tgaccttgga agatatatta gcaaaaaagg ggtacacaga  98340
ctcggcatag ccagttactt gcgaggtccc agccgtcggc atcaccgcca gaaactgaga  98400
attgaatatg ccatgctcgg caatgctctt tcccaacgcg tcccagcgat ggcgtggtac  98460
aaacgaagca tcctccccct cccatgtttg ccaatgaaac ctgcccttgg cgaagttact  98520
gacctcccag ccatgaaatg ggacaccctg tccctccaaa acaaggttgt gactagtctc  98580
caccgcggtg tagtacatag actggaatat attcttgtct aactcagcgc tctcagcatc  98640
```

-continued

```
gaggtacccg taccccaatt ccgcaaacac atccgccaac ccctgaacac caatccccat  98700
agacctctcc ttttgacctc gctcgacccc cggtgttgga tgggaaccac ccagaatgca  98760
ggcgttgatg acgaggactg ccacccttac tgcgtcgccc aaggcctcaa aacaaaaaaa  98820
cggcctgttg gcgtccgtgg tgccaaccct cgcgctttca acagttctca gacactttgg  98880
aaggcagata tttgccaggt tgcacaccga agtgtttctt cctggcagtt ggactatctc  98940
tgcacacaag tttgagcagt taatggccat gccctgagtg tcggtccagt ggtgttcatt  99000
gagcgcttct tttaaaagca cgtacggtga gcctgtcttt atgatggtgt ggataagagt  99060
gaacatcata gacttcaacg gcatgcaact aacgtacttt ccagcccgca ccaggcgctc  99120
gtattcgtta tcgaacgcag caccgtatag cttaatcaaa ttgggggcgg tggctggatc  99180
gaacaaatac cataacttgg atgggtcctt ttcatacatc ctgaaaaaca atgttgggat  99240
gcacacgccc tgaaagagac tgtgacatct gtcgggattc tccggtagtt tggcgttcaa  99300
aaaatcacag atttgactgt gccagagttc catgtatgcg ctcgcgccaa cgggcctgat  99360
gttattgtca ttgaaataat gaacctgggc atccaccagt ttgaggcaac tggctatgtt  99420
cttttggtgg gagaatgacg taacatccag acccacgcct gacttactgg ccagcaacgg  99480
actcatatcg tggtacaggg cgtccaaagt acccgactca ttcatcatgg agggctgcag  99540
aataaaacag ctggcgagtt gtccgccttc gactccagct gagcgcagta ttggcgtggc  99600
gcagcacacg tgctgcgcag cgaggtagcc aaaaacgtac tccactatag ccatctcaga  99660
tacagactta gcgtcctcaa taaggtcccg cgccaaccaa tacaggcatt catgctctaa  99720
gcactgacag gcaacaaaca cggaaaccct cataaacatt tgcgccacgc tttcatagac  99780
aggctctgtc cccatggtcc ttaggacgta agtatcatac aacctcacgg ccgataggta  99840
gccacagtta agtgtgtcct cgtaagcttt ggaccgtctg taggcgcaca acatatcttc  99900
caaggcatca atgttctttt gaataaacga ttccacccga tgtcccaaca cgcctcgaaa  99960
aatcccaaga tactgcttga gagtcgctgg gcacctagcc tccataattt ggtgccacag 100020
ccgccccgcc atggcattgg cccgcacgtc ccacccgacc ctaaccttta gaaagtctat 100080
gagagattgg gcacacatat caaaatccga caattgtccc gcagacacct gagacccgcg 100140
tcgctctggt gggacagctc ccaagtgaac ctgacaaaat gtccggacag acatgacctt 100200
acagaaacac agtccagggg ccacacgcgg cctcaaagtt cgcaaacacc agtacaggca 100260
aggacgtgcc cttcacgttc agactttggt gcaccggatg agaatcaaag ggaactgtgc 100320
ccagcgtaca aaccgcccca aaaacaagcc gatttatata cagctcgtgc ctcagctgaa 100380
tatacttggt ccggattaca tccgtaaagt gatcctttat catggccaca acctccgcaa 100440
agcccttccc agactggaaa aacgtcagcg ccatagatgg tctctggttc acacggagat 100500
aaaccaacga ggcataaata gtaacgttta ggcctgccgg ttcccggcgc tggaccatgg 100560
gacatgactc atccaaatca actagcatat cacaagggag ggtcaagcct acgtgtgcac 100620
ggggctcgtc ccgggccaac ccaactccct tcatggcgga ggtgaccttg gtcacgaagg 100680
tactgtggac actctggacc attggaccta ctggggtaag gagggtatga aactccccag 100740
tgtccatgag ttcactcaag ttagggatga aatccgccag gccggatcca cttccgtacc 100800
acacaccggc cactttgtga gtctgtggcg cttttgccgc ttccattcca gagagcataa 100860
acagggacgt gggtgttagc agcatatcca tagacgagcc gttgtcctcc tgcttgaatg 100920
aaaataaaaa ggttcccaga ggctcctggg gactaaaggt ctgtgaatac acgaggaaat 100980
```

-continued

```
ctccataggt cggctgccta aacggcgcct gccgcaaggc ctcatgcagc gagccaaccg 101040
tgggtcgtgt ggacgccgca tatttagaga gtaaatcccg cacccccctg gcaaactccg 101100
gtcctctagt gagggatacc cggtgagttg gtggaggtaa aagacccaac acttgcctac 101160
ccaggcgagc cgcattttca gcctgcacct tcatatccac gccggcaatg gacggcacag 101220
acgctcttga aaagcttacc aaaggcctga gtgggggagg cgggagcctt caccagacaa 101280
agctgttgat ggaatttcaa ctccgaggac tgccggtgcc tgccctctta aacagcagca 101340
caacagagca gtttttaaat actgttgccc aactgccgac ggacctatca aaatttatac 101400
gcgactatcg cgtgttcgca ctggttcgcg cggcgtattt tttagaaccc ccttctagca 101460
tcgacccccct tgaggcagcg cgcgctcttg gacgcctggt tgatatatta tcatcacaac 101520
caccgcagaa caccgcaccg gcgcagccac ccacctccga cgacaccctg aataactgta 101580
cattgctcaa actactagcc cactacgcgg atcagatagc aggtttcaaa acccccgctc 101640
tccctcccgt gccacctgga atcatcggcc tgttcacatg cgtggaacag atgtaccacg 101700
catgttttca gaaatactgg gcagctgcac tacccccaat gtggatactg acatacgacc 101760
ctcccacttc tccgttacag gactggctta tagtcgccta tggtaacaag gaaggactgc 101820
tactcccctc tggcataccc tcggaggagg tgttagccaa aacattagta acagaacacc 101880
acgagttgtt cgtatcgcgg tcgaattcga ccgagaccgc cgtcaccatg cccgtatcca 101940
aagaacgcgc cctcgccatc taccgggtgt tcgccaaggg tgaggtggtg gcggaaaata 102000
ctcccattct tgccttcacc gacgtggaac tatccacact caaaccccac tatctgttca 102060
tctatgattt tatcatagag gcattatgca agagctacac atactcatgc acccaggccc 102120
gcctggaatc ctttttgagc cgaggtatag acttcatgac tgacctaggt cagtacctag 102180
ataccgctac tagcggcaag cagcagctga cgcacagcca aataaaggaa atcaaataca 102240
ggctgctaag ctgcggtctc tcggcttccg cgtgtgatgt tttcagaact gtgatcatga 102300
ccctcccata tcgaccgacc cccaacctcg ctaacctgtc cacgtttatg gggatggttc 102360
accaactgac catgttcgga cactatttct accggtgcct gggcagctac agtcccaccg 102420
gcttggcctt cacagaattg caaaagatac tgacacgcgc cagcgcggag caaacggaac 102480
gtaacccgtg gagacatccg ggtatctcgg acattccact gcgttggaaa atatcgcgtg 102540
ctctagcatt cttcgtccct ccggccccca taaacacttt gcagcgcgtg tacgccgcgc 102600
tgccctcgca actcatgcgg gccatcttcg agatctcggt caagaccaca tggggaggcg 102660
ccgtaccggc aaacctggcg cgcgacattg acacaggacc gaacacacaa catatctcct 102720
ccacaccacc gcccaccctc aaggatgttg agacatactg tcaaggtctg cgggtgggag 102780
acacggagta cgatgaggac attgtgagaa gcccgctctt tgcagacgcg tttaccaaga 102840
gtcacttgtt gcctatactg cgcgaggttc tggaaaaccg cctgcagaaa aacagagctc 102900
tgtttcagat aagatggctg ataatatttg ctgccgaggc ggcaaccggg ctcatccctg 102960
ccaggcgccc gctagccaga gcctacttcc acatcatgga cattctggag gagagacatt 103020
cccaagacgc cctatacaac cttttggact gtatccagga gctcttcacc cacatcaggc 103080
aggctgttcc agacgcacag tgtccgcacg cctttctaca gtccctgttc gtctttcaat 103140
tccgcccttt cgtactcaaa caccagcagg gtgtaacctt gtttctagat ggcttgcaga 103200
catccctccc cccggtgata agtctggcca accttggaga caagctgtgt cgtctcgagt 103260
tcgagtacga cagcgagggc gacttcgtgc gcgtgccagt tgcaccgcca gaacaaccac 103320
cgcacgtaca tctgtcgcat ttcaagaaga caatacagac catcgaacag gccaccaggg 103380
```

```
aggccaccgt agccatgaca acaatcgcaa agccaatata ccccgcctac atccggttac 103440
tgcagcggct agaatatctt aacagactca accaccacat tctcaggatt cccttcccac 103500
aggacgccct ttctgaactc caggaaacct acctggcggc gtttgcacgg ttgacaaaat 103560
tggcagcgga cgcagcaaac acttgtagct actccctcac caagtacttt ggagttttat 103620
tccaacacca gctggtcccc acggccatcg ttaaaaaact gctacatttc gacgaggcta 103680
aagataccac agaagccttt ttacagagcc tggcacaacc cgtagtgcag ggacaacggc 103740
agggggcggc tggcgggtcg ggtgtcctga cgcagaaaga acttgagctc ttgaacaaaa 103800
taaacccaca gtttacagac gctcaggcta acattcctcc atctattaaa cgttcatatt 103860
caaataaata tgacgtccct gaggtctcag tcgactggga aacgtactcc cggtctgcct 103920
tcgaggcacc ggacgacgaa ctccgttttg tcccactgac gctggcaggc ctccggaaac 103980
tgtttgtcga atagaggcca tggcagccca gcctctgtac atggagggaa tggcctccac 104040
ccaccaagct aactgtatat tcggagaaca tgctggatcc cagtgcctca gcaactgcgt 104100
catgtacctg gcgtccagct attataacag cgaaaccccc ctcgtcgaca gagccagcct 104160
ggacgatgta cttgaacagg gcatgaggct ggacctcctc ctacgaaaat ctggcatgct 104220
gggatttaga caatatgccc aacttcatca catccccgga ttcctccgca cagacgactg 104280
ggccaccaag atcttccagt ctccagagtt ttatgggctc atcggacagg acgcggccat 104340
ccgcgagcca ttcatcgagt ccttgaggtc ggttttgagt cgaaactacg cgggcacggt 104400
acagtacctg atcattatct gccagtccaa agccggagca atcgtcgtca aggacaaaac 104460
gtattacatg tttgaccccc actgcatacc aaacatcccc aacagtcctg cacacgtcat 104520
aaagactaac gacgttggcg ttttattacc gtacatagcc acacatgaca ctgaatacac 104580
cgggtgcttc ctttacttta tcccacatga ctacatcagc ccagagcact acatcgcaaa 104640
ccactaccgc accattgtgt tcgaagaact ccacgggccc agaatggata tctcccgcgg 104700
ggtggaatca tgctccatca ccgaaatcac gtccccttct gtatcccccg cgcctagtga 104760
ggcaccattg cgcagggact ccacccaatc acaagacgaa acgcgcccgc gcagacctcg 104820
cgtcgtcatt cctccttacg atccgacaga ccgcccacga ccgcctcacc aagaccgccc 104880
gccagagcag gcagcgggat acggtggaaa caaaggacgc ggcggtaaca aaggacgcgg 104940
cggaaagacg ggacgtggcg gaaatgaagg acgcggtggc caccagccac cagacgagca 105000
ccagccccca cacatcaccg cggaacacat ggaccagtcc gacggacaag gcgccgatgg 105060
agacatggat agtacacccg caaatggtga gacatccgtt acggaaaccc cgggccccga 105120
acccaatccc ccagcacggc ctgacagaga gccaccgccc actcccccgg cgaccccagg 105180
cgccacagcg ctgctctctg acctaactgc cacaagaggg cagaaacgca aattttcctc 105240
gcttaaagaa tcttatccca tcgacagccc accctctgac gacgatgatg tgtcccagcc 105300
ctcccaacaa acggctccgg atactgaaga tatttggatt gacgacccac tcacaccctt 105360
gtacccacta acggatacac catctttcga cataacggcg gacgtcacac ccgacaacac 105420
ccaccccgag aaagcagcgg acggggactt taccaacaag accacaagca cggatgcgga 105480
caggtatgcc agcgccagtc aggaatcgct gggcaccctg gtctcgccat acgattttac 105540
aaacttggat acactgctgg cagagctggg ccggttggga acggcacagc ctatccctgt 105600
aatcgtggac agactaacat cgcgaccttt tcgagaagcc agcgctctac aggctatgga 105660
taggatacta acacacgtgg tcctagaata cggtctggtt tcgggttaca gcacagctgc 105720
```

-continued

```
cccatccaaa tgcacccacg tcctccagtt tttcattttg tggggcgaaa aactcggcat 105780
accaacggag gacgcaaaga cgctcctgga aagcgcactg gagatccccg caatgtgcga 105840
gatcgtccaa cagggccggt tgaaggagcc cacgttctcc cgccacatta taagcaagct 105900
aaacccctgc ttggaatccc tacacgccac tagtcgtcag gacttcaagt ccctgataca 105960
ggcattcaac gccgaaggga ttaggatcgc ctcgcgtgag agggagacgt ccatggccga 106020
actgatagaa acgataaccg cccgccttaa accaaatttt aacattgtct gtgcccgcca 106080
ggacgcacaa accattcaag acggcgtcgg tctcctcagg gccgaggtta acaagagaaa 106140
cgcacagata gcccaggagg ctgcgtattt tgagaatata atcacggccc tctccacatt 106200
ccaaccacct ccccaatcgc aacagacgtt cgaagtgctg ccggacctca aactgcgcac 106260
gctcgtggag cacctgaccc tggttgaggc gcaggtgaca acgcaaacgg tggaaagtct 106320
acaggcatac ctacagagcg ctgccactgc tgagcatcac cttaccaacg tgcccaacgt 106380
ccacagtata ctgtctaaca tatccaacac tctaaaagtt atagattatg taattccaaa 106440
atttataata aacaccgata cactggcccc atataaacag cagttttcat atctgggggg 106500
tgaactggca tctatgttct cccttgactg gcctcacgca cctgcagagg cggtagagcc 106560
actacccgtg ctgacttctc tgcgaggtaa aatcgcagag gcgctgacgc gtcaagaaaa 106620
caaaaacgct gtagatcaaa ttctaaccga cgccgaaggc ctccttaaga acattaccga 106680
tccaaacggc gcacacttcc acgcccaggc cgtatcaatt ccagtgttag aaaactacgt 106740
acataacgcg gggtccttc tcaagggcga aaagagcgag aggttctccc ggctgaagac 106800
cgccatccaa aacctggtat cctccgaatc atttatcacc gtgaccctac acagtacaaa 106860
ccttggaaac ctagttacca acgtaccaaa acttggtgag gcgttcaccg gggcccgca 106920
cctcctgaca agcccgtccg tgagacagtc cctttccacc ctgtgcacaa ccctgctgcg 106980
agatgccctg gacgccctgg aaaaaaagga tccggccctt cttggtgagg ggaccacgtt 107040
ggcgctggag acactcctag gatacgggtc ggtgcaggac tacaaggaga cggtacagat 107100
aatatccagc cttgtgggca tccaaaaatt agtcagggac cagggcgcgg acaagtgggc 107160
cactgccgtg acaaggctaa ctgacctcaa atcaactctg gccacgaccg ccatcgagac 107220
ggctacgaaa cggaaactat acagattgat ccaaagggac ctcaaagagg ctcaaaaaca 107280
cgagaccaat cgggccatgg aggaatggaa gcagaaagta ctggctcttg acaatgcgtc 107340
tccggaacgt gtcgccaccc tcctgcaaca ggctcccacc gcgaaggcta gagagtttgc 107400
agagaagcac ttcaaaatac tactccccgt acccgcggac gcccccgtcc aagcgtctcc 107460
aacgccgatg gaatacagcg ccagccccct cccggaccca aaggatatag acagagctac 107520
atccatccac ggggaacagg cgtggaagaa gatacagcag gcgttcaagg atttcaactt 107580
cgccgtcctg cggcccgctg actgggatgc cctggcagcg gagtaccaac gccgtggttc 107640
gcccctttccg gcggccgtgg gtccagcgct ctcagggttc ctggagacga tcctagggac 107700
gctgaacgac atctacatgg ataagctccg ctcctttctg cccgacgcgc agccttttca 107760
ggcgccgccc ttcgactggc taacgccgta tcaggaccaa gtcagctttt tcttgcgcac 107820
catagggctg ccgctggtgc gagcgctggc cgacaagatc agcgtgcagg cactgaggct 107880
tagccacgcg ctccagtccg gcgatttgca gcaggccacg gtgggcacgc ccctggagct 107940
ccctgccaca gagtacgcgc gcatcgcctc caacatgaag tccgtgttca acgaccacgg 108000
acttcaggtg cgatcagagg tcgcggatta tgtggaggcc caacgagccg acgcacacac 108060
gccacacgtc ccacgtccaa agatacaggc accaaagact ctgattccac atccggacgc 108120
```

-continued aatcgtcgcg gacggactac ccgcctttct taagacgtcc ctactgcagc aagaggccaa 108180
acttctggcg ctacagcggg cggacttcga gtcgctcgag agcgacatgc gcgccgcaga 108240
ggcccagaga aaagcatcgc gcgaggaaac ccagcgcaaa atggcacacg ccatcactca 108300
gctcttacag caggcaccca gtgcgatctc ggggcgcccg ctatccttac aggacccggt 108360
gggcttcctc gagggcatca tatacgacaa ggtcctggag cgcgaatcct acgagacggg 108420
tctcgaggga ctgtcctggc tcgagcagac catcaagtcc atcaccgtat acgctcccgt 108480
agaggagaag caaagaatgc acgtgctgct ggacgaggtg aaaaagcagc gagcaaacac 108540
tgagaccgct ctcgagctag aggccgcggc tacgcacggc gacgacgcta gactcctgca 108600
gcgagcggtc gatgagctgt caccgttgcg cgttaagggg gggaaggccg cggtggaatc 108660
ctggcggcag aaaatccaaa ccctgaaatc cctggtacag gaagcggagc aggccggcct 108720
cctgttggcc accatagaca cggtggccgg ccaggcccag gagaccatat caccatccac 108780
actccaggga ctgtaccaac agggacagga ggccatggcg gccattaagc ggtttaggga 108840
ctcgccccag ctagctggcc tgcaggaaaa gctggccgag ctacagcagt acgtcaagta 108900
caagaagcag tatctggaac actttgaggc cacccaaagc gtagtgttta cagcctttcc 108960
gctcacacag gaggttacga tcccagccct gcattacgcg ggacctttcg acaacttgga 109020
gcggctctca cgatacctac acatcggcca gacgcagccg gctccgggac agtggctcct 109080
gacacttccc acattcgacc ccacgcgccc ggcctgcgtc ccagccggcg gccacgaacc 109140
cccgttgcac agacaggtgg tgttctccag ctttttggag gcccagatcc gattagcgtt 109200
gtccgtagcg ggccccgtgc ctggacgggg tctgcccgga acaccgcaga tccgaagggg 109260
cgtggaggct gccgcttgtt tcctccacca gtgggacgag atatctcgcc tccttccaga 109320
ggtactggac accttttttcc acaacgcgcc ccttcccgca gagtcttcct ccaatgcttt 109380
cctggccatg tgcgtattga cgcaccttgt ctacctagct gggcgcgccg tcttgggccc 109440
acgggagccg gagcacgccg ccccggacgc gtacccaagg gaggtggcgc tggccccgcg 109500
cgacctgacc taccttctac tggccatgtg gccatcttgg atctcggcaa ttttgaaaca 109560
gccttcgcac gcggaggcgg cgcacgcatg tcttgtcacg ctgccaacaa tgctcaaggc 109620
tgtgccgtac ctcacgctgg aagcctcagc tggaccactg ccggcggaca tgcgccactt 109680
cgccacgcca gaagcgcgtc tgtttttccc cgcgcgatgg caccacgtca acgtgcagga 109740
gaaactgtgg ctgcgtaatg attttatgtc gctgtgtcac cgttccccgg ggcgcgcgcg 109800
catagccgtc ttggtgtggg ccgtcacttg cctagatcct gaggtaataa ggcagctgtg 109860
gtccaccttg cggcccctta ctgcggatga atccgacacg gcttctggac tgctgcgggt 109920
gctagtagaa atggagtttg gtccgccgcc caagacgccg cggcgggagg cggtggcgcc 109980
cggcgcaaca ctgccaccgt acccctacgg ccttgccacc ggcgagcgcc tggtcggcca 110040
ggcgcaggaa cgctctggcg gcgctggcaa gatgccggtg tccgggtttg agatagtttt 110100
aggcgcactg ctgttccgcg ccccccctacg cattttcagc accgcatcaa cccacaggat 110160
ctcagatttc gagggcggtt tccagatact gactcctctc ctggactgtt gcccagatcg 110220
cgagccattc gcctccctgg ccgccgcacc acgaaggacg gtgccactgg gagacccgtg 110280
cgccaacatt cacaccccccg aagagataca gatctttgcg cgtcaagccg cctggcttca 110340
atataccttc gcaaattacc agatccccag caccgacaac ccgataccga tcgttgtgct 110400
aaacgctaac aataaccttg aaaacagcta catccctcgc gatcgcaaag cggacccgct 110460

-continued acgaccattc tatgtagtcc ctctgaagcc gcagggtaga tggcctgaaa taatgaccac 110520
agcaacaacc ccctgccgcc taccgacatc gccagaagag gcgggatcac agttcgccag 110580
actccttcag agccaggtga gcgccacatg gtctgacatc ttctccaggg ttcccgagcg 110640
cctcgctccc aatgcgcctc agaagagttc ccagacaatg tcagaaatcc acgaggtcgc 110700
cgccacgccg ccactcacaa tcaccccaaa taaaccgacc ggaacccctc acgtctcccc 110760
ggaggctgat ccaataacag aacgcaaacg cggacagcag ccgaagattg tcgcggacaa 110820
catgcctagt cgtattctcc cgtcgctacc gaccccgaaa cccagagagc ctagaatcac 110880
gctaccccac gcactgcccg ttatatcacc cccagcacat cgcccgtcgc ctataccgca 110940
tctgccagca ccgcaggtaa cggagcccaa aggggttctc caaagcaaac gtggaactct 111000
cgtgctgcgg cccgccgcgg tcattgaccc acggaagccc gtctcggcac cgatcacgcg 111060
atatgagagg acggcgctcc agcccccccg gactgagggc gaaggccggc gccctcccga 111120
cacgcaaccc gtcactttaa cctttcgtct cccacctacc gcacccactc ccgcaactgc 111180
agccctagaa accaaaacaa ctcccccatc cacgccccca cacgccatag acattagccc 111240
accacagaca cctcccatgt ccacctcacc tcacgcgaga gacacaagcc cccccgcaga 111300
aaagcgggcc gcacccgtca ttcgagtaat ggcgcccacg caaccgtcgg gagaggcaag 111360
agtcaagcga gtggagatcg aacagggcct ttccacacgc aatgaagccc ctccccttga 111420
acgctcgaat cacgccgtgc ccgccgttac cccaaggcgc accgtagccc gcgaaatcag 111480
gatcccgccg gagataaagg cgggttggga cactgcaccg gacattcctc tgccccacag 111540
ctccccggag tcatccccac cgacttcccc ccagcctatc cgcgtggatg ataaatcgcc 111600
tcttcccaac ctcgtagaga gatacgcgcg gggtttcctg gacacgccct ctgtagaggt 111660
gatgtccctg gaaaatcagg acatcgccgt ggaccccgga ctgctaaccc gccggattcc 111720
atccgtggtg cccatgcccc atccaattat gtggtcaccc atagtaccca tcagtttaca 111780
aaacacagac atagacactg caaagataac actgattagt tttattagac gcatcaaaca 111840
aaaagtggcc gccctatcgg cgtccctggc ggagacggtt gacagaataa agaagtggta 111900
cttgtgactc cacggttgtc caatcgttgc ctatttcttt ttgccagagg ggggtttcct 111960
cgcgtcggcc accgcggggg cggccgtttc cgtcgtggat gagagggttg tgagaatgtc 112020
tgacgccggc gacaatgaat ggggaccaga ggacagggtg gttatactgc ttcccgagac 112080
ccccagtgag tcctggcccc cgggcgtggt gccggatgca gggcctggcc tcgaaggcac 112140
ggtgaacgtc cccgcgtcgt aagccgacgc cgcggaaact cggtcagcgc gctcgcgcgg 112200
tttctgatcc ctaagggtct gcagatgatc ccgcctttga attccaccca tcctcctcag 112260
ataggcctca taataatgat gggcaattaa gaacacgaga tagtgtctct tttgcacgag 112320
gtattcggcc tgcgacatat ttccctgatc cagggtattc atgcgagcca ccaggggatg 112380
gtgagcgtag tcatgatcca gtcgctcctg gatcacgggg tctctcacct taaagttgga 112440
catcttccac acaggcgggc gaaatagcct caggaggaac acttcccgca acagaactcc 112500
agcagctgtg aggtgagctg aagcagtccg cgcacgtcac ggtgctttaa tagggcagcc 112560
tcgcagtcgg gcgtcccaag gcaaggcact acaaaactga cagtttgatc taggtctcga 112620
atggcaaggg ccgcgttgtt agctagaaca gccctgatta cgacgcgtgc tagggtcccg 112680
cgtccggtaa tatcgcacag gggatacacc ctcatatgtt cgctgccaca gtaagaacag 112740
tagatcctcc ccgtggtcgc acagatggtg aactgcttct ctttcctgtc cctgctgaaa 112800
aacacgttgg tgggaggaaa attgacagta tgaaacttgc ccctgccaaa gttaagacag 112860

-continued

```
tgtccacact ccatgcacac aaccgcccga gcgcaacgcg cccgcttggc aagggccgcg 112920
cgggccacgc gagaacagat gacgggtatg gacacgcagg gggagagaac attgtatgcc 112980
agaagcctcc tgccaaggtt ccgcacgaga ccaggtccct cctgctcgca ggcgggcagc 113040
actacgtggc gggacttaat aaggctcaaa aaacacagtg acccaagcat ggcgtcgaac 113100
gggttaccgc agggaaccgt aggggcgacg cgctccaagg cctcccggag gccggtatct 113160
gccgccccta tcccgagccc gttaccgtct tcggtcgcag ccacaccgcg acgggtgtgc 113220
gagggcacct ccaggagggg acgacgcggc aacggcccat gccacttctt ccttagccag 113280
ggtagcgacg gtgggggctt cgaacagcag gtcactaacg gaaagcgaga gcaaagcgcc 113340
aacagcttgc agagttgggc acaggccttg gaaaatggaa gcgacaggta ttttgcccat 113400
acgtggcgcg gtatcgccct agcatggtcg gcggcctggg cacgggacag cgtcaccaca 113460
acccatacgt gggcgccaag cagctgctgc gccgcacaaa tctgcgcctg tttggcgacg 113520
gtgtctgagc cagcgcgcaa cacggcgatc gcctgcgcca gcgacgggcg gtccaacagg 113580
tgcctggccc aggagggcat gtttccctgg aaaccccgct ccccgaatat gacaaaagcc 113640
acatattcct ccactggcac gccattctcg ccctcgaaca cgcggtgggc cgtcagctgg 113700
gcctcatcca aaccaaacca agacacaaga aagcgatccc agcgctgatc cagggccatg 113760
accttctcac cagcgcgacc gcacggccta agctccactg aaaggcgccc agaatccgca 113820
ccgtcctacc cccctggccc gcccaatata ccgctgtgac gtctgatgta caggcccgcg 113880
cgtcgcggcc gttggtggga aaaccggcac caccctgtgc ggccgaatcc gccacggggg 113940
ctgccagaca gtacactgtc tccagcagcg acttcagtct cttgtgactt ttgggcgtca 114000
ccaccaaaaa ttgcaaaacc tgcctgtagt ccgtgaagta ggtacggcat attaccatgg 114060
agttgtacac gcccaggttc tttgagaaca ccaggctcgc cttgaacttt gtaaagtcat 114120
cctgccccag cacgacagac gtatttttgg caaggtatac gtccgactcc acgggaagga 114180
cgtgcccaaa ctgggacacg gcgtcgcttg gtcggcacag aaagcacttc agggttgtgg 114240
aaaggccatt attcgatata acaaagcagg gagagaacgg gtagtgcatc tcctccagga 114300
ggtgcgccca aaacttatac acaaactcta agtggtacac gcaaccgtgc tgcattctaa 114360
ccgtacatat ggcggtagca ccgcccttag cataaactgg ggccccgtcg atgcaccgtt 114420
ccaaatccag ggactgacca gactgtccca agtatgagga taccacccga cacagttcgt 114480
ccactacacg cttaccaacg acactcatgg cgacagcggg gtggggctgg caaggccccc 114540
aaagcgcgac acccgcagtc aatcagggcc gtgcccgcgc ctcggagaat acggcgtccg 114600
tgctcacgat cttgcgcagg acctgcctta ccgtgtccac cttgctctcc aacaccagag 114660
tatgatcgca ggctgcaggc tgtgcccgct ggacgagaaa ggtttttaaa tactgacagt 114720
agttgatggc gttcaatcta caatagatcg tgggaaataa aatttgcatg tcacgaggca 114780
gaagctggtc agacgcgtac tccatgttgg gttccacggg gaggggaaca cacgccccaa 114840
gacacgacgg cgcacatagg gagcggagca aacaattgat tcaaatattt gactccgcag 114900
cgagccggtt tgcagagtgg tcacctgccc tgctccacac ccacccccgc gtctcttcca 114960
actctcaact cacgatccag ggaaaccacc gtccagtggc catgtttgtt ccctggcaac 115020
tcggtacaat tacccgtcac cgagatgagc tccaaaaact actggcagcc tccctgctcc 115080
cggagcaccc ggaggagagc ctcggtaacc ccataatgac acagattcac cagtcgctcc 115140
aaccatcttc cccctgcagg gtctgtcagc tcctattttc tctggtccgc gattcgtcca 115200
```

-continued

```
cccccatggg tttcttcgag gactatgcct gcctctgctt cttctgtcta tacgccccac 115260
actgctggac ctcgaccatg gcggcagcgg cagacctgtg cgagatcatg catctgcact 115320
ttccagaaga ggaggcgaca tacgggctat tcggaccggg tcgccttatg ggtatcgact 115380
tgcagctgca cttctttgtt caaaagtgct ttaagaccac cgccgccgaa aaaatactgg 115440
gaatatccaa cctgcaattt ttaaaatcag aattcatccg gggcatgctc acaggcacca 115500
tcacctgcaa cttctgcttc aaaacgtcct ggcccaggac agacaaggag gaggccaccg 115560
gccccacccc atgctgccag attacagaca ccaccaccgc acccgcgagc ggcataccgg 115620
aactagcccg ggccacattc tgcggcgcaa gtcgccccac aaagcccagc ctacttcccg 115680
cgctaataga tatctggtcc acgagctcag agctccttga cgagccgcgc cctcgactga 115740
tcgcaagcga catgagtgaa ctcaaatccg tggtcgcatc ccacgatccg ttcttctctc 115800
ccccgcttca ggcagacacc tcacagggtc catgtctgat gcacccaacc ctggggctac 115860
gatacaaaaa cgggactgca tccgtctgcc tcctctgcga gtgccttgcg gcacacccag 115920
aggcacccaa ggcgctgcag acccttcagt gcgaggtaat gggccatata gaaaacaacg 115980
taaagctggt agacagaatt gcctttgtgt tggacaaccc attcgccatg ccatatgtat 116040
cagatccgct acttagagag ctgatccggg gctgtacccc acaggaaatt cacaagcacc 116100
tgttctgcga cccgctgtgc gccctcaatg ctaaggtggt gtcagaggac gtactattcc 116160
gcctgcccag ggagcaggag tataaaaagc tcagggcatc cgcggccgcc ggacagctcc 116220
tcgatgccaa caccctgttc gactgcgagg tcgtgcagac tttggtcttt ctctttaagg 116280
gtctccaaaa cgccagggtg gggaaaacca cctcactaga cattattcgg gagctaaccg 116340
cacaactaaa aagacaccgc ctagacctgg cccacccctc acagacgtca cacttgtacg 116400
cttgagctgg tcccgggcct tcgcacccca tccaccgatg ccgaaatcag tgtccagcca 116460
catcagcttg gcgacctcaa ccggtcgcag tggaccgcga gacatcagaa gatgcttgtc 116520
atcccgcctg cggtcggtcc cgcccggggc gcgaagcgcc agcgtcagca gcaagcacag 116580
aaacggcctt cgcaagttta tctcagacaa ggtatttttt agcatcctat cgcacagaca 116640
cgagctagga gtggactttc tccgtgagat ggagaccccg atatgcacct ccaaaacagt 116700
aatgctgccc ctagacctgt ctaccgtcgc acccggccgc tgcgtctccc tctctccgtt 116760
tggacactcc tcaaacatgg ggttccagtg cgctctgtgc ccatccacag aaaatcccac 116820
cgttgcccaa ggctcccggc ctcagacaat ggtgggcgat gcgctcaaaa aaaataacga 116880
gctatgctcg gtagcgctgg ccttttatca ccacgcagac aaagtgatcc aacacaagac 116940
gttttaccta tcactcctca gtcactccat ggatgtggtt cggcagagct tcctgcagcc 117000
tggtctactg tacgctaacc tggtcctaaa aacctttggg cacgatcccc tacccatctt 117060
cactaccaac aacggcatgc taacaatgtg catccttttt aaaacccggg cactacatct 117120
gggagaaact gcgcttaggc tgcttatgga taacctcccc aactacaaga tatcggcgga 117180
ctgctgcaga cagtcctacg tggtcaagtt tgtcccaacg cacccggaca ccgcaagcat 117240
tgcagtgcag gtacacacca tatgcgaagc ggttgcggcg ctagactgca ccgacgagat 117300
gcgggatgac attcaaaagg gaaccgcact tgtcaacgcc ctataacctc acatgtagcc 117360
tgtcacccca gctcctattg caactgacca tgttcaggtg gtaataaagt cattaaacga 117420
caaagtgatt cttttaatct gtttattgtt tttgaacatg tggcacacgc tgcaatgtac 117480
tgccatgaaa ggtggttcta tatccaccac ttggcgtctg ccgaagtcag tgccacaatt 117540
tcattaacaa acaaggtcaa tacattgtga gggagtgttt tttgccatgg taccattcgt 117600
```

-continued gtggtttggg agagcggacg ccatttgcgt gcaaaatgtg ctttgctgga ggccaacttc 117660
cgtcgcgctg gttgatgcgc ggcacattgt gtcaaccagg gcaccctccc ccaccgagtg 117720
ctttaatgcg gagaggaatg gtggcctggt tgacaccgcg tgccggccat ctgaactgtg 117780
actgtgttat gagccacggg tatgccctcg atacgcctgc tcttcagcat tgtatgtgtt 117840
taatgttgtg cttggtgcaa ccgtgattgt gtttttgtat tttattttac tgacactctt 117900
tgggagggca cgctagcttc agtgcgcgcc cgttgcaact cgtgtcctga atgctacggg 117960
gccacgctgg ccactcgggg ggacaacact aatcgccaac agacaaacga gtggtggtat 118020
cgccccaagc ctccagcgcc acccatttag taacacatcc gggacatgaa ctgccacaaa 118080
caccgttaag cctctatcca tgcattggga ttggagtgag gagggaggag ggcaccaggt 118140
tcccggggag gagggcacca ggttcccggg gaggagggca ccaggttccc ggggaggagg 118200
gcaccaggtt cccggggagg agggcaccag gttcccgggg aggagggcac caggttcccg 118260
gggaggaggg caccaggttc ccggggagga gggcaccagg ttcccgggga ggagggcacc 118320
aggttcccgg ggaggagggc accaggttcc cggggaggag ggcaccaggt tcccggggag 118380
gagggcacca ggttcccggg gaggagggca ccaggttccc ggggaggagg ctggggtgcg 118440
ccgcgccggg ttcctggggt gcgccgcgcc gggttcctgg ggtgcgccgc gccgggttcc 118500
tggggtgcgc cgcgccgggt tcctggggtg cgccgcgccg ggttcctggg gtgcgccgcg 118560
ccgggttcct ggggtgcgcc gcgccgggtt cctggggtgc ggggtgcggg ggaccgcgcc 118620
ggggtactgc agggttcgca gggttcgggg gtactacctg gtttcctggg gtgtgccagg 118680
acgggttcct ggggtgccac cgctcctcga tacgtgtaaa tccaagagat ccgtcctccg 118740
tgccgccgcg cgcgtaatgc gcgagggggg tcggtctccc ctcttcttta tagcgtttcc 118800
tgcgaagggg gcgtaaccgt aggacaaact gcttatgtag ggttagcca cccatttccc 118860 ggggccgcgc cagaggtgag cgtggaccta gcatcccgct cccatttacc gaaaccaccc 118920
agaggcgaga ttccagggcc gtgactcact agctcccctc ccatcgaaca accacgcttg 118980
gctaacacgg ctggagtggc ggtgggcggg gcccctataa tcctggcccc catctactga 119040
aacgacccag tagaaaaatc ccaaccccat gactcatcag gccctattat atagaatatc 119100
ccagtagagt gacccagctg gtttccataa atggatatac ttccggaaaa cgaaggaggg 119160
ttgaatacag ttgggggtag tccgctggta ttcccagctg aggttgcctt atttggtaat 119220
gcttccggaa ataccacctg agtaccccat tggtttatac cttgtttaat tgtagaatta 119280
cagctggatt tacccagccg ggtttacgca gctgcgtata cccagctgtg tttacgcagc 119340
ggggtttacg cagctgggta gacccagctg ggtataccta ctggaatagg ggctgcgatg 119400
actcagctgc gctaggatta aaggattata tatatatata taggaaaaat caaaacaaaa 119460
ctctaatcgc tgattggttc ccgctctggg ccaatcagct tgggagttct agggataggg 119520
gccaatggga ggcctccgaa tttgattgac ggctggggcg tccaatggaa tggcgcggtc 119580
gcctagctcg aacgggattg gtcggccgga tgggccaatg gcggctcgga aaactttgat 119640
tgacgggccg gcggaccaat gggagcgggg cagaggatta tgggggatta gcaaattcaa 119700
gatggcggcg cccatgaaat ggccaaaaat tataattttt cgagtcgctc acggtcccac 119760
ctagcggcgt gacctggagg tgaccccgtg cacccgggcg ctctgaattt ttctgcgcat 119820
gcgcgactcc tcatctacat aatttatgca cataaaagga ttagcgcatg caaattagtc 119880
agatagcagg gccatccaca ctttatgttg gccgcgtgcc aggcgccggc gtgggcgccg 119940

-continued cgcgcgtgct ctctcagtcg cgcctagctg cttccaacag acaaaagcgg ggcgttagtg 120000
agggagtgcg cgcgctgcgc tgacttggcc gatttccagt gcatgctttg tcaccccagc 120060
gcgagaatgg aattttcatt attgagcaat ttgggcaccc tgggcacgat aaccatacat 120120
ggatacacgg gttccaaata tgcaaagtag acactaaggt accatttggc atatttggac 120180
gtcctgggca ggttagctac ccaccagaat atatgggact ctgggcagga tagccaccca 120240
caattgtttt gcgcccctct ttggccaggg gaccaaggtc gtatggttcg cgctacacta 120300
agcccgaacg ttcagctttg cgtgctttcg acgtccaggc ggctggcaca cgggccgtga 120360
gcgccagcaa catgggatca tggtagtaag atacagcata aatccccgtc cggtggcgct 120420
caacgccaat atgcgcggct gcgtggtatc tcatcggtgg gcacgcgtac ggtggtctca 120480
tgggtattgg acttgtaggc gaggggaggc gcatacgaca aaaattgccg ccgtgaaggt 120540
cgggaacccg cccgcgcttc cgcaaggcac ggggccgcat cggacacagg ctaagcatta 120600
aggatcataa caccgcccta gaaatgttta agctgtgacc aaagcgaacc tcgcatgagg 120660
catacgcgag cgtggaggta ggattcccaa ggctattgag agacggtggg tgaaatgatg 120720
aagaacacac agaacaataa cgggcgacta gataaaaaga ctcgctcaac agcccgaaaa 120780
ccatcagccc gaccgccgat ggattaggtg ctgctggaca agtctttcta aacccgcgca 120840
gggtttgtgt cgatccagac gcttacgaac gcccgcttta aaaacactat tcataattaa 120900
cagaagttga caccagcccg cagttaccca accttctatt tttttggagt gttgacaagt 120960
ttccatcgcc cgtttggcgt ttcccgcatg gtgtcaaatt agtgacgcac cctccccccg 121020
tcactatggg tttaccctga tttagtaagt aaaactgccg cccccgccca ctcatttttt 121080
taccctgtta tttgctgtat ttacatctac ggaccccctt ttggtgagat tgccgtggtt 121140
ctaaataacg ttgtggtttt cggacccttt cagggaccaa atcttttacg tgttgccaag 121200
gtagcatttg ctggacccgc ataggttttt gtggcaccag gttatggtct tatgagcggg 121260
cttgaccggc aagttccagg catcctaagt gcttgatgta gacccttagg gcaccaggga 121320
ctacctaggt caaactcccc cttagtcatg acgccgtgcc cacgaggttt gagaggcgta 121380
gacatccgtg tcgactgctg gacggaggta gtataatcag ctaggcctca gtattctatg 121440
taacaaatga atgccctaga gtactgcggt ttagctagtt atactgcccg gttccaccag 121500
gcggcgttgt ggccacgggc ggttcgtcgc ttggacctgg aggggtgtca cattctgtga 121560
ccgcgacgtt gacgttagac acacgtcgct gccgtcctca gaatgtgata gcccatcaca 121620
ggcattgtag ctgttgcgtt ggttgggagt ttggggacca aatttctata attggtgtca 121680
ccgcggcagc tctagccctg gaagatctgg aagcttgctt caatggctca gatcgacccg 121740
gactacagtt agcgaagtag acccattata atcttaatct taaatctggt tgacggactt 121800
tcgcgccggg aacacgcagg tggcagcgga tgtgttttgc ccaaacacga gggttgcagg 121860
aaacaggtgc tgccggggat tatgtacagc ttacacccag tttcctgtaa tcgcccgcat 121920
ccggccgtcc tgggcagcac cgcaccctgc gtaaacaacc gcgtactttt tcctcctccc 121980 cccacccccca catccttcct cccaccctgc cagtccaacc cgcttcctgt tttattcgcc 122040
ttcaaacaga agcacgcatt ctaatgattc ttacaaaact tgttagtgtt tattaaatca 122100
gatacataca ttctacggac caaaaattag caacagcttg ttatctatgg tgtatggcga 122160
tagtgttggg agtgtgatgg gccggaaagg tgaaggccca ttagggtttg cacttggcgc 122220
tgtaggtcta ctcttgacaa agatctaagc attgacatta gggcatccac gtcagtggga 122280
cccagtaggt ctaagttttc catacagtac acccagtgta agaatgtctg tggtgtgctg 122340

-continued cgagacccta tagtgtcctt gcttaaaaat atcaaagacc taatatccct cgcacacagc 122400
tccccgtcta cgtggagaac agtgagctga taagggctga aataactcat tgtgcccgct 122460
aggtggcgct ctaaaaaacg cgggtctaag tgaagcaggt cgcgcaagag gtctctgcga 122520
cctgcacgaa acagacattc cgctaacagg ggaaacgtta acctgccctc ctcctttaaa 122580
gctctaagag ctccaattaa ttgggccagt gtgggttgag gtatgaacac gtttaggagg 122640
aacaatacca cttccctgtc atccgtgccc agtttccgcg ccacctcaca gagaacctcg 122700
taagtggcca tggtgccggc ttgtatatgt gaaggcaccg atgtggaaaa acaaaggaaa 122760
atttattttt ccgccctaaa caaaatcaca agcttaatag ctgtccagaa tgcgcagatc 122820
aaagtccgaa acagatgtta ggatctgttc cactgccgcc tgtagaacgg aaacatcgca 122880
tcccaatatg cttgccagct gaggaactac cccacccgag tgggtatcct gcggaatgac 122940
gttggcagga accaacagcg cacagcctgc agcgctgata atagaggcgg gcaatgagcc 123000
agtctttggg tcaactaagg cttttgtaat cagggtgttg acctcgtggt gccaaaagtc 123060
caggtgttgg gagcccccca gcaatttaag taacaagaag gaagtgacgt ccgtcgctaa 123120
gactgcctct gttcgccacg ccaacttctc aaggagttct ttctcctggt ctataagttc 123180
ttggcgggaa aaggagtctg ccgcggcata gcaaagtgaa ctggtagaaa taggcgtgag 123240
gcttctgagc ttactggcca ctaacaggca ggcgctccct gtcttttgaa agtgttcttt 123300
ggacacctgc tttataagta ggagtctgtc caaaagatta agggccaacg cgaccacgtt 123360
aggttctagg ttgtattcct ggcaaactga aaacatccat gtgcccagta acttacgcat 123420
atgcgaagta agagattgtt gaaaggtccc aaatacagag tcagaagtta aaaagcgcgg 123480
ctcaatttca agaatattgt aaaagatccg atcctcacat agcgtgggat ccagaagtcc 123540
cgagggcggg ttattggcag ttgccatata gagtggcgag cgtatgtggc ctacctgtag 123600
agcctggagt ttcagggtgc tctgtcaggt tctcccatcg acgacgctgg gccgcgagag 123660
tacgctagcc gttgtccgtg tgttcagttg aggtagatgg gtcgtgagaa cactgccccc 123720
cacacacacc agcacccatg gcgccaaatg caagtgcgga gcggcgacgg tggcttctag 123780
ggaggaaaaa gggggagagg tgtggctttt atgtcatttc ctgtggagag tccccaggac 123840
cttggttttc ccctggctgg gttaatggca ggggcttttt aaacttaact atggaagatt 123900
gtaggtttcc tgccaggggg tgactagctt cccaggctag gcgggccatt tgtactttct 123960
tacttgtgtc tttgttctga caatacacat atacacaata agttatgggc gactggtctg 124020
gtccagggtg gggcaagcag gacacggggc ctgcctttac tcctccaaac tggaaggcct 124080
gagataattt tttaagtccg tatgggtcat tgccccaaaa aatcactgca aacttccatt 124140
gacactttgg atctcgtctt ccatcctttc ccaaaaagcg tctataaaag atgtgttgtg 124200
gcctagcttt cgcaggacaa tcatctatct gtctgtaagg gaccggtggt tgttggtatc 124260
ttggatgtgg ctttttgggg tgggtaactg gaacgcgcct catacgaact ccaggtctgt 124320
ggggtggtga tgttctgagt acatagcggt attcgcgaga tgggccaggt tgtgggtcat 124380
cgtctggtgt attatctcct ggtgggctac tggcaatttg ttcatgtgtg ctaacaacag 124440
ggtaatccac ttccatttcg tcctcggatg acgacccgtg caagattatg ggctcttcca 124500
ccgtctcctg ctcctgctgt tccacccccct gctgctcctg ctcttccacc tcctctaact 124560
cctgctgctc ctgctcttcc acctcctcta actcctgctc ttcctgctct tccacctcct 124620
ctaactcctg ctcttcctgc tcttccacct cctctaactc ctgctcctcc tgctcctcct 124680
gctcctgctc ttgctcctcc acctcctcta attcctgctc ttcctgctcc tgctcttgct 124740
cttccacctc ctgctcttgc tcttccacct cctgctcctc taactcctgc tcctgctcct 124800
ctaactcctg ctcctgctcc tctaactcct gctcctgctc ctctaactcc tgctcctgct 124860
cctctaactc ctgctcctgc tcctctaact cctgctcctg ctcctctaac tcctgctcct 124920
gctcctctaa ctcctgctcc tgctcctcta actcctgctc ctgatcctct aactcctgct 124980
cctgctcctc taactcctgc tcctgctcct cctgctgctc ctgctcctcc tgctgctcct 125040
gttcatcctg ctgctgctgc tcatcctgct gctgctgctc atcctgctgc tgctgctcat 125100
cctgctgctg ctgctcatcc tgctgctgct gctcatcctg ctgctgctca tcctgctgct 125160
cctgctcatc ctgctgctcc tgctcatcct gctgctcctg ctcatcctgc tgctgctcat 125220
cctgctgctg ctcatcctgc tgctgctcat cctgctgctg ctcatcctgc tgctgctcat 125280
cctgctgctg ctcatcctgc tgctgctcat cctgctgctg ctcatcctgc tgctgctcat 125340
cctgctgctg ctcatcctgc tgctgctcat cctgctgctg ctcatcctgc tgctgctcat 125400
cctgctgctg ctcatcctgc tgctgctcat cctgctgctg ctcatcctgc tgctgctcat 125460
cctgctgctg ctcatcctgc tgctgctcat cctgctgctg ctcatcctgc tgctgtggct 125520
cccgctgctg tggctcccgc tgctgtggct cccgctgctg tggctcccgc tgctgtggct 125580
cccgctgctg tggctcccgc tgctgtggct cccgctgctg gggctcccgc tgctgtggct 125640
cccgctgctg tggctcctgc tgctgtggct cctgctgctg tggctcctgc tgctgtggct 125700
cctgctgctg tggctcctgc tgctgtggct cctgctgctg tggctcctgc tgctgtggct 125760
cctgctgctg tggctcctgc tgttgtggct cctgctgttg tggctcctgc aggggctcct 125820
gctgctgtgg ctcctgctgt tgtggctcct gcaggggctc ctgctgctgt ggctcctgct 125880
gctgtggctc ctgctgttgt ggctcctgca ggggctcctg ctgctgtggc tcctgctgct 125940
gtggctcctg ctgttgtggc tcctgctgct gttgtgaact ttggatgctc aacgttttgt 126000
ttccatcgcc cccgtcctcc tcgtcctcct tcttgtcctc ctcctcgtca tcctcctcgt 126060
cctcattgtc ctcatcatcg tcatcctcct cgtcctcctc ctcctcgtcc tcctcctcgt 126120
cctcctcctc gtcctcctcc tcgtcatcct cctcgtcatc ctcctcgtca tcctcctcgt 126180
catcctcctc gtcatcctcc tcgtcatcct cctcgtcatc ctcctcgtca tcctcctcgt 126240
catcctcctc gtcatcctcc tcgtcatcct cctcgtcctc ctcatctgtc tcctgctcct 126300
cctcatcatc cttattgtca ttgtcatcct tgtcaacctg actttccttg ctaatctcgt 126360
tgtccccatt atcctcgcca gcctgattat tttcggaaca ttctttttca ttcttggatg 126420
cttcttctgc aatctccgca aggagcacca acatggctgt gtcatcaccc caggatccct 126480
cagacgggga tgatgatcct atggagatgg gagatgtagg cggttggcgt ggcggagtat 126540
cgccatcgct ggatgatccc acgtagatcg gggactctgt ggcccatggg gggtacacac 126600
tacggttggc gaagtcacat ctagggggag agactggggg cgactgacat attgggttta 126660
gtgtagaggg accttggggg gacgatagcc ttctttttct caggctacgc agggtagacg 126720
gagctaaaga gtctggtgac gacttggagg gaggctcggg tggaggagtc gtgggtgagt 126780
gtggaggtgt agtctgctgc gagggtggcg gacgcatagg tgttgaagag tctggccttc 126840
ctgtaggact tgaaagcggt ggcctttgag aagactctgg agactgcgtg ggtggcaatg 126900
caggagatgg agaatgagta tccgtggtcc ccggagacac aggatgggat ggagggattg 126960
gggaggaaga cgtggttacg gggggtaaga gtgccggtgg aggtaaaggt gttgcgggag 127020
cgggtgaagg aatgggagcc accggtaaag taggactaga cacaaatgct ggcagcccgg 127080
atgtgaacac tgtgggactt ccaggtatag gcaaggtgtg gggtccacat tcccggccgt 127140
cgatggagtc ggcgacatgc ttccttcgcg gttgtagatg taggtcatcg ccaaggtcac 127200
atctttccgg agacctgttt cgtttcctac aacttcctct cgttaagggc gcgccggtgc 127260
tccgtcccga cctcaggcgc attcccgggg gcgccatcct cgggaaatct ggtctgacaa 127320
ccaaagtaaa attatggagg cggtggcagt atattcacat tatgcaatac ccgtagtgac 127380
cacaaggggg agctctcaga caattaagcg gttacacaca gtagcaggct gcagtaccgc 127440
ccatggccac aggatgtaga tcgcagacac tgaaacgctg aaacacagca ttaagctgca 127500
ataccgccga tggccaccag atggcacgcg ccgccagcaa atttaagtcc tggtggctca 127560
cctgccaggt aaacaaggtt aaagtgggtt tgctggcctt gcgttgccat ggatgctacc 127620
taggcaagtc cagatatata atccgggcgt gagaaacaga aacggccaat aacccatgtt 127680
tttcgaaaac caccacacac cttaacacaa atcatgtaca cctggtatta ctatttccca 127740
cacatcttat agcatttcaa agataagggt gccttacggg ccgcccgaaa caagtgggcg 127800
ggcgctactc actgtttata agtcagccgg accaagctgc tgctcttggg gacgtgactg 127860
cttcgtggcg cagctgcctc caaatgatac acacattttt tgattgtccc gggcgccgcg 127920
tagtggaggg cggagttata tcaagctact ttctgattgg tgccccaggc aggactgcca 127980
taaaaactga agaaggcgtg tctgctttgc agaatttacc ccccactgtg ctcccggttg 128040
ctggcaccgg ttcagtggtc cgacctgtcg tctgtgctcc cccgtggacg acgccgagtg 128100
cctctcgggg gtccatgtct agcctcttca tttcattacc ttgggtggcg ttcatctggc 128160
tagccctcct tggcgcggtt gggggtgccc gcgttcaggg gcccatgcgg ggctctgctg 128220
ccctcacctg cgccatcacg ccccgtgctg acatagttag cgttacctgg caaaaaaggc 128280
agctccccgg tcccgtaaac gtcgccacgt acagccattc atatggggtg gtggttcaga 128340
cccagtaccg ccacaaggca aatataacct gtcctgggct ttggaactct acccttgtta 128400
tccataacct tgcagtggat gatgagggct gttacctgtg tatctttaac tcatttggtg 128460
gccggcaggt gtcatgcaca gcctgcctgg aagtgacatc tccccctact ggacacgtgc 128520
aggtaaatag cacagaagac gcagacaccg tcacctgttt ggcaactggt cgcccacccc 128580
ccaatgtcac ctgggccgca ccctggaaca acgcctcttc tacccaggag cagttcactg 128640
acagtgatgg tcttacagtt gcgtggagga ccgtgaggct gccgcgtggg gataatacca 128700
ccccaagtga gggaatatgt ctcatcacct ggggaaatga gagcatatca atcccggctt 128760
ctattcaagg ccccttggcc catgaccttc ccgcggccca gggaactctt gccggggttg 128820
ccattactct ggtgggccta tttgggatat tcgcattaca tcattgccgc cgcaagcagg 128880
gcggtgcatc acctacttca gatgacatgg acccccctatc cacccagtga ctagatggac 128940
accccgtgaa ccgtcgtgct tacccacccc cttctgattc tgacagacaa cactactatg 129000
tcccaaagac tgttttttac agcccgatgg cccttcaggc ctccttgagt gtctagctgg 129060
tcccgtggtc attgtgtggt ttggcagtca cttccccatt ttggtgtcgc gttttgggtt 129120
ttgccctgcc cccagccaac gtggatcata ttctttcccg tcaggggagt gacaagctat 129180
aggacagaaa ggtcacctgg cccaaacgga ggatcctagg tgggtgtgca tttattagac 129240
gttggtgtgt tgaaggacgg atcaggcggg gaggaggggg tgggggagac ttactgcagc 129300
actaggttag gttgaaagcc ggggtaaaag gcgtggctaa acaacaccta tactacttgt 129360
tattgtaggc catggcggcc gaggatttcc taaccatctt cttagatgat gatgaatcct 129420

-continued

```
ggaatgaaac tctaaatatg agcggatatg actactctgg aaacttcagc ctagaagtga 129480
gcgtgtgtga gatgaccacc gtggtgcctt acacgtggaa cgttggaata ctctctctga 129540
ttttcctcat aaatgttctt ggaaatggat tggtcaccta catttttgc aagcaccgat 129600
cgcgggcagg agcgatagat atactgctcc tgggtatctg cctaaactcg ctgtgtctta 129660
gcatatctct attggcagaa gtgttgatgt ttttgtttcc caatatcatc tccacaggct 129720
tgtgcagact tgaaattttt ttttactatt tatatgtcta cttggatatc ttcagtgttg 129780
tgtgcgtcag tctagtgagg tacctcctgg tggcatattc tacgcgttcc tggcccaaga 129840
agcagtccct cggatgggta ctgacatccg ctgcactgtt aattgcattg gtgctgtcgg 129900
gggatgcctg tcgacacagg agcagggtgg tcgacccggt cagcaagcag gccatgtgtt 129960
atgagaacgc gggaaacatg actgcagact ggcgactgca tgtcagaacc gtgtcagtta 130020
ctgcaggttt cctgttaccc ctggccctcc ttattctgtt ttatgctctc acctggtgtg 130080
tggtgaggag gacaaagctg caagccaggc ggaaggtaag gggggtgatt gttgctgtgg 130140
tgctgctgtt ttttgtgttt tgcttccctt accacgtact aaatctactg gacactctgc 130200
taaggcgacg ctggatccgg gacagctgct atacgcgggg gttgataaac gtgggtctgg 130260
cagtaacctc gttactgcag gcactgtaca gcgccgtggt tcccctgata tactcctgcc 130320
tgggatccct ctttaggcag aggatgtacg gtctcttcca aagcctcagg cagtctttca 130380
tgtccggcgc caccacgtag cccgcggatg tctacgtgcc cttccccctt aatttaatct 130440
agcctcccgt tcccatgatg cagagaggcg aatttggttt gtacacagat gtgactatgt 130500
atttgtttta ttatgcgatt aaatgagggg tctgatccca aaagcaatgt ttagtggtgg 130560
tcgttgatct tcttgacgct ccataggtag attgactgga acgccatggc ccacggggac 130620
atggacaggg gtgttaggtc tggtggaaca tgctgccact gccacggatg gaacatcaga 130680
gatgggtcta tgatcagggc agcgtgtcgc ccgtcactgg atgtaagtcc ggccaccgtg 130740
gagttgcctg tggggtttct gggatagtgt ctggctggca gggtctcatc cgcggcattt 130800
ccatggtagg tgagggttat ctcgcctcgc tgtctcagta tgtactcgag ggcgtcctgc 130860
tcgtaccgga cccccaggta ctctccctgg gcccagctgg gcagcaccgt cccccgcaac 130920
actcggagga aaacgctctt agtgttctga gggatctgta tgtttagcca gtggctgtca 130980
tacagcttgg acacgttggt ctccaggttt accgcccagc gctggggtgg tgtgggtccg 131040
tacgtgtatg gtgaggattc cgaccggccc actacaccca gggccaccag cagctggaag 131100
cccacctcgc cacagcagat ggagaatgtg tcgggtctgt ttagaaactc tgtcagggtg 131160
gaggcacagg tagggtcgtt acacagcgcc aggacccatc ccctggcgct ggcgtagctg 131220
gcctggcagc ctgttctgag acatgtaatc agaccagaga accccgacaa ggactgtcct 131280
cgtttaagct cttccacagt caccgtggcc acctcaaagc ccgtgttctg caacgcggcc 131340
atgagcgcgt acggggcact gctcccaggc agcaccaacg cggccacacg gcgcggggag 131400
gtggggcacg aaaacaggcg cagctgactc ccaaggcaca tggcccttag gctgcccagg 131460
tgatgctcca gacgacccag gtccttcctg tgcatgtcct ccagtgggtg caggggaggc 131520
gtcaccaggt tccacatttc gtcagaaaag gaggtccatg agacttgcaa ggaagtcagg 131580
gtctcttgaa acacaactgt ctcgttctgc aaaaccgtga cgttgttgcc ttgtccctcg 131640
gggccaacgg tgcccagtgg gtgtgccacg cagcggtagt ccctggccgc ccgcagcacc 131700
tctgacaagt gtacctgggg cacctcaacc agtgccccag gggtctctga aaccataagt 131760
tcgagcgggt tagggtgggc gggtagtgag agctgcagtc ccctgcagcc ggccagggcc 131820
```

atctcgattg cagatgggag aagccctccg tcccctatgt cgtgcccaga tacaatgagc 131880
ctcttggaca tcaggtactt aacaagcatg aacaggctgg cgaccgtgga cgggttcaga 131940
gggggtattg ggtgcctgga tgccaggaag ttgtgctcga aggtggaccc ggctatgaga 132000
cagctctgat tcacggccag gtataccagg gcgttgcctt cgacctttac gtccggggtg 132060
accctgtatc tggatccctt gacctcggcc cagctggtaa acaccaccga gttgaaggga 132120
aggacctcca ccgtttcttg ctgttgtgtg atgcgcacat ggcgctccga aagcgtcgga 132180
gagctggcag ccgaggagat ggacagtgcc actcccagct cccggcagaa ttccttgcag 132240
gcgaagaggc actcctgtag gaggccggct tggtggtcct ctggactcca cgccacggcg 132300
ccagttagca ctacgtcctg gagcttggac acgggactga acatgaggtt ggtgagagcc 132360
tcggtgatgg cataggtggc cccggtggat acattagtag ccatcttgta ggcctgctcc 132420
cccatggcca ttgcctgacc cctccacgct ggcactggaa gcagctcctg gggcagggcc 132480
ttcacccagg tctcgaagtc cttgtgtagg aggttggcca tggacggagt gatggcctcc 132540
accgtgtcgg gcactctggg cgccaccctc tcggccagca tggacgagtg cagcaccagg 132600
tggtagtctg aaaccggtat gtccaggggt cccacgccag cctgttgggc gatgaggccg 132660
ttggagcatc ggtccatgtg tcgcgtaaag aactccttgc tgccaaccgt cgagtggcga 132720
agtaactggt ggattgtgga gccggtggca aaaaggcccc agtcaacatc ctcggggtgc 132780
cccgagacgc ggacaccatc ggacagcgcc agccaggggg acgggggggt ggacgacggc 132840
tggtctacag agaagaccct cgtggtctcc ccggtcaggt cgtctactat tctgatgcct 132900
gggtgctccg aggtcctccc gaggaccgtt acctggcacg cgcacaggcg cgcggcgcgc 132960
tgcagtacct ccaacggggt ctcgcccaga tccccaggca ccgcgcccga ctctgccacc 133020
accgcaaaca ccagggagca atacacgttg agaaagtgct ctgccaccgc cgccttcacg 133080
gcatccggac cggccgcggg atccgcaggc aggtgggtgc gcacctcgtc gggtagcttg 133140
gagacaaaca gctccaggcc ggtccgcggc gccagcgcct gcaggtgcct caccaccggg 133200
gccgggtcat gcgatctgtt tagtccggag aagatagggc ccttggcaag ccgctggacc 133260
agcttcaggg tctccaagat gcgcaccgca ttgtcggagc tgtcgcgata gaggttaggg 133320
taggtgtccg gtccatccgt gggctcaaac ctgcccagac acaccactgt ctgctggggg 133380
atcatccttc tcagggagat gcattctttg gaagtagtgg tagagatgga gcagactgcc 133440
agggcgttgc caggagtggt ggcgatggtg cgcaccgttt ttaagaaacc ccccagggtg 133500
gggactcccg ctccctgcag catctcggcc tgctgtacgc ccttggcgaa tatgcgacgg 133560
aatcggctgt gcgcacgggg tcccagggcc ggttcggtgg catacaggcc ggtgagggcc 133620
ccctgtgtct gtccgcctgg aaacagggtg ctgtgaaaca gcaggttgcc aaggccgcga 133680
atacccctct gcacgctgct gtggacgtgg gtgtacgctc cgtggatccc gaacgcctgt 133740
ctggcacagt tccagggcca ccgttccatg gtgcatcttc ccggtatcac aaagtacctg 133800
gccacgttat aattgtcccc ggttgaagcc tgcaccgcca gcggtagcag gtctgccccc 133860
agggatatca taacagcctg cataatgaca tcatcttcaa tgtgtggcct agccacgggc 133920
tggggaccct cgggcacttc caacccctcg tacggtacca ggtcggtatt ttgtgtaaat 133980
gccctgataa actgaggtgg gtgtggttct agcagggtct gtgtgatttt ggacaccagg 134040
tgcctgccca cttccactct agcccactcc tgcaatccta gctcttgcag cagaactgca 134100
agctctgttg acaatgttgt gggccggtgg tgcatgtttg gcccgtagcc aaaggataca 134160
acacgctcgc tcccccgtgg cacagaccgc ctgatgacat ggggatatcc aaggagcggt 134220
gacagcacag cgagcaccgt ctgtatttcc acatcccgtc tctctcgctc ctccctcgaa 134280
gtgggaggtc ttcggaaagt tatccatagc agatagtagc ctccggtgcc accgggtacg 134340
agagtgagtg tgcccgtacg gcttgtataa aagttcacaa aagcttcctc atccgcggtg 134400
agatcactct ccaaccacag cccagtgacg tcgtaggcca tgcctagagg gcgcaccgcc 134460
cccggggaca ccctctgtag tcaggctgcc gagaaacccg cgagatctct ggggagtagg 134520
aagaaactta gaatccccaa atatgtcgca gtcacaggtt gtcgggcaga gtctgtttcc 134580
gctttcatgg gatccacagt tacttgtagc catgtcacta acctcaaata ctcaaaaaaa 134640
gctatcgatg gaaaaatgct gtggtcctag gttagtccgt gggaaacaaa acttcctcat 134700
acacttcatc tgcaggctga aatggtggcg gatccagact ccttacacca cagttgctca 134760
cattagagat acctgattgg ttaatacaag cggacgcacg cgttggtgga ggcgtgttgt 134820
cgcccaagat actagcatag gtgactgtgc gttcgctatg tagttgctgc atttcaagtt 134880
gggtcgttac ttctgtgttg caaaccctta ctggagataa tgccatgtct gttgtggaac 134940
ttaaaatacg cgagtgtata acatttctag atggtagagg tggtaaacgg cgagctaaat 135000
gattaacatc gggacatatc ctgcctgcat gagcatgtgg tgtgtcgtgt ggtgtatata 135060
ttggtaatct tgttgttaca ttgttgaacg acacaagtct gctctctcgg tagagataac 135120
ccaccagtac ggcttggcca gtacctaata agaaaaaata aaatcgttaa tctctgtttt 135180
tatgtggcgc tggtgttcca attataaata aaaacacaac tcacttaata tcacaattac 135240
acaaatcagt cctgaagtaa cacctgtagt ccaaccgtca gtgtagagca ggactaactt 135300
aacacagcat ccagcacatg tccatgctaa ggaaataaac caaagttatg tttcggtttg 135360
ctttatgacc agggagctgc tacccaggta caaaaaatcc ttacccaaaa atagaaacag 135420
gaagccacca gagagtgaag ctttgtgaaa gctttgccag cagaagaaac aatataataa 135480
aaagccacag cctgctagta atgttatact ccctgtaaat aaaaaatatg gacagtaata 135540
atttatgaca cccaataagt atgtggaaaa aatgtaatgt aaaccactat actggtaaaa 135600
acataccttc gttattggtg tcttgttcgc gctttataaa cagtatccct attgttgtgg 135660
ttagtgtaac caacactcct ccttgtaaaa gtaaaaatga cataagcccc ttagttgatc 135720
caatccaatg tcgtttcatt gttataaaca agccggtcat acctgtaata aagttattca 135780
ttacaaaatg ttataatagt attggtaatg tttagttaag ataatgtaaa cttcacagta 135840
gtcatatacc aatatgtatg cagcttatgc atcctgcgat gattacagaa aggcatgaat 135900
gggaaacgca aaaaaaggcc ggtgttgcct tgagtatacc tgtagtaaaa aataaataat 135960
attgttggtt gcaatgctta ggtgcaagca gacataattg catagcagta aaaaccagac 136020
ttaccaccac atattgcaaa cacacatgca gcgagcttga gacaaggccc attatctgtt 136080
gcaaagatat gtataaaaaa aacaagcaac aatgtccata atggcaaaaa aaactggcaa 136140
tgtgtccagt tgttgtaaat ctgcaatccc attgagaata taagtaccaa caccataaca 136200
atgcacagta atccgctatc aatagtgcat ttaacgactc ttaatgttcc accaagtgat 136260
agaatggctg aaaaacacat acaggggaat tacgtttttt taaaaaattg gaaatattag 136320
atacataatt tttatttaat aaaaaacctt tagtaaaact taccagtaat tatagacaat 136380
aaacttataa tacaaacaca aacagtactc aaagtacttt gagtagagaa actccaactg 136440
gcaaaggcaa tacatcctaa aacaaaagac aaatacacga gacatttaaa caatgtatac 136500
ttagaaagaa ataagttaaa catttaaaaa atgtaactta ccaacaatta tagatggtcc 136560

```
aatgggaggg gaagcttgaa aacgttgttt ttttgactgc acatatatgt tgttattgta 136620

caaaaaagtt ggtagtaaac acttatgtta ctgagcaaaa atatggtgtt ttgtaaattt 136680

atagttaaaa gacaaaacat aatagacaaa cacccacaac atgttataag tgctgcaaac 136740

caagtacccc acaggtattt tttgtaattc attgtagaca aaaagcccaa ggcccaaaaa 136800

tgaagtggac aaaagaaata tgtaattaag tgtagttgga caaggaatta tatagctgga 136860

tgagttagtt ttgcacagaa ccagacatcc tatttttgtt tggaaaccta aaatccggat 136920

gaagggctta taaaatggca cagctgcaaa aagctgataa tgtaacactg catcctggtg 136980

tttttgattg tagcggaaaa atgtaataaa ttttacagac agttttgcct actgagaaca 137040

tgttgaaaaa aaggcactaa gggctttttt gccaaaggaa aaatgccccc gtggggttag 137100

gggaaagggg ggatggggtg atgggggaat ggtgggaaag gggggatggg gtgatggggg 137160

aatggtggga aaggggtgat ggggtgatgg gggaatgggg ggaaaggggg aatgggggga 137220

aagggggaat ggggggaaag ggggaatggg gggaaagggg ggatgggggg aaagggggaa 137280

tgggggggaaa gggggaatgg ggggaaaggg gggatggggg gaaaggggga atggggggaa 137340

agggggggatg gggggaaacg ggggatgggg ggaaaggggg gatggggggg aaaggggga 137400

tggggggggaa agggggggatg ggggggaaag gggggatggg ggggaaaggg gggatgggga 137460

agggggggggg gagggggaag ggggtgaagg gggaaggggg gaggcgaa             137508
```

```
<210> SEQ ID NO 60
<211> LENGTH: 3043
<212> TYPE: DNA
<213> ORGANISM: Homo sapiens

<400> SEQUENCE: 60

ttctcagagt ggctgcagtc tcgctgctgg atgtgcacat ggtggtcatt ccctctgctc     60

acaggggcag gggtccccccc ttactggact gaggttgccc cctgctccag gtcctgggtg    120

ggagcccatg tgaactgtca gtggggcagg tctgtgagag ctcccctcac actcaagtct    180

ctctcacagt ggccagagaa gaggaaggct ggagtcagaa tgaggcacca gggcgggcat    240

agcctgccca aaggcccctg ggattacagg caggatgggg agccctatct aagtgtctcc    300

cacgccccac cccagccatt ccaggccagg aagtccaaac tgtgcccctc agagggaggg    360

ggcagcctca ggcccattca gactgcccag ggagggctgg agagccctca ggaaggcggg    420

tgggtgggct gtcggttctt ggaaaggttc attaatgaaa acccccaagc ctgaccacct    480

agggaaaagg ctcaccgttc ccatgtgtgg ctgataaggg ccaggagatt ccacagttca    540

ggtagttccc ccgcctccct ggcattttgt ggtcaccatt aatcatttcc tctgtgtatt    600

taagagctct tttgccagtg agcccagcta cacagagaga aaggctaaag ttctctggag    660

gatgtggctg cagagcctgc tgctcttggg cactgtggcc tgcagcatct ctgcacccgc    720

ccgctcgccc agccccagca cgcagccctg ggagcatgtg aatgccatcc aggaggcccg    780

gcgtctcctg aacctgagta gagacactgc tgctgagatg gtaagtgaga gaatgtgggc    840

ctgtgctagg caccagtggc cctgactggc cacgcctgtc agcttgataa catgacattt    900

tccttttcta cagaatgaaa cagtagaagt catctcagaa atgtttgacc tccaggtaag    960

atgcttctct ctgacatagc tttccagaag cccctgccct ggggtggagg tggggactcc   1020

attttagatg gcaccacaca gggttgtcca ctttctctcc agtcagctgg ctgcaggagg   1080

agggggtagc aactgggtgc tcaagaggct gctggccgtg cccctatggc agtcacatga   1140
```

-continued

```
gctcctttat cagctgagcg gccatgggca gacctagcat tcaatggcca ggagtcacca   1200
ggggacaggt ggtaaagtgg gggtcacttc atgagacagg agctgtgggt ttggggcgct   1260
cactgtgccc cgagaccaag tcctgttgag acagtgctga ctacagagag gcacagaggg   1320
gtttcaggaa caacccttgc ccacccagca ggtccaggtg aggccccacc cccctctccc   1380
tgaatgatgg ggtgagagtc acctccttcc ctaaggctgg gctcctctcc aggtgccgct   1440
gagggtggcc tgggcggggc agtgagaagg gcaggttcgt gcctgccatg gacagggcag   1500
ggtctatgac tggacccagc ctgtgcccct cccaagccct actcctgggg gctgggggca   1560
gcagcaaaaa ggagtggtgg agagttcttg taccactgtg ggcacttggc cactgctcac   1620
cgacgaacga cattttccac aggagccgac ctgcctacag acccgcctgg agctgtacaa   1680
gcagggcctg cggggcagcc tcaccaagct caagggcccc ttgaccatga tggccagcca   1740
ctacaagcag cactgccctc caaccccggt gagtgcctac ggcagggcct ccagcaggaa   1800
tgtcttaatc tagggggtgg ggtcgacatg gggagagatc tatggctgtg gctgttcagg   1860
accccagggg gtttctgtgc caacagttat gtaatgatta gccctccaga gaggaggcag   1920
acagcccatt tcatcccaag gagtcagagc cacagagcgc tgaagcccac agtgctcccc   1980
agcaggagct gctcctatcc tggtcattat tgtcattacg gttaatgagg tcagaggtga   2040
gggcaaaccc aaggaaactt ggggcctgcc caaggcccag aggaagtgcc caggcccaag   2100
tgccaccttc tggcaggact ttcctctggc cccacatggg gtgcttgaat tgcagaggat   2160
caaggaaggg aggctacttg gaatggacaa ggacctcagg cactccttcc tgcgggaagg   2220
gagcaaagtt tgtggccttg actccactcc ttctgggtgc ccagagacga cctcagccca   2280
gctgccctgc tctgccctgg gaccaaaaag gcaggcgttt gactgcccag aaggccaacc   2340
tcaggctggc acttaagtca ggcccttgac tctggctgcc actggcagag ctatgcactc   2400
cttggggaac acgtgggtgg cagcagcgtc acctgaccca ggtcagtggg tgtgtcctgg   2460
agtgggcctc ctggcctctg agttctaaga ggcagtagag aaacatgctg gtgcttcctt   2520
cccccacgtt acccacttgc ctggactcaa gtgtttttta tttttctttt tttaaaggaa   2580
acttcctgtg caacccagat tatcaccttt gaaagtttca aagagaacct gaaggacttt   2640
ctgcttgtca tccccttgga ctgctgggag ccagtccagg agtgagaccg gccagatgag   2700
gctggccaag ccggggagct gctctctcat gaaacaagag ctagaaactc aggatggtca   2760
tcttggaggg accaaggggt gggccacagc catggtggga gtggcctgga cctgccctgg   2820
gcacactgac cctgatacag gcatggcaga agaatgggaa tattttatac tgacagaaat   2880
cagtaatatt tatatattta tatttttaaa atatttattt atttatttat ttaagttcat   2940
attccatatt tattcaagat gttttaccgt aataattatt attaaaaata tgcttctact   3000
tgtccagtgt tctagtttgt ttttaaccat gagcaaatgc cat                    3043
```